US012053459B2

(12) United States Patent
Kirman et al.

(10) Patent No.: US 12,053,459 B2
(45) Date of Patent: Aug. 6, 2024

(54) CDK2 INHIBITORS AND METHODS OF USING THE SAME

(71) Applicant: Cedilla Therapeutics, Inc., Foxboro, MA (US)

(72) Inventors: Louise Clare Kirman, Swampscott, MA (US); Carl Eric Schwartz, Marblehead, MA (US); Wojtek Michowski, Worthington, OH (US); Dale A. Porter, Jr., Cambridge, MA (US); Justin Ripper, Thebarton (AU); John Feutrill, Rosanna (AU)

(73) Assignee: Cedilla Therapeutics, Inc., Foxboro (MA)

( * ) Notice: Subject to any disclaimer, the term of this patent is extended or adjusted under 35 U.S.C. 154(b) by 18 days.

(21) Appl. No.: 17/849,321

(22) Filed: Jun. 24, 2022

(65) Prior Publication Data
US 2023/0121337 A1  Apr. 20, 2023

Related U.S. Application Data

(60) Provisional application No. 63/202,844, filed on Jun. 26, 2021.

(51) Int. Cl.
| | | |
|---|---|---|
| A61K 31/437 | (2006.01) | |
| A61K 31/444 | (2006.01) | |
| A61K 31/4709 | (2006.01) | |
| A61K 31/4725 | (2006.01) | |
| A61K 31/497 | (2006.01) | |
| A61K 31/498 | (2006.01) | |
| A61K 31/4985 | (2006.01) | |
| A61K 31/501 | (2006.01) | |
| A61K 31/506 | (2006.01) | |
| C07D 471/04 | (2006.01) | |
| C07D 519/00 | (2006.01) | |

(52) U.S. Cl.
CPC .......... *A61K 31/437* (2013.01); *A61K 31/444* (2013.01); *A61K 31/4709* (2013.01); *A61K 31/4725* (2013.01); *A61K 31/497* (2013.01); *A61K 31/498* (2013.01); *A61K 31/4985* (2013.01); *A61K 31/501* (2013.01); *A61K 31/506* (2013.01); *C07D 471/04* (2013.01); *C07D 519/00* (2013.01); *C07B 2200/09* (2013.01)

(58) Field of Classification Search
None
See application file for complete search history.

(56) References Cited

U.S. PATENT DOCUMENTS

| | | | |
|---|---|---|---|
| 7,351,719 B2 | 4/2008 | Stenkamp et al. | |
| 7,435,830 B2 | 10/2008 | Pennell et al. | |
| 7,435,831 B2 | 10/2008 | Chen et al. | |
| 7,452,911 B2 | 11/2008 | Stenkamp et al. | |
| 7,544,695 B2 | 6/2009 | Berk et al. | |
| 7,592,373 B2 | 9/2009 | Lehmann-Lintz et al. | |
| 7,638,526 B2 | 12/2009 | Mckittrick et al. | |
| 7,834,026 B2 | 11/2010 | Berk et al. | |
| 8,232,288 B2 | 7/2012 | Schunk et al. | |
| 8,349,825 B2 | 1/2013 | Mampreian et al. | |
| 8,455,475 B2 | 6/2013 | Schunk et al. | |
| 8,618,132 B2 | 12/2013 | Stenkamp et al. | |
| 8,629,147 B2 | 1/2014 | Anikin et al. | |
| 8,686,020 B2 | 4/2014 | Hamblett et al. | |
| 8,999,985 B2 | 4/2015 | Gao | |
| 9,150,587 B2 | 10/2015 | Chen et al. | |
| 9,493,486 B2 | 11/2016 | Hunziker et al. | |
| 9,527,856 B2 | 12/2016 | Braje et al. | |
| 9,579,314 B2 | 2/2017 | Rancati et al. | |
| 9,920,073 B2 | 3/2018 | Cocklin | |
| 10,004,728 B2 | 6/2018 | Rancati et al. | |
| 10,045,979 B2 | 8/2018 | Long et al. | |
| 10,059,690 B2 | 8/2018 | Ciblat et al. | |
| 10,106,526 B2 | 10/2018 | Sprott et al. | |
| 10,150,769 B2 | 12/2018 | Khan | |
| 10,196,369 B2 | 2/2019 | Pinkerton et al. | |
| 10,246,464 B2 | 4/2019 | Grembecka et al. | |
| 10,259,787 B2 | 4/2019 | Brown et al. | |
| 10,266,497 B2 | 4/2019 | Grice et al. | |
| 10,323,038 B2 | 6/2019 | Grice et al. | |
| 10,463,661 B2 | 11/2019 | Long et al. | |
| 10,519,135 B2 | 12/2019 | Sprott et al. | |
| 10,633,384 B2 | 4/2020 | Hunziker et al. | |

(Continued)

FOREIGN PATENT DOCUMENTS

| | | | |
|---|---|---|---|
| CN | 102952118 A | 3/2013 | |
| CN | 105461693 A | 4/2016 | |

(Continued)

OTHER PUBLICATIONS

Alexander et al., "Cyclin E overexpression as a biomarker for combination treatment strategies in inflammatory breast cancer", Oncotarget. Feb. 28, 2017;8(9):14897-14911.

Asghar et al., "The history and future of targeting cyclin-dependent kinases in cancer therapy", Nat Rev Drug Discov. Feb. 2015;14(2):130-46.

Au-Yeung et al., "Selective Targeting of Cyclin E1-Amplified High-Grade Serous Ovarian Cancer by Cyclin-Dependent Kinase 2 and AKT Inhibition", Clin Cancer Res. Apr. 1, 2017;23(7):1862-1874.

Ayhan et al., "CCNE1 copy-number gain and overexpression identify ovarian clear cell carcinoma with a poor prognosis", Mod Pathol. Feb. 2017;30(2):297-303.

(Continued)

*Primary Examiner* — Zinna Northington Davis
(74) *Attorney, Agent, or Firm* — Morrison & Foerster LLP

(57) ABSTRACT

The present disclosure relates generally to Cyclin-dependent kinase 2 (CDK2) inhibiting chemical compounds and uses thereof in the inhibition of the activity of CDK2. The disclosure also provides pharmaceutically acceptable compositions comprising compounds disclosed herein and methods of using said compounds and compositions in the treatment of various disorders related to CDK2 activity.

23 Claims, No Drawings

(56) References Cited

U.S. PATENT DOCUMENTS

| | | |
|---|---|---|
| 10,717,716 B2 | 7/2020 | Lee et al. |
| 10,759,751 B2 | 9/2020 | Brown et al. |
| 2004/0152742 A1 | 8/2004 | Stenkamp et al. |
| 2004/0209865 A1 | 10/2004 | Stenkamp et al. |
| 2005/0234034 A1 | 10/2005 | Pennell et al. |
| 2005/0267093 A1 | 12/2005 | Lehmann-Lintz et al. |
| 2006/0074121 A1 | 4/2006 | Chen et al. |
| 2007/0117824 A1 | 5/2007 | Berk et al. |
| 2007/0249648 A1 | 10/2007 | Bladh et al. |
| 2008/0089858 A1 | 4/2008 | Mckittrick et al. |
| 2008/0207635 A1 | 8/2008 | Anikin et al. |
| 2008/0247964 A1 | 10/2008 | Xu et al. |
| 2009/0069282 A1 | 3/2009 | Stenkamp et al. |
| 2009/0111794 A1 | 4/2009 | Bacani et al. |
| 2009/0156575 A1 | 6/2009 | Borjesson et al. |
| 2009/0209566 A1 | 8/2009 | Berk et al. |
| 2010/0249095 A1 | 9/2010 | Schunk et al. |
| 2011/0009382 A1 | 1/2011 | Schunk et al. |
| 2011/0098268 A1 | 4/2011 | Mampreian et al. |
| 2013/0131041 A1 | 5/2013 | Berk et al. |
| 2013/0224107 A1 | 8/2013 | Gao |
| 2013/0231327 A1 | 9/2013 | Schunk et al. |
| 2015/0099734 A1 | 4/2015 | Hunziker et al. |
| 2015/0344489 A1 | 12/2015 | Braje et al. |
| 2016/0176875 A1 | 6/2016 | Pinkerton et al. |
| 2016/0214998 A1 | 7/2016 | Cocklin |
| 2016/0235734 A1 | 8/2016 | Rancati et al. |
| 2017/0029425 A1 | 2/2017 | Hunziker et al. |
| 2017/0037050 A1 | 2/2017 | Wu et al. |
| 2017/0100394 A1 | 4/2017 | Long et al. |
| 2017/0119753 A1 | 5/2017 | Rancati et al. |
| 2017/0183355 A1 | 6/2017 | Sprott et al. |
| 2017/0247391 A1 | 8/2017 | Grembecka et al. |
| 2018/0105491 A1 | 4/2018 | Brown et al. |
| 2018/0208578 A1 | 7/2018 | Ciblat et al. |
| 2018/0230114 A1 | 8/2018 | Lee et al. |
| 2018/0291023 A1 | 10/2018 | Khan |
| 2018/0319772 A1 | 11/2018 | Sprott et al. |
| 2018/0327416 A1 | 11/2018 | Grice et al. |
| 2018/0338972 A1 | 11/2018 | Long et al. |
| 2018/0339970 A1 | 11/2018 | Grice et al. |
| 2019/0194200 A1 | 6/2019 | Khan |
| 2019/0202783 A1 | 7/2019 | Brown et al. |
| 2019/0218230 A1 | 7/2019 | Angibaud et al. |
| 2019/0330209 A1 | 10/2019 | Khan |
| 2020/0087304 A1 | 3/2020 | Grice et al. |
| 2020/0172573 A1 | 6/2020 | Zhang et al. |
| 2020/0207769 A1 | 7/2020 | Hunziker et al. |
| 2020/0216471 A1 | 7/2020 | Wu et al. |
| 2020/0290963 A1 | 9/2020 | Brown et al. |
| 2020/0407374 A1 | 12/2020 | Mach et al. |
| 2021/0214356 A1* | 7/2021 | Kouji ............... A61P 31/14 |
| 2023/0109076 A1 | 4/2023 | Kirman |

FOREIGN PATENT DOCUMENTS

| | | |
|---|---|---|
| CN | 111138358 A | 5/2020 |
| WO | 2004039764 A1 | 5/2004 |
| WO | 2004039780 A1 | 5/2004 |
| WO | 2005040167 A1 | 5/2005 |
| WO | 2005063239 A1 | 7/2005 |
| WO | 2005084667 A1 | 9/2005 |
| WO | 2007027734 A2 | 3/2007 |
| WO | 2007030061 A1 | 3/2007 |
| WO | 2007027734 A3 | 5/2007 |
| WO | 2007056155 A1 | 5/2007 |
| WO | 2007061880 A1 | 5/2007 |
| WO | 2007061978 A1 | 5/2007 |
| WO | 2007140383 A2 | 12/2007 |
| WO | 2007140383 A3 | 1/2008 |
| WO | 2008033456 A1 | 3/2008 |
| WO | 2007133561 A3 | 10/2008 |
| WO | 2010108651 A1 | 9/2010 |
| WO | 2010142402 A1 | 12/2010 |
| WO | WO-2011092198 A1 | 8/2011 |
| WO | 2012071684 A1 | 6/2012 |
| WO | 2013131010 A2 | 9/2013 |
| WO | 2013131010 A3 | 11/2013 |
| WO | 2013186159 A1 | 12/2013 |
| WO | 2015048567 A1 | 4/2015 |
| WO | 2015051230 A1 | 4/2015 |
| WO | 2015154039 A2 | 10/2015 |
| WO | 2015173392 A1 | 11/2015 |
| WO | 2015179414 A1 | 11/2015 |
| WO | 2015154039 A3 | 12/2015 |
| WO | 2016040330 A1 | 3/2016 |
| WO | 2016128456 A1 | 8/2016 |
| WO | 2015154039 A8 | 10/2016 |
| WO | 2017023133 A2 | 2/2017 |
| WO | 2017023133 A3 | 3/2017 |
| WO | 2017087863 A1 | 5/2017 |
| WO | 2018026798 A1 | 2/2018 |
| WO | 2018069732 A1 | 4/2018 |
| WO | 2018106818 A1 | 6/2018 |
| WO | 2018106820 A1 | 6/2018 |
| WO | 2018153312 A1 | 8/2018 |
| WO | 2018175746 A1 | 9/2018 |
| WO | 2018217805 A1 | 11/2018 |
| WO | 2018217809 A1 | 11/2018 |
| WO | 2019015644 A1 | 1/2019 |
| WO | 2019046330 A1 | 3/2019 |
| WO | 2019060365 A1 | 3/2019 |
| WO | 2019129121 A1 | 7/2019 |
| WO | 2019158051 A1 | 8/2019 |
| WO | 2020069027 A1 | 4/2020 |
| WO | 2020086739 A1 | 4/2020 |
| WO | 2020104494 A1 | 5/2020 |
| WO | 2020112905 A1 | 6/2020 |
| WO | 2020113071 A1 | 6/2020 |
| WO | 2020131627 A1 | 6/2020 |
| WO | 2022165513 A1 | 8/2022 |
| WO | 2022272106 A1 | 12/2022 |
| WO | 2024026479 A2 | 2/2024 |
| WO | 2024026481 A2 | 2/2024 |
| WO | 2024026483 A2 | 2/2024 |
| WO | 2024026484 A2 | 2/2024 |
| WO | 2024026486 A2 | 2/2024 |

OTHER PUBLICATIONS

Bukanov et al., "Long-lasting arrest of murine polycystic kidney disease with CDK inhibitor roscovitine", Nature. Dec. 14, 2006;444(7121):949-52.

Caldon et al., "Cyclin E2 overexpression is associated with endocrine resistance but not insensitivity to CDK2 inhibition in human breast cancer cells", Mol Cancer Ther. Jul. 2012;11(7):1488-99.

Chunder et al., "Cyclin-dependent kinase 2 controls peripheral immune tolerance", J Immunol. Dec. 15, 2012;189(12):5659-66.

Du et al., "Critical role of CDK2 for melanoma growth linked to its melanocyte-specific transcriptional regulation by MITF", Cancer Cell. Dec. 2004; 6(6): 565-576.

Ehedego et al., "Loss of Cyclin E1 attenuates hepatitis and hepatocarcinogenesis in a mouse model of chronic liver injury", Oncogene. Jun. 2018;37(25):3329-3339.

Elsawaf et al., "Triple-Negative Breast Cancer: Clinical and Histological Correlations", Breast Care (Basel). 2011;6(4):273-278.

Etemadmoghadam et al., "Resistance to CDK2 inhibitors is associated with selection of polyploid cells in CCNE1-amplified ovarian cancer", Clin Cancer Res. Nov. 1, 2013;19(21):5960-71.

Faber et al., "Review of rationale and progress toward targeting cyclin-dependent kinase 2 (CDK2) for male contraception", Biol Reprod. Aug. 4, 2020;103(2):357-367.

Herrera-Abreu et al., "Early Adaptation and Acquired Resistance to CDK4/6 Inhibition in Estrogen Receptor-Positive Breast Cancer", Cancer Res. Apr. 15, 2016;76(8):2301-13.

International Search Authority, International Search Report and Written Opinion issue in corresponding PCT/US22/70409, Mailing date: Jun. 2, 2022, 12 pages.

Keyomarsi et al., "Cyclin E and survival in patients with breast cancer", N Engl J Med. Nov. 14, 2002;347(20): 1566-75.

Liu et al., "Cyclin E-Mediated Human Proopiomelanocortin Regulation as a Therapeutic Target for Cushing Disease", J Clin Endocrinol Metab. Jul. 2015;100(7):2557-64.

(56) References Cited

OTHER PUBLICATIONS

Nakayama et al., "Gene amplification CCNE1 is related to poor survival and potential therapeutic target in ovarian cancer", Cancer. Jun. 1, 2010;116(11):2621-34.

Nevzorova et al., "Cyclin E1 controls proliferation of hepatic stellate cells and is essential for liver fibrogenesis in mice", Hepatology. Sep. 2012;56(3):1140-9.

Noske et al., "Detection of CCNE1/URI (19q12) amplification by in situ hybridisation is common in high grade and type II endometrial cancer", Oncotarget. Feb. 28, 2017;8(9):14794-14805.

Ooi et al., "Gene amplification of CCNE1, CCND1, and CDK6 in gastric cancers detected by multiplex ligation-dependent probe amplification and fluorescence in situ hybridization", Hum Pathol. Mar. 2017;61:58-67.

Ophascharoensuk et al., "The cyclin-dependent kinase inhibitor p27Kip1 safeguards against inflammatory injury", Nat Med. May 1998;4(5):575-80.

PCT International Search Report and Written Opinion from PCT/US2022/034963, dated Sep. 2, 2022.

PubChem Open Chemistry Database, "CID 143728706 Compound Summary: 1-N-cyclopentyl-7a-hydroxy-3-oxo-2-2-oxoethyl)-4-N-[4-(trifluoromethyl)phenyl]-1,3a,4,5,6,7-hexahydropyrrolo[3,4-c]pyridine-1,4-dicarboxamide," PubChem. Created Dec. 7, 2019: <https://pubchem.ncbi.nlm.nih.gov/compound/143728706>.

PubChem Open Chemistry Database, Compound Summary for SID 382817814, available Apr. 26, 2019 (5 pages).

Scaltriti et al., "Cyclin E amplification/overexpression is a mechanism of trastuzumab resistance in HER2+ breast cancer patients", Proc Natl Acad Sci U S A. Mar. 1, 2011;108(9):3761-6.

Yang et al., "Neuronal cell death is preceded by cell cycle events at all stages of Alzheimer's disease", J Neurosci. Apr. 1, 2003;23(7):2557-63.

International Search Report mailed Sep. 26, 2022 for PCT Application No. PCT/US2022/034963, filed Jun. 24, 2022, 2 pages.

U.S. Appl. No. 17/649,269, filed Jan. 28, 2022, for Kirman et al. (Also cited as U.S. Publication No. US-2023-0109076)(U.S. Patent Application is not submitted herewith pursuant to the waiver of 37 C.F.R. § 1.98(a)(2)(iii) issued by the Office on Sep. 21, 2004.).

U.S. Appl. No. 18/274,962, filed Jan. 28, 2022, for Kirman et al. (U.S. Patent Application is not submitted herewith pursuant to the waiver of 37 C.F.R. § 1.98(a)(2)(iii) issued by the Office on Sep. 21, 2004.).

U.S. Appl. No. 18/545,134, filed Dec. 19, 2023, for Kirman et al. (U.S. Patent Application is not submitted herewith pursuant to the waiver of 37 C.F.R. § 1.98(a)(2)(iii) issued by the Office on Sep. 21, 2004.).

* cited by examiner

CDK2 INHIBITORS AND METHODS OF USING THE SAME

CROSS REFERENCE TO RELATED APPLICATION

This application claims the benefit of U.S. Provisional Application No. 63/202,844, filed Jun. 26, 2021, which is hereby incorporated by reference in its entirety.

FIELD

The present disclosure relates generally to Cyclin-dependent kinase 2 (CDK2) inhibiting chemical compounds and uses thereof in the inhibition of the activity of CDK2. The disclosure also provides pharmaceutically acceptable compositions comprising compounds disclosed herein and methods of using said compounds and compositions in the treatment of various disorders related to CDK2 activity.

BACKGROUND

Cell cycle dysregulation, including uncontrolled cell growth, impaired cell differentiation and abnormal apoptosis have been shown to be caused by over activity of Cyclin-dependent kinases (CDKs). CDKs are important serine/threonine protein kinases that become active when combined with a specific cyclin partner. There are various subtypes of CDKs, each having a different role during the cell cycle, with varying levels of activity during each of the phases. CDK1, CDK2, CDK4 and CDK6 have been found to be specifically important subtypes, where over activity of one or more of these subtypes may lead to dysregulation of the cell cycle and the development of a variety of cancers. The S phase of the cell cycle is responsible for DNA replication and is the phase where aberrant DNA replication may occur. The CDK2/cyclin E complex is required for the cell cycle transition from the G1 phase to the S phase and the CDK2/cyclin A complex is required for the cell cycle transition from the S phase to the G2 phase. Therefore, selective inhibition of the CDK2/cyclin E and/or CDK2/cyclin A complexes can prevent aberrant DNA replication and can be used to treat certain cancers.

Accordingly, there is a need for the development of compounds capable of inhibiting the activity of CDK2/cyclin complexes, and pharmaceutical compositions thereof, for the prevention, and treatment of CDK2 related diseases or disorders.

SUMMARY

The present disclosure is based at least in part on the identification of compounds that bind and inhibit Cyclin-dependent kinase 2 (CDK2) and methods of using the same to treat diseases associated with CDK2 activity. Disclosed herein is a compound according to Formula I or a pharmaceutically acceptable salt thereof:

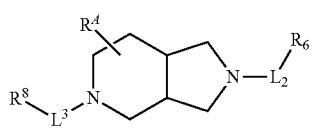

wherein each variable is as defined and described herein.

Compounds of the present disclosure, and pharmaceutically acceptable compositions thereof, are useful for treating a variety of diseases, disorders or conditions, associated with CDK2 activity. Such diseases, disorders, or conditions include those described herein.

DETAILED DESCRIPTION OF CERTAIN EMBODIMENTS

1. General Description of Compounds of the Disclosure

The present disclosure provides compounds capable of inhibiting Cyclin-dependent kinase 2 (CDK2) and/or CDK2/cyclin complexes.

In some embodiments, provided herein are compounds according to Formula I:

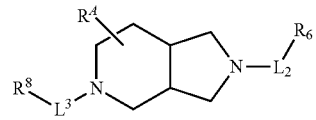

or a pharmaceutically acceptable salt thereof, wherein:
$R^A$ is

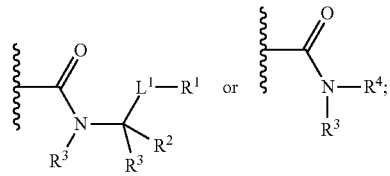

$L^1$ is a covalent bond or a saturated or unsaturated, straight or branched, optionally substituted bivalent $C_{1-6}$ hydrocarbon chain, wherein 0-2 methylene units of $L^1$ are independently replaced by —O—, —NR—, —S—, —OC(O)—, —C(O)O—, —C(O)—, —S(O)—, —S(O)$_2$—, —C(S)—, —NRS(O)$_2$—, —S(O)$_2$NR—, —NRC(O)—, —C(O)NR—, —OC(O)NR—, —NRC(O)O—, or —NRC(O)NR—;

$R^1$ is hydrogen, an optionally substituted $C_{1-6}$ aliphatic group, or an optionally substituted cyclic group selected from a 3-8 membered saturated or partially unsaturated monocyclic carbocyclic ring, a 7-12 membered saturated or partially unsaturated bicyclic carbocyclic ring, phenyl, an 8-10 membered bicyclic aromatic carbocyclic ring, a 3-8 membered saturated or partially unsaturated monocyclic heterocyclic ring (having 1-2 heteroatoms independently selected from nitrogen, oxygen, and sulfur), a 7-12 membered saturated or partially unsaturated bicyclic heterocyclic ring (having 1-4 heteroatoms independently selected from nitrogen, oxygen, and sulfur), a 5-6 membered monocyclic heteroaromatic ring (having 1-4 heteroatoms independently selected from nitrogen, oxygen, and sulfur), and an 8-10 membered bicyclic heteroaromatic ring (having 1-5 heteroatoms independently selected from nitrogen, oxygen, and sulfur);

$R^2$ is hydrogen, an optionally substituted $C_{1-6}$ aliphatic group, —C(O)OR, —C(O)NR$_2$, or an optionally substituted cyclic group selected from phenyl and a 5-6 membered monocyclic heteroaromatic ring (having 1-4 heteroatoms independently selected from nitrogen, oxygen, and sulfur);

each instance of $R^3$ is independently hydrogen or an optionally substituted $C_{1-6}$ aliphatic group;

$R^4$ is a cyclic group selected from a 3-8 membered saturated or partially unsaturated monocyclic carbocyclic ring, a 7-12 membered saturated or partially unsaturated bicyclic carbocyclic ring, phenyl, an 8-10 membered bicyclic aromatic carbocyclic ring, a 3-8 membered saturated or partially unsaturated monocyclic heterocyclic ring (having 1-2 heteroatoms independently selected from nitrogen, oxygen, and sulfur), a 7-12 membered saturated or partially unsaturated bicyclic heterocyclic ring (having 1-4 heteroatoms independently selected from nitrogen, oxygen, and sulfur), a 5-6 membered monocyclic heteroaromatic ring (having 1-4 heteroatoms independently selected from nitrogen, oxygen, and sulfur), and an 8-10 membered bicyclic heteroaromatic ring (having 1-5 heteroatoms independently selected from nitrogen, oxygen, and sulfur), wherein the cyclic group is optionally substituted with one or more instances of $R^5$;

each instance of $R^5$ is independently halogen, —CN, —$NO_2$, —OR, —SR, —$NR_2$, —$S(O)_2R$, —$S(O)_2NR_2$, —S(O)R, —$S(O)NR_2$, —C(O)R, —C(O)OR, —C(O)$NR_2$, —C(O)N(R)OR, —OC(O)R, —OC(O)$NR_2$, —N(R)C(O)OR, —N(R)C(O)R, —N(R)C(O)$NR_2$, —N(R)C(NR)$NR_2$, —N(R)S(O)$_2NR_2$, —N(R)$S(O)_2R$, an optionally substituted $C_{1-6}$ aliphatic group, or an optionally substituted —$C_{1-6}$ aliphatic-Cy group;

$L^2$ is a saturated or unsaturated, straight or branched, optionally substituted bivalent $C_{1-4}$ hydrocarbon chain, wherein 0-2 methylene units of $L^2$ are independently replaced by —O—, —NR—, —S—, —OC(O)—, —C(O)O—, —C(O)—, —S(O)—, —$S(O)_2$—, —C(S)—, —$NRS(O)_2$—, —$S(O)_2NR$—, —NRC(O)—, —C(O)NR—, —OC(O)NR—, —NRC(O)O—, or —NRC(O)NR—;

$R^6$ is an optionally substituted $C_{1-6}$ aliphatic group, or a cyclic group selected from a 3-8 membered saturated or partially unsaturated monocyclic carbocyclic ring, a 7-12 membered saturated or partially unsaturated bicyclic carbocyclic ring, phenyl, an 8-10 membered bicyclic aromatic carbocyclic ring, a 3-8 membered saturated or partially unsaturated monocyclic heterocyclic ring (having 1-2 heteroatoms independently selected from nitrogen, oxygen, and sulfur), a 7-12 membered saturated or partially unsaturated bicyclic heterocyclic ring (having 1-4 heteroatoms independently selected from nitrogen, oxygen, and sulfur), a 5-6 membered monocyclic heteroaromatic ring (having 1-4 heteroatoms independently selected from nitrogen, oxygen, and sulfur), and an 8-10 membered bicyclic heteroaromatic ring (having 1-5 heteroatoms independently selected from nitrogen, oxygen, and sulfur), wherein the cyclic group is optionally substituted with one or more instances of $R^7$;

each instance of $R^7$ is independently halogen, —CN, —$NO_2$, —OR, —SR, —$NR_2$, —$S(O)_2R$, —$S(O)_2NR_2$, —S(O)R, —$S(O)NR_2$, —C(O)R, —C(O)OR, —C(O)$NR_2$, —C(O)N(R)OR, —OC(O)R, —OC(O)$NR_2$, —N(R)C(O)OR, —N(R)C(O)R, —N(R)C(O)$NR_2$, —N(R)C(O)$S(O)_2R$, —N(R)C(NR)$NR_2$, —N(R)$S(O)_2NR_2$, —N(R)$S(O)_2R$, an optionally substituted $C_{1-6}$ aliphatic group, or Cy, or two instances of $R^6$ on the same carbon atom are taken together to form an oxo group;

$L^3$ is a saturated or unsaturated, straight or branched, optionally substituted bivalent $C_{1-4}$ hydrocarbon chain, wherein 0-2 methylene units of $L^3$ are independently replaced by —O—, —NR—, —S—, —OC(O)—, —C(O)O—, —C(O)—, —S(O)—, —$S(O)_2$—, —C(S)—, —$NRS(O)_2$—, —$S(O)_2NR$—, —NRC(O)—, —C(O)NR—, —OC(O)NR—, —NRC(O)O—, or —NRC(O)NR—;

$R^8$ is a cyclic group selected from a 3-8 membered saturated or partially unsaturated monocyclic carbocyclic ring, a 7-12 membered saturated or partially unsaturated bicyclic carbocyclic ring, phenyl, an 8-10 membered bicyclic aromatic carbocyclic ring, a 3-8 membered saturated or partially unsaturated monocyclic heterocyclic ring (having 1-2 heteroatoms independently selected from nitrogen, oxygen, and sulfur), a 7-12 membered saturated or partially unsaturated bicyclic heterocyclic ring (having 1-4 heteroatoms independently selected from nitrogen, oxygen, and sulfur), a 5-6 membered monocyclic heteroaromatic ring (having 1-4 heteroatoms independently selected from nitrogen, oxygen, and sulfur), and an 8-10 membered bicyclic heteroaromatic ring (having 1-5 heteroatoms independently selected from nitrogen, oxygen, and sulfur), wherein the cyclic group is optionally substituted with one or more instances of $R^9$;

each instance of $R^9$ is independently halogen, —CN, —$NO_2$, —OR, —SR, —$NR_2$, —$S(O)_2R$, —$S(O)_2NR_2$, —S(O)R, —$S(O)NR_2$, —C(O)R, —C(O)OR, —C(O)$NR_2$, —C(O)N(R)OR, —OC(O)R, —OC(O)$NR_2$, —N(R)C(O)OR, —N(R)C(O)R, —N(R)C(O)$NR_2$, —N(R)C(NR)$NR_2$, —N(R)$S(O)_2NR_2$, —N(R)$S(O)_2R$, an optionally substituted $C_{1-6}$ aliphatic group, an optionally substituted $C_{1-6}$ aliphatic-Cy group, or Cy;

each Cy is independently an optionally substituted cyclic group selected from a 3-8 membered saturated or partially unsaturated monocyclic carbocyclic ring, phenyl, a 3-8 membered saturated or partially unsaturated monocyclic heterocyclic ring (having 1-2 heteroatoms independently selected from nitrogen, oxygen, and sulfur), and a 5-6 membered monocyclic heteroaromatic ring (having 1-4 heteroatoms independently selected from nitrogen, oxygen, and sulfur); and each R is independently hydrogen, or an optionally substituted $C_{1-6}$ aliphatic group, an optionally substituted phenyl, an optionally substituted 3-7 membered saturated or partially unsaturated carbocyclic ring, an optionally substituted 3-7 membered saturated or partially unsaturated heterocyclic ring (having 1-2 heteroatoms independently selected from nitrogen, oxygen, and sulfur), or an optionally substituted 5-6 membered heteroaryl ring (having 1-4 heteroatoms independently selected from nitrogen, oxygen, and sulfur); or two R groups on the same nitrogen are taken together with their intervening atoms to form an optionally substituted 4-7 membered saturated, partially unsaturated, or heteroaryl ring (having 0-3 heteroatoms, in addition to the nitrogen, independently selected from nitrogen, oxygen, and sulfur);

wherein the compound is not Compound X, wherein Compound X is defined herein.

Overexpression of CDK2 is associated with abnormal regulation of the cell-cycle. The cyclin E/CDK2 complex plays an important role in regulation of the G1/S transition, histone biosynthesis and centrosome duplication. Progressive phosphorylation of retinoblastoma (Rb) by cyclin D/Cdk4/6 and cyclin E/Cdk2 releases the G1 transcription factor, E2F, and promotes S-phase entry. Activation of cyclin A/CDK2 during early S-phase promotes phosphorylation of endogenous substrates that permit DNA replication and inactivation of E2F, for S-phase completion. (Asghar et al., Nat. Rev. Drug. Discov. 2015; 14(2): 130-146).

Cyclin E, the regulatory cyclin for CDK2, is frequently overexpressed in cancer. Cyclin E amplification or overexpression has long been associated with poor outcomes in breast cancer. (Keyomarsi et al., Cyclin E and survival in patients with breast cancer. N Engl J Med. (2002) 347:1566-75). Cyclin E2 (CCNE2) overexpression is associated with endocrine resistance in breast cancer cells and CDK2 inhibition has been reported to restore sensitivity to tamoxifen or CDK4 inhibitors in tamoxifen-resistant and CCNE2 overexpressing cells. (Caldon et al., Mol. Cancer Ther. (2012) 11:1488-99; Herrera-Abreu et al., Cancer Res. (2016) 76: 2301-2313). Cyclin E amplification also reportedly contributes to trastuzumab resistance in HER2+ breast cancer. (Scaltriti et al., Proc Natl Acad Sci. (2011) 108: 3761-6). Cyclin E overexpression has also been reported to play a role in basal-like and triple negative breast cancer (TNBC), as well as inflammatory breast cancer. (Elsawaf & Sinn, Breast Care (2011) 6:273-278; Alexander et al., Oncotarget (2017) 8: 14897-14911.)

Amplification or overexpression of cyclin E1 (CCNE1) is also associated with poor outcomes in ovarian, gastric, endometrial and other cancers. (Nakayama et al., Gene amplification CCNE1 is related to poor survival and potential therapeutic target in ovarian cancer, Cancer (2010) 116: 2621-34; Etemadmoghadam et al., Clin Cancer Res (2013) 19: 5960-71; Au-Yeung et al., Clin. Cancer Res. (2017) 23:1862-1874; Ayhan et al., Modern Pathology (2017) 30: 297-303; Ooi et al., Hum Pathol. (2017) 61: 58-67; Noske et al., Oncotarget (2017) 8: 14794-14805).

There remains a need in the art for CDK inhibitors, especially selective CDK2 inhibitors, which may be useful for the treatment of cancer or other proliferative diseases or conditions. In particular, CDK2 inhibitors may be useful in treating CCNE1 or CCNE2 amplified tumors.

2. Compounds and Definitions

Compounds of this present disclosure include those described generally herein, and are further illustrated by the classes, subclasses, and species disclosed herein. As used herein, the following definitions shall apply unless otherwise indicated. For purposes of this disclosure, the chemical elements are identified in accordance with the Periodic Table of the Elements, CAS version, Handbook of Chemistry and Physics, 101$^{st}$ Ed. Additionally, general principles of organic chemistry are described in "Organic Chemistry", Thomas Sorrell, University Science Books, Sausalito: 2005, and "March's Advanced Organic Chemistry: Reactions Mechanisms and Structure", 8$^{th}$ Ed., Ed.: Smith, M. B., John Wiley & Sons, New York: 2019, the entire contents of which are hereby incorporated by reference.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle," "cycloaliphatic" or "cycloalkyl"), that has a single point of attachment to the rest of the molecule. Unless otherwise specified, aliphatic groups contain 1 to 6 aliphatic carbon atoms. In some embodiments, aliphatic groups contain 1 to 5 aliphatic carbon atoms. In other embodiments, aliphatic groups contain 1 to 4 aliphatic carbon atoms. In still other embodiments, aliphatic groups contain 1 to 3 aliphatic carbon atoms, and in yet other embodiments, aliphatic groups contain 1 to 2 aliphatic carbon atoms. In some embodiments, "cycloaliphatic" (or "carbocycle" or "cycloalkyl") refers to a monocyclic $C_3$-$C_6$ hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

As used herein, the term "bicyclic ring" or "bicyclic ring system" refers to any bicyclic ring system, i.e. carbocyclic or heterocyclic, saturated or having one or more units of unsaturation, having one or more atoms in common between the two rings of the ring system. Thus, the term includes any permissible ring fusion, such as ortho-fused or spirocyclic. As used herein, the term "heterobicyclic" is a subset of "bicyclic" that requires that one or more heteroatoms are present in one or both rings of the bicycle. Such heteroatoms may be present at ring junctions and are optionally substituted, and may be selected from nitrogen (including N-oxides), oxygen, sulfur (including oxidized forms such as sulfones and sulfonates), phosphorus (including oxidized forms such as phosphonates and phosphates), boron, etc. In some embodiments, a bicyclic group has 7-12 ring members and 0-4 heteroatoms independently selected from nitrogen, oxygen, and sulfur. As used herein, the term "bridged bicyclic" refers to any bicyclic ring system, i.e. carbocyclic or heterocyclic, saturated or partially unsaturated, having at least one bridge. As defined by IUPAC, a "bridge" is an unbranched chain of atoms or an atom or a valence bond connecting two bridgeheads, where a "bridgehead" is any skeletal atom of the ring system which is bonded to three or more skeletal atoms (excluding hydrogen). In some embodiments, a bridged bicyclic group has 7-12 ring members and 0-4 heteroatoms independently selected from nitrogen, oxygen, and sulfur. Such bridged bicyclic groups are well known in the art and include those groups set forth below where each group is attached to the rest of the molecule at any substitutable carbon or nitrogen atom. Unless otherwise specified, a bridged bicyclic group is optionally substituted with one or more substituents as set forth for aliphatic groups. Additionally or alternatively, any substitutable nitrogen of a bridged bicyclic group is optionally substituted. Exemplary bicyclic rings include:

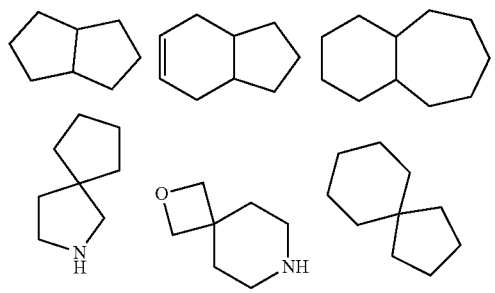

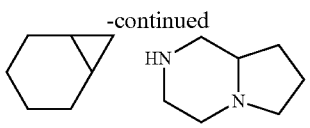

Exemplary bridged bicyclics include:

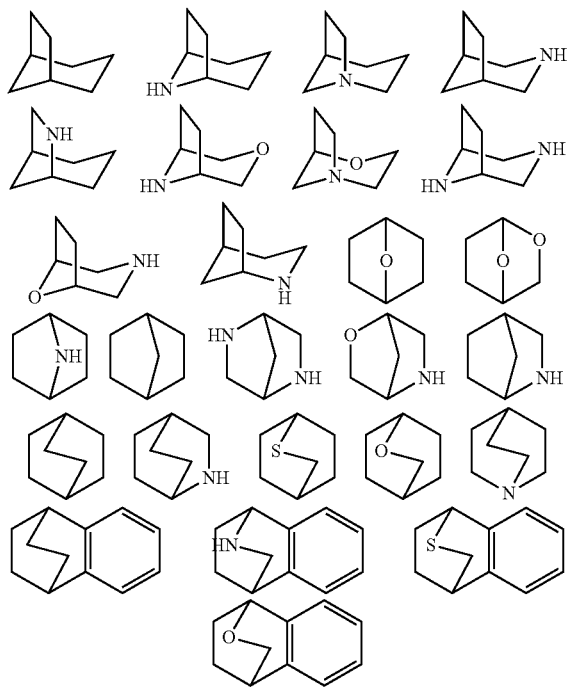

The term "Compound X" refers to 5-(2-(6-chloro-1H-indol-3-yl)acetyl)-2-(4-isopropoxy-3-methoxybenzoyl)-N-(1-(methylamino)-1-oxo-5-phenylpentan-2-yl)octahydro-1H-pyrrolo[3,4-c]pyridine-7-carboxamide. Compound X may also be depicted as

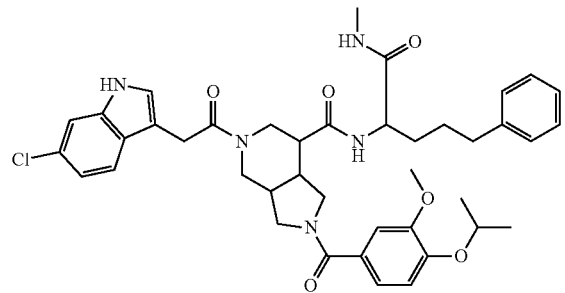

The term "lower alkyl" refers to a $C_{1-4}$ straight or branched alkyl group. Exemplary lower alkyl groups are methyl, ethyl, propyl, isopropyl, butyl, isobutyl, and tert-butyl.

The term "lower haloalkyl" refers to a $C_{1-4}$ straight or branched alkyl group that is substituted with one or more halogen atoms.

The term "heteroatom" means one or more of oxygen, sulfur, nitrogen, phosphorus, or silicon (including, any oxidized form of nitrogen, sulfur, phosphorus, or silicon; the quaternized form of any basic nitrogen; or an oxygen, sulfur, nitrogen, phosphorus, or silicon atom in a heterocyclic ring.

The term "unsaturated," as used herein, means that a moiety has one or more units of unsaturation.

As used herein, the term "bivalent $C_{1-8}$ (or $C_{1-6}$) saturated or unsaturated, straight or branched, hydrocarbon chain", refers to bivalent alkylene, alkenylene, and alkynylene chains that are straight or branched as defined herein.

The term "alkylene" refers to a bivalent alkyl group. An "alkylene chain" is a polymethylene group, i.e., $-(CH_2)_n-$, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

The term "alkenylene" refers to a bivalent alkenyl group. A substituted alkenylene chain is a polymethylene group containing at least one double bond in which one or more hydrogen atoms are replaced with a substituent. Suitable substituents include those described below for a substituted aliphatic group.

The term "halogen" means F, Cl, Br, or I.

The term "aryl" used alone or as part of a larger moiety as in "aralkyl," "aralkoxy," or "aryloxyalkyl," refers to monocyclic or bicyclic ring systems having a total of 4 to 14 ring members, wherein at least one ring in the system is aromatic and wherein each ring in the system contains three to seven ring members. The term "aryl" may be used interchangeably with the term "aryl ring". In certain embodiments of the present disclosure, "aryl" refers to an aromatic ring system which includes, but not limited to, phenyl, biphenyl, naphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" and "heteroar-," used alone or as part of a larger moiety, e.g., "heteroaralkyl," or "heteroaralkoxy," refer to groups having 5 to 10 ring atoms, preferably 5, 6, or 9 ring atoms; having 6, 10, or 14 π electrons shared in a cyclic array; and having, in addition to carbon atoms, from one to five heteroatoms. The term "heteroatom" in the context of "heteroaryl" particularly includes, but is not limited to, nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be monocyclic or bicyclic. A heteroaryl ring may include one or more oxo (=O) or thioxo (=S) substituent. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle," "heterocyclyl," "heterocyclic radical," and "heterocyclic ring" are used interchangeably and refer to a stable 5- to 7-membered monocyclic or 7 to 10-membered bicyclic heterocyclic moiety that is either saturated or partially unsaturated, and having, in addition to carbon atoms, one or more, preferably 1 to 4, heteroatoms, as defined above. When used in reference to a ring atom of a heterocycle, the term "nitrogen" includes a substituted nitrogen. As an example, in a saturated or partially unsaturated ring (having 0 to 3 heteroatoms selected from oxygen, sulfur and nitrogen.

A heterocyclic ring can be attached to a provided compound at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl. A heterocyclyl group may be monocyclic or bicyclic, bridged bicyclic, or spirocyclic. A heterocyclic ring may include one or more oxo (=O) or thioxo (=S) substituent. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As described herein, compounds of the present disclosure may contain "substituted" moieties. In general, the term "substituted" means that one or more hydrogens of the designated moiety are replaced with a suitable substituent. Unless otherwise indicated, an "optionally substituted" group may have a suitable substituent at one or more substitutable position of the group, and when more than one position in any given structure is substituted with more than one substituent selected from a specified group, the substituent may be either the same or different at every position. Combinations of substituents envisioned by the present disclosure are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; —$(CH_2)_{0-6}R°$; —$(CH_2)_{0-6}OR°$; —$O(CH_2)_{0-6}R°$, —O—$(CH_2)_{0-6}C(O)OR°$; —$(CH_2)_{0-6}CH(OR°)_2$; —$(CH_2)_{0-6}SR°$; —$(CH_2)_{0-6}$ Ph, which Ph may be substituted with R°; —$(CH_2)_{0-4}O(CH_2)_{0-1}$Ph which Ph may be substituted with R°; —CH=CHPh, which Ph may be substituted with R°; —$(CH_2)_{0-6}O(CH_2)_{0-1}$-pyridyl which pyridyl may be substituted with R°; —$NO_2$; —CN; —$N_3$; —$(CH_2)_{0-6}N(R°)_2$; —$(CH_2)_{0-6}N(R°)C(O)R°$; —N(R°)C(S) R°; —$(CH_2)_{0-6}N(R°)C(O)NR°_2$; —N(R°)C(S)NR°_2; —$(CH_2)_{0-6}N(R°)C(O)OR°$; —N(R°)N(R°)C(O)R°; —N(R°)N(R°)C(O)NR°_2; —N(R°)N(R°)C(O)OR°; —$(CH_2)_{0-6}C(O)R°$; —C(S)R°; —$(CH_2)_{0-6}C(O)OR°$; —$(CH_2)_{0-6}C(O)SR°$; —$(CH_2)_{0-6}C(O)OSiR°_3$; —$(CH_2)_{0-6}OC(O)R°$; —OC(O)$(CH_2)_{0-6}SR°$, —$(CH_2)_{0-6}SC(O)R°$; —$(CH_2)_{0-6}C(O)NR°_2$; —C(S)NR°_2; —C(S)SR°; —SC(S)SR°, —$(CH_2)_{0-6}OC(O)NR°_2$; —C(O)N(OR°)R°; —C(O)C(O)R°; —C(O)CH_2C(O)R°; —C(NOR°)R°; —$(CH_2)_{0-6}SSR°$; —$(CH_2)_{0-6}S(O)_2R°$; —$(CH_2)_{0-6}S(O)_2OR°$; —$(CH_2)_{0-6}OS(O)_2R°$; —S(O)_2NR°_2; —$(CH_2)_{0-6}S(O)R°$; —N(R°)S(O)_2NR°_2; —N(R°)S(O)_2R°; —N(OR°)R°; —C(NH)NR°_2; —P(O)_2R°; —P(O)R°_2; —P(O)(OR°)_2; —OP(O)(R°)OR°; —OP(O)R°_2; —OP(O)(OR°)_2; SiR°_3; —($C_{1-4}$ straight or branched) alkylene)O—N(R°_2; or —($C_{1-4}$ straight or branched)alkylene)C(O)O—N (R°_2, wherein each R° may be substituted as defined below and is independently hydrogen, $C_{1-6}$ aliphatic, —CH_2Ph, —O(CH_2)_{0-1}Ph, —CH*_2— (5- to 6-membered heteroaryl ring), or a 3- to 6-membered saturated, partially unsaturated, or aryl ring (having 0 to 4 heteroatoms independently selected from nitrogen, oxygen, and sulfur), or, notwithstanding the definition above, two independent occurrences of R°, taken together with their intervening atom(s), form a 3- to 12-membered saturated, partially unsaturated, or aryl mono- or bicyclic ring (having 0 to 4 heteroatoms independently selected from nitrogen, oxygen, and sulfur), which may be substituted as defined below.

Suitable monovalent substituents on R° (or the ring formed by taking two independent occurrences of R° together with their intervening atoms), are independently halogen, —$(CH_2)_{0-2}R^●$, -(haloR^●), —$(CH_2)_{0-2}OH$, —$(CH_2)_{0-2}R^●$, —$(CH_2)_{0-2}CH(OR^●)_2$; —O(haloR^●), —CN, —N_3, —$(CH_2)_{0-2}C(O)R^●$, —$(CH_2)_{0-2}C(O)OH$, —$(CH_2)_{0-2}C(O)OR^●$, —$(CH_2)_{0-2}SR^●$, —$(CH_2)_{0-2}SH$, —$(CH_2)_{0-2}NH_2$, —$(CH_2)_{0-2}NHR^●$, —$(CH_2)_{0-2}NR^●_2$, —$NO_2$, —OSiR^●_3, —C(O)SR^●, —($C_{1-4}$ straight or branched alkylene)C(O)OR^●, or —SSR^● wherein each R^● is unsubstituted or where preceded by "halo" is substituted only with one or more halogens, and is independently selected from $C_{1-4}$ aliphatic, —CH_2Ph, —O(CH_2)_{0-1}Ph, or a 5 to 6-membered saturated, partially unsaturated, or aryl ring (having 0 to 4 heteroatoms independently selected from nitrogen, oxygen, and sulfur). Suitable divalent substituents on a saturated carbon atom of R° include =O and =S.

Suitable divalent substituents on a saturated carbon atom of an "optionally substituted" group include the following: =O, =S, =NNR*_2, =NNHC(O)R*, =NNHC(O)OR*, =NNHS(O)_2R*, =NR*, =NOR*, —O(C(R*_2))_{2-3}O—, or —S(C(R*_2))_{2-3}S—, wherein each independent occurrence of R* is selected from hydrogen, $C_{1-6}$ aliphatic which may be substituted as defined below, and an unsubstituted 5 to 6-membered saturated, partially unsaturated, or aryl ring (having 0 to 4 heteroatoms independently selected from nitrogen, oxygen, and sulfur). Suitable divalent substituents that are bound to vicinal substitutable carbons of an "optionally substituted" group include: —O(CR*_2)_{2-3}O—, wherein each independent occurrence of R* is selected from hydrogen, $C_{1-6}$ aliphatic which may be substituted as defined below, and an unsubstituted 5 to 6-membered saturated, partially unsaturated, or aryl ring (having 0 to 4 heteroatoms independently selected from nitrogen, oxygen, and sulfur).

Suitable substituents on the aliphatic group of R* include halogen, —R^●, -(haloR^●), —OH, —OR^●, —O(haloR^●), —CN, —C(O)OH, —C(O)OR•, —NH$_2$, —NHR•, —NR•$_2$, or —NO$_2$, wherein each R• is unsubstituted or where preceded by "halo" is substituted only with one or more halogens, and is independently C$_{1-4}$ aliphatic, —CH$_2$Ph, —O(CH$_2$)$_{0-1}$Ph, or a 5 to 6-membered saturated, partially unsaturated, or aryl ring (having 0 to 4 heteroatoms independently selected from nitrogen, oxygen, and sulfur).

Suitable substituents on a substitutable nitrogen of an "optionally substituted" group include —R†, —NR†, —C(O)R†, —C(O)OR†, —C(O)C(O)R†, —C(O)CH$_2$C(O)R†, —S(O)$_2$R†, —S(O)$_2$NR†$_2$, —C(S)NR†$_2$, —C(NH)NR†$_2$, or —N(R†)S(O)$_2$R†; wherein each R† is independently hydrogen, C$_{1-6}$ aliphatic which may be substituted as defined below, unsubstituted —OPh, or an unsubstituted 5 to 6-membered saturated, partially unsaturated, or aryl ring (having 0 to 4 heteroatoms independently selected from nitrogen, oxygen, and sulfur), or, notwithstanding the definition above, two independent occurrences of R†, taken together with their intervening atom(s) form an unsubstituted 3 to 12-membered saturated, partially unsaturated, or aryl mono- or bicyclic ring (having 0 to 4 heteroatoms independently selected from nitrogen, oxygen, and sulfur).

Suitable substituents on the aliphatic group of R† are independently halogen, —R•, -(haloR•), —OH, —OR•, —O(haloR•), —CN, —C(O)OH, —C(O)OR•, —NH$_2$, —NHR•, —NR•$_2$, or —NO$_2$, wherein each R• is unsubstituted or where preceded by "halo" is substituted only with one or more halogens, and is independently C$_{1-4}$ aliphatic, —CH$_2$Ph, —O(CH$_2$)$_{0-1}$Ph, or a 5 to 6-membered saturated, partially unsaturated, or aryl ring (having 0 to 4 heteroatoms independently selected from nitrogen, oxygen, and sulfur).

As used herein, the term "provided compound" or "compound of the present disclosure" refers to any genus, subgenus, and/or species set forth herein.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, which is incorporated herein by reference. Pharmaceutically acceptable salts of the compounds of this disclosure include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium and N$^+$(C$_{1-4}$ alkyl)$_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the disclosure. Unless otherwise stated, all tautomeric forms of the compounds of the disclosure are within the scope of the disclosure. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}$C- or $^{14}$C-enriched carbon are within the scope of this disclosure. Such compounds are useful, for example, as analytical tools, as probes in biological assays, or as therapeutic agents in accordance with the present disclosure.

As used herein, the term "inhibitor" is defined as a compound that binds to and/or inhibits CDK2 with measurable affinity. In certain embodiments, an inhibitor has an IC$_{50}$ and/or binding constant of less than about 50 µM, less than about 1 µM, less than about 500 nM, less than about 100 nM, less than about 10 nM, or less than about 1 nM, when measured in an appropriate assay.

The term "patient," as used herein, means an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this disclosure include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

A "pharmaceutically acceptable derivative" means any non-toxic salt, ester, salt of an ester or other derivative of a compound of this disclosure that, upon administration to a recipient, is capable of providing, either directly or indirectly, a compound of this disclosure or an inhibitorily or degratorily active metabolite or residue thereof.

As used herein, the term "inhibitorily active metabolite or residue thereof" means that a metabolite or residue thereof is also an inhibitor of a CDK2 protein, or a mutant thereof.

3. Description of Exemplary Embodiments

In some embodiments, provided herein are compounds according to Formula I:

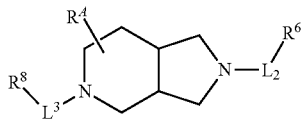

or a pharmaceutically acceptable salt thereof, wherein:
$R^4$ is

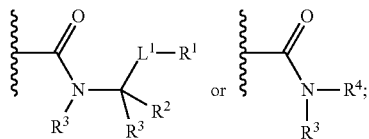

$L^1$ is a covalent bond or a saturated or unsaturated, straight or branched, optionally substituted bivalent $C_{1-6}$ hydrocarbon chain, wherein 0-2 methylene units of $L^1$ are independently replaced by —O—, —NR—, —S—, —OC(O)—, —C(O)O—, —C(O)—, —S(O)—, —S(O)$_2$—, —C(S)—, —NRS(O)$_2$—, —S(O)$_2$NR—, —NRC(O)—, —C(O)NR—, —OC(O)NR—, —NRC(O)O—, or —NRC(O)NR—;

$R^1$ is hydrogen, an optionally substituted $C_{1-6}$ aliphatic group, or an optionally substituted cyclic group selected from a 3-8 membered saturated or partially unsaturated monocyclic carbocyclic ring, a 7-12 membered saturated or partially unsaturated bicyclic carbocyclic ring, phenyl, an 8-10 membered bicyclic aromatic carbocyclic ring, a 3-8 membered saturated or partially unsaturated monocyclic heterocyclic ring (having 1-2 heteroatoms independently selected from nitrogen, oxygen, and sulfur), a 7-12 membered saturated or partially unsaturated bicyclic heterocyclic ring (having 1-4 heteroatoms independently selected from nitrogen, oxygen, and sulfur), a 5-6 membered monocyclic heteroaromatic ring (having 1-4 heteroatoms independently selected from nitrogen, oxygen, and sulfur), and an 8-10 membered bicyclic heteroaromatic ring (having 1-5 heteroatoms independently selected from nitrogen, oxygen, and sulfur);

$R^2$ is hydrogen, an optionally substituted $C_{1-6}$ aliphatic group, —C(O)OR, —C(O)NR$_2$, or an optionally substituted cyclic group selected from phenyl and a 5-6 membered monocyclic heteroaromatic ring (having 1-4 heteroatoms independently selected from nitrogen, oxygen, and sulfur);

each instance of $R^3$ is independently hydrogen or an optionally substituted $C_{1-6}$ aliphatic group;

$R^4$ is a cyclic group selected from a 3-8 membered saturated or partially unsaturated monocyclic carbocyclic ring, a 7-12 membered saturated or partially unsaturated bicyclic carbocyclic ring, phenyl, an 8-10 membered bicyclic aromatic carbocyclic ring, a 3-8 membered saturated or partially unsaturated monocyclic heterocyclic ring (having 1-2 heteroatoms independently selected from nitrogen, oxygen, and sulfur), a 7-12 membered saturated or partially unsaturated bicyclic heterocyclic ring (having 1-4 heteroatoms independently selected from nitrogen, oxygen, and sulfur), a 5-6 membered monocyclic heteroaromatic ring (having 1-4 heteroatoms independently selected from nitrogen, oxygen, and sulfur), and an 8-10 membered bicyclic heteroaromatic ring (having 1-5 heteroatoms independently selected from nitrogen, oxygen, and sulfur), wherein the cyclic group is optionally substituted with one or more instances of $R^5$;

each instance of $R^5$ is independently halogen, —CN, —NO$_2$, —OR, —SR, —NR$_2$, —S(O)$_2$R, —S(O)$_2$NR$_2$, —S(O)R, —S(O)NR$_2$, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)C(NR)NR$_2$, —N(R)S(O)$_2$NR$_2$, —N(R)S(O)$_2$R, an optionally substituted $C_{1-6}$ aliphatic group, or an optionally substituted —$C_{1-6}$ aliphatic-Cy group;

$L^2$ is a saturated or unsaturated, straight or branched, optionally substituted bivalent $C_{1-4}$ hydrocarbon chain, wherein 0-2 methylene units of $L^2$ are independently replaced by —O—, —NR—, —S—, —OC(O)—, —C(O)O—, —C(O)—, —S(O)—, —S(O)$_2$—, —C(S)—, —NRS(O)$_2$—, —S(O)$_2$NR—, —NRC(O)—, —C(O)NR—, —OC(O)NR—, —NRC(O)O—, or —NRC(O)NR—;

$R^6$ is an optionally substituted $C_{1-6}$ aliphatic group, or a cyclic group selected from a 3-8 membered saturated or partially unsaturated monocyclic carbocyclic ring, a 7-12 membered saturated or partially unsaturated bicyclic carbocyclic ring, phenyl, an 8-10 membered bicyclic aromatic carbocyclic ring, a 3-8 membered saturated or partially unsaturated monocyclic heterocyclic ring (having 1-2 heteroatoms independently selected from nitrogen, oxygen, and sulfur), a 7-12 membered saturated or partially unsaturated bicyclic heterocyclic ring (having 1-4 heteroatoms independently selected from nitrogen, oxygen, and sulfur), a 5-6 membered monocyclic heteroaromatic ring (having 1-4 heteroatoms independently selected from nitrogen, oxygen, and sulfur), and an 8-10 membered bicyclic heteroaromatic ring (having 1-5 heteroatoms independently selected from nitrogen, oxygen, and sulfur), wherein the cyclic group is optionally substituted with one or more instances of $R^7$;

each instance of $R^7$ is independently halogen, —CN, —NO$_2$, —OR, —SR, —NR$_2$, —S(O)$_2$R, —S(O)$_2$NR$_2$, —S(O)R, —S(O)NR$_2$, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)C(O)S(O)$_2$R, —N(R)C(NR)NR$_2$, —N(R)S(O)$_2$NR$_2$, —N(R)S(O)$_2$R, an optionally substituted $C_{1-6}$ aliphatic group, or Cy, or two instances of $R^6$ on the same carbon atom are taken together to form an oxo group;

$L^3$ is a saturated or unsaturated, straight or branched, optionally substituted bivalent $C_{1-4}$ hydrocarbon chain, wherein 0-2 methylene units of $L^3$ are independently replaced by —O—, —NR—, —S—, —OC(O)—, —C(O)O—, —C(O)—, —S(O)—, —S(O)$_2$—, —C(S)—, —NRS(O)$_2$—, —S(O)$_2$NR—, —NRC(O)—, —C(O)NR—, —OC(O)NR—, —NRC(O)O—, or —NRC(O)NR—;

$R^8$ is a cyclic group selected from a 3-8 membered saturated or partially unsaturated monocyclic carbocyclic ring, a 7-12 membered saturated or partially unsaturated bicyclic carbocyclic ring, phenyl, an 8-10 membered bicyclic aromatic carbocyclic ring, a 3-8 membered saturated or partially unsaturated monocyclic heterocyclic ring (having 1-2 heteroatoms independently selected from nitrogen, oxygen, and sulfur), a 7-12 membered saturated or partially unsaturated bicyclic heterocyclic ring (having 1-4 heteroatoms independently selected from nitrogen, oxygen, and sulfur), a 5-6 membered monocyclic heteroaromatic ring (having 1-4 heteroatoms independently selected from nitrogen, oxygen, and sulfur), and an 8-10 membered bicyclic heteroaromatic ring (having 1-5 heteroatoms independently selected from nitrogen, oxygen, and sulfur), wherein the cyclic group is optionally substituted with one or more instances of $R^9$;

each instance of $R^9$ is independently halogen, —CN, —$NO_2$, —OR, —SR, —$NR_2$, —$S(O)_2R$, —$S(O)_2NR_2$, —S(O)R, —$S(O)NR_2$, —C(O)R, —C(O)OR, —$C(O)NR_2$, —C(O)N(R)OR, —OC(O)R, —$OC(O)NR_2$, —N(R)C(O)OR, —N(R)C(O)R, —$N(R)C(O)NR_2$, —$N(R)C(NR)NR_2$, —$N(R)S(O)_2NR_2$, —$N(R)S(O)_2R$, an optionally substituted $C_{1-6}$ aliphatic group, an optionally substituted $C_{1-6}$ aliphatic-Cy group, or Cy;

each Cy is independently an optionally substituted cyclic group selected from a 3-8 membered saturated or partially unsaturated monocyclic carbocyclic ring, phenyl, a 3-8 membered saturated or partially unsaturated monocyclic heterocyclic ring (having 1-2 heteroatoms independently selected from nitrogen, oxygen, and sulfur), and a 5-6 membered monocyclic heteroaromatic ring (having 1-4 heteroatoms independently selected from nitrogen, oxygen, and sulfur); and each R is independently hydrogen, or an optionally substituted $C_{1-6}$ aliphatic group, an optionally substituted phenyl, an optionally substituted 3-7 membered saturated or partially unsaturated carbocyclic ring, an optionally substituted 3-7 membered saturated or partially unsaturated heterocyclic ring (having 1-2 heteroatoms independently selected from nitrogen, oxygen, and sulfur), or an optionally substituted 5-6 membered heteroaryl ring (having 1-4 heteroatoms independently selected from nitrogen, oxygen, and sulfur); or two R groups on the same nitrogen are taken together with their intervening atoms to form an optionally substituted 4-7 membered saturated, partially unsaturated, or heteroaryl ring (having 0-3 heteroatoms, in addition to the nitrogen, independently selected from nitrogen, oxygen, and sulfur);

wherein the compound is not Compound X, wherein Compound X is defined herein.

As defined generally above, $R^4$ is

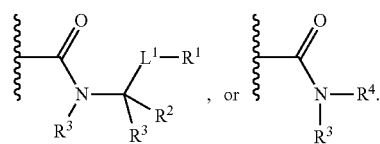

In some embodiments, $R^4$ is

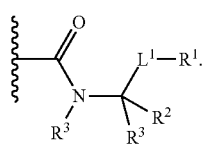

In some embodiments, $R^4$ is

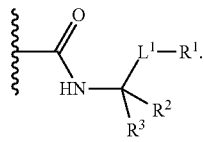

In some embodiments, $R^4$ is

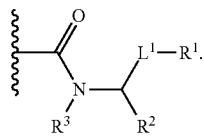

In some embodiments, $R^4$ is

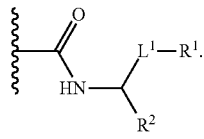

In some embodiments, $R^4$ is

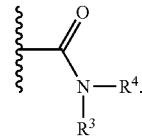

In some embodiments, $R^4$ is

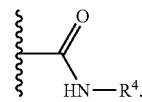

In some embodiments, $R^4$ is

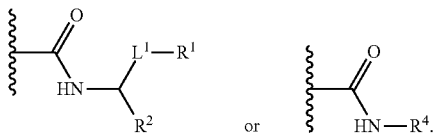

In some embodiments, $R^4$ is selected from those depicted in the compounds of the compounds of Table 1, below.

As defined generally above, $L^1$ is a covalent bond or a saturated or unsaturated, straight or branched, optionally substituted bivalent $C_{1-6}$ hydrocarbon chain, wherein 0-2 methylene units of $L^1$ are independently replaced by —O—, —NR—, —S—, —OC(O)—, —C(O)O—, —C(O)—, —S(O)—, —$S(O)_2$—, —C(S)—, —$NRS(O)_2$—, —$S(O)_2NR$—, —NRC(O)—, —C(O)NR—, —OC(O)NR—, —NRC(O)O—, or —NRC(O)NR—. In some embodiments, $L^1$ is a covalent bond. In some embodiments, $L^1$ is a saturated or unsaturated, straight or branched, optionally substituted bivalent $C_{1-6}$ hydrocarbon chain, wherein 0-2 methylene units of L are independently replaced by —O—, —NR—, —S—, —OC(O)—, —C(O)O—, —C(O)—, —S(O)—, —S(O)$_2$—, —C(S)—, —NRS(O)$_2$—, —S(O)$_2$NR—, —NRC(O)—, —C(O)NR—, —OC(O)NR—, —NRC(O)O—, or —NRC(O)NR—. In some embodiments, $L^1$ is a saturated or unsaturated, straight or branched, optionally substituted bivalent $C_{1-6}$ hydrocarbon chain. In some embodiments, $L^1$ is a saturated or unsaturated, straight or branched, optionally substituted bivalent $C_{1-4}$ hydrocarbon chain. In some embodiments, $L^1$ is a saturated or unsaturated, straight or branched, optionally substituted bivalent $C_{1-6}$ hydrocarbon chain, wherein 1 or 2 methylene units of $L^1$ are replaced by —O—, —NR—, —S—, —OC(O)—, —C(O)O—, —C(O)—, —S(O)—, —S(O)$_2$—, —C(S)—, —NRS(O)$_2$—, —S(O)$_2$NR—, —NRC(O)—, —C(O)NR—, —OC(O)NR—, —NRC(O)O—, or —NRC(O)NR—. In some embodiments, $L^1$ is an optionally substituted saturated, straight or branched, bivalent $C_{1-4}$ hydrocarbon chain. In some embodiments, $L^1$ is a partially unsaturated, straight or branched, bivalent $C_{1-4}$ hydrocarbon chain. In some embodiments, $L^1$ is an optionally substituted saturated, straight, bivalent $C_{1-6}$ hydrocarbon chain, wherein 1-2 methylene units of $L^1$ are independently replaced by —O—, —NR—, —S—, —OC(O)—, —C(O)O—, —C(O)—, —S(O)—, —S(O)$_2$—, —C(S)—, —NRS(O)$_2$—, —S(O)$_2$NR—, —NRC(O)—, —C(O)NR—, —OC(O)NR—, —NRC(O)O—, or —NRC(O)NR—. In some embodiments, $L^1$ is an optionally substituted straight or branched $C_{1-6}$ alkylene chain, wherein 1-2 methylene units of $L^1$ are independently replaced by —O—, —C(O)O—, —C(O)—, or —NRC(O)—. In some embodiments, $L^1$ is an optionally substituted straight or branched $C_{1-4}$ alkylene chain, wherein 1-2 methylene units of $L^1$ are independently replaced by —O—, —C(O)O—, —C(O)—, or —NRC(O)—. In some embodiments, $L^1$ is an optionally substituted straight or branched $C_{1-4}$ alkylene chain, wherein 1 methylene unit of $L^1$ is replaced by —O—. In some embodiments, $L^1$ is an optionally substituted straight or branched $C_{1-4}$ alkylene chain, wherein 1 methylene unit of $L^1$ is replaced by —NRC(O)—. In some embodiments, $L^1$ is an optionally substituted straight or branched $C_{1-4}$ alkylene chain, wherein 1 methylene unit of $L^1$ is replaced by —NHC(O)— or —N(CH$_3$)C(O)—. In some embodiments, $L^1$ is an unsubstituted straight chain $C_{1-4}$ alkylene. In some embodiments, $L^1$ is an unsubstituted straight chain $C_{1-4}$ alkenylene. In some embodiments, $L^1$ is an unsubstituted straight chain $C_{1-4}$ alkynylene. In some embodiments, $L^1$ is selected from those depicted in the compounds of Table 1, below.

In some embodiments, $L^1$ is

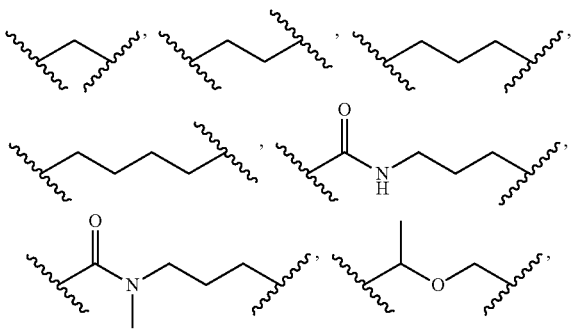

In some embodiments, $L^1$ is

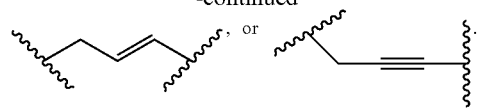

In some embodiments, $L^1$ is

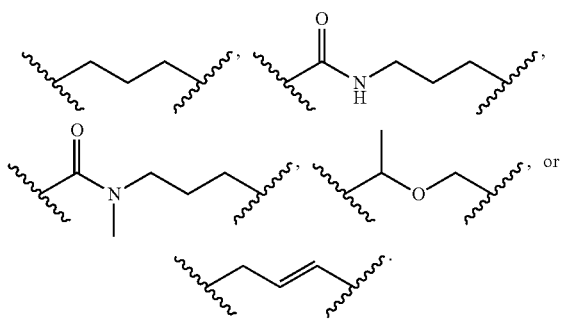

In some embodiments, $L^1$ is

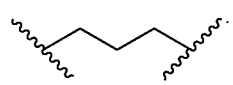 [SMILES: *CCC*]

In some embodiments, $L^1$ is

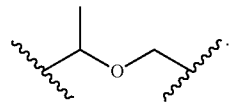 [SMILES: *COC(*)C]

As defined generally above, $R^1$ is hydrogen, an optionally substituted $C_{1-6}$ aliphatic group, or an optionally substituted cyclic group selected from a 3-8 membered saturated or partially unsaturated monocyclic carbocyclic ring, a 7-12 membered saturated or partially unsaturated bicyclic carbocyclic ring, phenyl, an 8-10 membered bicyclic aromatic carbocyclic ring, a 3-8 membered saturated or partially unsaturated monocyclic heterocyclic ring (having 1-2 heteroatoms independently selected from nitrogen, oxygen, and sulfur), a 7-12 membered saturated or partially unsaturated bicyclic heterocyclic ring (having 1-4 heteroatoms independently selected from nitrogen, oxygen, and sulfur), a 5-6 membered monocyclic heteroaromatic ring (having 1-4 heteroatoms independently selected from nitrogen, oxygen, and sulfur), and an 8-10 membered bicyclic heteroaromatic ring (having 1-5 heteroatoms independently selected from nitrogen, oxygen, and sulfur).

In some embodiments, $R^1$ is hydrogen. In some embodiments, $R^1$ is an optionally substituted $C_{1-6}$ aliphatic group. In some embodiments, $R^1$ is an optionally substituted $C_{1-4}$ aliphatic group. In some embodiments, $R^1$ is a $C_{1-4}$ aliphatic group. In some embodiments, $R^1$ is an isopropyl group. In some embodiments, $R^1$ is a tert-butyl group. In some embodiments, $R^1$ is methyl.

In some embodiments, $R^1$ is an optionally substituted cyclic group selected from a 3-8 membered saturated or partially unsaturated monocyclic carbocyclic ring, a 7-12 membered saturated or partially unsaturated bicyclic carbocyclic ring, phenyl, an 8-10 membered bicyclic aromatic carbocyclic ring, a 3-8 membered saturated or partially unsaturated monocyclic heterocyclic ring (having 1-2 heteroatoms independently selected from nitrogen, oxygen, and sulfur), a 7-12 membered saturated or partially unsaturated bicyclic heterocyclic ring (having 1-4 heteroatoms independently selected from nitrogen, oxygen, and sulfur), a 5-6 membered monocyclic heteroaromatic ring (having 1-4 heteroatoms independently selected from nitrogen, oxygen, and sulfur), and an 8-10 membered bicyclic heteroaromatic ring (having 1-5 heteroatoms independently selected from nitrogen, oxygen, and sulfur). In some embodiments, $R^1$ is an optionally substituted cyclic group selected from a 3-8 membered saturated or partially unsaturated monocyclic carbocyclic ring, phenyl, a 3-8 membered saturated or partially unsaturated monocyclic heterocyclic ring (having 1-2 heteroatoms independently selected from nitrogen, oxygen, and sulfur), a 5-6 membered monocyclic heteroaromatic ring (having 1-4 heteroatoms independently selected from nitrogen, oxygen, and sulfur), and an 8-10 membered bicyclic heteroaromatic ring (having 1-5 heteroatoms independently selected from nitrogen, oxygen, and sulfur). In some embodiments, $R^1$ is an optionally substituted cyclic group selected from phenyl, cyclohexyl, cyclopentyl, cycloheptyl, tetrahydrofuranyl, tetrahydropyranyl, pyridinyl, pyridazinyl, indole, and benzotriazole. In some embodiments, $R^1$ is an optionally substituted phenyl group. In some embodiments, $R^1$ is an optionally substituted cyclohexyl group. In some embodiments, $R^1$ is an optionally substituted cyclopentyl group. In some embodiments, $R^1$ is an optionally substituted cycloheptyl group. In some embodiments, $R^1$ is an optionally substituted pyridinyl group. In some embodiments, $R^1$ is an optionally substituted pyridazinyl group. In some embodiments, $R^1$ is an optionally substituted tetrahydrofuranyl group. In some embodiments, $R^1$ is an optionally substituted tetrahydropyranyl group. In some embodiments, $R^1$ is an optionally substituted indole group. In some embodiments, $R^1$ is an optionally substituted benzotriazole group. In some embodiments, $R^1$ is selected from those depicted in the compounds of Table 1, below.

In some embodiments, $R^1$ is hydrogen, methyl,

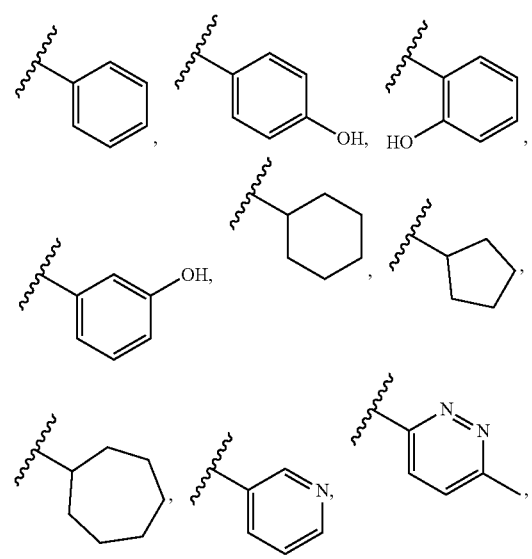

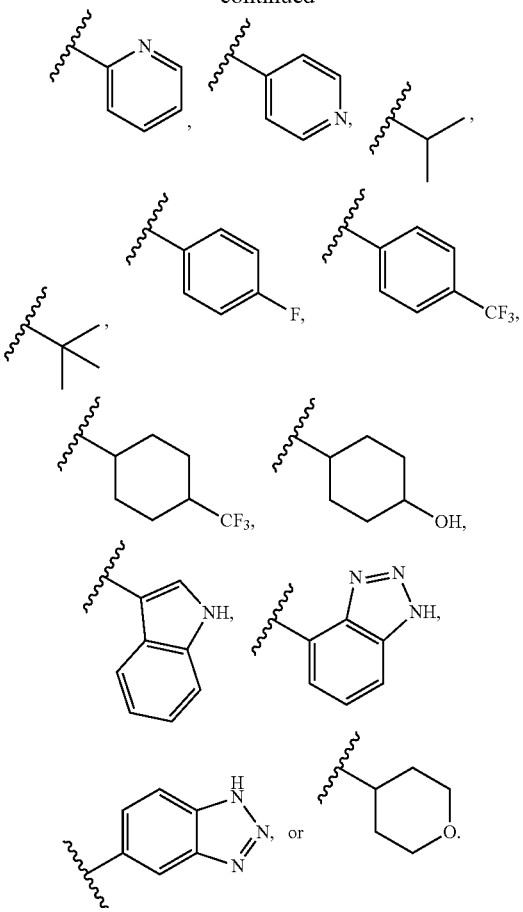

In some embodiments, $R^1$ is

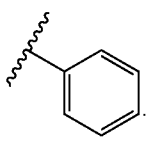 [SMILES: *c1ccccc1]

In some embodiments, $R^1$ is

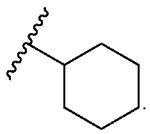 [SMILES: *C1CCCCC1]

As defined generally above, $R^2$ is hydrogen, an optionally substituted $C_{1-6}$ aliphatic group, —C(O)OR, —C(O)NR$_2$, or an optionally substituted cyclic group selected from phenyl and a 5-6 membered monocyclic heteroaromatic ring (having 1-4 heteroatoms independently selected from nitrogen, oxygen, and sulfur). In some embodiments, $R^2$ is an optionally substituted $C_{1-6}$ aliphatic group, —C(O)OR, —C(O)NR$_2$, or an optionally substituted cyclic group selected from phenyl and a 5-6 membered monocyclic heteroaromatic ring (having 1-4 heteroatoms independently selected from nitrogen, oxygen, and sulfur). In some embodiments, $R^2$ is hydrogen, methyl, —C(O)NHCH₃, —C(O)NH₂, —C(O)OCH₃, —C(O)OH, or an optionally substituted 5-6 membered monocyclic heteroaromatic ring (having 1-4 heteroatoms independently selected from nitrogen, oxygen, and sulfur). In some embodiments, R² is hydrogen, methyl, —C(O)NHCH₃, —C(O)NH₂, —C(O)OCH₃, or —C(O)OH. In some embodiments, R² is hydrogen. In some embodiments, R² is methyl. In some embodiments, R² is —C(O)NHCH₃. In some embodiments, R² is —C(O)NH₂. In some embodiments, R² is —C(O)OCH₃. In some embodiments, R² is —C(O)OH. In some embodiments, R² is a 5-6 membered monocyclic heteroaromatic ring (having 1-4 heteroatoms independently selected from nitrogen, oxygen, and sulfur). In some embodiments R² is an oxazolyl group. In some embodiments, R² is a pyrimidinyl group.

In some embodiments, R² is selected from those depicted in the compounds of Table 1, below.

As defined generally above, each instance of R³ is independently hydrogen or an optionally substituted C₁₋₆ aliphatic group. In some embodiments, each instance of R³ is hydrogen.

As defined generally above, R⁴ is a cyclic group selected from a 3-8 membered saturated or partially unsaturated monocyclic carbocyclic ring, a 7-12 membered saturated or partially unsaturated bicyclic carbocyclic ring, phenyl, an 8-10 membered bicyclic aromatic carbocyclic ring, a 3-8 membered saturated or partially unsaturated monocyclic heterocyclic ring (having 1-2 heteroatoms independently selected from nitrogen, oxygen, and sulfur), a 7-12 membered saturated or partially unsaturated bicyclic heterocyclic ring (having 1-4 heteroatoms independently selected from nitrogen, oxygen, and sulfur), a 5-6 membered monocyclic heteroaromatic ring (having 1-4 heteroatoms independently selected from nitrogen, oxygen, and sulfur), and an 8-10 membered bicyclic heteroaromatic ring (having 1-5 heteroatoms independently selected from nitrogen, oxygen, and sulfur), wherein the cyclic group is optionally substituted with one or more instances of R⁵.

In some embodiments, R⁴ is a cyclic group selected from a 3-8 membered saturated or partially unsaturated monocyclic heterocyclic ring (having 1-2 heteroatoms independently selected from nitrogen, oxygen, and sulfur), and a 5-6 membered monocyclic heteroaromatic ring (having 1-4 heteroatoms independently selected from nitrogen, oxygen, and sulfur), wherein the cyclic group is optionally substituted with one or more instances of R⁵. In some embodiments, R⁴ is a 3-8 membered saturated or partially unsaturated monocyclic heterocyclic ring (having 1-2 heteroatoms independently selected from nitrogen, oxygen, and sulfur), optionally substituted with one or more instances of R⁵. In some embodiments, R⁴ is a 5-6 membered monocyclic heteroaromatic ring (having 1-4 heteroatoms independently selected from nitrogen, oxygen, and sulfur), optionally substituted with one or more instances of R⁵. In some embodiments, R⁴ is a cyclic group selected from phenyl, pyridine, and piperidine, wherein the cyclic group is optionally substituted with one or more instances of R⁵. In some embodiments, R⁴ is phenyl, optionally substituted with one or more instances of R⁵. In some embodiments, R⁴ is pyridine, optionally substituted with one or more instances of R⁵. In some embodiments, R⁴ is piperidine, optionally substituted with one or more instances of R⁵. In some embodiments, R⁴ is selected from those depicted in the compounds of Table 1, below.

In some embodiments, R⁴ is substituted with 0, 1, or 2 instances of R⁵. In some embodiments, R⁴ is substituted with 1 instance of R⁵. R³ is substituted with 2 instances of R⁵. R⁴ is substituted with 3 instances of R⁵. In some embodiments, R⁴ is unsubstituted.

As defined generally above, each instance of R⁵ is independently halogen, —CN, —NO₂, —OR, —SR, —NR₂, —S(O)₂R, —S(O)₂NR₂, —S(O)R, —S(O)NR₂, —C(O)R, —C(O)OR, —C(O)NR₂, —C(O)N(R)OR, —OC(O)R, —OC(O)NR₂, —N(R)C(O)OR, —N(R)C(O)R, —N(R)C(O)NR₂, —N(R)C(NR)NR₂, —N(R)S(O)₂NR₂, —N(R)S(O)₂R, an optionally substituted C₁₋₆ aliphatic group, or an optionally substituted —C₁₋₆ aliphatic-Cy group.

In some embodiments, R⁵ is —OR, —C(O)R, an optionally substituted C₁₋₆ aliphatic group, or an optionally substituted —C₁₋₆ aliphatic-Cy group. In some embodiments, R⁵ is —OR. In some embodiments, R⁵ is —C(O)R. In some embodiments, R⁵ is an optionally substituted C₁₋₆ aliphatic group. In some embodiments, R⁵ is an optionally substituted —C₁₋₆ aliphatic-Cy group. In some embodiments, R⁵ is an optionally substituted benzyl group, an optionally substituted benzoyl group, an optionally substituted phenoxy group, or an optionally substituted phenylacetyl group. In some embodiments R⁵ is an optionally substituted benzyl group. In some embodiments R⁵ is an optionally substituted benzoyl group. In some embodiments R⁵ is an optionally substituted phenoxy group. In some embodiments R⁵ is an optionally substituted phenylacetyl group. In some embodiments, R⁵ is selected from those depicted in the compounds of Table 1, below.

In some embodiments, R⁴ is

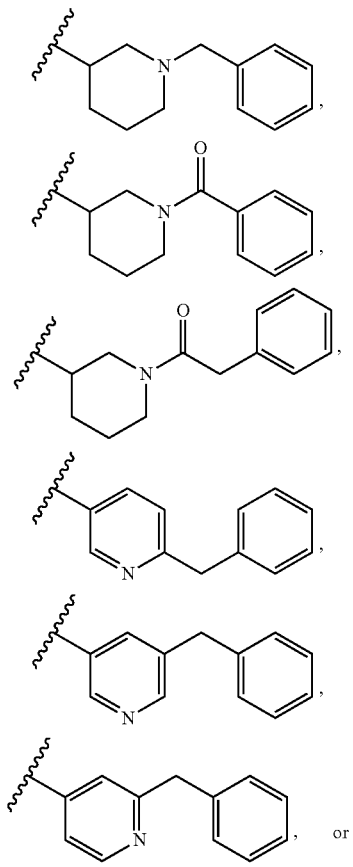

, or

-continued
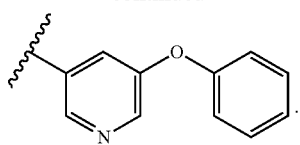
In some embodiments, $R^A$ is a substituent of Table A1 or Table A2:
TABLE A1
Exemplary $R^A$ substituents
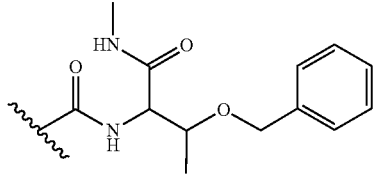
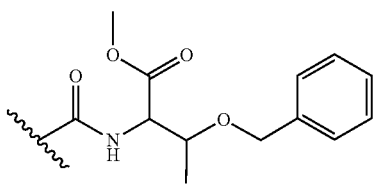 [SMILES: *C(=O)NC(C(=O)OC)C(C)OCc1ccccc1]
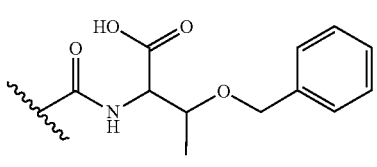 [SMILES: *C(=O)NC(C(=O)O)C(C)OCc1ccccc1]
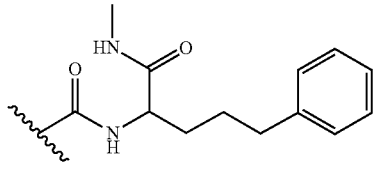
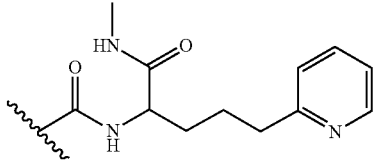 [SMILES: *C(=O)NC(CCCc1ccccn1)C(=O)NC]
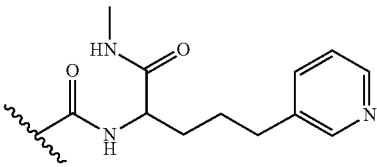 [SMILES: *C(=O)NC(CCCc1cccnc1)C(=O)NC]
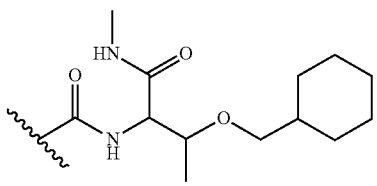 [SMILES: *C(=O)NC(C(=O)NC)C(C)OCC1CCCCC1]
TABLE A1-continued
Exemplary $R^A$ substituents
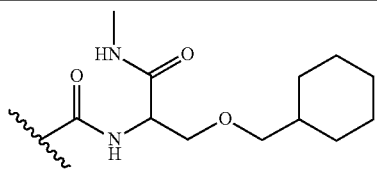
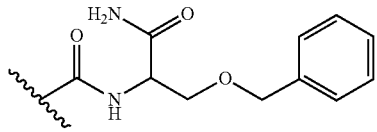 [SMILES: *C(=O)NC(COCc1ccccc1)C(N)=O]
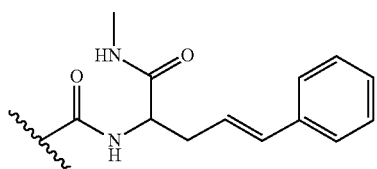 [SMILES: *C(=O)NC(C/C=C/c1ccccc1)C(=O)NC]
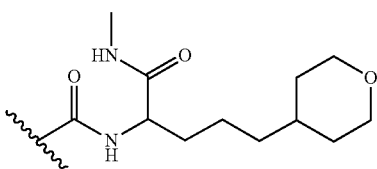 [SMILES: *C(=O)NC(CCCC1CCOCC1)C(=O)NC]
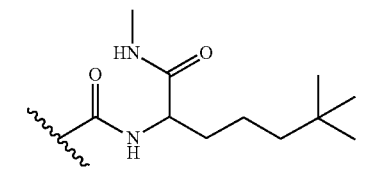 [SMILES: *C(=O)NC(CCCC(C)(C)C)C(=O)NC]
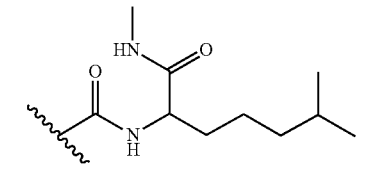 [SMILES: *C(=O)NC(CCCC(C)C)C(=O)NC]
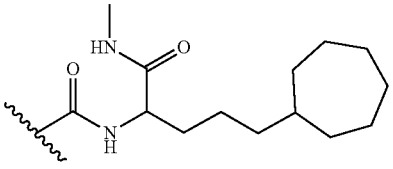 [SMILES: *C(=O)NC(CCCC1CCCCCC1)C(=O)NC]
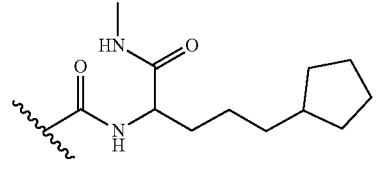 [SMILES: *C(=O)NC(CCCC1CCCC1)C(=O)NC]
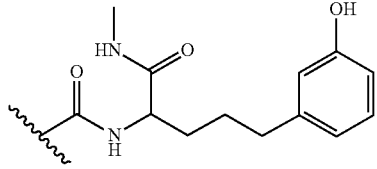 [SMILES: *C(=O)NC(CCCc1cccc(O)c1)C(=O)NC]

TABLE A1-continued

Exemplary R^A substituents

TABLE A1-continued

Exemplary R$^A$ substituents

TABLE A2

Additional Exemplary R$^A$ substituents

TABLE A2-continued

Additional Exemplary R$^A$ substituents

In some embodiments, R$^A$ is a substituent of Table A1 or Table A2. In some embodiments, R$^A$ is a substituent of Table A1. In some embodiments, R$^A$ is a substituent of Table A2.

In some embodiments, $R^4$ is

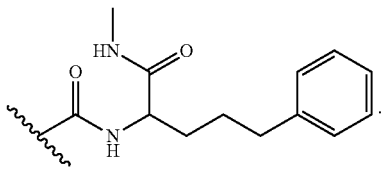 [SMILES: *C(=O)NC(CCCc1ccccc1)C(=O)NC]

As defined generally above, $L^2$ is a saturated or unsaturated, straight or branched, optionally substituted bivalent $C_{1-4}$ hydrocarbon chain, wherein 0-2 methylene units of $L^2$ are independently replaced by —O—, —NR—, —S—, —OC(O)—, —C(O)O—, —C(O)—, —S(O)—, —S(O)$_2$—, —C(S)—, —NRS(O)$_2$—, —S(O)$_2$NR—, —NRC(O)—, —C(O)NR—, —OC(O)NR—, —NRC(O)O—, or —NRC(O)NR—. In some embodiments, $L^2$ is a saturated, straight, optionally substituted bivalent $C_{1-4}$ hydrocarbon chain, wherein 0-2 methylene units of $L^2$ are independently replaced by —O—, —NR—, —OC(O)—, —C(O)O—, —C(O)—, —NRC(O)—, or —C(O)NR—. In some embodiments, $L^2$ is a saturated, straight, optionally substituted bivalent $C_{1-4}$ hydrocarbon chain. In some embodiments, $L^2$ is a saturated, straight, optionally substituted bivalent $C_{1-4}$ hydrocarbon chain, wherein 1 methylene unit of $L^2$ is replaced by —O—, —NR—, —OC(O)—, —C(O)O—, —C(O)—, —NRC(O)—, or —C(O)NR—. In some embodiments, $L^2$ is a saturated, straight, optionally substituted bivalent $C_{1-4}$ hydrocarbon chain, wherein 1 methylene unit of $L^2$ is replaced by —C(O)—. In some embodiments, $L^2$ is —CH$_2$— or —C(O)—. In some embodiments, $L^2$ is —CH$_2$—. In some embodiments, $L^2$ is —C(O)—. In some embodiments, $L^2$ is selected from those depicted in the compounds of Table 1, below.

As generally defined above, $R^6$ is an optionally substituted $C_{1-6}$ aliphatic group, or a cyclic group selected from a 3-8 membered saturated or partially unsaturated monocyclic carbocyclic ring, a 7-12 membered saturated or partially unsaturated bicyclic carbocyclic ring, phenyl, an 8-10 membered bicyclic aromatic carbocyclic ring, a 3-8 membered saturated or partially unsaturated monocyclic heterocyclic ring (having 1-2 heteroatoms independently selected from nitrogen, oxygen, and sulfur), a 7-12 membered saturated or partially unsaturated bicyclic heterocyclic ring (having 1-4 heteroatoms independently selected from nitrogen, oxygen, and sulfur), a 5-6 membered monocyclic heteroaromatic ring (having 1-4 heteroatoms independently selected from nitrogen, oxygen, and sulfur), and an 8-10 membered bicyclic heteroaromatic ring (having 1-5 heteroatoms independently selected from nitrogen, oxygen, and sulfur), wherein the cyclic group is optionally substituted with one or more instances of $R^7$.

In some embodiments, $R^6$ is an optionally substituted $C_{1-6}$ aliphatic group. In some embodiments, $R^6$ is a cyclic group selected from a 3-8 membered saturated or partially unsaturated monocyclic carbocyclic ring, a 7-12 membered saturated or partially unsaturated bicyclic carbocyclic ring, phenyl, an 8-10 membered bicyclic aromatic carbocyclic ring, a 3-8 membered saturated or partially unsaturated monocyclic heterocyclic ring (having 1-2 heteroatoms independently selected from nitrogen, oxygen, and sulfur), a 7-12 membered saturated or partially unsaturated bicyclic heterocyclic ring (having 1-4 heteroatoms independently selected from nitrogen, oxygen, and sulfur), a 5-6 membered monocyclic heteroaromatic ring (having 1-4 heteroatoms independently selected from nitrogen, oxygen, and sulfur), and an 8-10 membered bicyclic heteroaromatic ring (having 1-5 heteroatoms independently selected from nitrogen, oxygen, and sulfur), wherein the cyclic group is optionally substituted with one or more instances of $R^7$. In some embodiments, $R^6$ is a cyclic group selected from phenyl, an 8-10 membered bicyclic aromatic carbocyclic ring, a 5-6 membered monocyclic heteroaromatic ring (having 1-4 heteroatoms independently selected from nitrogen, oxygen, and sulfur), and an 8-10 membered bicyclic heteroaromatic ring (having 1-5 heteroatoms independently selected from nitrogen, oxygen, and sulfur), wherein the cyclic group is optionally substituted with one or more instances of $R^7$.

In some embodiments, $R^6$ is a cyclic group selected from cyclohexyl, phenyl, quinolinyl, isoquinolinyl, quinoxalinyl, 2,3-dihydrobenzo[b][1,4]dioxinyl, pyrazolyl, isoxazolyl, imidazolyl, thiazolyl, pyridinyl, pyrazinyl, pyridazinyl, pyrimidinyl, 2,3-dihydrobenzo[d]furanyl, benzofuranyl, indolyl, benzo[1,2,3]triazole, benzimidazolyl, imidazo[1,2-a]pyrimidinyl, imidazo[1,2-a]pyrazinyl, indazolyl, indolinyl, indolizinyl, isoindolinyl, and 2,3,-dihydrobenzo[d]oxazolyl, wherein the cyclic group is optionally substituted with one or more instances of $R^7$.

In some embodiments, $R^6$ is cyclohexyl, optionally substituted with one or more instances of $R^7$. In some embodiments, $R^6$ is phenyl, optionally substituted with one or more instances of $R^7$. In some embodiments, $R^6$ is quinolinyl, optionally substituted with one or more instances of $R^7$. In some embodiments, $R^6$ is isoquinolinyl, optionally substituted with one or more instances of $R^7$. In some embodiments, $R^6$ is quinoxalinyl, optionally substituted with one or more instances of $R^7$. In some embodiments, $R^6$ is 2,3-dihydrobenzo[b][1,4]dioxinyl, optionally substituted with one or more instances of $R^7$. In some embodiments, $R^6$ is pyrazolyl, optionally substituted with one or more instances of $R^7$. In some embodiments, $R^6$ is isoxazolyl, optionally substituted with one or more instances of $R^7$. In some embodiments, $R^6$ is imidazolyl, optionally substituted with one or more instances of $R^7$. In some embodiments, $R^6$ is thiazolyl, optionally substituted with one or more instances of $R^7$. In some embodiments, $R^6$ is pyridinyl, optionally substituted with one or more instances of $R^7$. In some embodiments, $R^6$ is pyrazinyl, optionally substituted with one or more instances of $R^7$. In some embodiments, $R^6$ is pyridazinyl, optionally substituted with one or more instances of $R^7$. In some embodiments, $R^6$ is pyrimidinyl, optionally substituted with one or more instances of $R^7$. In some embodiments, $R^6$ is 2,3-dihydrobenzo[d]furanyl, optionally substituted with one or more instances of $R^7$. In some embodiments, $R^6$ is benzofuranyl, optionally substituted with one or more instances of $R^7$. In some embodiments, $R^5$ is indolyl, optionally substituted with one or more instances of $R^7$. In some embodiments, $R^6$ is benzo[1,2,3]triazole, optionally substituted with one or more instances of $R^7$. In some embodiments, $R^6$ is benzimidazolyl, optionally substituted with one or more instances of $R^7$. In some embodiments, $R^6$ is imidazo[1,2-a]pyrimidinyl, optionally substituted with one or more instances of $R^7$. In some embodiments, $R^6$ is imidazo[1,2-a]pyrazinyl, optionally substituted with one or more instances of $R^7$. In some embodiments, $R^6$ is indazolyl, optionally substituted with one or more instances of $R^7$. In some embodiments, $R^6$ is indolinyl, optionally substituted with one or more instances of $R^7$. In some embodiments, $R^6$ is indolizinyl, optionally substituted with one or more instances of $R^7$. In some embodiments, $R^6$ is isoindolinyl, optionally substituted with one or more instances of $R^7$. In some embodiments, $R^6$ is 2,3,-dihydrobenzo[d]oxazolyl, optionally substituted with one or more instances of $R^7$. In some embodiments, $R^6$ is selected from those depicted in the compounds of Table 1, below.

In some embodiments, $R^6$ is substituted with 0, 1, 2 or 3 instances of $R^7$. In some embodiments, $R^6$ is substituted with 1 instance of $R^7$. $R^6$ is substituted with 2 instances of $R^7$. $R^6$ is substituted with 3 instances of $R^7$. In some embodiments, $R^6$ is unsubstituted.

As defined generally above, each $R^7$ is independently halogen, —CN, —NO$_2$, —OR, —SR, —NR$_2$, —S(O)$_2$R, —S(O)$_2$NR$_2$, —S(O)R, —S(O)NR$_2$, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)C(O)S(O)$_2$R, —N(R)C(NR)NR$_2$, —N(R)S(O)$_2$NR$_2$, —N(R)S(O)$_2$R, an optionally substituted C$_{1-6}$ aliphatic group, or Cy, or two instances of $R^6$ on the same carbon atom are taken together to form an oxo group.

In some embodiments, each $R^7$ is independently halogen, —CN, —OR, —NR$_2$, —S(O)$_2$NR$_2$, —N(R)C(O)R, —N(R)C(O)S(O)$_2$R, an optionally substituted C$_{1-6}$ aliphatic group, or Cy, or two instances of $R^7$ on the same carbon atom are taken together to form an oxo group. In some embodiments, each $R^7$ is independently —OR, an optionally substituted C$_{1-6}$ aliphatic group, Cy or two instances of $R^7$ on the same carbon atom are taken together to form an oxo group.

In some embodiments, each $R^7$ is independently fluoro, chloro, methoxy, ethoxy, isopropoxy, cyclopropoxy, isobutoxy, phenoxy, 2-cyclopropylethoxy, methyl, ethyl, cyclopropyl, isobutyl, phenyl, pyridinyl, pyrimidinyl, cyclopropanecarboxamido, 2-cyclopropylacetamido, (methylsulfonyl)methanamido, cyano, hydroxymethyl, trifluoromethoxy, trifluoromethyl, sulfamoyl, or amino, or two instances of $R^7$ on the same carbon atom are taken together to form an oxo group. In some embodiments, each $R^7$ is independently —OR. In some embodiments, each $R^7$ is independently selected from those depicted in the compounds of Table 1, below.

In some embodiments, -L$^2$-R$^6$ is a substituent of Table B1 or Table B2:

TABLE B1

Exemplary -L$^2$—R$^6$ substituents

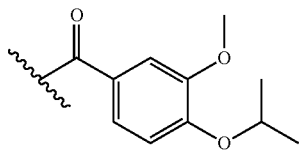 [SMILES: *C(=O)c1ccc(OC(C)C)c(OC)c1]

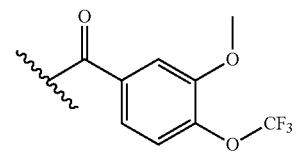 [SMILES: *C(=O)c1ccc(OC(F)(F)F)c(OC)c1]

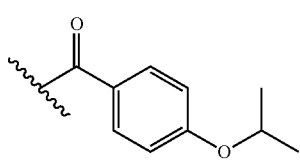 [SMILES: *C(=O)c1ccc(OC(C)C)cc1]

TABLE B1-continued

Exemplary -L$^2$—R$^6$ substituents

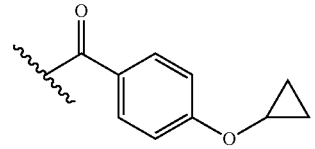 [SMILES: *C(=O)c1ccc(OC2CC2)cc1]

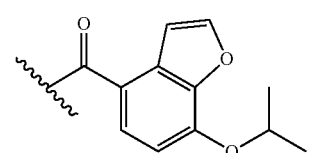

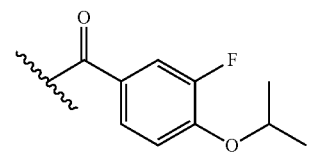 [SMILES: *C(=O)c1ccc(OC(C)C)c(F)c1]

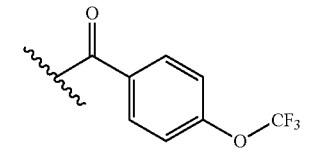 [SMILES: *C(=O)c1ccc(OC(F)(F)F)cc1]

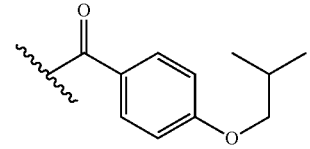 [SMILES: *C(=O)c1ccc(OCC(C)C)cc1]

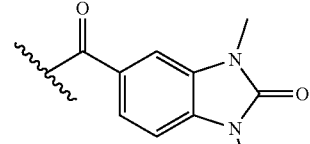

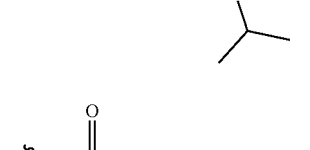

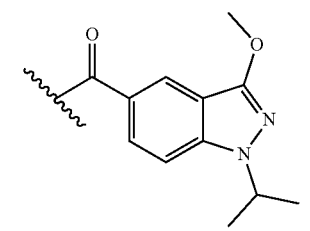 [SMILES: *C(=O)c1ccc2c(c1)c(OC)nn2C(C)C]

TABLE B1-continued
Exemplary -L²—R⁶ substituents
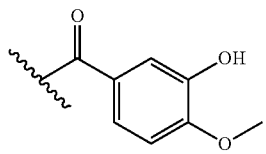 [SMILES: *C(=O)c1ccc(OC)c(O)c1]
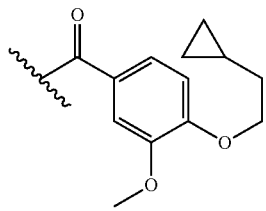 [SMILES: *C(=O)c1ccc(OCCC2CC2)c(OC)c1]
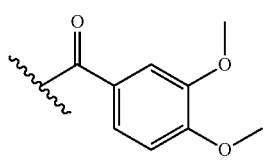 [SMILES: *C(=O)c1ccc(OC)c(OC)c1]
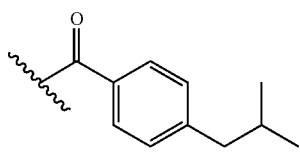 [SMILES: *C(=O)c1ccc(CC(C)C)cc1]
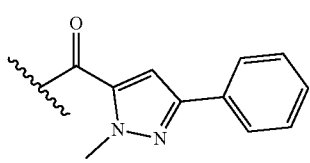 [SMILES: *C(=O)c1cc(-c2ccccc2)nn1C]
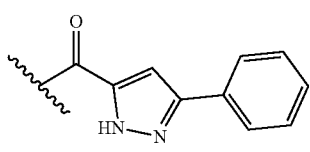 [SMILES: *C(=O)c1cc(-c2ccccc2)n[nH]1]
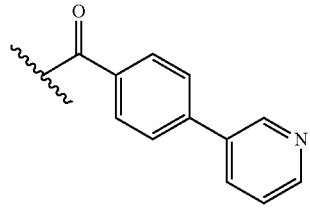 [SMILES: *C(=O)c1ccc(-c2cccnc2)cc1]
TABLE B2
Additional Exemplary -L²—R⁶ substituents
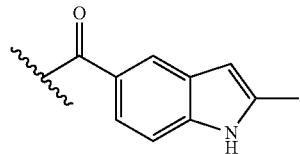 [SMILES: *C(=O)c1ccc2[nH]c(C)cc2c1]
TABLE B2-continued
Additional Exemplary -L²—R⁶ substituents
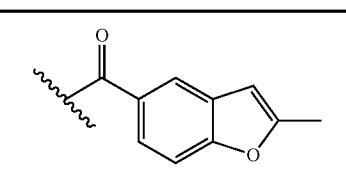
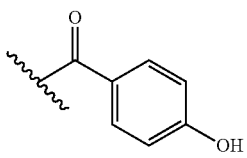 [SMILES: *C(=O)c1ccc(O)cc1]
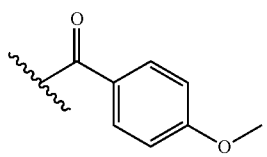 [SMILES: *C(=O)c1ccc(OC)cc1]
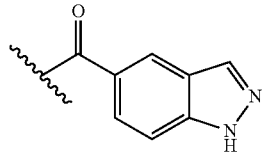 [SMILES: *C(=O)c1ccc2[nH]ncc2c1]
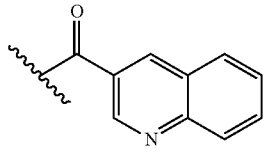 [SMILES: *C(=O)c1cnc2ccccc2c1]
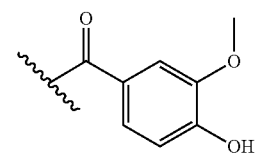 [SMILES: *C(=O)c1ccc(O)c(OC)c1]
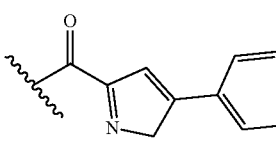
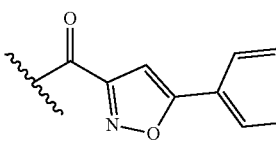
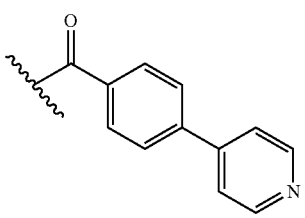 [SMILES: *C(=O)c1ccc(-c2ccncc2)cc1]

TABLE B2-continued
Additional Exemplary -L$^2$—R$^6$ substituents
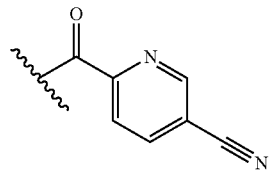 [SMILES: *C(=O)c1ccc(C#N)cn1]
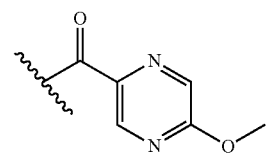 [SMILES: *C(=O)c1cnc(OC)cn1]
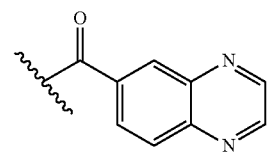 [SMILES: *C(=O)c1ccc2nccnc2c1]
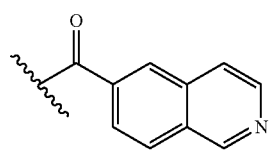 [SMILES: *C(=O)c1ccc2cnccc2c1]
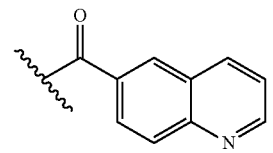 [SMILES: *C(=O)c1ccc2ncccc2c1]
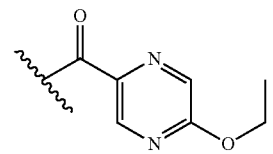 [SMILES: *C(=O)c1cnc(OCC)cn1]
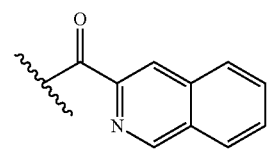 [SMILES: *C(=O)c1cc2ccccc2cn1]
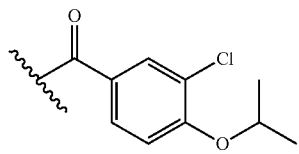 [SMILES: *C(=O)c1ccc(OC(C)C)c(Cl)c1]
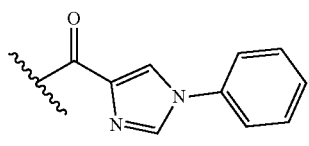 [SMILES: *C(=O)c1cn(-c2ccccc2)cn1]
TABLE B2-continued
Additional Exemplary -L$^2$—R$^6$ substituents
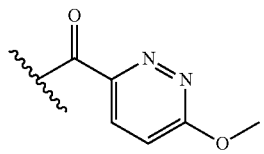 [SMILES: *C(=O)c1ccc(OC)nn1]
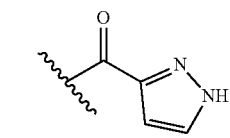 [SMILES: *C(=O)c1cc[nH]n1]
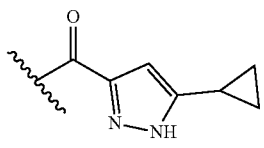 [SMILES: *C(=O)c1cc(C2CC2)[nH]n1]
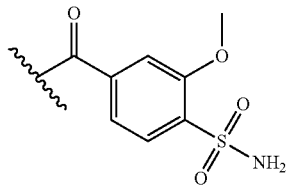 [SMILES: *C(=O)c1ccc(S(N)(=O)=O)c(OC)c1]
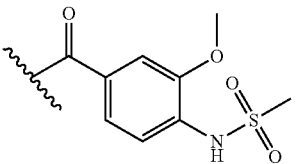 [SMILES: *C(=O)c1ccc(NS(C)(=O)=O)c(OC)c1]
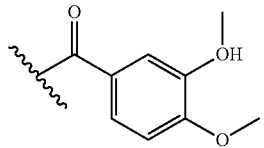 [SMILES: *C(=O)c1ccc(OC)c(OC)c1]
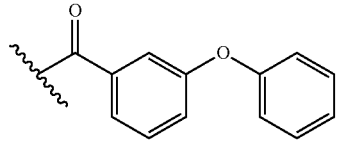 [SMILES: *C(=O)c1cccc(Oc2ccccc2)c1]
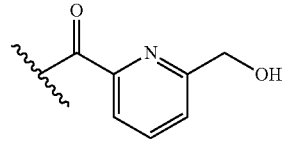 [SMILES: *C(=O)c1cccc(CO)n1]
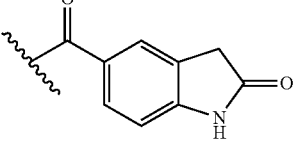

TABLE B2-continued
Additional Exemplary -L²—R⁶ substituents
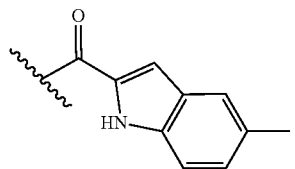 [SMILES: *C(=O)c1cc2cc(C)ccc2[nH]1]
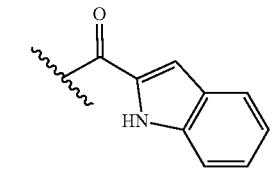 [SMILES: *C(=O)c1cc2ccccc2[nH]1]
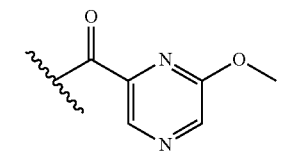 [SMILES: *C(=O)c1cncc(OC)n1]
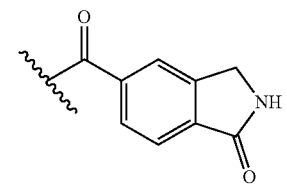 [SMILES: *C(=O)c1ccc2c(c1)CNC2=O]
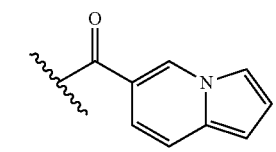 [SMILES: *C(=O)c1ccc2cccn2c1]
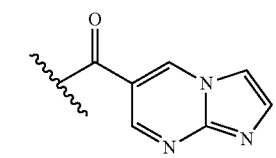 [SMILES: *C(=O)c1cnc2nccn2c1]
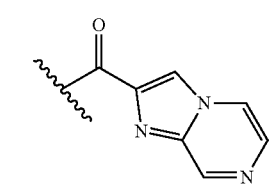 [SMILES: *C(=O)c1cn2ccncc2n1]
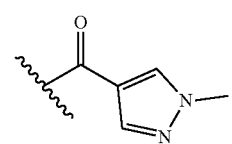 [SMILES: *C(=O)c1cnn(C)c1]
TABLE B2-continued
Additional Exemplary -L²—R⁶ substituents
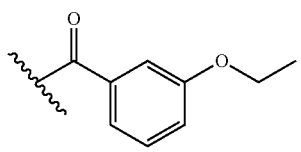 [SMILES: *C(=O)c1cccc(OCC)c1]
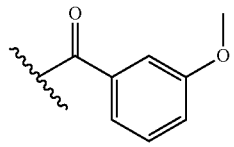 [SMILES: *C(=O)c1cccc(OC)c1]
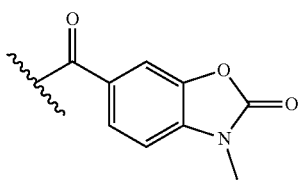 [SMILES: *C(=O)c1ccc2c(c1)oc(=O)n2C]
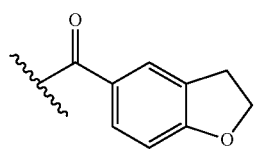 [SMILES: *C(=O)c1ccc2c(c1)CCO2]
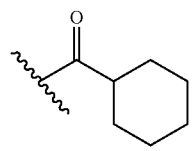 [SMILES: *C(=O)C1CCCCC1]
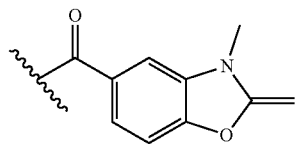 [SMILES: *C(=O)c1ccc2c(c1)N(C)C(=C)O2]
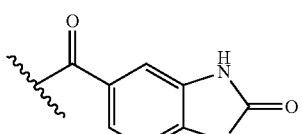
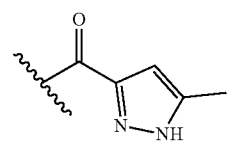 [SMILES: *C(=O)c1cc(C)[nH]n1]
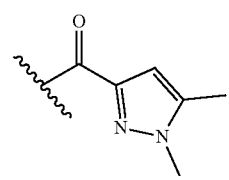 [SMILES: *C(=O)c1cc(C)n(C)n1]

TABLE B2-continued
Additional Exemplary -L²—R⁶ substituents
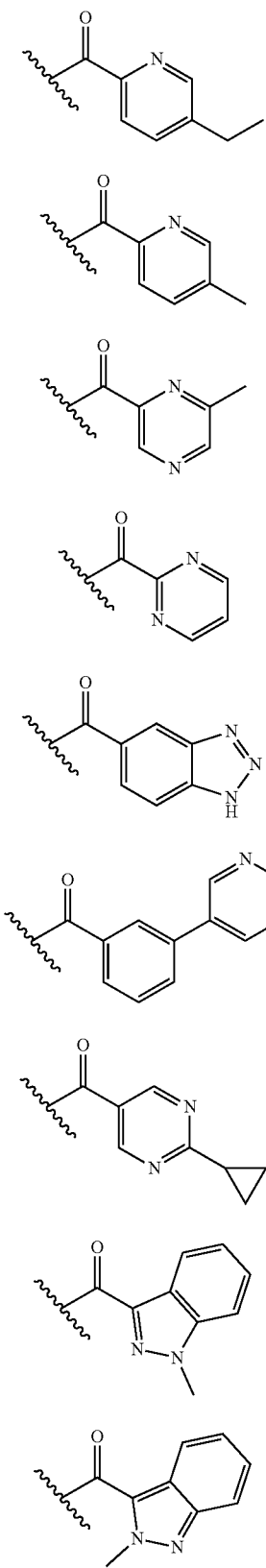
TABLE B2-continued
Additional Exemplary -L²—R⁶ substituents
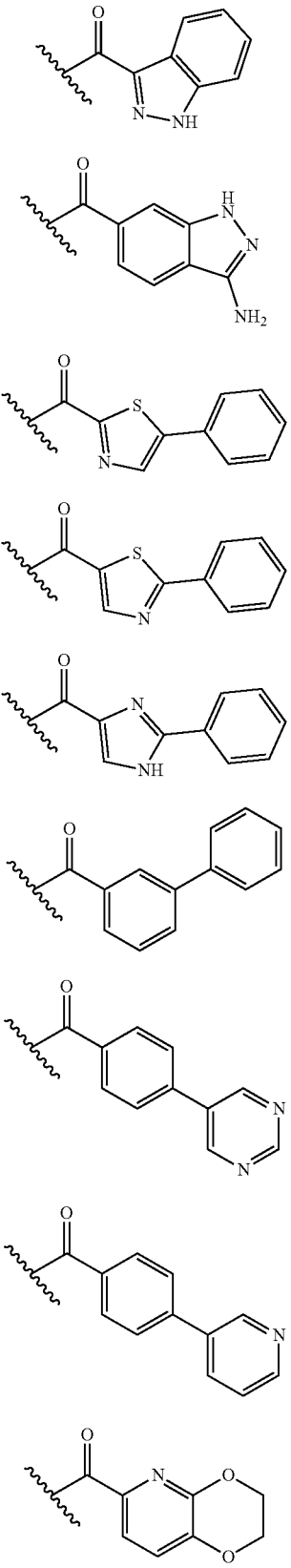

TABLE B2-continued

Additional Exemplary -L²—R⁶ substituents

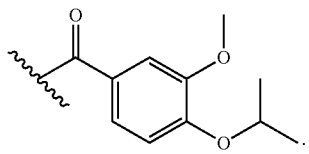 [SMILES: *C(=O)c1ccc(OC(C)C)c(OC)c1]

As defined generally above, $L^3$ is a saturated or unsaturated, straight or branched, optionally substituted bivalent $C_{1-4}$ hydrocarbon chain, wherein 0-2 methylene units of $L^3$ are independently replaced by —O—, —NR—, —S—, —OC(O)—, —C(O)O—, —C(O)—, —S(O)—, —S(O)$_2$—, —C(S)—, —NRS(O)$_2$—, —S(O)$_2$NR—, —NRC(O)—, —C(O)NR—, —OC(O)NR—, —NRC(O)O—, or —NRC(O)NR—. In some embodiments, $L^3$ is a saturated, straight, optionally substituted bivalent $C_{1-4}$ hydrocarbon chain, wherein 0-2 methylene units of $L^3$ are independently replaced by —O—, —NR—, —OC(O)—, —C(O)O—, —C(O)—, —NRC(O)—, or —C(O)NR. In some embodiments, $L^3$ is a saturated, straight, optionally substituted bivalent $C_{1-4}$ hydrocarbon chain. In some embodiments, $L^3$ is a saturated, straight, optionally substituted bivalent $C_{1-4}$ hydrocarbon chain, wherein 1 methylene unit of $L^3$ is replaced by —O—, —NR—, —OC(O)—, —C(O)O—, —C(O)—, —NRC(O)—, or —C(O)NR. In some embodiments, $L^3$ is a saturated, straight, optionally substituted bivalent $C_{1-4}$ hydrocarbon chain, wherein 1 methylene unit of $L^3$ is replaced by —C(O)—. In some embodiments, $L^3$ is a saturated, straight, substituted bivalent $C_{1-4}$ hydrocarbon chain, wherein 1 methylene unit of $L^3$ is replaced by —C(O)—, and wherein the $C_{1-4}$ hydrocarbon chain is substituted twice on the same carbon atom and forms a 3-6 membered saturated or partially unsaturated monocyclic carbocyclic ring. In some embodiments, $L^3$ is —C(O)CH$_2$—, —C(O)C(CH$_3$)H—, —C(O)C(CH$_3$)$_2$—, —C(O)CH$_2$CH$_2$—, C(O)CH$_2$CH$_2$CH$_2$—,

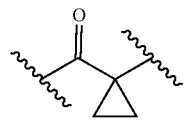 [SMILES: *C(=O)C1(*)CC1]

or —C(O)—. In some embodiments, $L^3$ is —C(O)CH$_2$—, or —C(O)C(CH$_3$)H—. In some embodiments, $L^3$ is —C(O)CH$_2$—. In some embodiments, $L^3$ is —C(O)C(CH$_3$)H—. In some embodiments, $L^3$ is —C(O)C(CH$_3$)$_2$—. In some embodiments, $L^3$ is —C(O)CH$_2$CH$_2$—. In some embodiments, $L^3$ is —C(O)CH$_2$CH$_2$CH$_2$—. In some embodiments, $L^3$ is —C(O)—. In some embodiments, $L^3$ is

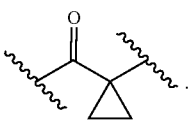 [SMILES: *C(=O)C1(*)CC1]

In some embodiments, -L²-R⁶ is a substituent of Table B1.
In some embodiments, -L²-R⁶ is a substituent of Table B2.
In some embodiments, -L²-R⁶ is In some embodiments, $L^3$ is —C(O)CH$_2$—,

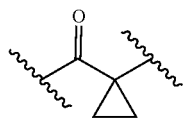 [SMILES: *C(=O)C1(*)CC1]

or —C(O)C(CH$_3$)H—. In some embodiments, $L^3$ is selected from those depicted in the compounds of Table 1, below.

As defined generally above, $R^8$ is a cyclic group selected from a 3-8 membered saturated or partially unsaturated monocyclic carbocyclic ring, a 7-12 membered saturated or partially unsaturated bicyclic carbocyclic ring, phenyl, an 8-10 membered bicyclic aromatic carbocyclic ring, a 3-8 membered saturated or partially unsaturated monocyclic heterocyclic ring (having 1-2 heteroatoms independently selected from nitrogen, oxygen, and sulfur), a 7-12 membered saturated or partially unsaturated bicyclic heterocyclic ring (having 1-4 heteroatoms independently selected from nitrogen, oxygen, and sulfur), a 5-6 membered monocyclic heteroaromatic ring (having 1-4 heteroatoms independently selected from nitrogen, oxygen, and sulfur), and an 8-10 membered bicyclic heteroaromatic ring (having 1-5 heteroatoms independently selected from nitrogen, oxygen, and sulfur), wherein the cyclic group is optionally substituted with one or more instances of $R^9$.

In some embodiments, $R^8$ is a cyclic group selected from phenyl, a 3-8 membered saturated or partially unsaturated monocyclic heterocyclic ring (having 1-2 heteroatoms independently selected from nitrogen, oxygen, and sulfur), a 7-12 membered saturated or partially unsaturated bicyclic heterocyclic ring (having 1-4 heteroatoms independently selected from nitrogen, oxygen, and sulfur), a 5-6 membered monocyclic heteroaromatic ring (having 1-4 heteroatoms independently selected from nitrogen, oxygen, and sulfur), and an 8-10 membered bicyclic heteroaromatic ring (having 1-5 heteroatoms independently selected from nitrogen, oxygen, and sulfur), wherein the cyclic group is optionally substituted with one or more instances of $R^9$. In some embodiments, $R^8$ is an 8-10 membered bicyclic heteroaromatic ring (having 1-5 heteroatoms independently selected from nitrogen, oxygen, and sulfur), optionally substituted with one or more instances of $R^9$. In some embodiments, $R^8$ is a cyclic group selected from indolyl, indazolyl, benzimidazolyl, benzofuranyl, phenyl, pyridinyl, pyrimidinyl, pyridazinyl, pyrazinyl, quinolinyl, isoquinolinyl, pyrazolyl, tetrazolyl, quinoxalinyl, indolizinyl, thiazolyl, oxazolyl, pyrrolyl, imidazo[1,2-a]pyrazinyl, and tetrahydropyranyl wherein the cyclic group is optionally substituted with one or more instances of $R^9$. In some embodiments, $R^8$ is a cyclic group selected from indolyl, indazolyl, benzofuranyl, and benzimidazolyl, wherein the cyclic group is optionally substituted with one or more instances of $R^9$.

In some embodiments, $R^8$ is indolyl optionally substituted with one or more instances of $R^9$. In some embodiments, $R^8$ is indazolyl, optionally substituted with one or more instances of $R^9$. In some embodiments, $R^8$ is benzimidazolyl, optionally substituted with one or more instances of $R^9$. In some embodiments, $R^8$ is benzofuranyl, optionally substituted with one or more instances of $R^9$. In some embodiments, $R^8$ is phenyl, optionally substituted with one or more instances of $R^9$. In some embodiments, $R^8$ is pyridinyl, optionally substituted with one or more instances of $R^9$. In some embodiments, $R^8$ is pyrimidinyl, optionally substituted with one or more instances of $R^9$. In some embodiments, $R^8$ is pyridazinyl, optionally substituted with one or more instances of $R^9$. In some embodiments, $R^8$ is pyrazinyl, optionally substituted with one or more instances of $R^9$. In some embodiments, $R^8$ is quinolinyl, optionally substituted with one or more instances of $R^9$. In some embodiments, $R^8$ is isoquinolinyl, optionally substituted with one or more instances of $R^9$. In some embodiments, $R^8$ is pyrazolyl, optionally substituted with one or more instances of $R^9$. In some embodiments, $R^8$ is tetrazolyl, optionally substituted with one or more instances of $R^9$. In some embodiments, $R^8$ is quinoxalinyl, optionally substituted with one or more instances of $R^9$. In some embodiments, $R^8$ is indolizinyl, optionally substituted with one or more instances of $R^9$. In some embodiments, $R^8$ is thiazolyl, optionally substituted with one or more instances of $R^9$. In some embodiments, $R^8$ is oxazolyl, optionally substituted with one or more instances of $R^9$. In some embodiments, $R^8$ is pyrrolyl, optionally substituted with one or more instances of $R^9$. In some embodiments, $R^8$ is imidazo[1,2-a]pyrazinyl, optionally substituted with one or more instances of $R^9$. In some embodiments, $R^8$ is tetrahydropyranyl, optionally substituted with one or more instances of $R^9$. In some embodiments, $R^8$ is selected from those depicted in the compounds of Table 1, below.

In some embodiments, $R^8$ is substituted with 0, 1 or 2 instances of $R^9$. In some embodiments, $R^8$ is substituted with 1 instance of $R^9$. $R^8$ is substituted with 2 instances of $R^9$. In some embodiments, $R^8$ is unsubstituted.

As defined generally above, each instance of $R^9$ is independently halogen, —CN, —NO$_2$, —OR, —SR, —NR$_2$, —S(O)$_2$R, —S(O)$_2$NR$_2$, —S(O)R, —S(O)NR$_2$, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)C(NR)NR$_2$, —N(R)S(O)$_2$NR$_2$, —N(R)S(O)$_2$R, an optionally substituted C$_{1-6}$ aliphatic group, an optionally substituted C$_{1-6}$ aliphatic-Cy group, or Cy.

In some embodiments, each instance of $R^9$ is independently halogen, —CN, —OR, an optionally substituted C$_{1-6}$ aliphatic group, or Cy. In some embodiments, each instance of $R^9$ is independently halogen, —CN, —OR, or a C$_{1-6}$ aliphatic group. In some embodiments, each instance of $R^9$ is independently fluoro, chloro, bromo, —CN, methyl, ethyl methoxy, hydroxymethyl, cyclopropylmethoxy, 2-methoxyethyl, phenyl or pyridinyl. In some embodiments, each instance of $R^9$ is independently chloro, bromo, —CN, methyl, or methoxy. In some embodiments, each $R^9$ is independently selected from those depicted in the compounds of Table 1, below.

In some embodiments, -L$^3$-R$^8$ is a substituent of Table C1 or Table C2:

TABLE C1

Exemplary -L$^3$—R$^8$ substituents

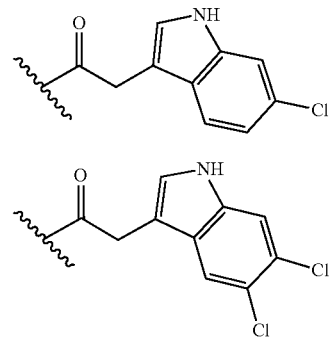

TABLE C1-continued

Exemplary -L³—R⁸ substituents

[Chemical structures of various -L³—R⁸ substituents featuring indole, benzimidazole, and benzofuran moieties with substituents including Cl, F, CN, Me, and other groups]

TABLE C2

Additional Exemplary -L³—R⁸ substituents

[Chemical structures showing additional substituents featuring phenyl, pyridine (2-, 3-, and 4-positions), and pyrazine rings attached via a ketone linker]

TABLE C2-continued

Additional Exemplary -L³—R⁸ substituents

TABLE C2-continued
Additional Exemplary -L³—R⁸ substituents
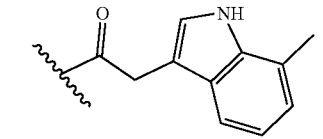 [SMILES: *C(=O)Cc1c[nH]c2c(C)cccc12]
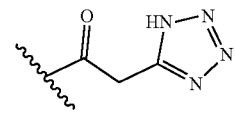
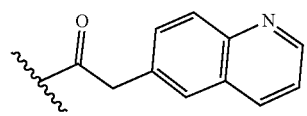 [SMILES: *C(=O)Cc1ccc2ncccc2c1]
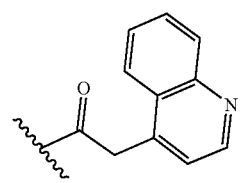 [SMILES: *C(=O)Cc1ccnc2ccccc12]
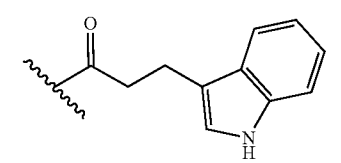 [SMILES: *C(=O)CCc1c[nH]c2ccccc12]
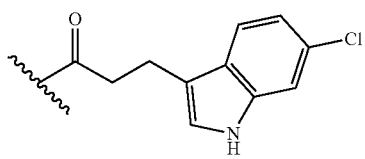 [SMILES: *C(=O)CCc1c[nH]c2cc(Cl)ccc12]
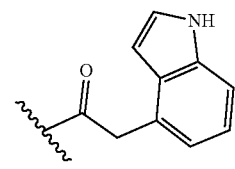 [SMILES: *C(=O)Cc1cccc2[nH]ccc12]
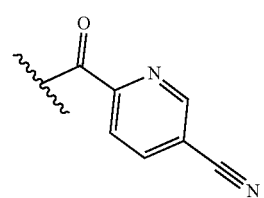 [SMILES: *C(=O)c1ccc(C#N)cn1]
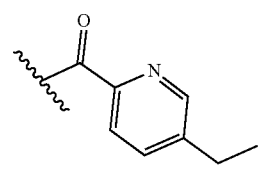 [SMILES: *C(=O)c1ccc(CC)cn1]
TABLE C2-continued
Additional Exemplary -L³—R⁸ substituents
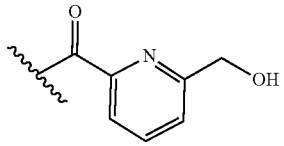 [SMILES: *C(=O)c1cccc(CO)n1]
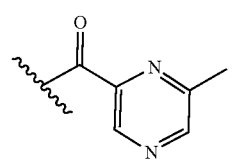 [SMILES: *C(=O)c1cncc(C)n1]
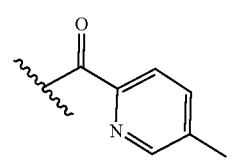 [SMILES: *C(=O)c1ccc(C)cn1]
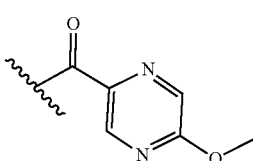
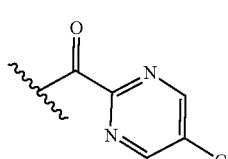
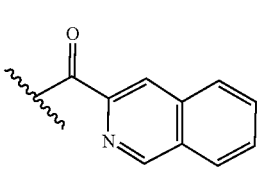 [SMILES: *C(=O)c1cc2ccccc2cn1]
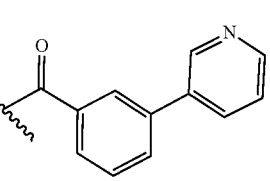
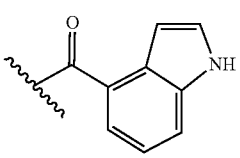 [SMILES: *C(=O)c1cccc2[nH]ccc12]
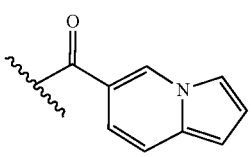 [SMILES: *C(=O)c1ccc2cccn2c1]

TABLE C2-continued
Additional Exemplary -L³—R⁸ substituents
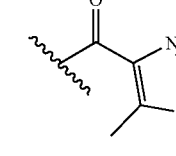
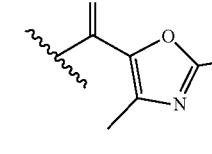
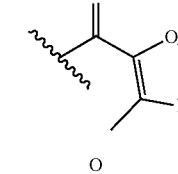
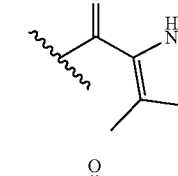
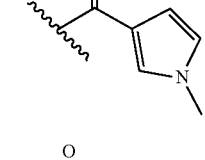
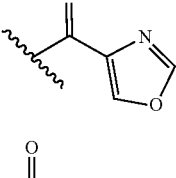
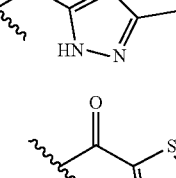
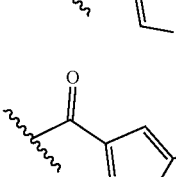
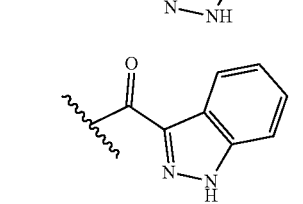

TABLE C2-continued

Additional Exemplary -L³—R⁸ substituents

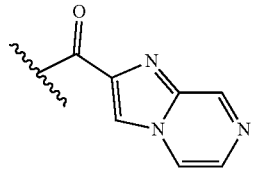 [SMILES: *C(=O)c1cn2ccncc2n1]
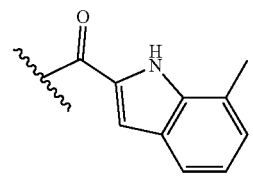 [SMILES: *C(=O)c1cc2cccc(C)c2[nH]1]
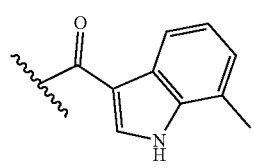 [SMILES: *C(=O)c1c[nH]c2c(C)cccc12]
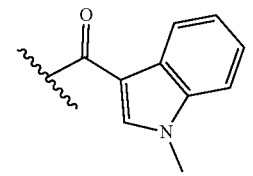 [SMILES: *C(=O)c1cn(C)c2ccccc12]
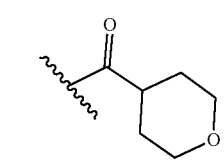 [SMILES: *C(=O)C1CCOCC1]
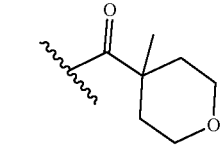 [SMILES: *C(=O)C1(C)CCOCC1]
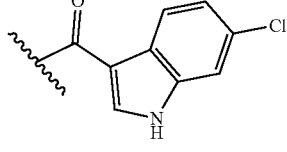
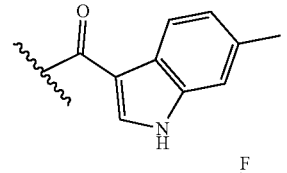
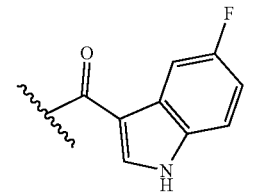 [SMILES: *C(=O)c1c[nH]c2ccc(F)cc12]

In some embodiments, -L³-R⁸ is a substituent of Table C1.
In some embodiments, -L³-R⁸ is a substituent of Table C2.
In some embodiments, -L³-R⁸ is

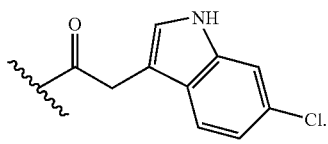 [SMILES: *C(=O)Cc1c[nH]c2cc(Cl)ccc12]

In some embodiments, each instance of Cy is independently phenyl or a 5-6 membered monocyclic heteroaromatic ring (having 1-4 heteroatoms independently selected from nitrogen, oxygen, and sulfur).

In some embodiments:

$R^A$ is

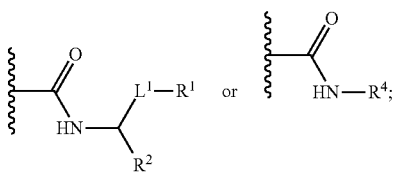

$L^1$ is 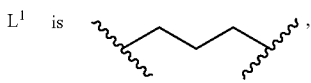,

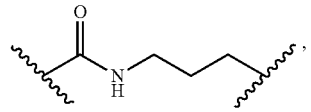,

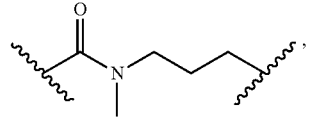,

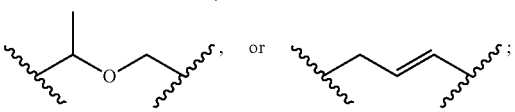;

$R^1$ is a $C_{1-4}$ aliphatic group or an optionally substituted cyclic group selected from a 3-8 membered saturated or partially unsaturated monocyclic carbocyclic ring, phenyl, a 3-8 membered saturated or partially unsaturated monocyclic heterocyclic ring (having 1-2 heteroatoms independently selected from nitrogen, oxygen, and sulfur), a 5-6 membered monocyclic heteroaromatic ring (having 1-4 heteroatoms independently selected from nitrogen, oxygen, and sulfur), and an 8-10 membered bicyclic heteroaromatic ring (having 1-5 heteroatoms independently selected from nitrogen, oxygen, and sulfur);

$R^2$ is hydrogen, methyl, —C(O)NHCH₃, —C(O)NH₂, —C(O)OCH₃, —C(O)OH, or an optionally substituted 5-6 membered monocyclic heteroaromatic ring (having 1-4 heteroatoms independently selected from nitrogen, oxygen, and sulfur);

R⁴ is a cyclic group selected from a 3-8 membered saturated or partially unsaturated monocyclic heterocyclic ring (having 1-2 heteroatoms independently selected from nitrogen, oxygen, and sulfur), and a 5-6 membered monocyclic heteroaromatic ring (having 1-4 heteroatoms independently selected from nitrogen, oxygen, and sulfur), wherein the cyclic group is optionally substituted with one or more instances of R⁵;

each R⁵ is independently —OR, —C(O)R, an optionally substituted $C_{1-6}$ aliphatic group, or an optionally substituted —$C_{1-6}$ aliphatic-Cy group;

L² is —C(O)—;

R⁶ is a cyclic group selected from phenyl, an 8-10 membered bicyclic aromatic carbocyclic ring, a 5-6 membered monocyclic heteroaromatic ring (having 1-4 heteroatoms independently selected from nitrogen, oxygen, and sulfur), and an 8-10 membered bicyclic heteroaromatic ring (having 1-5 heteroatoms independently selected from nitrogen, oxygen, and sulfur), wherein the cyclic group is optionally substituted with one or more instances of R⁷;

each R⁷ is independently —OR, an optionally substituted $C_{1-6}$ aliphatic group, Cy or two instances of R⁷ on the same carbon atom are taken together to form an oxo group;

L³ is —C(O)CH₂—,

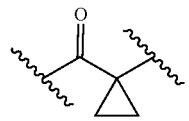 [SMILES: *C(=O)C1(*)CC1]

or —C(O)C(CH₃)H—;

R⁸ is an 8-10 membered bicyclic heteroaromatic ring (having 1-5 heteroatoms independently selected from nitrogen, oxygen, and sulfur), optionally substituted with one or more instances of R⁹;

each instance of R⁹ is independently halogen, —CN, —OR, or a $C_{1-6}$ aliphatic group; and each instance of Cy is independently phenyl or a 5-6 membered monocyclic heteroaromatic ring (having 1-4 heteroatoms independently selected from nitrogen, oxygen, and sulfur).

In some embodiments, the present disclosure provides a compound of Formula I, which is a compound of Formula II:

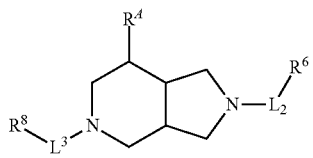

or a pharmaceutically acceptable salt thereof, wherein R⁴, L², R⁶, L³ and R⁸, and their constituent groups, are each as defined and described herein. In some embodiments, R⁴ is a substituent from Table A1. In some embodiments, -L²-R⁶ is a substituent from Table B1. In some embodiments, -L³-R⁸ is a substituent from Table C1. In some embodiments, R⁴ is a substituent from Table A1, and -L²-R⁶ is a substituent from Table B1. In some embodiments, R⁴ is a substituent from Table A1, and -L³-R⁸ is a substituent from Table C1. In some embodiments, -L²-R⁶ is a substituent from Table B1, and -L³-R⁸ is a substituent from Table C1. And in some embodiments, R⁴ is a substituent from Table A1, -L²-R⁶ is a substituent from Table B1, and -L³-R⁸ is a substituent from Table C1. In some embodiments:

R⁴ is

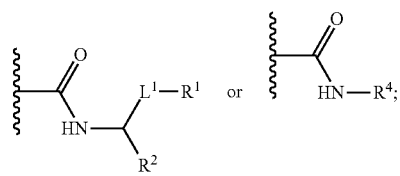

L¹ is

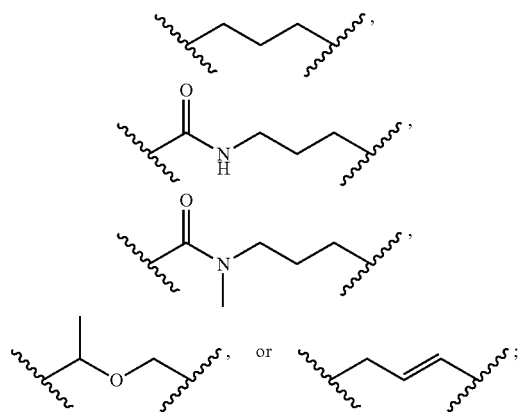

R¹ is a $C_{1-4}$ aliphatic group or an optionally substituted cyclic group selected from a 3-8 membered saturated or partially unsaturated monocyclic carbocyclic ring, phenyl, a 3-8 membered saturated or partially unsaturated monocyclic heterocyclic ring (having 1-2 heteroatoms independently selected from nitrogen, oxygen, and sulfur), a 5-6 membered monocyclic heteroaromatic ring (having 1-4 heteroatoms independently selected from nitrogen, oxygen, and sulfur), and an 8-10 membered bicyclic heteroaromatic ring (having 1-5 heteroatoms independently selected from nitrogen, oxygen, and sulfur);

R² is hydrogen, methyl, —C(O)NHCH₃, —C(O)NH₂, —C(O)OCH₃, —C(O)OH, or a 5-6 membered monocyclic heteroaromatic ring (having 1-4 heteroatoms independently selected from nitrogen, oxygen, and sulfur);

R⁴ is a 3-8 membered saturated or partially unsaturated monocyclic heterocyclic ring (having 1-2 heteroatoms independently selected from nitrogen, oxygen, and sulfur), optionally substituted with one or more instances of R⁵;

each R⁵ is independently —OR, —C(O)R, an optionally substituted $C_{1-6}$ aliphatic group, or an optionally substituted —$C_{1-6}$ aliphatic-Cy group;

L² is —C(O)—;

R⁶ is a cyclic group selected from phenyl, an 8-10 membered bicyclic aromatic carbocyclic ring, a 5-6 membered monocyclic heteroaromatic ring (having 1-4 heteroatoms independently selected from nitrogen, oxygen, and sulfur), and an 8-10 membered bicyclic heteroaromatic ring (having 1-5 heteroatoms independently selected from nitrogen, oxygen, and sulfur), wherein the cyclic group is optionally substituted with one or more instances of $R^7$;

each $R^7$ is independently —OR, an optionally substituted $C_{1-6}$ aliphatic group, Cy or two instances of $R^7$ on the same carbon atom are taken together to form an oxo group;

$L^3$ is —C(O)CH$_2$—,

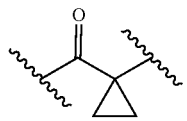 [SMILES: *C(=O)C1(*)CC1]

or —C(O)C(CH$_3$)H—;

$R^8$ is an 8-10 membered bicyclic heteroaromatic ring (having 1-5 heteroatoms independently selected from nitrogen, oxygen, and sulfur), optionally substituted with one or more instances of $R^9$;

each instance of $R^9$ is independently halogen, —CN, —OR, or a $C_{1-6}$ aliphatic group; and each instance of Cy is independently phenyl or a 5-6 membered monocyclic heteroaromatic ring (having 1-4 heteroatoms independently selected from nitrogen, oxygen, and sulfur).

In some embodiments, the present disclosure provides a compound of Formula I, which is a compound of Formula III:

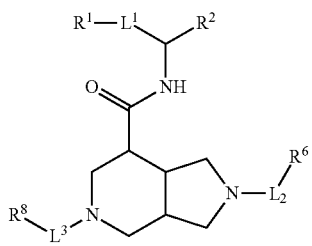

or a pharmaceutically acceptable salt thereof, wherein $R^1$, $R^2$, $L^1$, $L^2$, $R^6$, $L^3$ and $R^8$, and their constituent groups, are each as defined and described herein. In some embodiments, -$L^2$-$R^6$ is a substituent from Table B1. In some embodiments, -$L^3$-$R^8$ is a substituent from Table C1. In some embodiments, -$L^2$-$R^6$ is a substituent from Table B1, and -$L^3$-$R^8$ is a substituent from Table C1. In some embodiments, $R^1$ is optionally substituted phenyl. In some embodiments, $R^1$ is optionally substituted cyclohexyl. In some embodiments, $L^1$ is

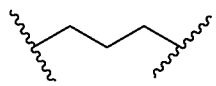

In some embodiments, $L^1$ is

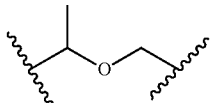

In some embodiments, $R^2$ is —C(O)NHCH$_3$. In some embodiments, $L^2$ is —C(O)—. In some embodiments, $R^6$ is phenyl optionally substituted with one or more instances of $R^7$. In some embodiments, $R^6$ is pyrazolyl optionally substituted with one or more instances of $R^7$. In some embodiments, $L^3$ is —C(O)CH$_2$—. In some embodiments, $L^3$ is —C(O)C(CH$_3$)H—. In some embodiments, $R^8$ is a cyclic group selected from indolyl, indazolyl, benzofuranyl, and benzimidazolyl, wherein the cyclic group is optionally substituted with one or more instances of $R^9$. In some embodiments, $R^8$ is indolyl optionally substituted with one or more instances of $R^9$.

In some embodiments, the present disclosure provides a compound of Formula I, which is a compound of Formula IV:

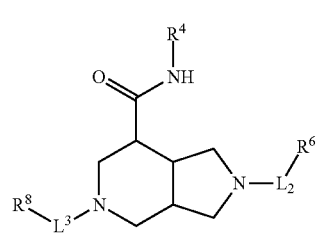

or a pharmaceutically acceptable salt thereof, wherein $R^4$, $L^2$, $R^6$, $L^3$ and $R^8$, and their constituent groups, are each as defined and described herein. In some embodiments, -$L^2$-$R^6$ is a substituent from Table B1. In some embodiments, -$L^3$-$R^8$ is a substituent from Table C1. In some embodiments, -$L^2$-$R^6$ is a substituent from Table B1, and -$L^3$-$R^8$ is a substituent from Table C1. In some embodiments, $R^4$ is pyridinyl, optionally substituted with one or more instances of $R^5$. In some embodiments, $R^4$ is piperidinyl, optionally substituted with one or more instances of $R^5$. In some embodiments, $L^2$ is —C(O)—. In some embodiments, $R^6$ is phenyl optionally substituted with one or more instances of $R^7$. In some embodiments, $R^6$ is pyrazolyl optionally substituted with one or more instances of $R^7$. In some embodiments, $L^3$ is —C(O)CH$_2$—. In some embodiments, $L^3$ is —C(O)C(CH$_3$)H—. In some embodiments, $R^8$ is a cyclic group selected from indolyl, indazolyl, benzofuranyl, and benzimidazolyl, wherein the cyclic group is optionally substituted with one or more instances of $R^9$. In some embodiments, $R^8$ is indolyl optionally substituted with one or more instances of $R^9$.

In some embodiments, the present disclosure provides a compound of Formula I, which is a compound of Formula V:

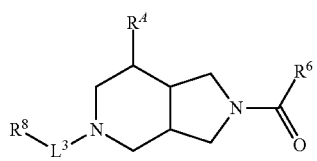

or a pharmaceutically acceptable salt thereof, wherein $R^4$, $R^6$, $L^3$ and $R^8$, and their constituent groups, are each as defined and described herein. In some embodiments, $R^4$ is a substituent from Table A1. In some embodiments, $-L^3-R^8$ is a substituent from Table C1. In some embodiments, $R^4$ is a substituent from Table A1, and $-L^3-R^8$ is a substituent from Table C1. In some embodiments, $R^6$ is phenyl optionally substituted with one or more instances of $R^7$. In some embodiments, $R^6$ is pyrazolyl optionally substituted with one or more instances of $R^7$.

In some embodiments, the present disclosure provides a compound of Formula I, which is a compound of Formula Va or Vb:

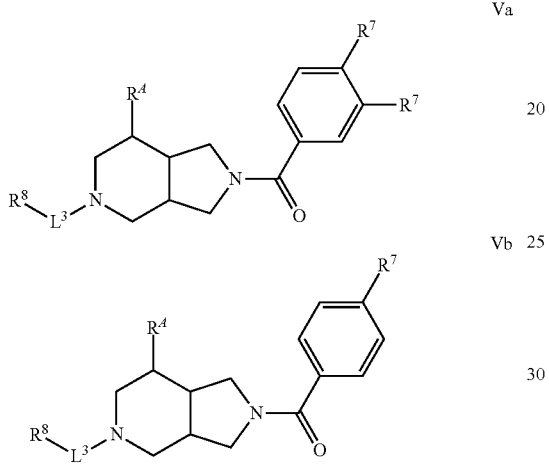

Va

Vb or a pharmaceutically acceptable salt thereof, wherein $R^4$, $R^7$, $L^3$ and $R^8$, and their constituent groups, are each as defined and described herein. In some embodiments, $R^4$ is a substituent from Table A1. In some embodiments, $-L^3-R^8$ is a substituent from Table C1. In some embodiments, $R^4$ is a substituent from Table A1, and $-L^3-R^8$ is a substituent from Table C1. In some embodiments, each instance of $R^7$ is —OR or a halogen. In some embodiments, each instance of $R^7$ is —OR. In some embodiments, $L^3$ is —C(O)CH$_2$—. In some embodiments, $L^3$ is —C(O)C(CH$_3$)H—. In some embodiments, $R^8$ is a cyclic group selected from indolyl, indazolyl, benzofuranyl, and benzimidazolyl, wherein the cyclic group is optionally substituted with one or more instances of $R^9$. In some embodiments, $R^8$ is indolyl optionally substituted with one or more instances of $R^9$.

In some embodiments, the present disclosure provides a compound of Formula I, which is a compound of Formula VI:

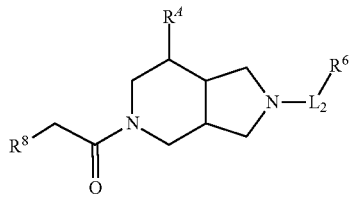

VI or a pharmaceutically acceptable salt thereof, wherein $R^4$, $L^2$, $R^6$, and $R^8$, and their constituent groups, are each as defined and described herein. In some embodiments, $R^4$ is a substituent from Table A1. In some embodiments, $-L^2-R^6$ is a substituent from Table B1. In some embodiments, $R^4$ is a substituent from Table A1, and $-L^2-R^6$ is a substituent from Table B1. In some embodiments, $R^8$ is a cyclic group selected from indolyl, indazolyl, benzofuranyl, and benzimidazolyl, wherein the cyclic group is optionally substituted with one or more instances of $R^9$. In some embodiments, $R^8$ is indolyl optionally substituted with one or more instances of $R^9$.

In some embodiments, the present disclosure provides a compound of Formula I, which is a compound of Formula VIa:

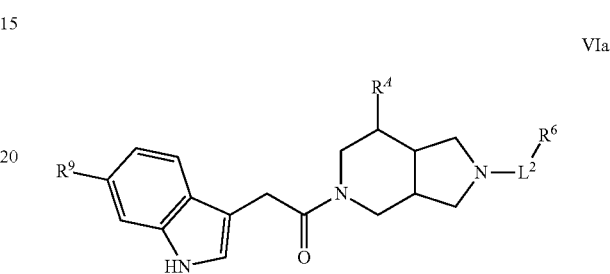

VIa or a pharmaceutically acceptable salt thereof, wherein $R^4$, $L^2$, $R^6$, and $R^9$, and their constituent groups, are each as defined and described herein. In some embodiments, $R^4$ is a substituent from Table A1. In some embodiments, $-L^2-R^6$ is a substituent from Table B1. In some embodiments, $R^4$ is a substituent from Table A1, and $-L^2-R^6$ is a substituent from Table B1. In some embodiments, $R^9$ is a halogen, methyl or —CN. In some embodiments, $R^9$ is chloro.

In some embodiments, the present disclosure provides a compound of Formula I, which is a compound of Formula VIIa:

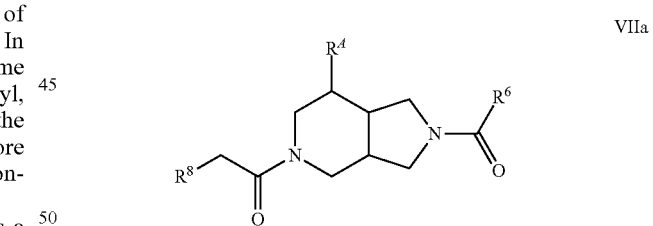

VIIa or a pharmaceutically acceptable salt thereof, wherein $R^4$, $R^6$, and $R^8$, and their constituent groups, are each as defined and described herein. In some embodiments, $R^4$ is a substituent from Table A1. In some embodiments, $R^6$ is phenyl optionally substituted with one or more instances of $R^7$. In some embodiments, $R^6$ is pyrazolyl optionally substituted with one or more instances of $R^7$. In some embodiments, $R^8$ is a cyclic group selected from indolyl, indazolyl, benzofuranyl, and benzimidazolyl, wherein the cyclic group is optionally substituted with one or more instances of $R^9$. In some embodiments, $R^8$ is indolyl optionally substituted with one or more instances of $R^9$.

In some embodiments, the present disclosure provides a compound of Formula I, which is a compound of Formula VIIb:

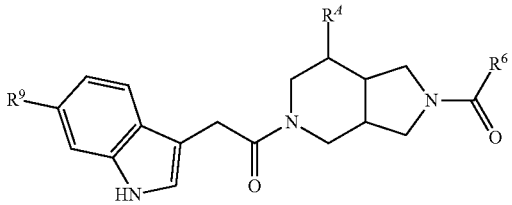

VIIb or a pharmaceutically acceptable salt thereof, wherein $R^4$, $R^6$, and $R^9$, and their constituent groups, are each as defined and described herein. In some embodiments, $R^4$ is a substituent from Table A1. In some embodiments, $R^6$ is phenyl optionally substituted with one or more instances of $R^7$. In some embodiments, $R^6$ is pyrazolyl optionally substituted with one or more instances of $R^7$. In some embodiments, $R^9$ is a halogen, methyl or —CN. In some embodiments, $R^9$ is chloro.

In some embodiments, the present disclosure provides a compound of Formula I, which is a compound of Formula VIIc:

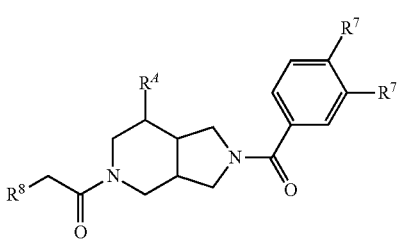

VIIc

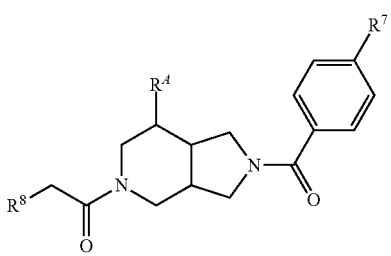

VIId or a pharmaceutically acceptable salt thereof, wherein $R^4$, $R^7$, and $R^8$, and their constituent groups, are each as defined and described herein. In some embodiments, $R^4$ is a substituent from Table A1. In some embodiments, each instance of $R^7$ is —OR or a halogen. In some embodiments, each instance of $R^7$ is —OR. In some embodiments, $L^3$ is —C(O)CH$_2$—. In some embodiments, $L^3$ is —C(O)C(CH$_3$)H—. In some embodiments, $R^8$ is a cyclic group selected from indolyl, indazolyl, benzofuranyl, and benzimidazolyl, wherein the cyclic group is optionally substituted with one or more instances of $R^9$. In some embodiments, $R^8$ is indolyl optionally substituted with one or more instances of $R^9$.

In some embodiments, the present disclosure provides a compound of Formula I, which is a compound of Formula VIIe or VIIf:

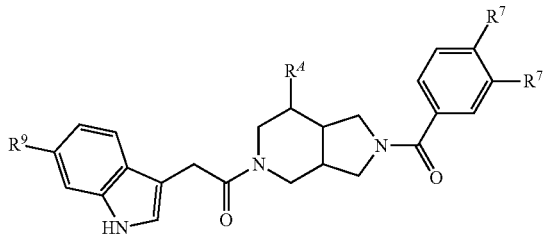

VIIe

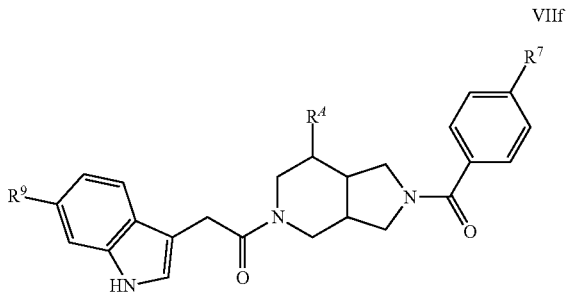

VIIf or a pharmaceutically acceptable salt thereof, wherein $R^4$, $R^7$, and $R^9$, and their constituent groups, are each as defined and described herein. In some embodiments, $R^4$ is a substituent from Table A1. In some embodiments, each instance of $R^7$ is —OR or a halogen. In some embodiments, each instance of $R^7$ is —OR. In some embodiments, $R^9$ is a halogen, methyl or —CN. In some embodiments, $R^9$ is chloro.

In some embodiments, the present disclosure provides a compound of Formula I, which is a compound of Formula VIIIa or VIIIb

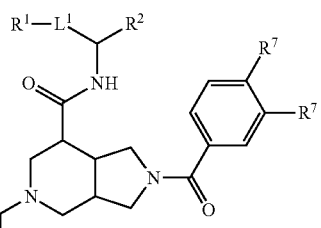

VIIIa

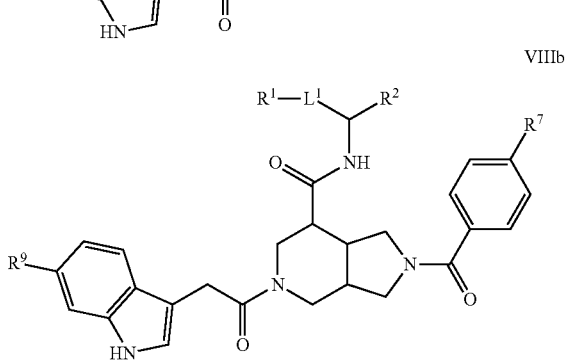

VIIIb or a pharmaceutically acceptable salt thereof, wherein $R^1$, $R^2$, $R^7$, and $R^9$, and their constituent groups, are each as defined and described herein. In some embodiments, $R^1$ is optionally substituted phenyl. In some embodiments, $R^1$ is optionally substituted cyclohexyl. In some embodiments, $L^1$ is

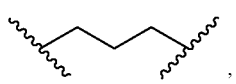 [SMILES: *CCC*]

In some embodiments, $L^1$ is

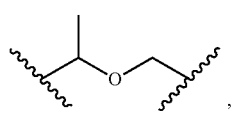 [SMILES: *COC(*)C]

In some embodiments, $R^2$ is —C(O)NHCH$_3$. In some embodiments, each instance of $R^7$ is —OR or a halogen. In some embodiments, each instance of $R^7$ is —OR. In some embodiments, $R^9$ is a halogen, methyl or —CN. In some embodiments, $R^9$ is chloro.

In some embodiments, the present disclosure provides a compound of Formula I, which is a compound of Formula VIIIc or VIIId:

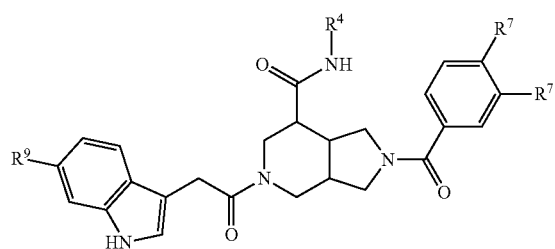

VIIIc

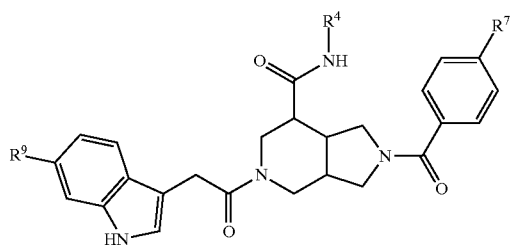

VIIId or a pharmaceutically acceptable salt thereof, wherein $R^4$, $R^7$, and $R^9$, and their constituent groups, are each as defined and described herein. In some embodiments, $R^4$ is pyridinyl, optionally substituted with one or more instances of $R^5$. In some embodiments, $R^4$ is piperidinyl, optionally substituted with one or more instances of $R^5$. In some embodiments, each instance of $R^7$ is —OR or a halogen. In some embodiments, each instance of $R^7$ is —OR. In some embodiments, $R^9$ is a halogen, methyl or —CN. In some embodiments, $R^9$ is chloro.

Exemplary compounds of the present disclosure are set forth in Table 1, below.

TABLE 1

| | Exemplary Compounds |
|---|---|
| # | Structure |
| I-1 |  |

TABLE 1-continued
Exemplary Compounds
| # | Structure |
|---|---|
| I-2 | 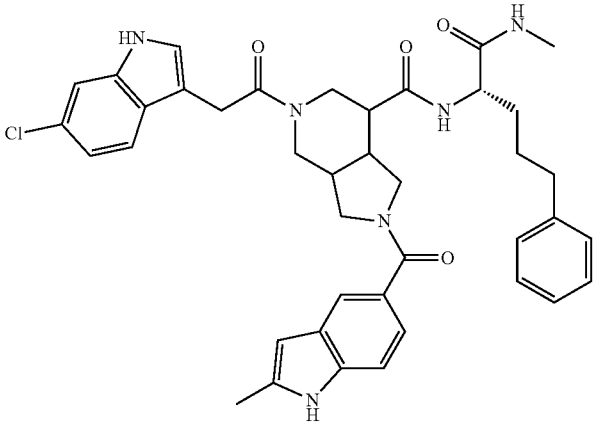 [SMILES: CNC(=O)[C@H](CCCc1ccccc1)NC(=O)C1CN(C(=O)Cc2c[nH]c3cc(Cl)ccc23)CC2CN(C(=O)c3ccc4[nH]c(C)cc4c3)CC21] |
| I-3 | 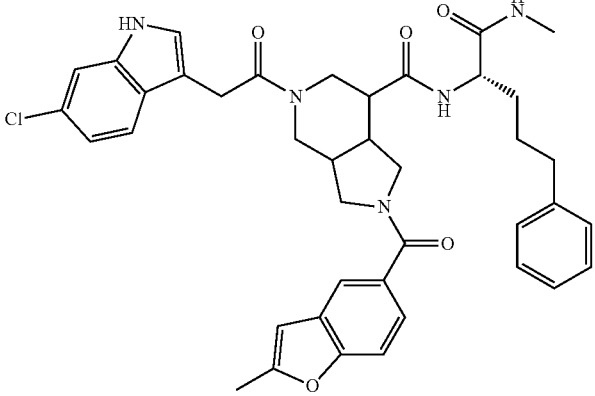 |
| I-4 | 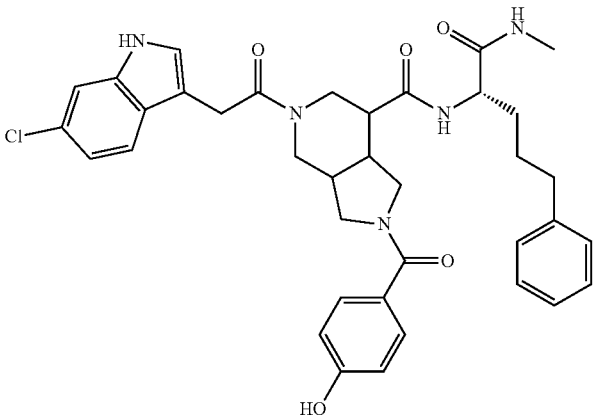 [SMILES: CNC(=O)[C@H](CCCc1ccccc1)NC(=O)C1CN(C(=O)Cc2c[nH]c3cc(Cl)ccc23)CC2CN(C(=O)c3ccc(O)cc3)CC21] |

TABLE 1-continued

Exemplary Compounds

| # | Structure |
|---|---|
| I-5 | 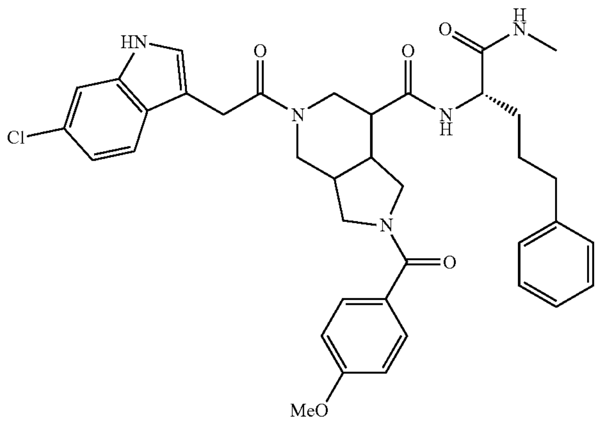 [SMILES: CNC(=O)[C@H](CCCc1ccccc1)NC(=O)C1CN(C(=O)Cc2c[nH]c3cc(Cl)ccc23)CC2CN(C(=O)c3ccc(OC)cc3)CC21] |
| I-6 | 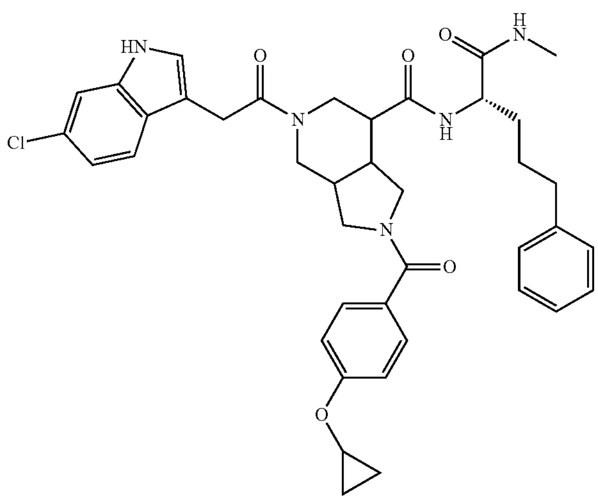 [SMILES: CNC(=O)[C@H](CCCc1ccccc1)NC(=O)C1CN(C(=O)Cc2c[nH]c3cc(Cl)ccc23)CC2CN(C(=O)c3ccc(OC4CC4)cc3)CC21] |
| I-7 | 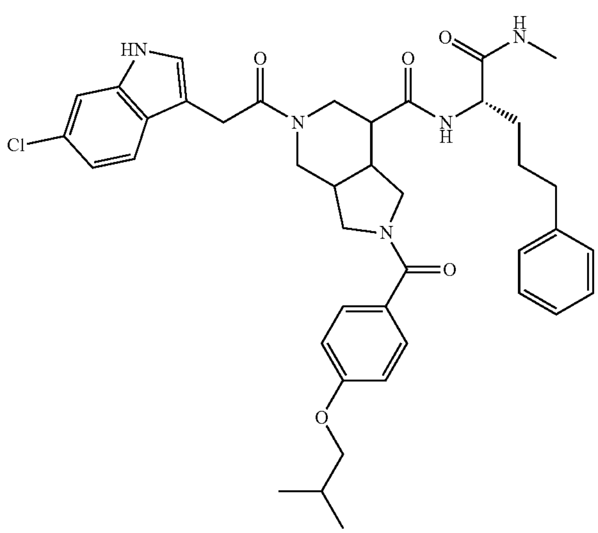 [SMILES: CNC(=O)[C@H](CCCc1ccccc1)NC(=O)C1CN(C(=O)Cc2c[nH]c3cc(Cl)ccc23)CC2CN(C(=O)c3ccc(OCC(C)C)cc3)CC21] |

TABLE 1-continued

Exemplary Compounds

| # | Structure |
|---|---|
| I-8 | 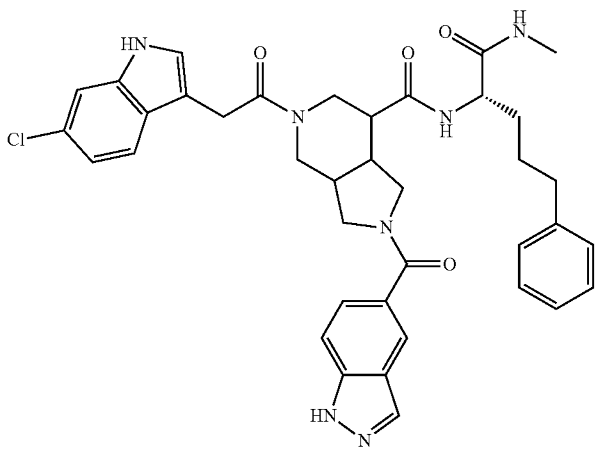 [SMILES: CNC(=O)[C@H](CCCc1ccccc1)NC(=O)C1CN(C(=O)Cc2c[nH]c3cc(Cl)ccc23)CC2CN(C(=O)c3ccc4[nH]ncc4c3)CC21] |
| I-9 | 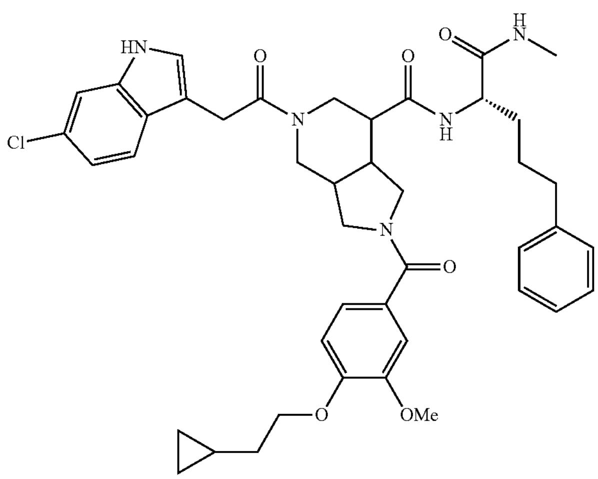 [SMILES: CNC(=O)[C@H](CCCc1ccccc1)NC(=O)C1CN(C(=O)Cc2c[nH]c3cc(Cl)ccc23)CC2CN(C(=O)c3ccc(OCCC4CC4)c(OC)c3)CC21] |
| I-10 | 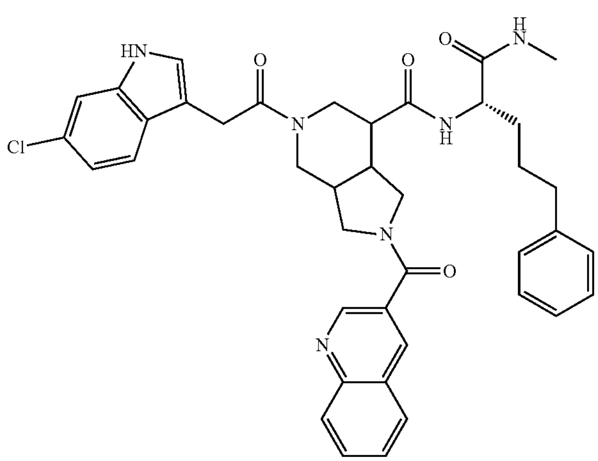 [SMILES: CNC(=O)[C@H](CCCc1ccccc1)NC(=O)C1CN(C(=O)Cc2c[nH]c3cc(Cl)ccc23)CC2CN(C(=O)c3cnc4ccccc4c3)CC21] |

TABLE 1-continued

| Exemplary Compounds | |
|---|---|
| # | Structure |
| I-11 | |
| I-12 | |
| I-13 | |

TABLE 1-continued

Exemplary Compounds

| # | Structure |
|---|---|
| I-14 | 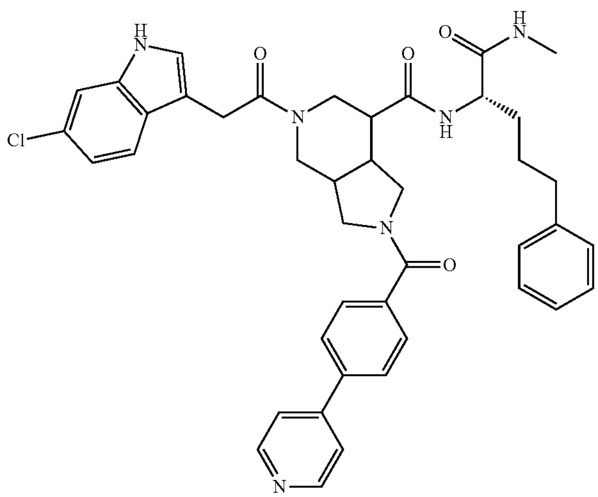 |
| I-15 | 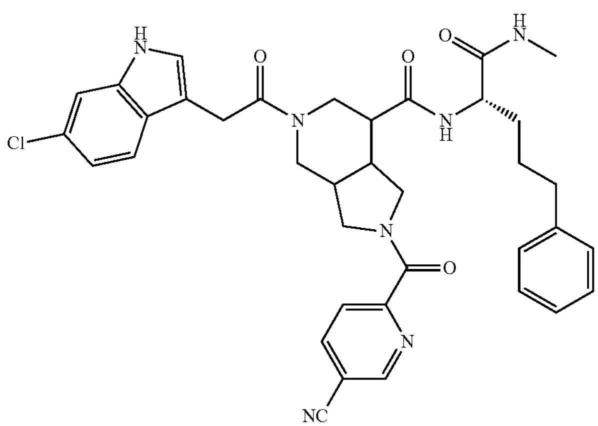 [SMILES: CNC(=O)[C@H](CCCc1ccccc1)NC(=O)C1CN(C(=O)Cc2c[nH]c3cc(Cl)ccc23)CC2CN(C(=O)c3ccc(C#N)cn3)CC21] |
| I-16 | 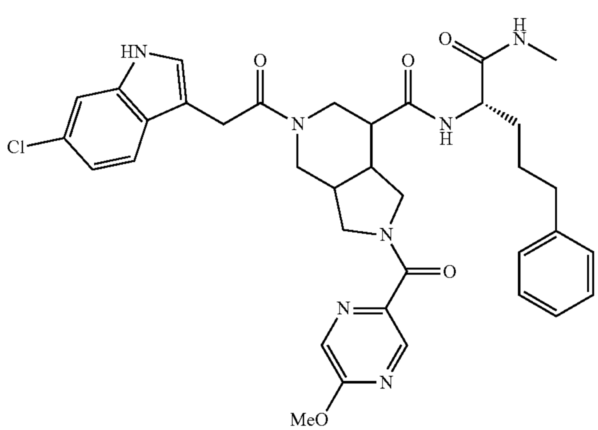 [SMILES: CNC(=O)[C@H](CCCc1ccccc1)NC(=O)C1CN(C(=O)Cc2c[nH]c3cc(Cl)ccc23)CC2CN(C(=O)c3cnc(OC)cn3)CC21] |

TABLE 1-continued

Exemplary Compounds

| # | Structure |
|---|---|
| I-17 | 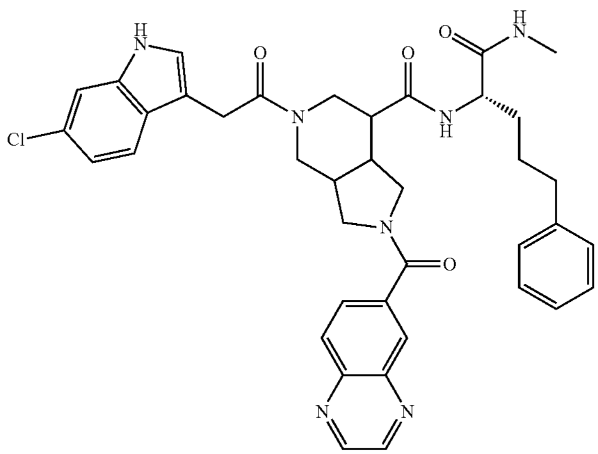 [SMILES: CNC(=O)[C@H](CCCc1ccccc1)NC(=O)C1CN(C(=O)Cc2c[nH]c3cc(Cl)ccc23)CC2CN(C(=O)c3ccc4nccnc4c3)CC21] |
| I-18 | 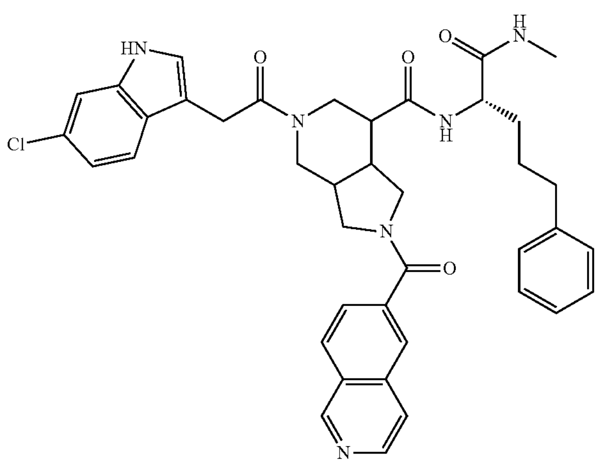 [SMILES: CNC(=O)[C@H](CCCc1ccccc1)NC(=O)C1CN(C(=O)Cc2c[nH]c3cc(Cl)ccc23)CC2CN(C(=O)c3ccc4cnccc4c3)CC21] |
| I-19 | 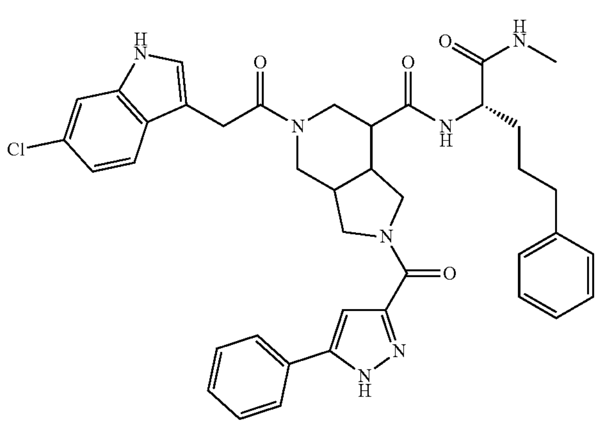 [SMILES: CNC(=O)[C@H](CCCc1ccccc1)NC(=O)C1CN(C(=O)Cc2c[nH]c3cc(Cl)ccc23)CC2CN(C(=O)c3cc(-c4ccccc4)[nH]n3)CC21] |

TABLE 1-continued

Exemplary Compounds

| # | Structure |
|---|---|
| I-20 | 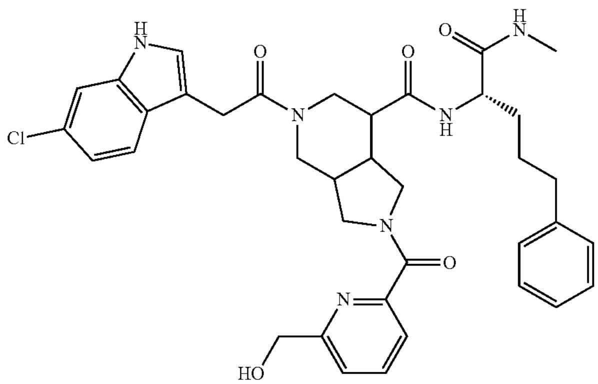 [SMILES: CNC(=O)[C@H](CCCc1ccccc1)NC(=O)C1CN(C(=O)Cc2c[nH]c3cc(Cl)ccc23)CC2CN(C(=O)c3cccc(CO)n3)CC21] |
| I-21 | 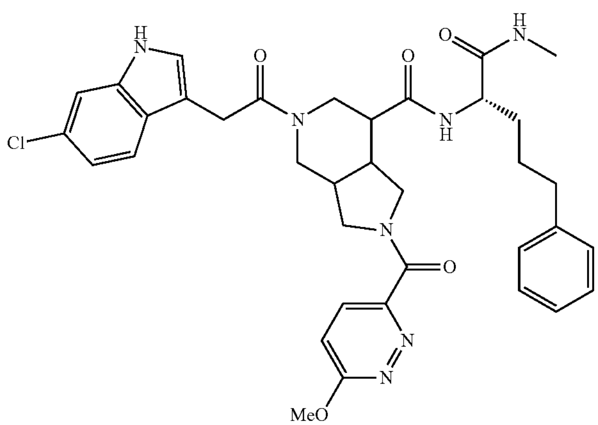 |
| I-22 | 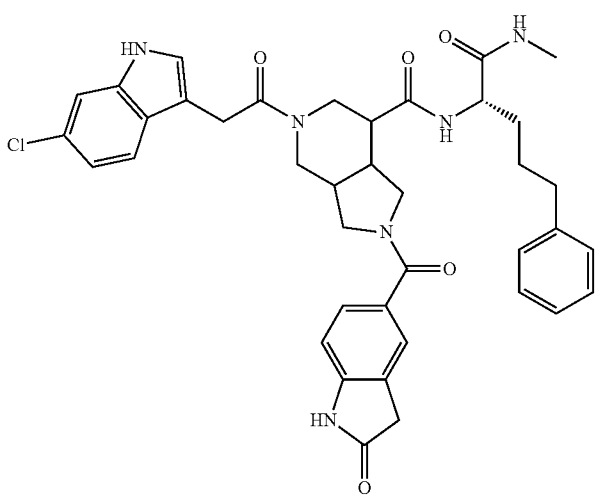 [SMILES: CNC(=O)[C@H](CCCc1ccccc1)NC(=O)C1CN(C(=O)Cc2c[nH]c3cc(Cl)ccc23)CC2CN(C(=O)c3ccc4c(c3)CC(=O)N4)CC21] |

First eluting diastereomer

TABLE 1-continued
Exemplary Compounds
| # | Structure |
|---|---|
| I-23 | 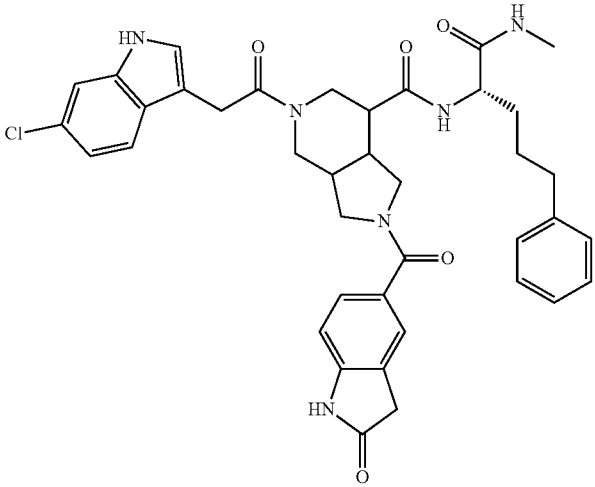 Second eluting diastereomer |
| I-24 | 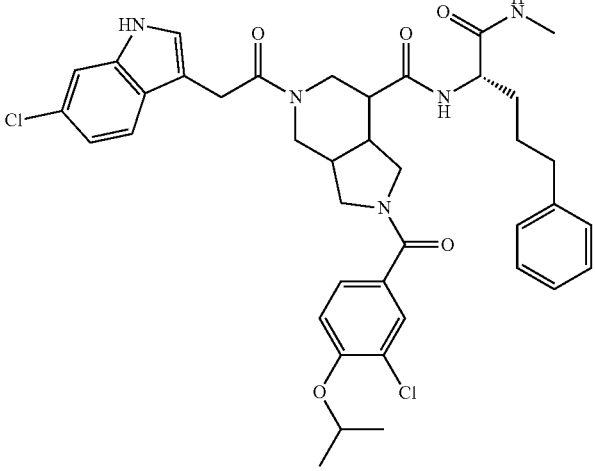 |
| I-25 | 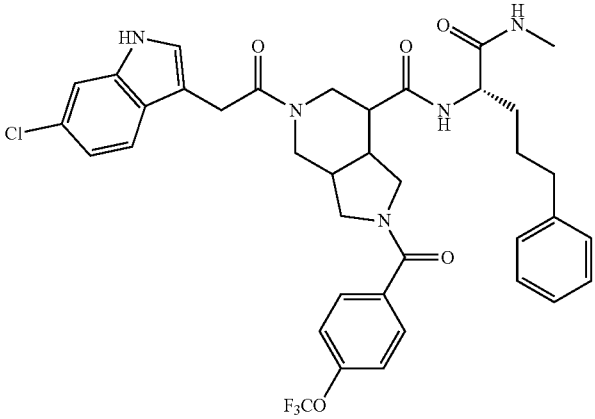 [SMILES: CNC(=O)[C@H](CCCc1ccccc1)NC(=O)C1CN(C(=O)Cc2c[nH]c3cc(Cl)ccc23)CC2CN(C(=O)c3ccc(OC(F)(F)F)cc3)CC21] |

TABLE 1-continued

Exemplary Compounds

| # | Structure |
|---|---|
| I-26 | 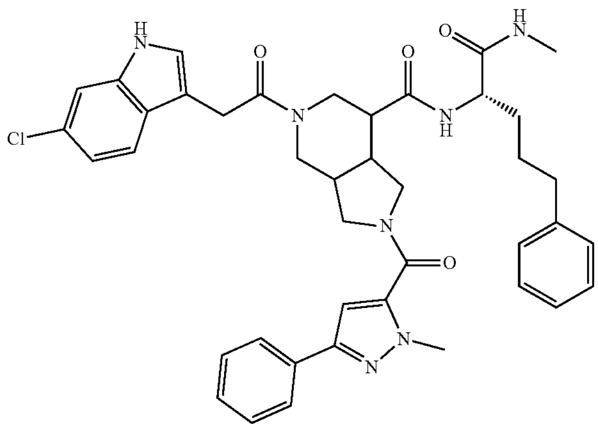 [SMILES: CNC(=O)[C@H](CCCc1ccccc1)NC(=O)C1CN(C(=O)Cc2c[nH]c3cc(Cl)ccc23)CC2CN(C(=O)c3cc(-c4ccccc4)nn3C)CC21] |
| I-27 | 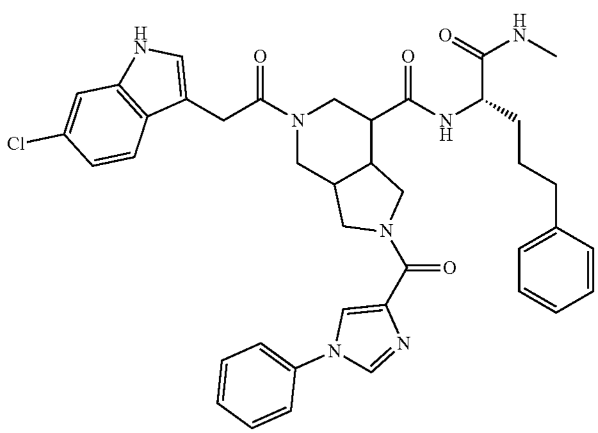 [SMILES: CNC(=O)[C@H](CCCc1ccccc1)NC(=O)C1CN(C(=O)Cc2c[nH]c3cc(Cl)ccc23)CC2CN(C(=O)c3cn(-c4ccccc4)cn3)CC21] |
| I-28 | 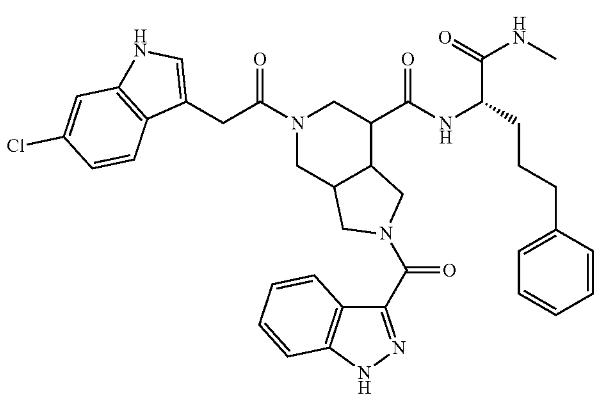 [SMILES: CNC(=O)[C@H](CCCc1ccccc1)NC(=O)C1CN(C(=O)Cc2c[nH]c3cc(Cl)ccc23)CC2CN(C(=O)c3n[nH]c4ccccc34)CC21] |

TABLE 1-continued
Exemplary Compounds
| # | Structure |
|---|---|
| I-29 | 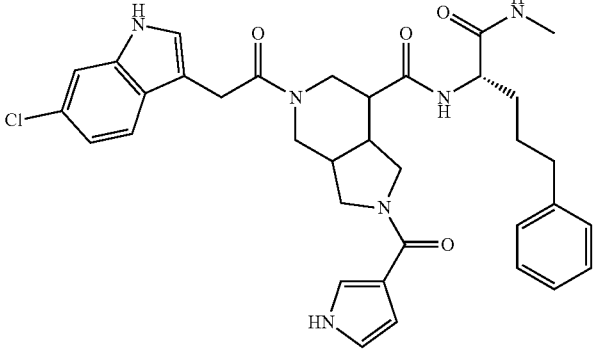 |
| I-30 | 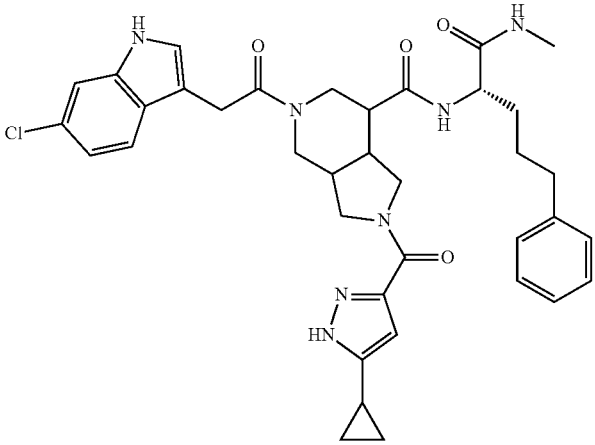 [SMILES: CNC(=O)[C@H](CCCc1ccccc1)NC(=O)C1CN(C(=O)Cc2c[nH]c3cc(Cl)ccc23)CC2CN(C(=O)c3cc(C4CC4)[nH]n3)CC21] |
| I-31 | 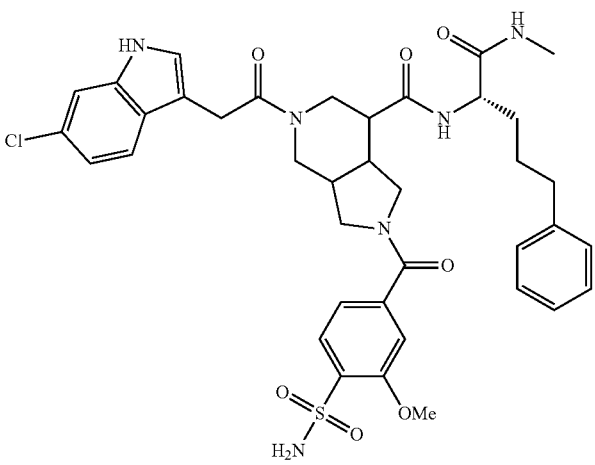 [SMILES: CNC(=O)[C@H](CCCc1ccccc1)NC(=O)C1CN(C(=O)Cc2c[nH]c3cc(Cl)ccc23)CC2CN(C(=O)c3ccc(S(N)(=O)=O)c(OC)c3)CC21] |

TABLE 1-continued

Exemplary Compounds

| # | Structure |
|---|---|
| I-32 | 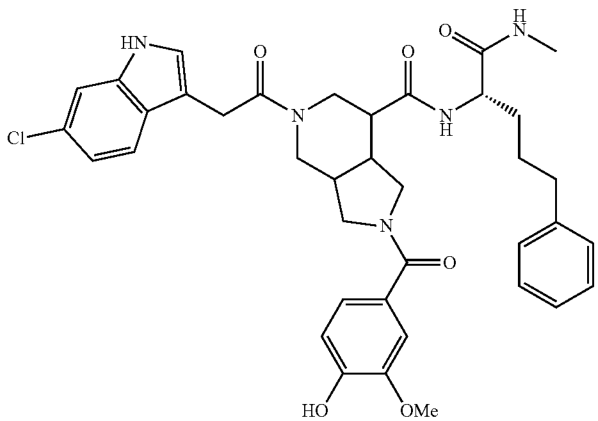 [SMILES: CNC(=O)[C@H](CCCc1ccccc1)NC(=O)C1CN(C(=O)Cc2c[nH]c3cc(Cl)ccc23)CC2CN(C(=O)c3ccc(O)c(OC)c3)CC21] |
| I-33 | 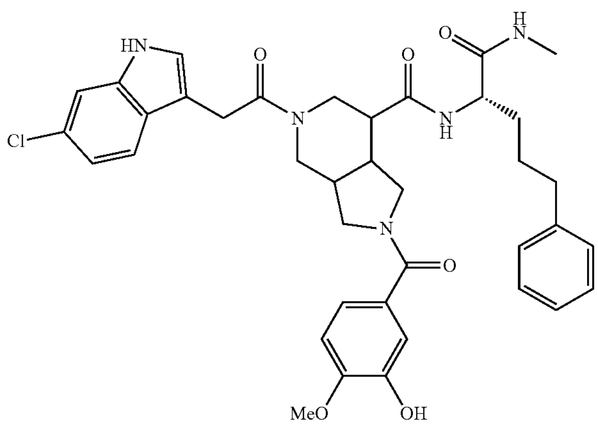 [SMILES: CNC(=O)[C@H](CCCc1ccccc1)NC(=O)C1CN(C(=O)Cc2c[nH]c3cc(Cl)ccc23)CC2CN(C(=O)c3ccc(OC)c(O)c3)CC21] |
| I-34 | 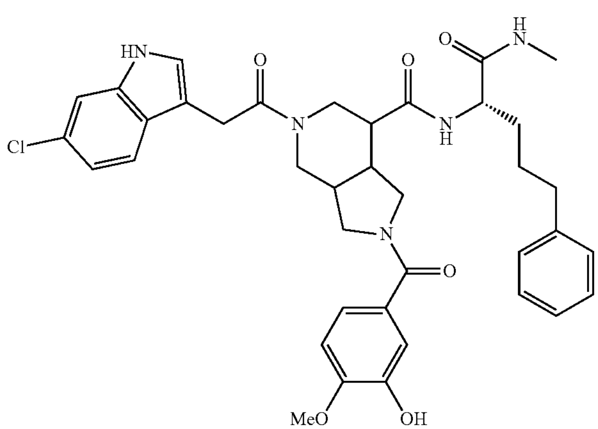 [SMILES: CNC(=O)[C@H](CCCc1ccccc1)NC(=O)C1CN(C(=O)Cc2c[nH]c3cc(Cl)ccc23)CC2CN(C(=O)c3ccc(OC)c(O)c3)CC21] |

TABLE 1-continued

Exemplary Compounds

| # | Structure |
|---|---|
| I-35 | 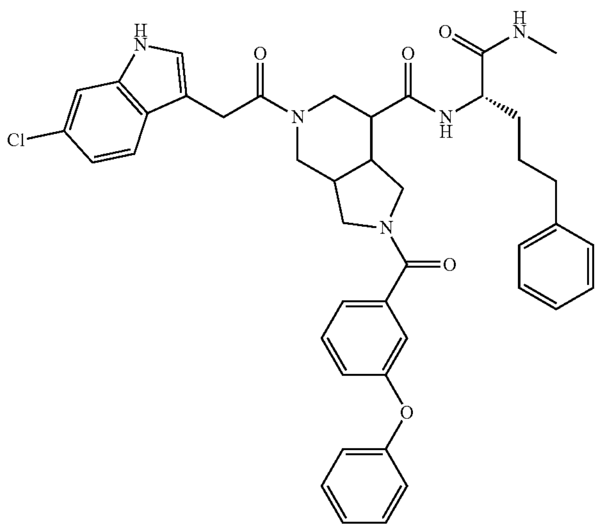 [SMILES: CNC(=O)[C@H](CCCc1ccccc1)NC(=O)C1CN(C(=O)Cc2c[nH]c3cc(Cl)ccc23)CC2CN(C(=O)c3cccc(Oc4ccccc4)c3)CC21] |
| I-36 | 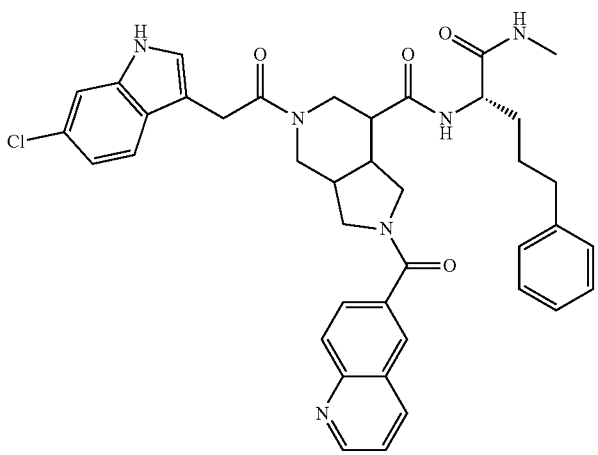 [SMILES: CNC(=O)[C@H](CCCc1ccccc1)NC(=O)C1CN(C(=O)Cc2c[nH]c3cc(Cl)ccc23)CC2CN(C(=O)c3ccc4ncccc4c3)CC21] |
| I-37 | 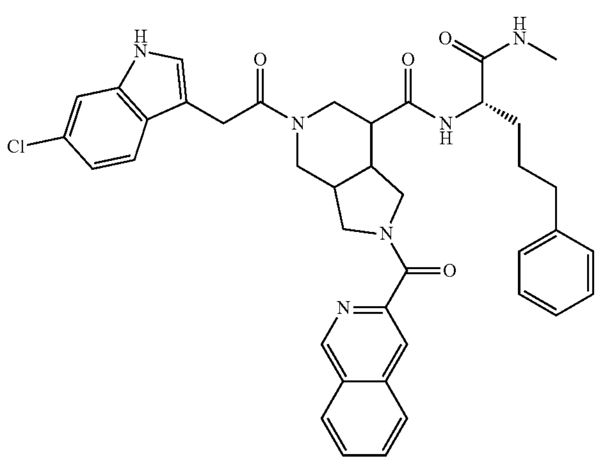 [SMILES: CNC(=O)[C@H](CCCc1ccccc1)NC(=O)C1CN(C(=O)Cc2c[nH]c3cc(Cl)ccc23)CC2CN(C(=O)c3cc4ccccc4cn3)CC21] |

TABLE 1-continued

Exemplary Compounds

| # | Structure |
|---|---|
| I-38 | 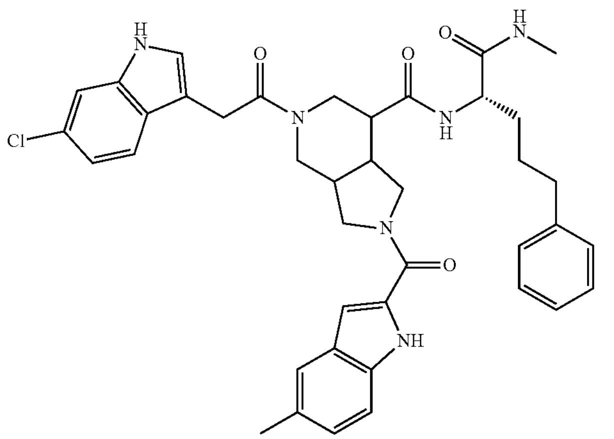 [SMILES: CNC(=O)[C@H](CCCc1ccccc1)NC(=O)C1CN(C(=O)Cc2c[nH]c3cc(Cl)ccc23)CC2CN(C(=O)c3cc4cc(C)ccc4[nH]3)CC21] |
| I-39 | 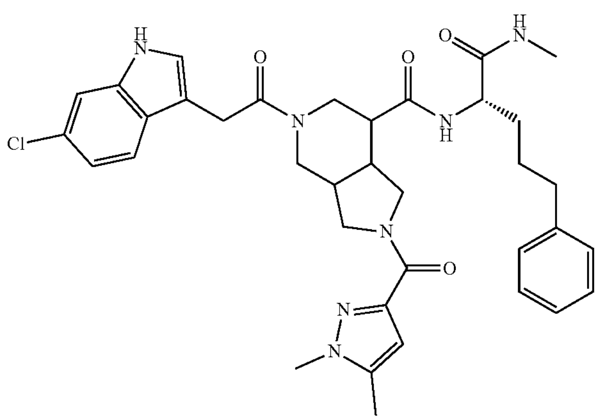 [SMILES: CNC(=O)[C@H](CCCc1ccccc1)NC(=O)C1CN(C(=O)Cc2c[nH]c3cc(Cl)ccc23)CC2CN(C(=O)c3cc(C)n(C)n3)CC21] |
| I-40 | 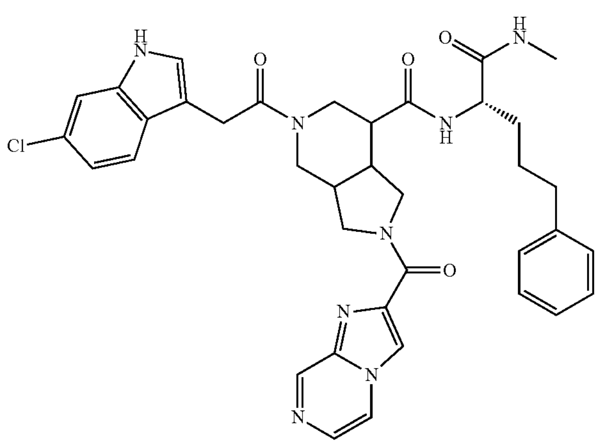 [SMILES: CNC(=O)[C@H](CCCc1ccccc1)NC(=O)C1CN(C(=O)Cc2c[nH]c3cc(Cl)ccc23)CC2CN(C(=O)c3cn4ccncc4n3)CC21] |

TABLE 1-continued

Exemplary Compounds

| # | Structure |
|---|---|
| I-41 | 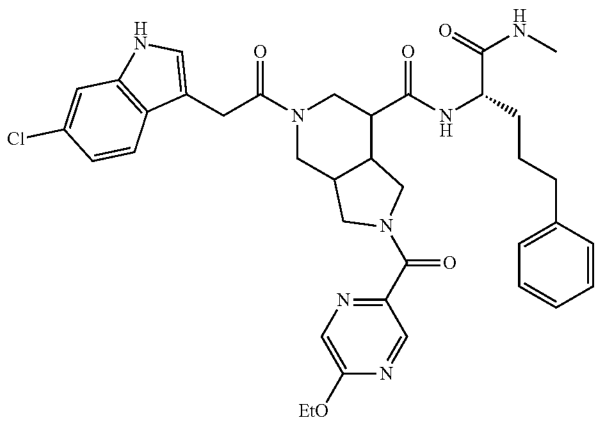 [SMILES: CCOc1cnc(C(=O)N2CC3CN(C(=O)Cc4c[nH]c5cc(Cl)ccc45)CC(C(=O)N[C@@H](CCCc4ccccc4)C(=O)NC)C3C2)cn1] |
| I-42 | 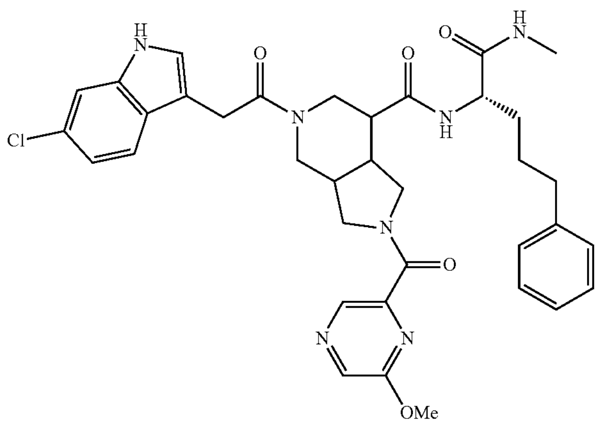 |
| I-43 | 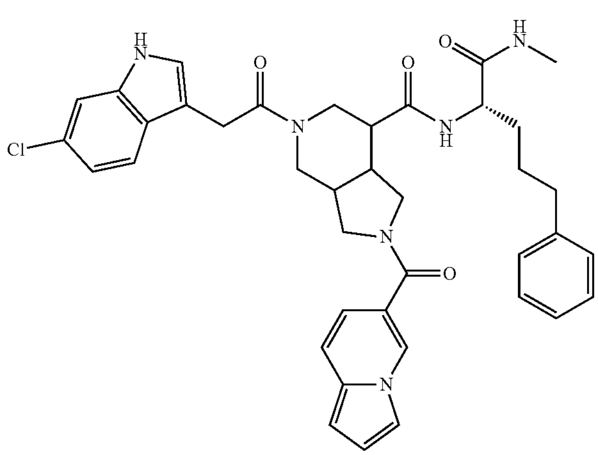 [SMILES: CNC(=O)[C@H](CCCc1ccccc1)NC(=O)C1CN(C(=O)Cc2c[nH]c3cc(Cl)ccc23)CC2CN(C(=O)c3ccc4cccn4c3)CC21] |

TABLE 1-continued
Exemplary Compounds
| # | Structure |
|---|---|
| I-44 | 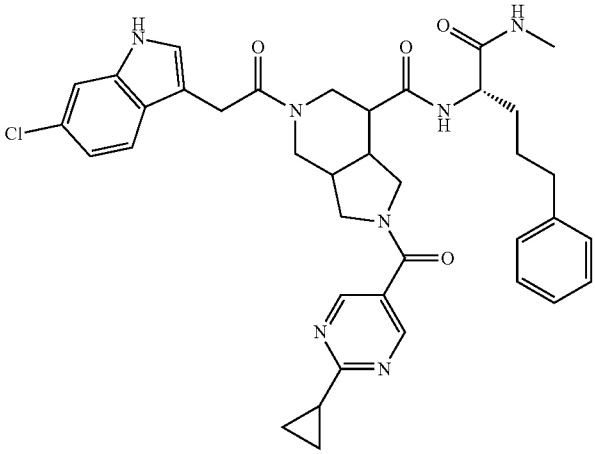 [SMILES: CNC(=O)[C@H](CCCc1ccccc1)NC(=O)C1CN(C(=O)Cc2c[nH]c3cc(Cl)ccc23)CC2CN(C(=O)c3cnc(C4CC4)nc3)CC21] |
| I-45 | 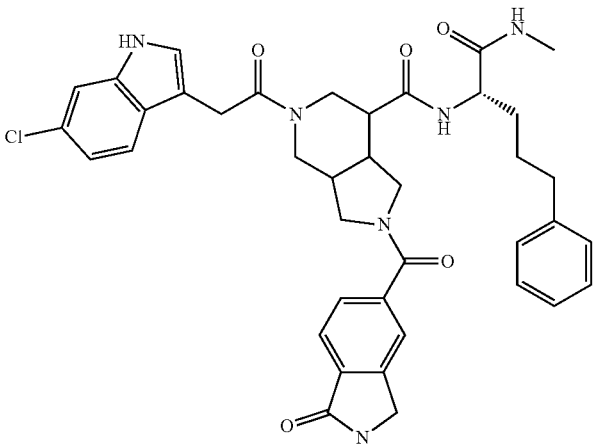 |
| I-46 | 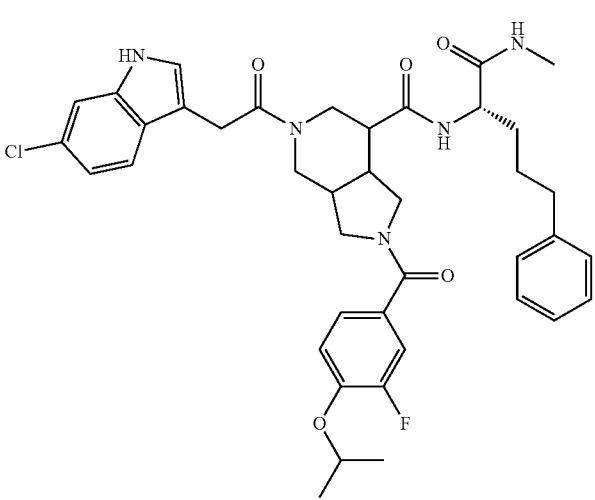 [SMILES: CNC(=O)[C@H](CCCc1ccccc1)NC(=O)C1CN(C(=O)Cc2c[nH]c3cc(Cl)ccc23)CC2CN(C(=O)c3ccc(OC(C)C)c(F)c3)CC21] |

TABLE 1-continued
Exemplary Compounds
| # | Structure |
|---|---|
| I-47 | 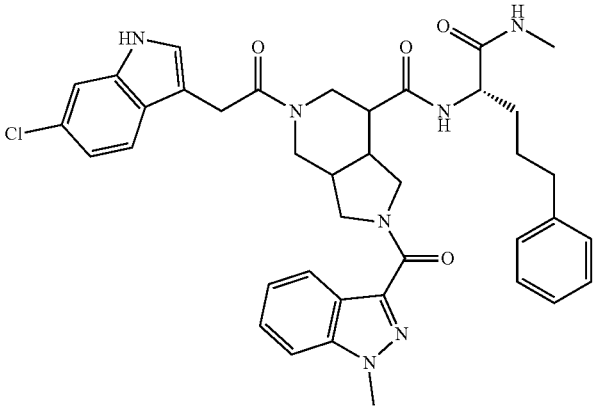 [SMILES: CNC(=O)[C@H](CCCc1ccccc1)NC(=O)C1CN(C(=O)Cc2c[nH]c3cc(Cl)ccc23)CC2CN(C(=O)c3nn(C)c4ccccc34)CC21] |
| I-48 | 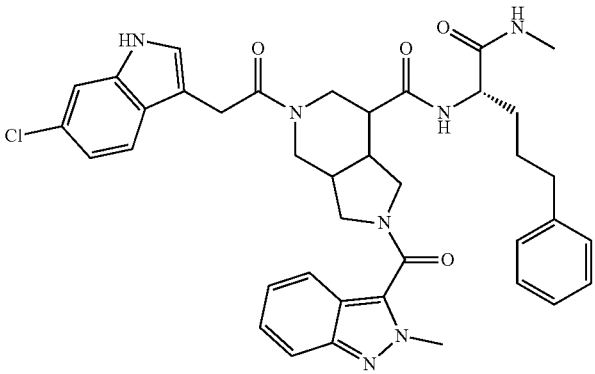 [SMILES: CNC(=O)[C@H](CCCc1ccccc1)NC(=O)C1CN(C(=O)Cc2c[nH]c3cc(Cl)ccc23)CC2CN(C(=O)c3c4ccccc4nn3C)CC21] |
| I-49 | 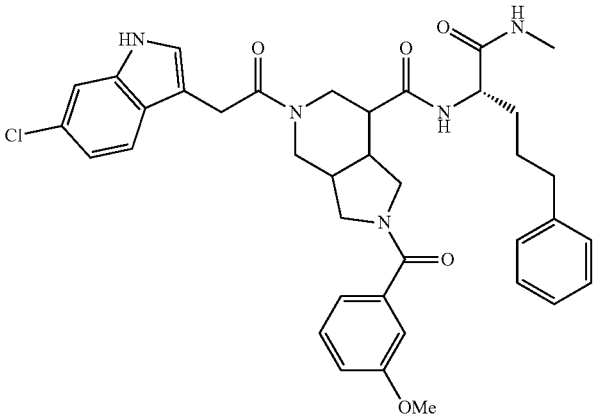 [SMILES: CNC(=O)[C@H](CCCc1ccccc1)NC(=O)C1CN(C(=O)Cc2c[nH]c3cc(Cl)ccc23)CC2CN(C(=O)c3cccc(OC)c3)CC21] |

TABLE 1-continued

Exemplary Compounds

| # | Structure |
|---|---|
| I-50 | 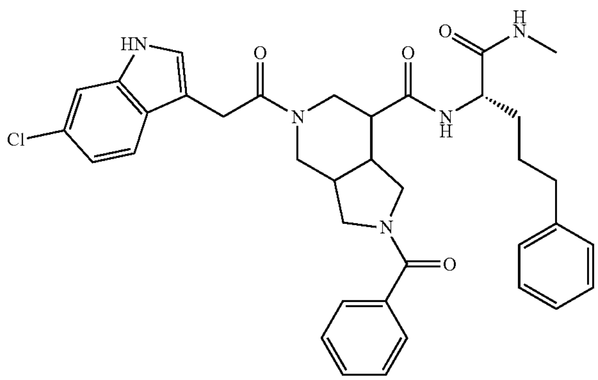 [SMILES: CNC(=O)[C@H](CCCc1ccccc1)NC(=O)C1CN(C(=O)Cc2c[nH]c3cc(Cl)ccc23)CC2CN(C(=O)c3ccccc3)CC21] |
| I-51 | 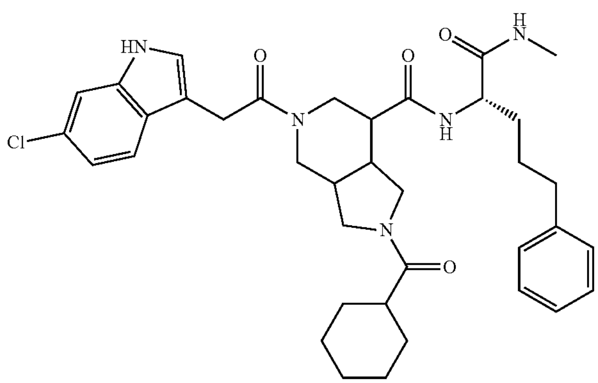 [SMILES: CNC(=O)[C@H](CCCc1ccccc1)NC(=O)C1CN(C(=O)Cc2c[nH]c3cc(Cl)ccc23)CC2CN(C(=O)C3CCCCC3)CC21] |
| I-52 | 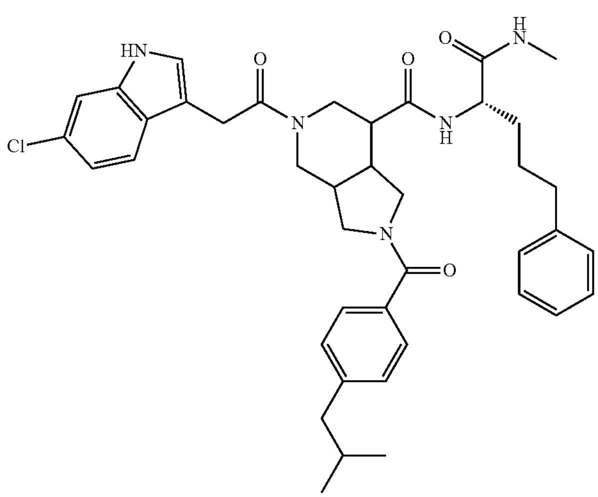 |

TABLE 1-continued
Exemplary Compounds
| # | Structure |
|---|---|
| I-53 | 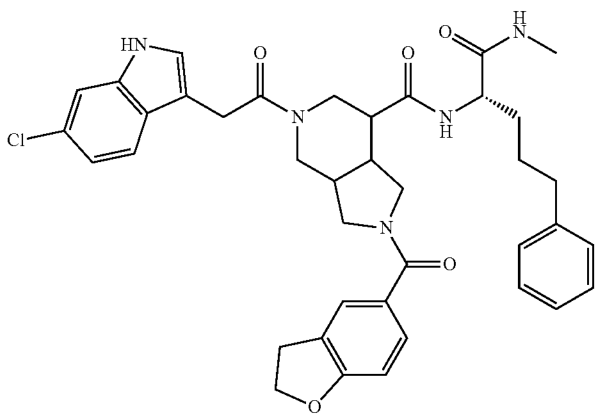 [SMILES: CNC(=O)[C@H](CCCc1ccccc1)NC(=O)C1CN(C(=O)Cc2c[nH]c3cc(Cl)ccc23)CC2CN(C(=O)c3ccc4c(c3)CCO4)CC21] |
| I-54 | 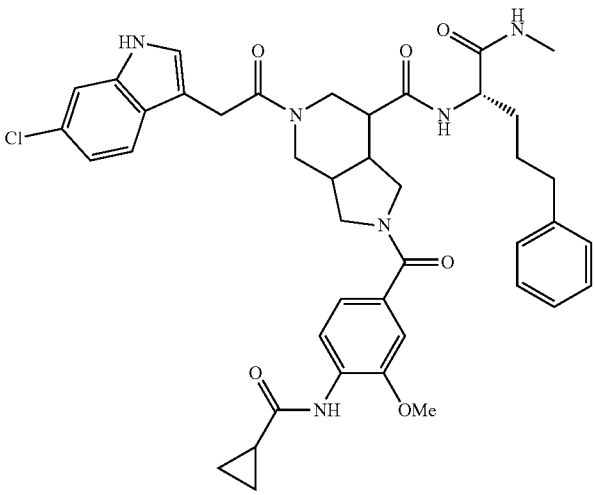 [SMILES: CNC(=O)[C@H](CCCc1ccccc1)NC(=O)C1CN(C(=O)Cc2c[nH]c3cc(Cl)ccc23)CC2CN(C(=O)c3ccc(NC(=O)C4CC4)c(OC)c3)CC21] |
| I-55 | 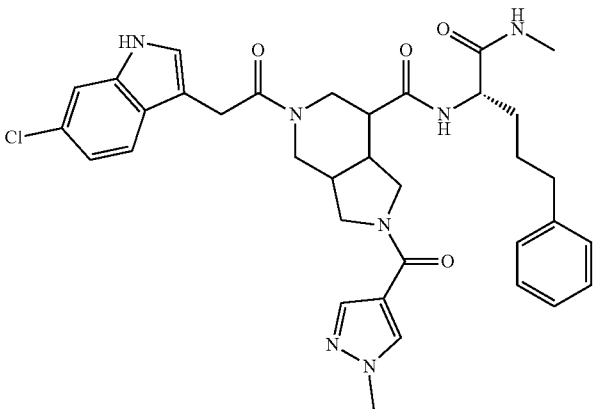 [SMILES: CNC(=O)[C@H](CCCc1ccccc1)NC(=O)C1CN(C(=O)Cc2c[nH]c3cc(Cl)ccc23)CC2CN(C(=O)c3cnn(C)c3)CC21] |

TABLE 1-continued
| Exemplary Compounds | |
|---|---|
| # | Structure |
| I-56 | 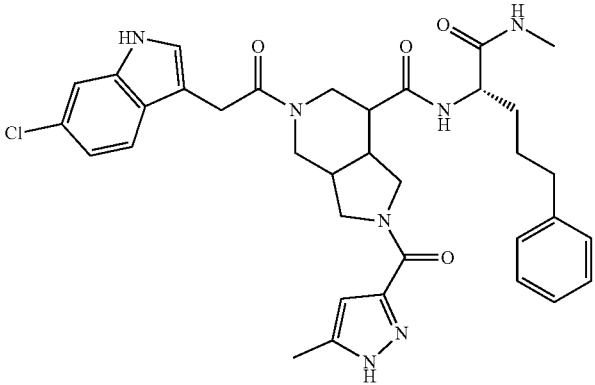 [SMILES: CNC(=O)[C@H](CCCc1ccccc1)NC(=O)C1CN(C(=O)Cc2c[nH]c3cc(Cl)ccc23)CC2CN(C(=O)c3cc(C)[nH]n3)CC21] |
| I-57 | 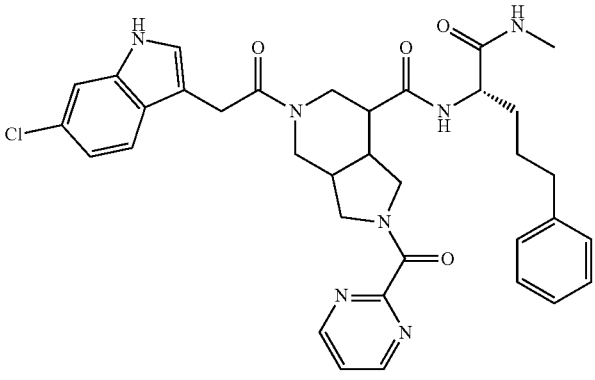 [SMILES: CNC(=O)[C@H](CCCc1ccccc1)NC(=O)C1CN(C(=O)Cc2c[nH]c3cc(Cl)ccc23)CC2CN(C(=O)c3ncccn3)CC21] |
| I-58 | 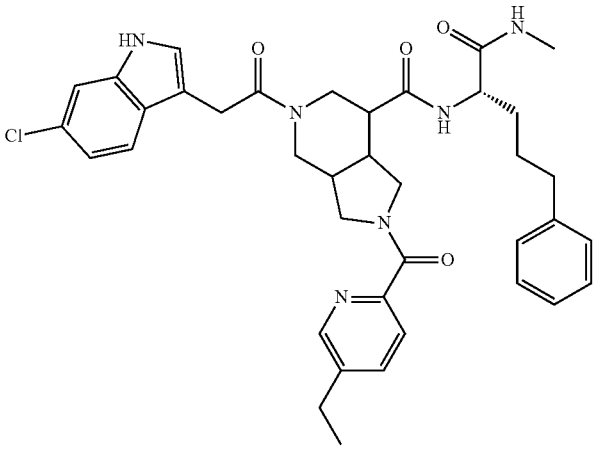 [SMILES: CCc1ccc(C(=O)N2CC3CN(C(=O)Cc4c[nH]c5cc(Cl)ccc45)CC(C(=O)N[C@@H](CCCc4ccccc4)C(=O)NC)C3C2)nc1] |

TABLE 1-continued
Exemplary Compounds
| # | Structure |
|---|---|
| I-59 | 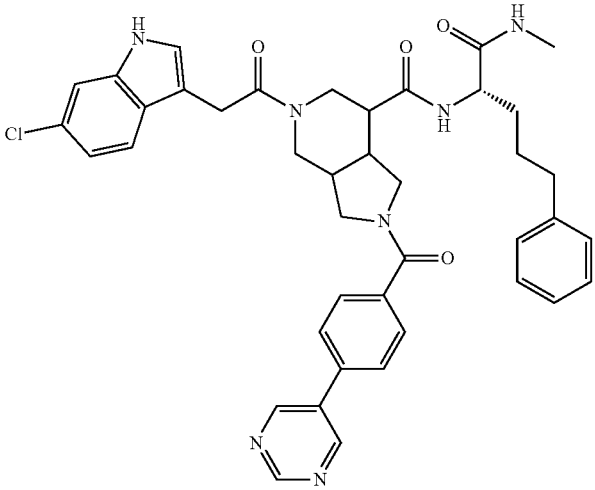 [SMILES: CNC(=O)[C@H](CCCc1ccccc1)NC(=O)C1CN(C(=O)Cc2c[nH]c3cc(Cl)ccc23)CC2CN(C(=O)c3ccc(-c4cncnc4)cc3)CC21] |
| I-60 | 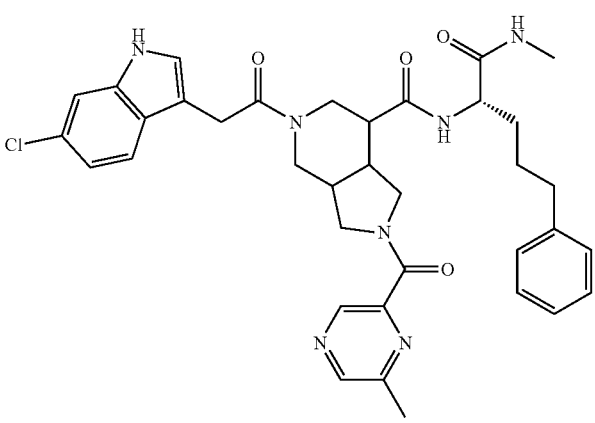 [SMILES: CNC(=O)[C@H](CCCc1ccccc1)NC(=O)C1CN(C(=O)Cc2c[nH]c3cc(Cl)ccc23)CC2CN(C(=O)c3cncc(C)n3)CC21] |
| I-61 | 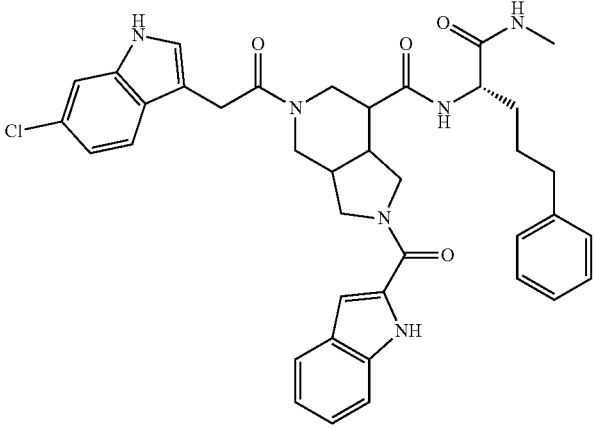 [SMILES: CNC(=O)[C@H](CCCc1ccccc1)NC(=O)C1CN(C(=O)Cc2c[nH]c3cc(Cl)ccc23)CC2CN(C(=O)c3cc4ccccc4[nH]3)CC21] |

TABLE 1-continued
Exemplary Compounds
| # | Structure |
|---|---|
| I-62 | 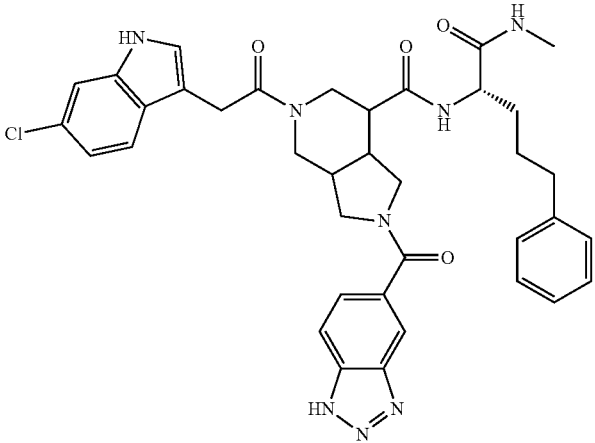 [SMILES: CNC(=O)[C@H](CCCc1ccccc1)NC(=O)C1CN(C(=O)Cc2c[nH]c3cc(Cl)ccc23)CC2CN(C(=O)c3ccc4[nH]nnc4c3)CC21] |
| I-63 | 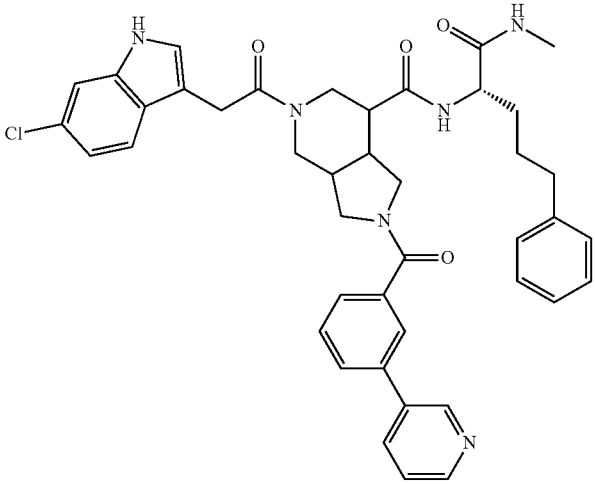 [SMILES: CNC(=O)[C@H](CCCc1ccccc1)NC(=O)C1CN(C(=O)Cc2c[nH]c3cc(Cl)ccc23)CC2CN(C(=O)c3cccc(-c4cccnc4)c3)CC21] |
| I-64 | 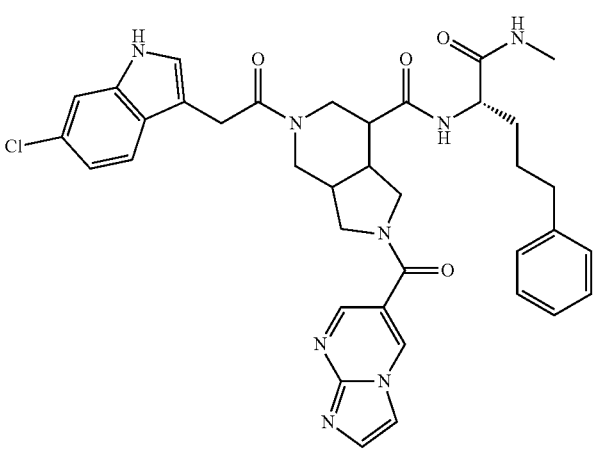 |

TABLE 1-continued
Exemplary Compounds
| # | Structure |
|---|---|
| I-65 | 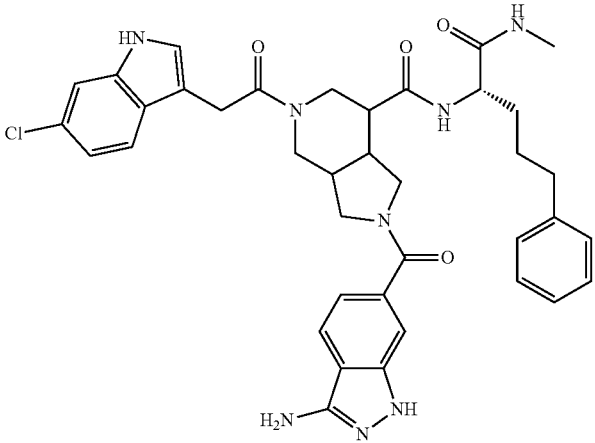 [SMILES: CNC(=O)[C@H](CCCc1ccccc1)NC(=O)C1CN(C(=O)Cc2c[nH]c3cc(Cl)ccc23)CC2CN(C(=O)c3ccc4c(N)n[nH]c4c3)CC21] |
| I-66 | 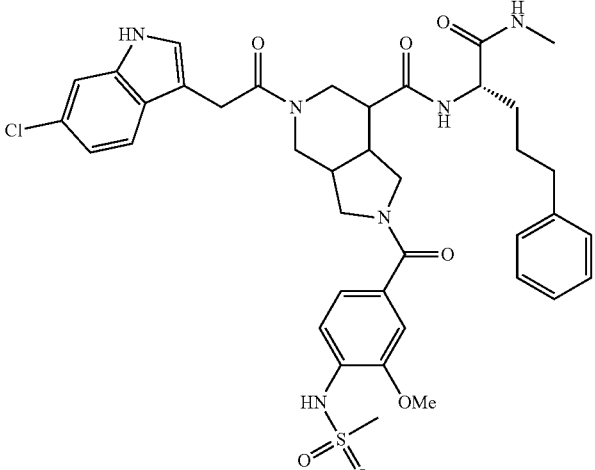 |
| I-67 | 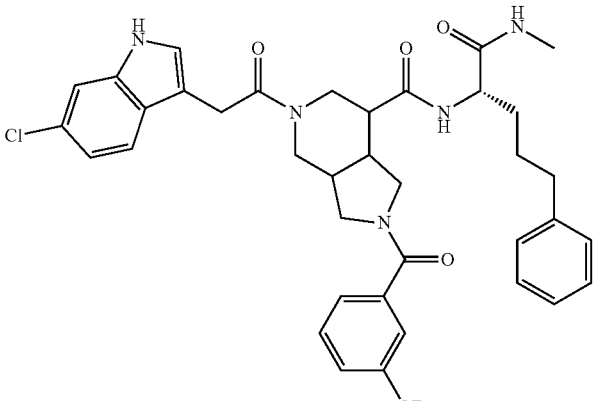 |

TABLE 1-continued

Exemplary Compounds

| # | Structure |
|---|---|
| I-68 | 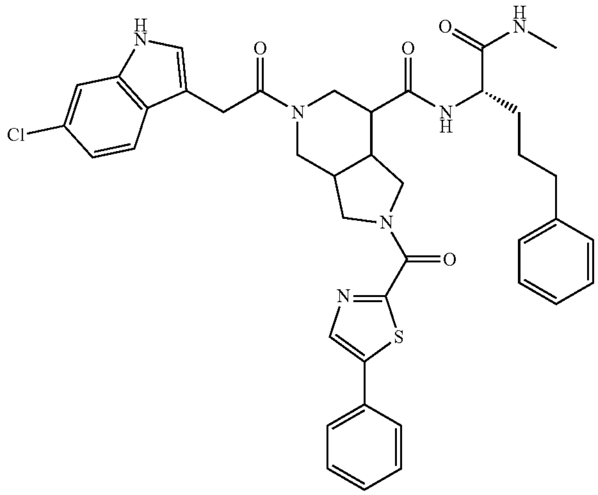 [SMILES: CNC(=O)[C@H](CCCc1ccccc1)NC(=O)C1CN(C(=O)Cc2c[nH]c3cc(Cl)ccc23)CC2CN(C(=O)c3ncc(-c4ccccc4)s3)CC21] |
| I-69 | 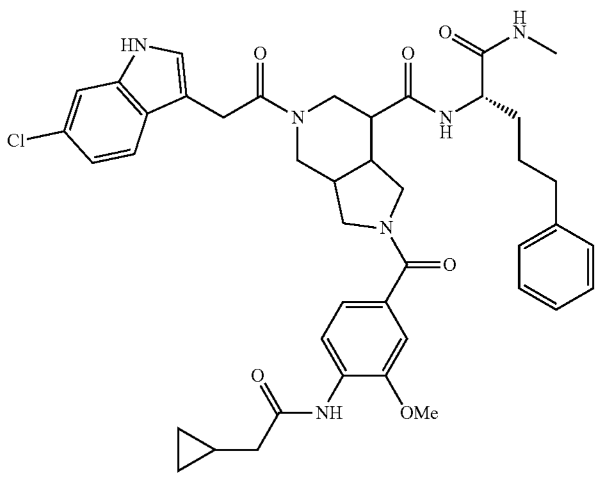 [SMILES: CNC(=O)[C@H](CCCc1ccccc1)NC(=O)C1CN(C(=O)Cc2c[nH]c3cc(Cl)ccc23)CC2CN(C(=O)c3ccc(NC(=O)CC4CC4)c(OC)c3)CC21] |
| I-70 | 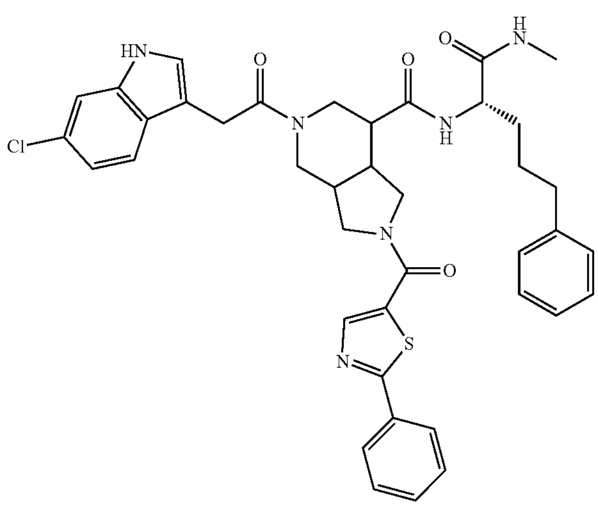 [SMILES: CNC(=O)[C@H](CCCc1ccccc1)NC(=O)C1CN(C(=O)Cc2c[nH]c3cc(Cl)ccc23)CC2CN(C(=O)c3cnc(-c4ccccc4)s3)CC21] |

TABLE 1-continued

Exemplary Compounds

| # | Structure |
|---|-----------|
| I-71 | 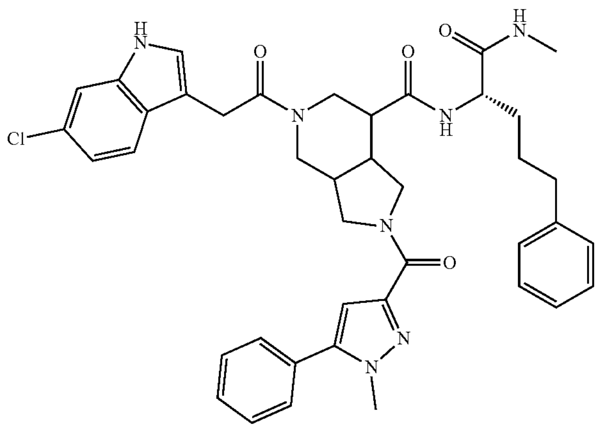 [SMILES: CNC(=O)[C@H](CCCc1ccccc1)NC(=O)C1CN(C(=O)Cc2c[nH]c3cc(Cl)ccc23)CC2CN(C(=O)c3cc(-c4ccccc4)n(C)n3)CC21] |
| I-72 | 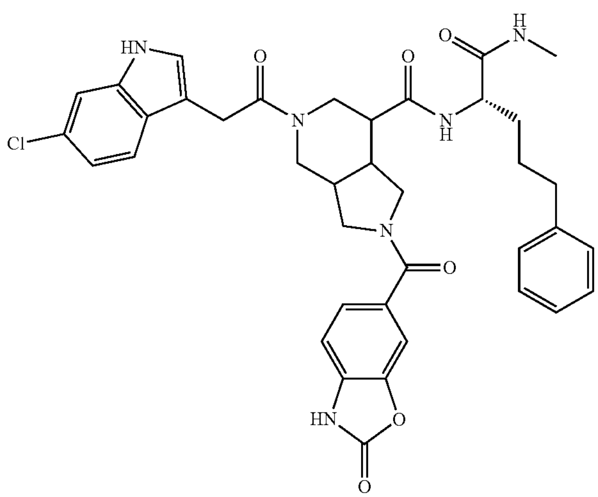 |
| I-73 | 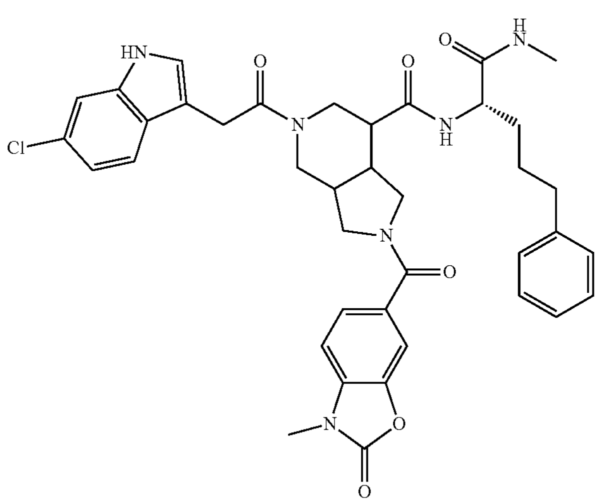 [SMILES: CNC(=O)[C@H](CCCc1ccccc1)NC(=O)C1CN(C(=O)Cc2c[nH]c3cc(Cl)ccc23)CC2CN(C(=O)c3ccc4c(c3)oc(=O)n4C)CC21] |

TABLE 1-continued
Exemplary Compounds
| # | Structure |
|---|---|
| I-74 | 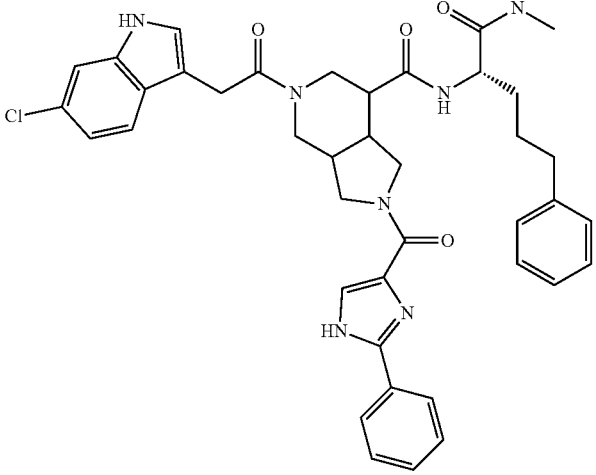 |
| I-75 | 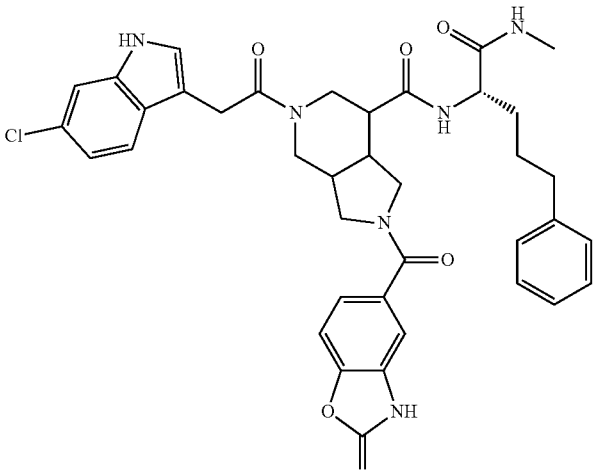 |
| I-76 | 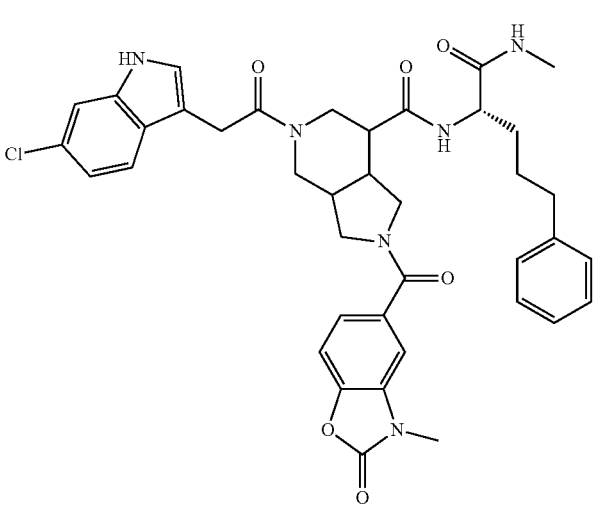 [SMILES: CNC(=O)[C@H](CCCc1ccccc1)NC(=O)C1CN(C(=O)Cc2c[nH]c3cc(Cl)ccc23)CC2CN(C(=O)c3ccc4oc(=O)n(C)c4c3)CC21] |

TABLE 1-continued
Exemplary Compounds
| # | Structure |
|---|---|
| I-77 | 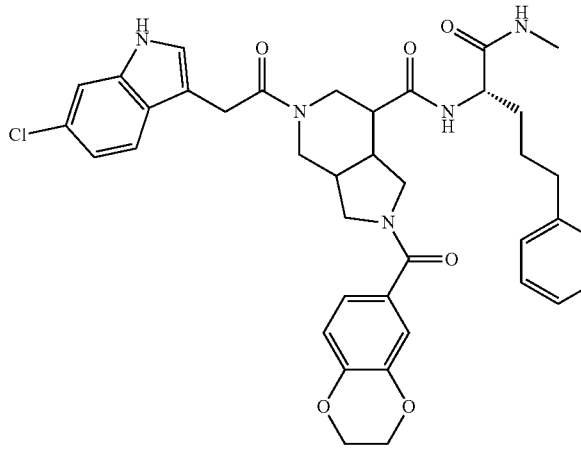 |
| I-78 | 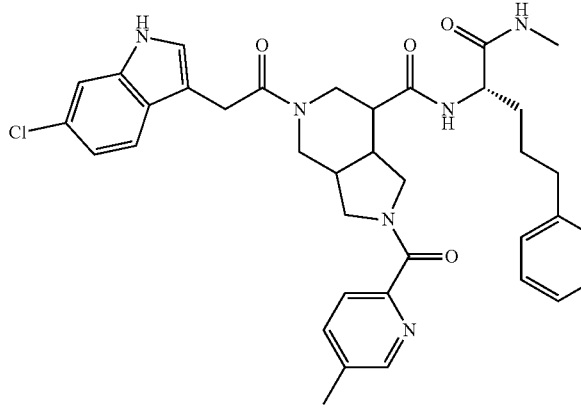 |
| I-79 | 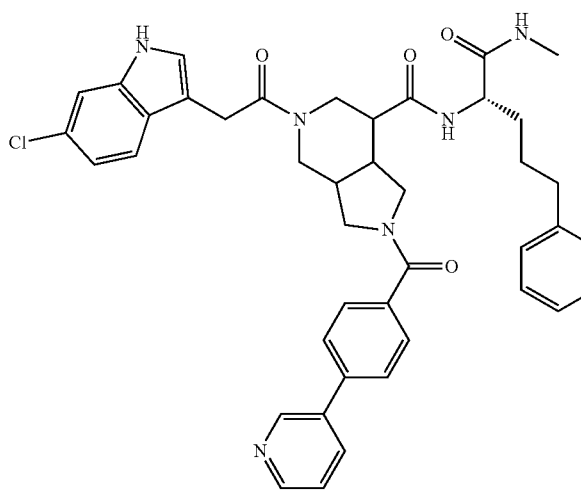 |

TABLE 1-continued
Exemplary Compounds
| # | Structure |
|---|---|
| I-80 | 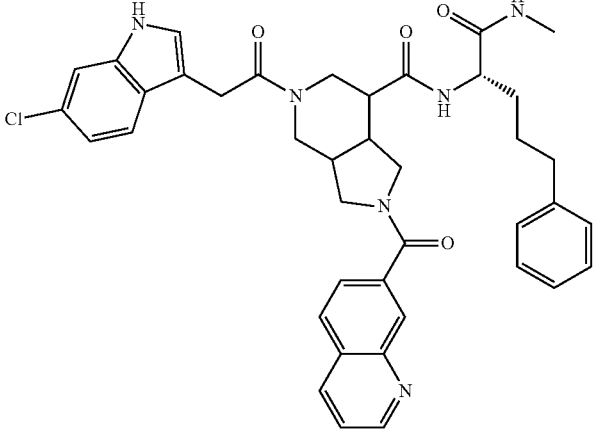 |
| I-81 | 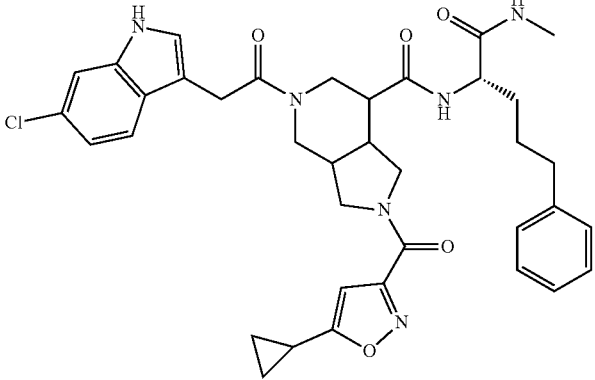 |
| I-82 | 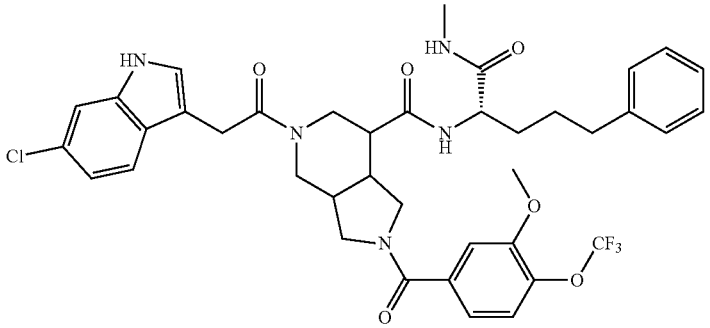 [SMILES: CNC(=O)[C@H](CCCc1ccccc1)NC(=O)C1CN(C(=O)Cc2c[nH]c3cc(Cl)ccc23)CC2CN(C(=O)c3ccc(OC(F)(F)F)c(OC)c3)CC21] |
| I-83 | 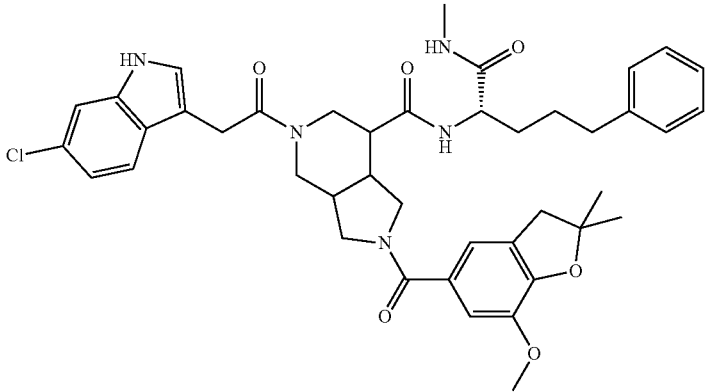 [SMILES: CNC(=O)[C@H](CCCc1ccccc1)NC(=O)C1CN(C(=O)Cc2c[nH]c3cc(Cl)ccc23)CC2CN(C(=O)c3cc4c(c(OC)c3)OC(C)(C)C4)CC21] |

TABLE 1-continued
Exemplary Compounds
| # | Structure |
|---|---|
| I-84 | 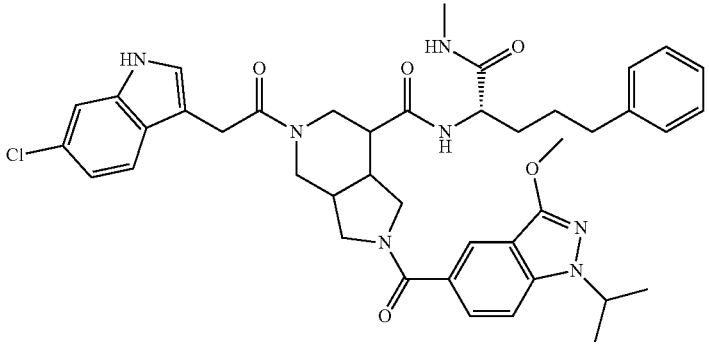 [SMILES: CNC(=O)[C@H](CCCc1ccccc1)NC(=O)C1CN(C(=O)Cc2c[nH]c3cc(Cl)ccc23)CC2CN(C(=O)c3ccc4c(c3)c(OC)nn4C(C)C)CC21] |
| I-85 | 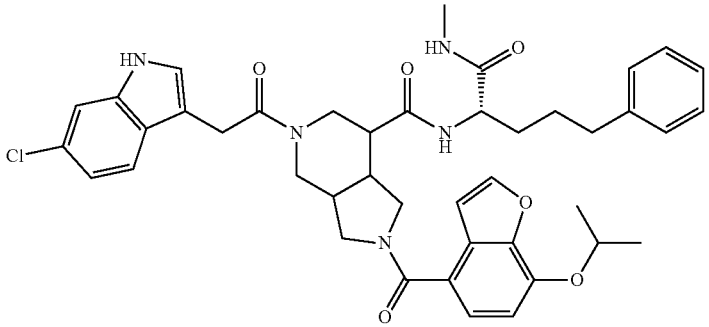 [SMILES: CNC(=O)[C@H](CCCc1ccccc1)NC(=O)C1CN(C(=O)Cc2c[nH]c3cc(Cl)ccc23)CC2CN(C(=O)c3ccc(OC(C)C)c4occc34)CC21] |
| I-86 | 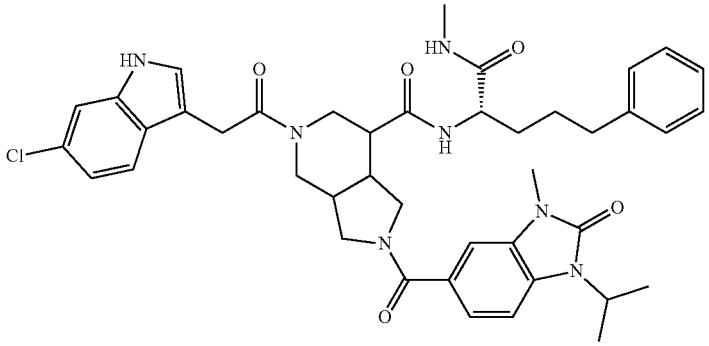 [SMILES: CNC(=O)[C@H](CCCc1ccccc1)NC(=O)C1CN(C(=O)Cc2c[nH]c3cc(Cl)ccc23)CC2CN(C(=O)c3ccc4c(c3)n(C)c(=O)n4C(C)C)CC21]<br>First eluting diastereomer |
| I-87 | 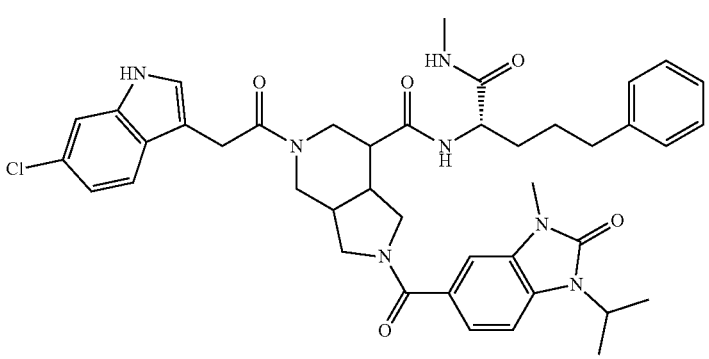 [SMILES: CNC(=O)[C@H](CCCc1ccccc1)NC(=O)C1CN(C(=O)Cc2c[nH]c3cc(Cl)ccc23)CC2CN(C(=O)c3ccc4c(c3)n(C)c(=O)n4C(C)C)CC21]<br>Second eluting diastereomer |

TABLE 1-continued
Exemplary Compounds
| # | Structure |
|---|---|
| I-88 | 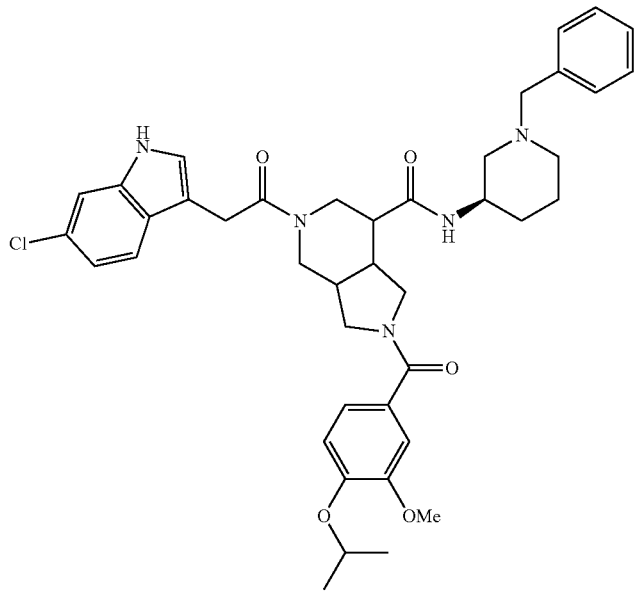 [SMILES: COc1cc(C(=O)N2CC3CN(C(=O)Cc4c[nH]c5cc(Cl)ccc45)CC(C(=O)N[C@@H]4CCCN(Cc5ccccc5)C4)C3C2)ccc1OC(C)C] |
| I-89 | 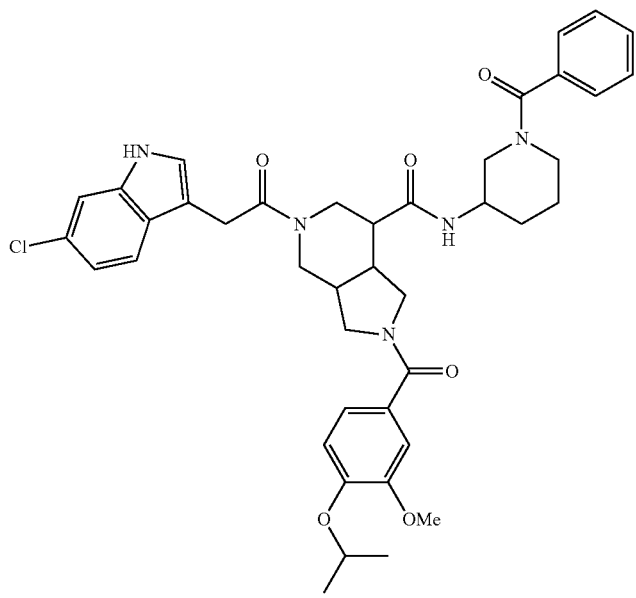 [SMILES: COc1cc(C(=O)N2CC3CN(C(=O)Cc4c[nH]c5cc(Cl)ccc45)CC(C(=O)NC4CCCN(C(=O)c5ccccc5)C4)C3C2)ccc1OC(C)C] |

TABLE 1-continued
Exemplary Compounds
| # | Structure |
|---|---|
| I-90 | 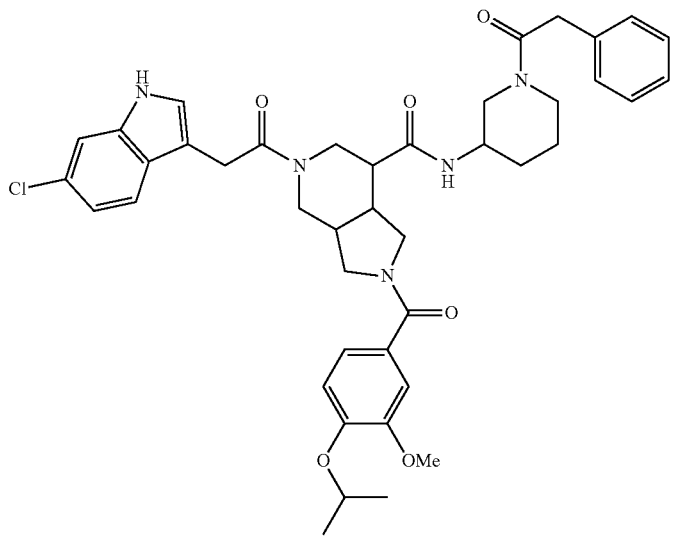 [SMILES: COc1cc(C(=O)N2CC3CN(C(=O)Cc4c[nH]c5cc(Cl)ccc45)CC(C(=O)NC4CCCN(C(=O)Cc5ccccc5)C4)C3C2)ccc1OC(C)C] |
| I-91 | 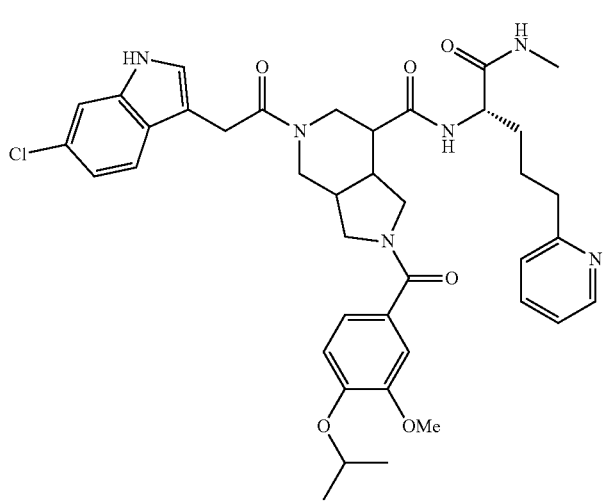 |
| I-92 | 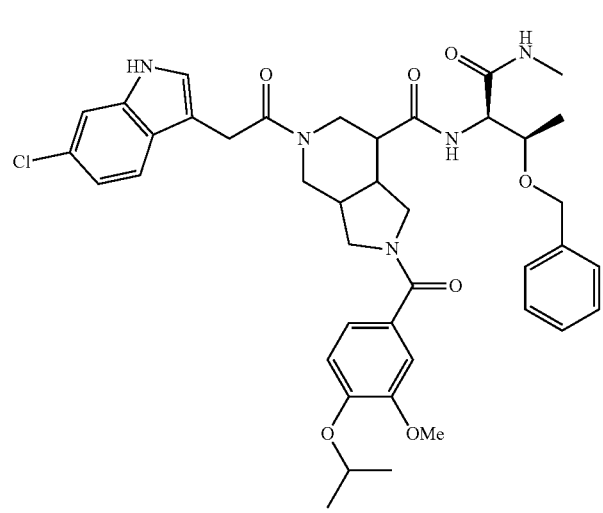 [SMILES: CNC(=O)[C@H](NC(=O)C1CN(C(=O)Cc2c[nH]c3cc(Cl)ccc23)CC2CN(C(=O)c3ccc(OC(C)C)c(OC)c3)CC21)[C@@H](C)OCc1ccccc1] |

TABLE 1-continued
Exemplary Compounds
| # | Structure |
|---|---|
| I-93 | 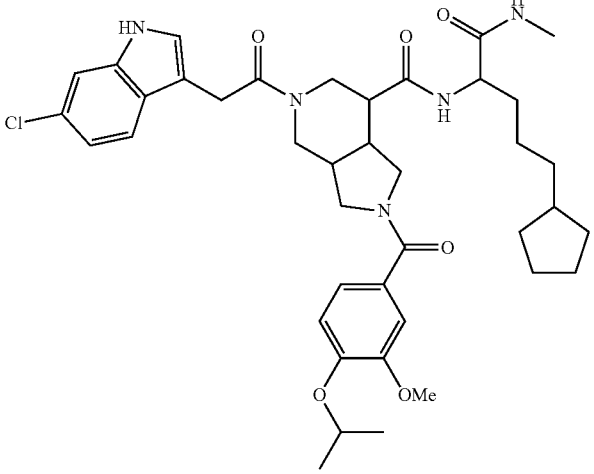 |
| I-94 | 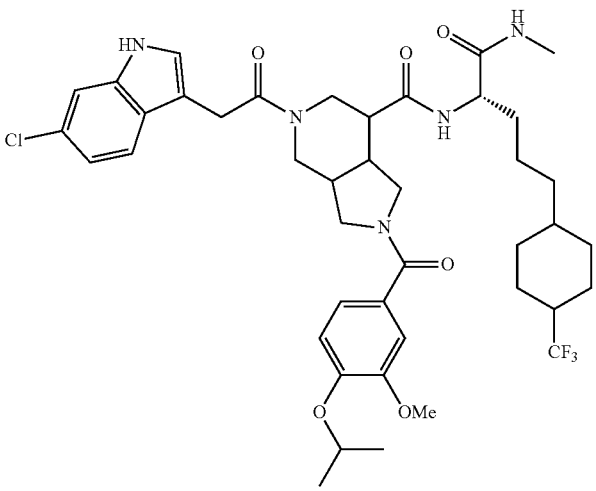 [SMILES: CNC(=O)[C@H](CCCC1CCC(C(F)(F)F)CC1)NC(=O)C1CN(C(=O)Cc2c[nH]c3cc(Cl)ccc23)CC2CN(C(=O)c3ccc(OC(C)C)c(OC)c3)CC21] |
| I-95 | 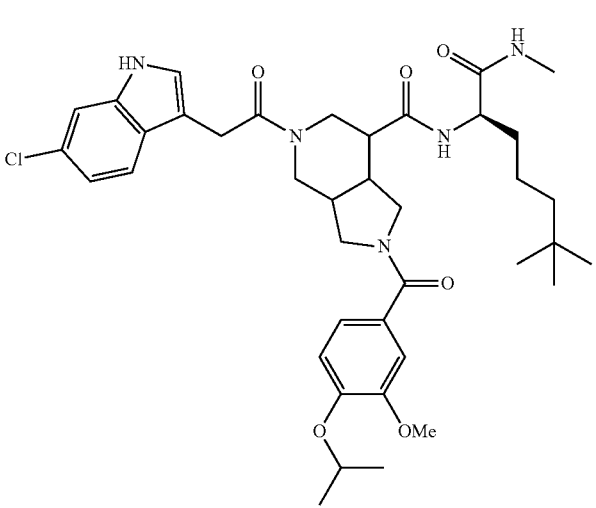 [SMILES: CNC(=O)[C@@H](CCCC(C)(C)C)NC(=O)C1CN(C(=O)Cc2c[nH]c3cc(Cl)ccc23)CC2CN(C(=O)c3ccc(OC(C)C)c(OC)c3)CC21] |

127
TABLE 1-continued
Exemplary Compounds
| # | Structure |
|---|---|
| I-96 | 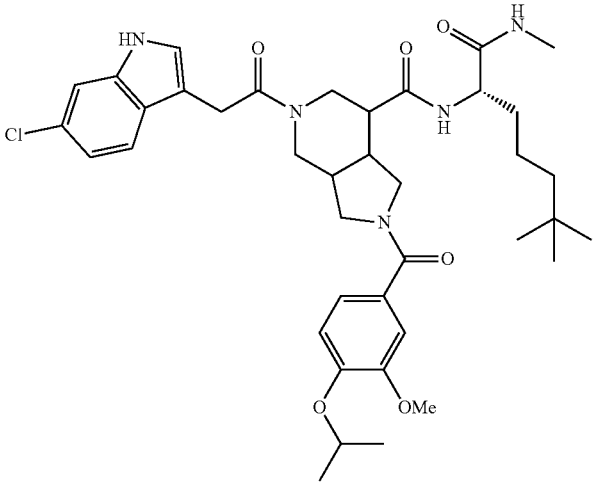 [SMILES: CNC(=O)[C@H](CCCC(C)(C)C)NC(=O)C1CN(C(=O)Cc2c[nH]c3cc(Cl)ccc23)CC2CN(C(=O)c3ccc(OC(C)C)c(OC)c3)CC21] |
| I-97 | 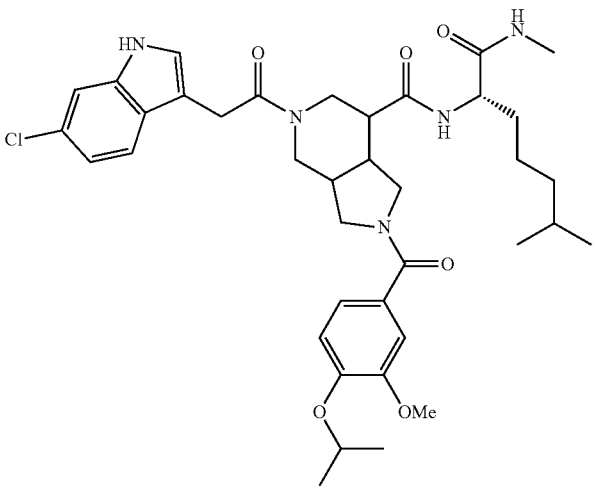 [SMILES: CNC(=O)[C@H](CCCC(C)C)NC(=O)C1CN(C(=O)Cc2c[nH]c3cc(Cl)ccc23)CC2CN(C(=O)c3ccc(OC(C)C)c(OC)c3)CC21] |
| I-98 | 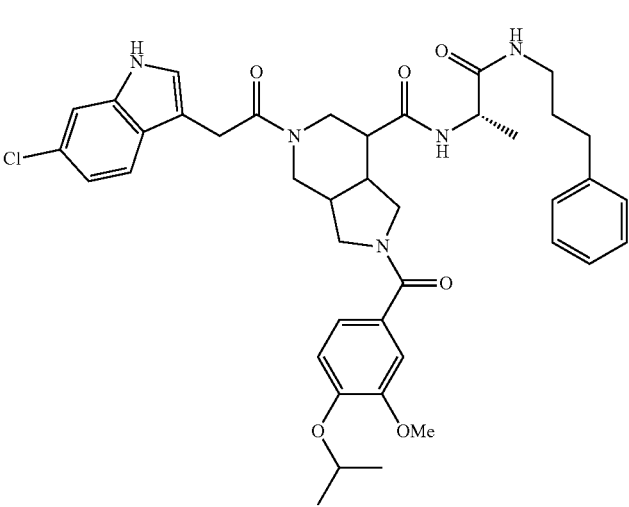 [SMILES: COc1cc(C(=O)N2CC3CN(C(=O)Cc4c[nH]c5cc(Cl)ccc45)CC(C(=O)N[C@@H](C)C(=O)NCCCc4ccccc4)C3C2)ccc1OC(C)C] |

TABLE 1-continued
Exemplary Compounds
| # | Structure |
|---|---|
| I-99 | 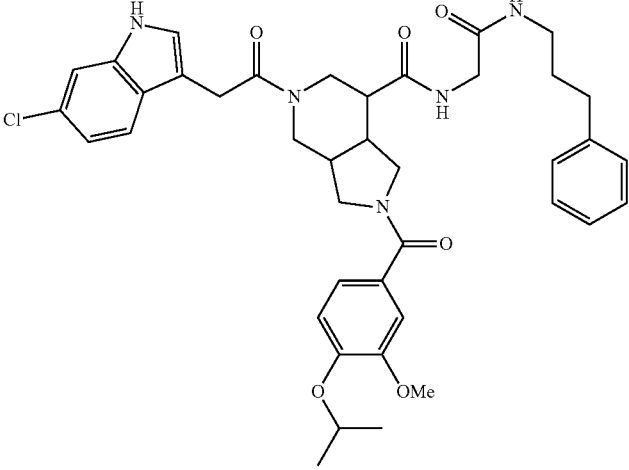 |
| I-100 | 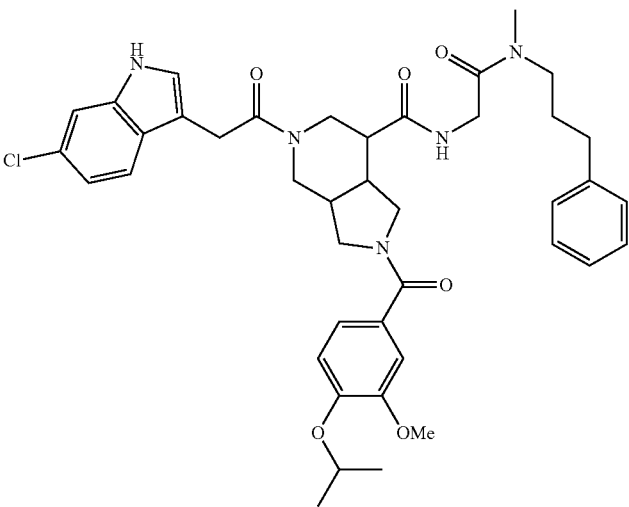 [SMILES: COc1cc(C(=O)N2CC3CN(C(=O)Cc4c[nH]c5cc(Cl)ccc45)CC(C(=O)NCC(=O)N(C)CCCc4ccccc4)C3C2)ccc1OC(C)C]
First eluting diastereomer |
| I-101 | 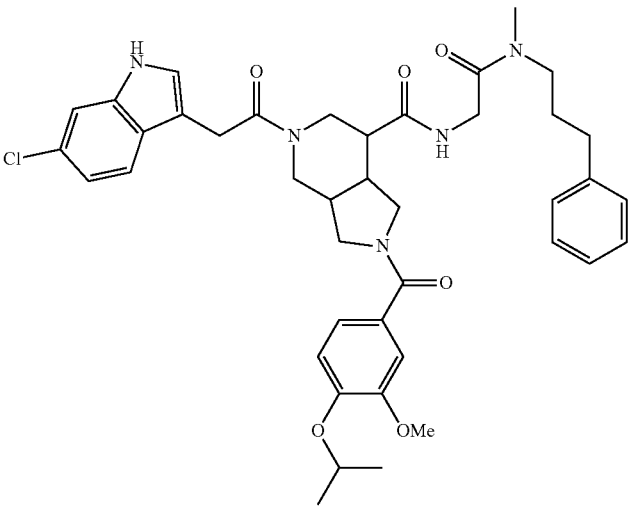 [SMILES: COc1cc(C(=O)N2CC3CN(C(=O)Cc4c[nH]c5cc(Cl)ccc45)CC(C(=O)NCC(=O)N(C)CCCc4ccccc4)C3C2)ccc1OC(C)C]
Second eluting diastereomer |

TABLE 1-continued
Exemplary Compounds
| # | Structure |
|---|---|
| I-102 | 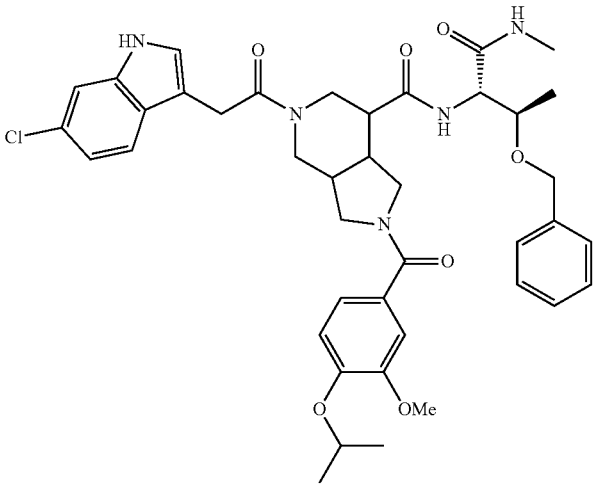 |
| I-103 | 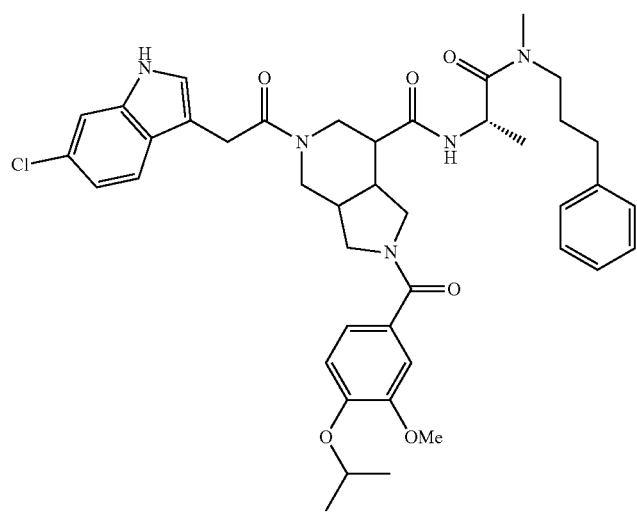 [SMILES: COc1cc(C(=O)N2CC3CN(C(=O)Cc4c[nH]c5cc(Cl)ccc45)CC(C(=O)N[C@@H](C)C(=O)N(C)CCCc4ccccc4)C3C2)ccc1OC(C)C] |
| I-104 | 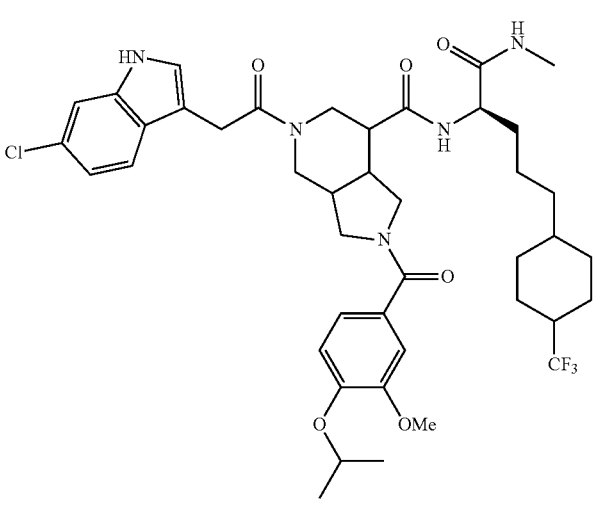 |

TABLE 1-continued
Exemplary Compounds
| # | Structure |
|---|---|
| I-105 | 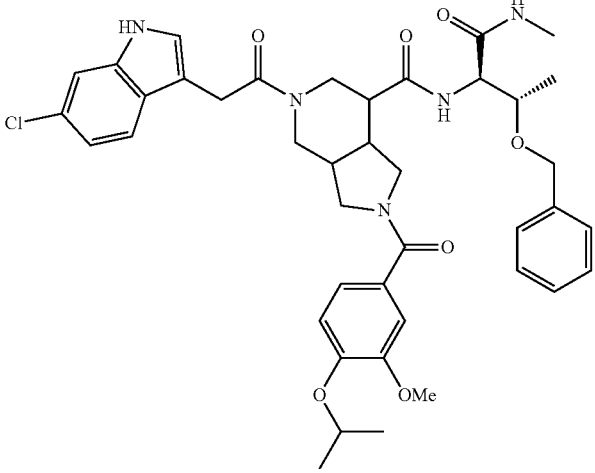 |
| I-106 | 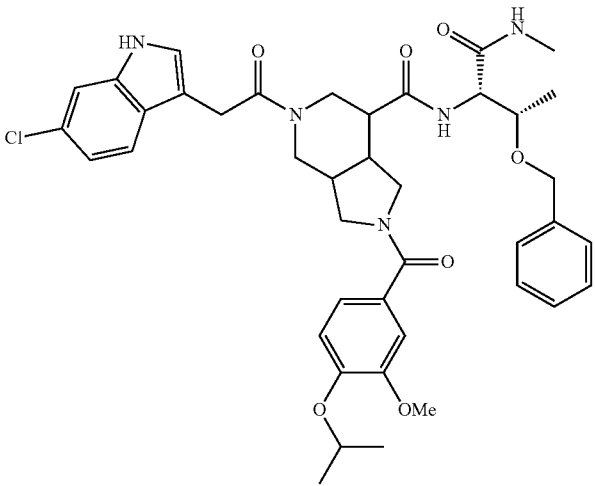 [SMILES: CNC(=O)[C@@H](NC(=O)C1CN(C(=O)Cc2c[nH]c3cc(Cl)ccc23)CC2CN(C(=O)c3ccc(OC(C)C)c(OC)c3)CC21)[C@H](C)OCc1ccccc1] |
| I-107 | 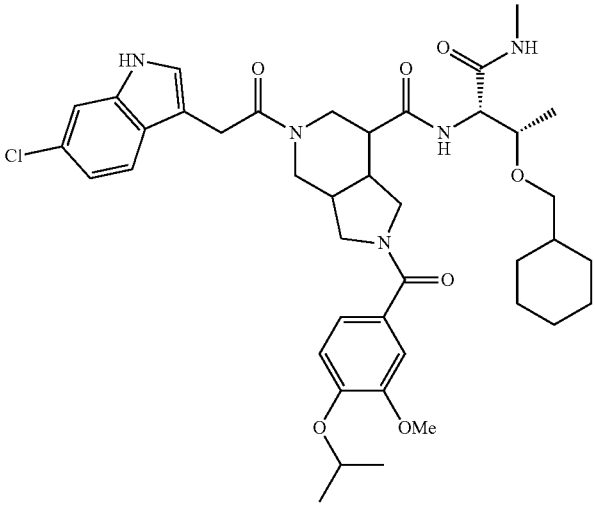 [SMILES: CNC(=O)[C@@H](NC(=O)C1CN(C(=O)Cc2c[nH]c3cc(Cl)ccc23)CC2CN(C(=O)c3ccc(OC(C)C)c(OC)c3)CC21)[C@H](C)OCC1CCCCC1] |

TABLE 1-continued
Exemplary Compounds
| # | Structure |
|---|---|
| I-108 | 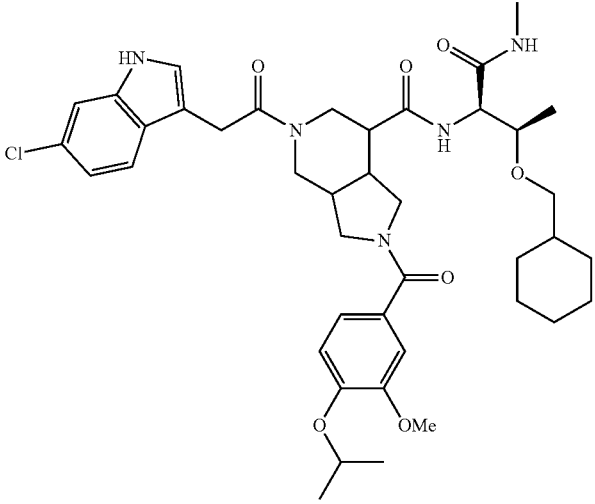 [SMILES: CNC(=O)[C@H](NC(=O)C1CN(C(=O)Cc2c[nH]c3cc(Cl)ccc23)CC2CN(C(=O)c3ccc(OC(C)C)c(OC)c3)CC21)[C@@H](C)OCC1CCCCC1] |
| I-109 | 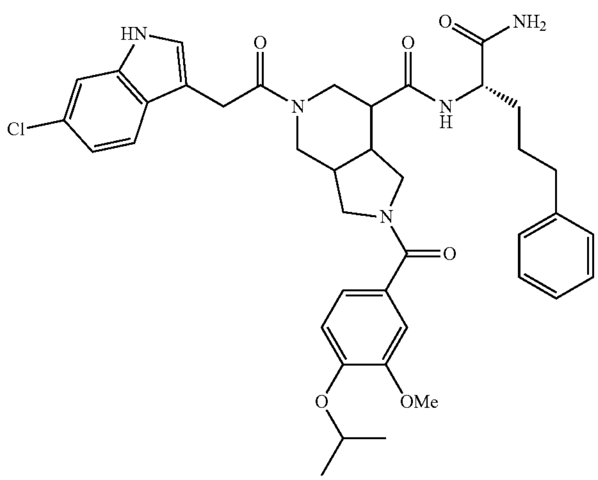 [SMILES: COc1cc(C(=O)N2CC3CN(C(=O)Cc4c[nH]c5cc(Cl)ccc45)CC(C(=O)N[C@@H](CCCc4ccccc4)C(N)=O)C3C2)ccc1OC(C)C] |
| I-110 | 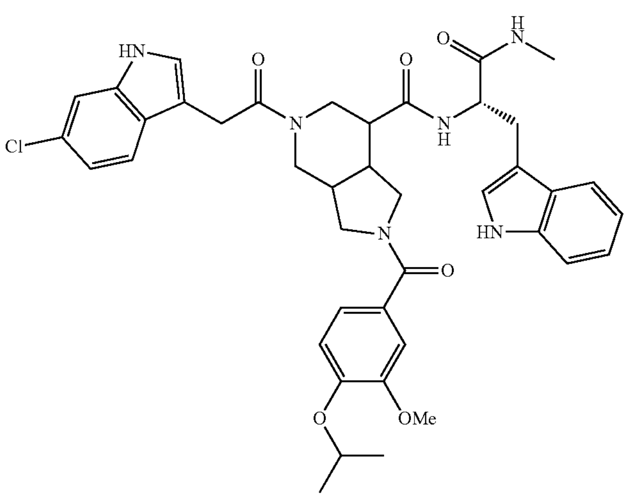 [SMILES: CNC(=O)[C@H](Cc1c[nH]c2ccccc12)NC(=O)C1CN(C(=O)Cc2c[nH]c3cc(Cl)ccc23)CC2CN(C(=O)c3ccc(OC(C)C)c(OC)c3)CC21] |
First eluting diastereomer TABLE 1-continued
Exemplary Compounds
| # | Structure |
|---|---|
| I-111 | 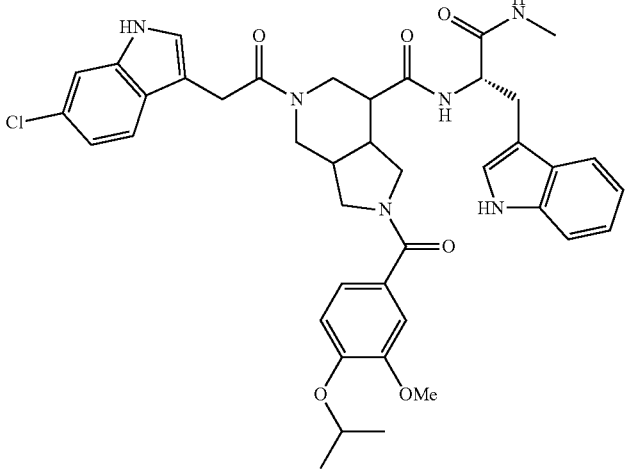<br>Second eluting diastereomer |
| I-112 | 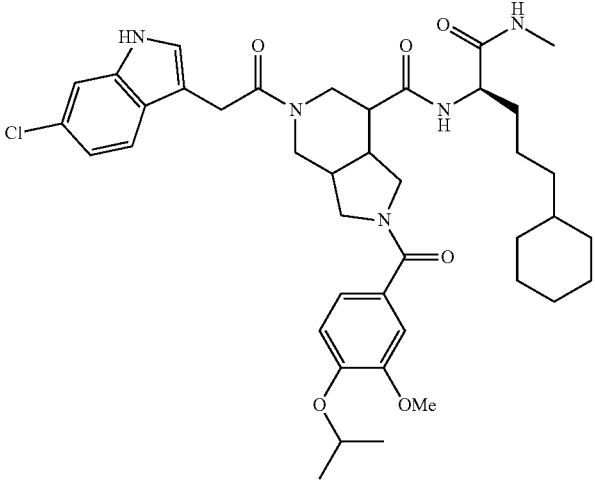 [SMILES: CNC(=O)[C@@H](CCCC1CCCCC1)NC(=O)C1CN(C(=O)Cc2c[nH]c3cc(Cl)ccc23)CC2CN(C(=O)c3ccc(OC(C)C)c(OC)c3)CC21] |
| I-113 | 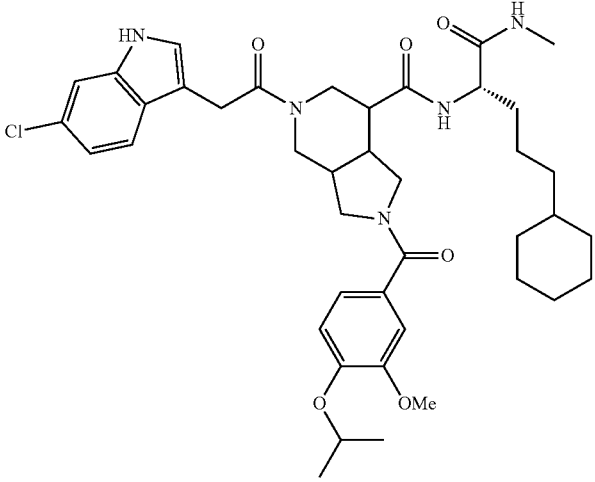 |

TABLE 1-continued
| Exemplary Compounds |
|---|
| # Structure |
I-114
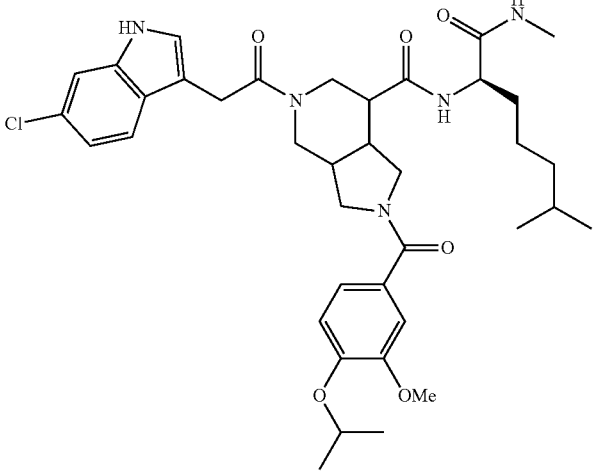
I-115
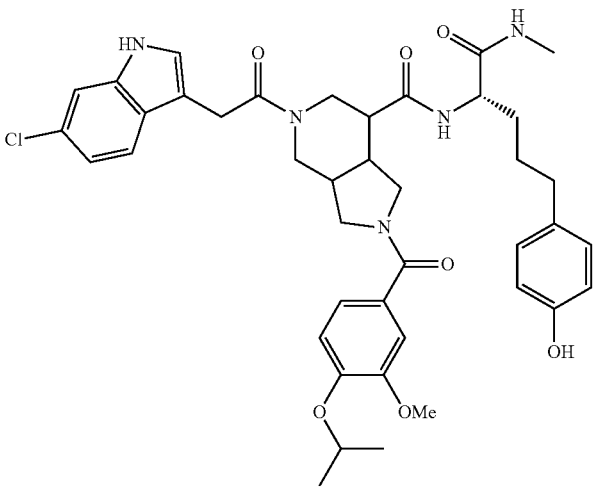 [SMILES: CNC(=O)[C@H](CCCc1ccc(O)cc1)NC(=O)C1CN(C(=O)Cc2c[nH]c3cc(Cl)ccc23)CC2CN(C(=O)c3ccc(OC(C)C)c(OC)c3)CC21]
I-116
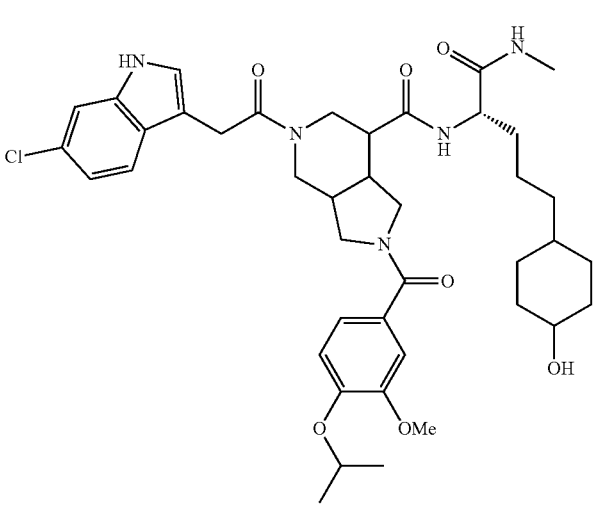 [SMILES: CNC(=O)[C@H](CCCC1CCC(O)CC1)NC(=O)C1CN(C(=O)Cc2c[nH]c3cc(Cl)ccc23)CC2CN(C(=O)c3ccc(OC(C)C)c(OC)c3)CC21]

TABLE 1-continued
| Exemplary Compounds | |
|---|---|
| # | Structure |
I-117
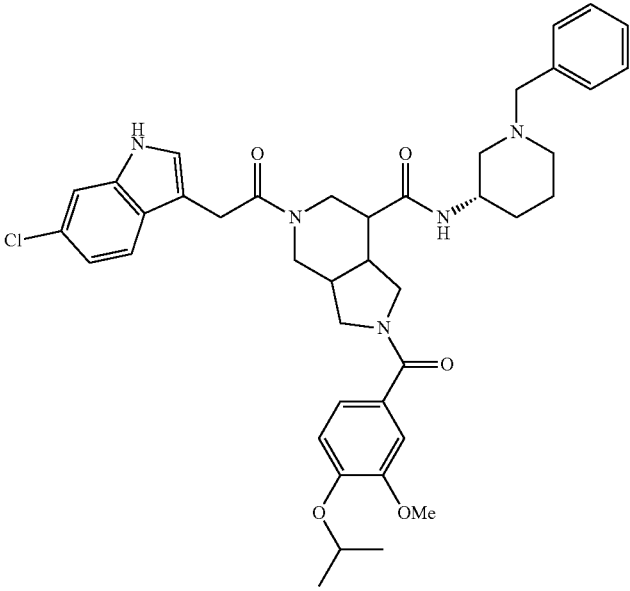 [SMILES: COc1cc(C(=O)N2CC3CN(C(=O)Cc4c[nH]c5cc(Cl)ccc45)CC(C(=O)N[C@H]4CCCN(Cc5ccccc5)C4)C3C2)ccc1OC(C)C]
First eluting diastereomer
I-118
Second eluting diastereomer TABLE 1-continued
Exemplary Compounds
| # | Structure |
|---|---|
| I-119 | 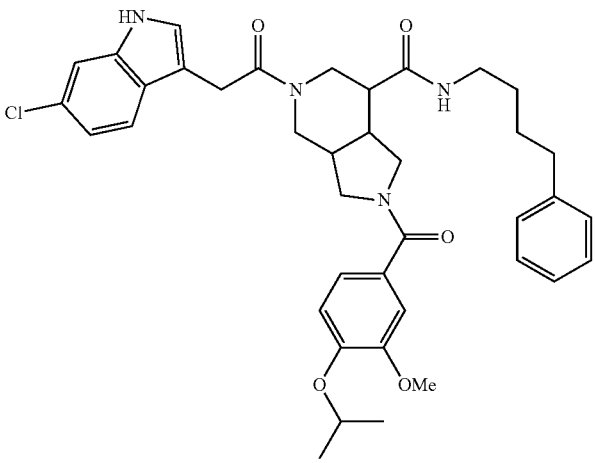 [SMILES: COc1cc(C(=O)N2CC3CN(C(=O)Cc4c[nH]c5cc(Cl)ccc45)CC(C(=O)NCCCCc4ccccc4)C3C2)ccc1OC(C)C] |
| I-120 | 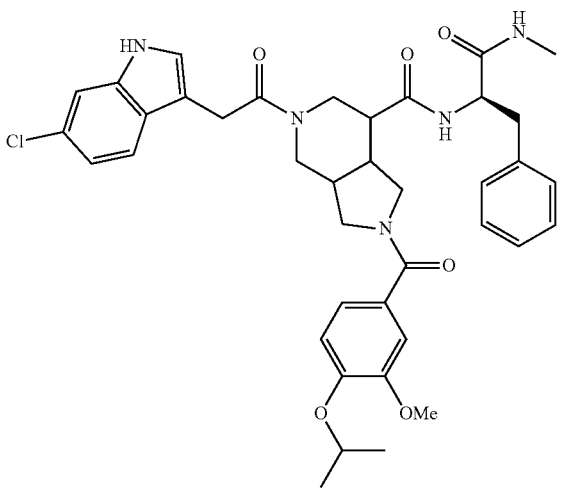 [SMILES: CNC(=O)[C@@H](Cc1ccccc1)NC(=O)C1CN(C(=O)Cc2c[nH]c3cc(Cl)ccc23)CC2CN(C(=O)c3ccc(OC(C)C)c(OC)c3)CC21] |
| I-121 | 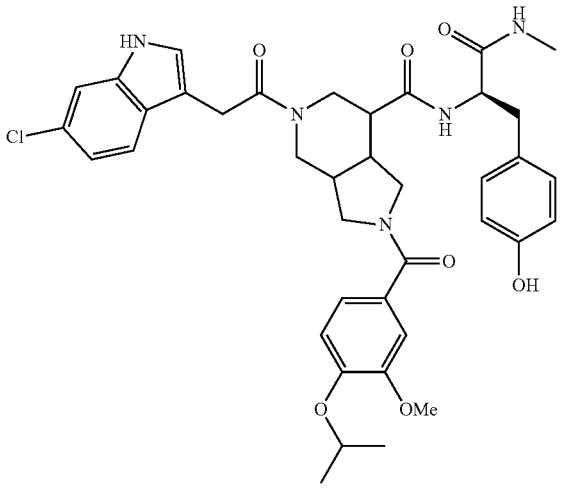 [SMILES: CNC(=O)[C@@H](Cc1ccc(O)cc1)NC(=O)C1CN(C(=O)Cc2c[nH]c3cc(Cl)ccc23)CC2CN(C(=O)c3ccc(OC(C)C)c(OC)c3)CC21] |

TABLE 1-continued

Exemplary Compounds

| # | Structure |
|---|---|
| I-122 | 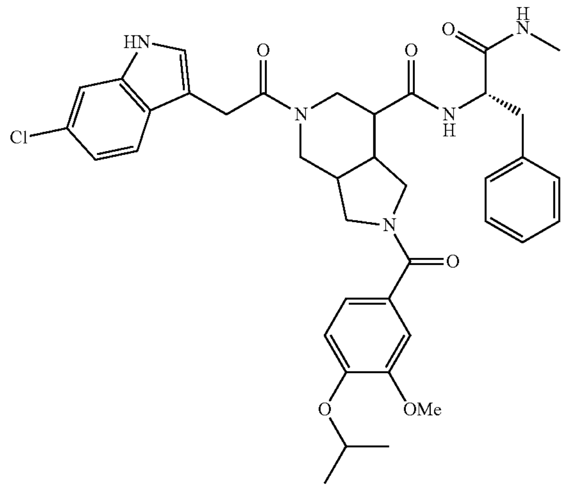 [SMILES: CNC(=O)[C@H](Cc1ccccc1)NC(=O)C1CN(C(=O)Cc2c[nH]c3cc(Cl)ccc23)CC2CN(C(=O)c3ccc(OC(C)C)c(OC)c3)CC21] |
| I-123 | 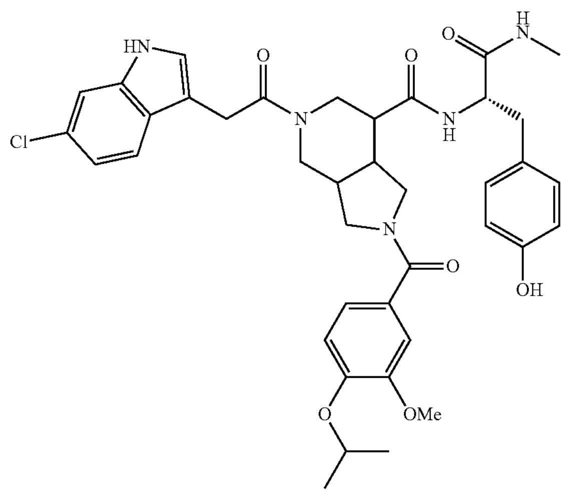 [SMILES: CNC(=O)[C@H](Cc1ccc(O)cc1)NC(=O)C1CN(C(=O)Cc2c[nH]c3cc(Cl)ccc23)CC2CN(C(=O)c3ccc(OC(C)C)c(OC)c3)CC21] |
| I-124 | 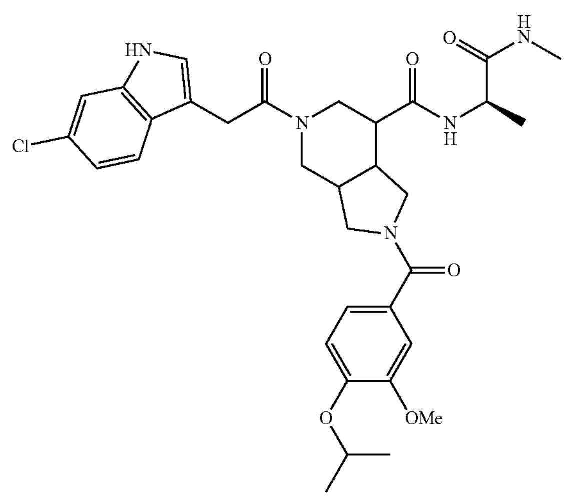 [SMILES: CNC(=O)[C@@H](C)NC(=O)C1CN(C(=O)Cc2c[nH]c3cc(Cl)ccc23)CC2CN(C(=O)c3ccc(OC(C)C)c(OC)c3)CC21] |

TABLE 1-continued
Exemplary Compounds
| # | Structure |
|---|---|
| I-125 | 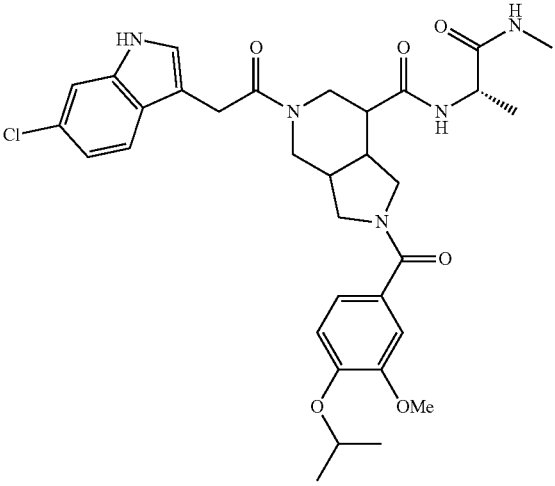 [SMILES: CNC(=O)[C@H](C)NC(=O)C1CN(C(=O)Cc2c[nH]c3cc(Cl)ccc23)CC2CN(C(=O)c3ccc(OC(C)C)c(OC)c3)CC21] |
| I-126 | 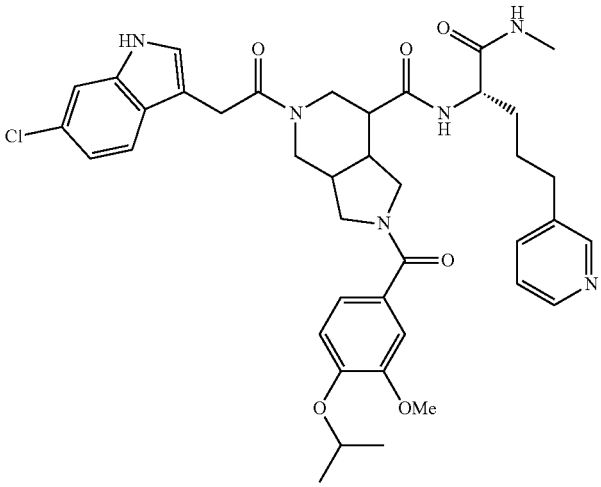 |
| I-127 | 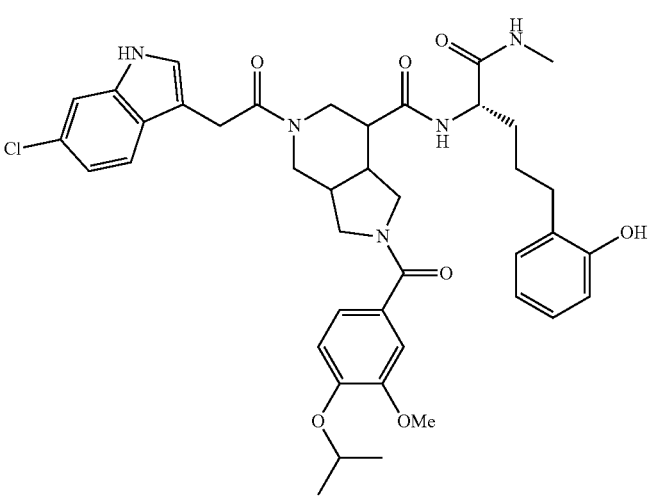 [SMILES: CNC(=O)[C@H](CCCc1ccccc1O)NC(=O)C1CN(C(=O)Cc2c[nH]c3cc(Cl)ccc23)CC2CN(C(=O)c3ccc(OC(C)C)c(OC)c3)CC21] |

TABLE 1-continued

Exemplary Compounds

| # | Structure |
|---|---|
| I-128 | 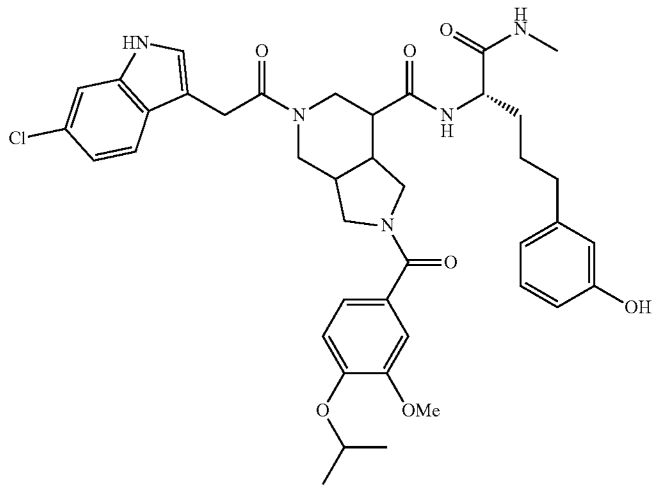 [SMILES: CNC(=O)[C@H](CCCc1cccc(O)c1)NC(=O)C1CN(C(=O)Cc2c[nH]c3cc(Cl)ccc23)CC2CN(C(=O)c3ccc(OC(C)C)c(OC)c3)CC21] |
| I-129 | 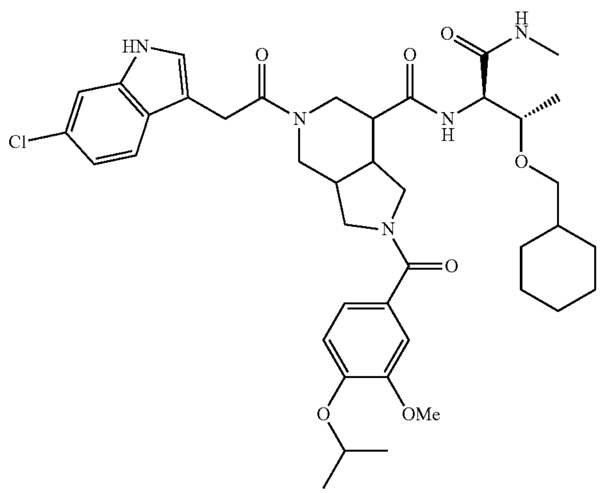 [SMILES: CNC(=O)[C@H](NC(=O)C1CN(C(=O)Cc2c[nH]c3cc(Cl)ccc23)CC2CN(C(=O)c3ccc(OC(C)C)c(OC)c3)CC21)[C@H](C)OCC1CCCCC1] |
| I-130 | 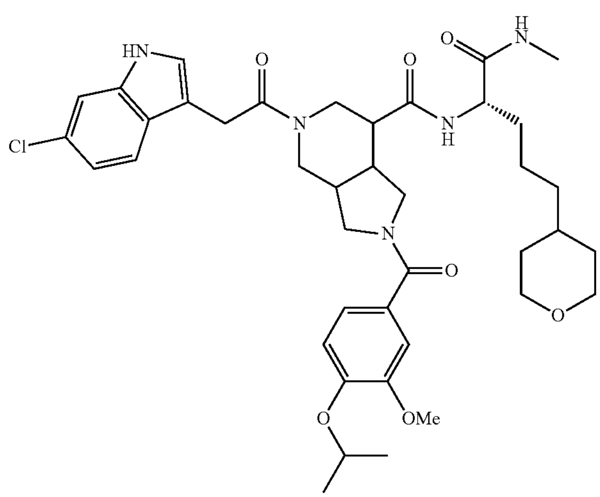 [SMILES: CNC(=O)[C@H](CCCC1CCOCC1)NC(=O)C1CN(C(=O)Cc2c[nH]c3cc(Cl)ccc23)CC2CN(C(=O)c3ccc(OC(C)C)c(OC)c3)CC21] |

TABLE 1-continued

Exemplary Compounds

| # | Structure |
|---|---|
| I-131 | 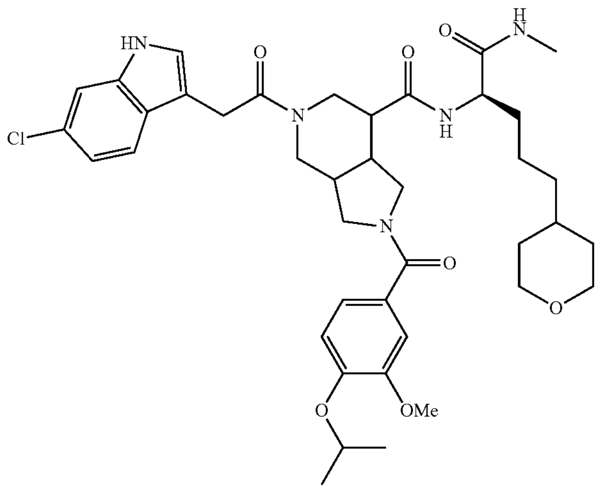 |
| I-132 | 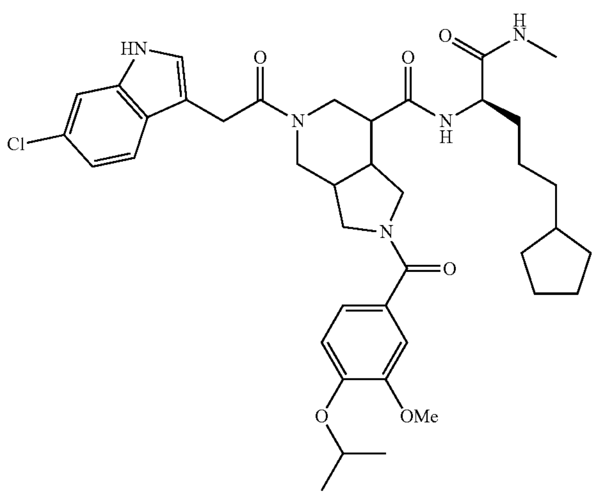 [SMILES: CNC(=O)[C@@H](CCCC1CCCC1)NC(=O)C1CN(C(=O)Cc2c[nH]c3cc(Cl)ccc23)CC2CN(C(=O)c3ccc(OC(C)C)c(OC)c3)CC21] |
| I-133 | 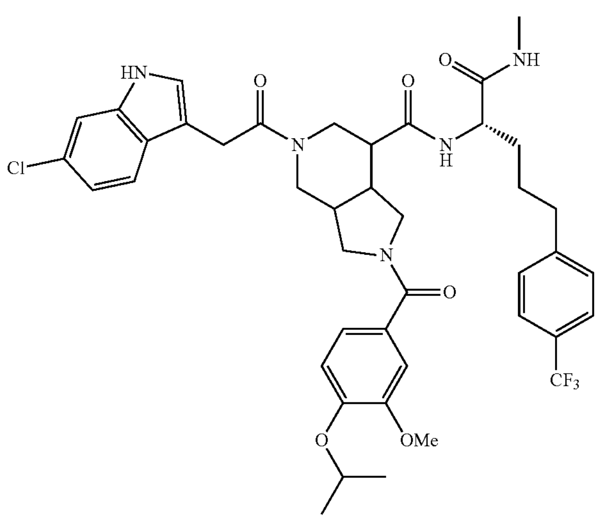 [SMILES: CNC(=O)[C@H](CCCc1ccc(C(F)(F)F)cc1)NC(=O)C1CN(C(=O)Cc2c[nH]c3cc(Cl)ccc23)CC2CN(C(=O)c3ccc(OC(C)C)c(OC)c3)CC21] |

TABLE 1-continued

Exemplary Compounds

| # | Structure |
|---|---|
| I-134 | 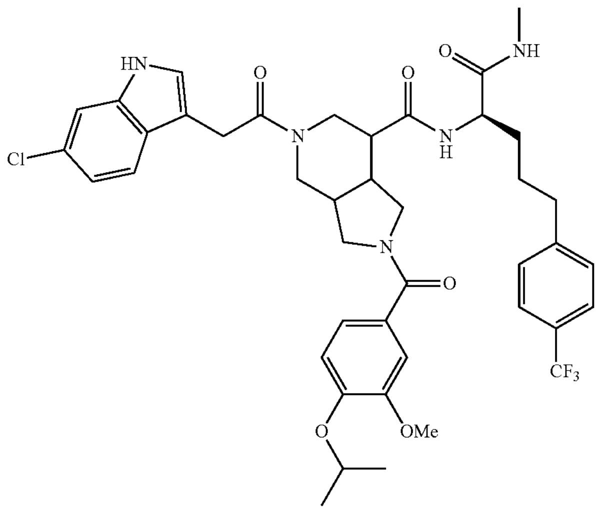 [SMILES: CNC(=O)[C@@H](CCCc1ccc(C(F)(F)F)cc1)NC(=O)C1CN(C(=O)Cc2c[nH]c3cc(Cl)ccc23)CC2CN(C(=O)c3ccc(OC(C)C)c(OC)c3)CC21] |
| I-135 | 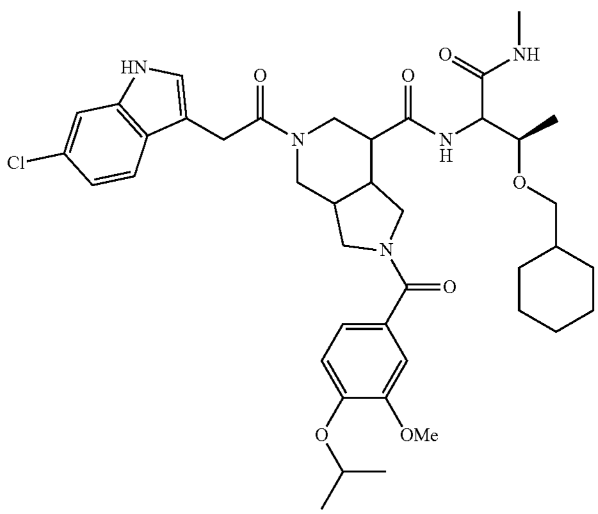 |
| I-136 | 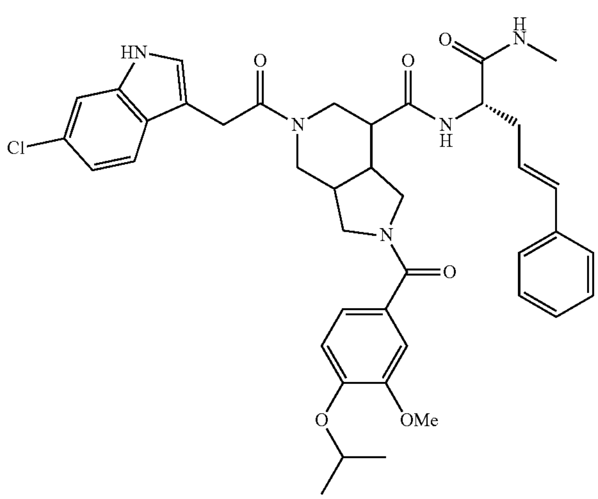 [SMILES: CNC(=O)[C@H](C/C=C/c1ccccc1)NC(=O)C1CN(C(=O)Cc2c[nH]c3cc(Cl)ccc23)CC2CN(C(=O)c3ccc(OC(C)C)c(OC)c3)CC21] |

TABLE 1-continued

Exemplary Compounds

| # | Structure |
|---|---|
| I-137 | 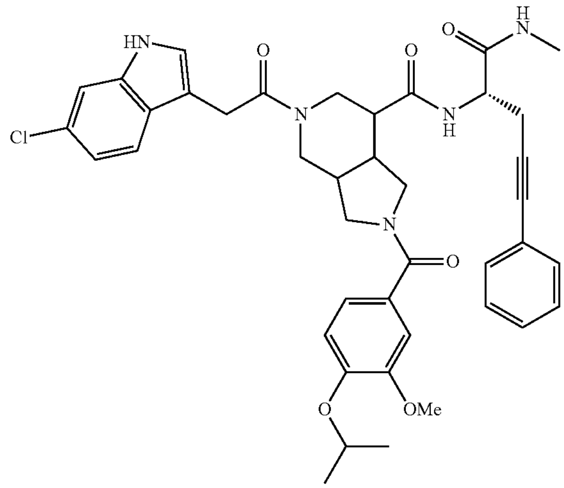 [SMILES: CNC(=O)[C@H](CC#Cc1ccccc1)NC(=O)C1CN(C(=O)Cc2c[nH]c3cc(Cl)ccc23)CC2CN(C(=O)c3ccc(OC(C)C)c(OC)c3)CC21] |
| I-138 | 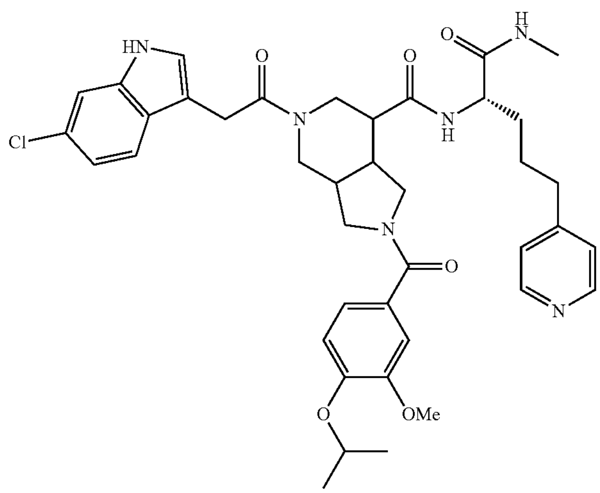 [SMILES: CNC(=O)[C@H](CCCc1ccncc1)NC(=O)C1CN(C(=O)Cc2c[nH]c3cc(Cl)ccc23)CC2CN(C(=O)c3ccc(OC(C)C)c(OC)c3)CC21] |
| I-139 | 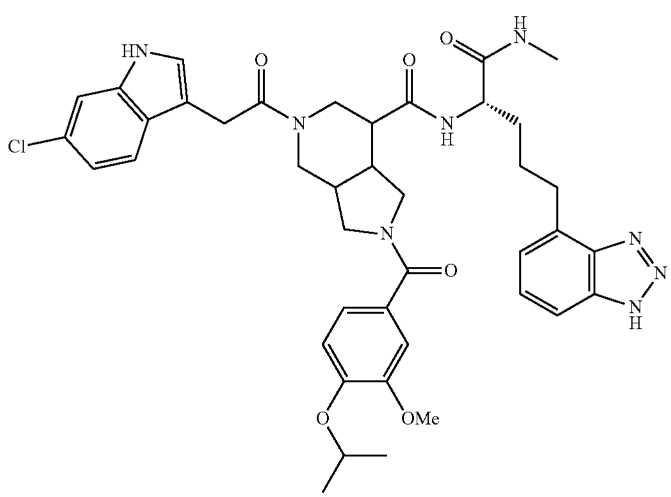 [SMILES: CNC(=O)[C@H](CCCc1cccc2[nH]nnc12)NC(=O)C1CN(C(=O)Cc2c[nH]c3cc(Cl)ccc23)CC2CN(C(=O)c3ccc(OC(C)C)c(OC)c3)CC21] |

TABLE 1-continued
Exemplary Compounds
| # | Structure |
|---|---|
| I-140 | 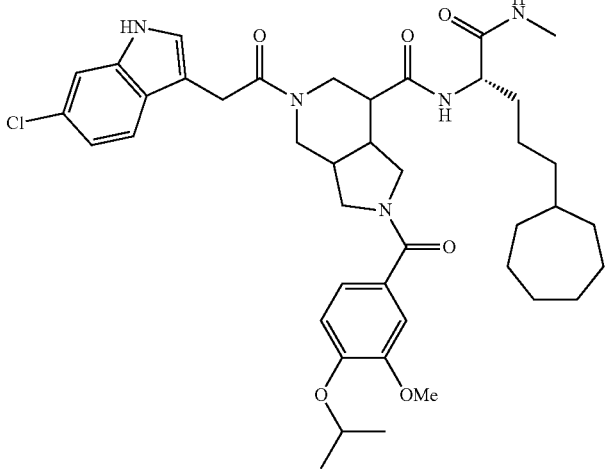 |
| I-141 | 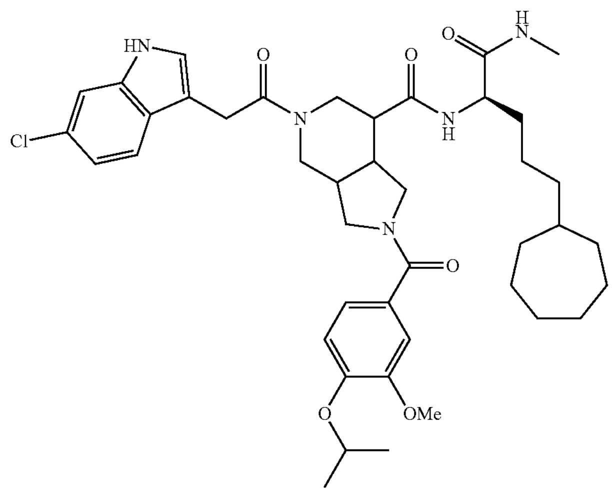 [SMILES: CNC(=O)[C@@H](CCCC1CCCCCC1)NC(=O)C1CN(C(=O)Cc2c[nH]c3cc(Cl)ccc23)CC2CN(C(=O)c3ccc(OC(C)C)c(OC)c3)CC21] |
| I-142 | 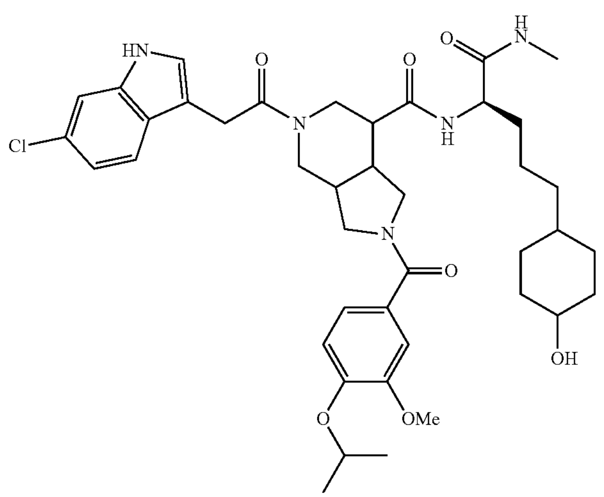 [SMILES: CNC(=O)[C@@H](CCCC1CCC(O)CC1)NC(=O)C1CN(C(=O)Cc2c[nH]c3cc(Cl)ccc23)CC2CN(C(=O)c3ccc(OC(C)C)c(OC)c3)CC21] |

TABLE 1-continued
Exemplary Compounds
| # | Structure |
|---|---|
| I-143 | 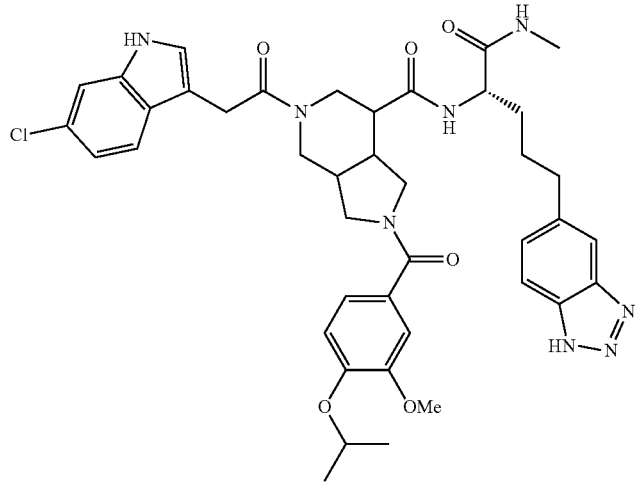 [SMILES: CNC(=O)[C@H](CCCc1ccc2[nH]nnc2c1)NC(=O)C1CN(C(=O)Cc2c[nH]c3cc(Cl)ccc23)CC2CN(C(=O)c3ccc(OC(C)C)c(OC)c3)CC21] |
| I-144 | 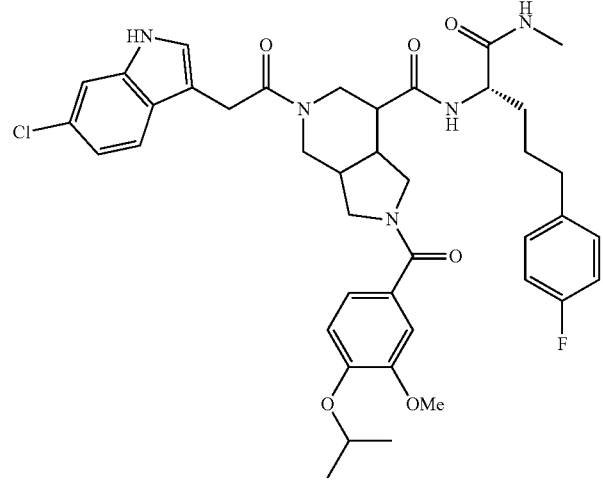 [SMILES: CNC(=O)[C@H](CCCc1ccc(F)cc1)NC(=O)C1CN(C(=O)Cc2c[nH]c3cc(Cl)ccc23)CC2CN(C(=O)c3ccc(OC(C)C)c(OC)c3)CC21] |
| I-145 | 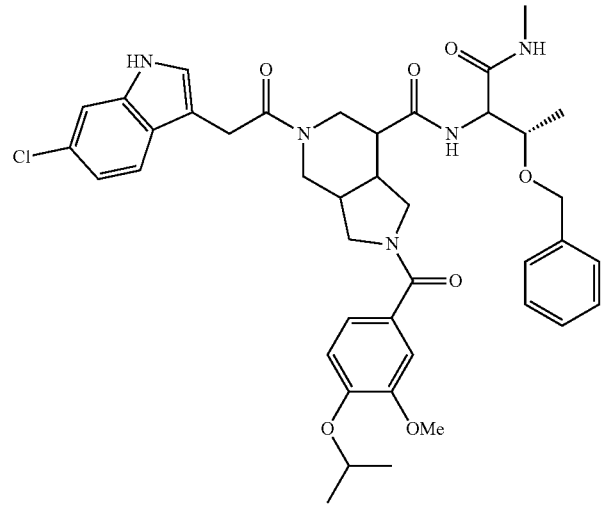 [SMILES: CNC(=O)C(NC(=O)C1CN(C(=O)Cc2c[nH]c3cc(Cl)ccc23)CC2CN(C(=O)c3ccc(OC(C)C)c(OC)c3)CC21)[C@H](C)OCc1ccccc1] |
First eluting diastereomer - n-Hexane/EtOH TABLE 1-continued
Exemplary Compounds
| # | Structure |
|---|---|
| I-146 | 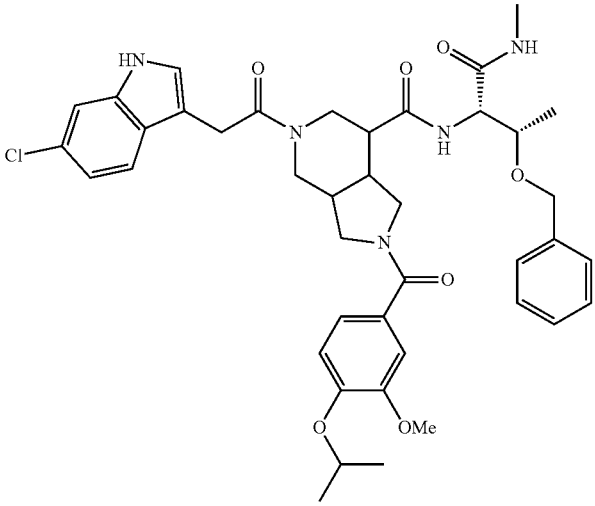<br>Second eluting diastereomer - n-Hexane/EtOH |
| I-147 | 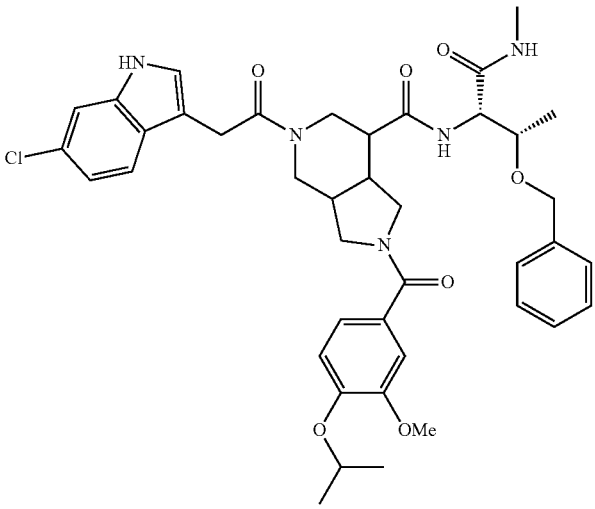 [SMILES: CNC(=O)[C@@H](NC(=O)C1CN(C(=O)Cc2c[nH]c3cc(Cl)ccc23)CC2CN(C(=O)c3ccc(OC(C)C)c(OC)c3)CC21)[C@H](C)OCc1ccccc1]<br>First eluting diastereomer - H₂O/Acetonitrile |

TABLE 1-continued
Exemplary Compounds
| # | Structure |
|---|-----------|
| I-148 | 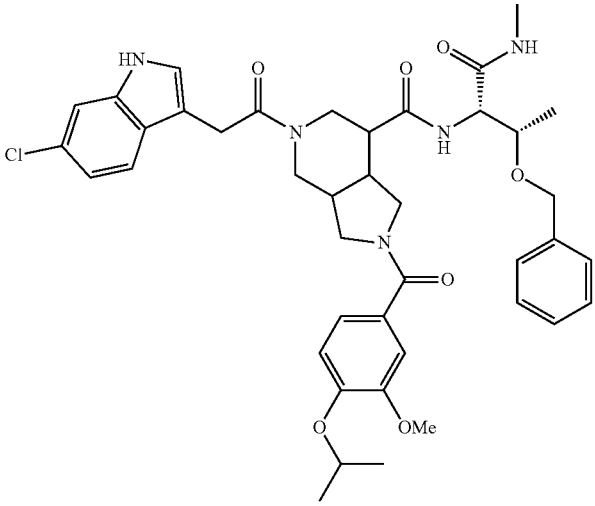 [SMILES: CNC(=O)[C@@H](NC(=O)C1CN(C(=O)Cc2c[nH]c3cc(Cl)ccc23)CC2CN(C(=O)c3ccc(OC(C)C)c(OC)c3)CC21)[C@H](C)OCc1ccccc1] Second eluting diastereomer - H₂O/Acetonitrile |
| I-149 | 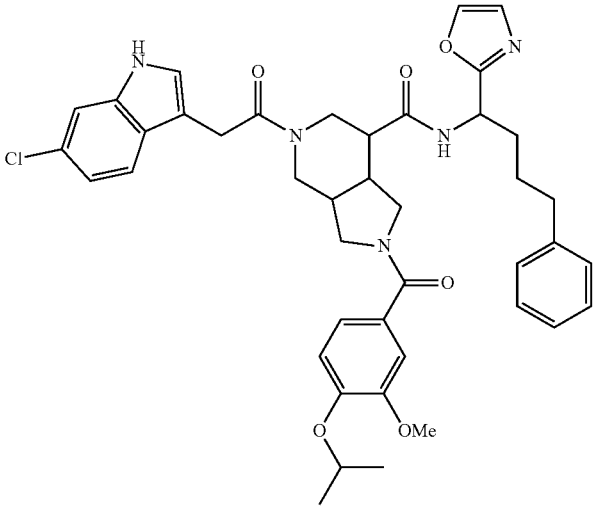 [SMILES: COc1cc(C(=O)N2CC3CN(C(=O)Cc4c[nH]c5cc(Cl)ccc45)CC(C(=O)NC(CCCc4ccccc4)c4ncco4)C3C2)ccc1OC(C)C] |

TABLE 1-continued
Exemplary Compounds
| # | Structure |
|---|---|
| I-150 | 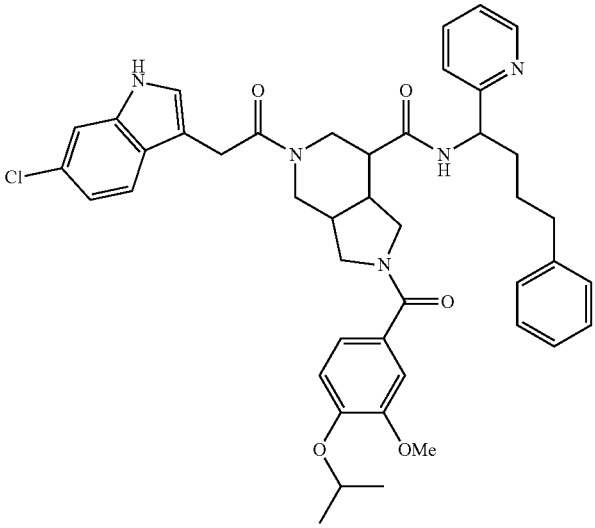 |
| I-151 | 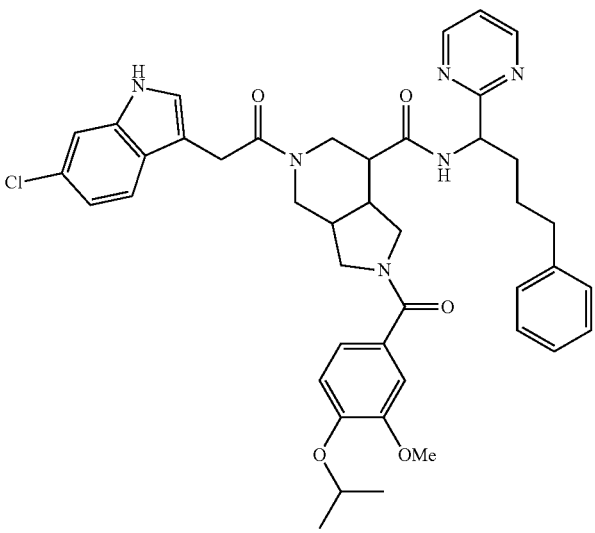 [SMILES: COc1cc(C(=O)N2CC3CN(C(=O)Cc4c[nH]c5cc(Cl)ccc45)CC(C(=O)NC(CCCc4ccccc4)c4ccccn4)C3C2)ccc1OC(C)C] |
| I-152 | 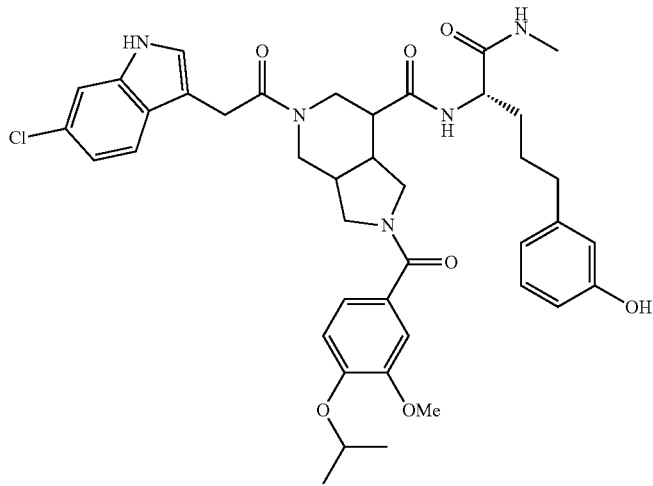 [SMILES: CNC(=O)[C@H](CCCc1cccc(O)c1)NC(=O)C1CN(C(=O)Cc2c[nH]c3cc(Cl)ccc23)CC2CN(C(=O)c3ccc(OC(C)C)c(OC)c3)CC21]<br>First eluting diastereomer |

TABLE 1-continued
Exemplary Compounds
| # | Structure |
|---|---|
| I-153 | 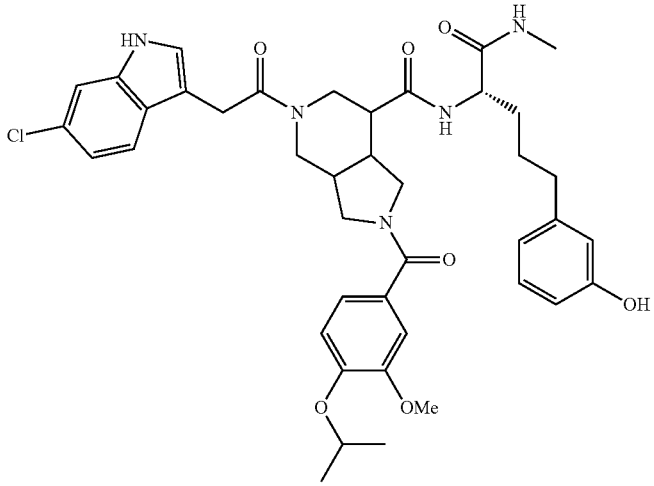 [SMILES: CNC(=O)[C@H](CCCc1cccc(O)c1)NC(=O)C1CN(C(=O)Cc2c[nH]c3cc(Cl)ccc23)CC2CN(C(=O)c3ccc(OC(C)C)c(OC)c3)CC21]<br>Second eluting diastereomer |
| I-154 | 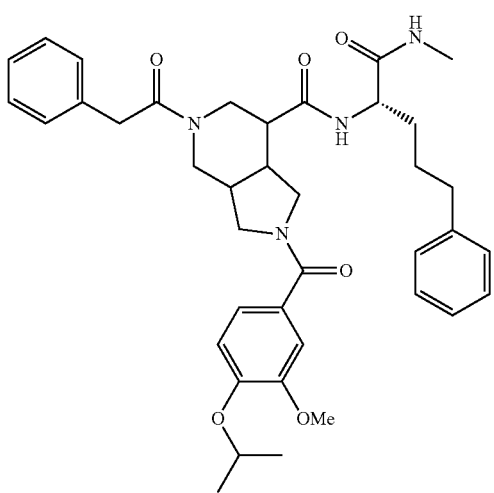 [SMILES: CNC(=O)[C@H](CCCc1ccccc1)NC(=O)C1CN(C(=O)Cc2ccccc2)CC2CN(C(=O)c3ccc(OC(C)C)c(OC)c3)CC21] |
| I-155 | 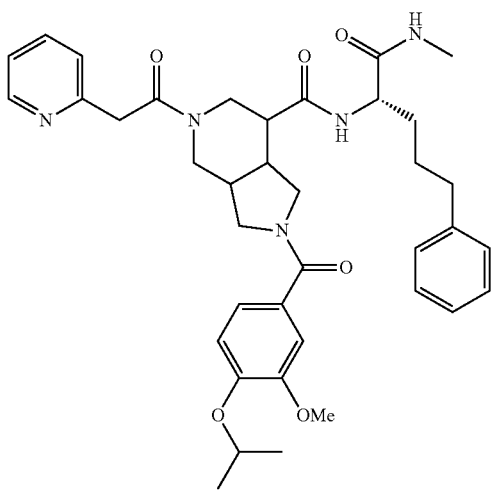 |

TABLE 1-continued
Exemplary Compounds
| # | Structure |
|---|---|
| I-156 | 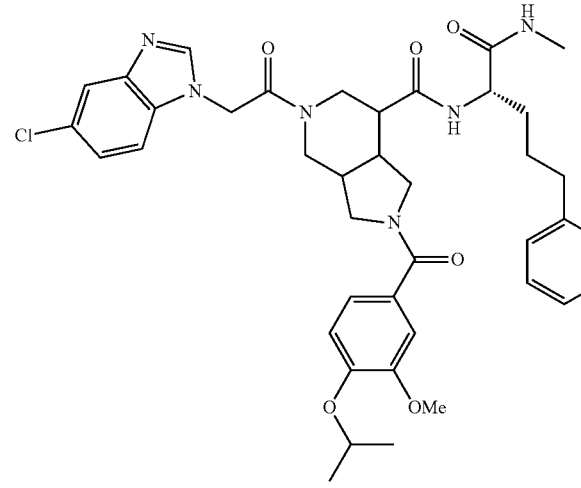 |
| I-157 | 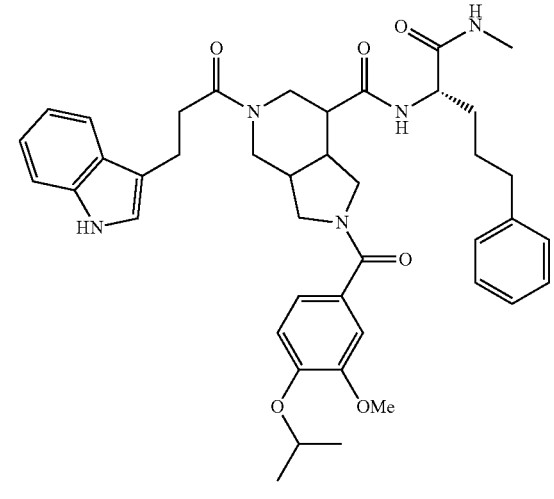 [SMILES: CNC(=O)[C@H](CCCc1ccccc1)NC(=O)C1CN(C(=O)CCc2c[nH]c3ccccc23)CC2CN(C(=O)c3ccc(OC(C)C)c(OC)c3)CC21] |
| I-158 | 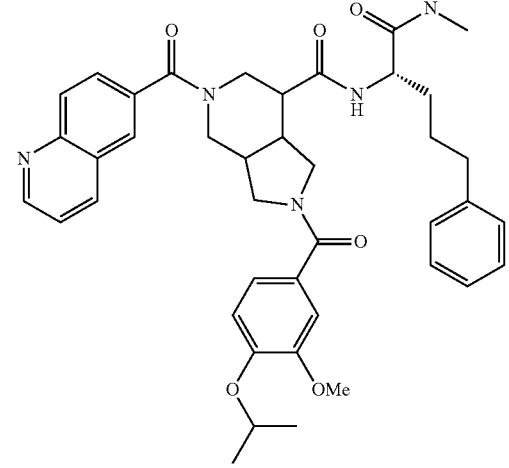 |

171
172
TABLE 1-continued
Exemplary Compounds
| # | Structure |
|---|---|
| I-159 | 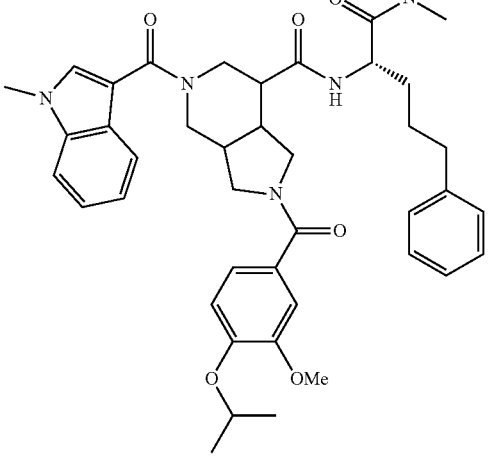 |
| I-160 | 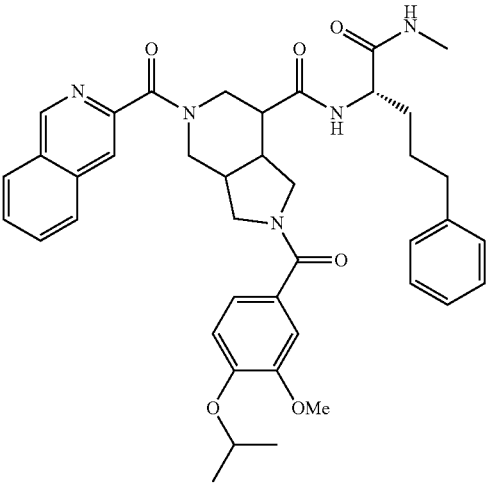 [SMILES: CNC(=O)[C@H](CCCc1ccccc1)NC(=O)C1CN(C(=O)c2cc3ccccc3cn2)CC2CN(C(=O)c3ccc(OC(C)C)c(OC)c3)CC21] |
| I-161 | 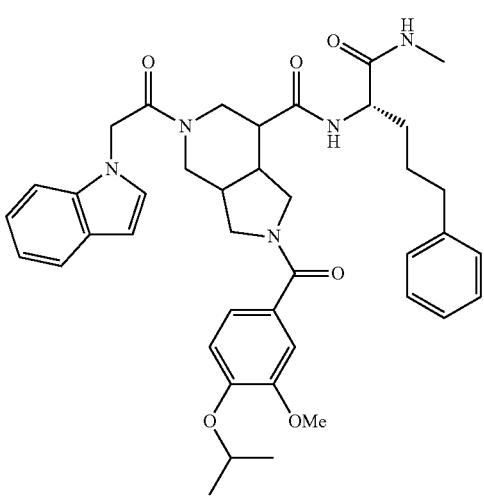 [SMILES: CNC(=O)[C@H](CCCc1ccccc1)NC(=O)C1CN(C(=O)Cn2ccc3ccccc32)CC2CN(C(=O)c3ccc(OC(C)C)c(OC)c3)CC21] |

TABLE 1-continued
Exemplary Compounds
| # | Structure |
|---|---|
| I-162 | 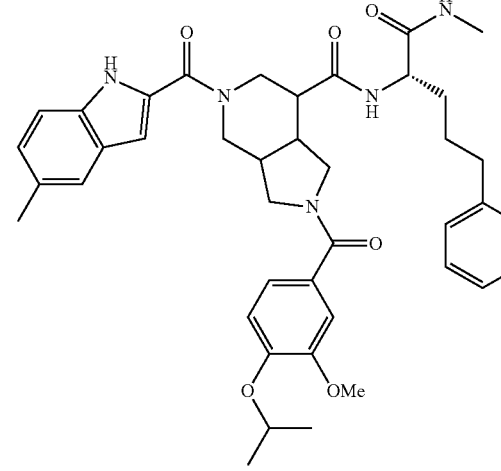 |
| I-163 | 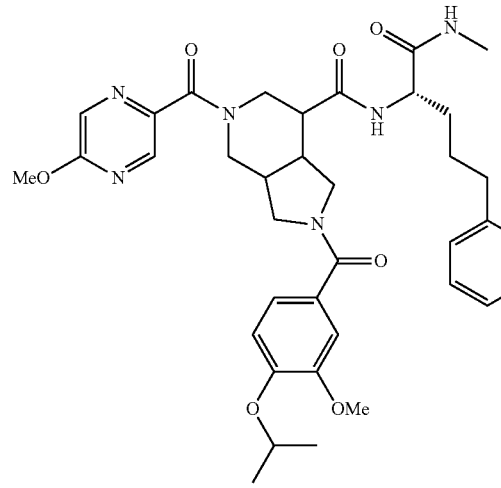 |
| I-164 | 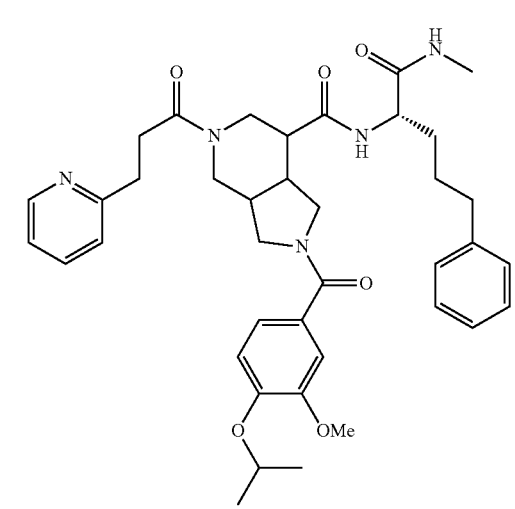 [SMILES: CNC(=O)[C@H](CCCc1ccccc1)NC(=O)C1CN(C(=O)CCc2ccccn2)CC2CN(C(=O)c3ccc(OC(C)C)c(OC)c3)CC21] |

TABLE 1-continued
Exemplary Compounds
| # | Structure |
|---|---|
| I-165 | 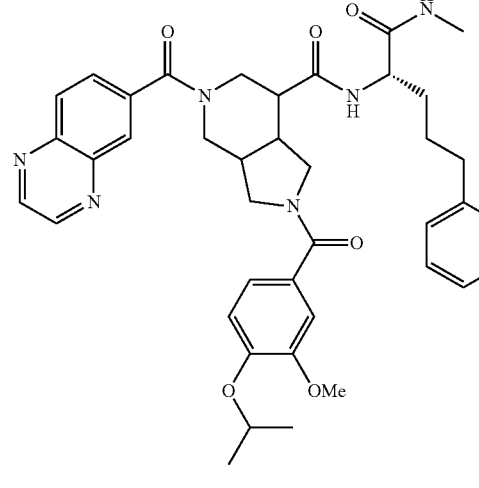 |
| I-166 | 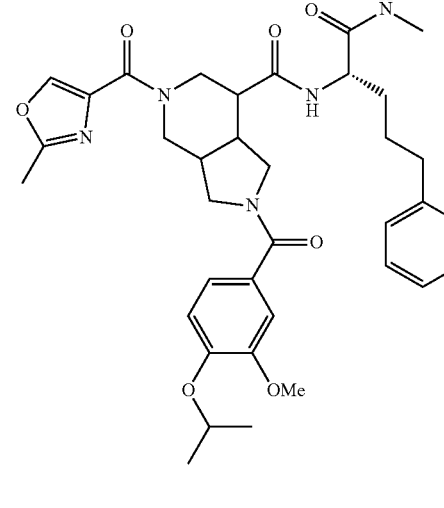 |
| I-167 | 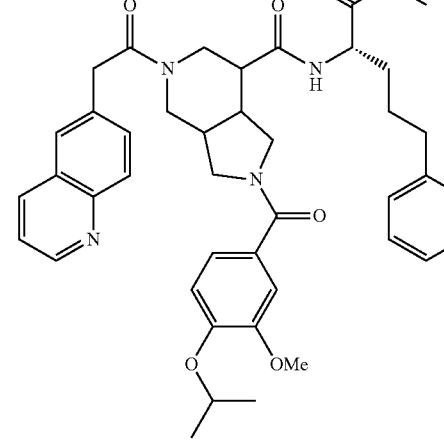 |

TABLE 1-continued
Exemplary Compounds
| # | Structure |
|---|---|
| I-168 | 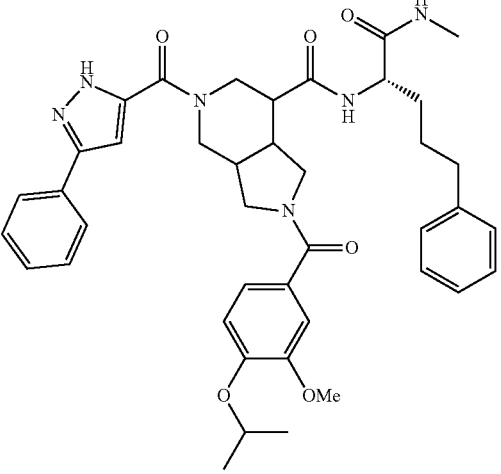 |
| I-169 | 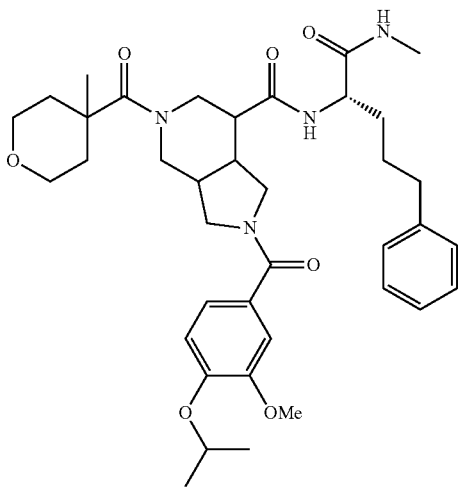 [SMILES: CNC(=O)[C@H](CCCc1ccccc1)NC(=O)C1CN(C(=O)C2(C)CCOCC2)CC2CN(C(=O)c3ccc(OC(C)C)c(OC)c3)CC21] |
| I-170 | 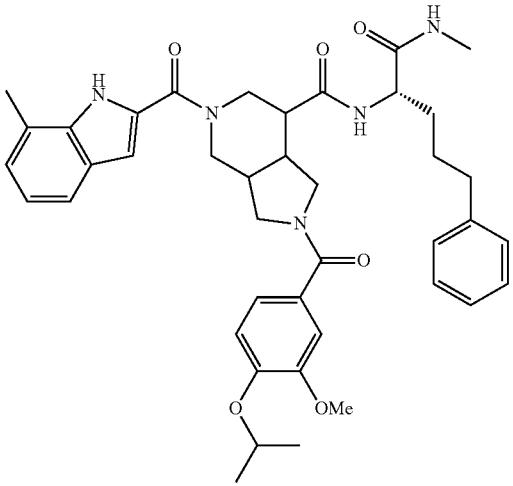 [SMILES: CNC(=O)[C@H](CCCc1ccccc1)NC(=O)C1CN(C(=O)c2cc3cccc(C)c3[nH]2)CC2CN(C(=O)c3ccc(OC(C)C)c(OC)c3)CC21] |

TABLE 1-continued

Exemplary Compounds

| # | Structure |
|---|---|
| I-171 | 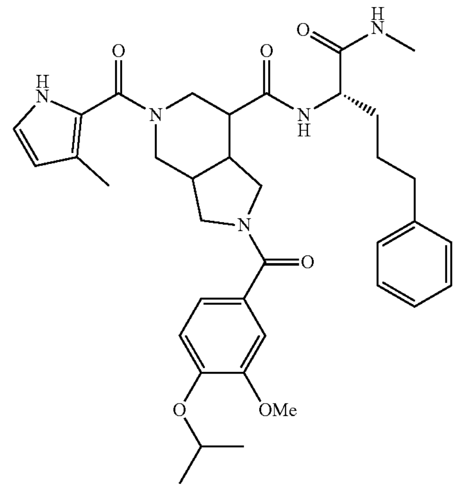 [SMILES: CNC(=O)[C@H](CCCc1ccccc1)NC(=O)C1CN(C(=O)c2[nH]ccc2C)CC2CN(C(=O)c3ccc(OC(C)C)c(OC)c3)CC21] |
| I-172 | 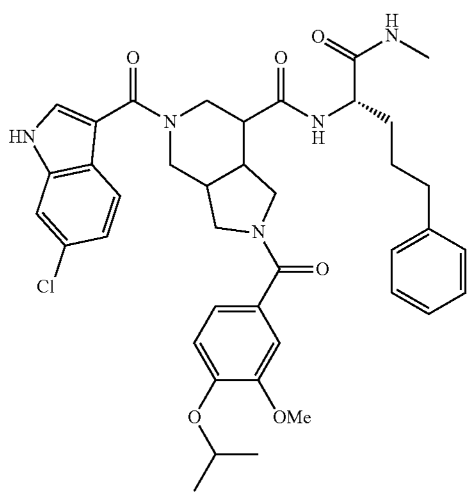 |
| I-173 | 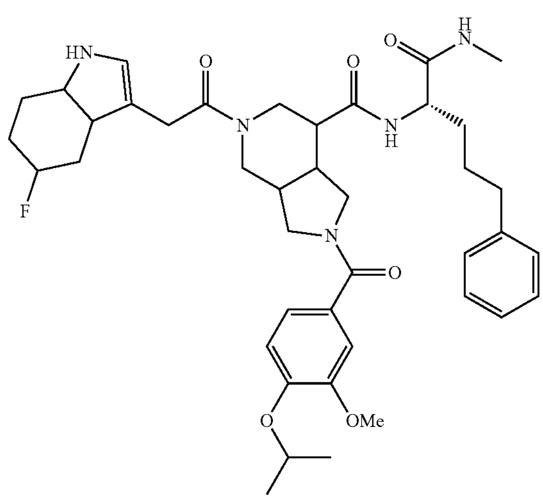 [SMILES: CNC(=O)[C@H](CCCc1ccccc1)NC(=O)C1CN(C(=O)CC2=CNC3CCC(F)CC23)CC2CN(C(=O)c3ccc(OC(C)C)c(OC)c3)CC21] |

TABLE 1-continued
Exemplary Compounds
| # | Structure |
|---|---|
| I-174 | 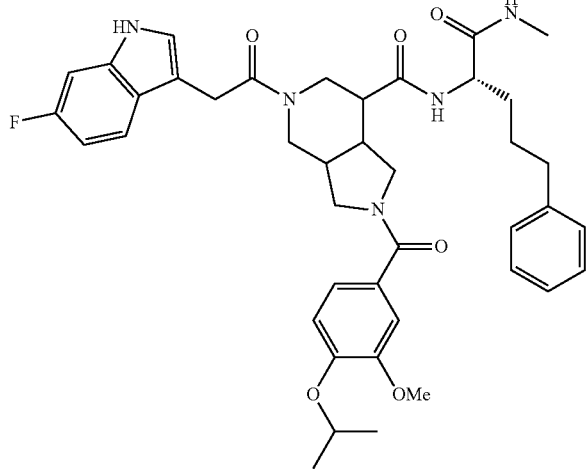 |
| I-175 | 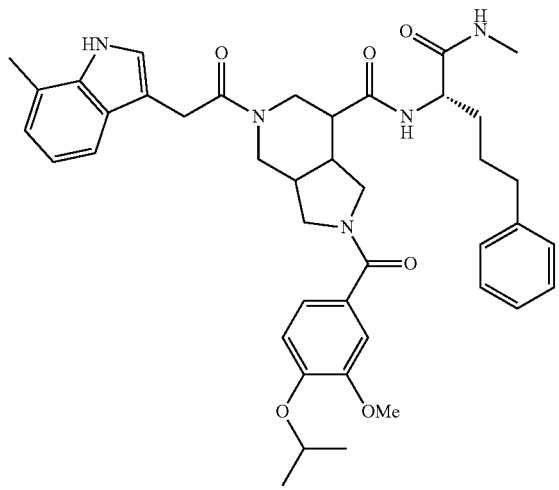 [SMILES: CNC(=O)[C@H](CCCc1ccccc1)NC(=O)C1CN(C(=O)Cc2c[nH]c3c(C)cccc23)CC2CN(C(=O)c3ccc(OC(C)C)c(OC)c3)CC21] |
| I-176 | 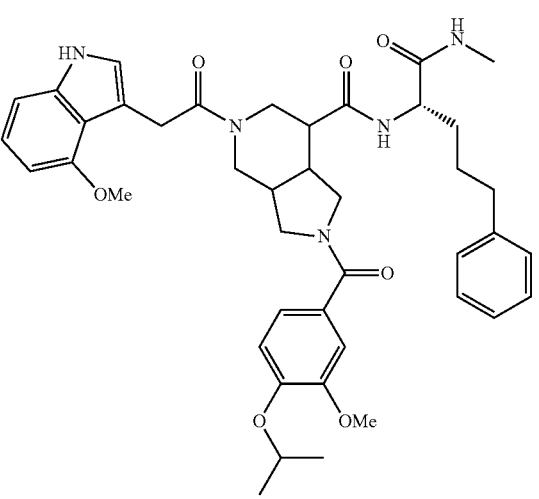 [SMILES: CNC(=O)[C@H](CCCc1ccccc1)NC(=O)C1CN(C(=O)Cc2c[nH]c3cccc(OC)c23)CC2CN(C(=O)c3ccc(OC(C)C)c(OC)c3)CC21] |

TABLE 1-continued
Exemplary Compounds
| # | Structure |
|---|---|
| I-177 | 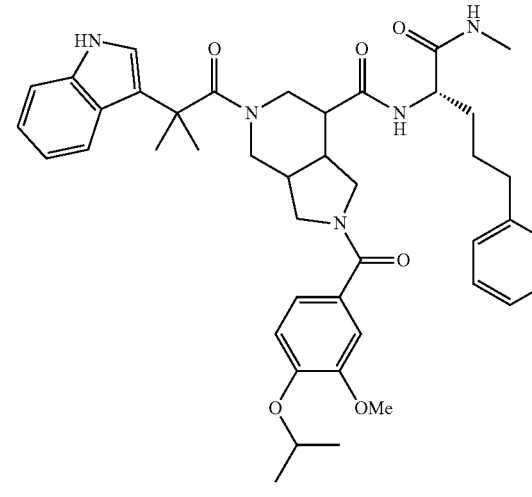 |
| I-178 | 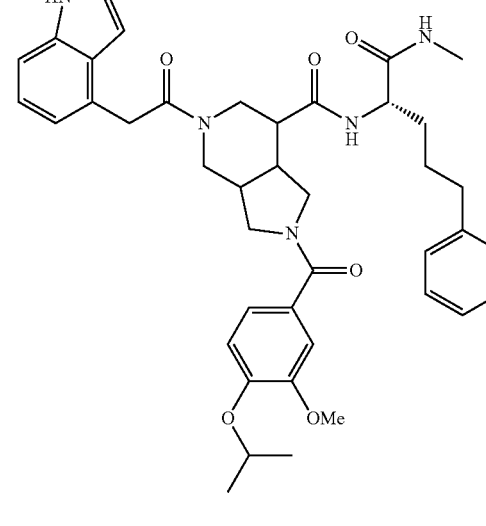 |
| I-179 | 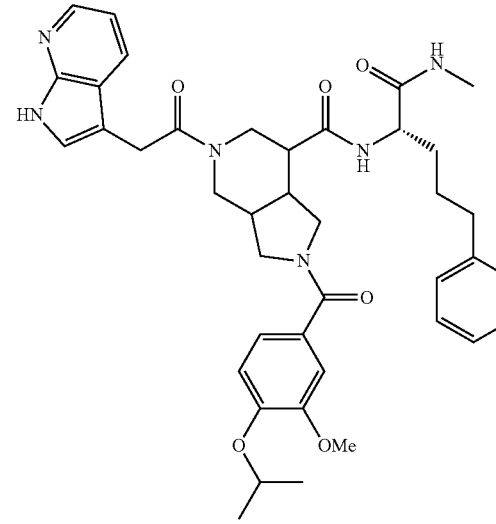 |

TABLE 1-continued
Exemplary Compounds
| # | Structure |
|---|---|
| I-180 | 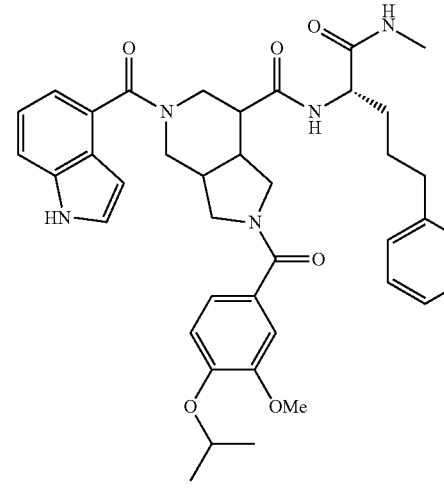 |
| I-181 | 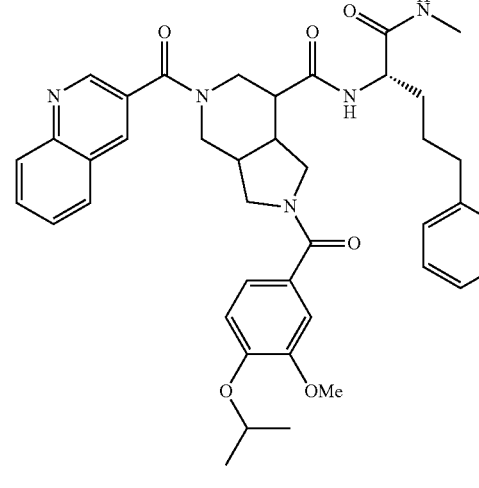 |
| I-182 | 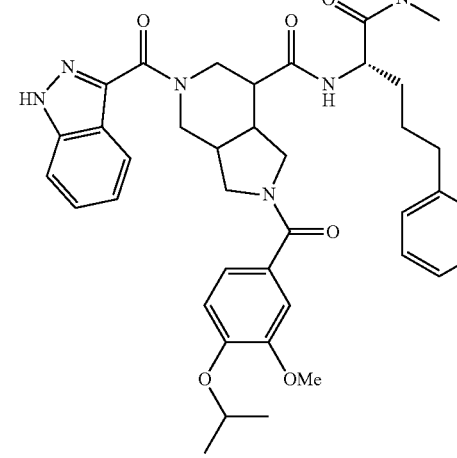 |

187 188
TABLE 1-continued
Exemplary Compounds
| # | Structure |
|---|---|
| I-183 | 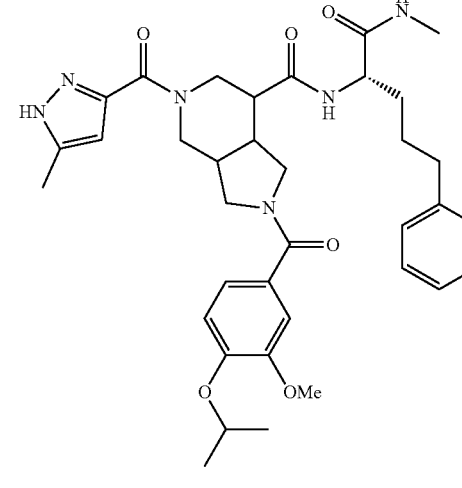 |
| I-184 | 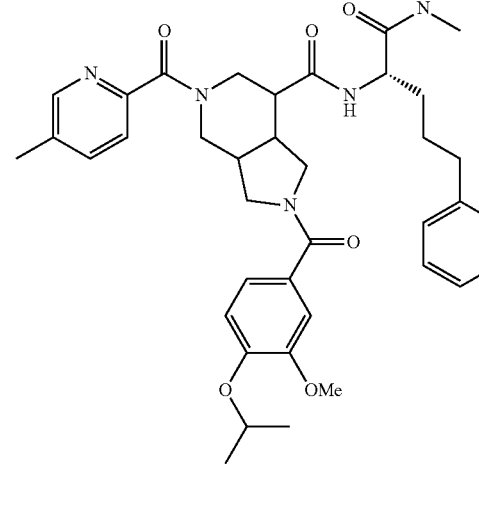 |
| I-185 | 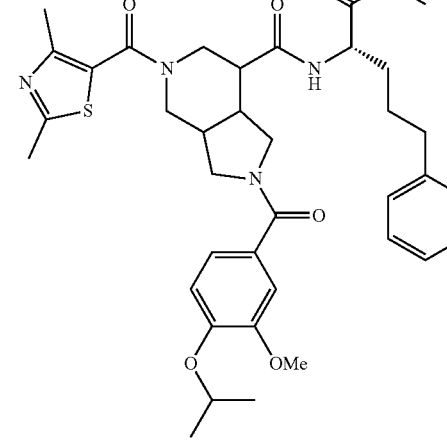 |

TABLE 1-continued

Exemplary Compounds

| # | Structure |
|---|---|
| I-186 | *(chemical structure)* |
| I-187 | *(chemical structure)* |
| I-188 | *(chemical structure)* |

TABLE 1-continued
Exemplary Compounds
| # | Structure |
|---|---|
| I-189 | 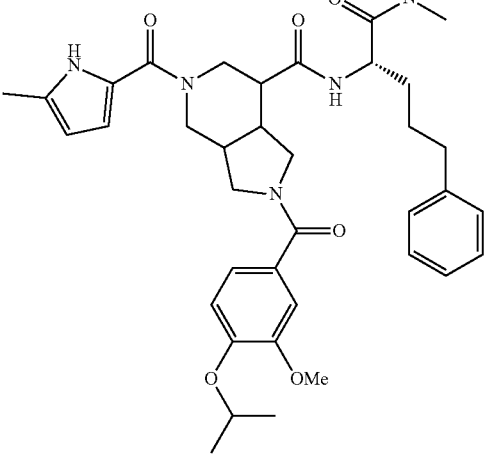 |
| I-190 | 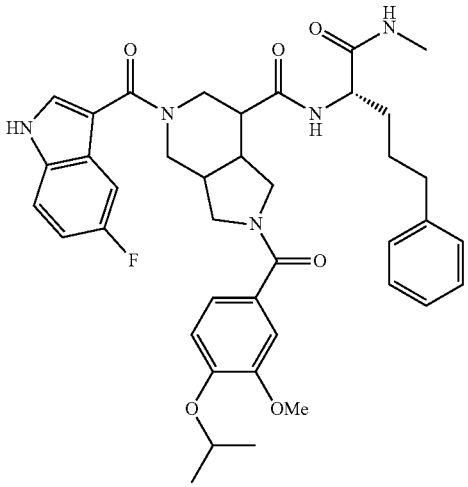 [SMILES: CNC(=O)[C@H](CCCc1ccccc1)NC(=O)C1CN(C(=O)c2c[nH]c3ccc(F)cc23)CC2CN(C(=O)c3ccc(OC(C)C)c(OC)c3)CC21] |
| I-191 | 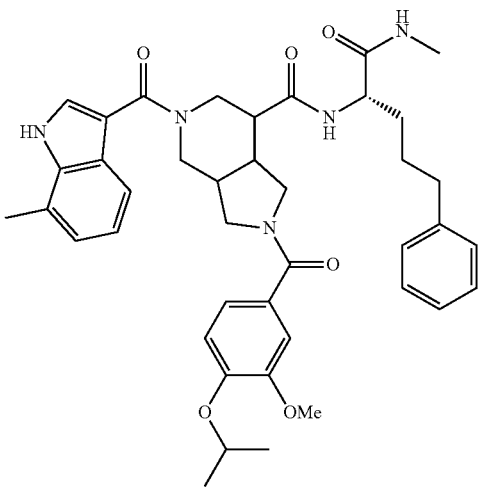 [SMILES: CNC(=O)[C@H](CCCc1ccccc1)NC(=O)C1CN(C(=O)c2c[nH]c3c(C)cccc23)CC2CN(C(=O)c3ccc(OC(C)C)c(OC)c3)CC21] |

TABLE 1-continued

Exemplary Compounds

| # | Structure |
|---|---|
| I-192 | 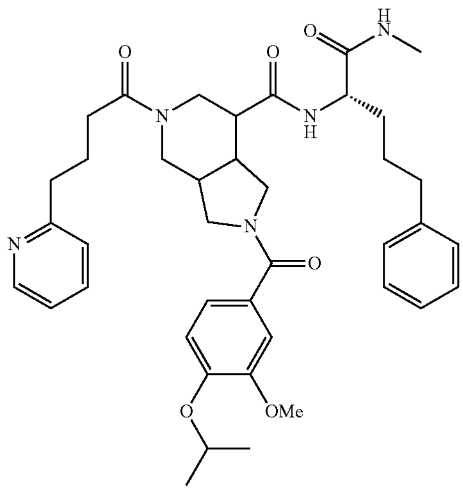 [SMILES: CNC(=O)[C@H](CCCc1ccccc1)NC(=O)C1CN(C(=O)CCCc2ccccn2)CC2CN(C(=O)c3ccc(OC(C)C)c(OC)c3)CC21] |
| I-193 | 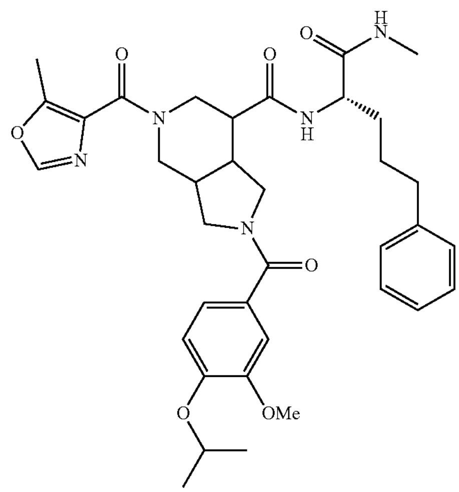 [SMILES: CNC(=O)[C@H](CCCc1ccccc1)NC(=O)C1CN(C(=O)c2ncoc2C)CC2CN(C(=O)c3ccc(OC(C)C)c(OC)c3)CC21] |
| I-194 | 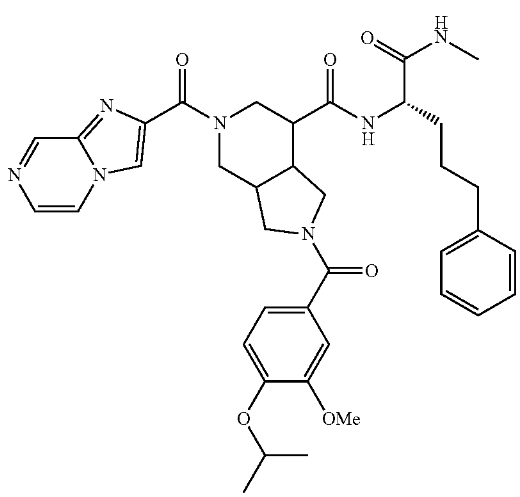 [SMILES: CNC(=O)[C@H](CCCc1ccccc1)NC(=O)C1CN(C(=O)c2cn3ccncc3n2)CC2CN(C(=O)c3ccc(OC(C)C)c(OC)c3)CC21] |

First eluting diastereomer 195 196
TABLE 1-continued
Exemplary Compounds
| # | Structure |
|---|---|
| I-195 | 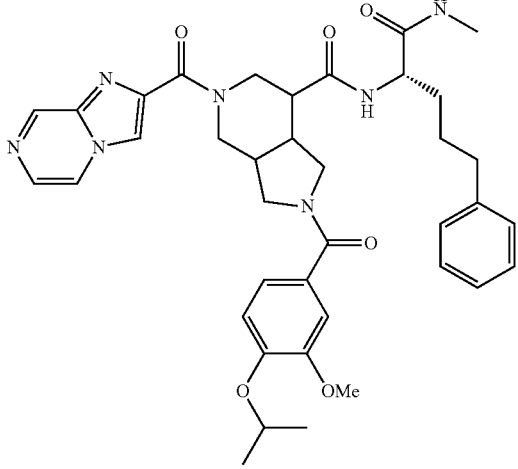<br>Second eluting diastereomer |
| I-196 | 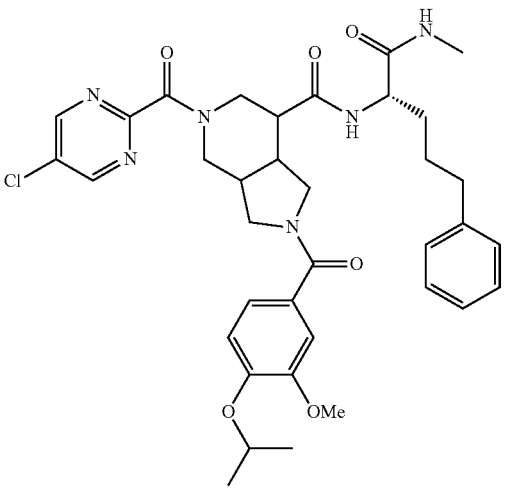 [SMILES: CNC(=O)[C@H](CCCc1ccccc1)NC(=O)C1CN(C(=O)c2ncc(Cl)cn2)CC2CN(C(=O)c3ccc(OC(C)C)c(OC)c3)CC21] |
| I-197 | 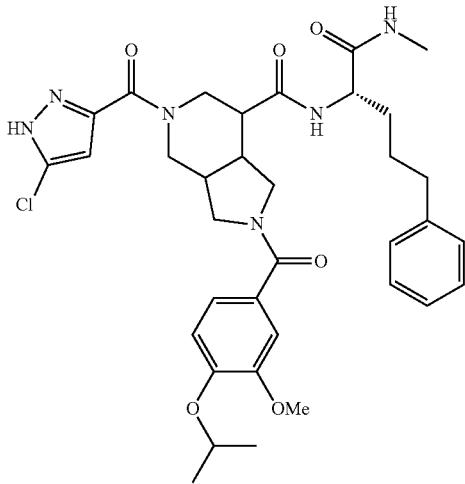 |

TABLE 1-continued
Exemplary Compounds
| # | Structure |
|---|---|
| I-198 | 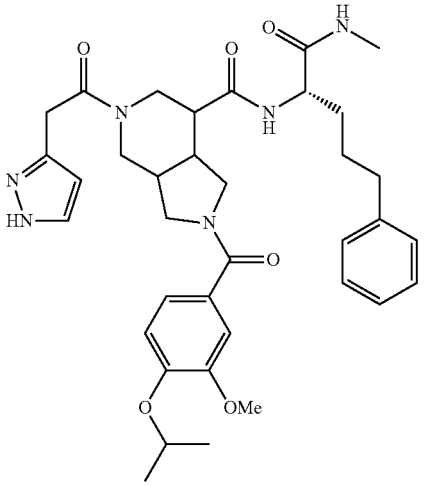 [SMILES: CNC(=O)[C@H](CCCc1ccccc1)NC(=O)C1CN(C(=O)Cc2cc[nH]n2)CC2CN(C(=O)c3ccc(OC(C)C)c(OC)c3)CC21] |
| I-199 | 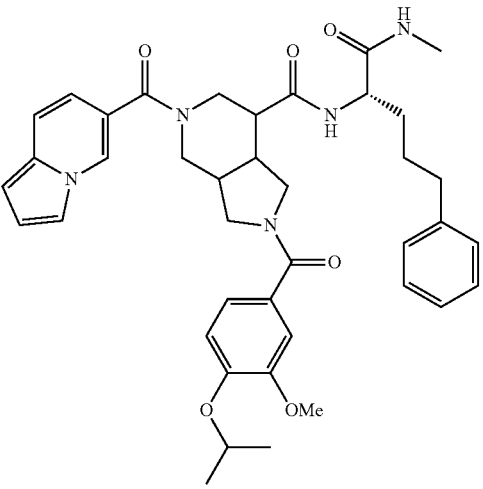 [SMILES: CNC(=O)[C@H](CCCc1ccccc1)NC(=O)C1CN(C(=O)c2ccc3cccn3c2)CC2CN(C(=O)c3ccc(OC(C)C)c(OC)c3)CC21] |
| I-200 | 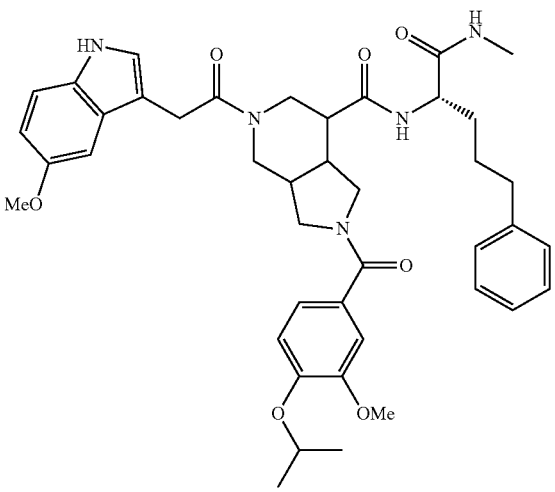 [SMILES: CNC(=O)[C@H](CCCc1ccccc1)NC(=O)C1CN(C(=O)Cc2c[nH]c3ccc(OC)cc23)CC2CN(C(=O)c3ccc(OC(C)C)c(OC)c3)CC21] |

TABLE 1-continued
Exemplary Compounds
| # | Structure |
|---|---|
| I-201 | 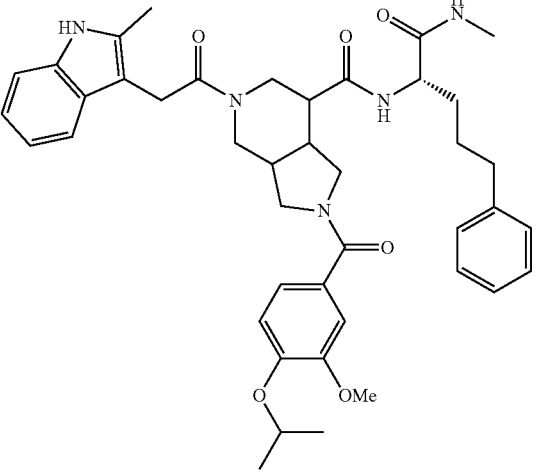 |
| I-202 | 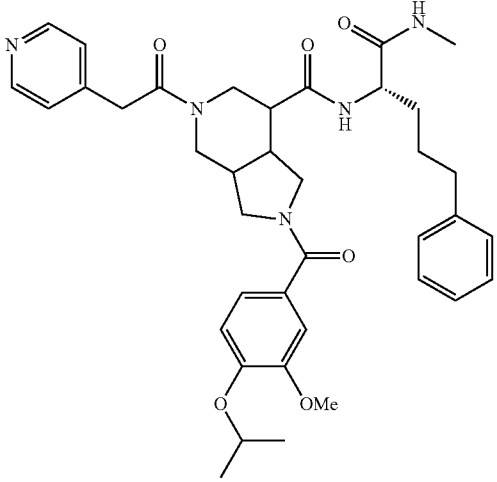 [SMILES: CNC(=O)[C@H](CCCc1ccccc1)NC(=O)C1CN(C(=O)Cc2ccncc2)CC2CN(C(=O)c3ccc(OC(C)C)c(OC)c3)CC21] |
| I-203 | 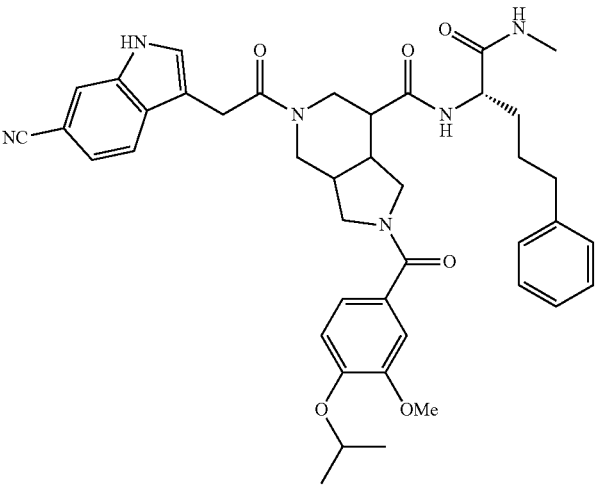 [SMILES: CNC(=O)[C@H](CCCc1ccccc1)NC(=O)C1CN(C(=O)Cc2c[nH]c3cc(C#N)ccc23)CC2CN(C(=O)c3ccc(OC(C)C)c(OC)c3)CC21] |

TABLE 1-continued
Exemplary Compounds
| # | Structure |
|---|---|
| I-204 | 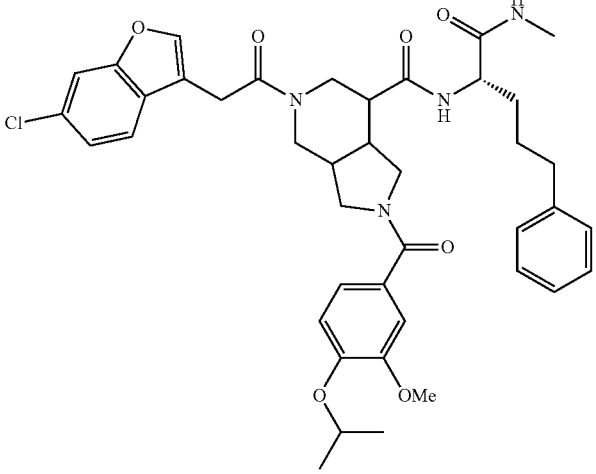 |
| I-205 | 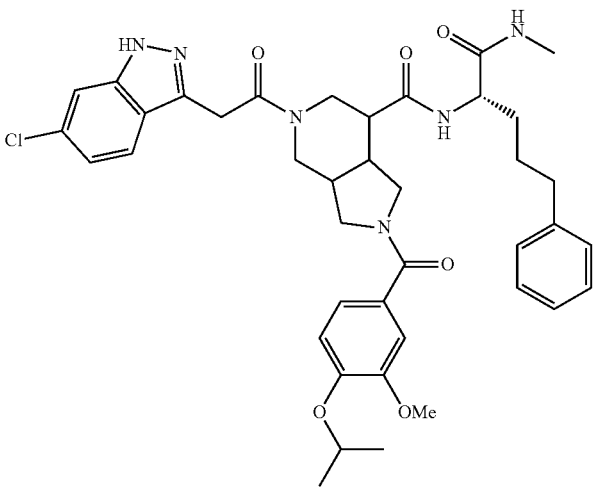 [SMILES: CNC(=O)[C@H](CCCc1ccccc1)NC(=O)C1CN(C(=O)Cc2n[nH]c3cc(Cl)ccc23)CC2CN(C(=O)c3ccc(OC(C)C)c(OC)c3)CC21] |
| I-206 | 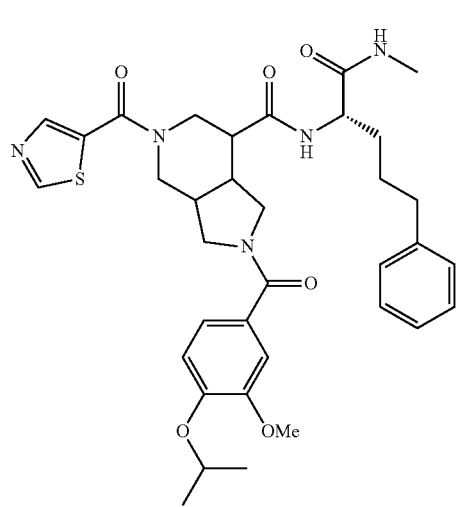 [SMILES: CNC(=O)[C@H](CCCc1ccccc1)NC(=O)C1CN(C(=O)c2cncs2)CC2CN(C(=O)c3ccc(OC(C)C)c(OC)c3)CC21] |

TABLE 1-continued

Exemplary Compounds

| # | Structure |
|---|---|
| I-207 | 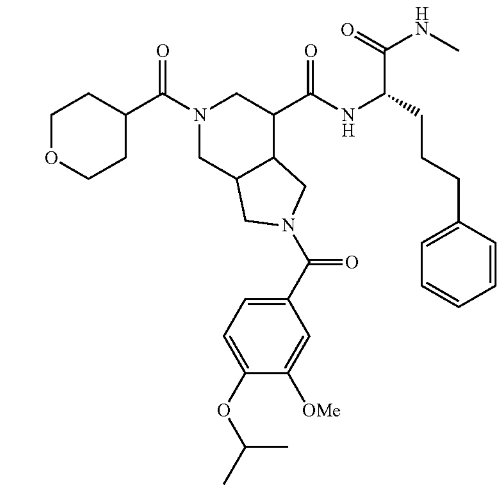 [SMILES: CNC(=O)[C@H](CCCc1ccccc1)NC(=O)C1CN(C(=O)C2CCOCC2)CC2CN(C(=O)c3ccc(OC(C)C)c(OC)c3)CC21] |
| I-208 | 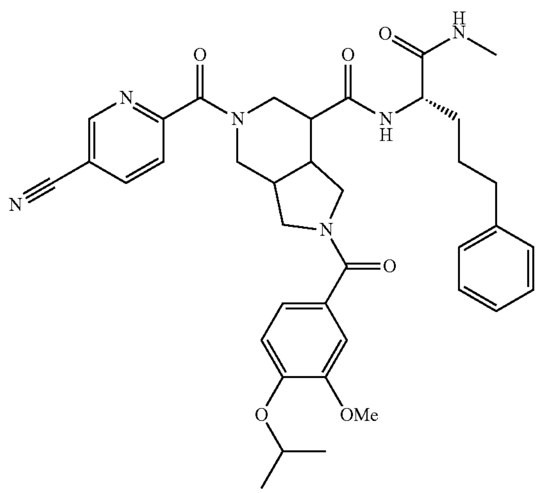 [SMILES: CNC(=O)[C@H](CCCc1ccccc1)NC(=O)C1CN(C(=O)c2ccc(C#N)cn2)CC2CN(C(=O)c3ccc(OC(C)C)c(OC)c3)CC21] |
| I-209 | 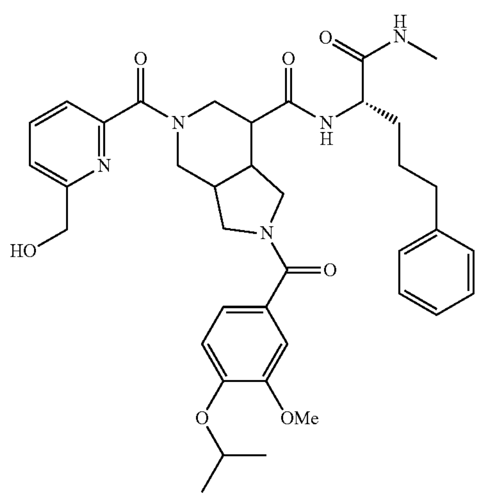 [SMILES: CNC(=O)[C@H](CCCc1ccccc1)NC(=O)C1CN(C(=O)c2cccc(CO)n2)CC2CN(C(=O)c3ccc(OC(C)C)c(OC)c3)CC21] |

TABLE 1-continued
Exemplary Compounds
| # | Structure |
|---|---|
| I-210 | 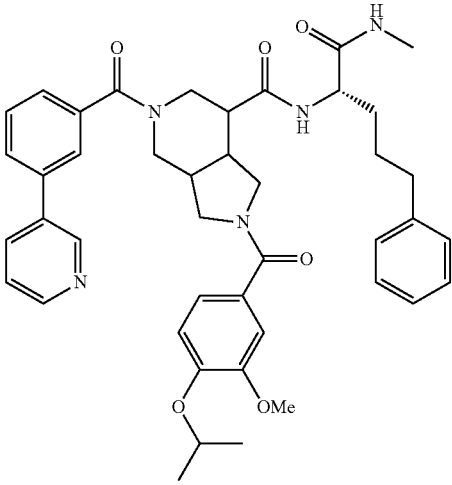 [SMILES: CNC(=O)[C@H](CCCc1ccccc1)NC(=O)C1CN(C(=O)c2cccc(-c3cccnc3)c2)CC2CN(C(=O)c3ccc(OC(C)C)c(OC)c3)CC21] |
| I-211 | 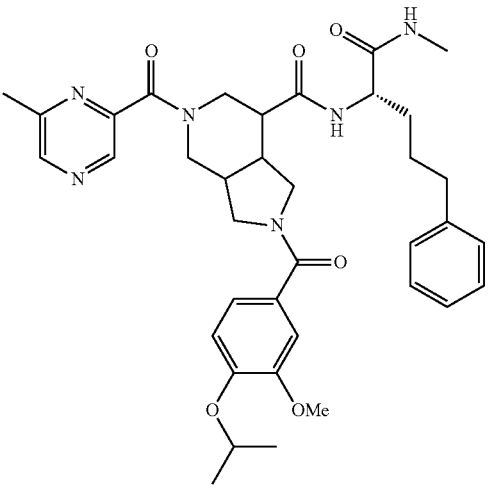 [SMILES: CNC(=O)[C@H](CCCc1ccccc1)NC(=O)C1CN(C(=O)c2cncc(C)n2)CC2CN(C(=O)c3ccc(OC(C)C)c(OC)c3)CC21] |
| I-212 | 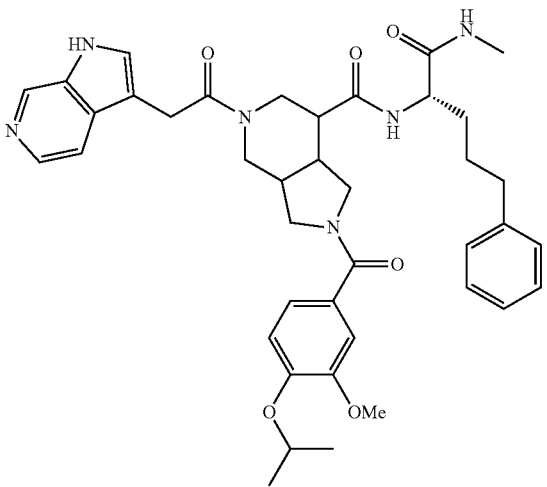 [SMILES: CNC(=O)[C@H](CCCc1ccccc1)NC(=O)C1CN(C(=O)Cc2c[nH]c3cnccc23)CC2CN(C(=O)c3ccc(OC(C)C)c(OC)c3)CC21] |

TABLE 1-continued
Exemplary Compounds
| # | Structure |
|---|---|
| I-213 | 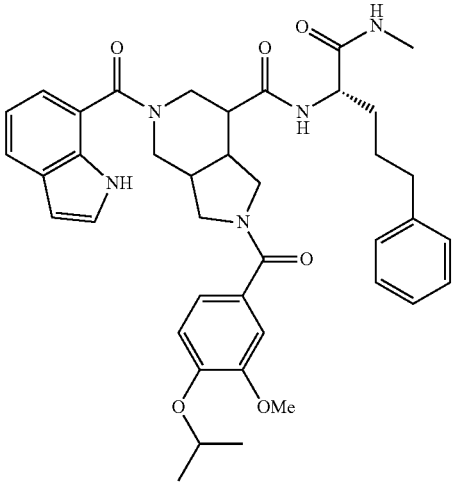 [SMILES: CNC(=O)[C@H](CCCc1ccccc1)NC(=O)C1CN(C(=O)c2cccc3cc[nH]c23)CC2CN(C(=O)c3ccc(OC(C)C)c(OC)c3)CC21] |
| I-214 | 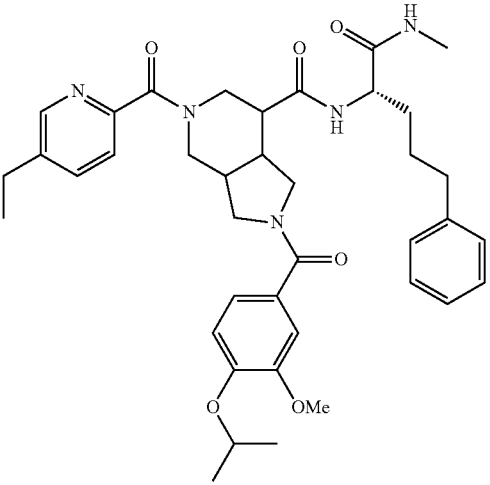 |
| I-215 | 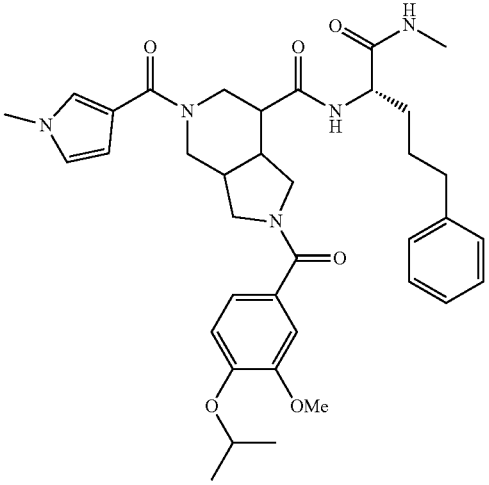 [SMILES: CNC(=O)[C@H](CCCc1ccccc1)NC(=O)C1CN(C(=O)c2ccn(C)c2)CC2CN(C(=O)c3ccc(OC(C)C)c(OC)c3)CC21] |

TABLE 1-continued
Exemplary Compounds
| # | Structure |
|---|---|
| I-216 | 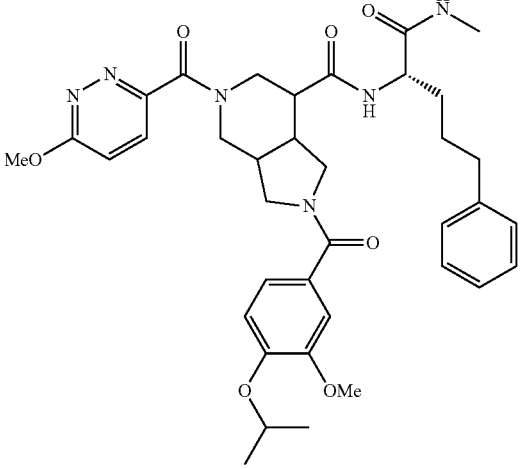 |
| I-217 | 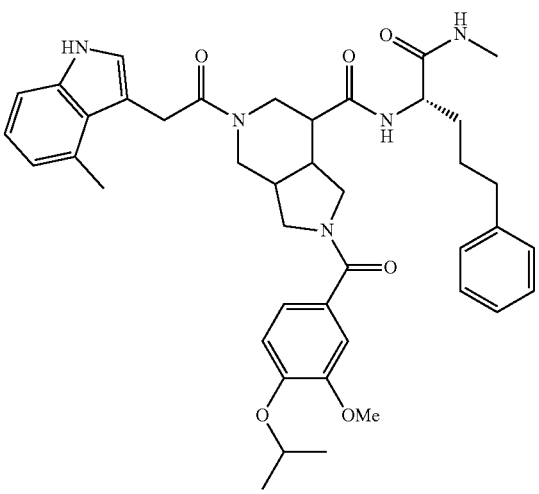 [SMILES: CNC(=O)[C@H](CCCc1ccccc1)NC(=O)C1CN(C(=O)Cc2c[nH]c3cccc(C)c23)CC2CN(C(=O)c3ccc(OC(C)C)c(OC)c3)CC21] |
| I-218 | 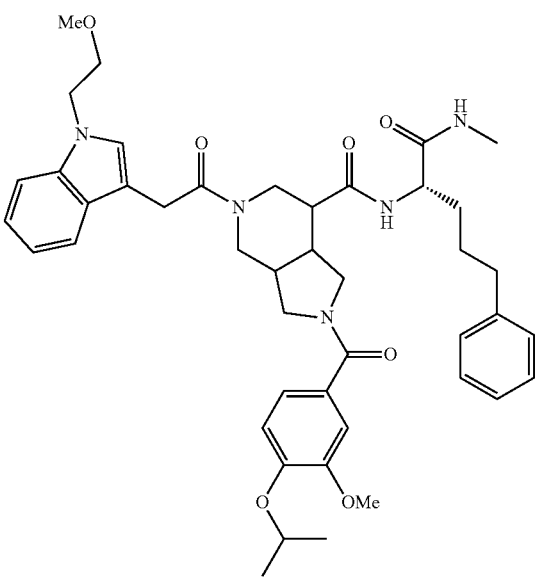 [SMILES: CNC(=O)[C@H](CCCc1ccccc1)NC(=O)C1CN(C(=O)Cc2cn(CCOC)c3ccccc23)CC2CN(C(=O)c3ccc(OC(C)C)c(OC)c3)CC21] |

TABLE 1-continued

Exemplary Compounds

| # | Structure |
|---|---|
| I-219 | 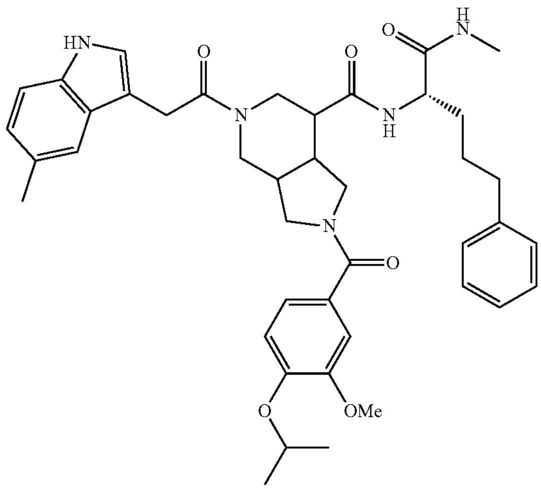 |
| I-220 | 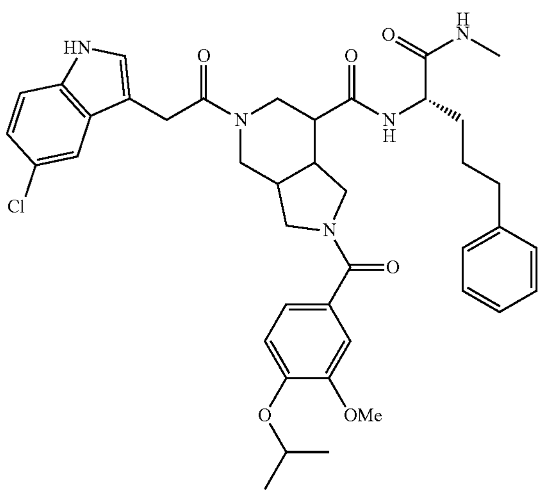 |
| I-221 | 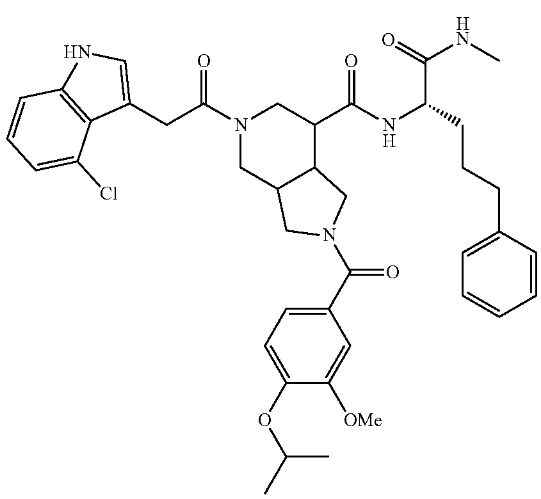 [SMILES: CNC(=O)[C@H](CCCc1ccccc1)NC(=O)C1CN(C(=O)Cc2c[nH]c3cccc(Cl)c23)CC2CN(C(=O)c3ccc(OC(C)C)c(OC)c3)CC21] |

TABLE 1-continued

Exemplary Compounds

| # | Structure |
|---|---|
| I-222 | 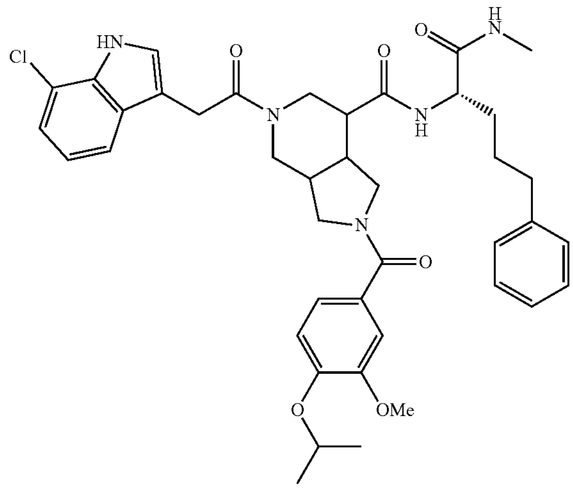 [SMILES: CNC(=O)[C@H](CCCc1ccccc1)NC(=O)C1CN(C(=O)Cc2c[nH]c3c(Cl)cccc23)CC2CN(C(=O)c3ccc(OC(C)C)c(OC)c3)CC21] |
| I-223 | 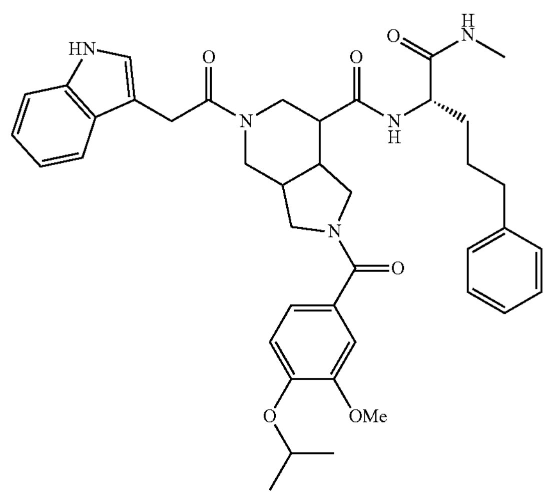 [SMILES: CNC(=O)[C@H](CCCc1ccccc1)NC(=O)C1CN(C(=O)Cc2c[nH]c3ccccc23)CC2CN(C(=O)c3ccc(OC(C)C)c(OC)c3)CC21] |
| I-224 | 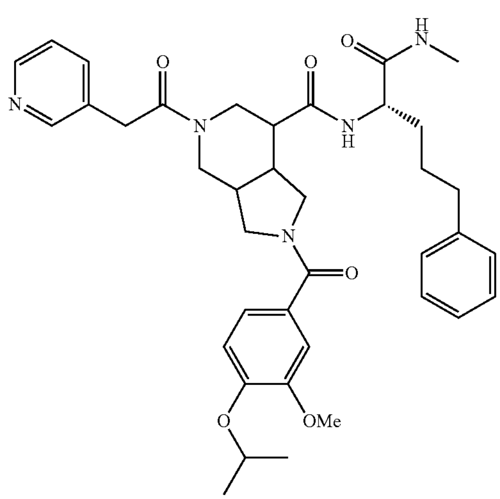 [SMILES: CNC(=O)[C@H](CCCc1ccccc1)NC(=O)C1CN(C(=O)Cc2cccnc2)CC2CN(C(=O)c3ccc(OC(C)C)c(OC)c3)CC21] |

TABLE 1-continued
Exemplary Compounds
| # | Structure |
|---|---|
| I-225 | 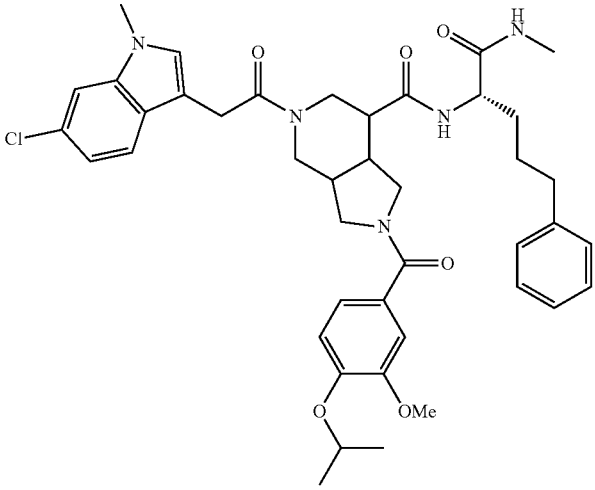 [SMILES: CNC(=O)[C@H](CCCc1ccccc1)NC(=O)C1CN(C(=O)Cc2cn(C)c3cc(Cl)ccc23)CC2CN(C(=O)c3ccc(OC(C)C)c(OC)c3)CC21] |
| I-226 | 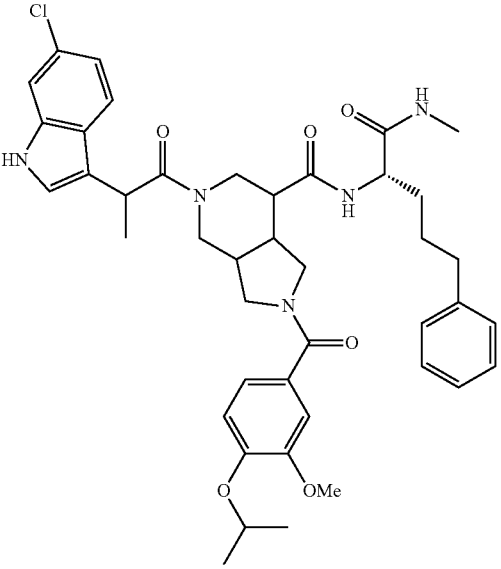 [SMILES: CNC(=O)[C@H](CCCc1ccccc1)NC(=O)C1CN(C(=O)C(C)c2c[nH]c3cc(Cl)ccc23)CC2CN(C(=O)c3ccc(OC(C)C)c(OC)c3)CC21] |
| I-227 | 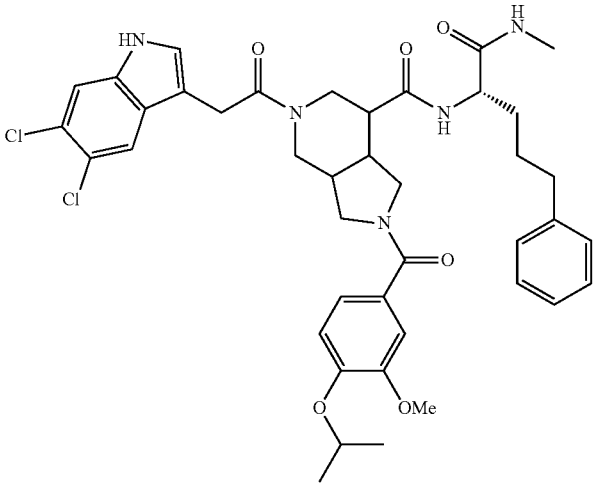 [SMILES: CNC(=O)[C@H](CCCc1ccccc1)NC(=O)C1CN(C(=O)Cc2c[nH]c3cc(Cl)c(Cl)cc23)CC2CN(C(=O)c3ccc(OC(C)C)c(OC)c3)CC21] |

TABLE 1-continued

Exemplary Compounds

| # | Structure |
|---|---|
| I-228 | 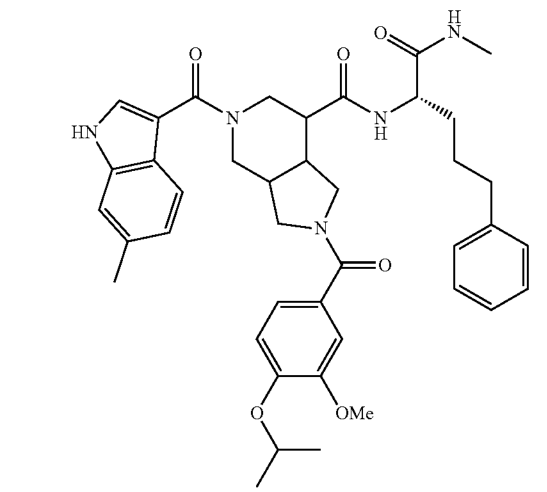 [SMILES: CNC(=O)[C@H](CCCc1ccccc1)NC(=O)C1CN(C(=O)c2c[nH]c3cc(C)ccc23)CC2CN(C(=O)c3ccc(OC(C)C)c(OC)c3)CC21] |
| I-229 | 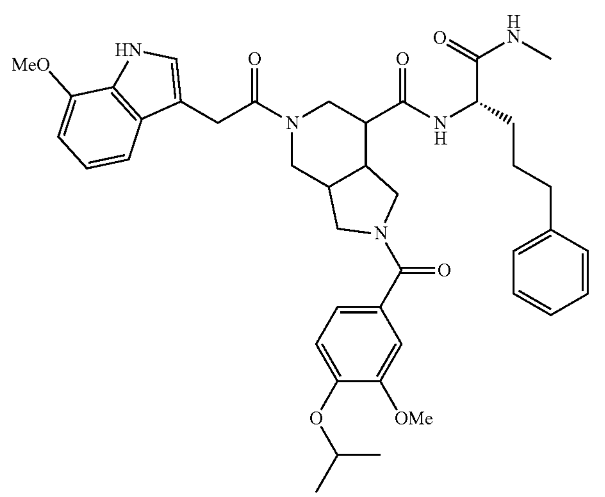 [SMILES: CNC(=O)[C@H](CCCc1ccccc1)NC(=O)C1CN(C(=O)Cc2c[nH]c3c(OC)cccc23)CC2CN(C(=O)c3ccc(OC(C)C)c(OC)c3)CC21] |
| I-230 | 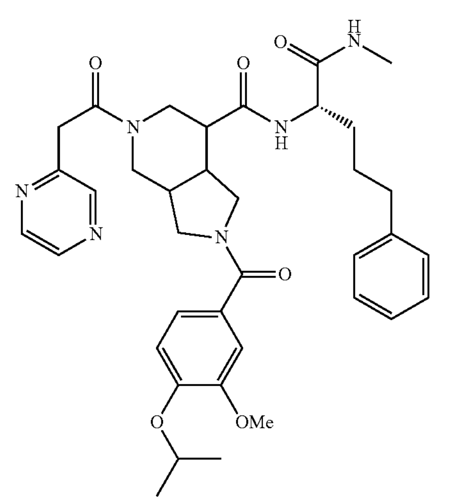 [SMILES: CNC(=O)[C@H](CCCc1ccccc1)NC(=O)C1CN(C(=O)Cc2cnccn2)CC2CN(C(=O)c3ccc(OC(C)C)c(OC)c3)CC21] |

TABLE 1-continued
Exemplary Compounds
| # | Structure |
|---|---|
| I-231 | 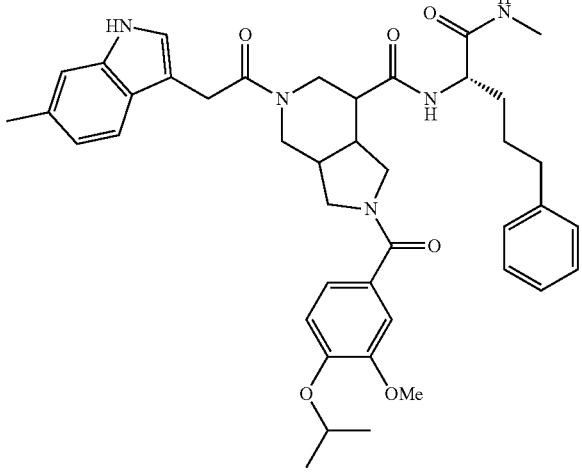 |
| I-232 | 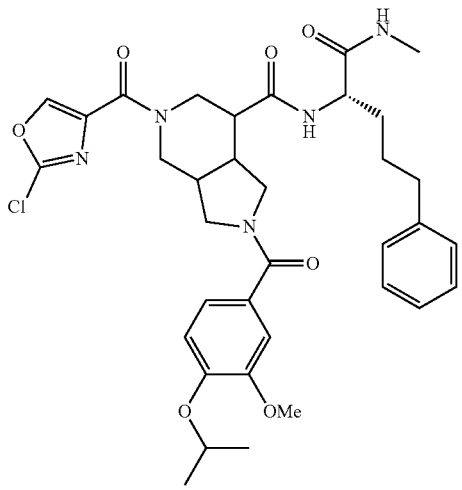 [SMILES: CNC(=O)[C@H](CCCc1ccccc1)NC(=O)C1CN(C(=O)c2coc(Cl)n2)CC2CN(C(=O)c3ccc(OC(C)C)c(OC)c3)CC21]
First eluting diastereomer |
| I-233 | 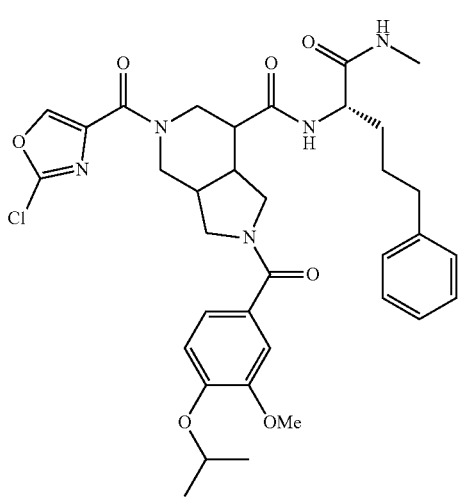 [SMILES: CNC(=O)[C@H](CCCc1ccccc1)NC(=O)C1CN(C(=O)c2coc(Cl)n2)CC2CN(C(=O)c3ccc(OC(C)C)c(OC)c3)CC21]
Second eluting diastereomer |

TABLE 1-continued
Exemplary Compounds
| # | Structure |
|---|---|
| I-234 | 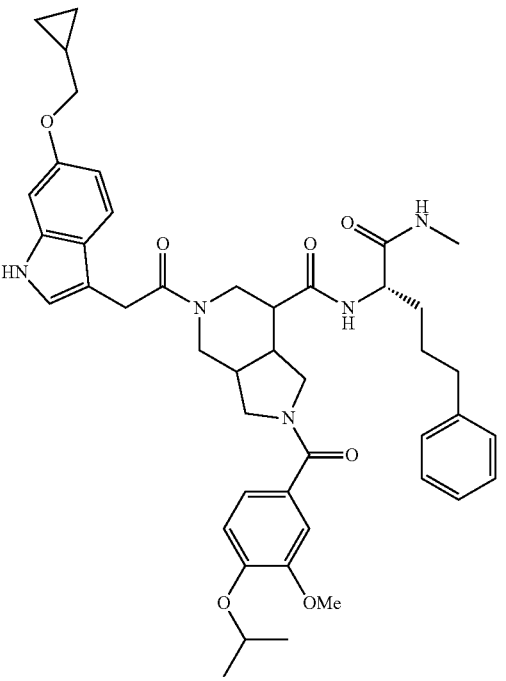 [SMILES: CNC(=O)[C@H](CCCc1ccccc1)NC(=O)C1CN(C(=O)Cc2c[nH]c3cc(OCC4CC4)ccc23)CC2CN(C(=O)c3ccc(OC(C)C)c(OC)c3)CC21] |
| I-235 | 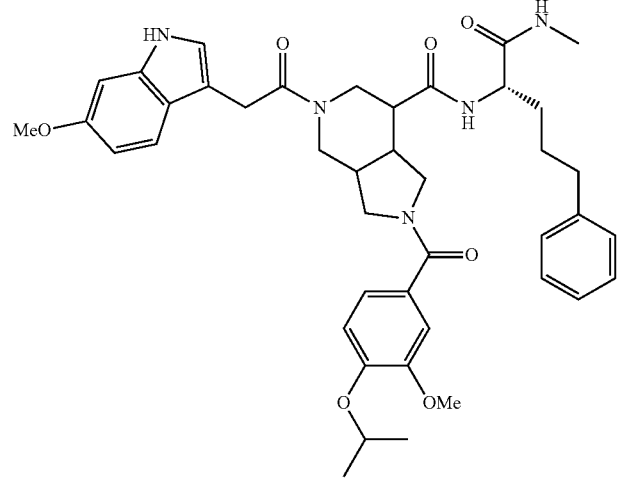 [SMILES: CNC(=O)[C@H](CCCc1ccccc1)NC(=O)C1CN(C(=O)Cc2c[nH]c3cc(OC)ccc23)CC2CN(C(=O)c3ccc(OC(C)C)c(OC)c3)CC21] |
| I-236 | 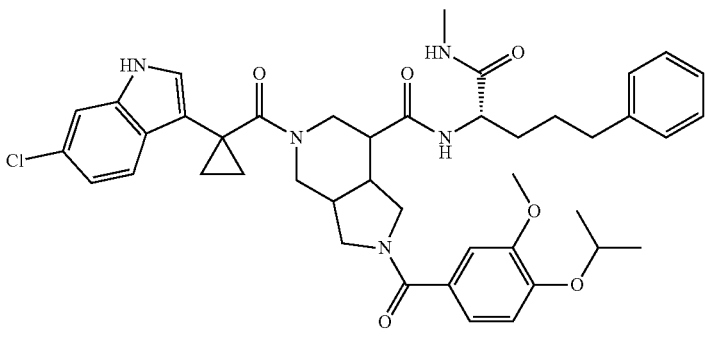 [SMILES: CNC(=O)[C@H](CCCc1ccccc1)NC(=O)C1CN(C(=O)C2(c3c[nH]c4cc(Cl)ccc34)CC2)CC2CN(C(=O)c3ccc(OC(C)C)c(OC)c3)CC21] |

TABLE 1-continued
Exemplary Compounds
| # | Structure |
|---|---|
| I-237 | 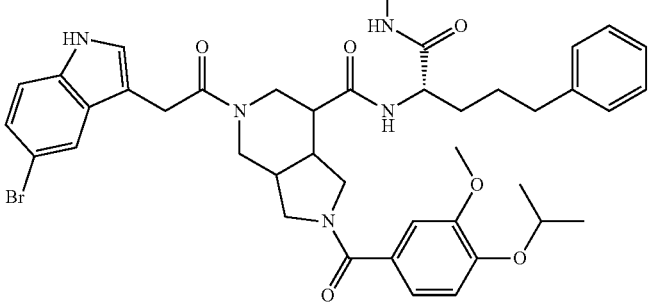 |
| I-238 | 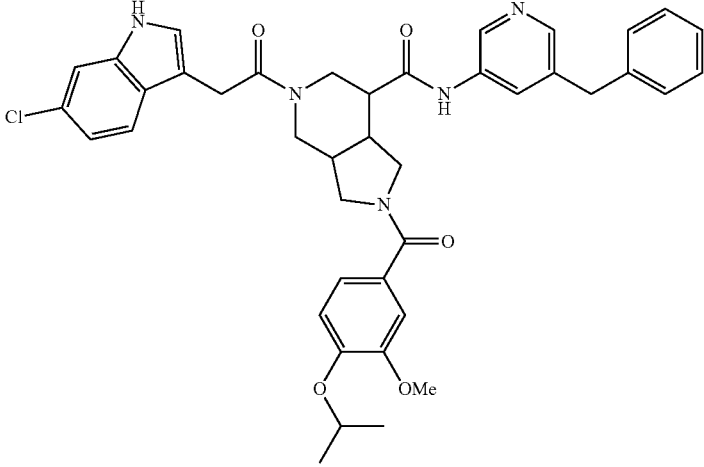 [SMILES: COc1cc(C(=O)N2CC3CN(C(=O)Cc4c[nH]c5cc(Cl)ccc45)CC(C(=O)Nc4cncc(Cc5ccccc5)c4)C3C2)ccc1OC(C)C] |
| I-239 | 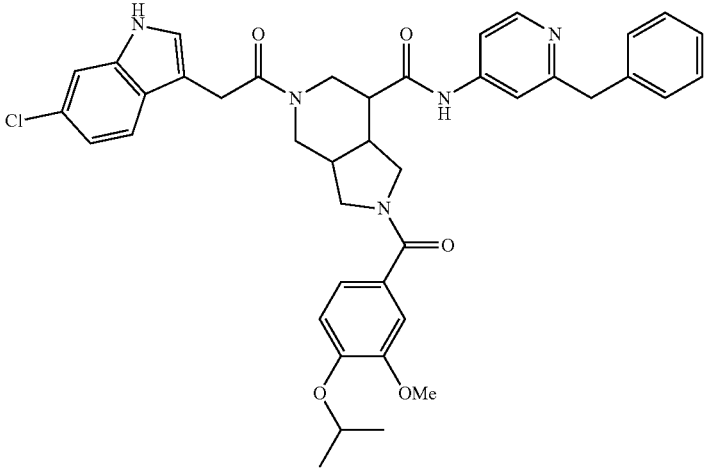 [SMILES: COc1cc(C(=O)N2CC3CN(C(=O)Cc4c[nH]c5cc(Cl)ccc45)CC(C(=O)Nc4ccnc(Cc5ccccc5)c4)C3C2)ccc1OC(C)C] |

TABLE 1-continued

Exemplary Compounds

| # | Structure |
|---|---|
| I-240 | 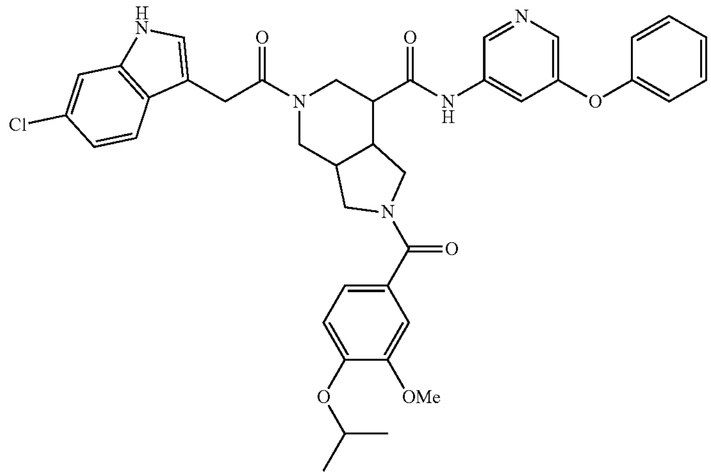 |
| I-241 | 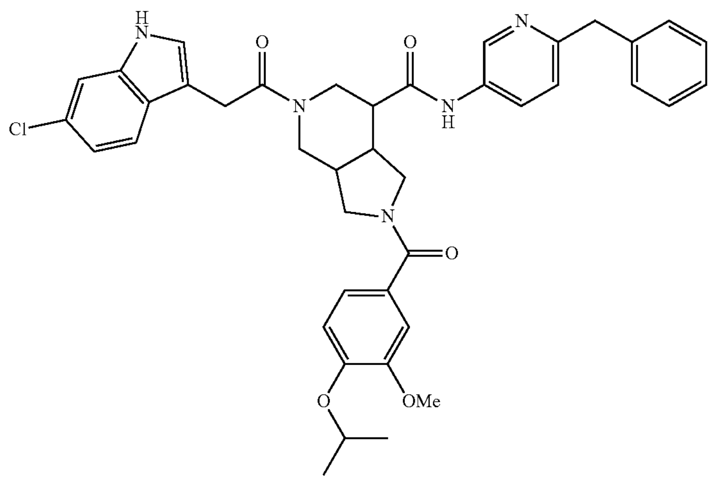 [SMILES: COc1cc(C(=O)N2CC3CN(C(=O)Cc4c[nH]c5cc(Cl)ccc45)CC(C(=O)Nc4ccc(Cc5ccccc5)nc4)C3C2)ccc1OC(C)C] |
| I-242 | 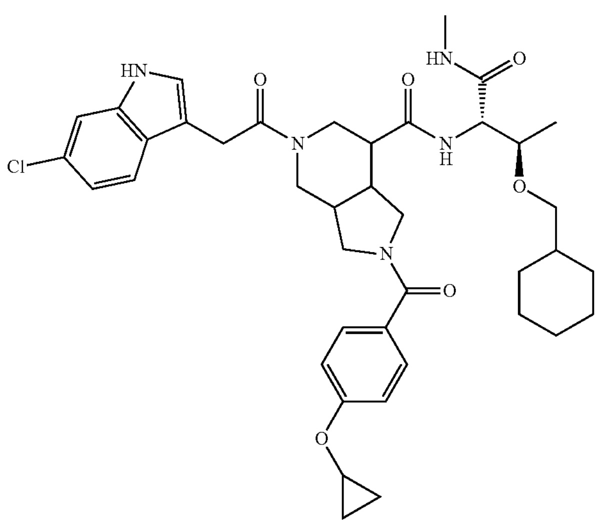 [SMILES: CNC(=O)[C@@H](NC(=O)C1CN(C(=O)Cc2c[nH]c3cc(Cl)ccc23)CC2CN(C(=O)c3ccc(OC4CC4)cc3)CC21)[C@@H](C)OCC1CCCCC1] |

TABLE 1-continued

Exemplary Compounds

| # | Structure |
|---|---|
| I-243 | 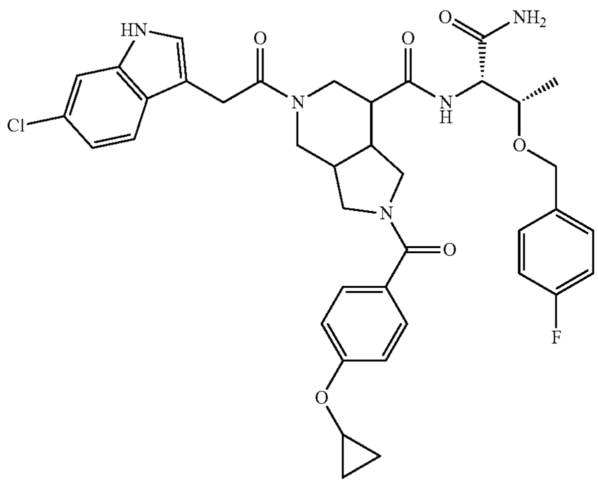 [SMILES: C[C@H](OCc1ccc(F)cc1)[C@H](NC(=O)C1CN(C(=O)Cc2c[nH]c3cc(Cl)ccc23)CC2CN(C(=O)c3ccc(OC4CC4)cc3)CC21)C(N)=O] |
| I-244 | 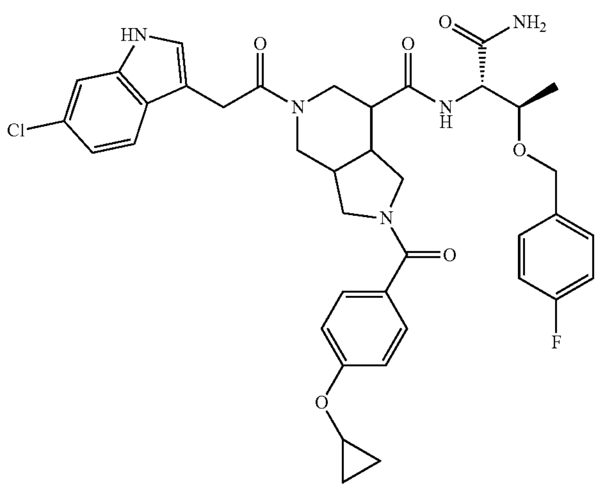 [SMILES: C[C@@H](OCc1ccc(F)cc1)[C@H](NC(=O)C1CN(C(=O)Cc2c[nH]c3cc(Cl)ccc23)CC2CN(C(=O)c3ccc(OC4CC4)cc3)CC21)C(N)=O] |
| I-245 | 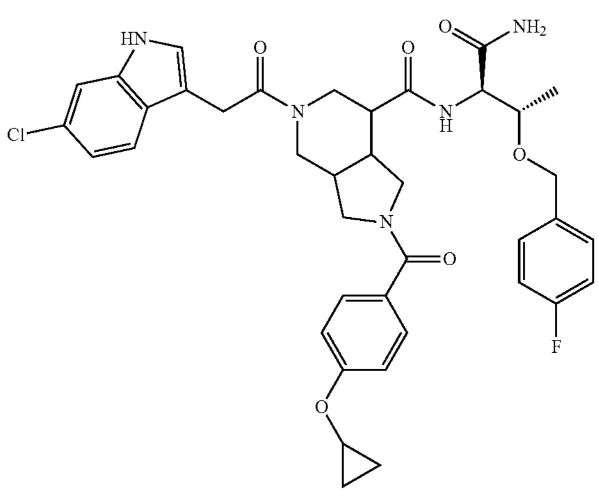 |

TABLE 1-continued

Exemplary Compounds

| # | Structure |
|---|---|
| I-246 | 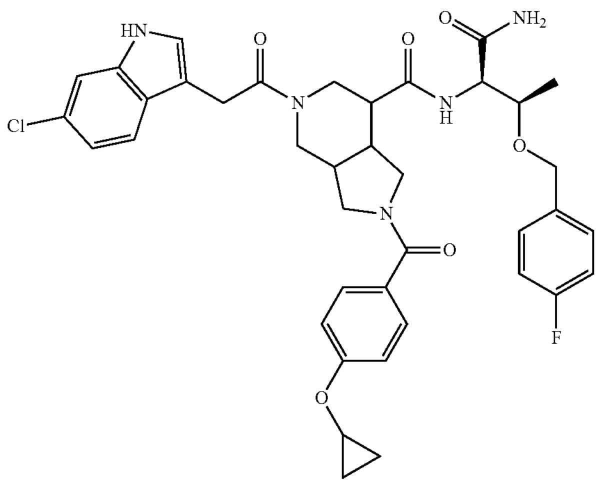 [SMILES: C[C@@H](OCc1ccc(F)cc1)[C@@H](NC(=O)C1CN(C(=O)Cc2c[nH]c3cc(Cl)ccc23)CC2CN(C(=O)c3ccc(OC4CC4)cc3)CC21)C(N)=O] |
| I-247 | 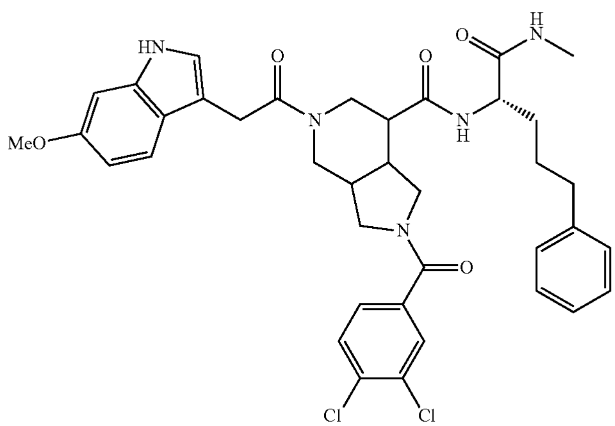 [SMILES: CNC(=O)[C@H](CCCc1ccccc1)NC(=O)C1CN(C(=O)Cc2c[nH]c3cc(OC)ccc23)CC2CN(C(=O)c3ccc(Cl)c(Cl)c3)CC21] |
| I-248 | 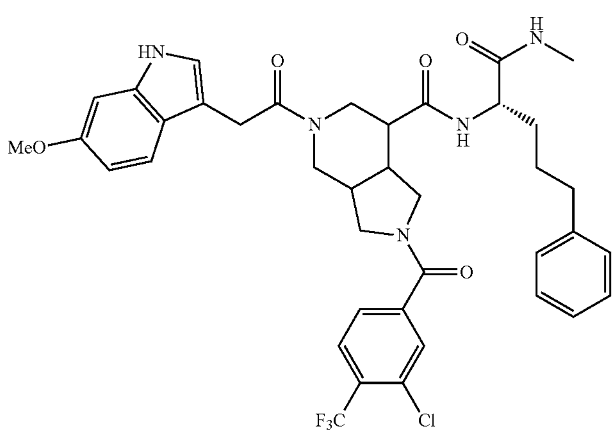 [SMILES: CNC(=O)[C@H](CCCc1ccccc1)NC(=O)C1CN(C(=O)Cc2c[nH]c3cc(OC)ccc23)CC2CN(C(=O)c3ccc(C(F)(F)F)c(Cl)c3)CC21] |

TABLE 1-continued

Exemplary Compounds

| # | Structure |
|---|---|
| I-249 | 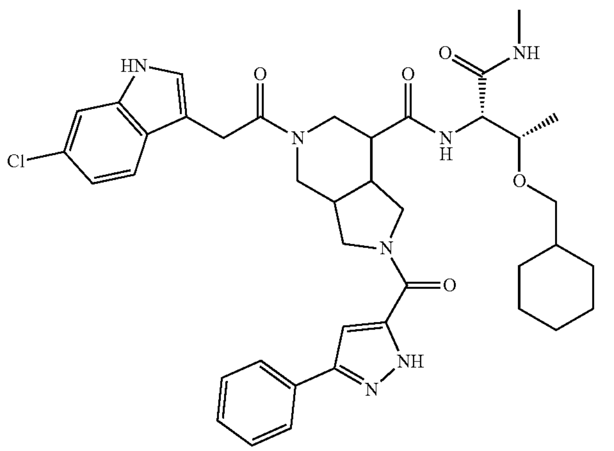 [SMILES: CNC(=O)[C@@H](NC(=O)C1CN(C(=O)Cc2c[nH]c3cc(Cl)ccc23)CC2CN(C(=O)c3cc(-c4ccccc4)n[nH]3)CC21)[C@H](C)OCC1CCCCC1] |
| I-250 | 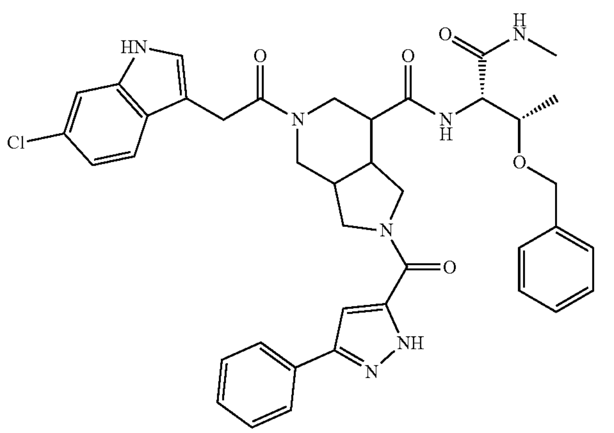 [SMILES: CNC(=O)[C@@H](NC(=O)C1CN(C(=O)Cc2c[nH]c3cc(Cl)ccc23)CC2CN(C(=O)c3cc(-c4ccccc4)n[nH]3)CC21)[C@H](C)OCc1ccccc1] |
| I-251 | 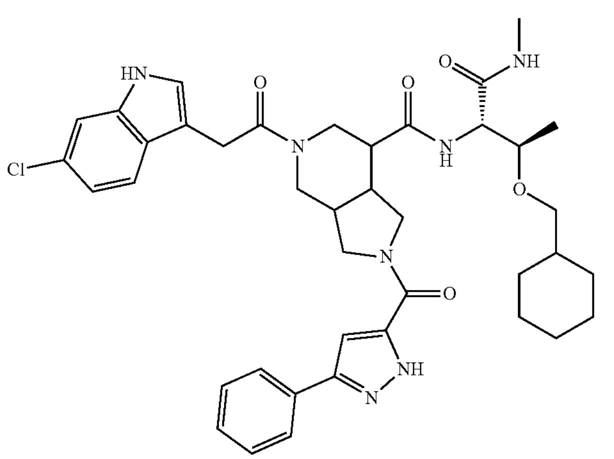 [SMILES: CNC(=O)[C@@H](NC(=O)C1CN(C(=O)Cc2c[nH]c3cc(Cl)ccc23)CC2CN(C(=O)c3cc(-c4ccccc4)n[nH]3)CC21)[C@@H](C)OCC1CCCCC1] |

TABLE 1-continued
Exemplary Compounds
| # | Structure |
|---|---|
| I-252 | 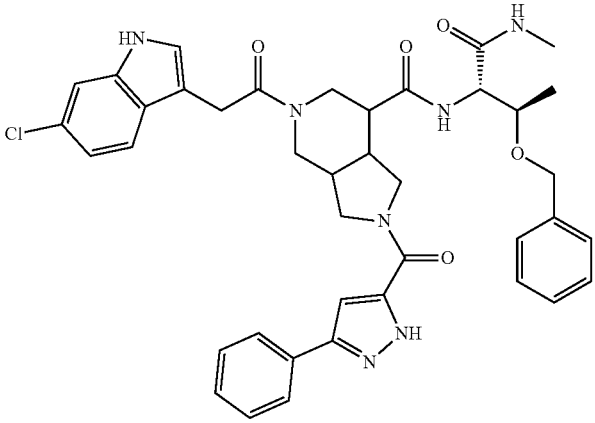 [SMILES: CNC(=O)[C@@H](NC(=O)C1CN(C(=O)Cc2c[nH]c3cc(Cl)ccc23)CC2CN(C(=O)c3cc(-c4ccccc4)n[nH]3)CC21)[C@@H](C)OCc1ccccc1] |
| I-253 | 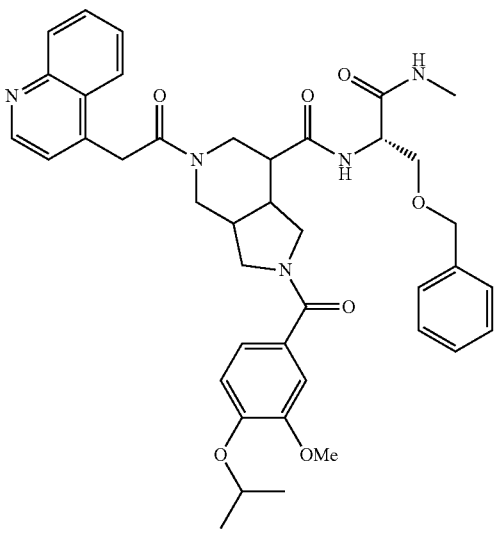 [SMILES: CNC(=O)[C@H](COCc1ccccc1)NC(=O)C1CN(C(=O)Cc2ccnc3ccccc23)CC2CN(C(=O)c3ccc(OC(C)C)c(OC)c3)CC21] |
| I-254 | 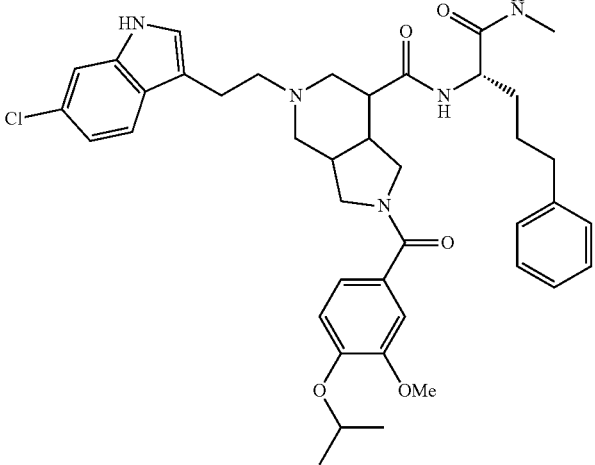 |

TABLE 1-continued

Exemplary Compounds

| # | Structure |
|---|---|
| I-255 | 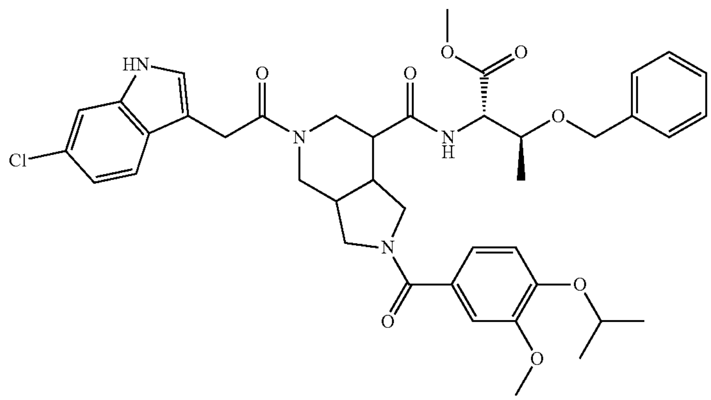 [SMILES: COC(=O)[C@@H](NC(=O)C1CN(C(=O)Cc2c[nH]c3cc(Cl)ccc23)CC2CN(C(=O)c3ccc(OC(C)C)c(OC)c3)CC21)[C@H](C)OCc1ccccc1] |
| I-256 | 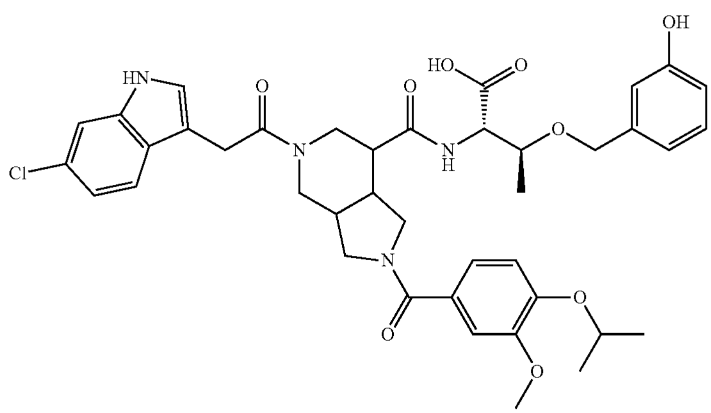 [SMILES: COc1cc(C(=O)N2CC3CN(C(=O)Cc4c[nH]c5cc(Cl)ccc45)CC(C(=O)N[C@H](C(=O)O)[C@H](C)OCc4cccc(O)c4)C3C2)ccc1OC(C)C] |
| I-257 | Synthesized from first eluting intermediate |

TABLE 1-continued
Exemplary Compounds
| # | Structure |
|---|---|
| I-258 | 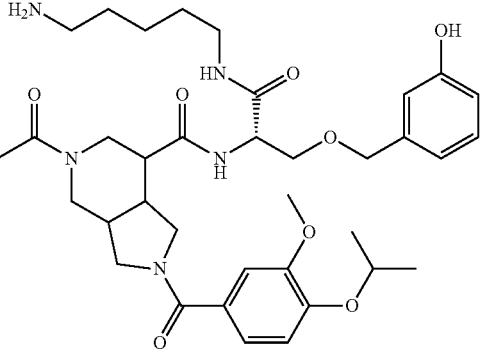<br>Synthesized from second eluting intermediate |
| I-259 | 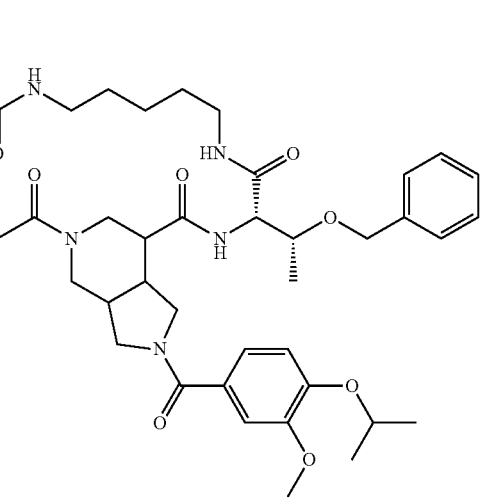<br>First eluting diastereomer |
| I-260 | 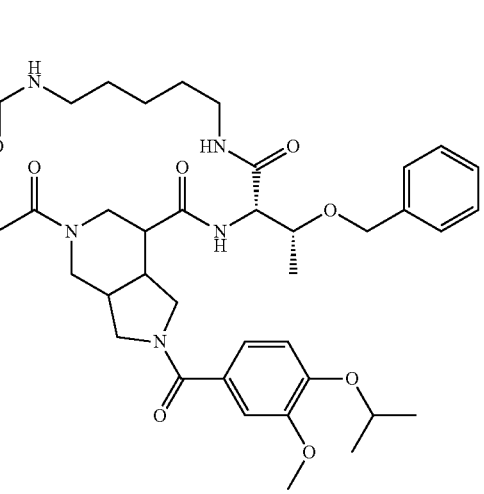<br>Second eluting diastereomer |

TABLE 1-continued

Exemplary Compounds

| # | Structure |
|---|---|
| I-261 | 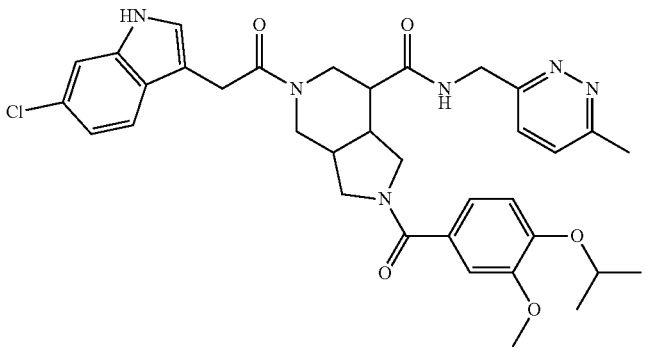 [SMILES: COc1cc(C(=O)N2CC3CN(C(=O)Cc4c[nH]c5cc(Cl)ccc45)CC(C(=O)NCc4ccc(C)nn4)C3C2)ccc1OC(C)C]<br>First eluting enantiomer |
| I-262 | 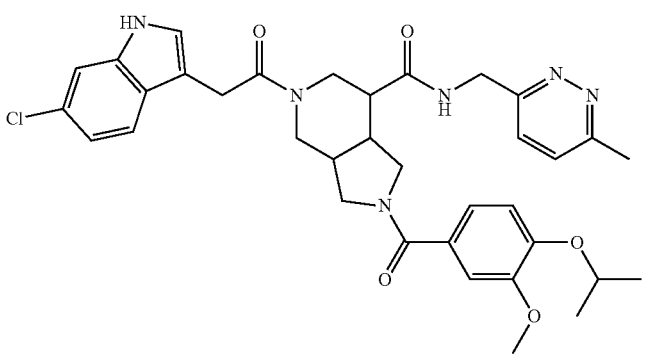 [SMILES: COc1cc(C(=O)N2CC3CN(C(=O)Cc4c[nH]c5cc(Cl)ccc45)CC(C(=O)NCc4ccc(C)nn4)C3C2)ccc1OC(C)C]<br>Second eluting enantiomer |

In some embodiments, the present disclosure provides a compound set forth in Table 1, above, or a pharmaceutically acceptable salt thereof. In some embodiments, the disclosure provides a compound set forth in Table 1, above, or a pharmaceutically acceptable salt thereof, and any enantiomers, diastereomers, or conformation isomers thereof.

In some embodiments, the present disclosure provides a pharmaceutical composition comprising a compound of the present disclosure, or a pharmaceutically acceptable salt thereof, together with a pharmaceutically acceptable carrier, excipient, vehicle, adjuvant or diluent. In some embodiments, the present disclosure provides a pharmaceutical composition comprising a compound set forth in Table 1 above, or a pharmaceutically acceptable salt thereof, together with a pharmaceutically acceptable carrier, excipient, vehicle, adjuvant or diluent. In some embodiments, the pharmaceutical composition further comprises an additional therapeutic agent.

In some embodiments, the present disclosure provides a complex comprising a CDK2 protein and a compound of the present disclosure.

In some embodiments, the present disclosure provides a method of inhibiting the activity of a cyclin-dependent kinase (CDK). In some embodiments, the method comprises contacting a compound of the present disclosure with a CDK. In some embodiments, the compound and the CDK are contacted in vivo. In some embodiments, the compound and the CDK are contacted in vitro.

In some embodiments, the present disclosure provides compounds that selectively inhibit CDK2 over other cyclin-dependent kinases (CDKs). In some embodiments, the compounds of the present disclosure selectively inhibit CDK2 over one or more other CDKs, selected from CDK1, CDK3, CDK4, CDK5, CDK6, CDK7, CDK8, CDK9, CDK10, CDK11, CDK12 and CDK13. In some embodiments, the compounds of the present disclosure selectively inhibit CDK2 over CDK4. In some embodiments, the compounds of the present disclosure selectively inhibit CDK2 over CDK6. In some embodiments, the compounds of the present disclosure selectively inhibit CDK2 over CDK4 and CDK6.

In some embodiments, the present disclosure provides compounds that selectively inhibit CDK2/cyclin E complexes over other CDK complexes.

In any of the preceding embodiments, the central bicyclic core of any of the compounds or formulas described herein can be in one of a number of stereochemical configurations, or a mixture of two or more stereochemical configurations.

In some embodiments, the present disclosure provides a compound of Formula I, which is a compound of Formula Ia:

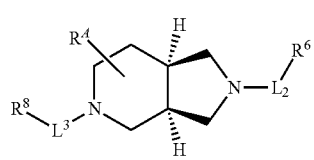

Ia or a pharmaceutically acceptable salt thereof, wherein $R^4$, $L^2$, $R^6$, $L^3$ and $R^8$, and their constituent groups, are each as defined and described herein.

In some embodiments, the present disclosure provides a compound of Formula I, which is a compound of Formula Ib:

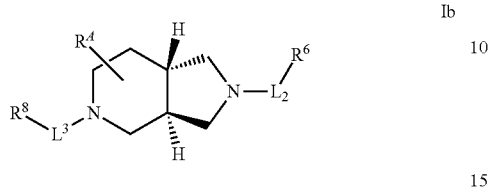

Ib or a pharmaceutically acceptable salt thereof, wherein $R^4$, $L^2$, $R^6$, $L^3$ and $R^8$, and their constituent groups, are each as defined and described herein.

In some embodiments, the present disclosure provides a compound of Formula I, which is a compound of Formula Ic:

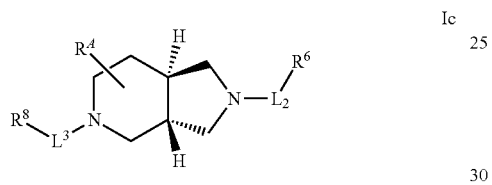

Ic or a pharmaceutically acceptable salt thereof, wherein $R^4$, $L^2$, $R^6$, $L^3$ and $R^8$, and their constituent groups, are each as defined and described herein.

In some embodiments, the present disclosure provides a compound of Formula I, which is a compound of Formula Id:

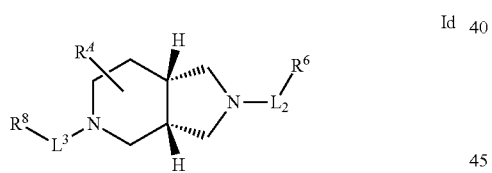

Id or a pharmaceutically acceptable salt thereof, wherein $R^4$, $L^2$, $R^6$, $L^3$ and $R^8$, and their constituent groups, are each as defined and described herein.

In some embodiments, the present disclosure provides a compound of any one of Formulas II, III, IV, V, Va, Vb, VI, VIa, VIIa, VIIb, VIIc, VIId, VIIe, VIIf, VIIIa, VIIIb, VIIIc, or VIIId, or a compound of Table 1, or a pharmaceutically acceptable salt thereof, wherein the central bicyclic core of said Formula or compound has a stereochemical configuration as shown below:

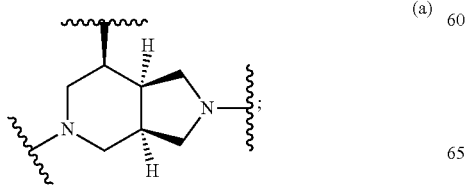

(a)

-continued

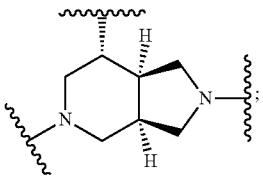

(b)

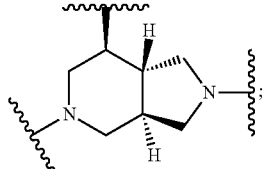

(c)

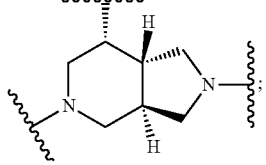

(d)

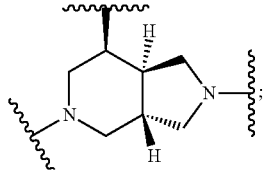

(e)

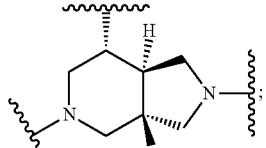

(f)

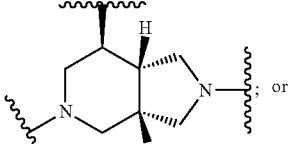

(g)

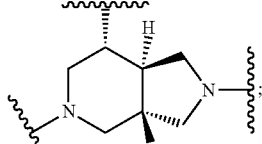

(h)

or a combination of two or more of the aforementioned stereochemical configurations. In some embodiments, the compound has stereochemical configuration "(a)". In some embodiments, the compound has stereochemical configuration "(b)". In some embodiments, the compound has stereochemical configuration "(c)". In some embodiments, the compound has stereochemical configuration "(d)". In some embodiments, the compound has stereochemical configuration "(e)". In some embodiments, the compound has stereochemical configuration "(f)". In some embodiments, the compound has stereochemical configuration "(g)". In some embodiments, the compound has stereochemical configuration "(h)".

4. General Methods of Providing the Present Compounds

The compounds of this disclosure may be prepared or isolated in general by synthetic and/or semi-synthetic methods known to those skilled in the art for analogous compounds and by methods described in detail in the Examples, herein.

In the Schemes below, where a particular protecting group ("PG"), leaving group ("LG"), or transformation condition is depicted, one of ordinary skill in the art will appreciate that other protecting groups, leaving groups, and transformation conditions are also suitable and are contemplated. Such groups and transformations are described in detail in *March's Advanced Organic Chemistry: Reactions, Mechanisms, and Structure*, M. B. Smith and J. March, 5$^{th}$ Edition, John Wiley & Sons, 2001, *Comprehensive Organic Transformations*, R. C. Larock, 2$^{nd}$ Edition, John Wiley & Sons, 1999, and *Protecting Groups in Organic Synthesis*, T. W. Greene and P. G. M. Wuts, 3$^{rd}$ edition, John Wiley & Sons, 1999, the entirety of each of which is hereby incorporated herein by reference.

As used herein, the phrase "leaving group" (LG) includes, but is not limited to, halogens (e.g. fluoride, chloride, bromide, iodide), sulfonates (e.g. mesylate, tosylate, benzenesulfonate, brosylate, nosylate, triflate), diazonium, and the like.

Amino protecting groups are well known in the art and include those described in detail in *Protecting Groups in Organic Synthesis*, T. W. Greene and P. G. M. Wuts, 3$^{rd}$ edition, John Wiley & Sons, 1999, the entirety of which is incorporated herein by reference. Suitable amino protecting groups include, but are not limited to, aralkylamines, carbamates, cyclic imides, allyl amines, amides, and the like. Examples of such groups include t-butyloxycarbonyl (BOC), ethyloxycarbonyl, methyloxycarbonyl, trichloroethyloxycarbonyl, allyloxycarbonyl (Alloc), benzyloxocarbonyl (CBZ), allyl, phthalimide, benzyl (Bn), fluorenylmethylcarbonyl (Fmoc), formyl, acetyl, chloroacetyl, dichloroacetyl, trichloroacetyl, phenylacetyl, trifluoroacetyl, benzoyl, and the like.

Compounds of the present disclosure, including those of Formula I and the compounds of Table 1, can generally be prepared according the methods described below. Reagents and conditions can be modified and substituted using knowledge common to one of ordinary skill in the art, as needed, in order to arrive at the compounds of the present disclosure.

Scheme 1: General Synthesis Method 1

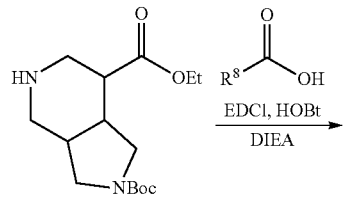

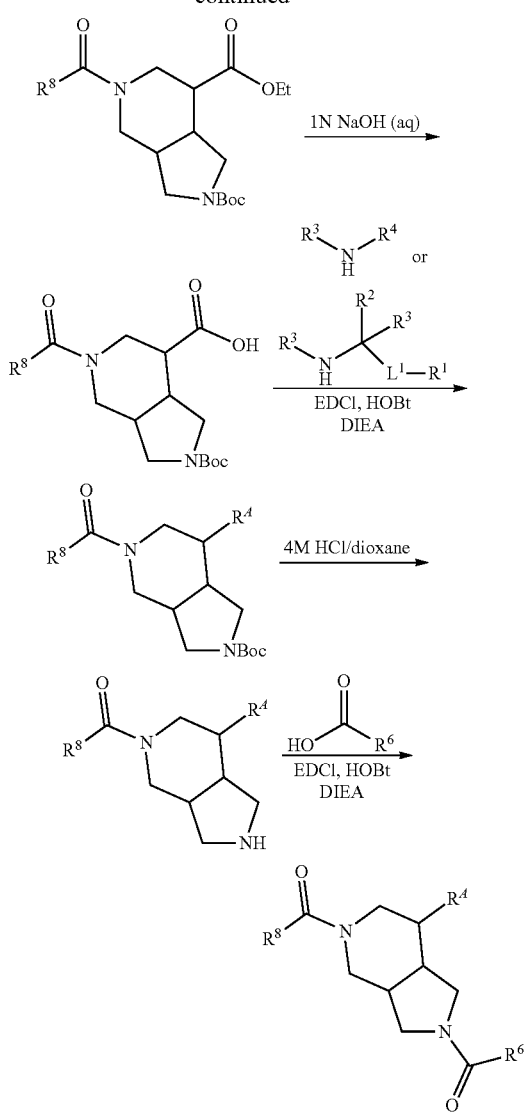

Scheme 2: General Synthesis Method 2

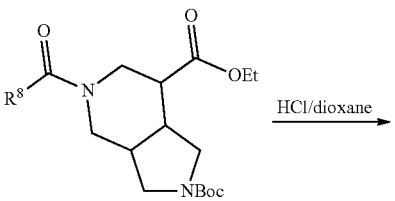

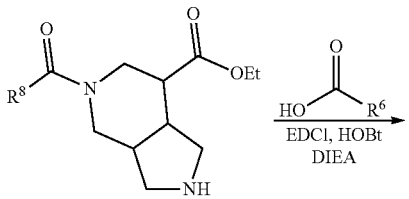

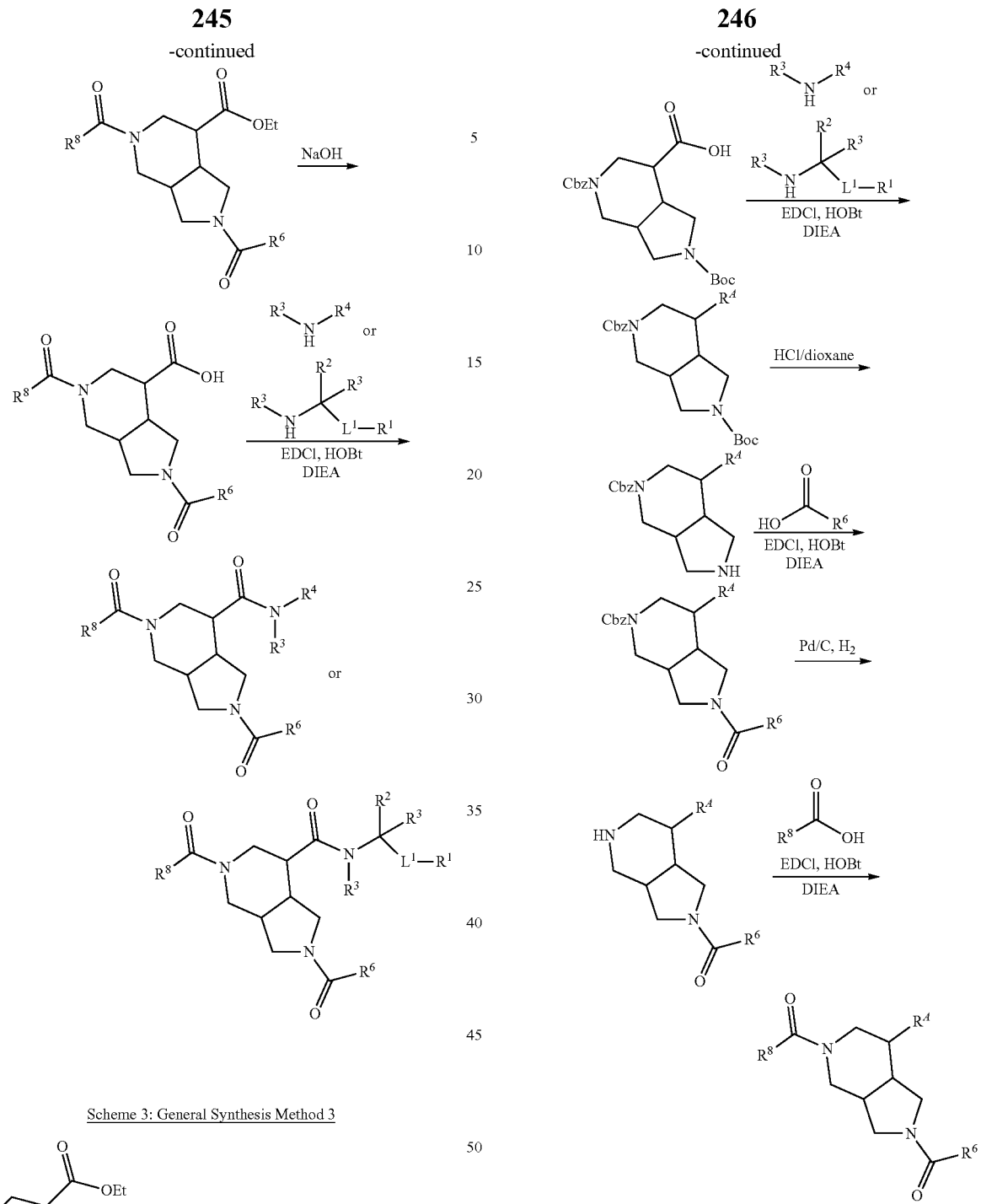

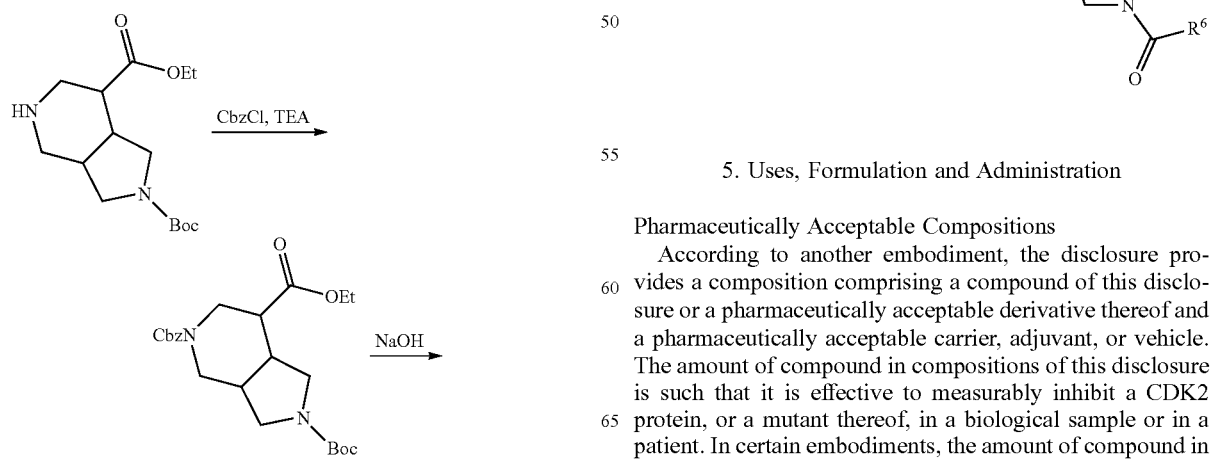

5. Uses, Formulation and Administration

Pharmaceutically Acceptable Compositions

According to another embodiment, the disclosure provides a composition comprising a compound of this disclosure or a pharmaceutically acceptable derivative thereof and a pharmaceutically acceptable carrier, adjuvant, or vehicle. The amount of compound in compositions of this disclosure is such that it is effective to measurably inhibit a CDK2 protein, or a mutant thereof, in a biological sample or in a patient. In certain embodiments, the amount of compound in compositions of this disclosure is such that it is effective to measurably inhibit a CDK2 protein, or a mutant thereof, in a biological sample or in a patient. In certain embodiments, a composition of this disclosure is formulated for administration to a patient in need of such composition. In some embodiments, a composition of this disclosure is formulated for oral administration to a patient.

Compositions of the present disclosure may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this disclosure may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Pharmaceutically acceptable compositions of this disclosure may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, pharmaceutically acceptable compositions of this disclosure may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Pharmaceutically acceptable compositions of this disclosure may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, provided pharmaceutically acceptable compositions may be formulated in a suitable ointment containing the active component suspended or dissolved in one or more carriers. Carriers for topical administration of compounds of this disclosure include, but are not limited to, mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, provided pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

Pharmaceutically acceptable compositions of this disclosure may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, pharmaceutically acceptable compositions of this disclosure are formulated for oral administration. Such formulations may be administered with or without food. In some embodiments, pharmaceutically acceptable compositions of this disclosure are administered without food. In other embodiments, pharmaceutically acceptable compositions of this disclosure are administered with food.

The amount of compounds of the present disclosure that may be combined with the carrier materials to produce a composition in a single dosage form will vary depending upon the host treated, the particular mode of administration. Preferably, provided compositions should be formulated so that a dosage of between 0.01-100 mg/kg body weight/day of the compound can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present disclosure in the composition will also depend upon the particular compound in the composition.

Uses of Compounds and Pharmaceutically Acceptable Compositions

Compounds and compositions described herein are generally useful for the modulation of the activity CDK2. In some embodiments, the compounds and compositions described herein are CDK2 inhibitors.

In some embodiments, the compounds and compositions of the present disclosure are useful for treating diseases and disorders associated with CDK2 activity, including, but not limited to cancers, myeloproliferative disorders, autoimmune disorders, inflammatory disorders, viral infections, fibrotic disorders, and neurodegenerative disorders.

In some embodiments, the disclosure provides a method of inhibiting the activity of a CDK2, the method comprising contacting a compound of the present disclosure, or a pharmaceutically acceptable salt thereof with the CDK2. In some embodiments, the contacting takes place in vitro. In some embodiments, the contacting takes place in vivo.

In some embodiments, the disclosure provides a method of treating, preventing or lessening the severity of a disease or disorder associated with CDK2 activity in a patient, including, but not limited to cancers, myeloproliferative disorders, autoimmune disorders, inflammatory disorders, fibrotic disorders, and neurodegenerative disorders, said method comprising administering to a patient in need thereof, a compound of the present disclosure, or a pharmaceutically acceptable salt thereof, or a pharmaceutical composition comprising an effective amount of a compound of the present disclosure, or a pharmaceutically acceptable salt thereof.

The disclosure further provides a compound of the present disclosure, or a pharmaceutically acceptable salt thereof, or a pharmaceutical composition comprising an effective amount of a compound of the present disclosure, or a pharmaceutically acceptable salt thereof, for use in the treatment of a disease or disorder associated with CDK2 activity.

The disclosure further provides a compound of the present disclosure, or a pharmaceutically acceptable salt thereof, or a pharmaceutical composition comprising an effective amount of a compound of the present disclosure, or a pharmaceutically acceptable salt thereof, for use in the manufacture of a medicament for treating a disease or disorder associated with CDK2 activity.

In some embodiments, the disease or disorder associated with CDK2 activity is a CDK2-mediated disease or disorder. In some embodiments, the disease or disorder associated with CDK2 activity is a disease or disorder caused by CDK2 over-activity.

In some embodiments, the disease or disorder associated with CDK2 activity is cancer.

In some embodiments, the cancer is selected from breast cancer, ovarian cancer, bladder cancer, uterine cancer, prostate cancer, lung cancer, esophageal cancer, head and neck cancer, colorectal cancer, kidney cancer, liver cancer, pancreatic cancer, stomach cancer, melanoma and thyroid cancer.

In some embodiments, the cancer is characterized by amplification or overexpression of CCNE1 and/or CCNE2.

In some embodiments, the cancer is breast cancer. In some embodiments, the breast cancer is a breast cancer selected from ER-positive/HR-positive breast cancer, HER2-negative breast cancer, ER-positive/HR-positive breast cancer, HER2-positive breast cancer, triple negative breast cancer (TNBC), inflammatory breast cancer, endocrine resistant breast cancer, trastuzumab resistant breast cancer, breast cancer with primary or acquired resistance to CDK4/CDK6 inhibition, advanced breast cancer and metastatic breast cancer. In some embodiments the breast cancer is characterized by amplification or overexpression of CCNE1 and/or CCNE2.

In some embodiments, the cancer is ovarian cancer. In some embodiments, the ovarian cancer is high-grade serous ovarian cancer (HGSOC). In some embodiments the ovarian cancer is characterized by amplification or overexpression of CCNE1 and/or CCNE2.

In some embodiments, the cancer is bladder cancer. In some embodiments, the bladder cancer is characterized by amplification or overexpression of CCNE1 and/or CCNE2.

In some embodiments, the cancer is uterine cancer. In some embodiments, the uterine cancer is characterized by amplification or overexpression of CCNE1 and/or CCNE2.

In some embodiments, the cancer is prostate cancer. In some embodiments, the prostate cancer is characterized by amplification or overexpression of CCNE1 and/or CCNE2.

In some embodiments, the cancer is lung cancer. In some embodiments, the lung cancer is a lung cancer selected from non-small cell lung cancer, small cell lung cancer, squamous cell carcinoma, adenocarcinoma, and mesothelioma. In some embodiments, the lung cancer is characterized by amplification or overexpression of CCNE1 and/or CCNE2. In some embodiments, the lung cancer is CCNE1 amplified squamous cell carcinoma or CCNE1 amplified adenocarcinoma.

In some embodiments, the cancer is head and neck cancer. In some embodiments, the head and neck cancer is characterized by amplification or overexpression of CCNE1 and/or CCNE2.

In some embodiments, the cancer is colorectal cancer. In some embodiments, the colorectal cancer is characterized by amplification or overexpression of CCNE1 and/or CCNE2.

In some embodiments, the cancer is kidney cancer. In some embodiments, the kidney cancer is renal cell carcinoma (RCC). In some embodiments, the kidney cancer is characterized by amplification or overexpression of CCNE1 and/or CCNE2.

In some embodiments, the cancer is liver cancer. In some embodiments, the liver cancer is hepatocellular carcinoma (HCC). In some embodiments, the liver cancer is characterized by amplification or overexpression of CCNE1 and/or CCNE2.

In some embodiments, the cancer is pancreatic cancer. In some embodiments, the pancreatic cancer is characterized by amplification or overexpression of CCNE1 and/or CCNE2.

In some embodiments, the cancer is stomach cancer. In some embodiments, the stomach cancer is characterized by amplification or overexpression of CCNE1 and/or CCNE2.

In some embodiments, the cancer is melanoma. In some embodiments, the melanoma is characterized by amplification or overexpression of CCNE1 and/or CCNE2. CDK2 expression is regulated by essential melanocytic transcription factor MITF. It has been found that CDK2 depletion suppresses the growth of melanoma (Du et al., Cancer Cell. 2004 December; 6(6): 565-576)

In some embodiments, the cancer is thyroid cancer. In some embodiments, the thyroid cancer is characterized by amplification or overexpression of CCNE1 and/or CCNE2.

In some embodiments, the disease or disorder associated with CDK2 activity is a myeloproliferative disorder.

In some embodiments, the disease or disorder associated with CDK2 activity is a neurodegenerative disease or disorder. In some embodiments, the neurodegenerative disease or disorder is Alzheimer's disease (AD). It has been reported that neuronal cell death in subjects suffering from AD is preceded by cell cycle events. Inhibition of one or more CDKs can inhibit cell cycle events and therefore stave off neuronal cell death (Yang et al., J Neurosci. 2003 Apr. 1; 23(7):2557-2563).

In some embodiments, the disease or disorder associated with CDK2 activity is a liver disease.

In some embodiments, the disease or disorder associated with CDK2 activity is liver fibrosis. It has been reported that CCNE1 knockout mice do not develop liver fibrosis upon exposure to pro-fibrotic toxin $CCl_4$, suggesting that liver fibrosis can be treated via administration of a CDK2 inhibitor (Nevzorova, et al., *Hepatology.* 2012 September; 56(3): 1140-1149.)

In some embodiments, the disease or disorder associated with CDK2 activity is Cushing disease. Pituitary cyclin E/E2F1 signaling is a molecular mechanism underlying neuroendocrine regulation of the hypothalamic-pituitary-adrenal axis, and therefore provides a subcellular therapeutic target for CDK2 inhibitors of pituitary ACTH-dependent hypercortisolism, also known as Cushing disease (Liu, et al., *J Clin Endocrinol Metab.* 2015 July; 100(7): 2557-2564).

In some embodiments, the disease or disorder associated with CDK2 activity is a kidney disease.

In some embodiments, the disease or disorder associated with CDK2 activity is polycystic kidney disease. It has been reported that CDK2/CDK5 inhibitor roscovitine yields effective arrest of cystic kidney disease in mouse models of polycystic kidney disease (Bukanov, et al., *Nature.* 2006 Dec. 14; 444(7121):949-52).

In some embodiments, the disease or disorder associated with CDK2 activity is an autoimmune disorder. CDK2 ablation has been shown to promote immune tolerance by supporting the function of regulatory T cells (Chunder et al., J Immunol. 2012 Dec. 15; 189(12):5659-66).

In some embodiments, the disease or disorder associated with CDK2 activity is an inflammatory disorder. Cyclin E ablation has been shown to attenuate hepatitis in mice, while p27 knockout mice display exacerbation of renal inflammation (Ehedego et al., Oncogene. 2018 June; 37(25):3329-3339; Ophascharoensuk et al., Nat Med. 1998 May; 4(5): 575-80). In some embodiments, the inflammatory disorder is hepatitis.

In some embodiments, the compounds and compositions of the present disclosure are useful as male contraceptives. Based on the finding that male CDK2 knockout mice are sterile, CDK2 inhibitors have been studied as possible male contraceptives (Faber, et al., *Biol Reprod.* 2020 August; 103(2): 357-367). In some embodiments, the present disclosure provides a method of reducing male fertility comprising administering to a patient in need thereof, a compound of the present disclosure, or a pharmaceutically acceptable salt thereof, or a pharmaceutical composition comprising an effective amount of a compound of the present disclosure, or a pharmaceutically acceptable salt thereof.

Combination Therapies

Depending upon the particular condition, or disease, to be treated, additional therapeutic agents, which are normally administered to treat that condition, may be administered in combination with compounds and compositions of this disclosure. As used herein, additional therapeutic agents that are normally administered to treat a particular disease, or condition, are known as "appropriate for the disease, or condition, being treated."

In certain embodiments, a provided combination, or composition thereof, is administered in combination with another therapeutic agent.

In some embodiments, the present disclosure provides a method of treating a disclosed disease or condition comprising administering to a patient in need thereof an effective amount of a compound disclosed herein or a pharmaceutically acceptable salt thereof and co-administering simultaneously or sequentially an effective amount of one or more additional therapeutic agents, such as those described herein. In some embodiments, the method includes co-administering one additional therapeutic agent. In some embodiments, the method includes co-administering two additional therapeutic agents. In some embodiments, the combination of the disclosed compound and the additional therapeutic agent or agents acts synergistically.

Examples of agents that the compounds of the present disclosure may also be combined with include, without limitation: endocrine therapeutic agents, chemotherapeutic agents and other CDK inhibitory compounds.

In some embodiments, the present disclosure provides a method of treating a disclosed disease or condition comprising administering to a patient in need thereof an effective amount of a compound disclosed herein or a pharmaceutically acceptable salt thereof and co-administering simultaneously or sequentially an effective amount of an endocrine therapeutic agent.

In some embodiments, the present disclosure provides a method of treating a disclosed disease or condition comprising administering to a patient in need thereof an effective amount of a compound disclosed herein or a pharmaceutically acceptable salt thereof and co-administering simultaneously or sequentially an effective amount of one or more additional CDK inhibitory compounds. In some embodiments, the CDK inhibitory compounds are CDK4 or CDK4/CDK6 inhibitors.

In some embodiments, the present disclosure provides a method of treating a disclosed disease or condition comprising administering to a patient in need thereof an effective amount of a compound disclosed herein or a pharmaceutically acceptable salt thereof and co-administering simultaneously or sequentially an effective amount of a chemotherapeutic agent. In some embodiments, the chemotherapeutic agent is a taxane. In some embodiments, the chemotherapeutic agent is a platinum agent. In some embodiments, the chemotherapeutic agent is trastuzumab.

As used herein, the term "combination," "combined," and related terms refers to the simultaneous or sequential administration of therapeutic agents in accordance with this disclosure. For example, a combination of the present disclosure may be administered with another therapeutic agent simultaneously or sequentially in separate unit dosage forms or together in a single unit dosage form.

The amount of additional therapeutic agent present in the compositions of this disclosure will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

One or more other therapeutic agent may be administered separately from a compound or composition of the present disclosure, as part of a multiple dosage regimen. Alternatively, one or more other therapeutic agents may be part of a single dosage form, mixed together with a compound of this disclosure in a single composition. If administered as a multiple dosage regime, one or more other therapeutic agent and a compound or composition of the present disclosure may be administered simultaneously, sequentially or within a period of time from one another, for example within 1, 2, 3, 4, 5, 6, 7, 8, 9, 10, 11, 12, 13, 14, 15, 16, 17, 18, 18, 20, 21, 22, 23, or 24 hours from one another. In some embodiments, one or more other therapeutic agent and a compound or composition the present disclosure are administered as a multiple dosage regimen within greater than 24 hours a parts.

In one embodiment, the present disclosure provides a composition comprising a provided compound or a pharmaceutically acceptable salt thereof and one or more additional therapeutic agents. The therapeutic agent may be administered together with a provided compound or a pharmaceutically acceptable salt thereof, or may be administered prior to or following administration of a provided compound or a pharmaceutically acceptable salt thereof. Suitable therapeutic agents are described in further detail below. In certain embodiments, a provided compound or a pharmaceutically acceptable salt thereof may be administered up to 5 minutes, 10 minutes, 15 minutes, 30 minutes, 1 hour, 2 hours, 3 hours, 4 hours, 5, hours, 6 hours, 7 hours, 8 hours, 9 hours, 10 hours, 11 hours, 12 hours, 13 hours, 14 hours, 15 hours, 16 hours, 17 hours, or 18 hours before the therapeutic agent. In other embodiments, a provided compound or a pharmaceutically acceptable salt thereof may be administered up to 5 minutes, 10 minutes, 15 minutes, 30 minutes, 1 hour, 2 hours, 3 hours, 4 hours, 5, hours, 6 hours, 7 hours, 8 hours, 9 hours, 10 hours, 11 hours, 12 hours, 13 hours, 14 hours, 15 hours, 16 hours, 17 hours, or 18 hours following the therapeutic agent.

EXAMPLES

As depicted in the Examples below, in certain exemplary embodiments, compounds are prepared according to the general procedures provided herein. It will be appreciated that, although the general methods depict the synthesis of certain compounds of the present disclosure, the general methods, and other methods known to one of ordinary skill in the art, can be applied to all compounds and subclasses and species of each of these compounds, as described herein.

General Procedures

Abbreviations: Chloroform-d (deuterated chloroform); DMSO-$d_6$ (deuterated dimethylsulfoxide); Boc (tert-butoxycarbonyl); Boc$_2$O (di-tert-butyl dicarbonate); DMF (N,N-dimethylformamide); NMP (1-methyl-2-pyrrolidinone); DMSO (dimethylsulfoxide); PE (petroleum ether); EDCI (1-ethyl-3-(3-dimethylaminopropyl) carbodiimide); ESI (electrospray atmospheric pressure ionization); TEA (tri ethyl amine); TFA (trifluoroacetic acid); dioxane (1,4-dioxane); THF (tetrahydrofuran); EtOAc (ethyl acetate); g (gram); h (hour); nm (nanometer); $^1$H NMR (proton nuclear magnetic resonance); Hz (hertz); LCMS (liquid chromatography-mass spectrometry); MS (mass spectrometry); mg (milligrams); MHz (megahertz); min (minutes); mL (millilitres), mmol (millimoles); ppm (parts per million); R$_t$ (retention time); RT (room temperature); TLC (thin layer chromatography); v/v (volume/volume); m/z (mass charge ratio); HCl (hydrochloric acid); KOAc (potassium acetate); NaOAc (sodium acetate); Pd/C (palladium on activated carbon); n-BuLi (n-butyllithium); MeI (iodomethane); EtI (iodoethane); LiHMDS (lithium bis(trimethylsilyl)amide); NaHMDS (sodium bis(trimethylsilyl)amide); TMSOI (trimethyl sulfoxonium iodide); TMSCHN$_2$ (trimethylsilyldiazomethane); LDA (lithium diisopropylamide); DIAD (diisopropyl azodicarboxylate); DEAD (diethyl azodicarboxylate); DBAD (di-tert-butyl azodicarboxylate); TMSCF$_3$ (Trimethyl(trifluoromethyl)silane); X-Phos (2-(dicyclohexylphosphino)-2',4',6'-triisopropylbiphenyl); NCS (N-chlorosuccinimide); NBS (N-bromosuccinimide); SEMCl (2-(trimethylsilyl)ethoxymethyl chloride); AIBN (2,2'-azobis(isobutyronitrile)); CO (carbon monoxide); DIPEA or DIEA (N,N-diisopropylethylamine); TBAF (tetrabutylammonium fluoride); TBAI (tetrabutylammonium iodide); DAST (diethylaminosulfur trifluoride); MW (microwave); Pd(PPh$_3$)$_4$ (tetrakis(triphenylphosphine)palladium); Pd$_2$(dba)$_3$ (tris(dibenzylideneacetone)dipalladium); Pd(dppf)Cl$_2$ ([1,1'-Bis(diphenylphosphino)ferrocene]dichloropalladium); NaH (sodium hydride); PPh$_3$ (triphenylphosphine); HATU (2-(7-aza-1H-benzotriazole-1-yl)-1,1,3,3-tetramethyluronium hexafluorophosphate); TBSCl (tert-butyldimethylchlorosilane); ee (enantiomeric excess); NiCl$_2$(dme) (dichloro(dimethoxyethane)nickel); HOBt (hydroxybenzotriazole); DCM (dicloromethane); DMA (dimethylacetamide); prep-TLC (preparative thin layer chromatography), prep-HPLC (preparative HPLC); DEA (diethylamine); CbzCl (benzyl chloroformate); ACN (acetonitrile), DCC (dicyclohexylcarbodiimide), HOSu (N-hydroxysuccinimide); quant. (quantitative yield); MTBE (methyl tert-butyl ether); DIBAL-H (diisobutylaluminium hydride); DCE (1,2-dichloro ethane); DMAP (4-(dimethylamino)pyridine); IPA (isopropyl alcohol); LDA (lithium diisopropylamide); TBN (tert-butyl nitrite); PMBCl (4-methoxybenzyl chloride); CAN (ceric ammonium nitrate); CDI (N,N'-carbonyldiimidazole); FmocOSu (N-(9H-fluoren-9-ylmethoxycarbonyloxy)succinimide).

Materials and Methods

NMR: $^1$H NMR spectra were recorded at 400 MHz using a Bruker AVANCE 400 MHz spectrometer. Data for $^1$H are reported as chemical shift (ppm) and multiplicity (s=singlet, d=doublet, t=triplet, q=quartet, m=multiplet).

LCMS (Shimadzu 3 min method):
LC: Shimadzu LC-20AD series, Binary Pump, Diode Array Detector. Agilent Poroshell 120 EC-C18, 2.7 µm, 4.6×50 mm column. Mobile phase: A: 0.05% formic acid in water (v/v), B: 0.05% formic acid in MeCN (v/v). Acquire time: 3 min. LC gradient: hold 15% B for 0.28 min; then 15% to 90% in 2.1 min; then 90% to 100% in 0.01 min; then hold 100% for 0.3 min; then 100% to 15% in 0.01 min; hold at 15% for 0.3 min. Flow Rate: 1.5 mL/min at 25° C. Detection wavelength: 214 nm, 254 nm.
MS: 2020, Quadrupole LC/MS, Ion Source: API-ESI, TIC: 100~900 m/z, Drying gas flow: 15 L/min, Nebulizer pressure: 1.5 L/min, Drying gas temperature: 250° C., Vcap: 4500V.
LC-MS (Shimadzu 5 min method):
LC: Shimadzu LC-20AD series, Binary Pump, Diode Array Detector. Agilent Poroshell 120 EC-C18, 2.7 µm, 4.6×50 mm column. Mobile phase: A: 0.05% formic acid in water (v/v), B: 0.05% formic acid in MeCN (v/v). Acquire time: 5 min. LC gradient: hold 15% B for 0.5 min; then 15% to 85% in 3.5 min; then 85% to 100% in 0.01 min; then hold 100% for 0.49 min; then 100% to 15% in 0.01 min; hold at 15% for 0.49 min. Flow Rate: 1 mL/min at 25° C. Detection wavelength: 214 nm, 254 nm.

MS: 2020, Quadrupole LC/MS, Ion Source: API-ESI, TIC: 100~900 m/z, Drying gas flow: 15 L/min, Nebulizer pressure: 1.5 L/min, Drying gas temperature: 250° C., Vcap: 4500V.

LC-MS (Agilent 5 min method):

LC: Agilent Technologies 1290 series, Binary Pump, Diode Array Detector. Agilent Poroshell 120 EC-C18, 2.7 μm, 4.6×50 mm column. Mobile phase: A: 0.05% formic acid in water (v/v), B: 0.05% formic acid in MeCN (v/v). Acquire time: 5 min. LC gradient: hold 10% B for 0.5 min; then 10% to 90% in 3.5 min; then 90% to 100% in 0.01 min; then hold 100% for 0.49 min; then 100% to 10% in 0.01 min; hold at 10% for 0.49 min. Flow Rate: 1 mL/min at 25° C. Detection wavelength: 214 nm, 254 nm.

MS: G6120A, Quadrupole LC/MS, Ion Source: API-ESI, TIC: 70~1000 m/z, Fragmentor: 70, Drying gas flow: 12 L/min, Nebulizer pressure: 36 psi, Drying gas temperature: 350° C., Vcap: 3000V.

Preparative HPLC Generic Methods:

HPLC Instruments: Shimadzu 20AP UV detector: SPD-20A. UV wavelength: 214 nm and 254 nm.

Condition 1: Mobile phase A: water with 0.1% trifluoroacetic acid; Mobile phase B: methanol.

Condition 2: Mobile phase A: water with 0.1% trifluoroacetic acid; Mobile phase B: acetonitrile.

Column: Agilent 10 Prep-C18 250×21.2 mm. Column temperature: Ambient

LC gradient: 20% to 85% in 20 min; then 85% to 100% in 0.01 min; then hold 100% for 5 min; then 100% to 20% in 0.01 min; hold at 20% for 5 min.

LC Flow rate: 20 mL/min binary pump.

Example 1: Synthesis of Precursor Compounds and Intermediates

Synthesis of Int-1 and Int-2

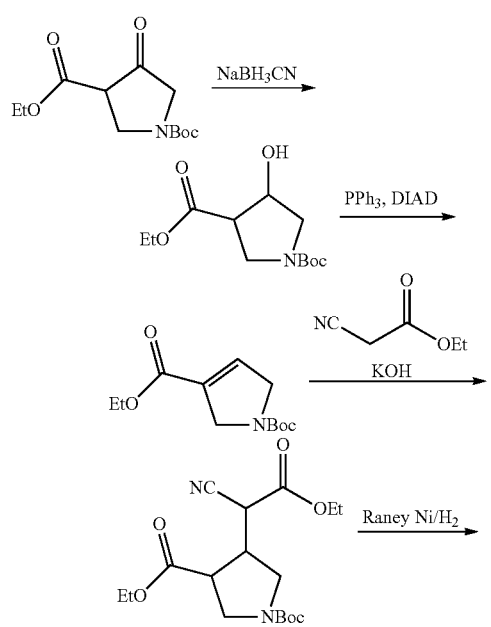

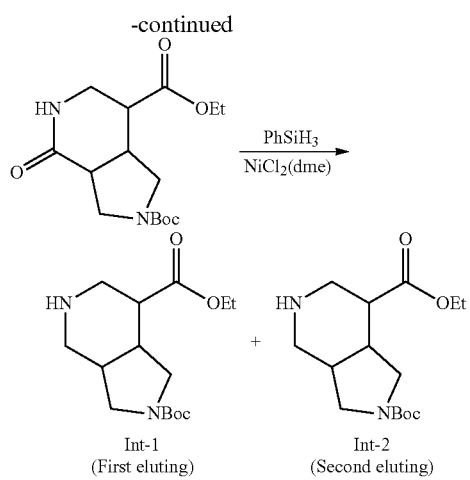

Step 1: 1-(tert-butyl) 3-ethyl 4-hydroxypyrrolidine-1,3-dicarboxylate

To a solution of 1-(tert-butyl) 3-ethyl 4-oxopyrrolidine-1,3-dicarboxylate (30.0 g, 0.117 mol) in MeOH (500 mL) was added NaBH$_3$CN (8.04 g, 0.128 mol). Aqueous HCl (1M, 110 mL) was added dropwise with stirring maintaining the pH at ~3-4. When the addition was complete the reaction was stirred for 5 h and extracted with EtOAc three times. The combined organic layers were washed with aqueous NaHCO$_3$, brine, dried over Na$_2$SO$_4$ and concentrated in vacuo. The crude residue was purified by column chromatography (20% EtOAc/PE) to give the product (27.0 g, 89.4%) as a colourless oil. LCMS m/z=260.1 [M+H]$^+$; $^1$H NMR (400 MHz, CDCl$_3$) δ 4.57-4.49 (m, 1H), 4.17 (dq, J=7.2, 1.6 Hz, 2H), 3.78-3.41 (m, 3H), 3.37-2.64 (m, 3H), 1.44 (app d, J=1.4 Hz, 9H), 1.32-1.19 (m, 3H).

Step 2: 1-(tert-butyl) 3-ethyl 2,5-dihydro-1H-pyrrole-1,3-dicarboxylate

To a solution of 1-(tert-butyl) 3-ethyl 4-hydroxypyrrolidine-1,3-dicarboxylate (27.0 g, 0.104 mol) and PPh$_3$ (32.8 g, 0.125 mol) in dry toluene (300 mL) at 0° C. was added DIAD (25.3 g, 0.125 mol) dropwise. The mixture was allowed to warm to room temperature and stirred overnight. The solvent was removed under vacuum and the residue purified by column chromatography (10% EtOAc/PE) to give the product (19.0 g, 76.4%) as a colourless oil. $^1$H NMR (400 MHz, DMSO-d$_6$) δ 6.77 (dt, J=13.4, 1.9 Hz, 1H), 4.23-4.07 (m, 6H), 1.41 (d, J=2.3 Hz, 9H), 1.22 (t, J=7.1 Hz, 3H).

Step 3: 1-(tert-butyl) 3-ethyl 4-(1-cyano-2-ethoxy-2-oxoethyl)pyrrolidine-1,3-dicarboxylate To a solution of 1-(tert-butyl) 3-ethyl 2,5-dihydro-1H-pyrrole-1,3-dicarboxylate (19.0 g, 0.079 mol) and ethyl 2-cyanoacetate (17.8 g, 0.157 mol) in DMF (250 mL) was added KOH (8.83 g, 0.158 mol). The mixture was stirred for 4 h, then extracted with EtOAc three times. The combined organic layers were washed with water and brine, dried over Na$_2$SO$_4$ and concentrated in vacuo. The crude was purified by column chromatography (30% EtOAc/PE) to give the product (19.8 g, 71%) as a colourless oil. 1H NMR (400

MHz, CD$_3$OD) δ 4.38-4.19 (m, 4H), 3.85-3.38 (m, 6H), 3.19-3.09 (m, 1H), 1.54-1.50 (m, 9H), 1.42-1.23 (m, 6H).

Step 4: 2-(tert-butyl) 7-ethyl 4-oxooctahydro-2H-pyrrolo[3,4-c]pyridine-2,7-dicarboxylate To a solution of 1-(tert-butyl) 3-ethyl 4-(1-cyano-2-ethoxy-2-oxoethyl)pyrrolidine-1,3-dicarboxylate (19.8 g, 0.056 mol) in EtOH (250 mL) was added Raney Ni (5 g). The resulting mixture was stirred under an atmosphere of H$_2$ overnight. The reaction mixture was filtered through a pad of celite and the filtrate was concentrated in vacuo. The crude was purified by column chromatography (50% EtOAc/PE) to give the product (13.9 g, 79%) as a colourless oil. $^1$H NMR (400 MHz, CD$_3$OD) δ 4.25-4.14 (m, 2H), 3.84-3.33 (m, 6H), 3.28-2.67 (m, 3H), 1.46 (d, J=3.7 Hz, 9H), 1.28 (dt, J=7.2, 3.0 Hz, 3H).

Step 5: 2-(tert-butyl) 7-ethyl octahydro-2H-pyrrolo[3,4-c]pyridine-2,7-dicarboxylate (Int-1) and (Int-2)

To a solution of 2-(tert-butyl) 7-ethyl 4-oxooctahydro-2H-pyrrolo[3,4-c]pyridine-2,7-dicarboxylate (13.9 g, 0.044 mol) and PhSiH$_3$ (12.11 g, 0.112 mol) in dry toluene (300 mL) was added NiCl$_2$(dme) (1.23 g, 0.006 mol). The mixture was heated at reflux under N$_2$ overnight. The solvent was removed and the residue taken up in EtOAc. The organic phase was washed with aqueous NaHCO$_3$ and brine, dried over Na$_2$SO$_4$ and concentrated in vacuo. The crude residue was purified by column chromatography (2.5% MeOH/DCM) to give Int-1 (4.0 g, 30%) as the first eluting diastereomer and Int-2 (2.1 g, 14%) as the second eluting diastereomer. Int-1: LCMS m/z=299.1 [M+H]$^+$; $^1$H NMR (400 MHz, CD$_3$OD) δ 4.16-4.04 (m, 2H), 3.36-3.18 (m, 4H), 3.10-3.02 (m, 1H), 2.86-2.75 (m, 2H), 2.69-2.57 (m, 1H), 2.47-2.39 (m, 1H), 2.38-2.28 (m, 2H), 1.43-1.37 (m, 9H), 1.24-1.17 (m, 3H). Int-2: LCMS m/z=299.1 [M+H]$^+$; $^1$H NMR (400 MHz, CD$_3$OD) δ 4.21-4.10 (m, 2H), 3.46-3.34 (m, 2H), 3.30-3.25 (m, 1H), 3.18-3.00 (m, 2H), 2.95-2.68 (m, 4H), 2.41-2.22 (m, 2H), 1.50-1.43 (m, 9H), 1.30-1.23 (m, 3H).

Alternative Synthesis of 1-(tert-butyl) 3-ethyl 4-(1-cyano-2-ethoxy-2-oxoethyl)pyrrolidine-1,3-dicarboxylate

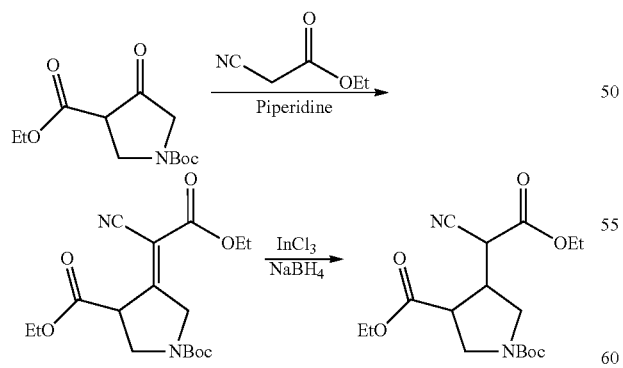

Step 1: 1-(tert-butyl) 3-ethyl 4-(1-cyano-2-ethoxy-2-oxoethylidene)pyrrolidine-1,3-dicarboxylate A mixture of 1-(tert-butyl) 3-ethyl 4-oxopyrrolidine-1,3-dicarboxylate (20.0 g, 0.078 mol), ethyl 2-cyanoacetate (8.8 g, 0.093 mol) and piperidine (20.0 g, 0.078 mol) was stirred for 2 days under N$_2$. The resulting mixture was concentrated in vacuo and the crude purified by column chromatography (6% EtOAc/PE) to afford the product (8.11 g, 29.6%) as a yellow oil. $^1$H NMR (400 MHz, CD$_3$OD) δ 4.66-4.49 (m, 1H), 4.46-3.60 (m, 8H), 1.53-1.44 (m, 9H), 1.39-1.22 (m, 6H).

Step 2: 1-(tert-butyl) 3-ethyl 4-(1-cyano-2-ethoxy-2-oxoethyl)pyrrolidine-1,3-dicarboxylate To a solution of InCl$_3$ (204 mg, 0.92 mmol) and NaBH$_4$ (387 mg, 10.2 mmol) in acetonitrile (10 mL) was added a solution of 1-(tert-butyl) 3-ethyl 4-(1-cyano-2-ethoxy-2-oxoethylidene)pyrrolidine-1,3-dicarboxylate (2.4 g, 6.8 mmol) in acetonitrile (15 mL). The mixture was stirred at room temperature for 3 h. The reaction mixture was quenched with water and extracted with EtOAc three times. The combined organic layers were washed with water, brine, and dried over Na$_2$SO$_4$. The solvent was removed and the crude purified by column chromatography (30% EtOAc/PE) to afford the product (1.5 g, 62.2%) as a colorless oil. LCMS m/z=299.1 [M-tBu+H]$^+$; $^1$H NMR (400 MHz, CD$_3$OD) δ 4.39-4.17 (m, 4H), 3.85-3.65 (m, 2H), 3.64-3.35 (m, 4H), 3.18-3.05 (m, 1H), 1.55-1.48 (m, 9H), 1.41-1.28 (m, 6H).

Synthesis of (S)-2-amino-N-methyl-5-phenylpentanamide

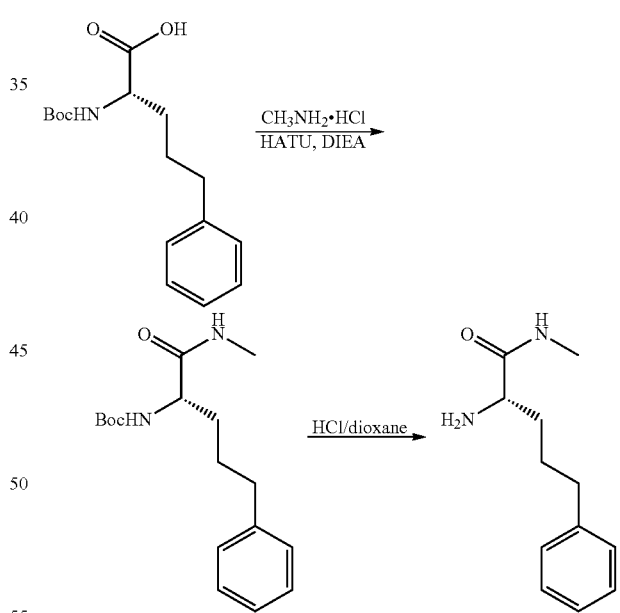

Step 1: tert-butyl (S)-(1-(methylamino)-1-oxo-5-phenylpentan-2-yl)carbamate

A solution of (S)-2-((tert-butoxycarbonyl)amino)-5-phenylpentanoic acid (3.0 g, 10.2 mmol), HATU (5.83 g, 15.3 mmol) and DIEA (5.3 g, 40.8 mmol) in DMF (15 mL) was stirred at room temperature for 30 min Methylamine hydrochloride (830 mg, 12.3 mmol) was then added and the mixture stirred for another 6 h. Water was added and the precipitate collected by filtration, then washed with water and dried under vacuum to afford the product (2.1 g, 67%) as a white solid. LCMS m/z=307.2 [M+H]⁺.

Step 2: (S)-2-amino-N-methyl-5-phenylpentanamide

To a solution of tert-butyl (S)-(1-(methylamino)-1-oxo-5-phenylpentan-2-yl)carbamate (2.1 g, 6.85 mmol) in DCM (20 mL) was added HCl (4M in dioxane, 20 mL) and the mixture was stirred at room temperature for 2 h. The solvent was removed to afford the product (1.65 g, quant.) as white solid. LCMS m/z=207.1 [M+H]⁺.

Synthesis of (S)-2-amino-3-(1H-indol-3-yl)-N-methylpropanamide

Made using a similar method as described for the synthesis of (S)-2-amino-N-methyl-5-phenylpentanamide, starting with (tert-butoxycarbonyl)-L-tryptophan in place of (S)-2-((tert-butoxycarbonyl)amino)-5-phenylpentanoic acid. LCMS m/z=218.0 [M+H]⁺.

Synthesis of (R)-2-amino-N-methyl-3-phenylpropanamide

Made using a similar method as described for the synthesis of (S)-2-amino-N-methyl-5-phenylpentanamide, starting with (tert-butoxycarbonyl)-D-phenylalanine in place of (S)-2-((tert-butoxycarbonyl)amino)-5-phenylpentanoic acid. LCMS m/z=179.1 [M+H]⁺.

Synthesis of (R)-2-amino-3-(4-hydroxyphenyl)-N-methylpropanamide

Made using a similar method as described for the synthesis of (S)-2-amino-N-methyl-5-phenylpentanamide, starting with (tert-butoxycarbonyl)-D-tyrosine in place of (S)-2-((tert-butoxycarbonyl)amino)-5-phenylpentanoic acid. LCMS m/z=195.2 [M+H]⁺.

Synthesis of (R)-2-amino-3-(4-hydroxyphenyl)-N-methylpropanamide

Made using a similar method as described for the synthesis of (S)-2-amino-N-methyl-5-phenylpentanamide, starting with (tert-butoxycarbonyl)-L-phenylalanine in place of (S)-2-((tert-butoxycarbonyl)amino)-5-phenylpentanoic acid. LCMS m/z=179.2 [M+H]⁺.

Synthesis of 4-(2-cyclopropylethoxy)-3-methoxybenzoic acid

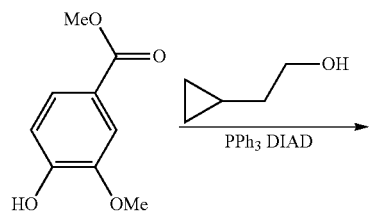

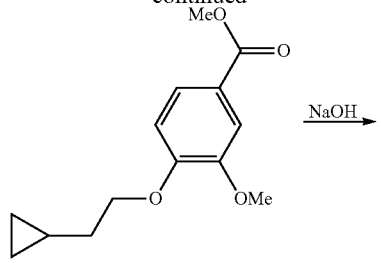

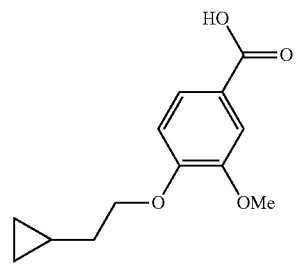

Step 1: methyl 4-(2-cyclopropylethoxy)-3-methoxybenzoate

To a solution of methyl 4-hydroxy-3-methoxybenzoate (100 mg, 0.55 mmol) in dry THF (3 mL) was added 2-cyclopropylethan-1-ol (57 mg, 0.66 mmol) and PPh₃ (288 mg, 1.10 mmol). After stirring at 0° C. for 10 min, DIAD (166 mg, 082 mmol) was added and the reaction mixture was allowed to warm to room temperature and stirred for another 2 h. Water was added and the aqueous extracted with EtOAc three times. The combined organic layers were washed with water, brine and dried over Na₂SO₄. The solvent was removed and the residue purified by prep-TLC (50% PE/EtOAc) to afford methyl 4-(2-cyclopropylethoxy)-3-methoxybenzoate (80 mg, 59%) as a white solid. ¹H NMR (400 MHz, CD₃OD) δ 7.63 (dd, J=8.4, 2.0 Hz, 1H), 7.54 (d, J=2.0 Hz, 1H), 7.01 (d, J=8.4 Hz, 1H), 4.13 (t, J=6.5 Hz, 2H), 3.87 (d, J=1.5 Hz, 6H), 1.71 (q, J=6.7 Hz, 2H), 0.96-0.84 (m, 1H), 0.53-0.45 (m, 2H), 0.18-0.11 (m, 2H).

Step 2: 4-(2-cyclopropylethoxy)-3-methoxybenzoic acid 0

To a solution of methyl 4-(2-cyclopropylethoxy)-3-methoxybenzoate (80 mg, 0.32 mmol) in MeOH (2 mL) was added aqueous NaOH (1M, 0.5 mL). The resulting mixture was stirred for 3 h. The residue obtained after concentration was diluted with water and the pH adjusted to ~1 by addition of 1M HCl. The aqueous layer was extracted with EtOAc three times and the combined organic layers were washed with water, brine and dried over Na₂SO₄. 4-(2-cyclopropylethoxy)-3-methoxybenzoic acid (50 mg, 67%) was obtained after removal of the solvent as a white solid. ¹H NMR (400 MHz, CD₃OD) δ 7.65 (dd, J=8.4, 2.0 Hz, 1H), 7.56 (d, J=2.0 Hz, 1H), 7.01 (d, J=8.4 Hz, 1H), 4.13 (t, J=6.6 Hz, 2H), 3.87 (s, 3H), 1.71 (q, J=6.7 Hz, 2H), 0.89 (td, J=7.3, 4.0 Hz, 2H), 0.55-0.45 (m, 1H), 0.22-0.11 (m, 2H).

Synthesis of 2-phenyloxazole-5-carboxylic acid

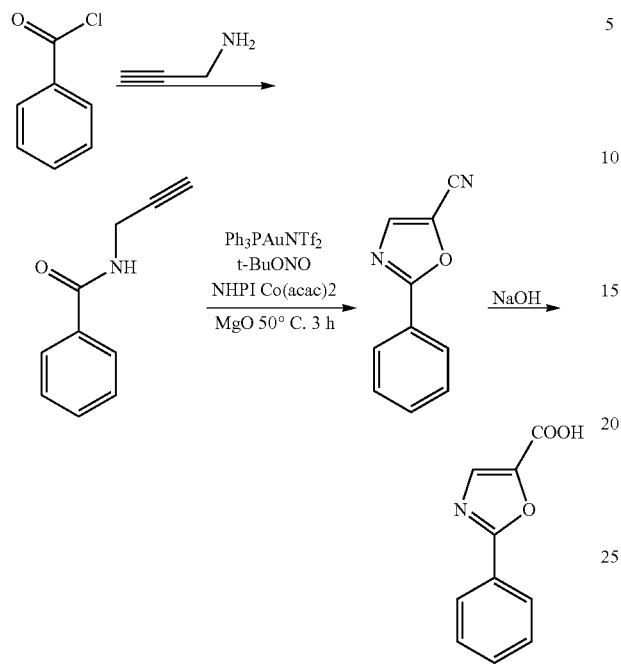

Step 1: N-(prop-2-yn-1-yl)benzamide

To a solution of benzoyl chloride (1.0 g, 7.14 mmol) and TEA (2.7 g, 26.7 mmol) in DCM (5 mL) was added prop-2-yn-1-amine (0.43 g, 7.80 mmol) dropwise. The mixture was stirred at r.t. overnight. The resulting mixture was extracted with EtOAc three times. The combined organic layers were washed with water and brine, dried over $Na_2SO_4$ and concentrated in vacuo. The obtained residue was purified by column chromatography (10% EtOAc/PE) to afford N-(prop-2-yn-1-yl)benzamide (0.80 g, 71.4%) as a colourless solid. LCMS m/z=160.1 $[M+H]^+$; $^1H$ NMR (400 MHz, DMSO-$d_6$) δ 8.92 (t, J=5.6 Hz, 1H), 7.90-7.80 (m, 2H), 7.58-7.42 (m, 3H), 4.05 (dd, J=5.6, 2.5 Hz, 2H), 3.11 (t, J=2.5 Hz, 1H).

Step 2: 2-phenyloxazole-5-carbonitrile

To a solution of N-(prop-2-yn-1-yl)benzamide (350 mg, 2.201 mmol) in acetonitrile (5 mL) was added $Ph_3PauNTf_2$ (23.2 mg, 0.110 mmol), t-BuONO (680.1 mg, 6.603 mmol), N-Hydroxyphthalimide (107.6 mg, 0.660 mmol), bis(2,4-pentanedionato)cobalt (42.2 mg, 0.165 mmol) and magnesium oxide (266.1 mg, 6.603 mmol). The mixture was heated at 50° C. for 3 h. The solvent was removed under vacuum and the residue was purified by prep-TLC (6.6% MeOH/DCM) to give 2-phenyloxazole-5-carbonitrile (34 mg, 9.1%) as a colorless oil. LCMS m/z=171.1 $[M+H]^+$; $^1H$ NMR (400 MHz, DMSO-$d_6$) δ 8.42 (s, 1H), 8.12-8.03 (m, 2H), 7.69-7.57 (m, 3H).

Step 3: 2-phenyloxazole-5-carboxylic acid

To a solution of 2-phenyloxazole-5-carbonitrile (35 mg, 0.205 mmol) in a mixture of DMSO (1 mL) and $H_2O$ (0.5 mL) was added NaOH (24.6 mg, 0.615 mmol). The mixture was heated at 100° C. for 3 h. After pH was adjusted to ~1 with adding of 1M HCl, the aqueous was extracted with EtOAc three times. 2-phenyloxazole-5-carboxylic acid (34 mg, 87.2%) was obtained after removal of the solvent as a white solid. LCMS m/z=190.0 $[M+H]^+$.

Synthesis of 3-methoxy-4-sulfamoylbenzoic acid

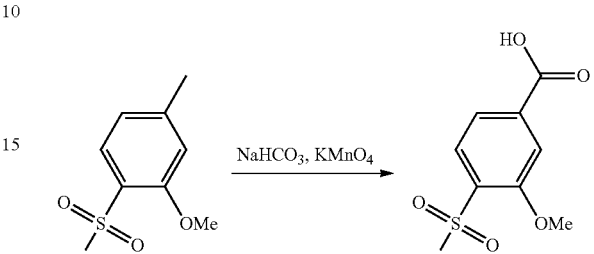

To a solution of 2-methoxy-4-methylbenzenesulfonamide (1.00 g, 4.97 mmol) in $H_2O$ (5 mL) was added $NaHCO_3$ (0.34 g, 3.98 mmol) and $KMnO_4$ (3.14 g 19.88 mmol). The resulting mixture was stirred at 100° C. overnight. After filtration, the filtrate was acidified by adding of 1M HCl until pH to ~2 then extracted by EtOAc three times. The combined organic layers were washed with water, brine, dried over $Na_2SO_4$. 3-methoxy-4-sulfamoylbenzoic acid (200 mg, 17%) was obtained after removal of the solvent as a white solid. LCMS m/z=232.1 $[M+H]^+$.

Synthesis of 4-(cyclopropanecarboxamido)-3-methoxybenzoic acid

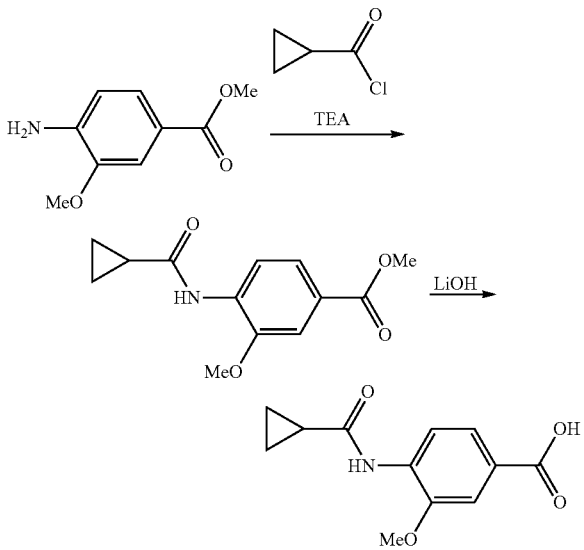

Step 1: methyl 4-(cyclopropanecarboxamido)-3-methoxybenzoate

To a solution of methyl 4-amino-3-methoxybenzoate (500 mg, 2.76 mmol) in DCM (5 mL) at 0° C. was added TEA (836 mg, 8.26 mmol) and cyclopropanecarbonyl chloride (346 mg, 3.31 mmol). The resulting mixture was stirred at 0° C. for 1 h. The residue after concentration was purified by column chromatography (30% EtOAc/PE) to afford methyl 4-(cyclopropanecarboxamido)-3-methoxybenzoate (400 mg, 58.2%) as a white solid. LCMS m/z=250.1 [M+H]$^+$.

Step 2: 4-(cyclopropanecarboxamido)-3-methoxybenzoic acid

To a solution of methyl 4-(cyclopropanecarboxamido)-3-methoxybenzoate (150.0 mg, 0.60 mmol) in a mixture of THF (2 mL) and H$_2$O (2 mL) was added LiOH (43 mg, 1.8 mmol). The resulting mixture was stirred at room temperature for 3 h. The pH of reaction mixture was adjusted to ~2 by adding of 1M HCl then extracted with EtOAc three times. The combined organic layers were washed with water and brine, dried over Na$_2$SO$_4$. 4-(Cyclopropanecarboxamido)-3-methoxybenzoic acid (140 mg, 98.9%) was obtained after removal of the solvent as a white solid. LCMS m/z=236.0 [M+H]$^+$.

Synthesis of 3-methoxy-4-(methylsulfonamido)benzoic acid

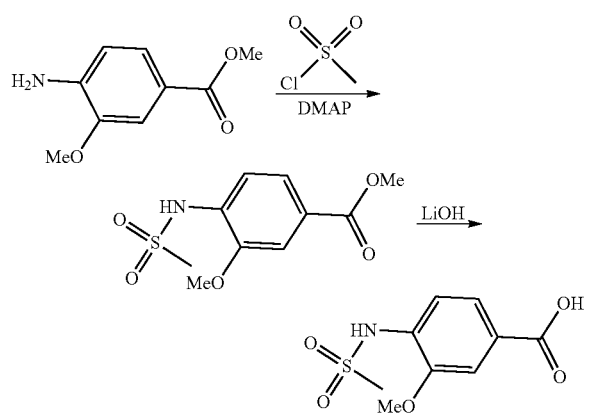

Step 1: methyl 3-methoxy-4-(methylsulfonamido)benzoate

To a solution of methyl 4-amino-3-methoxybenzoate (500 mg, 2.7 mmol) in DCM (5 mL) and pyridine (0.5 mL) was added methanesulfonyl chloride (720 mg, 4.2 mmol) and DMAP (20 mg, 0.135 mmol) at 0° C. The resulting mixture was stirred for 4 h. Water was added and the aqueous extracted with EtOAc three times. The combined organic layers were washed with water, brine and dried over Na$_2$SO$_4$. The residue after concentration was purified by column chromatography (2% MeOH/DCM) to afford methyl 3-methoxy-4-(methylsulfonamido)benzoate (680 mg, 97%) as a white solid. $^1$H NMR (400 MHz, CDCl$_3$) δ 7.68 (dd, J=8.4, 1.7 Hz, 1H), 7.58 (d, J=1.4 Hz, 2H), 7.12 (s, 1H), 3.92 (d, J=13.0 Hz, 6H), 3.03 (s, 3H).

Step 2: 3-methoxy-4-(methylsulfonamido)benzoic acid

To a solution of methyl 3-methoxy-4-(methylsulfonamido)benzoate (680 mg, 2.62 mmol) in MeOH (10 mL) and THF (5 mL) was added LiOH (275 mg, 6.55 mmol). The mixture was stirred for 2 h. The solvent was removed under vacuum and the residue obtained was diluted with water and the pH adjusted to ~1 by addition of 1M HCl. The aqueous layer was extracted with EtOAc three times. The combined organic layers were washed with water and brine, dried over Na$_2$SO$_4$ and the solvent removed to afford methyl 3-methoxy-4-(methylsulfonamido)benzoate (563 mg, 87.8%) as a white solid. $^1$H NMR (400 MHz, CD$_3$OD) δ 6.83 (t, J=1.0 Hz, 2H), 6.77-6.69 (m, 1H), 3.14 (d, J=0.9 Hz, 3H), 2.20 (d, J=1.0 Hz, 3H).

Synthesis of (3-aminopiperidin-1-yl)(phenyl)methanone hydrochloride

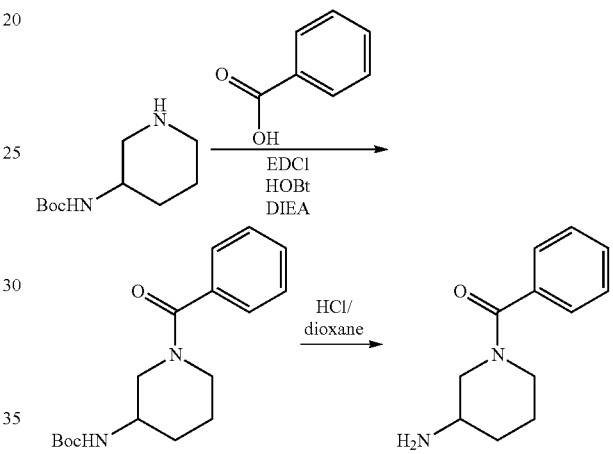

Step 1: tert-butyl (1-benzoylpiperidin-3-yl)carbamate

To a solution of tert-butyl piperidin-3-ylcarbamate (300 mg, 1.5 mmol) in DMA (5 mL) was added benzoic acid (275.0 mg, 28.2 mmol), EDCI (430.7 mg, 2.25 mmol), HOBt (243 mg, 1.85 mmol) and DIPEA (232.3 mg, 1.85 mmol). The resulting mixture was stirred overnight. Water was added into the reaction mixture then extracted with EtOAc three times. The combined organic layers were washed with water, brine, dried over Na$_2$SO$_4$. The residue after concentration was purified by column chromatography (10% EtOAc/PE) to afford tert-butyl (1-benzoylpiperidin-3-yl)carbamate (367 mg, 81%) as a white solid. LCMS m/z=305.2 [M+H]$^+$; $^1$H NMR (400 MHz, CD$_3$OD) δ 7.54-7.31 (m, 5H), 3.46 (d, J=58.1 Hz, 2H), 3.05 (d, J=47.2 Hz, 2H), 2.11-1.68 (m, 3H), 1.66-1.20 (m, 12H).

Step 2: (3-aminopiperidin-1-yl)(phenyl)methanone hydrochloride

To a solution of tert-butyl (1-benzoylpiperidin-3-yl)carbamate (367 mg, 1.2 mmol) in DCM (5 mL) was added HCl (4M in dixoane, 3 mL). The resulting mixture was stirred for 4 h. The solvent was removed to afford (3-aminopiperidin-1-yl)(phenyl)methanone hydrochloride (390 mg, quant.) LCMS m/z=205.1 [M+H]$^+$.

265
Synthesis of 1-(3-aminopiperidin-1-yl)-2-phenylethan-1-one hydrochloride

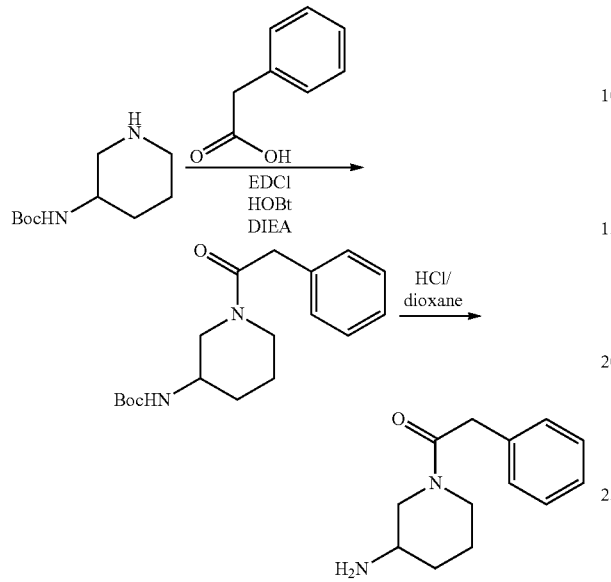

Step 1: tert-butyl (1-(2-phenylacetyl)piperidin-3-yl)carbamate

To a solution of tert-butyl piperidin-3-ylcarbamate (200 mg, 1.0 mmol) in DMA (5 mL) was added 2-phenylacetic acid (204.0 mg, 1.5 mmol), EDCI (287.1 mg, 1.5 mmol), HOBt (162.0 mg, 1.2 mmol) and DIPEA (154.9 mg, 1.2 mmol). The resulting mixture was stirred overnight. Water was added into the reaction mixture then extracted with EtOAc three times. The combined organic layers were washed with water, brine and dried over $Na_2SO_4$. The solvent was removed and the residue purified by column chromatography (10% EtOAc/PE) to afford tert-butyl (1-(2-phenylacetyl)piperidin-3-yl)carbamate (234 mg, 74%) as a white solid. LCMS m/z=319.2 [M+H]$^+$; $^1$H NMR (400 MHz, $CD_3OD$) δ 7.39-7.17 (m, 5H), 3.94-3.66 (m, 4H), 3.44-3.34 (m, 1H), 3.19-3.05 (m, 2H), 2.01-1.66 (m, 1H), 1.57-1.36 (m, 12H).

Step 2: 1-(3-aminopiperidin-1-yl)-2-phenylethan-1-one hydrochloride

To a solution of tert-butyl (1-(2-phenylacetyl)piperidin-3-yl)carbamate (367 mg, 1.2 mmol) in DCM (5 mL) was added HCl (4M in dioxane, 3 mL). The resulting mixture was stirred for 4 h. The solvent was removed to afford 1-(3-aminopiperidin-1-yl)-2-phenylethan-1-one hydrochloride (240 mg, quant.) LCMS m/z=219.1 [M+H]$^+$.

266
Synthesis of (S)-2-amino-N-methyl-5-(pyridin-2-yl)pentanamide

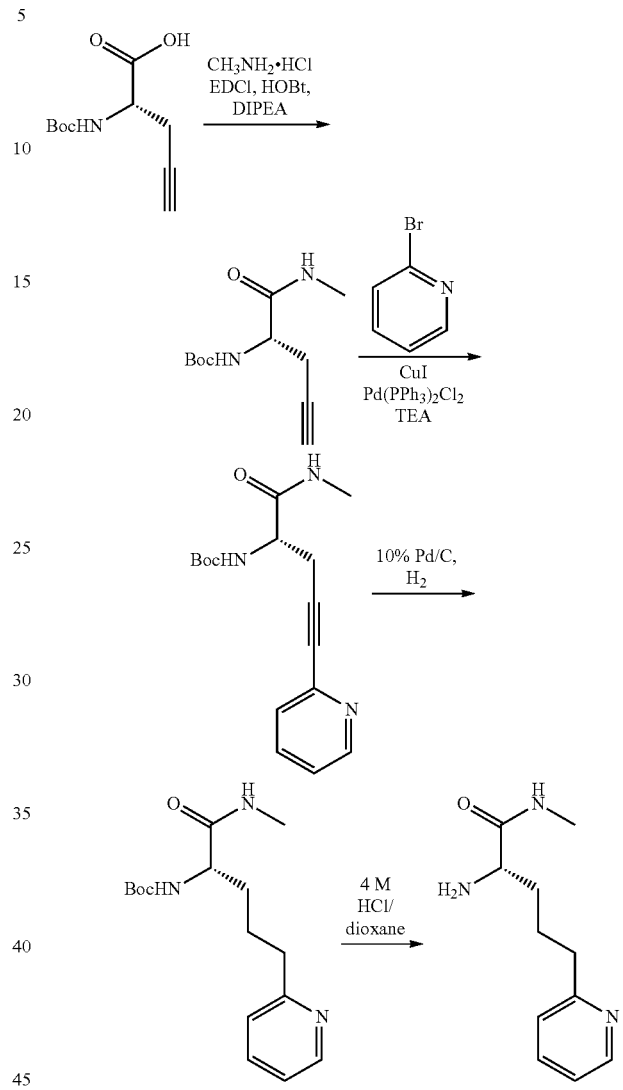

Step 1: tert-butyl (S)-(1-(methylamino)-1-oxopent-4-yn-2-yl) carbamate

To a solution of methanamine hydrochloride (950 mg, 14.07 mmol) in DMF (20 mL) was added (S)-2-((tert-butoxycarbonyl)amino)pent-4-ynoic acid (2.0 g, 9.38 mmol), EDCI (2.7 g, 14.07 mmol), HOBt (1.9 g, 14.07 mmol) and DIPEA (3.6 g, 28.14 mmol). The resulting mixture was stirred at room temperature for 4 h. Water was added and the aqueous extracted with EtOAc three times. The combined organic layers were washed with water, brine and dried over $Na_2SO_4$. The solvent was removed and the residue purified by column chromatography (5% MeOH/DCM) to afford tert-butyl (S)-(1-(methylamino)-1-oxopent-4-yn-2-yl) carbamate (1.6 g, 76%) as a white solid. $^1$H NMR (400 MHz, $CD_3OD$) δ 4.18 (t, J=6.7 Hz, 1H), 2.74 (s, 3H), 2.67-2.60 (m, 1H) 2.58-2.49 (m, 1H), 2.36 (s, 1H), 1.45 (s, 9H).

Step 2: tert-butyl (S)-(1-(methylamino)-1-oxo-5-(pyridin-2-yl)pent-4-yn-2-yl) carbamate A mixture of tert-butyl (S)-(1-(methylamino)-1-oxopent-4-yn-2-yl) carbamate (300 mg, 1.33 mmol), 2-bromopyridine (210 mg, 1.33 mmol), Pd(PPh$_3$)$_4$ (116 mg, 0.13 mmol), CsF (445 mg, 2.93 mmol), CuI (25 mg, 0.13 mmol) in DMF (5 mL) was heated at 100° C. for 3 h under an atmosphere of N$_2$. Water was added and the aqueous extracted with EtOAc three times. The combined organic layers were washed with water, brine and dried over Na$_2$SO$_4$. The solvent was removed and the residue purified by prep-TLC (7% MeOH/DCM) to afford tert-butyl (S)-(1-(methylamino)-1-oxo-5-(pyridin-2-yl)pent-4-yn-2-yl) carbamate (142 mg, 35%) as a brown oil. LCMS m/z=304 [M+H]$^+$; $^1$H NMR (400 MHz, CD$_3$OD) δ 8.47 (d, J=5.4 Hz, 1H), 7.80 (tt, J=7.7, 1.2 Hz, 1H), 7.49 (d, J=7.9 Hz, 1H), 7.40-7.33 (m, 1H), 4.32 (t, J=6.6 Hz, 1H), 2.95-2.81 (m, 2H), 2.76 (s, 3H), 1.44 (d, J=0.9 Hz, 9H).

Step 3: tert-butyl (S)-(1-(methylamino)-1-oxo-5-(pyridin-2-yl)pentan-2-yl)carbamate To a solution of tert-butyl (S)-(1-(methylamino)-1-oxo-5-(pyridin-2-yl)pent-4-yn-2-yl) carbamate (100 mg, 0.33 mmol) in MeOH (2 mL) was added Pd/C (10%, 10 mg). The resulting mixture was stirred for 3 h under an atmosphere of H$_2$. The reaction mixture was filtered through celite, the solvent removed and the residue purified by prep-TLC (7% MeOH/DCM) to afford tert-butyl (S)-(1-(methylamino)-1-oxo-5-(pyridin-2-yl)pentan-2-yl)carbamate (30 mg, 33%) as a colorless oil LCMS m/z=308 [M+H]$^+$.

Step 4: (S)-2-amino-N-methyl-5-(pyridin-2-yl)pentanamide

To a solution of tert-butyl (S)-(1-(methylamino)-1-oxo-5-(pyridin-2-yl)pentan-2-yl)carbamate (30 mg, 0.098 mmol) in MeOH (1 mL) was added HCl (4M in dioxane, 1 mL). The resulting mixture was stirred at room temperature for 3 h. The solvent was removed under reduced pressure to afford (S)-2-amino-N-methyl-5-(pyridin-2-yl)pentanamide (22 mg, quant.). LCMS m/z=208 [M+H]$^+$.

Synthesis of (2R,3R)-2-amino-3-(benzyloxy)-N-methylbutanamide

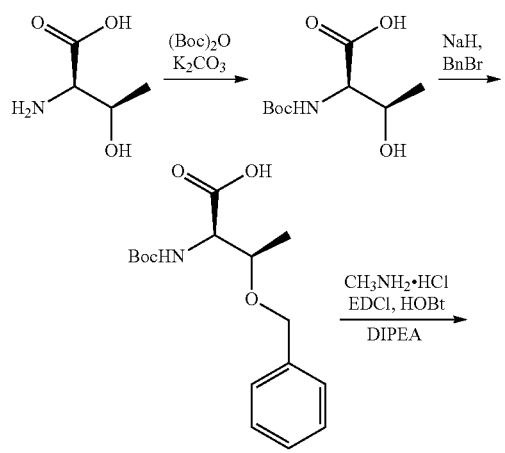

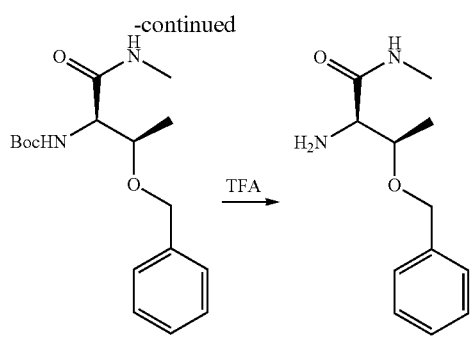

Step 1: (tert-butoxycarbonyl)-D-allothreonine

To a solution of D-allothreonine (1.0 g, 8.4 mmol) in a mixture of THF and H$_2$O (10 mL/2 mL) was added K$_2$CO$_3$ (2.3 g, 16.8 mmol) and Boc anhydride (2.0 g, 9.2 mmol). The resulting mixture was stirred overnight. Water was added and the aqueous extracted with EtOAc. The combined organic layers were washed with water, brine and dried over Na$_2$SO$_4$. The solvent was removed to afford (tert-butoxycarbonyl)-D-allothreonine (700 mg, 39%) as a yellow oil. $^1$H NMR (400 MHz, DMSO-d$_6$) δ 6.78 (d, J=7.7 Hz, 1H), 3.90-3.79 (m, 2H), 1.38 (s, 9H), 1.08 (d, J=5.5 Hz, 3H).

Step 2: O-benzyl-N-(tert-butoxycarbonyl)-D-allothreonine

To a solution of (tert-butoxycarbonyl)-D-allothreonine (700 mg, 3.2 mmol) in DMF (5.0 mL) was added NaH (270 mg, 6.7 mmol) portionwise at 0° C. After stirring for 1 h, BnBr (544 mg, 3.2 mmol) was added and the reaction mixture was stirred for another 14 h. The solvent was removed and the residue purified by RP column to afford O-benzyl-N-(tert-butoxycarbonyl)-D-allothreonine (345 mg, 35%) as a white solid. $^1$H NMR (400 MHz, CD$_3$OD) δ 7.38-7.23 (m, 5H), 4.63-4.51 (m, 2H), 4.46 (d, J=4.9 Hz, 1H), 3.92 (p, J=6.5 Hz, 1H), 1.45 (s, 9H), 1.21 (d, J=6.4 Hz, 3H).

Step 3: tert-butyl ((2R,3R)-3-(benzyloxy)-1-(methylamino)-1-oxobutan-2-yl)carbamate To a solution of O-benzyl-N-(tert-butoxycarbonyl)-D-allothreonine (100 mg, 0.32 mmol) in DMF (2 mL) was added CH$_3$NH$_2$·HCl (26 mg, 0.39 mmol), EDCI (93 mg, 0.48 mmol), HOBt (66 mg, 0.48 mmol) and DIPEA (209 mg, 1.62 mmol). The resulting mixture was stirred at room temperature for 14 h. Water was added and the aqueous extracted with EtOAc. The combined organic layers were washed with water, brine and dried over Na$_2$SO$_4$. The solvent was removed and the residue purified by column chromatography (1% MeOH/DCM) to afford tert-butyl ((2R,3R)-3-(benzyloxy)-1-(methylamino)-1-oxobutan-2-yl)carbamate (80 mg, 80%) as a white solid. $^1$H NMR (400 MHz, CD$_3$OD) δ 7.35-7.21 (m, 5H), 4.52 (q, J=11.5 Hz, 2H), 3.83 (t, J=6.4 Hz, 1H), 2.73 (s, 3H), 2.45-2.30 (m, 1H), 1.44 (s, 9H), 1.19 (t, J=6.7 Hz, 3H).

Step 4: (2R,3R)-2-amino-3-(benzyloxy)-N-methylbutanamide

To a solution of tert-butyl ((2R,3R)-3-(benzyloxy)-1-(methylamino)-1-oxobutan-2-yl)carbamate (80 mg, 0.25 mmol) in DCM (2 mL) was added TFA (0.5 mL). The resulting mixture was stirred for 3 h. The solvent was removed under reduced pressure to afford (2R,3R)-2-amino-3-(benzyloxy)-N-methylbutanamide (55 mg, quant.). This product was used directly in next step.

Synthesis of (2S,3S)-2-amino-3-(benzyloxy)-N-methylbutanamide

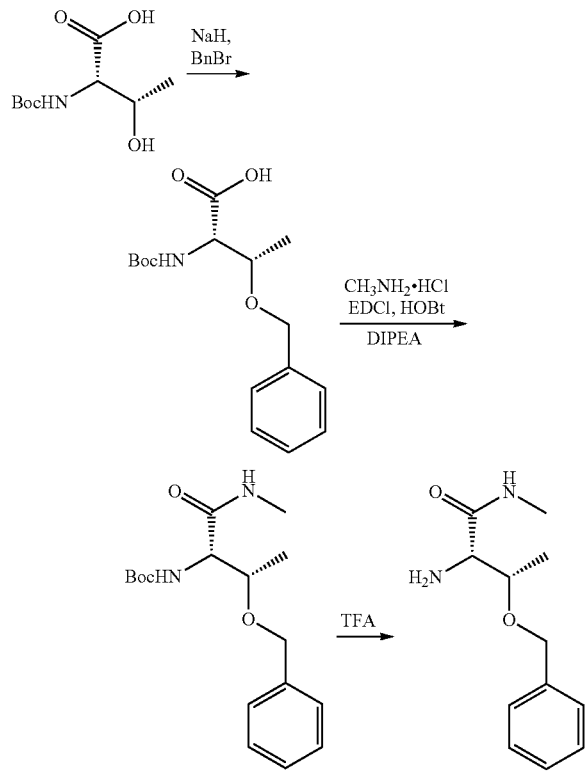

Made using a similar method as described for the synthesis of (2R,3R)-2-amino-3-(benzyloxy)-N-methylbutanamide. LCMS m/z=223.1 [M+H]+.

Synthesis of (S)-2-amino-5-cyclopentyl-N-methylpentanamide

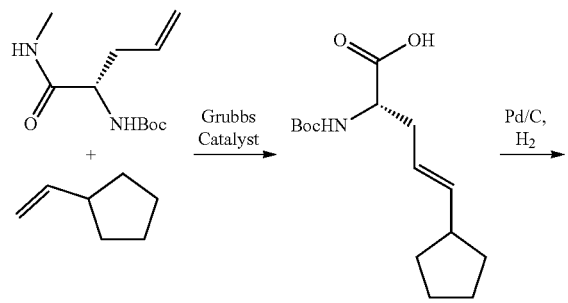

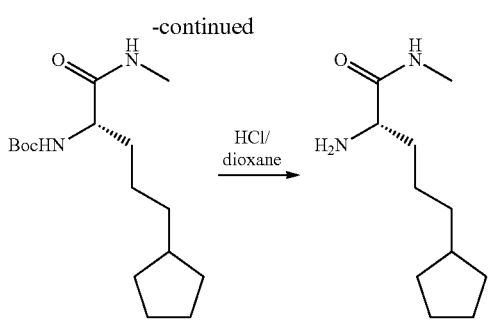

Step 1: tert-butyl (S)-(5-cyclopentyl-1-(methylamino)-1-oxopent-4-en-2-yl)carbamate To a solution of tert-butyl (S)-(1-(methylamino)-1-oxopent-4-en-2-yl)carbamate (200 mg, 0.877 mmol) in DCM (3 mL) was added vinylcyclopentane (169 mg, 1.754 mmol) and Grubbs catalyst (150 mg, 0.17 mmol). The resulting mixture was stirred at room temperature for 12 h. Water was added and the aqueous extracted with EtOAc. The combined organic layers were washed with water, brine and dried over $Na_2SO_4$. The solvent was removed and the residue purified by column chromatography (33% EtOAc/PE) to afford tert-butyl (S)-(5-cyclopentyl-1-(methylamino)-1-oxopent-4-en-2-yl)carbamate (58 mg, 22%) as a white solid. LCMS m/z=297 [M+H]+; $^1$H NMR (400 MHz, $CD_3OD$) δ 5.61-5.17 (m, 2H), 4.05-3.84 (m, 1H), 2.72 (d, J=3.6 Hz, 3H), 2.32 (ddt, J=61.8, 14.6, 7.8 Hz, 3H), 1.81-1.52 (m, 6H), 1.44 (s, 9H), 1.34-1.24 (m, 2H).

Step 2: tert-butyl (S)-(5-cyclopentyl-1-(methylamino)-1-oxopentan-2-yl)carbamate To a solution of tert-butyl (S)-(5-cyclopentyl-1-(methylamino)-1-oxopent-4-en-2-yl)carbamate (58 mg, 0.196 mmol) in MeOH (1 mL) was added 10% Pd/C (10 mg). The resulting mixture was stirred at room temperature for 3 h under an atmosphere of $H_2$. The filtrate through a pad of celite was concentrated to afford tert-butyl (S)-(5-cyclopentyl-1-(methylamino)-1-oxopentan-2-yl)carbamate (50 mg, 99%) as a white solid. $^1$H NMR (400 MHz, $CD_3OD$) δ 3.97 (dd, J=9.2, 5.3 Hz, 1H), 2.73 (s, 3H), 1.87-1.47 (m, 9H), 1.44 (s, 9H), 1.41-0.82 (m, 7H).

Step 3: (S)-2-amino-5-cyclopentyl-N-methylpentanamide

To a solution of tert-butyl (S)-(5-cyclopentyl-1-(methylamino)-1-oxopentan-2-yl)carbamate (50 mg, 0.167 mmol) in MeOH (1 mL) was added HCl (4M in dioxane, 1 ml). The mixture was stirred at room temperature for 3 h. The mixture was concentrated to afford (S)-2-amino-5-cyclopentyl-N-methylpentanamide.

Synthesis of (S)-2-amino-N-methyl-5-(4-(trifluoromethyl)cyclohexyl)pentanamide

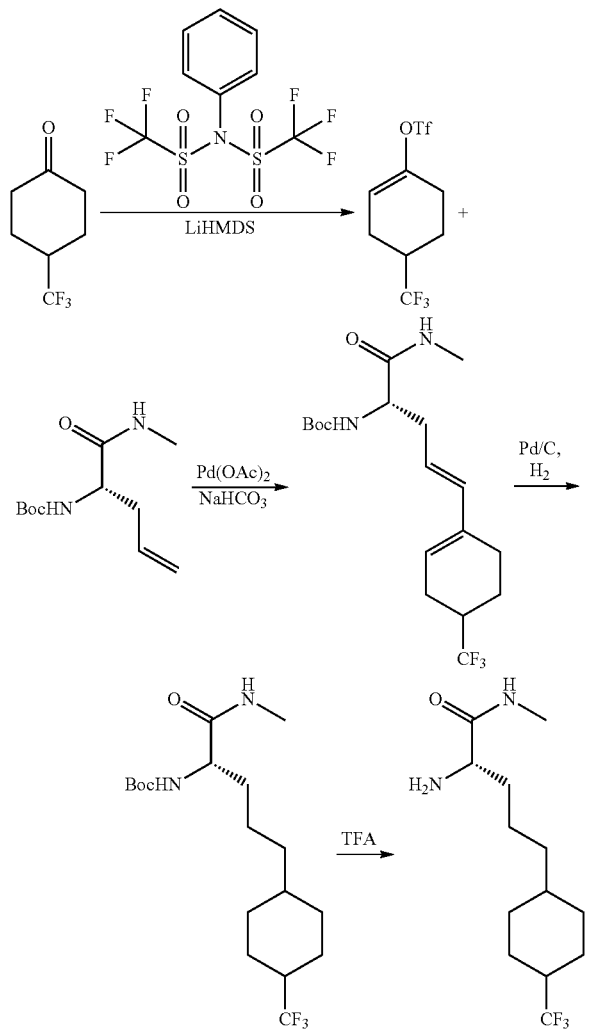

Step 1: 4-(trifluoromethyl)cyclohex-1-en-1-yl trifluoromethanesulfonate

To a solution of 4-(trifluoromethyl)cyclohexan-1-one (500 mg, 3.01 mmol) in THF (8 mL) at −78° C. was added LiHMDS (3.6 mL, 3.61 mmol) dropwise and stirred for 30 minute. Then a solution of 1,1,1-trifluoro-N-phenyl-N-((trifluoromethyl)sulfonyl)methanesulfonamide (1.18 g, 3.31 mmol) in THF (1 mL) was added thereto and the mixture was stirred at room temperature overnight. Water was added and the aqueous extracted with EtOAc. The combined organic layers were washed with water, brine and dried over $Na_2SO_4$. The solvent was removed and the residue purified by column chromatography (2% MeOH/DCM) to afford 4-(trifluoromethyl)cyclohex-1-en-1-yl trifluoromethanesulfonate (400 mg, 45%). $^1H$ NMR (400 MHz, Chloroform-d) δ 5.81-5.76 (m, 1H), 2.55-2.39 (m, 3H), 2.38-2.25 (m, 2H), 2.15 (ddt, J=13.1, 4.9, 2.5 Hz, 1H), 1.77 (dtd, J=13.0, 11.1, 6.3 Hz, 1H).

Step 2: tert-butyl ((2S,E)-1-(methylamino)-1-oxo-5-(4-(trifluoromethyl)cyclohex-1-en-1-yl)pent-4-en-2-yl)carbamate A mixture of 4-(trifluoromethyl)cyclohex-1-en-1-yl trifluoromethanesulfonate (250 mg, 0.838 mmol), tert-butyl (S)-(1-(methylamino)-1-oxopent-4-en-2-yl)carbamate (172 mg, 0.755 mmol), $Pd(OAc)_2$ (19 mg, 0.084 mmol) and $NaHCO_3$ (211 mg, 2.52 mmol) in $DMF/H_2O$ (4 mL/1 mL) was stirred at 70° C. overnight. Water was added and the aqueous extracted with EtOAc. The combined organic layers were washed with water, brine and dried over $Na_2SO_4$. The solvent was removed and the residue purified by column chromatography (1.5% MeOH/DCM) to afford tert-butyl ((2S,E)-1-(methylamino)-1-oxo-5-(4-(trifluoromethyl)cyclohex-1-en-1-yl)pent-4-en-2-yl)carbamate (120 mg, 38%). LCMS m/z=377 $[M+H]^+$; $^1H$ NMR (400 MHz, $CDCl_3$) δ 6.23-5.63 (m, 2H), 5.56-4.80 (m, 2H), 4.12 (d, J=7.1 Hz, 1H), 2.82 (d, J=4.9 Hz, 3H), 2.60-2.26 (m, 3H), 2.27-1.92 (m, 3H), 1.48-1.39 (m, 9H), 1.29-1.23 (m, 2H).

Step 3: tert-butyl (S)-(1-(methylamino)-1-oxo-5-(4-(trifluoromethyl)cyclohexyl)pentan-2-yl)carbamate To a solution of ((2S,E)-1-(methylamino)-1-oxo-5-(4-(trifluoromethyl)cyclohex-1-en-1-yl)pent-4-en-2-yl)carbamate (120 mg, 0.319 mmol) in MeOH (2 mL) was added 10% Pd/C (12 mg). The resulting mixture was stirred under $H_2$ overnight. The mixture was filtered through a pad of celite and the solvent remove from the filtrate to afford tert-butyl (S)-(1-(methylamino)-1-oxo-5-(4-(trifluoromethyl)cyclohexyl)pentan-2-yl)carbamate (100 mg, 83%). LCMS m/z=381 $[M+H]^+$.

Step 4: (S)-2-amino-N-methyl-5-(4-(trifluoromethyl)cyclohexyl)pentanamide

To a solution of tert-butyl (S)-(1-(methylamino)-1-oxo-5-(4-(trifluoromethyl)cyclohexyl)pentan-2-yl)carbamate (100 mg, 0.263 mmol) in DCM (3 mL) was added TFA (3 mL). The mixture was stirred for 3 h. The solvent was removed to afford (S)-2-amino-N-methyl-5-(4-(trifluoromethyl)cyclohexyl)pentanamide (76 mg, quant.). LCMS m/z=281 $[M+H]^+$

Synthesis of (S)-2-amino-5-cycloheptyl-N-methylpentanamide

Made using a similar method as described for the synthesis of (S)-2-amino-N-methyl-5-(4-(trifluoromethyl)cyclohexyl)pentanamide, starting from cycloheptanone, in place of 4-(trifluoromethyl)cyclohexan-1-one. LCMS m/z=227.1 $[M+H]^+$.

Synthesis of (S)-2-amino-N,6,6-trimethylheptanamide

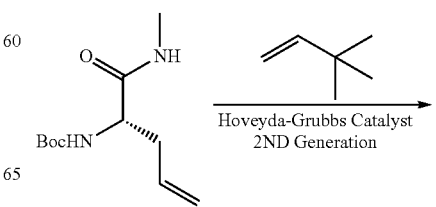

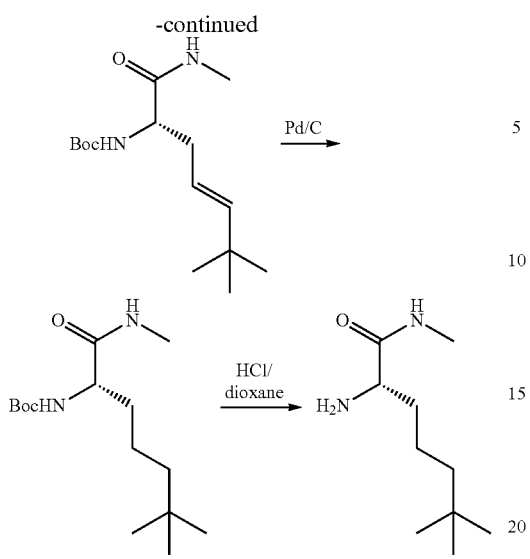

Step 1: tert-butyl (S,E)-(6,6-dimethyl-1-(methyl-amino)-1-oxohept-4-en-2-yl)carbamate To a solution of tert-butyl (S)-(1-(methylamino)-1-oxopent-4-en-2-yl)carbamate (500 mg, 2.19 mmol) and 3,3-dimethylbut-1-ene (992.0 mg, 10.9 mmol) in toluene (10 mL) was added Hoveyda-Grubbs Catalyst 2nd Generation (274.4 mg, 0.428 mmol). The mixture was stirred at 100° C. for two days. The resulting mixture was concentrated in vacuo. The solvent was removed and the residue purified by column chromatography (25% EtOAc/PE) to afford tert-butyl (S,E)-(6,6-dimethyl-1-(methylamino)-1-oxohept-4-en-2-yl)carbamate (85.0 mg, 14%) as colourless oil. $^1$H NMR (400 MHz, CDCl$_3$) δ 6.15 (s, 1H), 5.56 (m, 1H), 5.41-5.04 (m, 1H), 2.80 (d, J=4.9 Hz, 3H), 2.54-2.22 (m, 2H), 1.43 (s, 9H), 0.98 (s, 9H).

Step 2: tert-butyl (S)-(6,6-dimethyl-1-(methyl-amino)-1-oxoheptan-2-yl)carbamate To a solution of tert-butyl (S,E)-(6,6-dimethyl-1-(methylamino)-1-oxohept-4-en-2-yl)carbamate (85 mg, 0.299 mmol) in MeOH (3 mL) was added Pd/C (10 mg). The mixture was stirred under an atmosphere of H$_2$ for 8 h. The mixture was filtered through a pad of celite and the solvent removed from the filtrate to afford tert-butyl (S)-(6,6-dimethyl-1-(methylamino)-1-oxoheptan-2-yl)carbamate (76.0 mg, 80%) as colourless oil. LCMS m/z=287 [M+H]$^+$.

Step 3: (S)-2-amino-N,6,6-trimethylheptanamide

To a solution of tert-butyl (S)-(6,6-dimethyl-1-(methyl-amino)-1-oxoheptan-2-yl)carbamate (76.0 mg, 0.27 mmol) in DCM (5 mL) was added HCl (4 M in dioxane, 3 mL). The resulting mixture was stirred for 3 h. The solvent was removed to afford (S)-2-amino-N,6,6-trimethylheptanamide (80 mg, quant.). LCMS m/z=186 [M+H]$^+$.

Synthesis of (S)-2-amino-N,6-dimethylheptanamide

Made using a similar method as described for the synthesis of (S)-2-amino-N,6,6-trimethylheptanamide, using 3-methylbut-1-ene and Grubbs catalyst in place of 3,3-dimethylbut-1-ene and Hoveyda-Grubbs catalyst, respectively. The solvent was removed in vacuo and the crude product was used directly in the synthesis of additional compounds.

Synthesis of (S)-2-amino-5-cyclohexyl-N-methylpentanamide

Made using a similar method as described for the synthesis of (S)-2-amino-N,6,6-trimethylheptanamide, using vinylcyclohexane and Grubbs catalyst in place of 3,3-dimethylbut-1-ene and Hoveyda-Grubbs catalyst, respectively LCMS m/z=213.1 [M+H]$^+$.

Synthesis of 2-amino-N-(3-phenylpropyl)acetamide

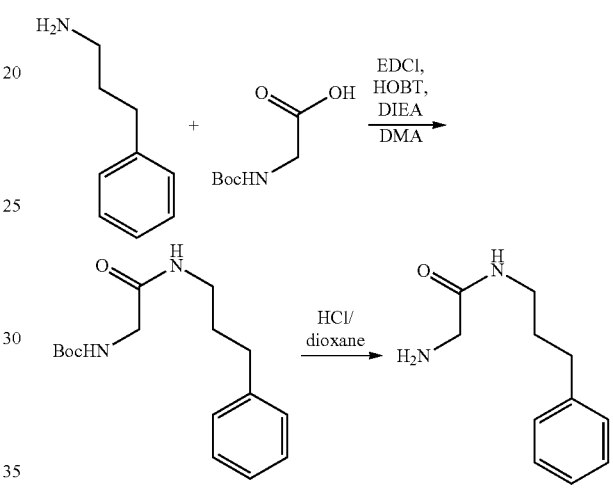

Step 1: tert-butyl (2-oxo-2-(3-phenylpropyl)amino)ethyl)carbamate

To a solution of (tert-butoxycarbonyl)glycine (500 mg, 2.85 mmol), EDCI (821 mg, 4.28 mmol) and HOBt (463 mg, 3.42 mmol) in DMA (10 mL) was added 3-phenylpropan-1-amine (424 mg, 3.14 mmol) and DIEA (1.11 g, 8.56 mmol). The mixture was stirred at room temperature overnight. Water was added and the aqueous extracted with EtOAc three times. The combined organic layers were washed with water and brine, dried over Na$_2$SO$_4$ and the solvent removed in vacuo. The crude was purified by column chromatography (2.5% MeOH/DCM) to give tert-butyl (2-oxo-2-((3-phenylpropyl)amino)ethyl)carbamate (538 mg, 64%). LCMS m/z=293.3 [M+H]$^+$.

Step 2: 2-amino-N-(3-phenylpropyl)acetamide

A solution of tert-butyl (2-oxo-2-((3-phenylpropyl)amino)ethyl)carbamate (500 mg, 1.71 mmol) in HCl (4M in dioxane, 5 mL) was stirred for 1 h. The volatiles were removed in vacuo to give 2-amino-N-(3-phenylpropyl)acetamide (486 mg, quant.).

Synthesis of (S)-2-amino-N-methyl-N-(3-phenylpropyl)propanamide

Made using a similar method as described for the synthesis of 2-amino-N-(3-phenylpropyl)acetamide, starting from N-methyl-3-phenylpropan-1-amine and (tert-butoxycarbonyl)-L-alanine. LCMS m/z=221.3 [M+H]+.

Synthesis of 2-amino-N-methyl-N-(3-phenylpropyl)acetamide Made using a similar method as described for the synthesis of 2-amino-N-(3-phenylpropyl)acetamide, starting from N-methyl-3-phenylpropan-1-amine and (tert-butoxycarbonyl)glycine. LCMS m/z=207.2 [M+H]+.

Synthesis of (2S,3R)-2-amino-3-(cyclohexylmethoxy)-N-methylbutanamide

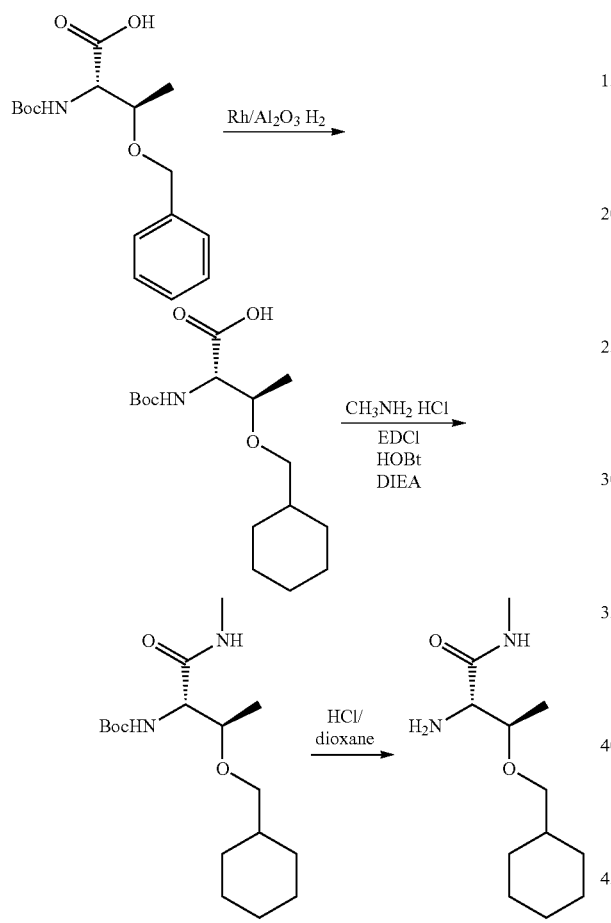

Step 1: N-(tert-butoxycarbonyl)-O-(cyclohexylmethyl)-L-threonine

To a solution of O-benzyl-N-(tert-butoxycarbonyl)-L-threonine (400 mg, 1.29 mmol) in IPA (15 mL) was added Rh—Al₂O₃ (5%, 50 mg). The resulting mixture was stirred overnight under H₂. The reaction mixture was filtered through a pad of celite, the solvent removed and the residue purified by column chromatography (10% MeOH/DCM) to afford N-(tert-butoxycarbonyl)-O-(cyclohexylmethyl)-L-threonine (390 mg, 95.6%) as a colorless oil. $^1$H NMR (400 MHz, CD₃OD) δ 4.09 (d, J=2.8 Hz, 1H), 4.04-3.94 (m, 1H), 3.39-3.33 (m, 1H), 3.17-3.09 (m, 1H), 1.79-1.62 (m, 4H), 1.53-1.40 (m, 9H), 1.34-1.09 (m, 8H), 1.00-0.81 (m, 2H).

Step 2: tert-butyl ((2S,3R)-3-(cyclohexylmethoxy)-1-(methylamino)-1-oxobutan-2-yl) carbamate To a solution of N-(tert-butoxycarbonyl)-O-(cyclohexylmethyl)-L-threonine (390 mg, 1.24 mmol) in DMF (8 mL) was added methylamine hydrochloride (167 mg, 2.47 mmol), EDCI (357 mg, 1.86 mmol), HOBt (202 mg, 1.49 mmol) and DIPEA (320 mg, 2.47 mmol). The resulting mixture was stirred at room temperature overnight. Water was added and the aqueous extracted with EtOAc three times. The combined organic layers were washed with water, brine and dried over Na₂SO₄. The solvent was removed and the residue purified by column chromatography (1.9% MeOH/DCM) to afford tert-butyl ((2S,3R)-3-(cyclohexylmethoxy)-1-(methylamino)-1-oxobutan-2-yl) carbamate (360 mg, 88%) as a white solid. LCMS m/z=329.3 [M+H]+; $^1$H NMR (400 MHz, CDCl₃) δ 6.53 (br, 1H), 5.47 (d, J=6.8 Hz, 1H), 4.20-4.13 (m, 1H), 3.99-3.90 (m, 1H), 3.41-3.21 (m, 2H), 2.83 (d, J=4.9 Hz, 3H), 1.75-1.61 (m, 6H), 1.45 (s, 9H), 1.29-1.04 (m, 6H), 0.96-0.83 (m, 2H)

Step 3: (2S,3R)-2-amino-3-(cyclohexylmethoxy)-N-methylbutanamide

To a solution of tert-butyl ((2S,3R)-3-(cyclohexylmethoxy)-1-(methylamino)-1-oxobutan-2-yl) carbamate (350 mg, 1.06 mmol) in DCM (2 mL) was added TFA (1 mL). The resulting mixture was stirred for 2 h. The solvent was removed to afford (2S,3R)-2-amino-3-(cyclohexylmethoxy)-N-methylbutanamide (370 mg, quant.). LCMS m/z=229.2 [M+H]+.

Synthesis of (2R,3R)-2-amino-3-(cyclohexylmethoxy)-N-methylbutanamide

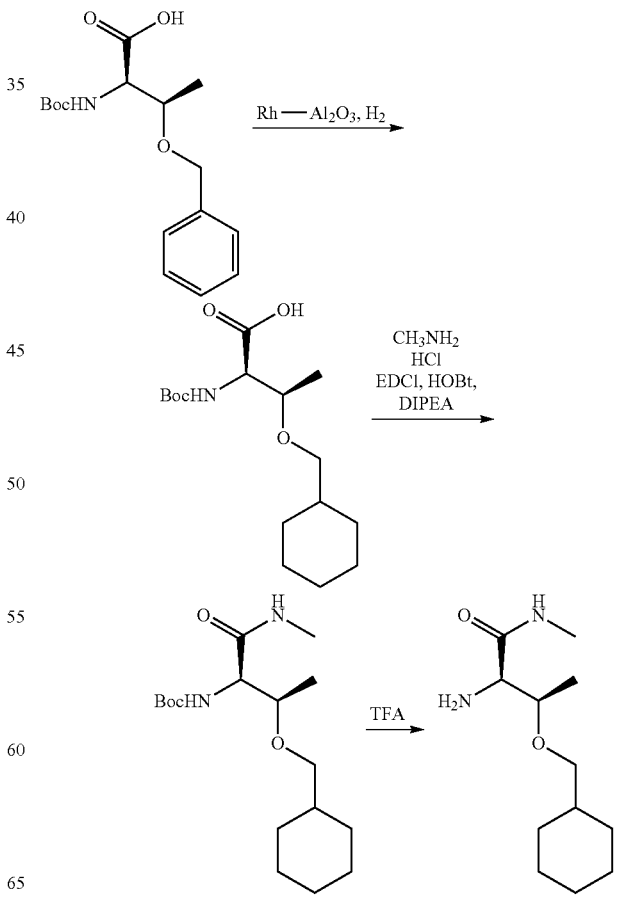

Step 1: N-(tert-butoxycarbonyl)-O-(cyclohexylmethyl)-D-allothreonine

To a solution of O-benzyl-N-(tert-butoxycarbonyl)-D-allothreonine (70 mg, 0.22 mmol) in IPA (2 mL) was added Rh—Al$_2$O$_3$ (5%, 20 mg). The resulting mixture was stirred overnight under an atmosphere of H$_2$. The reaction mixture was filtered through celite and the solvent removed to afford N-(tert-butoxycarbonyl)-O-(cyclohexylmethyl)-D-allothreonine (50 mg, 71%) as a colorless oil. LCMS m/z=316.1 [M+H]$^+$.

Step 2: tert-butyl ((2R,3R)-3-(cyclohexylmethoxy)-1-(methylamino)-1-oxobutan-2-yl)carbamate To a solution of N-(tert-butoxycarbonyl)-O-(cyclohexylmethyl)-D-allothreonine (50 mg, 0.16 mmol) in DMF (1 mL) was added methylamine hydrochloride (13 mg, 0.19 mmol), EDCI (46 mg, 0.24 mmol), HOBt (32 mg, 0.24 mmol) and DIPEA (62 mg, 0.48 mmol). The resulting mixture was stirred overnight. Water was added and the aqueous extracted with EtOAc. The combined organic layers were washed with water, brine and dried over Na$_2$SO$_4$. The solvent was removed and the residue purified by column chromatography (2% MeOH/DCM) to afford tert-butyl ((2R,3R)-3-(cyclohexylmethoxy)-1-(methylamino)-1-oxobutan-2-yl)carbamate (38 mg, 73%) as a white solid. LCMS m/z=329.3 [M+H]$^+$.

Step 3: (2R,3R)-2-amino-3-(cyclohexylmethoxy)-N-methylbutanamide

To a solution of tert-butyl ((2R,3R)-3-(cyclohexylmethoxy)-1-(methylamino)-1-oxobutan-2-yl)carbamate (38 mg, 0.12 mmol) in a mixture of DCM (1 mL) and MeOH (1 mL) was added TFA (1 mL). The resulting mixture was stirred for 2 h. The solvent was removed under reduced pressure to afford (2R,3R)-2-amino-3-(cyclohexylmethoxy)-N-methylbutanamide (27 mg, quant.) as a yellow oil. LCMS m/z=229.2 [M+H]$^+$.

Synthesis of (2S,3S)-2-amino-3-(cyclohexylmethoxy)-N-methylbutanamide

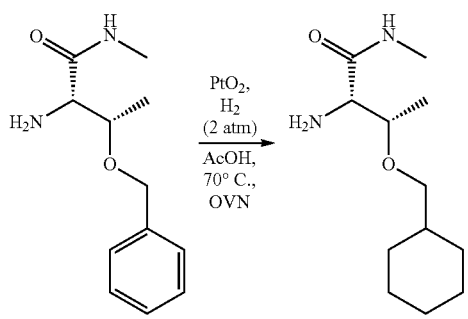 [SMILES: CNC(=O)[C@@H](N)[C@H](C)OCc1ccccc1 ; CNC(=O)[C@@H](N)[C@H](C)OCC1CCCCC1]

To a solution of (2S,3S)-2-amino-3-(benzyloxy)-N-methylbutanamide (100 mg, 0.45 mmol) in AcOH (2 mL) was added PtO$_2$ (20 mg) and the mixture was stirred under an atmosphere of H$_2$ (2 atm) overnight. The mixture was filtered through a pad of celite and the filtrate concentrated to afford (2S,3S)-2-amino-3-(cyclohexylmethoxy)-N-methylbutanamide (90 mg, 87%). LCMS m/z=229.2 [M+H]$^+$.

Synthesis of (S)-2-amino-5-(4-hydroxyphenyl)-N-methylpentanamide

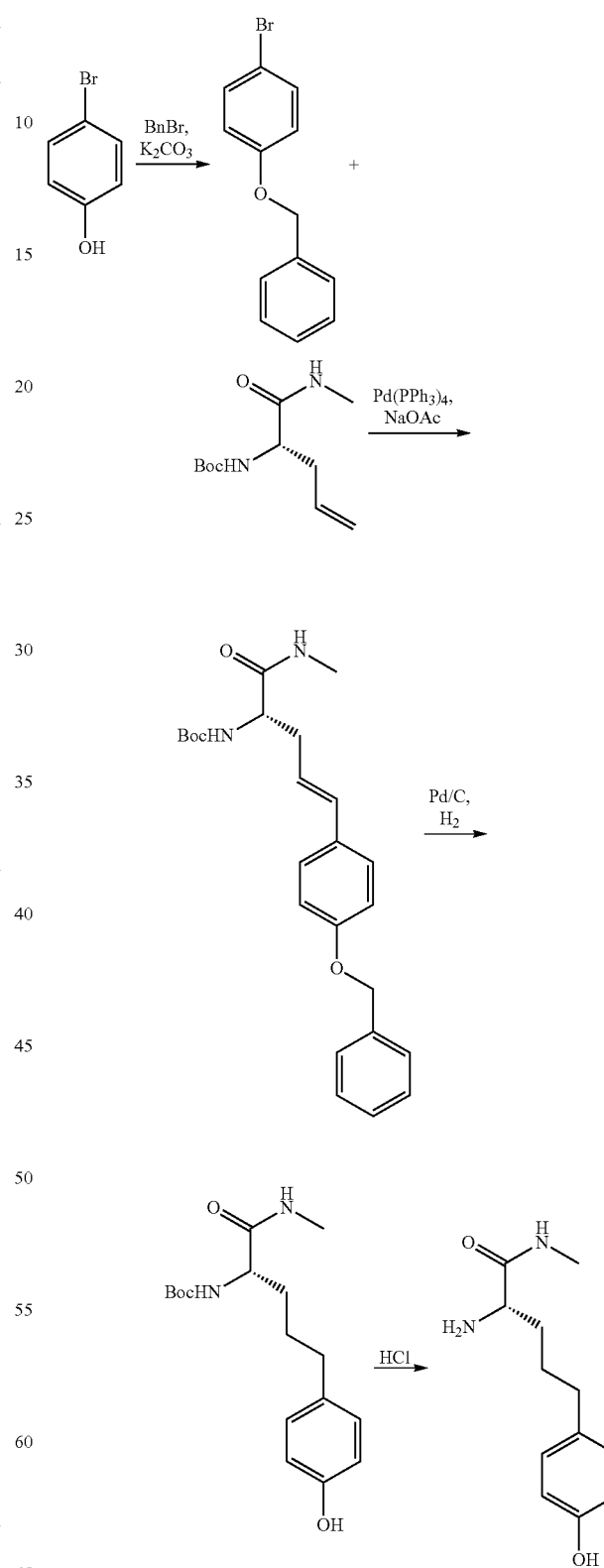

Step 1: 1-(benzyloxy)-4-bromobenzene

To a solution of 4-bromophenol (1 g, 5.78 mmol) in DMF (20 mL) was added BnBr (1.037 g, 6.07 mmol) and $K_2CO_3$ (2.4 g, 17.3 mmol). The resulting mixture was stirred at room temperature for 4 h. Water was added and the aqueous extracted with EtOAc three times. The combined organic layers were washed with water, brine and dried over $Na_2SO_4$. The solvent was removed and the residue purified by column chromatography (5% MeOH/DCM) to afford 1-(benzyloxy)-4-bromobenzene (1.215 g, 80%) as a white solid. 1H NMR (400 MHz, $CD_3OD$) δ 7.44-7.27 (m, 7H), 6.94-6.88 (m, 2H), 5.04 (s, 2H).

Step 2: tert-butyl (S,E)-(5-(4-(benzyloxy)phenyl)-1-(methylamino)-1-oxopent-4-en-2-yl)carbamate To a solution of 1-(benzyloxy)-4-bromobenzene (100 mg, 0.38 mmol) in NMP (2 mL) was added tert-butyl (S)-(1-(methylamino)-1-oxopent-4-en-2-yl)carbamate (86.6 mg, 0.38 mmol), $Pd(PPh_3)_4$ (22 mg, 0.019 mmol) and NaOAc (62.3 mg, 0.76 mmol). The mixture was heated at 110° C. overnight. Water was added and the aqueous extracted with EtOAc three times. The combined organic layers were washed with water, brine and dried over $Na_2SO_4$. The solvent was removed and the residue purified by column chromatography (50% EtOAc/PE) to afford tert-butyl (S,E)-(5-(4-(benzyloxy)phenyl)-1-(methylamino)-1-oxopent-4-en-2-yl)carbamate (37.8 mg, 24.3%) as a white solid. LCMS m/z=411.2 $[M+H]^+$.

Step 3: tert-butyl (S)-(5-(4-hydroxyphenyl)-1-(methylamino)-1-oxopentan-2-yl)carbamate To a solution of tert-butyl (S,E)-(5-(4-(benzyloxy)phenyl)-1-(methylamino)-1-oxopent-4-en-2-yl)carbamate (37.8 mg, 0.092 mmol) in MeOH (1 mL) was added Pd/C (10%, 50 mg). The resulting mixture was stirred for 3 h under an atmosphere of $H_2$. The reaction mixture was filtered through celite and the solvent was removed to afford tert-butyl (S)-(5-(4-hydroxyphenyl)-1-(methylamino)-1-oxopentan-2-yl)carbamate (33 mg, quant) as a colorless oil. LCMS m/z=323.2 $[M+H]^+$.

Step 4: (S)-2-amino-5-(4-hydroxyphenyl)-N-methylpentanamide

To a solution of tert-butyl (S)-(5-(4-hydroxyphenyl)-1-(methylamino)-1-oxopentan-2-yl)carbamate (33 mg, 0.102 mmol) in DCM (1 mL) was added HCl (4M in dioxane, 0.5 mL). The mixture was stirred at room temperature for 2 h. The solvent was removed to afford (S)-2-amino-5-(4-hydroxyphenyl)-N-methylpentanamide (25.5 g, quant.). LCMS m/z=223.1 $[M+H]^+$.

Synthesis of (S)-2-amino-5-(4-hydroxycyclohexyl)-N-methylpentanamide

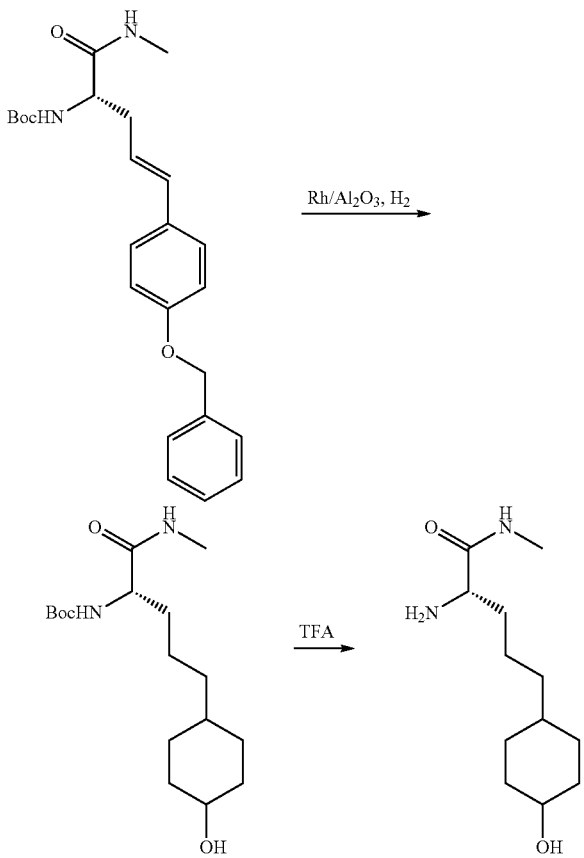

Step 1: tert-butyl (S)-(5-(4-hydroxycyclohexyl)-1-(methylamino)-1-oxopentan-2-yl)carbamate To a solution of tert-butyl (S)-(5-(4-hydroxycyclohexyl)-1-(methylamino)-1-oxopentan-2-yl)carbamate (200 mg, 0.048 mmol) in IPA (1 mL) was added $Rh/Al_2O_3$ (5%, 49 mg). The mixture was stirred at room temperature under $H_2$ for 2 h. The reaction mixture was filtered through celite and the filterate concentrated to afford tert-butyl (S)-(5-(4-hydroxycyclohexyl)-1-(methylamino)-1-oxopentan-2-yl)carbamate (16.7 mg, quant.) as a colorless oil LCMS m/z=329.2 $[M+H]^+$.

Step 2: (S)-2-amino-5-(4-hydroxycyclohexyl)-N-methylpentanamide

To a solution of tert-butyl (S)-(5-(4-hydroxycyclohexyl)-1-(methylamino)-1-oxopentan-2-yl)carbamate (16 mg, 0.048 mmol) in DCM (1 mL) was added TFA (1 mL). The mixture was stirred at room temperature for 1 h. The solvent was removed to afford (S)-2-amino-5-(4-hydroxycyclohexyl)-N-methylpentanamide (16 mg, quant). LCMS m/z=226.9 $[M-H]^-$.

Synthesis of 2-(5-chloro-1H-benzo[d]imidazol-1-yl)acetic acid

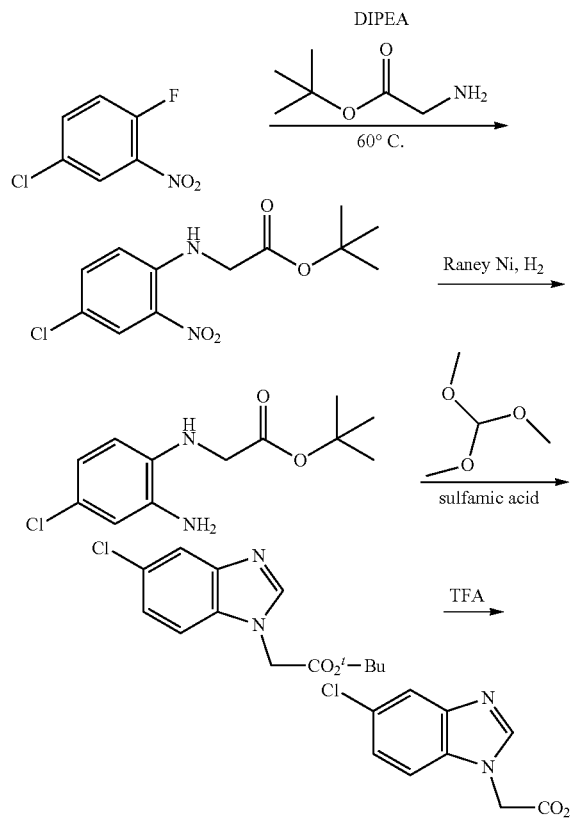

Step 1: tert-butyl (4-chloro-2-nitrophenyl)glycinate

To a solution of 4-chloro-1-fluoro-2-nitrobenzene (200 mg, 1.14 mmol) in DMSO (3 mL) was added tert-butyl glycinate (164 mg, 1.25 mmol) and DIPEA (294 mg, 2.28 mmol). The resulting mixture was stirred and heated to 60° C. overnight. Water was added into the reaction mixture and the aqueous extracted with EtOAc. The combined organic layers were washed with water, brine and dried over $Na_2SO_4$. The residue, after concentration was purified by column chromatography (10% EtOAc/PE) to afford tert-butyl (4-chloro-2-nitrophenyl)glycinate (1.1 g, 73%) as a yellow solid. $^1$H NMR (400 MHz, DMSO-$d_6$) δ 8.42 (t, J=5.6 Hz, 1H), 8.10 (d, J=9.1 Hz, 1H), 6.99 (d, J=2.1 Hz, 1H), 6.76 (dd, J=9.1, 2.1 Hz, 1H), 4.19 (d, J=5.6 Hz, 2H), 1.44 (s, 9H).

Step 2: tert-butyl (2-amino-4-chlorophenyl)glycinate

To a solution of tert-butyl (4-chloro-2-nitrophenyl)glycinate (100 mg, 0.33 mmol) in MeOH (2 mL) was added Raney Ni (0.2 mL). The resulting mixture was stirred for 3 h under an atmosphere of $H_2$. The residue was filtered through celite, the solvent removed and the residue purified by prep-TLC (50% PE/EtOAc) to afford tert-butyl (2-amino-4-chlorophenyl)glycinate (40 mg, 42%) as a light yellow solid. $^1$H NMR (400 MHz, DMSO-$d_6$) δ 6.52 (d, J=8.2 Hz, 1H), 6.43 (dd, J=8.2, 2.3 Hz, 1H), 6.20 (d, J=2.3 Hz, 1H), 5.21 (t, J=6.3 Hz, 1H), 4.66 (s, 2H), 3.79 (d, J=6.2 Hz, 2H), 1.42 (s, 9H).

Step 3: tert-butyl 2-(5-chloro-1H-benzo[d]imidazol-1-yl)acetate

To a solution of tert-butyl (2-amino-4-chlorophenyl)glycinate (20 mg, 0.078 mmol) in MeOH (1 mL) was added trimethoxymethane (10 mg, 0.093 mmol) and sulfamic acid (1 mg, 0.008 mmol). The resulting mixture was stirred overnight. The solvent was removed under reduced pressure and the residue was purified by prep-TLC (50% PE/EtOAc) to afford tert-butyl 2-(5-chloro-1H-benzo[d]imidazol-1-yl)acetate (7 mg, 33%) as a light yellow solid. $^1$H NMR (400 MHz, $CD_3OD$) δ 8.22 (d, J=1.4 Hz, 1H), 7.67 (d, J=8.7 Hz, 1H), 7.56 (d, J=2.0 Hz, 1H), 7.29 (dd, J=8.6, 2.0 Hz, 1H), 5.07 (s, 2H), 1.47 (s, 9H).

Step 4: 2-(5-chloro-1H-benzo[d]imidazol-1-yl)acetic acid

To a solution of tert-butyl 2-(5-chloro-1H-benzo[d]imidazol-1-yl)acetate (50 mg, 0.19 mmol) in DCM (2 mL) was added TFA (1.5 mL). The resulting mixture was stirred overnight. The solvent was removed under reduced pressure to afford 2-(5-chloro-1H-benzo[d]imidazol-1-yl)acetic acid as a yellow oil. LCMS m/z=210.9 [M+H]$^+$.

Synthesis of 2-(6-cyano-1H-indol-3-yl)acetic acid

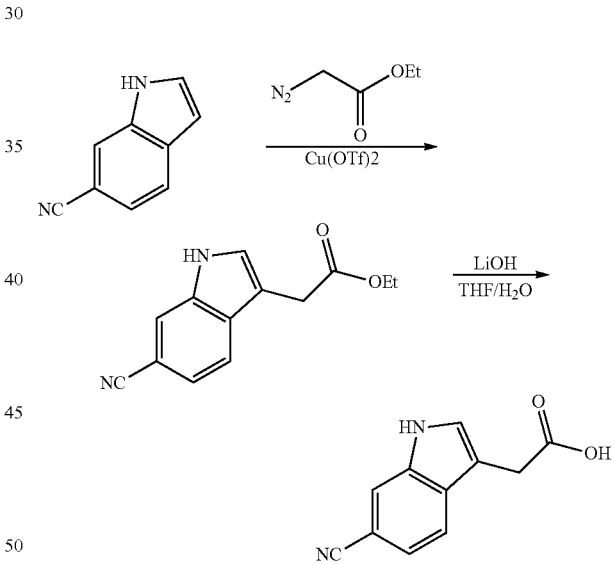

Step 1: ethyl 2-(6-cyano-1H-indol-3-yl)acetate

To a solution of 1H-indole-6-carbonitrile (200 mg, 1.41 mmol) in DCM (5 mL) was added ethyl 2-diazoacetate (293 mg, 2.57 mmol) and $Cu(OTf)_2$ (62 mg, 0.17 mmol). The resulting mixture was stirred at room temperature overnight. The residue, after concentration, was purified by column chromatography (10% EtOAc/PE) to afford ethyl 2-(6-cyano-1H-indol-3-yl)acetate (40 mg, 12.4%) as a colorless oil.

Step 2: 2-(6-cyano-1H-indol-3-yl)acetic acid

To a solution of ethyl 2-(6-cyano-1H-indol-3-yl)acetate (40 mg, 0.18 mmol) in THF/$H_2O$ (1.5 mL/1.5 mL) was added LiOH·H₂O (22.1 mg, 0.53 mmol). The resulting mixture was stirred at room temperature for 3 h. The aqueous was acidified to pH=2-3 by adding 1 M HCl and extracted with EtOAc three times. The combined organic phases were concentrated under reduced pressure to afford 2-(6-cyano-1H-indol-3-yl)acetic acid (28 mg, 79.8%) as a white solid. LCMS m/z=199.0 [M–H]⁻.

Synthesis of 2-(6-chlorobenzofuran-3-yl)acetic acid

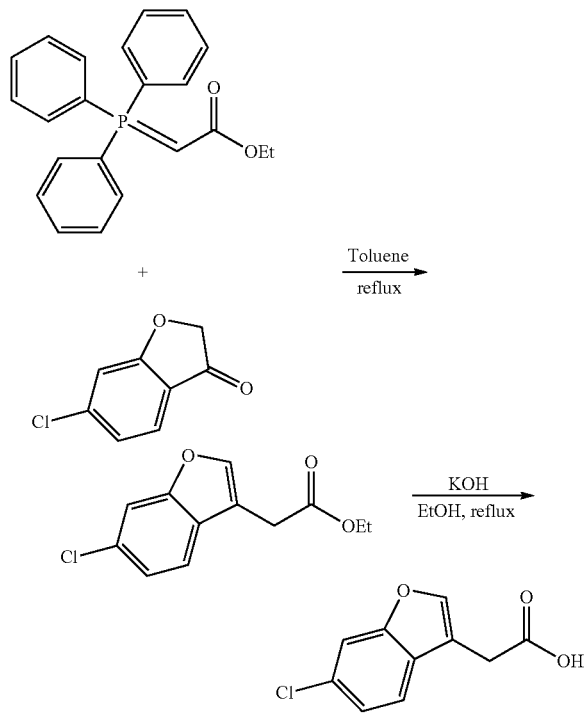

Step 1: ethyl 2-(6-chlorobenzofuran-3-yl)acetate

A mixture of 6-chlorobenzofuran-3(2H)-one (169 mg, 1.0 mmol) and ethyl (triphenylphosphoranylidene)acetate (524 mg, 1.5 mmol) in toluene (10 mL) was heated at reflux for 24 h. The reaction mixture was concentrated in vacuo and the residue purified by column chromatography (10% EtOAc/PE) to give ethyl 2-(6-chlorobenzofuran-3-yl)acetate (171 mg, 72%). ¹H NMR (400 MHz, DMSO-d₆) δ 7.95 (d, J=1.1 Hz, 1H), 7.74 (d, J=1.8 Hz, 1H), 7.61 (d, J=8.4 Hz, 1H), 7.32 (dd, J=8.4, 1.9 Hz, 1H), 4.11 (q, J=7.1 Hz, 2H), 3.79 (d, J=1.1 Hz, 2H), 1.19 (t, J=7.1 Hz, 3H).

Step 2: 2-(6-chlorobenzofuran-3-yl)acetic acid

A mixture of ethyl 2-(6-chlorobenzofuran-3-yl)acetate (155 mg, 0.65 mmol) and KOH (55 mg, 0.98 mmol) in EtOH (5 mL) was heated at 80° C. for 1 h. The reaction mixture was acidified by adding of 1M HCl and extracted with EtOAc three times. The combined organic layers were washed with water and brine, dried over Na₂SO₄ and concentrated in vacuo to give 2-(6-chlorobenzofuran-3-yl)acetic acid (132 mg, 96% yield).

Synthesis of (S)-2-amino-N-methyl-5-(pyridin-2-yl)pentanamide

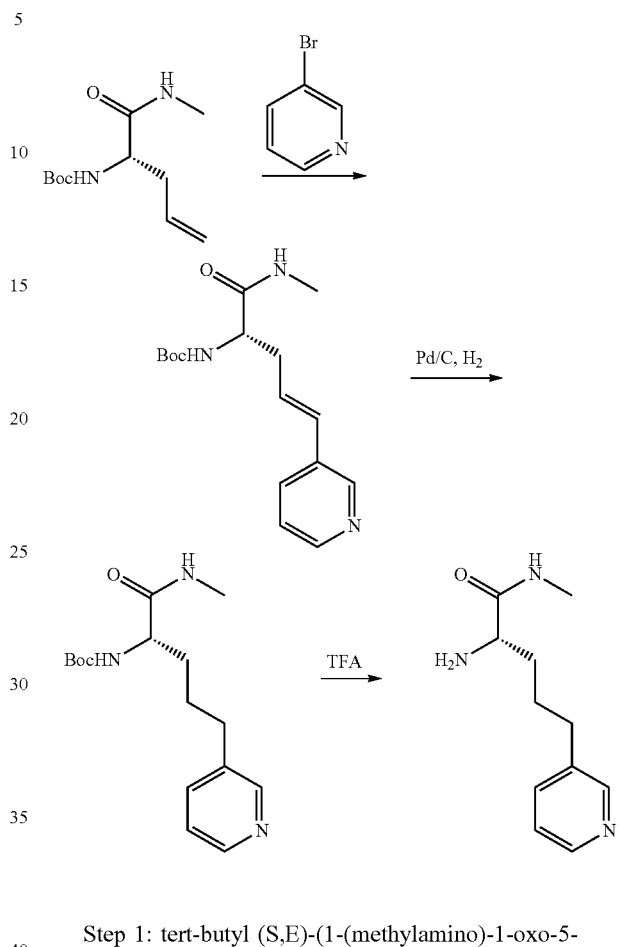

Step 1: tert-butyl (S,E)-(1-(methylamino)-1-oxo-5-(pyridin-3-yl)pent-4-en-2-yl)carbamate A mixture of tert-butyl (S)-(1-(methylamino)-1-oxopent-4-en-2-yl)carbamate (50 mg, 0.22 mmol), 3-bromopyridine (31 mg, 0.20 mmol), Pd(OAc)₂ (5 mg), NaHCO₃ (55 mg, 0.66 mmol) in DMF/H₂O (1 mL/0.2 mL) wad heated at 70° C. for 4 h under an atmosphere of N₂. Water was added and the aqueous extracted with EtOAc. The combined organic layers were washed with water, brine and dried over Na₂SO₄. The solvent was removed and the residue purified by prep-TLC (8% MeOH/DCM) to afford tert-butyl (S,E)-(1-(methylamino)-1-oxo-5-(pyridin-3-yl)pent-4-en-2-yl)carbamate (24 mg, 35%) as a yellow oil. LCMS m/z=306.1 [M+H]⁺.

Step 2: tert-butyl (S)-(1-(methylamino)-1-oxo-5-(pyridin-3-yl)pentan-2-yl)carbamate To a solution of tert-butyl (S,E)-(1-(methylamino)-1-oxo-5-(pyridin-3-yl)pent-4-en-2-yl)carbamate (80 mg, 0.26 mmol) in MeOH (10 mL) was added Pd/C (10%, 8 mg). The resulting mixture was stirred for 14 h under an atmosphere of H₂. The reaction mixture was filtered through celite and the filtrate was concentrated to afford tert-butyl (S)-(1-(methylamino)-1-oxo-5-(pyridin-3-yl)pentan-2-yl)carbamate (80.5 mg, quant.) as a yellow oil. LCMS m/z=308.2 [M+H]⁺.

Step 3: (S)-2-amino-N-methyl-5-(pyridin-2-yl)pentanamide

To a solution of tert-butyl (S)-(1-(methylamino)-1-oxo-5-(pyridin-3-yl)pentan-2-yl)carbamate (74 mg, 0.23 mmol) in DCM (3.0 mL) was added TFA (0.5 mL). The resulting mixture was stirred for 3 h. The solvent was removed under reduced pressure to afford (S)-2-amino-N-methyl-5-(pyridin-2-yl)pentanamide (51 mg, quant.).

Synthesis of 5-benzylpyridin-3-amine

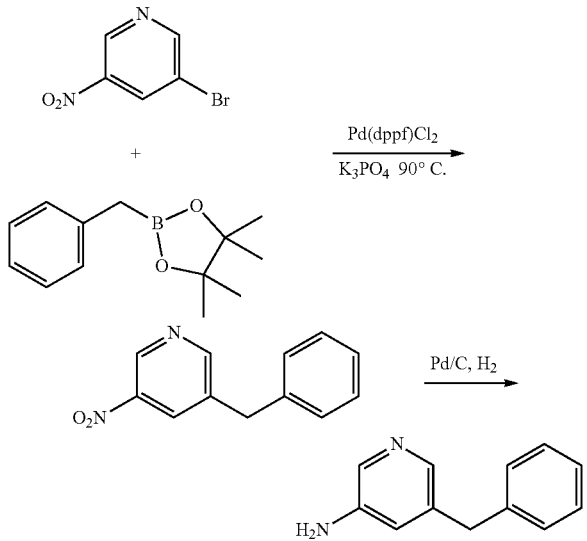

Step 1: 3-benzyl-5-nitropyridine

To a solution of 3-bromo-5-nitropyridine (200 mg, 0.985 mmol) in a mixture of dioxane (15 mL) and water (3 mL) was added 2-benzyl-4,4,5,5-tetramethyl-1,3,2-dioxaborolane (322.3 mg, 1.48 mmol), Pd(dppf)$_2$Cl$_2$ (144.2 mg, 0.197 mmol) and K$_3$PO$_4$ (627.4 mg, 2.96 mmol). The resulting mixture was heated at 90° C. for 5 h. Water was added into the reaction mixture and the aqueous extracted with EtOAc three times. The combined organic layers were washed with water, brine and dried over Na$_2$SO$_4$. The residue, after concentration was purified by column chromatography (25% EtOAc/PE) to afford 3-benzyl-5-nitropyridine (92 mg, 44%). LCMS m/z=215.0 [M+H]$^+$; $^1$H NMR (400 MHz, CD$_3$OD) δ 9.20 (d, J=2.4 Hz, 1H), 8.79 (d, J=1.9 Hz, 1H), 8.39 (t, J=2.2 Hz, 1H), 7.38-7.21 (m, 5H), 4.16 (s, 2H).

Step 2: 5-benzylpyridin-3-amine

To a solution of 3-benzyl-5-nitropyridine (92 mg, 0.43 mmol) in MeOH (3 mL) was added Pd/C (10.0 mg). The reaction mixture was stirred under H$_2$ for 5 h. After filtration through a pad of celite, the filtrate was concentrated to afford 5-benzylpyridin-3-amine (60 mg, 75%) as a white solid. LCMS m/z=185.1 [M+H]$^+$; $^1$H NMR (400 MHz, DMSO-d$_6$) δ 7.75 (d, J=2.6 Hz, 1H), 7.66 (d, J=1.9 Hz, 1H), 7.35-7.25 (m, 2H), 7.20 (d, J=7.5 Hz, 3H), 6.68 (s, 1H), 5.21 (s, 2H), 3.79 (s, 2H).

Synthesis of 2-benzylpyridin-4-amine

Made using a similar method as described for the synthesis of 5-benzylpyridin-3-amine, using 2-bromo-4-nitropyridine in place of 3-bromo-5-nitropyridine

Synthesis of 5-phenoxypyridin-3-amine

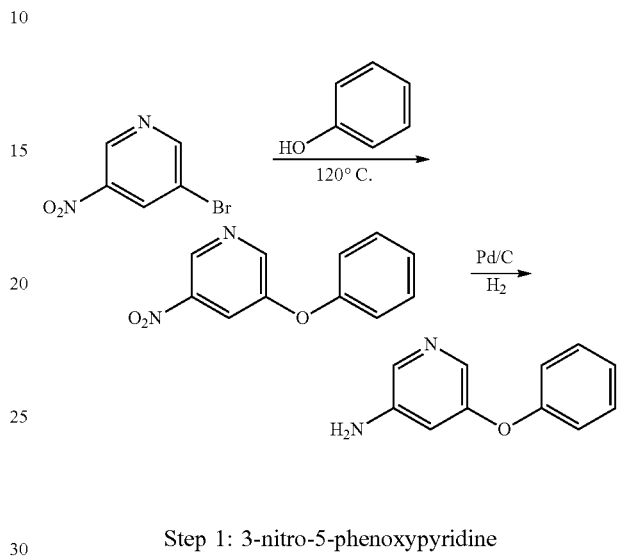

Step 1: 3-nitro-5-phenoxypyridine

A mixture of 3-bromo-5-nitropyridine (500 mg, 2.46 mmol), phenol (255 mg, 2.71 mmol) and K$_2$CO$_3$ (408 mg, 2.96 mmol) in DMSO (6 mL) was stirred at 120° C. for 3 h. Water was added into the reaction mixture and the aqueous extracted with EtOAc three times. The combined organic layers were washed with water, brine, dried over Na$_2$SO$_4$. The residue, after concentration was purified by column chromatography (10% EtOAc/PE) to afford 3-nitro-5-phenoxypyridine (93 mg, 17%) as a white solid. LCMS m/z=217.0 [M+H]$^+$.

Step 2: 5-phenoxypyridin-3-amine

To a solution of 3-nitro-5-phenoxypyridine (93 mg, 0.43 mmol) in MeOH (1 mL) was added 10% Pd/C (10 mg). The resulting mixture was stirred under H$_2$ for 3 h. After filtration through a pad of celite, the filtrate was concentrated to afford 5-phenoxypyridin-3-amine (50 mg, 62%) as a white solid. LCMS m/z=187.1 [M+H]$^+$.

Synthesis of (2S,3S)-2-amino-3-((4-fluorobenzyl)oxy)butanamide

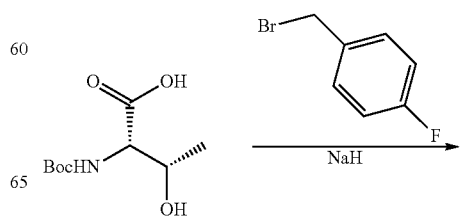

Step 1: N-(tert-butoxycarbonyl)-O-(4-fluorobenzyl)-L-allothreonine

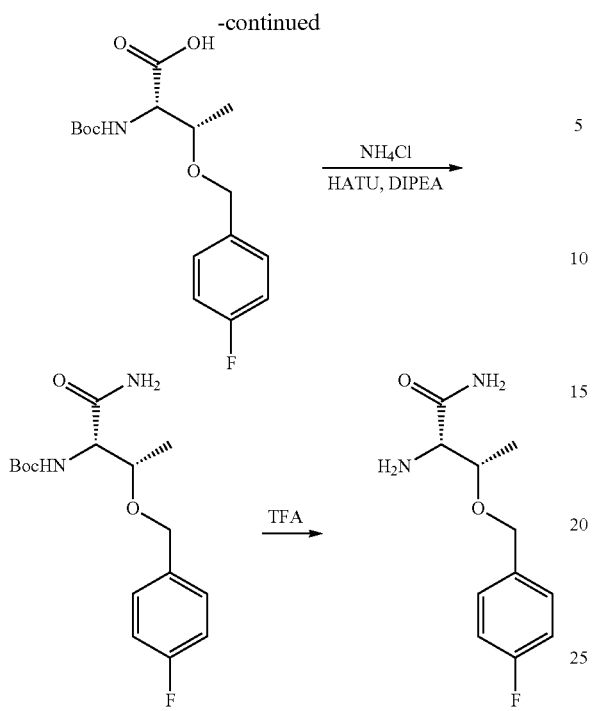

To a solution of (tert-butoxycarbonyl)-L-allothreonine (500 mg, 2.28 mmol) in DMF (5.0 mL) was added NaH (187 mg, 4.67 mmol) portionwise at 0° C. After stirring for 1 h, 1-(bromomethyl)-4-fluorobenzene (431 mg, 2.28 mmol) was added and the reaction mixture was stirred for another 14 h. The residue, after concentration was purified by reverse-phase column to afford N-(tert-butoxycarbonyl)-O-(4-fluorobenzyl)-L-allothreonine (140 mg, 19%) as off-white solid. LCMS m/z=328.2 [M+H]+.

Step 2: tert-butyl ((2S,3S)-1-amino-3-(4-fluorobenzyl)oxy)-1-oxobutan-2-yl)carbamate HATU (179 mg, 0.47 mmol) was added to the solution of N-(tert-butoxycarbonyl)-O-(4-fluorobenzyl)-L-allothreonine (100 mg, 0.92 mmol) in DMF (2.0 mL) at 0° C. After stirring for 30 min, NH4Cl (50 mg, 0.93 mmol) was added and the solution was stirred for another 2 h. The residue, after concentration was purified by reverse-phase column to afford tert-butyl ((2S,3S)-1-amino-3-((4-fluorobenzyl)oxy)-1-oxobutan-2-yl)carbamate (50 mg, 50%) as a colorless oil. LCMS m/z=327.1 [M+1]+; 1H NMR (400 MHz, CD3OD) δ 7.40-7.33 (m, 2H), 7.07-7.00 (m, 2H), 4.53 (s, 2H), 4.33 (d, J=6.0 Hz, 1H), 3.85 (t, J=6.4 Hz, 1H), 1.45 (s, 9H), 1.19 (d, J=6.3 Hz, 3H).

Step 3: (2S,3S)-2-amino-3-(4-fluorobenzyl)oxy)butanamide

TFA (2.0 mL) was added to the solution of tert-butyl ((2S,3S)-1-amino-3-((4-fluorobenzyl)oxy)-1-oxobutan-2-yl)carbamate (50 mg, 0.15 mmol) in DCM (2.0 mL) and the reaction mixture was stirred for 3 h. The solvent was removed under reduced pressure to afford (2S,3S)-2-amino-3-((4-fluorobenzyl)oxy)butanamide (209 mg, quant.) as a yellow oil. LCMS m/z=226.9 [M+H]+.

Synthesis of (2S,3R)-2-amino-3-((4-fluorobenzyl)oxy)butanamide

Made using a similar method as described for the synthesis of (2S,3S)-2-amino-3-((4-fluorobenzyl)oxy)butanamide, starting from (tert-butoxycarbonyl)-L-threonine. LCMS m/z=227.0 [M+H]+.

Synthesis of 4-(2-cyclopropylacetamido)-3-methoxybenzoic acid

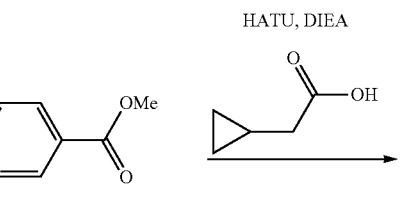

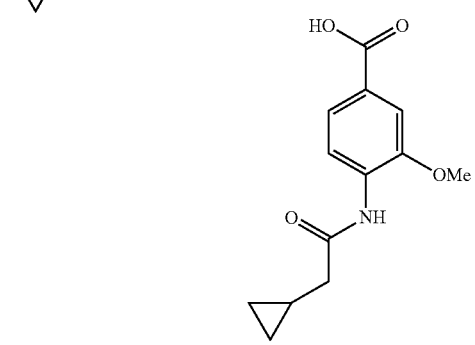

Step 1: Methyl 4-(2-cyclopropylacetamido)-3-methoxybenzoate 2-cyclopropylacetic acid (332 mg, 3.31 mmol) was added to the solution of methyl 4-amino-3-methoxybenzoate (500 mg, 2.76 mmol), DIEA (1.07 g, 8.28 mmol) and HATU (380.23 mg, 4.14 mmol) in DMA (15.0 mL). The solution was stirred at room temperature for 14 h. The reaction was treated with water and extracted with EtOAc three times. The combined organic layers were washed with water and brine, dried over Na2SO4 and concentrated. The residue was purified by column chromatography (2% MeOH/DCM) to give methyl 4-(2-cyclopropylacetamido)-3-methoxybenzoate (333 mg, 46%) as a white solid. LCMS m/z=264.1 [M+H]+.

Step 2: 4-(2-cyclopropylacetamido)-3-methoxybenzoic acid

To a solution of methyl 4-(2-cyclopropylacetamido)-3-methoxybenzoate (50 mg, 0.19 mmol) in MeOH/H$_2$O (1 mL/0.2 mL) was added NaOH (22.8 mg, 0.57 mmol). The resulting mixture was stirred for 4 h. The reaction was treated with water and pH of the aqueous was adjusted to ~1 by adding of 1M HCl then extracted with EtOAc. The combined organic layers were washed with water, brine and dried over Na$_2$SO$_4$. Concentration afforded 4-(2-cyclopropylacetamido)-3-methoxybenzoic acid (40 mg, 85%) as a yellow solid. LCMS m/z=250.1 [M+H]$^+$.

Synthesis of (S)-2-amino-5-(2-hydroxyphenyl)-N-methylpentanamide

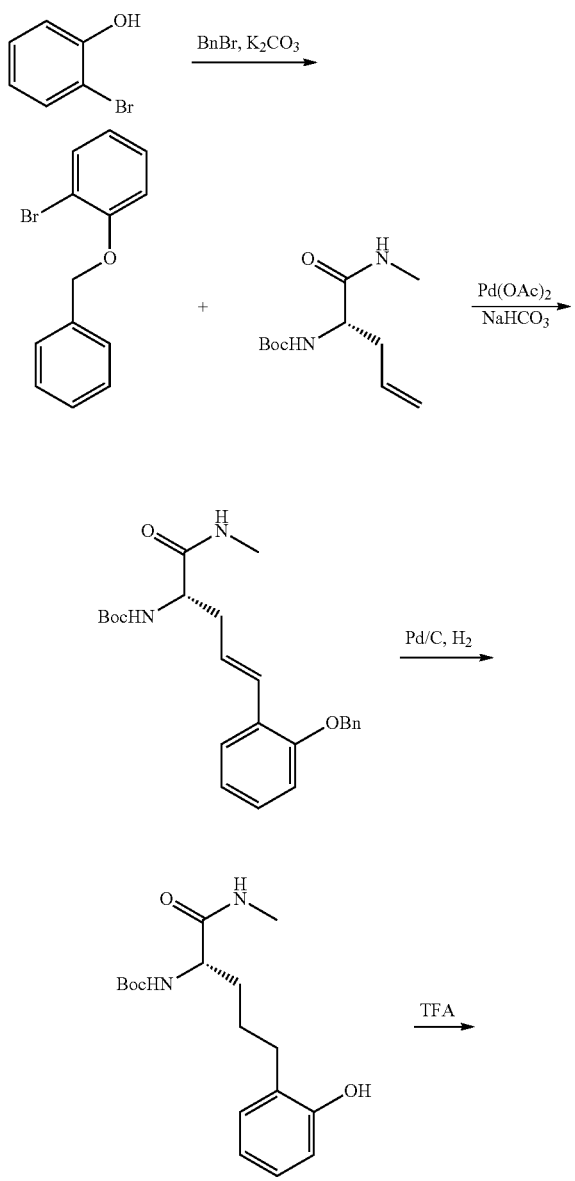

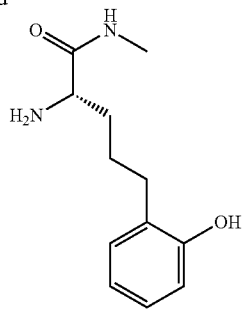

Step 1: 1-(benzyloxy)-2-bromobenzene ( )

BnBr (2.17 g, 12.7 mmol) was added to the solution of 3-bromophenol (2 g, 11.6 mmol) and K$_2$CO$_3$ (3.2 g, 23.2 mmol) in DMF (10.0 mL). The solution was stirred at room temperature for 3 h. The reaction was treated with water and extracted with EtOAc three times. The combined organic layers were washed with water and brine, dried over Na$_2$SO$_4$ and concentrated. The residue was purified by column chromatography (20% EtOAc/PE) to afford 1-(benzyloxy)-2-bromobenzene (2.8 g, 92%) as a yellow oil. $^1$H NMR (400 MHz, CD$_3$OD) δ 7.58-7.20 (m, 7H), 7.00-6.82 (m, 2H), 5.04 (s, 2H).

Step 2: tert-butyl (S,Z)-(5-(2-(benzyloxy)phenyl)-1-(methylamino)-1-oxopent-4-en-2-yl)carbamate To a solution of 1-(benzyloxy)-2-bromobenzene (1 g, 3.80 mmol) in NMP (10.0 mL) was added tert-butyl (S)-(1-(methylamino)-1-oxopent-4-en-2-yl)carbamate (1.04 g, 4.56 mmol), Pd(PPh$_3$)$_4$ (218 mg, 1.90 mmol) and NaOAc (1.55 g, 11.4 mmol). The resulting mixture was heated at 100° C. for 14 h. The reaction was treated with water and extracted with EtOAc. The combined organic layers were washed with water and brine, dried over Na$_2$SO$_4$ and concentrated. The residue was purified by column chromatography (20% EtOAc/PE) to afford tert-butyl (S,Z)-(5-(2-(benzyloxy)phenyl)-1-(methylamino)-1-oxopent-4-en-2-yl)carbamate (300 mg, 40%) as a yellow oil. LCMS m/z=411.1 [M+H]$^+$.

Step 3: tert-butyl (S)-(5-(2-hydroxyphenyl)-1-(methylamino)-1-oxopentan-2-yl)carbamate Pd/C (5 mg) was added to the solution of tert-butyl (S,Z)-(5-(2-(benzyloxy)phenyl)-1-(methylamino)-1-oxopent-4-en-2-yl)carbamate (50 mg, 0.12 mmol) in MeOH (1.5 mL) and the reaction was stirred at room temperature for 14 h under an atmosphere of H$_2$. The mixture was filtered through a pad of celite and the filtrate was concentrated to afford tert-butyl (S)-(5-(2-hydroxyphenyl)-1-(methylamino)-1-oxopentan-2-yl)carbamate (35 mg, quant.) which was used in next step without further purification. LCMS m/z=323.3 [M+H]$^+$.

Step 4: (S)-2-amino-5-(2-hydroxyphenyl)-N-methylpentanamide

TFA (1.5 mL) was added to a solution of tert-butyl (S)-(5-(2-hydroxyphenyl)-1-(methylamino)-1-oxopentan-2-yl)carbamate (40 mg, 0.12 mmol) in DCM (2.0 mL) and the reaction was stirred for 4 h. The solvent was removed to afford (S)-2-amino-5-(2-hydroxyphenyl)-N-methylpentanamide (30 mg, quant.) which was used without further purification.

Synthesis of (S)-2-amino-5-(3-hydroxyphenyl)-N-methylpentanamide

Made using a similar method as described for the synthesis of (S)-2-amino-5-(2-hydroxyphenyl)-N-methylpentanamide. LCMS m/z=223.1 [M+H]+.

Synthesis of 2-(6-chloro-1H-indol-3-yl)propanoic acid

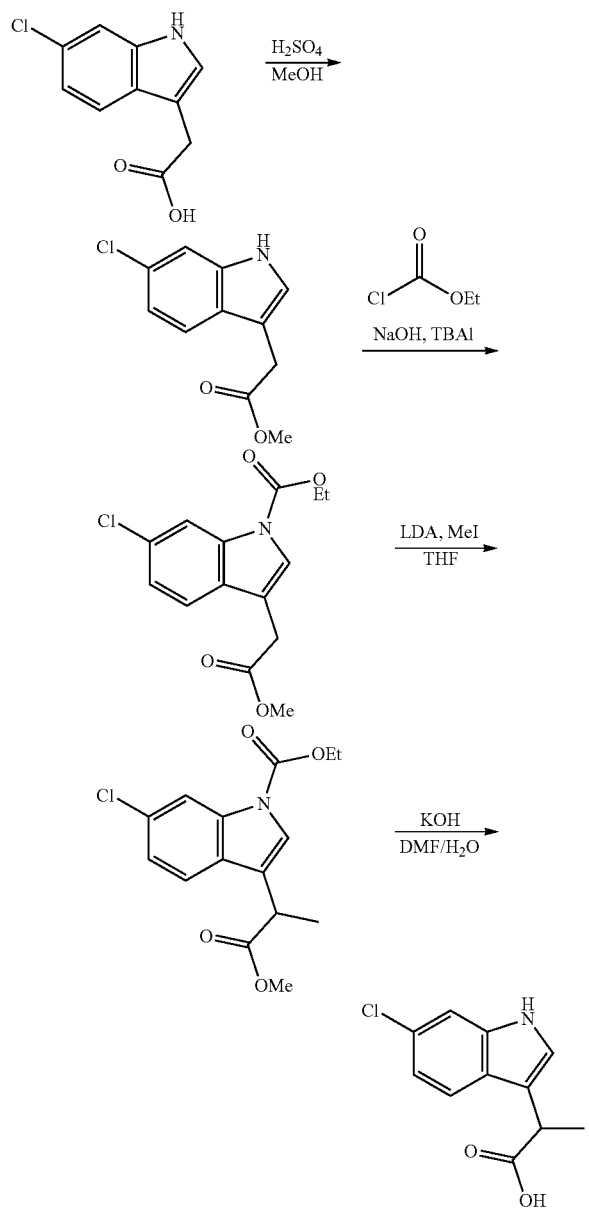

Step 1: methyl 2-(6-chloro-1H-indol-3-yl)acetate

To a solution of 2-(6-chloro-1H-indol-3-yl)acetic acid (500 mg, 2.392 mmol) in MeOH (5 mL) was added conc. $H_2SO_4$ (1 mL). The resulting mixture was heated at 80° C. for 2 h then the solvent removed under vacuum. The residue obtained was diluted with water and the pH adjusted to ~8 by addition of 10% NaOH. The aqueous layer was extracted with EtOAc three times and the combined organic layers were washed with water and brine, dried over $Na_2SO_4$ and concentrated to afford methyl 2-(6-chloro-1H-indol-3-yl)acetate (490 mg, 92%) as a white solid. LCMS m/z=223.9 [M+H]+; 1H NMR (400 MHz, $CD_3OD$) δ 7.46 (d, J=8.4 Hz, 1H), 7.34 (d, J=1.9 Hz, 1H), 7.18 (d, J=0.9 Hz, 1H), 6.99 (dd, J=8.4, 1.9 Hz, 1H), 3.75 (d, J=0.8 Hz, 2H), 3.67 (s, 3H).

Step 2: ethyl 6-chloro-3-(2-methoxy-2-oxoethyl)-1H-indole-1-carboxylate

To a solution of methyl 2-(6-chloro-1H-indol-3-yl)acetate (350 mg, 1.569 mmol) in DCM (3 ml) was added ethyl carbonochloridate (340 mg, 3.139 mmol) and TBAI (57 mg, 0.157 mmol). The resulting mixture was stirred at 0° C. for 2 h. The mixture was diluted with water and extracted with EtOAc three times. The combined organic layers were washed with water and brine, dried over $Na_2SO_4$ and concentrated. The residue was purified by column chromatography (20% EtOAc/PE) to afford ethyl 6-chloro-3-(2-methoxy-2-oxoethyl)-1H-indole-1-carboxylate (440 mg, 95%) as a white solid. 1H NMR (400 MHz, $CD_3OD$) δ 8.13 (d, J=1.9 Hz, 1H), 7.61 (t, J=1.1 Hz, 1H), 7.49 (d, J=8.4 Hz, 1H), 7.23 (dd, J=8.4, 1.9 Hz, 1H), 4.48 (q, J=7.1 Hz, 2H), 3.74 (d, J=1.0 Hz, 2H), 3.70 (s, 3H), 1.45 (t, J=7.1 Hz, 3H).

Step 3: ethyl 6-chloro-3-(1-methoxy-1-oxopropan-2-yl)-1H-indole-1-carboxylate

To a solution of ethyl 6-chloro-3-(2-methoxy-2-oxoethyl)-1H-indole-1-carboxylate (440 mg, 1.49 mmol) in dry THF (3 mL) was added LDA (2M in THF, 1.2 mL, 2.4 mmol) and MeI (318 mg, 2.24 mmol) under $N_2$ atmosphere at −70° C. The mixture was allowed to warm to room temperature and stirred for another 5 h. Water was added and the aqueous extracted with EtOAc three times. The combined organic layers were washed with water, brine and dried over $Na_2SO_4$. The residue obtained after concentration was purified by column chromatography (10% EtOAc/PE) to afford ethyl 6-chloro-3-(1-methoxy-1-oxopropan-2-yl)-1H-indole-1-carboxylate (70 mg, 15%) as a white solid. 1H NMR (400 MHz, $CD_3OD$) δ 8.08 (s, 1H), 7.57 (dd, J=2.5, 1.3 Hz, 1H), 7.45 (dt, J=8.5, 1.9 Hz, 1H), 7.20 (dq, J=8.5, 1.6 Hz, 1H), 4.46 (qd, J=7.1, 1.0 Hz, 2H), 3.70 (d, J=7.3 Hz, 6H), 1.44 (t, J=7.1 Hz, 4H).

Step 4: 2-(6-chloro-1H-indol-3-yl)propanoic acid

To a solution of ethyl 6-chloro-3-(1-methoxy-1-oxopropan-2-yl)-1H-indole-1-carboxylate (70 mg, 0.226 mmol) in DMF (1 mL) was added 10% NaOH (1 ml). The resulting mixture was stirred for 3 h then the solvent removed under vacuum. The residue obtained was diluted with water and the pH adjusted to ~2 by addition of 1M HCl. The aqueous layer was extracted with EtOAc three times and the combined organic layers were washed with water and brine, dried over $Na_2SO_4$ and concentrated to afford 2-(6-chloro-1H-indol-3-yl)propanoic acid (45 mg, 90%) as a white solid. LCMS m/z=221.9 [M−H]−.

Synthesis of (S)-2-amino-N-methyl-5-(tetrahydro-2H-pyran-4-yl)pentanamide

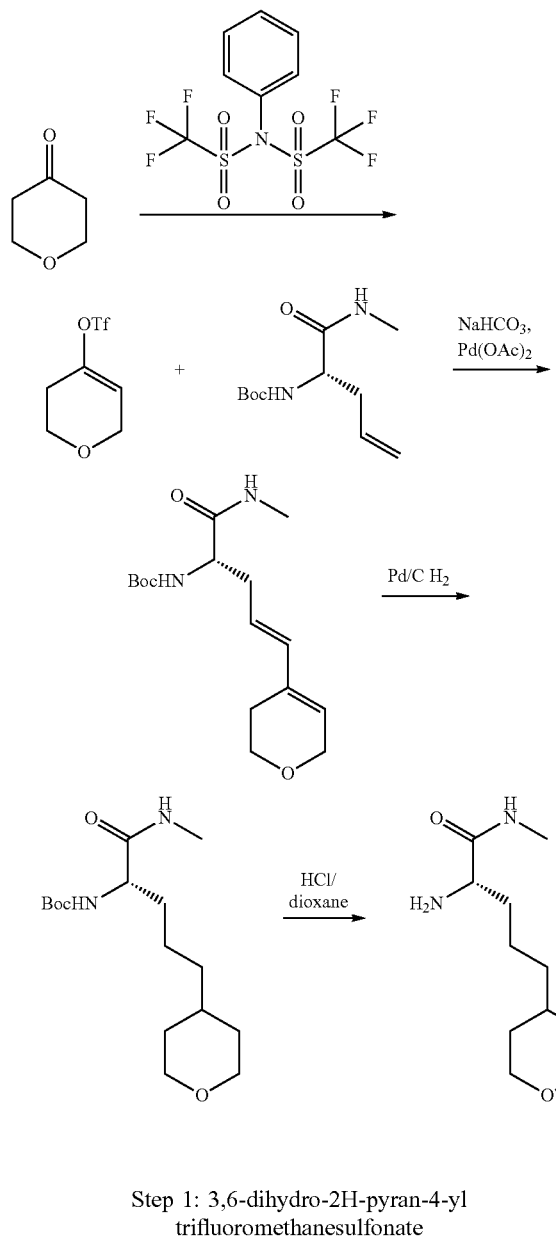

Step 1: 3,6-dihydro-2H-pyran-4-yl trifluoromethanesulfonate

To a solution of tetrahydro-4H-pyran-4-one (500 mg, 4.995 mmol) in dry THF (3 mL) was added LiHMDS (1M in THF, 6 mL, 5.994 mmol) and phenyl triflimide (1.96 g, 5.494 mmol) at ~78° C. The resulting mixture was stirred at room temperature overnight. Water was added and the aqueous extracted with EtOAc three times. The combined organic layers were washed with water, brine and dried over $Na_2SO_4$. The residue, after concentration was purified by column chromatography (6% EtOAc/PE) to afford 3,6-dihydro-2H-pyran-4-yl trifluoromethanesulfonate (350 mg, 30%) as a yellow oil. $^1$H NMR (400 MHz, $CD_3OD$) δ 5.92 (tt, J=2.9, 1.4 Hz, 1H), 4.24 (q, J=2.9 Hz, 2H), 3.87 (t, J=5.5 Hz, 2H), 2.46 (ttd, J=5.5, 2.8, 1.4 Hz, 2H).

Step 2: tert-butyl (S,E)-(5-(3,6-dihydro-2H-pyran-4-yl)-1-(methylamino)-1-oxopent-4-en-2-yl)carbamate To a solution of 3,6-dihydro-2H-pyran-4-yl trifluoromethanesulfonate (300 mg, 1.293 mmol) in a mixture of DMF (4 mL) and $H_2O$ (1 mL) was added tert-butyl (S)-(1-(methylamino)-1-oxopent-4-en-2-yl)carbamate (265 mg, 1.164 mmol), $NaHCO_3$ (326 mg, 3.879 mmol) and $Pd(OAc)_2$ (29 mg, 0.129 mmol). The resulting mixture was heated at 100° C. overnight under $N_2$ atmosphere. Water was added and the aqueous extracted with EtOAc three times. The combined organic layers were washed with water, brine and dried over $Na_2SO_4$. The residue after concentration was purified by column chromatography (20% EtOAc/PE) to afford tert-butyl (S,E)-(5-(3,6-dihydro-2H-pyran-4-yl)-1-(methylamino)-1-oxopent-4-en-2-yl)carbamate (180 mg, 45%) as a yellow oil. LCMS m/z=311.2 $[M+H]^+$.

Step 3: tert-butyl (S)-(1-(methylamino)-1-oxo-5-(tetrahydro-2H-pyran-4-yl)pentan-2-yl)carbamate To a solution of tert-butyl (S,E)-(5-(3,6-dihydro-2H-pyran-4-yl)-1-(methylamino)-1-oxopent-4-en-2-yl)carbamate (45 mg, 0.145 mmol) in MeOH (1 mL) was added 10% Pd/C (10 mg). The resulting mixture was stirred at room temperature for 3 h under $H_2$ atmosphere. The mixture was filtered through celite and the filtrate was concentrated to afford tert-butyl (S)-(1-(methylamino)-1-oxo-5-(tetrahydro-2H-pyran-4-yl)pentan-2-yl)carbamate (40 mg, 88%) as a white oil. LCMS m/z=315.2 $[M+H]^+$.

Step 4: (S)-2-amino-N-methyl-5-(tetrahydro-2H-pyran-4-yl)pentanamide

To a solution of tert-butyl (S)-(1-(methylamino)-1-oxo-5-(tetrahydro-2H-pyran-4-yl)pentan-2-yl)carbamate (40 mg, 0.127 mmol) in MeOH (1 mL) was added HCl (4M in dioxane, 1 mL). The mixture was stirred at room temperature for 3 h. The solvent was removed under reduced pressure to afford (S)-2-amino-N-methyl-5-(tetrahydro-2H-pyran-4-yl)pentanamide which was used directly in next step. LCMS m/z=215.1 $[M+H]^+$.

Synthesis of 2-(5,6-dichloro-1H-indol-3-yl)acetic acid

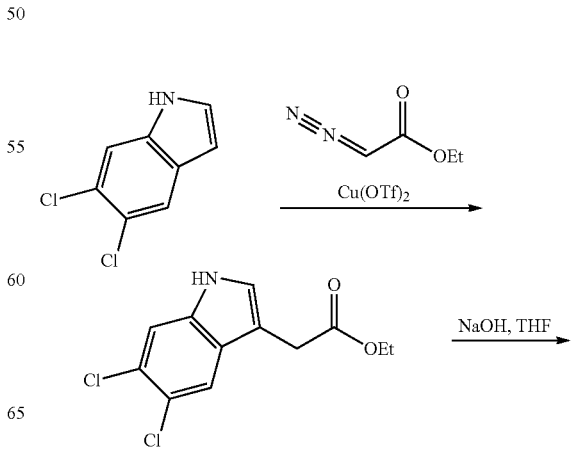

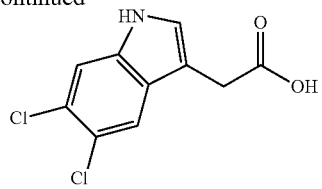

Step 1: ethyl 2-(5,6-dichloro-1H-indol-3-yl)acetate

To a solution of 5,6-dichloro-1H-indole (2.0 g, 10.82 mmol) in DCM (10 mL) was added ethyl 2-diazoacetate (1.8 g, 16.2 mmol) and Cu(OTf)$_2$ (180 mg, 1.1 mmol). The resulting mixture was stirred at room temperature overnight. Water was added and the aqueous extracted with DCM three times. The combined organic layers were washed with water, brine, dried over Na$_2$SO$_4$. The residue after concentration was purified by column chromatography (20% EtOAc/PE) to afford ethyl 2-(5,6-dichloro-1H-indol-3-yl)acetate (700 mg, 24%) as a yellow oil. LCMS m/z=269.8 [M−H]$^−$.

Step 2: 2-(5,6-dichloro-1H-indol-3-yl)acetic acid

To a solution of ethyl 2-(5,6-dichloro-1H-indol-3-yl)acetate (100 mg, 0.37 mmol) in THF (1 mL) was added 10% NaOH (1 mL). The resulting mixture was stirred for 3 h then the solvent removed under vacuum. The residue obtained was diluted with water and the pH adjusted to ~2 by addition of 1M HCl. The aqueous layer was extracted with EtOAc three times and the combined organic layers were washed with water and brine, dried over Na$_2$SO$_4$ and concentrated to afford 2-(5,6-dichloro-1H-indol-3-yl)acetic acid (70 mg, 78%) as a white solid. LCMS m/z=241.8 [M−H]$^−$. $^1$H NMR (400 MHz, CD$_3$OD) δ 7.68 (d, J=9.1 Hz, 1H), 7.49 (d, J=2.1 Hz, 1H), 7.23 (d, J=7.3 Hz, 1H), 3.70 (d, J=0.9 Hz, 2H).

Synthesis of 2-(7-methoxy-1H-indol-3-yl)acetic acid

Made using a similar method as described for the synthesis of 2-(5,6-dichloro-1H-indol-3-yl)acetic acid, starting from 7-methoxy-1H-indole. LCMS m/z=206.0 [M+H]$^+$.

Synthesis of (S)-2-amino-N-methyl-5-(4-(trifluoromethyl)phenyl)pentanamide

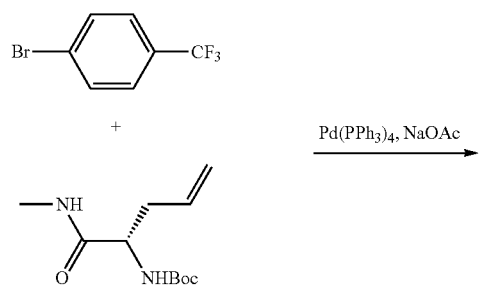

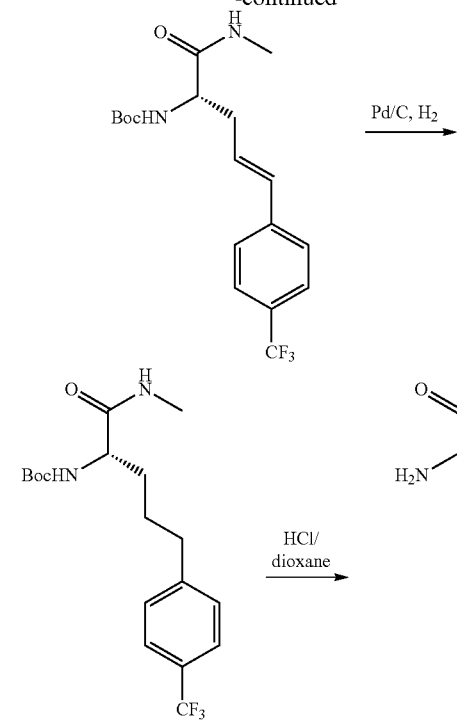

Step 1: tert-butyl (S,E)-(1-(methylamino)-1-oxo-5-(4-(trifluoromethyl)phenyl)pent-4-en-2-yl)carbamate To a solution of tert-butyl (S)-(1-(methylamino)-1-oxo-pent-4-en-2-yl)carbamate (100 mg, 0.446 mmol) in NMP (3 mL) was added 1-bromo-4-(trifluoromethyl)benzene (100 mg, 0.446 mmol), Pd(PPh$_3$)$_4$ (25 mg, 0.023 mmol) and NaOAc (73 mg, 0.892 mmol). The resulting mixture was heated at 100° C. for 4 h. Water was added and the aqueous extracted with EtOAc three times. The combined organic layers were washed with water, brine and dried over Na$_2$SO$_4$. The residue after concentration was purified by column chromatography (20% EtOAc/PE) to afford tert-butyl (S,E)-(1-(methylamino)-1-oxo-5-(4-(trifluoromethyl)phenyl)pent-4-en-2-yl)carbamate (140 mg, 84%) as a white oil. LCMS m/z=373.0 [M+H]$^+$.

Step 2: tert-butyl (S)-(1-(methylamino)-1-oxo-5-(4-(trifluoromethyl)phenyl)pentan-2-yl)carbamate To a solution of tert-butyl (S,E)-(1-(methylamino)-1-oxo-5-(4-(trifluoromethyl)phenyl)pent-4-en-2-yl)carbamate (100 mg, 0.27 mmol) in MeOH (1 mL) was added 10% Pd/C (14 mg). The resulting mixture was stirred at room temperature for 6 h under H$_2$ atmosphere. The mixture was filtered through a pad of celite and the filtrate was concentrated to afford tert-butyl (S)-(1-(methylamino)-1-oxo-5-(4-(trifluoromethyl)phenyl)pentan-2-yl)carbamate (70 mg, 71%) as a colorless oil. LCMS m/z=375.1 [M+H]$^+$.

Step 3: (S)-2-amino-N-methyl-5-(4-(trifluoromethyl)phenyl)pentanamide

To a solution of tert-butyl (S)-(1-(methylamino)-1-oxo-5-(4-(trifluoromethyl)phenyl)pentan-2-yl)carbamate (50 mg, 0.167 mmol) in MeOH (1 mL) was added HCl (4M in dioxane, 1 mL). The mixture was stirred at room temperature for 3 h. The solvent was removed under reduced pressure and the product was used directly. LCMS m/z=275.0 [M+H]$^+$.

Synthesis of (S,E)-2-amino-N-methyl-5-phenylpent-4-enamide

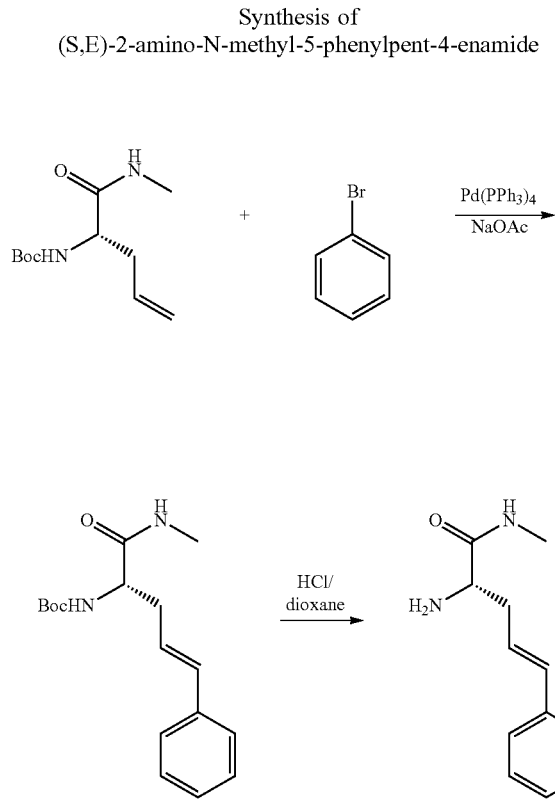

Step 1: tert-butyl (S,E)-(1-(methylamino)-1-oxo-5-phenylpent-4-en-2-yl)carbamate To a solution of tert-butyl (S)-(1-(methylamino)-1-oxo-pent-4-en-2-yl)carbamate (450 mg, 1.973 mmol) in NMP (3 mL) was added bromobenzene (300 mg, 1.923 mmol), Pd(PPh$_3$)$_4$ (114 mg, 0.099 mmol) and NaOAc (324 mg, 3.946 mmol). The resulting mixture was heated at 100° C. for 4 h. Water was added and the aqueous extracted with EtOAc three times. The combined organic layers were washed with water, brine and dried over Na$_2$SO$_4$. The residue after concentration was purified by column chromatography (20% EtOAc/PE) to afford tert-butyl (S,E)-(1-(methylamino)-1-oxo-5-phenylpent-4-en-2-yl)carbamate (140 mg, 84%) as a white solid. LCMS m/z=305.0 [M+H]$^+$.

Step 2: (S,E)-2-amino-N-methyl-5-phenylpent-4-enamide

To a solution of tert-butyl (S,E)-(1-(methylamino)-1-oxo-5-phenylpent-4-en-2-yl)carbamate (50 mg, 0.167 mmol) in MeOH (1 mL) was added HCl (4M in dioxane, 1 mL). The mixture was stirred at room temperature for 3 h. The solvent was removed under reduced pressure to afford (S,E)-2-amino-N-methyl-5-phenylpent-4-enamide which was used directly. LCMS m/z=205.0 [M+H]$^+$.

Synthesis of (S)-2-amino-N-methyl-5-phenylpent-4-ynamide

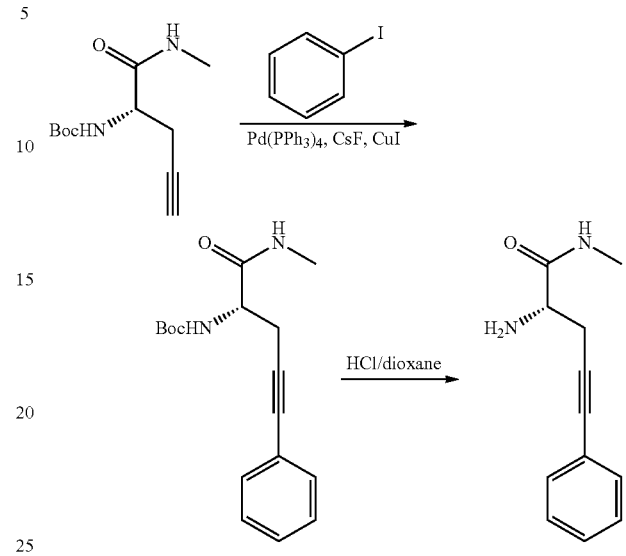

Step 1: tert-butyl (S)-(1-(methylamino)-1-oxo-5-phenylpent-4-yn-2-yl)carbamate To a solution of tert-butyl (S)-(1-(methylamino)-1-oxo-pent-4-en-2-yl)carbamate (100 mg, 0.442 mmol) in NMP (3 mL) was added iodobenzene (300 mg, 1.923 mmol), PdCl$_2$(PPh$_3$)$_2$ (30 mg, 0.044 mmol) and CuI (8 mg, 0.044 mmol). The resulting mixture was heated at 100° C. for 4 h under N$_2$ atmosphere. Water was added and the aqueous extracted with EtOAc three times. The combined organic layers were washed with water, brine and dried over Na$_2$SO$_4$. The residue after concentration was purified by column chromatography (20% EtOAc/PE) to afford tert-butyl (S)-(1-(methylamino)-1-oxo-5-phenylpent-4-yn-2-yl)carbamate (82 mg, 62%) as a white solid. LCMS m/z=303.2 [M+H]$^+$.

Step 2: (S)-2-amino-N-methyl-5-phenylpent-4-ynamide

To a solution of tert-butyl (S)-(1-(methylamino)-1-oxo-5-phenylpent-4-yn-2-yl)carbamate (50 mg, 0.167 mmol) in MeOH (1 mL) was added HCl (4M in dioxane, 1 mL). The mixture was stirred at room temperature for 3 h. The solvent was removed under reduced pressure to afford (S)-2-amino-N-methyl-5-phenylpent-4-ynamide which was used directly in next step. LCMS m/z=203.2 [M+H]$^+$.

Synthesis of (S)-2-amino-N-methyl-5-(pyridin-4-yl)pentanamide

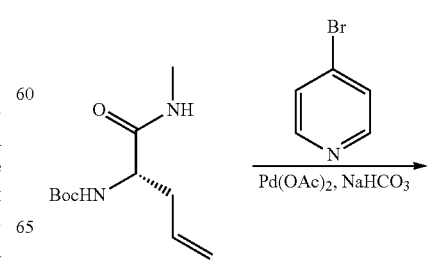

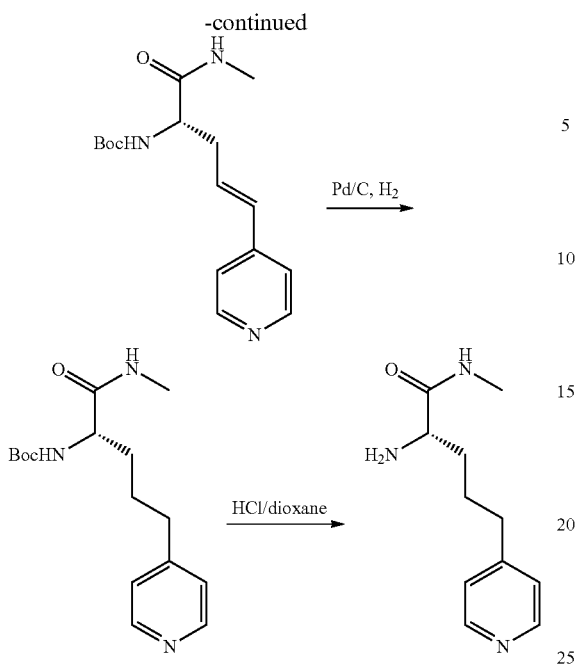

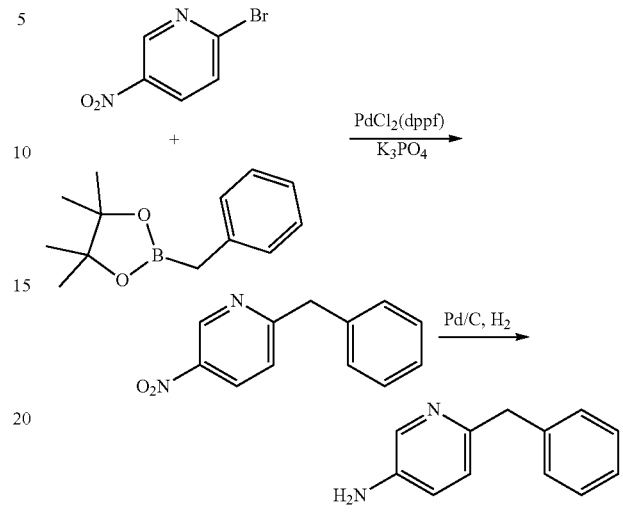

Step 1: tert-butyl (S,E)-(1-(methylamino)-1-oxo-5-(pyridin-4-yl)pent-4-en-2-yl)carbamate To a solution of tert-butyl (S)-(1-(methylamino)-1-oxo-pent-4-en-2-yl)carbamate (200 mg, 0.877 mmol) in a mixture of DMF (4 mL) and H₂O (2 mL) was added 4-bromopyridine (187 mg, 0.964 mmol), Pd(OAc)₂ (20 mg) and NaHCO₃ (294 mg, 3.5 mmol). The resulting mixture was heated at 70° C. overnight. Water was added and the aqueous extracted with EtOAc three times. The combined organic layers were washed with water, brine and dried over Na₂SO₄. Residue after concentration was purified by prep-HPLC to afford tert-butyl (S,E)-(1-(methylamino)-1-oxo-5-(pyridin-4-yl)pent-4-en-2-yl)carbamate (70 mg, 26%) as a white solid. LCMS m/z=306.0 [M+H]⁺.

Step 2: tert-butyl (S)-(1-(methylamino)-1-oxo-5-(pyridin-4-yl)pentan-2-yl)carbamate To a solution of tert-butyl (S,E)-(1-(methylamino)-1-oxo-5-(pyridin-4-yl)pent-4-en-2-yl)carbamate (70 mg, 0.23 mmol) in THF (2 mL) was added Pd/C (10%, 50 mg). The mixture was stirred at room temperature for 2 h under an atmosphere of H₂. The reaction mixture was filtered through celite and the filtrate was concentrated to afford tert-butyl (S)-(1-(methylamino)-1-oxo-5-(pyridin-4-yl)pentan-2-yl)carbamate (70 mg, quant.) as a colorless oil. LCMS m/z=308.0 [M+H]⁺.

Step 3: (S)-2-amino-N-methyl-5-(pyridin-4-yl)pentanamide

To a solution of tert-butyl (S)-(1-(methylamino)-1-oxo-5-(pyridin-4-yl)pentan-2-yl)carbamate (70 mg, 0.228 mmol) in MeOH (1 mL) was added HCl (4M in dioxane, 2 mL). The resulting mixture was stirred at room temperature for 1 h. The solvent was removed to afford (S)-2-amino-N-methyl-5-(pyridin-4-yl)pentanamide (50 mg, quant.) LCMS m/z=208.0 [M+H]⁺.

Synthesis of 6-benzylpyridin-3-amine

Step 1: 2-benzyl-5-nitropyridine

A mixture of 2-bromo-5-nitropyridine (500 mg, 2.46 mmol), 2-benzyl-4,4,5,5-tetramethyl-1,3,2-dioxaborolane (218 mg, 3.69 mmol) Pd(dppf)Cl₂ (cat.) and K₃PO₄ (1.57 g, 7.39 mmol) in a mixture of dioxane (5 mL) and H₂O (1 mL) was heated at 90° C. for 2 h. Water was added and the aqueous extracted with EtOAc three times. The combined organic layers were washed with water and brine, dried over Na₂SO₄ and concentrated. The residue was purified by column chromatography (10% EtOAc/PE) to afford 2-benzyl-5-nitropyridine (249 mg, 47%) as a white solid. LCMS m/z=215.2 [M+H]⁺.

Step 2: 6-benzylpyridin-3-amine

To a solution of 2-benzyl-5-nitropyridine (249 mg, 1.16 mmol) in MeOH (3 mL) was added 10% Pd/C (10 mg). The resulting mixture was stirred for 3 h under an atmosphere of H₂. The mixture was filtered through celite and the filtrate was concentrated to afford 6-benzylpyridin-3-amine (100 mg, 47% yield) as a white solid. LCMS m/z=185.1 [M+H]⁺.

Synthesis of (S)-2-amino-5-(1H-benzo[d][1,2,3]triazol-4-yl)-N-methylpentanamide

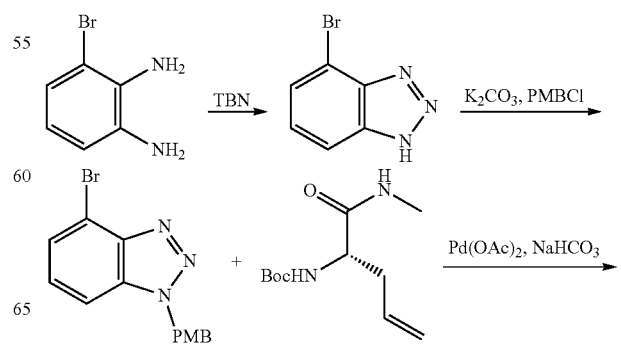

-continued

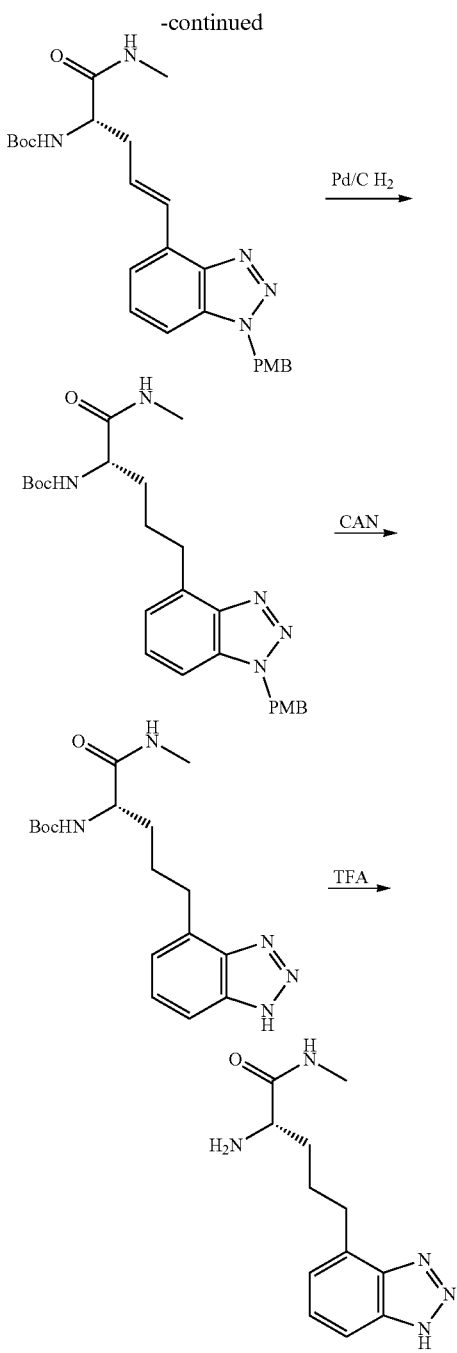

Step 1: 4-bromo-1H-benzo[d][1,2,3]triazole

TBN (2.2 g, 21.4 mmol) was added to a solution of 3-bromobenzene-1,2-diamine (2 g, 10.7 mmol) in DCM (15 mL). The solution was stirred at room temperature for 2 h. The solvent was removed and the residue was purified by column chromatography (2% MeOH/DCM) to give 4-bromo-1H-benzo[d][1,2,3]triazole (1.7 g, 81%) as a yellow oil. LCMS m/z=197.9 [M+H]$^+$.

Step 2: 4-bromo-1-(4-methoxybenzyl)-1H-benzo[d][1,2,3]triazole

To a solution of 4-bromo-1H-benzo[d][1,2,3]triazole (1.6 mg, 8.04 mmol) in DCM (10.0 mL) was added PMBCl (1.38 g, 8.84 mmol) and TEA (2.9 g, 27.21 mmol). The resulting mixture was stirred for 4 h. The solvent was removed and the residue was purified by column chromatography (2% MeOH/DCM) to give 4-bromo-1-(4-methoxybenzyl)-1H-benzo[d][1,2,3]triazole (1.1 g, 41%) as a yellow solid. LCMS m/z=317.8 [M+H]$^+$.

Step 3: tert-butyl (S,E)-(5-(1-(4-methoxybenzyl)-1H-benzo[d][1,2,3]triazol-4-yl)-1-(methylamino)-1-oxopent-4-en-2-yl)carbamate To a solution of 4-bromo-1-(4-methoxybenzyl)-1H-benzo[d][1,2,3]triazole (950 mg, 2.99 mmol) in a mixture of DMF (10 mL) and H$_2$O (2 mL) was added tert-butyl (S)-(1-(methylamino)-1-oxopent-4-en-2-yl)carbamate (820 mg, 3.60 mmol), Pd(OAc)$_2$ (67 mg, 0.03 mmol) and NaHCO$_3$ (754 mg, 8.97 mmol). The resulting mixture was heated at 70° C. for 14 h. Water was added and the aqueous extracted with EtOAc three times. The combined organic layers were washed with water and brine, dried over Na$_2$SO$_4$ and concentrated. The residue was purified by column chromatography (2% MeOH/DCM) to afford tert-butyl (S,E)-(5-(1-(4-methoxybenzyl)-1H-benzo[d][1,2,3]triazol-4-yl)-1-(methylamino)-1-oxopent-4-en-2-yl)carbamate (600 mg, 43%) as a white solid. LCMS m/z=466.1 [M+H]$^+$.

Step 4: tert-butyl (S)-(5-(1-(4-methoxybenzyl)-1H-benzo[d][1,2,3]triazol-4-yl)-1-(methylamino)-1-oxopentan-2-yl)carbamate Pd/C (10%, 84 mg) was added to a solution of tert-butyl (S,E)-(5-(1-(4-methoxybenzyl)-1H-benzo[d][1,2,3]triazol-4-yl)-1-(methylamino)-1-oxopent-4-en-2-yl)carbamate (280 mg, 0.77 mmol) in MeOH (5 mL) and the reaction mixture was stirred under H$_2$ atmosphere for 14 h. The mixture was filtered through a pad of celite and the filtrate was concentrated to afford tert-butyl (S)-(5-(1-(4-methoxybenzyl)-1H-benzo[d][1,2,3]triazol-4-yl)-1-(methylamino)-1-oxopentan-2-yl)carbamate (250 mg, quant.) which was used in next step without further purification. LCMS m/z=468.1 [M+H]$^+$.

Step 5: tert-butyl (S)-(5-(1H-benzo[d][1,2,3]triazol-4-yl)-1-(methylamino)-1-oxopentan-2-yl)carbamate To a solution of tert-butyl (S)-(5-(1-(4-methoxybenzyl)-1H-benzo[d][1,2,3]triazol-4-yl)-1-(methylamino)-1-oxopentan-2-yl)carbamate (180 mg, 0.48 mmol) in a mixture of DMF (5 mL) and H$_2$O (1 mL) was added CAN (808 mg, 1.48 mmol). The resulting mixture was stirred at room temperature for 4 h. Water was added and the aqueous extracted with EtOAc three times. The combined organic layers were washed with water and brine, dried over Na$_2$SO$_4$ and concentrated. The residue was purified by prep-TLC to give tert-butyl (S)-(5-(1H-benzo[d][1,2,3]triazol-4-yl)-1-(methylamino)-1-oxopentan-2-yl)carbamate (40 mg, 34%) as a yellow solid. LCMS m/z=348.0 [M+H]$^+$.

Step 6: (S)-2-amino-5-(1H-benzo[d][1,2,3]triazol-4-yl)-N-methylpentanamide

TFA (0.5 mL) was added to a solution of tert-butyl (S)-(5-(1H-benzo[d][1,2,3]triazol-4-yl)-1-(methylamino)-1-oxopentan-2-yl)carbamate (40 mg, 0.11 mmol) in DCM (1.5 mL) and the reaction was stirred for 4 h. The solvent was removed to afford (S)-2-amino-5-(1H-benzo[d][1,2,3]tri-

Synthesis of 2-(6-(cyclopropylmethoxy)-1H-indol-3-yl)acetic acid

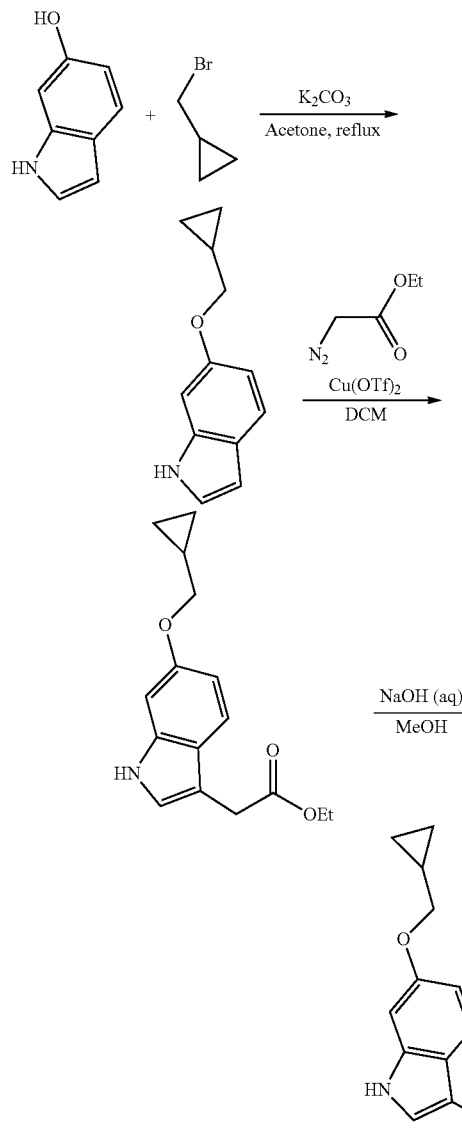

Step 1: 6-(cyclopropylmethoxy)-1H-indole

To a solution of 1H-indol-6-ol (500 mg, 3.76 mmol) in acetone (10 mL) was added (bromom-ethyl)cyclopropane (0.8 mL) and K$_2$CO$_3$ (1.55 g, 11.3 mmol). The mixture was heated at reflux for 24 h and an additional amount of (bromomethyl)cyclopropane (0.5 mL) was added. The mixture was heated at reflux for additional 2 days. The reaction mixture was concentrated in vacuo. The crude was purified by column chromatography (15% EtOAc/PE) to give 6-(cyclopropylmethoxy)-1H-indole (570 mg, 81%). LCMS m/z=188.0 [M+H]$^+$.

Step 2: ethyl 2-(6-(cyclopropylmethoxy)-1H-indol-3-yl)acetate

To a solution of 6-(cyclopropylmethoxy)-1H-indole (100 mg, 0.53 mmol) and Cu(OTf)$_2$ (19 mg, 0.05 mmol) in DCM (3 mL) was added ethyl diazoacetate (430 mg, 3.77 mmol) dropwise. The mixture was stirred at room temperature for 24 h. The reaction mixture was concentrated in vacuo and the residue was purified by column chromatography (12% EtOAc/PE) to give ethyl 2-(6-(cyclopropylmethoxy)-1H-indol-3-yl)acetate (122 mg, 14.6%). LCMS m/z=274.1 [M+H]$^+$.

Step 3: 2-(6-(cyclopropylmethoxy)-1H-indol-3-yl)acetic acid

To a solution of ethyl 2-(6-(cyclopropylmethoxy)-1H-indol-3-yl)acetate (122 mg, 0.45 mmol) in MeOH (1 mL) was added 10% NaOH (4 mL). The mixture was stirred at room temperature for 3 h. The pH was adjusted to ~2 by addition of 1M HCl and the aqueous extracted with EtOAc three times. The combined organic layers were concentrated in vacuo to afford 2-(6-(cyclopropylmethoxy)-1H-indol-3-yl)acetic acid which was used directly in the synthesis of further compounds.

Synthesis of 1-(oxazol-2-yl)-4-phenylbutan-1-amine

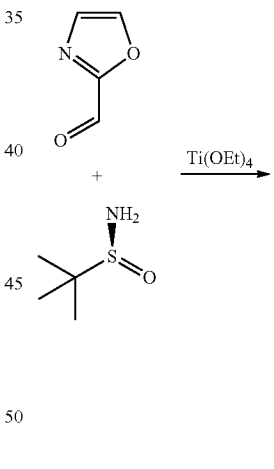

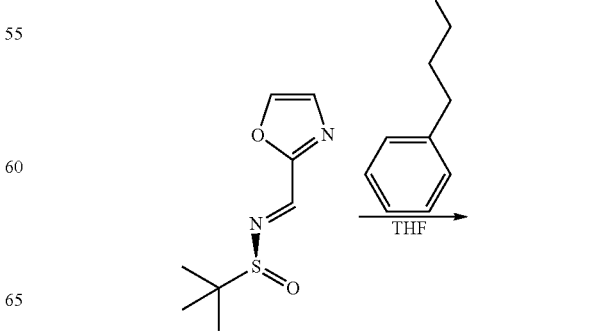

305

-continued

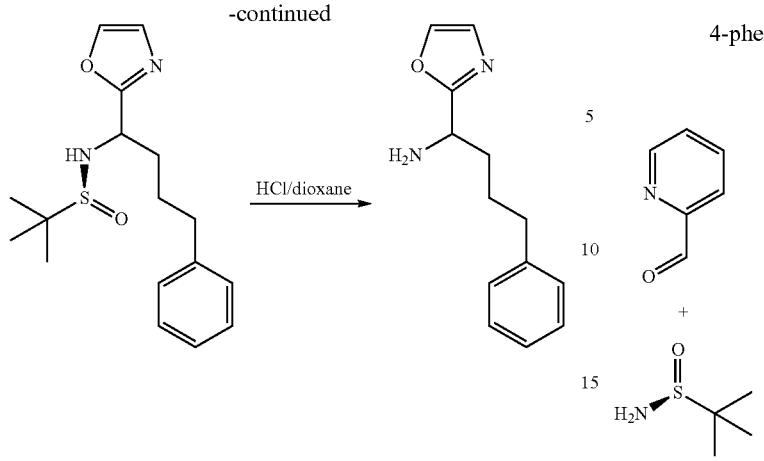

Step 1: (S)-2-methyl-N-(oxazol-2-ylmethylene)propane-2-sulfinamide

A mixture of oxazole-2-carbaldehyde (300 mg, 3.09 mmol), (S)-2-methylpropane-2-sulfinamide (450 mg, 3.71 mmol) and Ti(OEt)$_4$ (1.41 g, 6.18 mmol) in THF (10.0 mL) was stirred at room temperature overnight. Water was added and the aqueous extracted with EtOAc three times. The organic layers were washed with water, brine, dried over Na$_2$SO$_4$ and concentrated in vacuo. The crude was purified by silica column chromatography (30% EtOAc/PE) to give (S)-2-methyl-N-(oxazol-2-ylmethylene)propane-2-sulfinamide (300 mg, 49%). LCMS m/z=201.2 [M+H]$^+$; $^1$H NMR (400 MHz, CDCl$_3$) δ 8.52 (d, J=1.0 Hz, 1H), 7.84 (s, 1H), 7.41 (s, 1H), 1.29 (d, J=1.1 Hz, 9H).

Step 2: (S)-2-methyl-N-(1-(oxazol-2-yl)-4-phenylbutyl)propane-2-sulfinamide To a solution of (S)-2-methyl-N-(oxazol-2-ylmethylene)propane-2-sulfinamide (300 mg, 1.5 mmol) in dry THF was added (3-phenylpropyl)magnesium bromide (1.67 g, 7.49 mmol) at ~78° C. The mixture was stirred at room temperature under an atmosphere of N$_2$. NH$_4$Cl solution was added and the aqueous extracted with EtOAc three times. The combined organic layers were washed with water, brine, dried over Na$_2$SO$_4$ and concentrated in vacuo. The crude was purified by prep-HPLC to give (S)-2-methyl-N-(1-(oxazol-2-yl)-4-phenylbutyl)propane-2-sulfinamide (82 mg, 17%). LCMS m/z=321.2 [M+H]$^+$.

Step 3: 1-(oxazol-2-yl)-4-phenylbutan-1-amine

A solution of (S)-2-methyl-N-(1-(oxazol-2-yl)-4-phenylbutyl)propane-2-sulfinamide (82 mg, 0.256 mmol) in HCl (4M in dioxane, 3 mL) was stirred at room temperature for 3 h. The reaction mixture was concentrated in vacuo to give 1-(oxazol-2-yl)-4-phenylbutan-1-amine (60 mg, quant.). LCMS m/z=217.2 [M+H]$^+$.

306

Synthesis of 4-phenyl-1-(pyridin-2-yl)butan-1-amine

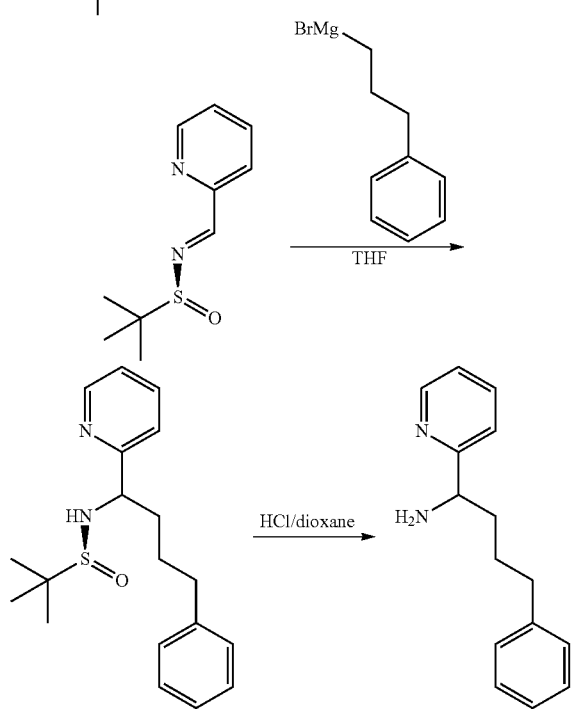

Step 1: (S)-2-methyl-N-(pyridin-2-ylmethylene)propane-2-sulfinamide

A mixture of picolinaldehyde (3.0 g, 28.0 mmol), (S)-2-methylpropane-2-sulfinamide (4.06 g, 33.6 mmol) and Ti(OEt)$_4$ (12.8 g, 56 mmol) in THF (50 mL) was stirred at room temperature overnight. Water was then added and the mixture extracted with EtOAc three times. The combined organic layers were washed with water, brine and dried over Na$_2$SO$_4$. The solvent was removed and the residue purified by silica column chromatography (10% EtOAc/PE) to afford (S,E)-2-methyl-N-(pyridin-2-ylmethylene)propane-2-sulfinamide (1.1 g, 21%): $^1$H NMR (400 MHz, CD$_3$OD) δ 8.72 (ddd, J=4.9, 1.7, 0.9 Hz, 1H), 8.62 (s, 1H), 8.13 (dt, J=8.0, 1.1 Hz, 1H), 8.00 (td, J=7.7, 1.7 Hz, 1H), 7.58 (ddd, J=7.6, 4.8, 1.2 Hz, 1H), 1.29 (s, 9H).

Step 2: (S)-2-methyl-N-(4-phenyl-1-(pyridin-2-yl)butyl)propane-2-sulfinamide To a solution of (S)-2-methyl-N-(pyridin-2-ylmethylene)propane-2-sulfinamide (300 mg, 1.4 mmol) in dry THF was added (3-phenylpropyl)magnesium bromide (466 mg, 2.1 mmol) dropwise at −78° C. under N$_2$. The reaction mixture was stirred at this temperature for 2 hours. The reaction was quenched with sat. aq. NH$_4$Cl solution and extracted with EtOAc three times. The combined organic layers were washed with water, brine and dried over Na$_2$SO$_4$. The residue was concentrated and purified by silica column chromatography (5% MeOH/DCM) to give (S)-2-methyl-N-(4-phenyl-1-(pyridin-2-yl)butyl)propane-2-sulfinamide (86 mg, 18%) as a mixture of diastereomers (2/5). $^1$H NMR (400 MHz, CD$_3$OD) δ 8.48 (ddd, J=4.9, 1.7, 1.0 Hz, 1H), 7.80 (qd, J=7.6, 1.8 Hz, 1H), 7.44 (ddt, J=10.8, 8.0, 1.1 Hz, 1H), 7.33-7.27 (m, 1H), 7.26-7.18 (m, 2H), 7.13 (td, J=6.1, 5.6, 2.9 Hz, 3H), 4.47-4.37 (m, 1H), 2.62 (t, J=7.5 Hz, 2H), 2.02-1.54 (m, 4H), 1.19 (s, 9H, major isomer), 1.15 (s, 9H, minor isomer).

Step 3: 4-phenyl-1-(pyridin-2-yl)butan-1-amine

A solution of (S)-2-methyl-N-(4-phenyl-1-(pyridin-2-yl)butyl)propane-2-sulfinamide (30 mg, 0.09 mmol) in HCl (4 M in dioxane, 2 mL) was stirred at room temperature for 3 h. The reaction mixture was concentrated to afford 4-phenyl-1-(pyridin-2-yl)butan-1-amine which was used directly.

Synthesis of
4-phenyl-1-(pyrimidin-2-yl)butan-1-amine

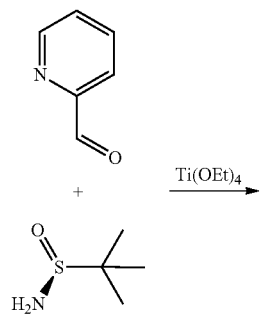

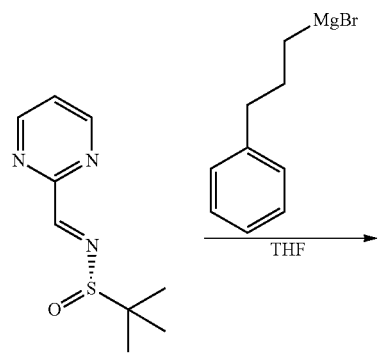

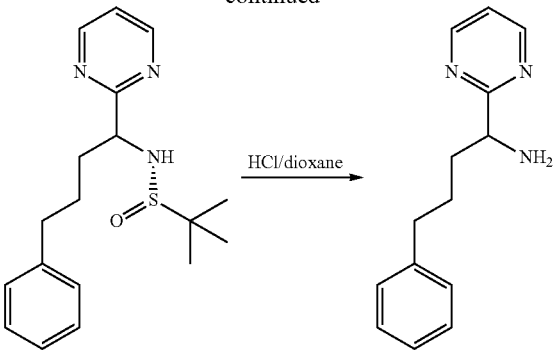

Step 1: (S)-2-methyl-N-(pyrimidin-2-ylmethylene)propane-2-sulfinamide (S)-2-methylpropane-2-sulfinamide (353 mg, 2.91 mmol) was added to a solution of pyrimidine-2-carbaldehyde (300 mg, 2.78 mmol) and KHSO$_4$ (397 mg, 2.91 mmol) in toluene (20 mL) and the mixture was heated at 50° C. for 14 h. The reaction mixture was concentrated in vacuo and the residue purified by silica column chromatography (30% EtOAc/PE) to give (S)-2-methyl-N-(pyrimidin-2-ylmethylene)propane-2-sulfinamide (330 mg, 56%). LCMS m/z=212.0 [M+H]$^+$; $^1$H NMR (400 MHz, CD$_3$OD) δ 9.00 (d, J=4.8 Hz, 2H), 8.61 (s, 1H), 7.61 (t, J=4.8 Hz, 1H), 1.31 (s, 9H).

Step 2: (S)-2-methyl-N-(4-phenyl-1-(pyrimidin-2-yl)butyl)propane-2-sulfinamide

To a solution of (S)-2-methyl-N-(pyrimidin-2-ylmethylene)propane-2-sulfinamide (130 mg, 0.62 mmol) in THF (3.0 mL) was added (3-phenylpropyl)magnesium bromide (1M in THF, 2.0 mL) at −78° C. under N$_2$. The mixture stirred at −78° C. for 10 min then allowed to warm to room temperature and stirring continued for 2 h. The reaction mixture was concentrated in vacuo and the residue purified by silica column chromatography (50% EtOAc/PE) to give (S)-2-methyl-N-(4-phenyl-1-(pyrimidin-2-yl)butyl)propane-2-sulfinamide (54 mg, 26%).

Step 3: 4-phenyl-1-(pyrimidin-2-yl)butan-1-amine

A solution of (S)-2-methyl-N-(4-phenyl-1-(pyrimidin-2-yl)butyl)propane-2-sulfinamide (54 mg, 0.16 mmol) in HCl (4 M in dioxane, 2 mL) was stirred at room temperature for 1 h. The reaction mixture was concentrated in vacuo to give 4-phenyl-1-(pyrimidin-2-yl)butan-1-amine 4-phenyl-1-(pyrimidin-2-yl)butan-1-amine (37 mg, quant.) which was used directly.

Synthesis of
3-methoxy-4-(trifluoromethoxy)benzoic acid

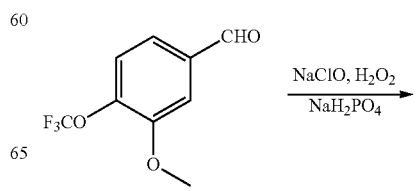

-continued

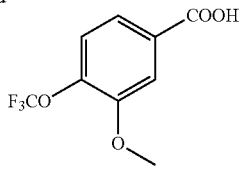

H$_2$O$_2$ (72 mg, 1.19 mmol) was added to a solution of 3-methoxy-4-(trifluoromethoxy)benzaldehyde (80 mg, 0.36 mmol), NaH$_2$PO$_4$ (282 mg, 1.19 mmol) and NaClO (164 mg, 1.19 mmol) in DMSO/H$_2$O (2.0 mL/0.5 mL). The solution was stirred at room temperature for 5 h. Water was added and pH adjusted to ~1 by addition of 1M HCl. The aqueous was extracted with EtOAc three times. The combined organic layers were washed with water, brine and dried over Na$_2$SO$_4$. The residue was concentrated and used without further purification. LCMS m/z=234.9 [M−H]$^-$.

Synthesis of 1-(1H-indol-3-yl)cyclopropane-1-carboxylic acid

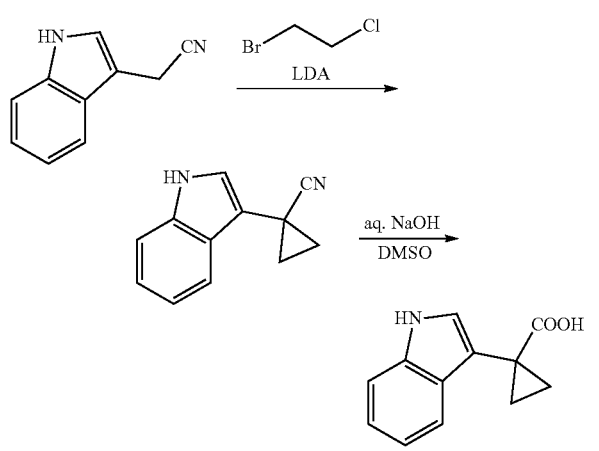

Step 1: 1-(1H-indol-3-yl)cyclopropane-1-carbonitrile

A solution of 2-(1H-indol-3-yl)acetonitrile (500 mg, 3.20 mmol) in THF was treated with LDA (2M in THF, 6.4 mL, 12.8 mmol) at −30° C. The solution was allowed to warm to −5° C. and stirred for 30 min, then cooled to −30° C. and 1-bromo-2-chloroethane (550 mg, 3.84 mmol) was added dropwise. The reaction mixture was stirred at room temperature for 2 h. Water was added and the pH adjusted to ~1 by addition of 1M HCl. The aqueous was extracted with EtOAc three times and the combined organic layers washed with, water, brine and dried over Na$_2$SO$_4$. The residue after concentration was purified by silica gel column (20% EtOAc/PE) to afford 1-(1H-indol-3-yl)cyclopropane-1-carbonitrile (235 mg, 40%) as a yellow solid. $^1$H NMR (400 MHz, DMSO-d$_6$) δ 11.17 (s, 1H), 7.72-7.66 (m, 1H), 7.43-7.35 (m, 2H), 7.19-7.05 (m, 2H), 1.69-1.56 (m, 2H), 1.41-1.28 (m, 2H).

Step 2: 1-(1H-indol-3-yl)cyclopropane-1-carboxylic acid

To a solution of 1-(1H-indol-3-yl)cyclopropane-1-carbonitrile (40 mg, 0.22 mmol) in DMSO (2 mL) was added NaOH (35.2 mg, 0.88 mmol). The mixture was heated at 70° C. overnight. Water was added and pH adjusted to ~1 by addition of 1M HCl. The aqueous was extracted with EtOAc three times and the combined organic layers were washed with water, brine and dried over Na$_2$SO$_4$. The solvent was removed to afford 1-(1H-indol-3-yl)cyclopropane-1-carboxylic acid (43 mg, 97%) as a colorless oil, which was used directly.

Synthesis of 7-methoxy-2,2-dimethyl-2,3-dihydrobenzofuran-5-carboxylic acid

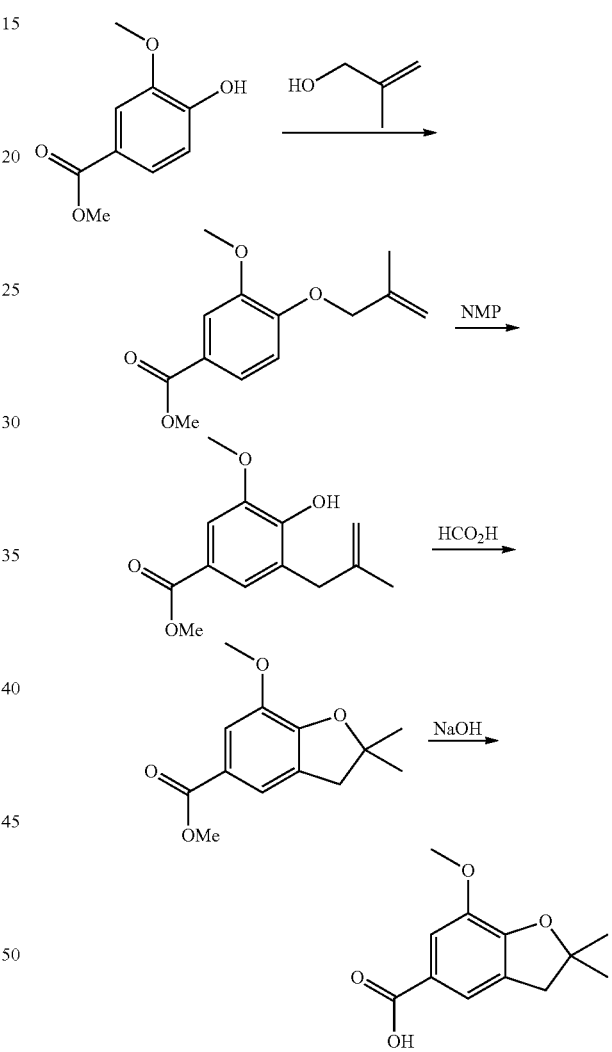

Step 1: methyl 3-methoxy-4-((2-methylallyl)oxy)benzoate 2-methylprop-2-en-1-ol (396 mg, 5.49 mmol) was added to a solution of methyl 4-hydroxy-3-methoxybenzoate (1 g, 5.49 mmol), DIAD (258 mg, 5.49 mmol) and PPh$_3$ (1.44 g, 5.49 mmol) in THF (8.0 mL). The reaction mixture was stirred at room temperature for 14 h. The solvent was removed and the residue purified by silica gel column (3% EtOAc/PE) to afford methyl 3-methoxy-4-((2-methylallyl)oxy)benzoate (1 g, 77%) as a yellow solid. $^1$H NMR (400

MHz, DMSO-d$_6$) δ 7.54 (dd, J=8.4, 2.4 Hz, 1H), 7.45 (d, J=2.0 Hz, 1H), 7.04 (d, J=8.4 Hz, 1H), 5.05 (s, 1H), 4.96 (s, 1H), 4.53 (s, 2H), 3.82 (s, 3H), 3.81 (s, 3H), 1.76 (s, 3H).

Step 2: methyl 4-hydroxy-3-methoxy-5-(2-methylallyl)benzoate

Methyl 3-methoxy-4-((2-methylallyl)oxy)benzoate (100 mg, 0.42 mmol) was dissolved in NMP (1.5 mL) and the solution heated at 205° C. for 7 h. The reaction was allowed to cool, water added and the aqueous extracted with EtOAc three times. The combined organic layers were washed with water, brine and dried over Na$_2$SO$_4$. The residue was concentrated and purified by prep-TLC (5% MeOH/DCM) to afford methyl 4-hydroxy-3-methoxy-5-(2-methylallyl)benzoate (80 mg, 80%) as a white solid. $^1$H NMR (400 MHz, DMSO-d$_6$) δ 9.61 (s, 1H), 7.42-7.29 (m, 2H), 4.75 (s, 1H), 4.61 (s, 1H), 3.84 (s, 3H), 3.78 (s, 3H), 3.28 (s, 2H), 1.64 (s, 3H).

Step 3: methyl 7-methoxy-2,2-dimethyl-2,3-dihydrobenzofuran-5-carboxylate

To a solution of methyl 4-hydroxy-3-methoxy-5-(2-methylallyl)benzoate (60 mg, 0.25 mmol) in DCM (1.5 mL) was added formic acid (0.5 mL). The resulting mixture was heated at 45° C. for 14 h in a sealed tube. The solvent was removed and the residue purified by prep-TLC (7% MeOH/DCM) to afford methyl 7-methoxy-2,2-dimethyl-2,3-dihydrobenzofuran-5-carboxylate (55 mg, 92%) as a white oil. LCMS m/z=237.0 [M+H]$^+$.

Step 4: 7-methoxy-2,2-dimethyl-2,3-dihydrobenzofuran-5-carboxylic acid

NaOH (18.6 mg, 0.47 mmol) was added to a solution of methyl 7-methoxy-2,2-dimethyl-2,3-dihydrobenzofuran-5-carboxylate (55 mg, 0.23 mmol) in a mixture of MeOH (2 mL) and H$_2$O (0.4 mL). The reaction mixture was stirred at room temperature for 14 h. Water was added and the pH adjusted to ~1 by addition of 1M HCl. The aqueous was extracted with EtOAc three times and the combined organic layers were washed with water, brine and dried over Na$_2$SO$_4$. The solvent was removed to afford 7-methoxy-2,2-dimethyl-2,3-dihydrobenzofuran-5-carboxylic acid (205 mg, quant.) which was used without further purification. $^1$H NMR (400 MHz, DMSO-d$_6$) δ 7.43 (d, J=1.6 Hz, 1H), 7.35 (d, J=1.6 Hz, 1H), 3.78 (s, 3H), 3.04 (s, 2H), 1.42 (s, 6H).

Synthesis of isopropyl-3-methyl-2-oxo-2,3-dihydro-1H-benzo[d]imidazole-5-carboxylic acid

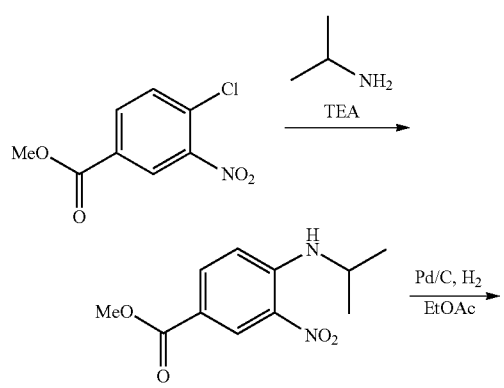

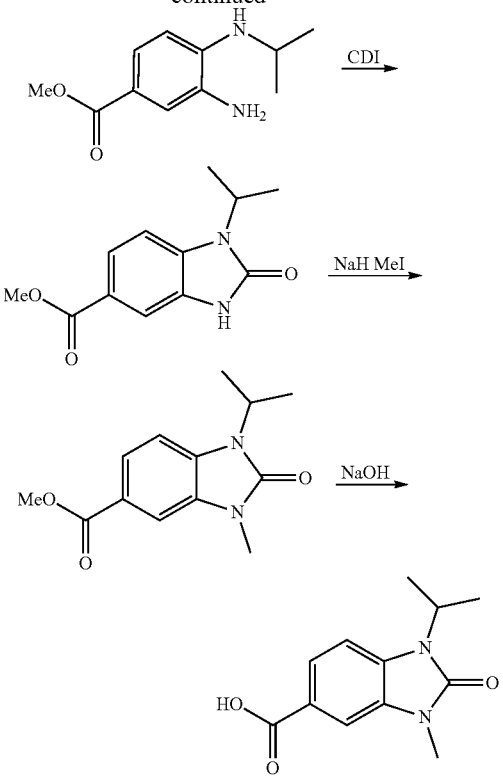

Step 1: methyl 4-(isopropylamino)-3-nitrobenzoate

To a solution of propan-2-amine (274 mg, 4.64 mmol) in THF (5 mL) was added methyl 4-chloro-3-nitrobenzoate (500 mg, 2.32 mmol) and Et$_3$N (704 mg, 6.96 mmol). The mixture was stirred at room temperature overnight. Water was added and the aqueous extracted with EtOAc three times. The combined organic layers were washed with water, brine and dried over Na$_2$SO$_4$. The crude obtained, after concentration, was purified by silica gel column (20% EtOAc/PE) to afford methyl 4-(isopropylamino)-3-nitrobenzoate (552 mg, quant.). LCMS m/z=239.2 [M+H]$^+$.

Step 2: methyl 3-amino-4-(isopropylamino)benzoate

To a solution of methyl 4-(isopropylamino)-3-nitrobenzoate (552 mg, 2.32 mmol) in MeOH (5 mL) was added Pd/C (10%, 52 mg). The mixture was stirred at room temperature overnight under an atmosphere of H$_2$. The reaction mixture was filtered through celite and the filtrate was concentrated under reduced pressure to afford methyl 3-amino-4-(isopropylamino)benzoate (442 mg, 92%). LCMS m/z=209.2 [M+H]$^+$.

Step 3: methyl 1-isopropyl-2-oxo-2,3-dihydro-1H-benzo[d]imidazole-5-carboxylate To a solution of methyl 3-amino-4-(isopropylamino)benzoate (370 mg, 1.78 mmol) in dioxane (4 mL) was added CDI (346 mg, 2.13 mmol) and the reaction mixture stirred at room temperature overnight. Water was added and the aqueous extracted with EtOAc three times. The combined organic layers were washed with water, brine, dried over Na$_2$SO$_4$ and concentrated in vacuo. The crude was purified by silica gel column (5% MeOH/DCM) to afford methyl 1-isopropyl-2-oxo-2,3-dihydro-1H-benzo[d]imidazole-5-carboxylate (224 mg, 54%).

Step 4: methyl 1-isopropyl-3-methyl-2-oxo-2,3-dihydro-1H-benzo[d]imidazole-5-carboxylate To a solution of methyl 1-isopropyl-2-oxo-2,3-dihydro-1H-benzo[d]imidazole-5-carboxylate (100 mg, 0.43 mmol) in DMF (2 mL) at RT was added NaH (51 mg, 1.28 mmol). The mixture was stirred for 30 min then MeI (91 mg, 0.64 mmol) was added. The reaction mixture was then stirred for a further 4 h. Water was added and the aqueous extracted with EtOAc three times. The combined organic layers were washed with water, brine, dried over $Na_2SO_4$ and concentrated in vacuo. The crude was purified by silica gel column (3% MeOH/DCM) to afford methyl 1-isopropyl-3-methyl-2-oxo-2,3-dihydro-1H-benzo[d]imidazole-5-carboxylate (93 mg, 88%). LCMS m/z=249.2 [M+H]$^+$.

Step 5: isopropyl-3-methyl-2-oxo-2,3-dihydro-1H-benzo[d]imidazole-5-carboxylic acid To a solution of methyl 1-isopropyl-3-methyl-2-oxo-2,3-dihydro-1H-benzo[d]imidazole-5-carboxylate (93 mg, 0.37 mmol) in MeOH (1 mL) was added NaOH (10%, 1 mL) and the reaction stirred for 2 h. Water was added and the pH adjusted to ~1 by addition of 1 M HCl. The aqueous was extracted with EtOAc three times and the combined organic layers were washed with water, brine, dried over $Na_2SO_4$ and concentrated in vacuo to afford isopropyl-3-methyl-2-oxo-2,3-dihydro-1H-benzo[d]imidazole-5-carboxylic acid (86 mg, quant.).

Synthesis of 1-isopropyl-3-methoxy-1H-indazole-6-carboxylic acid

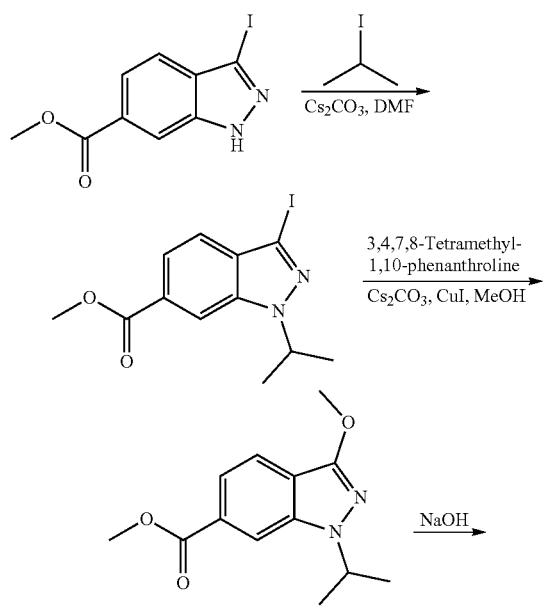

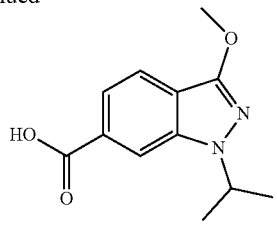

Step 1: methyl 3-iodo-1-isopropyl-1H-indazole-6-carboxylate

To a solution of methyl 3-iodo-1H-indazole-6-carboxylate (300 mg, 1 mmol) in DMF (5 mL) was added 2-iodopropane (336 mg, 2 mmol) and $Cs_2CO_3$ (972 mg, 3 mmol). The resulting mixture was stirred at room temperature overnight. Water was added and the aqueous extracted with EtOAc three times. The combined organic layers were washed with water, brine and dried over $Na_2SO_4$. The residue was concentrated and purified by silica gel column (20% EtOAc/PE) to afford methyl 3-iodo-1-isopropyl-1H-indazole-6-carboxylate (280 mg, 81%) as a yellow oil. LCMS m/z=345.0 [M+H]$^+$.

Step 2: methyl 1-isopropyl-3-methoxy-JH-indazole-6-carboxylate

To a solution of methyl 3-iodo-1-isopropyl-1H-indazole-6-carboxylate (150 mg, 0.43 mmol) in MeOH (1 mL) was added $Cs_2CO_3$ (281 mg, 0.87 mmol), 3,4,7,8-tetramethyl-1,10-phenanthroline (20 mg, 0.085 mmol) and CuI (8 mg, 0.043 mmol). The resulting mixture was heated at 140° C. for 2 h in a microwave reactor. Water was added and the aqueous extracted with EtOAc three times. The combined organic layers were washed with water, brine and dried over $Na_2SO_4$. The residue was concentrated and purified by silica gel column (12% EtOAc/PE) to afford methyl 1-isopropyl-3-methoxy-1H-indazole-6-carboxylate (45 mg, 42%) as a yellow oil. LCMS m/z=249.2 [M+H]$^+$. $^1$H NMR (400 MHz, $CD_3OD$) δ 8.31 (dd, J=1.6, 0.8 Hz, 1H), 7.97 (dd, J=9.0, 1.6 Hz, 1H), 7.43 (d, J=9.0 Hz, 1H), 4.83-4.77 (m, 1H), 4.09 (s, 3H), 3.91 (s, 3H), 1.49 (d, J=6.4 Hz, 6H).

Step 3: 1-isopropyl-3-methoxy-JH-indazole-6-carboxylic acid

To a solution of methyl 1-isopropyl-3-methoxy-1H-indazole-6-carboxylate (45 mg, 0.18 mmol) in MeOH (1 mL) was added 10% aq NaOH (1 mL) and the reaction stirred at room temperature for 3 h. The solvent was removed and water added. The pH was adjusted to ~1 by addition of 1 M HCl and the aqueous extracted with EtOAc three times. The combined organic layers were washed with water, brine, dried over $Na_2SO_4$ and concentrated to afford 1-isopropyl-3-methoxy-1H-indazole-6-carboxylic acid (30 mg, 71%) as a colourless oil. LCMS m/z=235.1 [M+H]$^+$.

Synthesis of 7-isopropoxybenzofuran-4-carboxylic acid

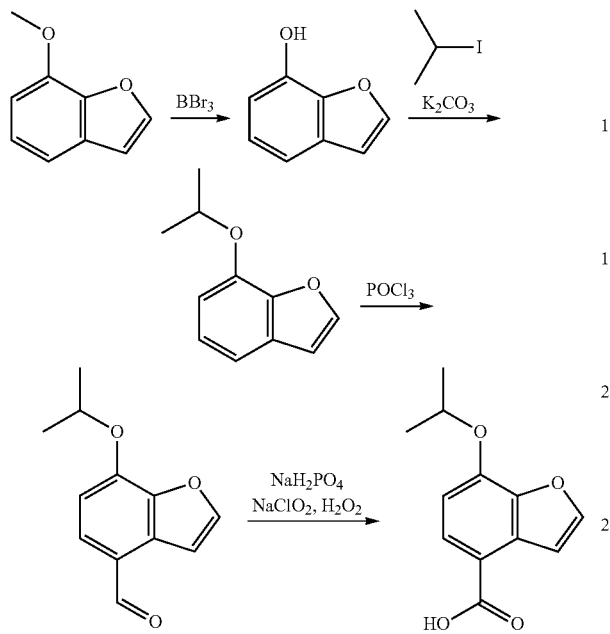

Step 1: benzofuran-7-ol

To a solution of BBr$_3$ (1M in DCM, 2 mL, 2 mmol) at −78° C. was added a solution of 7-methoxybenzofuran (150 mg, 1 mmol) in DCM (2 mL) dropwise. The resulting mixture was allowed to warm to room temperature and stirred for 4 hours under N$_2$. Water was added and the aqueous extracted with diethylether three times. The combined organic layers were washed with water, brine, dried over Na$_2$SO$_4$ and concentrated. The residue was purified by prep-TLC (30% EtOAc/PE) to afford benzofuran-7-ol (55 mg, 31%) as a black oil. $^1$H NMR (400 MHz, CDCl$_3$) δ 7.61 (d, J=2.2 Hz, 1H), 7.20-7.08 (m, 2H), 6.84 (dd, J=7.8, 1.2 Hz, 1H), 6.78 (d, J=2.2 Hz, 1H).

Step 2: 7-isopropoxybenzofuran

To a solution of benzofuran-7-ol (50 mg, 0.37 mmol) in DMF (1 mL) was added 2-iodopropane (76 mg, 0.45 mmol) and K$_2$CO$_3$ (155 mg, 1.1 mmol). The resulting mixture was stirred at room temperature for 4 hours. The solvent was removed in vacuo and the residue purified by prep-TLC (30% EtOAc/PE) to afford 7-isopropoxybenzofuran (44 mg, 68%) as a yellow oil. $^1$H NMR (400 MHz, CDCl$_3$) δ 7.61 (d, J=2.2 Hz, 1H), 7.20-7.09 (m, 2H), 6.82 (dd, J=7.8, 1.2 Hz, 1H), 6.75 (d, J=2.2 Hz, 1H), 4.80 (p, J=6.0 Hz, 1H), 1.43 (d, J=6.0 Hz, 6H).

Step 3: 7-isopropoxybenzofuran-4-carbaldehyde

To a solution of 7-isopropoxybenzofuran (44 mg, 0.25 mmol) in DMF (1 mL) was added POCl$_3$ (230 mg, 1.5 mmol) and the reaction heated at 100° C. for 4 hours under N$_2$. The reaction was cooled to room temperature and the mixture was poured into saturated Na$_2$CO$_3$ solution and extracted with ether three times. The combined organic layers were washed with water, brine and dried over Na$_2$SO$_4$. The residue was purified by prep-TLC (30% EtOAc/PE) to afford 7-isopropoxybenzofuran-4-carbaldehyde (40 mg, 78%) as a yellow oil. LCMS m/z=205.1 [M+H]$^+$.

Step 4: 7-isopropoxybenzofuran-4-carboxylic acid

To a solution of 7-isopropoxybenzofuran-4-carbaldehyde (40 mg, 0.2 mmol) in a mixture of DMSO (1 mL) and H$_2$O (1 mL) was added NaClO$_2$ (115 mg, 1.0 mmol), NaH$_2$PO$_4$ (160 mg, 1.0 mmol) and 30% H$_2$O$_2$ (113 mg, 1.0 mmol). The resulting mixture was stirred at room temperature for 4 hours under N$_2$. Water was added and the pH adjusted to ~1 by addition of 1M HCl. The aqueous was extracted with EtOAc three times. The combined organic layers were washed with water, brine and dried over Na$_2$SO$_4$. The residue was purified by prep-TLC (20% EtOAc/PE) to afford 7-isopropoxybenzofuran-4-carboxylic acid (20 mg, 45%) as a white solid. LCMS m/z=221.0 [M+H]$^+$.

Synthesis of methyl O-benzyl-L-allothreoninate

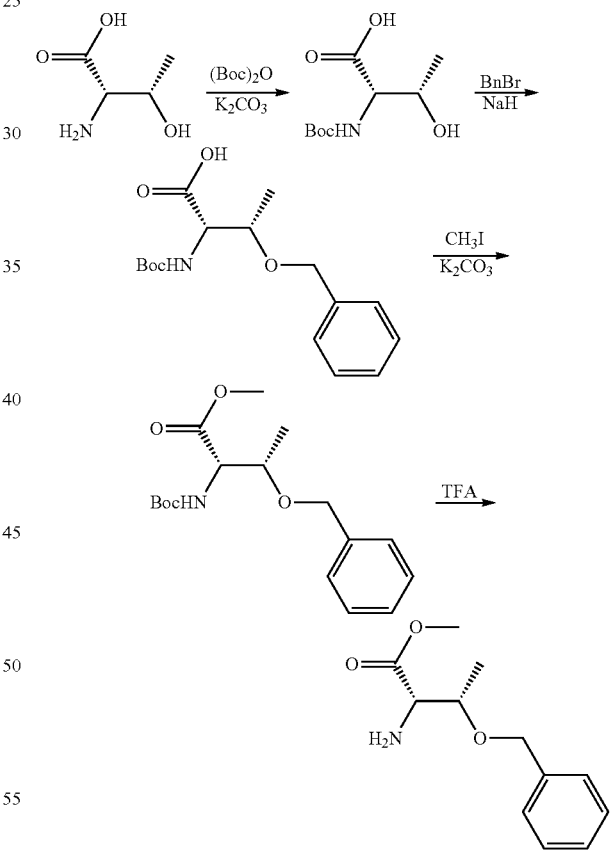

Step 1: (tert-butoxycarbonyl)-L-allothreonine

To a solution of L-allothreonine (1.0 g, 8.4 mmol) and K$_2$CO$_3$ (2.3 g, 16.8 mmol) in a mixture of THF (10 mL) and H$_2$O (2 mL) at 0° C. was added (Boc)$_2$O (2.0 g, 9.2 mmol). The resulting mixture was stirred for 5 hours, then water was added and the aqueous extracted with Et$_2$O three times and the organic layers discarded. The pH of the aqueous layer was adjusted to ~1 by addition of 1M HCl and extracted with 20% MeOH/DCM three times. The combined organic layers were washed with water and brine, dried over Na$_2$SO$_4$ and concentrated to afford (tert-butoxycarbonyl)-L-allothreonine (1.0 g, 55%). LCMS m/z=164.1 [M−$^t$Butyl+H]$^+$.

Step 2: O-benzyl-N-(tert-butoxycarbonyl)-L-allothreonine

To a solution of (tert-butoxycarbonyl)-L-allothreonine (2.0 g, 9.12 mmol) in DMF (20 mL) at 0° C. was added NaH (728 mg, 18.2 mmol) and the resulting mixture stirred for 30 minutes. Benzyl bromide (1.1 mL, 9.12 mmol) was then added and the reaction mixture stirred for another 3 hours at room temperature. Water was added and the aqueous extracted with EtOAc three times. The combined organic layers were washed with water, brine and dried over Na$_2$SO$_4$. The residue was concentrated and purified by reverse-phase column to afford O-benzyl-N-(tert-butoxycarbonyl)-L-allothreonine (1.7 g, 61%). LCMS m/z=254.2 [M−$^t$Butyl+H]$^+$; $^1$H NMR (400 MHz, DMSO-d$_6$) δ 12.64 (s, 1H), 7.39-7.21 (m, 5H), 7.01 (d, J=8.8 Hz, 1H), 4.47 (s, 2H), 4.28 (dd, J=9.0, 5.6 Hz, 1H), 3.88-3.77 (m, 1H), 1.39 (s, 9H), 1.11 (d, J=6.4 Hz, 3H).

Step 3: methyl O-benzyl-N-(tert-butoxycarbonyl)-L-allothreoninate

To a solution of O-benzyl-N-(tert-butoxycarbonyl)-L-allothreonine (480 mg, 1.55 mmol) and K$_2$CO$_3$ (429 mg, 3.10 mmol) in DMF (15 mL) was added CH$_3$I (330.7 mg, 2.33 mmol) and the reaction stirred for 4 hours. Water was added and the aqueous extracted with EtOAc three times. The combined organic layers were washed with water, brine and dried over Na$_2$SO$_4$. The residue was concentrated and purified by silica gel column (20% EtOAc/PE) to afford methyl O-benzyl-N-(tert-butoxycarbonyl)-L-allothreoninate (498 mg, 99%) as a colourless oil. LCMS m/z=268.2 [M−$^t$Butyl+H]$^+$; $^1$H NMR (400 MHz, CDCl$_3$) δ 7.37-7.26 (m, 5H), 5.25 (d, J=8.8 Hz, 1H), 4.60-4.49 (m, 3H), 3.97-3.80 (m, 1H), 3.75 (s, 3H), 1.43 (s, 9H), 1.23 (d, J=6.4 Hz, 3H).

Step 4: methyl O-benzyl-L-allothreoninate

To a solution of methyl O-benzyl-N-(tert-butoxycarbo-nyl)-L-allothreoninate (480 mg, 1.49 mmol) in DCM (5 mL) was added TFA (2.5 mL). The mixture was stirred for 4 hours. The solvent was removed to afford methyl O-benzyl-L-allothreoninate (400 mg, quant). LCMS m/z=224.2 [M+H]$^+$.

Synthesis of (9H-fluoren-9-yl)methyl (S)-(5-(2-amino-5-(3-hydroxyphenyl)pentanamido)pentyl) carbamate

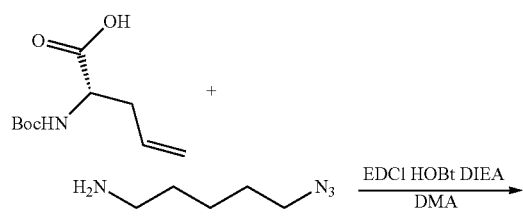

Step 1: tert-butyl (S)-(1-((5-azidopentyl)amino)-1-oxopent-4-en-2-yl)carbamate

A solution of (S)-2-((tert-butoxycarbonyl)amino)pent-4-enoic acid (517 mg, 2.4 mmol), 5-azidopentan-1-amine (280 mg, 2.18 mmol), EDCI (630 mg, 3.3 mmol), HOBt (443 mg, 3.3 mmol) and DIEA (1.12 g, 8.8 mmol) in DMA (5 mL) was stirred at room temperature overnight. Water was added and the aqueous extracted with EtOAc. The combined organic layers were washed with water and brine and dried over Na₂SO₄. The residue after concentration was purified by silica gel column (50% EtOAc/PE) to afford tert-butyl (S)-(1-((5-azidopentyl)amino)-1-oxopent-4-en-2-yl)carbamate (330 mg, 46%) as a yellow oil. LCMS m/z=326.2 [M+H]⁺.

Step 2: tert-butyl (S,E)-(1-((5-azidopentyl)amino)-5-(3-(benzyloxy)phenyl)-1-oxopent-4-en-2-yl)carbamate To a solution of tert-butyl (S)-(1-((5-azidopentyl)amino)-1-oxopent-4-en-2-yl)carbamate (1.07 g, 3.3 mmol) and 1-(benzyloxy)-3-iodobenzene (1.02 g, 3.3 mmol) in a mixture of DMF (8 mL) and H₂O (2 mL) was added Pd(OAc)₂ (73 mg, 0.33 mmol) and NaHCO₃ (1.1 g, 13.2 mmol). The reaction mixture was heated at 75° C. for 4 h. Water was added and the aqueous extracted with EtOAc. The combined organic layers were washed with water and brine and dried over Na₂SO₄. The residue after concentration was purified by silica gel column (50% EtOAc/PE) to afford tert-butyl (S,E)-(1-((5-azidopentyl)amino)-5-(3-(benzyloxy)phenyl)-1-oxopent-4-en-2-yl)carbamate (1.38 g, 82%) as a white solid. ¹H NMR (400 MHz, CD₃OD) δ 7.46-7.40 (m, 2H), 7.39-7.27 (m, 3H), 7.19 (t, J=8.0 Hz, 1H), 7.00 (t, J=2.0 Hz, 1H), 6.95 (d, J=7.6 Hz, 1H), 6.85 (dd, J=8.0, 2.4 Hz, 1H), 6.47-6.38 (m, 1H), 6.24-6.12 (m, 1H), 5.07 (s, 2H), 4.16-4.07 (m, 1H), 3.29-3.20 (m, 1H), 3.17-3.06 (m, 3H), 2.68-2.43 (m, 2H), 1.51-1.39 (m, 12H), 1.37-1.27 (m, 3H).

Step 3: tert-butyl (S)-(1-(5-aminopentyl)amino)-5-(3-hydroxyphenyl)-1-oxopentan-2-yl)carbamate To a solution of tert-butyl (S,E)-(1-((5-azidopentyl)amino)-5-(3-(benzyloxy)phenyl)-1-oxopent-4-en-2-yl)carbamate (1.4 g, 2.76 mmol) in MeOH (8 mL) was added Pd/C (10%, 200 mg). The reaction mixture was stirred at room temperature overnight. The solution was filtered through celite and the filtrate was concentrated to afford tert-butyl (S)-(1-((5-aminopentyl)amino)-5-(3-hydroxyphenyl)-1-oxopentan-2-yl)carbamate (970 mg, 89%) which was used in next step directly. ¹H NMR (400 MHz, CD₃OD) δ 7.05 (t, J=8.0 Hz, 1H), 6.66-6.56 (m, 3H), 4.03-3.90 (m, 1H), 3.26-3.09 (m, 2H), 2.67-2.50 (m, 4H), 1.73-1.48 (m, 7H), 1.44 (s, 9H), 1.40-1.28 (m, 3H).

Step 4: tert-butyl (S)-(1-((5-((((9H-fluoren-9-yl)methoxy)carbonyl)amino)pentyl)amino)-5-(3-hydroxyphenyl)-1-oxopentan-2-yl)carbamate To a solution of tert-butyl (S)-(1-((5-aminopentyl)amino)-5-(3-hydroxyphenyl)-1-oxopentan-2-yl)carbamate (200 mg, 0.5 mmol) and FmocOSu (189 mg, 0.55 mmol) in a mixture of THF (4 mL) and H₂O (1 mL) was added NaHCO₃ (85 mg, 1 mmol). The reaction mixture was stirred at room temperature for 4 h. Water was added and the aqueous extracted with EtOAc. The combined organic layers were washed with water, brine and dried over Na₂SO₄. The residue after concentration was purified by silica gel column (50% EtOAc/PE) to afford tert-butyl (S)-(1-((5-((((9H-fluoren-9-yl)methoxy)carbonyl)amino)pentyl)amino)-5-(3-hydroxyphenyl)-1-oxopentan-2-yl)carbamate (137 mg, 44%) as a white solid. LCMS m/z=616.2 [M+H]⁺

Step 5: (9H-fluoren-9-yl)methyl (S)-(5-(2-amino-5-(3-hydroxyphenyl)pentanamido)pentyl)carbamate To a solution of tert-butyl (S)-(1-((5-((((9H-fluoren-9-yl)methoxy)carbonyl)amino)pentyl)amino)-5-(3-hydroxyphenyl)-1-oxopentan-2-yl)carbamate (50 mg, 0.08 mmol) in DCM (2 mL) was added TFA (2 mL) and the reaction mixture was stirred at room temperature for 2 h. The solvent was removed under reduced pressure to afford the product (57 mg, quant.) as a white solid. LCMS m/z=516.2 [M+H]⁺.

Synthesis of (2S,3S)-2-amino-N-(5-azidopentyl)-3-(benzyloxy)butanamide

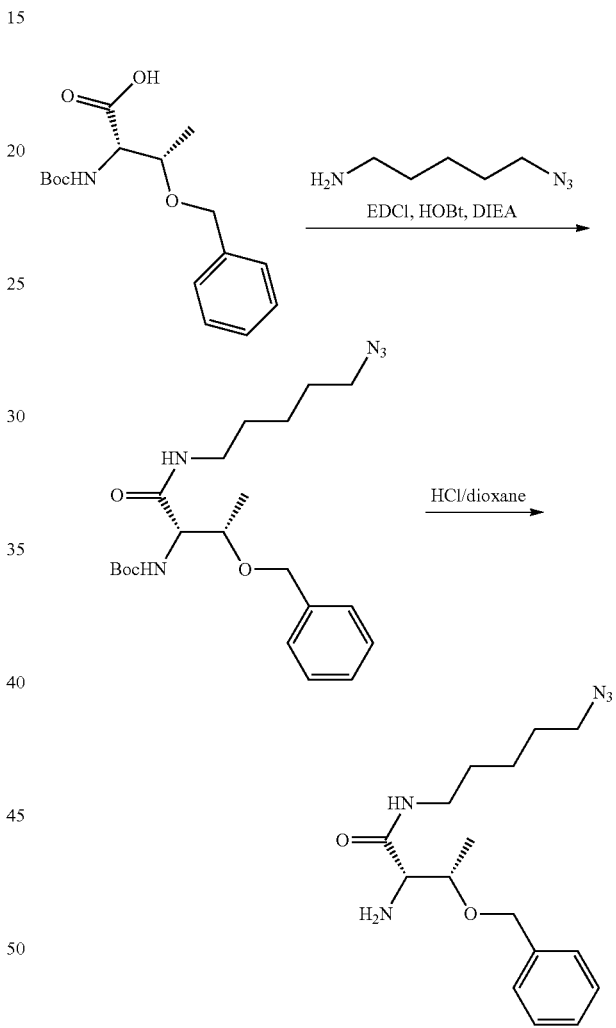

Step 1: tert-butyl ((2S,3S)-1-(5-azidopentyl)amino)-3-(benzyloxy)-1-oxobutan-2-yl)carbamate To a solution of O-benzyl-N-(tert-butoxycarbonyl)-L-allothreonine (220 mg, 0.71 mmol) in DMA (1 mL) was added 5-azidopentan-1-amine (100 mg, 0.78 mmol), EDCI (205 mg, 1.07 mmol), HOBt (144 mg, 1.07 mmol) and DIEA (460 mg, 3.56 mmol). The resulting mixture was stirred at room temperature for 4 hours under N₂. Water was added and the aqueous extracted with EtOAc three times. The combined organic layers were washed with water and brine and dried over Na₂SO₄. The residue obtained after concentration was purified by silica gel column (30% EtOAc/PE) to afford tert-butyl ((2S,3S)-1-((5-azidopentyl)amino)-3-(benzyloxy)-1-oxobutan-2-yl)carbamate (220 mg, 73%) as a yellow oil. LCMS m/z=420.3 [M+H]⁺.

Step 2: (2S,3S)-2-amino-N-(5-azidopentyl)-3-(benzyloxy)butanamide

To a solution of tert-butyl ((2S,3S)-1-((5-azidopentyl)amino)-3-(benzyloxy)-1-oxobutan-2-yl)carbamate (244 mg, 0.58 mmol) in MeOH (1 mL) was added HCl (4M in dixoane, 2 mL). The resulting mixture was stirred at room temperature for 1 h. The solvent was removed to afford (2S,3S)-2-amino-N-(5-azidopentyl)-3-(benzyloxy)butanamide (220 mg, quant.) LCMS m/z=320.3 [M+H]⁺.

Example 2: Synthesis of Exemplary Compounds

Synthesis of 5-(2-(6-chloro-1H-indol-3-yl)acetyl)-2-(4-isopropoxy-3-methoxybenzoyl)-N-((S)-1-(methylamino)-1-oxo-5-phenylpentan-2-yl)octahydro-1H-pyrrolo[3,4-c]pyridine-7-carboxamide I-1

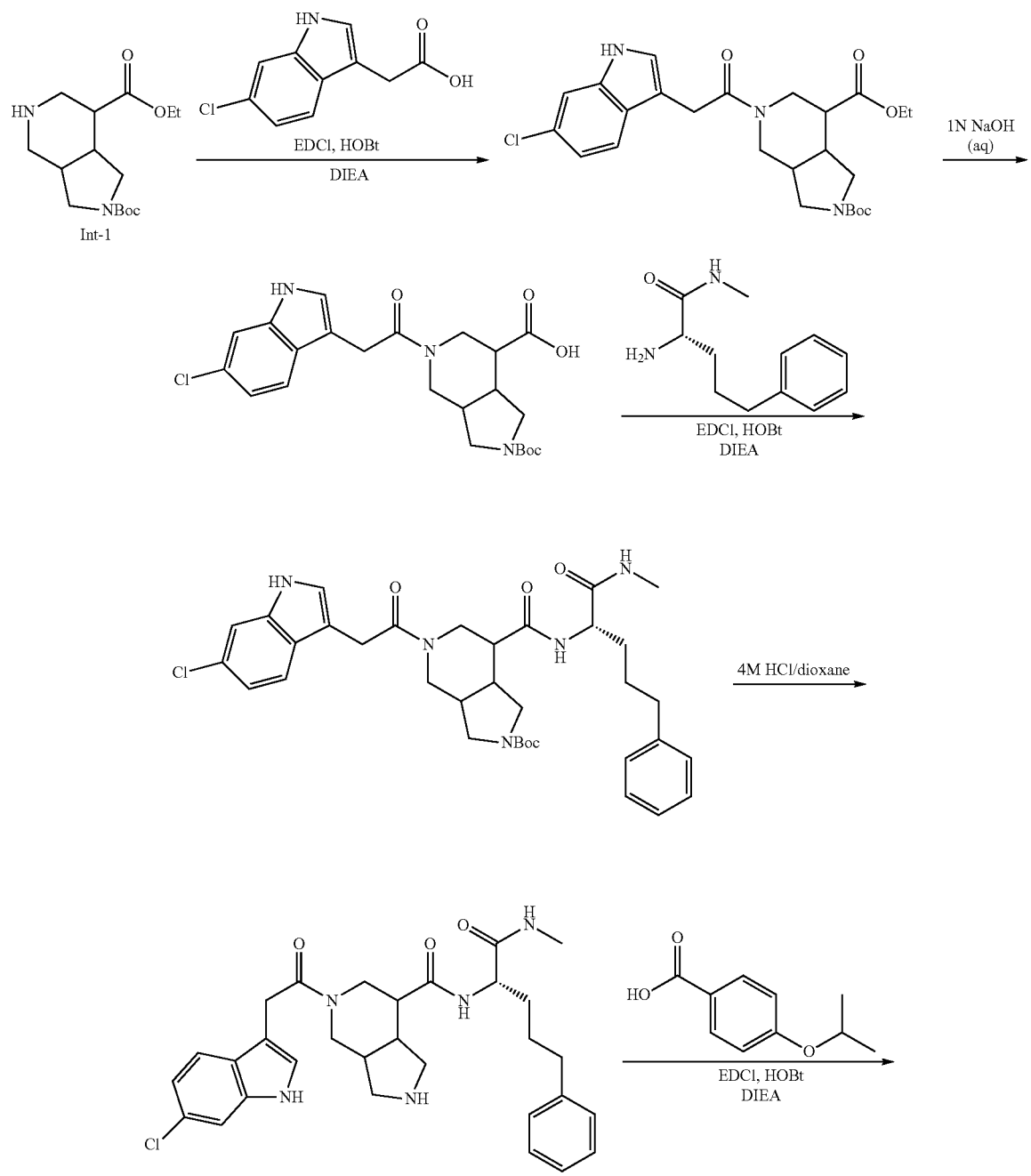

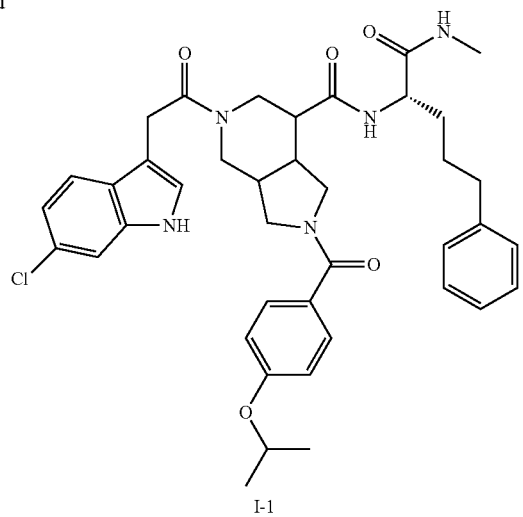

I-1

Step 1: 2-(tert-butyl) 7-ethyl 5-(2-(6-chloro-1H-indol-3-yl)acetyl)octahydro-2H-pyrrolo[3,4-c]pyridine-2,7-dicarboxylate To a solution of 2-(tert-butyl) 7-ethyl octahydro-2H-pyrrolo[3,4-c]pyridine-2,7-dicarboxylate (Int-1, 6.4 g, 21.5 mmol) in DMF (60 mL) was added 2-(6-chloro-1H-indol-3-yl)acetic acid (5.9 g, 28.2 mmol), EDCI (6.8 g, 35.3 mmol), HOBt (4.8 g, 35.3 mmol) and DIPEA (9.1 g, 70.5 mmol). The resulting mixture was stirred at room temperature for 14 h. Water was then added and the aqueous layer was extracted with EtOAc. The combined organic layers were washed with water and brine, dried over $Na_2SO_4$ and the solvent removed in vacuo. The residue was purified by column chromatography (2% MeOH/DCM) to afford the product (5.3 g, 46%) as a white solid. LCMS m/z=490.0 $[M+H]^+$; $^1H$ NMR (400 MHz, $CD_3OD$) δ 7.64-7.50 (m, 1H), 7.37-7.31 (m, 1H), 7.24-7.14 (m, 1H), 7.04-6.96 (m, 1H), 4.68-3.66 (m, 5H), 3.52-3.37 (m, 1H), 3.29-2.06 (m, 7H), 1.98-1.77 (m, 1H), 1.46-1.35 (m, 9H), 1.24 (t, J=7.2 Hz, 3H).

Step 2: 2-(tert-butoxycarbonyl)-5-(2-(6-chloro-1H-indol-3-yl)acetyl)octahydro-1H-pyrrolo[3,4-c]pyridine-7-carboxylic acid To a solution of 2-(tert-butyl) 7-ethyl 5-(2-(6-chloro-1H-indol-3-yl)acetyl)octahydro-2H-pyrrolo[3,4-c]pyridine-2,7-dicarboxylate (2.0 g, 4.1 mmol) in MeOH (20 mL) was added aqueous NaOH (1M, 4.1 mL). The resulting mixture was stirred for 3 h then the solvent removed under vacuum. The residue obtained was diluted with water and the pH adjusted to ~1 by addition of 1M HCl. The aqueous layer was extracted with EtOAc three times and the combined organic layers washed with water and brine, dried over $Na_2SO_4$ and concentrated to afford the product (1.7 g, 90%) as a white solid. LCMS m/z=462.2 $[M+H]^+$; $^1H$ NMR (400 MHz, $CD_3OD$) δ 7.63-7.47 (m, 1H), 7.37-7.31 (m, 1H), 7.25-7.15 (m, 1H), 7.05-6.96 (m, 1H), 4.71-4.11 (m, 2H), 4.07-3.70 (m, 2H), 3.54-3.36 (m, 1H), 3.29-2.04 (m, 7H), 2.00-1.77 (m, 1H), 1.47-1.35 (m, 9H).

Step 3: tert-butyl 5-(2-(6-chloro-1H-indol-3-yl)acetyl)-7-(((S)-1-(methylamino)-1-oxo-5-phenylpentan-2-yl)carbamoyl)octahydro-2H-pyrrolo[3,4-c]pyridine-2-carboxylate In a similar manner to the procedure reported for Step 1, the coupling of 2-(tert-butoxycarbonyl)-5-(2-(6-chloro-1H-indol-3-yl)acetyl)octahydro-1H-pyrrolo[3,4-c]pyridine-7-carboxylic acid and (S)-2-amino-N-methyl-5-phenylpentanamide gave the product (1.8 g, quant.) after column chromatography (2% MeOH/DCM) as a white solid. LCMS m/z=650.3 $[M+H]^+$; $^1H$ NMR (400 MHz, $CD_3OD$) δ 7.68-6.87 (m, 9H), 4.53-3.66 (m, 5H), 3.56-3.38 (m, 1H), 3.28-2.77 (m, 4H), 2.76-1.98 (m, 9H), 1.87-1.51 (m, 4H), 1.50-1.33 (m, 9H).

Step 4: 5-(2-(6-chloro-1H-indol-3-yl)acetyl)-N—((S)-1-(methylamino)-1-oxo-5-phenylpentan-2-yl)octahydro-1H-pyrrolo[3,4-c]pyridine-7-carboxamide hydrochloride To a solution of tert-butyl 5-(2-(6-chloro-1H-indol-3-yl)acetyl)-7-(((S)-1-(methylamino)-1-oxo-5-phenylpentan-2-yl)carbamoyl)octahydro-2H-pyrrolo[3,4-c]pyridine-2-carboxylate (1.8 g, 2.77 mmol) in a mixture of DCM and MeOH (20 mL/10 mL) was added HCl in dioxane (4M, 6 mL). The resulting mixture was stirred for 3 h, then the solvent removed under reduced pressure to afford the product (1.7 g, quant.). LCMS m/z=550.2 $[M+H]^+$; $^1H$ NMR (400 MHz, $CD_3OD$) δ 7.68-6.89 (m, 9H), 4.49-3.73 (m, 5H), 3.61-3.34 (m, 1H), 3.30-2.81 (m, 4H), 2.78-2.28 (m, 8H), 1.89-1.55 (m, 4H).

Step 5: 5-(2-(6-chloro-1H-indol-3-yl)acetyl)-2-(4-isopropoxy-3-methoxybenzoyl)-N—((S)-1-(methylamino)-1-oxo-5-phenylpentan-2-yl)octahydro-1H-pyrrolo[3,4-c]pyridine-7-carboxamide (I-1)

A mixture of the product of Step 4 (73 mg, 0.12 mmol), 4-isopropoxy-3-methoxybenzoic acid (27 mg, 0.15 mmol), EDCI (36 mg 0.19 mmol), HOBt (20 mg, 0.15 mmol) and DIEA (65 mg, 0.5 mmol) in DMF (2.0 mL) was stirred overnight. The reaction mixture was diluted with water and extracted with EtOAc three times. The combined organic layers were washed with water and brine, dried over Na$_2$SO$_4$ and concentrated in vacuo. The residue was purified by column chromatography (3.3% MeOH/DCM) to give I-1 (33.4 mg, 39%) as a white solid. LCMS m/z=712.4 [M+H]$^+$; $^1$H NMR (400 MHz, CD$_3$OD) δ 7.66-6.77 (m, 13H), 4.79-3.35 (m, 9H), 3.29-2.98 (m, 2H), 2.98-2.76 (m, 1H), 2.76-2.48 (m, 6H), 2.43 (ddd, J=12.4, 7.2, 3.8 Hz, 1H), 2.37-1.99 (m, 1H), 1.97-1.43 (m, 4H), 1.42-1.22 (m, 7H).

The compounds listed in Table 2 were synthesized using analogous methods to those shown for I-1, using the appropriate commercially available reagents and/or intermediates. Final examples were obtained as a mixture of diastereomers unless indicated otherwise.

TABLE 2

Compounds made by a method analogous to I-1

| # | $^1$H NMR Chromatography conditions, if applicable | LCMS |
|---|---|---|
| I-2 | $^1$H NMR (400 MHz, CD$_3$OD) δ 7.71-6.80 (m, 12H), 4.61-3.34 (m, 7H), 3.28-2.78 (m, 2H), 2.78-2.58 (m, 5H), 2.57-2.34 (m, 6H), 2.30-1.98 (m, 1H), 1.84-0.86 (m, 5H). | m/z = 707.3 [M + H]$^+$ |
| I-3 | $^1$H NMR (400 MHz, CD$_3$OD) δ 7.82-6.86 (m, 12H), 6.57-6.39 (m, 1H), 4.60-4.15 (m, 2H), 4.15-3.69 (m, 3H), 3.69-3.39 (m, 3H), 3.27-2.97 (m, 2H), 2.93-2.34 (m, 11H), 2.35-2.18 (m, 1H), 2.09-1.34 (m, 4H), 1.24-1.88 (m, 1H). | m/z = 708.3 [M + H]$^+$ |
| I-4 | $^1$H NMR (400 MHz, CD$_3$OD) δ 7.55-7.76 (m, 13H), 4.51-4.30 (m, 1H), 4.28-3.84 (m, 4H), 3.71-3.64 (m, 1H), 3.55-3.37 (m, 2H), 3.27-2.80 (m, 3H), 2.76-2.60 (m, 6H), 2.45-2.07 (m, 2H), 1.65-1.28 (m, 5H). | m/z = 670.3 [M + H]$^+$ |
| I-5 | $^1$H NMR (400 MHz, CD$_3$OD) δ 7.66-6.76 (m, 13H), 4.44-3.72 (m, 8H), 3.68-3.40 (m, 3H), 3.13-2.95 (m, 1H), 2.78-2.56 (m, 6H), 2.46-2.37 (m, 1H), 2.21-2.00 (m, 1H), 1.82-1.49 (m, 4H), 1.41-1.32 (m, 2H). | m/z = 684.3 [M + H]$^+$ |
| I-6 | $^1$H NMR (400 MHz, CD$_3$OD) δ 7.65-6.91 (m, 13H), 4.57-4.36 (m 1H), 4.35-3.74 (m, 5H), 3.70-3.36 (m, 4H), 3.30-2.78 (m, 3H), 2.77-1.99 (m, 9H), 1.80-1.37 (m, 4H), 0.88-0.58 (m, 4H). | m/z = 710.3 [M + H]$^+$ |
| I-7 | $^1$H NMR (400 MHz, CD$_3$OD) δ 7.67-6.80 (m, 13H), 4.61-3.72 (m, 6H), 3.72-3.34 (m, 4H), 3.30-2.75 (m, 3H), 2.75-1.92 (m, 9H), 1.85-1.33 (m, 4H), 1.24-0.88 (m, 7H). | m/z = 726.4 [M + H]$^+$ |
| I-8 | $^1$H NMR (400 MHz, CD$_3$OD) δ 8.22-8.06 (m, 1H), 8.01-7.77 (m, 1H), 7.65-6.78 (m, 11H), 4.62-4.06 (m, 3H), 4.05-3.33 (m, 7H), 3.30-3.01 (m, 2H), 3.00-1.83 (m, 10H), 1.81-1.34 (m, 4H). | m/z = 694.3 [M + H]$^+$ |
| I-9 | $^1$H NMR (400 MHz, CD$_3$OD) δ 7.67-7.45 (m, 1H), 7.45-6.62 (m, 11H), 4.63-3.35 (m, 14H), 3.29-2.33 (m, 11H),, 1.87-1.50 (m, 5H), 1.05-0.73 (m, 1H), 0.58-0.35 (m, 2H), 0.19-0.05 (m, 2H). | m/z = 768.3 [M + H]$^+$ |
| I-10 | $^1$H NMR (400 MHz, CD$_3$OD) δ 8.97-6.76 (m, 15H), 4.52-4.10 (m, 3H), 3.94-3.72 (m, 3H), 3.64-3.35 (m, 3H), 3.30-2.83 (m, 2H), 2.86-2.28 (m, 8H), 2.08-2.00 (m, 1H), 1.77-1.41 (m, 3H), 1.12-0.90 (m, 1H). | m/z = 705.2 [M + H]$^+$ |
| I-11 | $^1$H NMR (400 MHz, CD$_3$OD) δ 7.86-6.88 (m, 18H), 4.63-4.02 (m, 2H), 3.88 (m, 2H), 3.74-3.34 (m, 3H), 3.27-2.94 (m, 2H), 2.93-1.91 (m, 9H), 1.87-1.22 (m, 5H). | m/z = 730.3 [M + H]$^+$ |
| I-12 | $^1$H NMR (400 MHz, CD$_3$OD) δ 7.92-6.68 (m, 13H), 4.63-3.84 (m, 7H), 3.83-3.33 (m, 3H), 3.25-2.75 (m, 2H), 2.75-2.23 (m, 8H), 1.79-1.57 (m, 3H), 1.54-1.35 (m, 1H). | m/z = 694.2 [M + H]$^+$ |
| I-13 | $^1$H NMR (400 MHz, CD$_3$OD) δ 7.96-7.80 (m, 2H), 7.56-7.48 (m, 4H), 7.38-6.92 (m, 8H), 4.53-4.45 (m, 1H), 4.28-4.03 (m, 2H), 3.94-3.49 (m, 6H), 3.20-2.81 (m, 2H), 2.78-2.33 (m, 7H), 2.20-2.03 (m, 1H), 1.71-1.50 (m, 4H), 1.36-1.25 (m, 3H). | m/z = 721.2 [M + H]$^+$ |
| I-14 | $^1$H NMR (400 MHz, CD$_3$OD) δ 8.74-8.52 (m, 2H), 7.87-6.84 (m, 15H), 4.70-3.87 (m, 5H), 3.85-3.33 (m, 4H), 3.29-2.81 (m, 3H), 2.80-2.49 (m, 7H), 2.42-2.13 (m, 1H), 1.86-1.51 (m, 3H). | m/z = 731.3 [M + H]$^+$ |
| I-15 | $^1$H NMR (400 MHz, CD$_3$OD) δ 8.92-6.92 (m, 12H), 4.56-4.46 (m, 1H), 4.39-4.30 (m, 1H), 4.21-4.06 (m, 1H), 3.94-3.78 (m, 3H), 3.63-3.40 (m, 3H), 3.30-2.91 (m, 2H), 2.74-2.68 (m, 8H), 2.35-2.00 (m, 1H), 1.83-1.44 (m, 4H). | m/z = 680.3 [M + H]$^+$ |
| I-16 | $^1$H NMR (400 MHz, CD$_3$OD) δ 8.72-8.33 (m, 1H), 8.22-7.84 (m, 1H), 7.60-6.83 (m, 9H), 4.56-3.76 (m, 9H), 3.73-3.43 (m, 3H), 3.23-2.76 (m, 2H), 2.75-2.55 (m, 6H), 2.54-2.16 (m, 2H), 1.79-1.45 (m, 4H). | m/z = 686.3 [M + H]$^+$ |
| I-17 | $^1$H NMR (400 MHz, CD$_3$OD) δ 9.12-8.87 (m, 2H), 8.32-6.70 (m, 12H), 4.68-3.87 (m, 6H), 3.85-3.40 (m, 4H), 3.30-3.02 (m, 2H), 3.01-2.63 (m, 6H), 2.61-2.44 (m, 2H), 2.41-2.01 (m, 2H), 1.80-1.39 (m, 3H), 1.25-0.85 (m, 1H). | m/z = 706.3 [M + H]$^+$ |
| I-18 | $^1$H NMR (400 MHz, CD$_3$OD) δ 9.40-9.16 (m, 1H), 8.58-8.43 (m, 1H), 8.16-6.58 (m, 13H), 4.53-3.87 (m, 5H), 3.64-3.41 (m, 3H), 3.06-2.44 (m, 10H), 2.29-1.42 (m, 5H). | m/z = 705.3 [M + H]$^+$ |
| I-19 | $^1$H NMR (400 MHz, CD$_3$OD) δ 8.01-6.68 (m, 15H), 4.63-4.36 (m, 1H), 4.36-3.81 (m, 5H), 3.80-3.35 (m, 3H), 3.19-1.89 (m, 10H), 1.80-1.40 (m, 4H).eb;normal | m/z = 720.3 [M + H]$^+$ |
| I-20 | $^1$H NMR (400 MHz, CD$_3$OD) δ 7.96-6.91 (m, 12H), 4.78-4.17 (m, 4H), 4.06-3.34 (m, 6H), 3.24-2.16 (m, 10H), 1.74-1.29 (m, 5H). | m/z = 685.3 [M + H]$^+$ |

TABLE 2-continued

Compounds made by a method analogous to I-1

| # | ¹H NMR Chromatography conditions, if applicable | LCMS |
|---|---|---|
| I-21 | ¹H NMR (400 MHz, CD₃OD) δ 8.29-6.69 (m, 11H), 4.56-3.41 (m, 11H), 3.27-2.76 (m, 2H), 2.75-2.46 (m, 7H), 2.38-1.96 (m, 1H), 1.80-1.42 (m, 4H), 1.37-1.30 (m, 1H). | m/z = 686.3 [M + H]⁺ |
| I-22 | ¹H NMR (400 MHz, CD₃OD) δ 7.63-6.88 (m, 12H), 4.54-3.84 (m, 5H), 3.71-3.36 (m, 5H), 3.26-1.96 (m, 12H), 1.83-1.40 (m, 4H). First eluting diastereomer purified by Prep-TLC (6% MeOH/DCM). Rf = 0.40 | m/z = 709.3 [M + H]⁺ |
| I-23 | ¹H NMR (400 MHz, CD3OD) δ 7.67-6.79 (m, 12H), 4.66-3.39 (m, 10H), 3.32-2.35 (m, 11H), 2.33-1.52 (m, 4H). Second eluting diastereomer purified by Prep-TLC (6% MeOH/DCM). Rf = 0.32 | m/z = 709.3 [M + H]⁺ |
| I-24 | ¹H NMR (400 MHz, CD₃OD) δ 7.61-6.92 (m, 12H), 4.59-4.27 (m, 3H), 4.89-3.80 (m, 3H), 3.69-3.40 (m, 3H), 3.23-3.01 (m, 2H), 2.98-2.75 (m, 1H), 2.72-2.41 (m, 7H), 2.29-2.13 (m, 1H), 1.78-1.55 (m, 3H), 1.43-1.24 (m, 8H). | m/z = 746.3 [M + H]⁺ |
| I-25 | ¹H NMR (400 MHz, CD₃OD) δ 7.67-6.91 (m, 13H), 4.62-3.35 (m, 8H), 3.29-2.80 (m, 3H), 2.78-2.54 (m, 6H), 2.49-2.40 (m, 1H), 2.35-1.92 (m, 1H), 1.82-1.56 (m, 3H), 1.38-1.28 (m, 1H). | m/z = 738.3 [M + H]⁺ |
| I-26 | ¹H NMR (400 MHz, CD₃OD) δ 7.82-7.77 (m, 2H), 7.56-6.74 (m, 13H), 4.20-4.00 (m, 3H), 3.98-3.45 (m, 9H), 3.20-3.07 (m, 2H), 2.97-2.91 (m, 1H), 2.74-2.29 (m, 8H), 1.84-1.27 (m, 5H). | m/z = 734.3 [M + H]⁺ |
| I-27 | ¹H NMR (400 MHz, CD₃OD) δ 9.31-6.60 (m, 15H), 4.78-3.34 (m, 9H), 3.28-2.81 (m, 2H), 2.81-2.24 (m, 8H), 2.22-1.76 (m, 1H), 1.74-1.32 (m, 4H). | m/z = 720.4 [M + H]⁺ |
| I-28 | ¹H NMR (400 MHz, CD₃OD) δ 8.17 (m, 1H), 7.70-6.76 (m, 12H), 4.58-4.36 (m, 1H), 4.35-4.06 (m, 2H), 4.04-3.57 (m, 5H), 3.56-3.35 (m, 1H), 3.23-2.85 (m, 2H), 2.77-2.45 (m, 7H), 2.47-1.93 (m, 1H), 1.87-1.33 (m, 5H). | m/z = 694.4 [M + H]⁺ |
| I-29 | ¹H NMR (400 MHz, CD₃OD) δ 8.12-6.24 (m, 11H), 4.66-4.11 (m, 2H), 4.10-3.75 (m, 4H), 3.72-3.34 (m, 2H), 3.24-2.80 (m, 2H), 2.79-2.03 (m, 9H), 1.87-1.37 (m, 6H). | m/z = 644.4 [M + H]⁺ |
| I-30 | ¹H NMR (400 MHz, CD₃OD) δ 7.58-6.21 (m, 10H), 4.55-3.34 (m, 9H), 3.27-2.86 (m, 2H), 2.75-2.49 (m, 7H), 2.27-1.34 (m, 6H), 1.05-0.63 (m, 4H). | m/z = 684.4 [M + H]⁺ |
| I-31 | ¹H NMR (400 MHz, CD₃OD) δ 7.99-6.80 (m, 12H), 4.58-4.06 (m, 2H), 4.04-3.34 (m, 9H), 3.29-2.96 (m, 2H), 2.94-2.35 (m, 9H), 2.31-1.34 (m, 4H). | m/z = 763.3 [M + H]⁺ |
| I-32 | ¹H NMR (400 MHz, CD₃OD) δ 7.71-6.62 (m, 12H), 4.50-3.44 (m, 11H), 3.24-2.79 (m, 3H), 2.77-1.87 (m, 9H), 1.81-1.34 (m, 7H). | m/z = 700.4 [M + H]⁺ |
| I-33 | ¹H NMR (400 MHz, CD₃OD) δ 7.67-6.66 (m, 12H), 4.56-3.74 (m, 11H), 3.70-3.41 (m, 3H), 3.27-2.79 (m, 3H), 2.74-2.00 (m, 9H), 1.81-1.49 (m, 3H). | m/z = 714.3 [M + H]⁺ |
| I-34 | ¹H NMR (400 MHz, CD₃OD) δ 7.44-6.41 (m, 12H), 4.38-3.20 (m, 11H), 3.09-2.57 (m, 3H), 2.56-2.29 (m, 7H), 1.62-1.33 (m, 3H), 1.19-0.97 (m, 2H). | m/z = 700.4 [M + H]⁺ |
| I-35 | ¹H NMR (400 MHz, CD₃OD) δ 7.61-6.89 (m, 18H), 4.54-3.37 (m, 8H), 3.26-2.82 (m, 3H), 2.80-2.32 (m, 8H), 2.28-1.97 (m, 1H), 1.84-1.55 (m, 3H) | m/z = 746.4 [M + H]⁺ |
| I-36 | ¹H NMR (400 MHz, CD₃OD) δ 9.07-6.72 (m, 15H), 4.60-3.80 (m, 5H), 3.79-3.47 (m, 3H), 3.26-3.03 (m, 2H), 2.96-2.42 (m, 8H), 2.36-1.97 (m, 2H), 1.84-1.47 (m, 3H), 1.15-0.90 (m, 1H). | m/z = 705.3 [M + H]⁺ |
| I-37 | ¹H NMR (400 MHz, CD₃OD) δ 9.33-8.72 (m, 1H), 8.26-7.50 (m, 6H), 7.41-6.77 (m, 8H), 4.62-3.42 (m, 8H), 3.21-2.97 (m, 1H), 2.91-2.39 (m, 8H), 2.28-2.10 (m, 1H), 1.87-1.43 (m, 4H), 1.22-0.84 (m, 1H). | m/z = 705.3 [M + H]⁺ |
| I-38 | ¹H NMR (400 MHz, CD₃OD) δ 7.65-6.70 (m, 13H), 4.66-3.37 (m, 10H), 3.25-2.83 (m, 2H), 2.78-2.32 (m, 11H), 2.30-2.14 (m, 1H), 1.92-1.42 (m, 4H). | m/z = 707.3 [M + H]⁺ |
| I-39 | ¹H NMR (400 MHz, CD₃OD) δ 7.73-6.12 (m, 10H), 4.56-3.39 (m, 12H), 3.24-1.93 (m, 14H), 1.77-1.46 (m, 4H). | m/z = 672.4 [M + H]⁺ |
| I-40 | ¹H NMR (400 MHz, CD₃OD) δ 9.12-8.26 (m, 3H), 7.99-6.61 (m, 10H), 4.61-3.47 (m, 9H), 3.27-2.84 (m, 2H), 2.75-1.98 (m, 8H), 1.79-1.41 (m, 4H). | m/z = 695.3 [M + H]⁺ |
| I-41 | ¹H NMR (400 MHz, CD₃OD) δ 8.62-7.82 (m, 2H), 7.60-6.84 (m, 9H), 4.57-3.47 (m, 11H), 3.17-2.77 (m, 2H), 2.76-2.47 (m, 7H), 2.39-2.08 (m, 1H), 1.77-1.35 (m, 7H). | m/z = 700.3 [M + H]⁺ |
| I-42 | ¹H NMR (400 MHz, CD₃OD) δ 8.62-8.21 (m, 2H), 7.60-6.84 (m, 9H), 4.59-3.46 (m, 13H), 3.25-2.88 (m, 2H), 2.78-2.45 (m, 8H), 2.36-2.01 (m, 1H), 1.77-1.49 (m, 3H). | m/z = 686.4 [M + H]⁺ |
| I-43 | ¹H NMR (400 MHz, CD₃OD) δ 8.44-8.12 (m, 1H), 7.63-6.39 (m, 13H), 4.53-3.81 (m, 5H), 3.74-3.38 (m, 4H), 3.22-2.81 (m, 2H), 2.77-1.96 (m, 8H), 1.83-1.42 (m, 4H), 1.27-1.05 (m, 1H). | m/z = 693.3 [M + H]⁺ |
| I-44 | ¹H NMR (400 MHz, CD₃OD) δ 8.92-8.39 (m, 2H), 7.69-6.91 (m, 9H), 4.63-3.39 (m, 10H), 3.29-2.78 (m, 3H), 2.73-2.59 (m, 5H), 2.54-2.05 (m, 3H), 1.86-1.52 (m, 4H), 1.34-1.22 (m, 4H). | m/z = 696.3 [M + H]⁺ |
| I-45 | ¹H NMR (400 MHz, CD₃OD) δ 7.97-6.87 (m, 12H), 4.60-3.34 (m, 10H), 3.30-1.93 (m, 12H), 1.78-1.48 (m, 3H). | m/z = 709.4 [M + H]⁺ |

TABLE 2-continued

Compounds made by a method analogous to I-1

| # | $^1$H NMR Chromatography conditions, if applicable | LCMS |
|---|---|---|
| I-46 | $^1$H NMR (400 MHz, CD$_3$OD) δ 7.64-6.88 (m, 12H), 4.84-3.33 (m, 9H), 3.29-1.89 (m, 12H), 1.85-1.55 (m, 3H), 1.45-1.30 (m, 6H). | m/z = 730.4 [M + H]$^+$ |
| I-47 | $^1$H NMR (400 MHz, CD$_3$OD) δ 8.47-6.58 (m, 12H), 4.77-4.16 (m, 2H), 4.16-3.34 (m, 9H), 3.27-2.47 (m, 8H), 2.46-1.58 (m, 4H), 1.58-0.84 (m, 3H). | m/z = 707.3 [M + H]$^+$ |
| I-48 | $^1$H NMR (400 MHz, CD$_3$OD) δ 7.87-6.77 (m, 13H), 4.67-3.37 (m, 11H), 3.28-2.28 (m, 11H), 1.96-1.42 (m, 4H). | m/z = 708.4 [M + H]$^+$ |
| I-49 | $^1$H NMR (400 MHz, CD$_3$OD) δ 8.10-6.86 (m, 13H), 4.53-4.26 (m, 1H), 4.13-3.93 (m, 2H), 3.85-3.71 (m, 4H), 3.69-3.40 (m, 2H), 3.24-2.81 (m, 2H), 2.76-2.42 (m, 7H), 2.03-1.25 (m, 7H). | m/z = 684.3 [M + H]$^+$ |
| I-50 | $^1$H NMR (400 MHz, CD$_3$OD) δ 7.65-6.90 (m, 14H), 4.60-3.40 (m, 6H), 3.25-2.80 (m, 3H), 2.80-2.39 (m, 7H), 2.26-1.53 (m, 4H), 1.38-1.22 (m, 2H). | m/z = 654.3 [M + H]$^+$ |
| I-51 | $^1$H NMR (400 MHz, CD$_3$OD) δ 7.70-6.79 (m, 9H), 4.60-3.47 (m, 6H), 2.77-2.21 (m, 10H), 1.78-1.18 (m, 19H). | m/z = 660.3 [M + H]$^+$ |
| I-52 | $^1$H NMR (400 MHz, CD$_3$OD) δ 7.65-6.97 (m, 13H), 4.57-3.39 (m, 6H), 3.27-2.83 (m, 2H), 2.80-2.39 (m, 10H), 2.16-1.21 (m, 8H), 0.96-0.85 (m, 6H). | m/z = 710.3 [M + H]$^+$ |
| I-53 | $^1$H NMR (400 MHz, CD$_3$OD) δ 7.62-6.61 (m, 12H), 4.73-3.37 (m, 9H), 3.25-2.97 (m, 4H), 2.77-2.36 (m, 8H), 1.85-1.52 (m, 3H), 1.45-1.23 (m, 3H). | m/z = 695.3 [M + H]$^+$ |
| I-54 | $^1$H NMR (400 MHz, CD$_3$OD) δ 8.20-6.66 (m, 12H), 4.59-3.82 (m, 7H), 3.75-3.33 (m, 4H), 3.28-2.47 (m, 9H), 2.46-2.13 (m, 2H), 2.10-1.21 (m, 6H), 1.16-0.76 (m, 4H). | m/z = 767.4 [M + H]$^+$ |
| I-55 | $^1$H NMR (400 MHz, CD$_3$OD) δ 8.18-7.75 (m, 2H), 7.39 (m, 2H), 7.25-7.11 (m, 5H), 7.06 (m, 1H), 4.60-3.64 (m, 8H), 3.55-3.44 (m, 2H), 3.22-2.81 (m, 2H), 2.77-2.57 (m, 7H), 2.37-1.99 (m, 1H), 1.86-1.51 (m, 4H), 1.37-1.24 (m, 3H). | m/z = 658.3 [M + H]$^+$ |
| I-56 | $^1$H NMR (400 MHz, CD$_3$OD) δ 7.59-6.82 (m, 9H), 6.45-6.37 (m, 1H), 4.65-3.64 (m, 7H), 3.63-3.41 (m, 2H), 3.15-2.50 (m, 9H), 2.39-2.09 (m, 4H), 1.80-1.33 (m, 5H). | m/z = 658.3 [M + H]$^+$ |
| I-57 | $^1$H NMR (400 MHz, CD$_3$OD) δ 8.94-8.52 (m, 2H), 7.66-6.90 (m, 10H), 4.62-3.35 (m, 8H), 3.26-2.18 (m, 10H), 1.77-1.28 (m, 5H). | m/z = 656.3 [M + H]$^+$ |
| I-58 | $^1$H NMR (400 MHz, CD$_3$OD) δ 8.53-6.87 (m, 12H), 4.61-4.21 (m, 2H), 4.20-3.74 (m, 3H), 3.73-3.37 (m, 4H), 3.22-2.93 (m, 1H), 2.85-2.55 (m, 10H), 1.78-1.33 (m, 6H), 1.28-1.15 (m, 2H). | m/z = 683.3 [M + H]$^+$ |
| I-59 | $^1$H NMR (400 MHz, CD$_3$OD) δ 9.34-8.87 (m, 3H), 7.89-6.83 (m, 13H), 4.58-3.42 (m, 8H), 3.28-2.01 (m, 11H), 1.90-1.37 (m, 4H). | m/z = 732.3 [M + H]$^+$ |
| I-60 | $^1$H NMR (400 MHz, CD$_3$OD) δ 8.85-6.67 (m, 11H), 4.64-3.37 (m, 10H), 3.21-2.34 (m, 13H), 1.74-1.44 (m, 3H). | m/z = 670.4 [M + H]$^+$ |
| I-61 | $^1$H NMR (400 MHz, CD$_3$OD) δ 8.07-6.79 (m, 14H), 4.57-3.37 (m, 10H), 3.26-2.83 (m, 2H), 2.76-2.01 (m, 8H), 1.75-1.45 (m, 3H). | m/z = 693.4 [M + H]$^+$ |
| I-62 | $^1$H NMR (400 MHz, CD$_3$OD) δ 8.13-6.67 (m, 12H), 4.59-4.01 (m, 2H), 3.98-3.41 (m, 4H), 3.26-2.31 (m, 10H), 2.23-1.97 (m, 1H), 1.80-1.49 (m, 3H), 1.40-1.03 (m, 4H). | m/z = 695.3 [M + H]$^+$ |
| I-63 | $^1$H NMR (400 MHz, CD$_3$OD) δ 8.87-8.73 (m, 1H), 8.59-8.49 (m, 1H), 8.14-8.02 (m, 1H), 7.87-6.87 (m, 14H), 4.63-3.44 (m, 8H), 3.27-2.40 (m, 10H), 2.38-2.19 (m, 1H), 2.01-1.40 (m, 4H). | m/z = 731.5 [M + H]$^+$ |
| I-64 | $^1$H NMR (400 MHz, CD$_3$OD) δ 9.23-8.95 (m, 1H), 8.74-8.39 (m, 1H), 7.97-6.84 (m, 11H), 4.63-3.92 (m, 9H), 3.23-2.41 (m, 9H), 2.39-2.19 (m, 1H), 2.12-1.41 (m, 4H). | m/z = 695.3 [M + H]$^+$ |
| I-65 | $^1$H NMR (400 MHz, CD$_3$OD) δ 7.81-6.79 (m, 12H), 4.62-3.36 (m, 8H), 3.27-2.38 (m, 10H), 2.32-2.11 (m, 1H), 1.98-1.41 (m, 4H). | m/z = 709.3 [M + H]$^+$ |
| I-66 | $^1$H NMR (400 MHz, CD$_3$OD) δ 7.60-6.69 (m, 12H), 4.55-3.84 (m, 8H), 3.71-3.36 (m, 3H), 3.13-2.88 (m, 5H), 2.78-2.17 (m, 9H), 1.82-1.33 (m, 4H). | m/z = 777.4 [M + H]$^+$ |
| I-67 | $^1$H NMR (400 MHz, CD$_3$OD) δ 7.62-6.71 (m, 13H), 4.55-3.82 (m, 6H), 3.72-3.37 (m, 3H), 3.29-2.38 (m, 11H), 2.38-1.96 (m, 1H), 1.79-1.33 (m, 7H). | m/z = 698.2 [M + H]$^+$ |
| I-68 | $^1$H NMR (400 MHz, CD$_3$OD) δ 8.25-6.76 (m, 15H), 4.65-3.40 (m, 9H), 3.28-2.78 (m, 2H), 2.76-2.49 (m, 7H), 1.77-1.50 (m, 5H), 1.44-1.27 (m, 2H). | m/z = 737.3 [M + H]$^+$ |
| I-69 | $^1$H NMR (400 MHz, CD$_3$OD) δ 8.46-6.53 (m, 12H), 4.60-3.82 (m, 8H), 3.68-3.44 (m, 3H), 3.36-3.34 (m, 2H), 3.30-2.79 (m, 3H), 2.57-1.71 (m, 13H), 0.96-0.20 (m, 5H). | m/z = 781.4 [M + H]$^+$ |
| I-70 | $^1$H NMR (400 MHz, CD$_3$OD) δ 8.23-6.91 (m, 15H), 4.65-3.37 (m, 9H), 3.12-1.36 (m, 15H). | m/z = 737.4 [M + H]$^+$ |
| I-71 | $^1$H NMR (400 MHz, CD$_3$OD) δ 7.62-6.67 (m, 15H), 4.57-4.12 (m, 2H), 4.12-3.35 (m, 10H), 3.21-2.41 (m, 9H), 1.79-1.46 (m, 4H). | m/z = 734.4 [M + H]$^+$ |
| I-72 | $^1$H NMR (400 MHz, CD$_3$OD) δ 8.45-6.88 (m, 12H), 4.57-3.37 (m, 7H), 3.27-1.93 (m, 11H), 1.86-1.11 (m, 5H). | m/z = 711.4 [M + H]$^+$ |
| I-73 | $^1$H NMR (400 MHz, CD$_3$OD) δ 7.65-6.88 (m, 12H), 4.58-3.36 (m, 10H), 3.28-2.80 (m, 4H), 2.78-2.24 (m, 8H), 1.99-1.40 (m, 5H). | m/z = 725.4 [M + H]$^+$ |
| I-74 | $^1$H NMR (400 MHz, CD$_3$OD) δ 8.11-6.79 (m, 15H), 4.60-3.46 (m, 8H), 3.25-2.46 (m, 9H), 2.40-1.34 (m, 5H). | m/z = 720.4 [M + H]$^+$ |

TABLE 2-continued

Compounds made by a method analogous to I-1

| # | ¹H NMR Chromatography conditions, if applicable | LCMS |
|---|---|---|
| I-75 | ¹H NMR (400 MHz, CD₃OD) δ 7.59-6.88 (m, 12H), 4.62-3.41 (m, 8H), 3.20-2.45 (m, 10H), 2.41-1.30 (m, 7H). | m/z = 711.3 [M + H]⁺ |
| I-76 | ¹H NMR (400 MHz, CD₃OD) δ 7.91-6.81 (m, 12H), 4.56-3.02 (m, 13H), 2.79-2.12 (m, 10H), 1.63-1.35 (m, 8H). | m/z = 725.3 [M + H]⁺ |
| I-77 | ¹H NMR (400 MHz, CD₃OD) δ 7.60-6.67 (m, 12H), 4.60-4.38 (m, 1H), 4.36-4.16 (m, 5H), 4.07-3.81 (m, 2H), 3.73-3.34 (m, 3H), 3.29-2.36 (m, 11H), 2.35-1.91 (m, 1H), 1.87-1.37 (m, 4H). | m/z = 712.2 [M + H]⁺ |
| I-78 | ¹H NMR (400 MHz, CD₃OD) δ 8.47-6.83 (m, 12H), 4.62-3.38 (m, 9H), 3.25-2.19 (m, 14H), 1.81-1.41 (m, 4H). | m/z = 669.4 [M + H]⁺ |
| I-79 | ¹H NMR (400 MHz, CD₃OD) δ 9.00-8.49 (m, 2H), 8.26-7.94 (m, 1H), 7.77-6.84 (m, 14H), 4.59-3.33 (m, 8H), 3.28-2.76 (m, 3H), 2.75-2.23 (m, 8H), 2.22-1.97 (m, 1H), 1.83-1.54 (m, 3H). | m/z = 731.3 [M + H]⁺ |
| I-80 | ¹H NMR (400 MHz, CD₃OD) δ 9.08-8.85 (m, 1H), 8.53-6.97 (m, 13H), 6.89-6.50 (m, 1H), 4.58-3.33 (m, 8H), 3.28-2.74 (m, 3H), 2.73-2.55 (m, 5H), 2.54-2.21 (m, 2H), 2.13-1.42 (m, 4H), 1.36-1.29 (m, 1H). | m/z = 705.3 [M + H]⁺ |
| I-81 | ¹H NMR (400 MHz, CD₃OD) δ 7.64-6.85 (m, 9H), 6.35-6.20 (m, 1H), 4.70-3.34 (m, 9H), 3.27-2.79 (m, 2H), 2.74-2.54 (m, 6H), 2.35-1.96 (m, 2H), 1.77-1.49 (m, 4H), 1.41-1.30 (m, 1H), 1.19-0.87 (m, 4H). | m/z = 685.4 [M + H]⁺ |
| I-82 | ¹H NMR (400 MHz, CD₃OD) δ 7.68-6.68 (m, 12H), 4.62-3.44 (m, 11H), 3.20-2.24 (m, 11H), 2.01-1.36 (m, 4H). | m/z = 768.4 [M + H]⁺ |
| I-83 | ¹H NMR (400 MHz, CD₃OD) δ 7.60-6.79 (m, 11H), 4.58-3.34 (m, 11H), 3.27-2.22 (m, 12H), 2.05-1.15 (m, 11H). | m/z = 754.5 [M + H]⁺ |
| I-84 | ¹H NMR (400 MHz, CD₃OD) δ 7.86-6.79 (m, 12H), 4.82-3.96 (m, 7H), 3.94-3.38 (m, 5H), 3.28-2.32 (m, 9H), 2.29-1.61 (m, 4H), 1.60-1.23 (m, 8H). | m/z = 766.3 [M + H]⁺ |
| I-85 | ¹H NMR (400 MHz, CD₃OD) δ 7.84-6.73 (m, 13H), 4.62-3.38 (m, 7H), 3.24-2.92 (m, 2H), 2.84-2.20 (m, 9H), 1.83-1.61 (m, 3H), 1.51-1.28 (m, 9H). | m/z = 752.4 [M + H]⁺ |
| I-86 | ¹H NMR (400 MHz, CD₃OD) δ 7.64-6.80 (m, 12H), 4.80-4.55 (m, 1H), 4.55-4.16 (m, 2H), 4.15-3.87 (m, 2H), 3.84-3.43 (m, 3H), 3.41-3.35 (m, 3H), 3.27-3.11 (m, 1H), 3.10-3.06 (m, 1H), 3.05-2.77 (m, 1H), 2.74-2.55 (m, 5H), 2.22-0.85 (m, 14H).<br>First eluting diastereomer purified by prep-HPLC on an Agilent 10 Prep-C18 column (21.2 mm I.D. × 25 cm, 10 um), using H₂O/MeOH 0.1% TFA at a flow rate of 20 mL/min (wave length 214 nm). Rt = 10.5 min. | m/z = 766.5 [M + H]⁺ |
| I-87 | ¹H NMR (400 MHz, CD₃OD) δ 7.63-6.87 (m, 12H), 4.80-4.60 (m, 1H), 4.55-3.36 (m, 11H), 3.27-2.96 (m, 2H), 2.89-2.42 (m, 8H), 1.87-1.44 (m, 10H), 1.39-1.26 (m, 1H).<br>Second eluting diastereomer purified by prep-HPLC on an Agilent 10 Prep-C18 column (21.2 mm I.D. × 25 cm, 10 um), using H₂O/MeOH 0.1% TFA at a flow rate of 20 mL/min (wave length 214 nm). Rt = 12.7 min. | m/z = 766.5 [M + H]⁺ |

Synthesis of N—((R)-1-benzylpiperidin-3-yl)-5-(2-(6-chloro-1H-indol-3-yl)acetyl)-2-(4-isopropoxy-3-methoxybenzoyl)octahydro-1H-pyrrolo[3,4-c]pyridine-7-carboxamide I-88

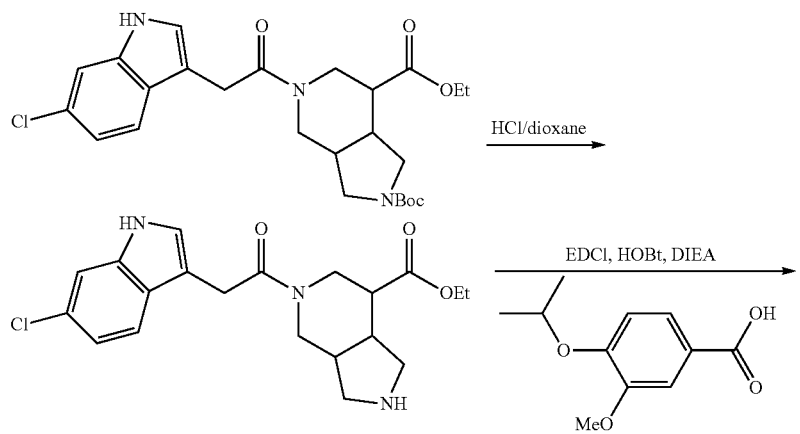

-continued

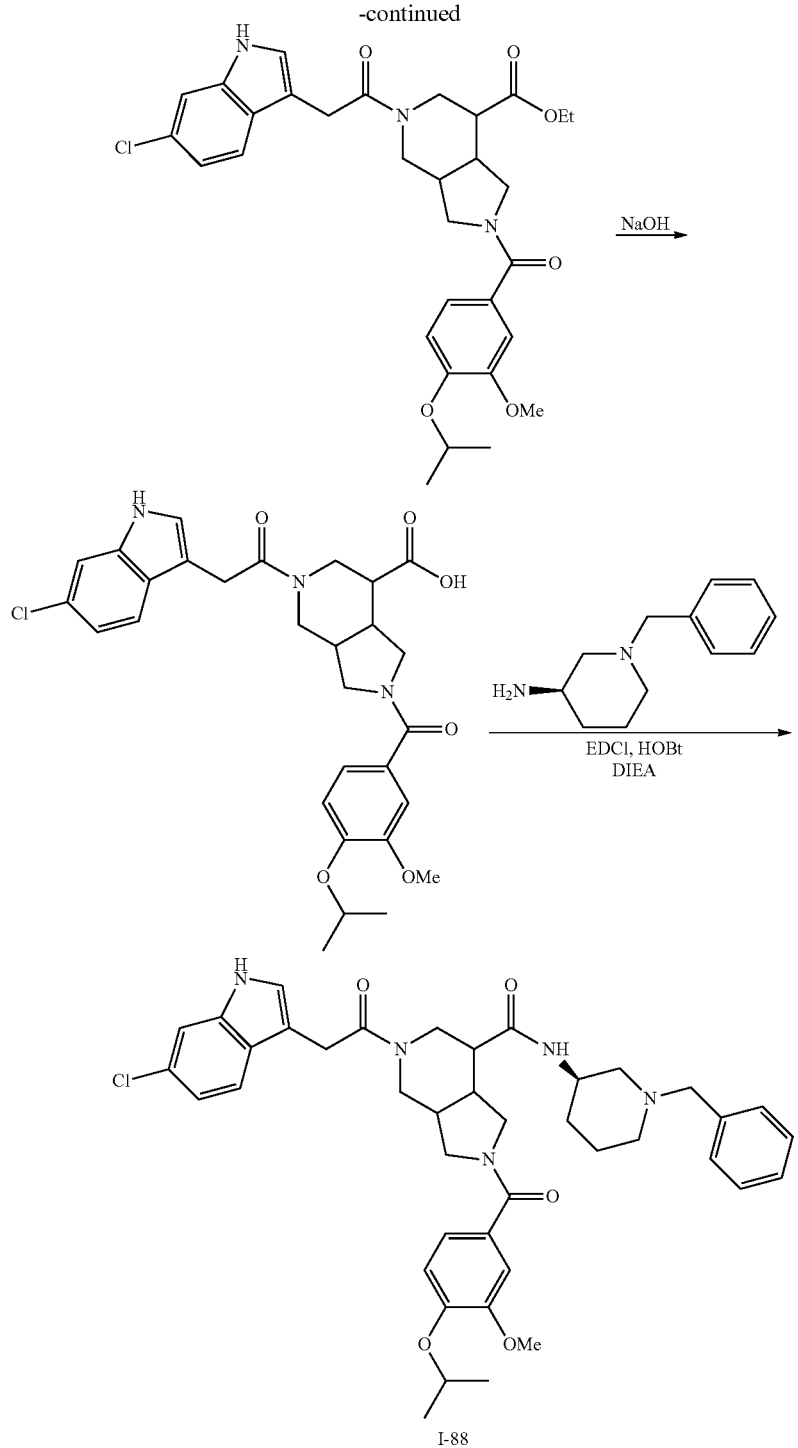

I-88

Step 1: ethyl 5-(2-(6-chloro-1H-indol-3-yl)acetyl) octahydro-1H-pyrrolo[3,4-c]pyridine-7-carboxylate hydrochloride To a solution of the product of 2-(tert-butyl) 7-ethyl 5-(2-(6-chloro-1H-indol-3-yl)acetyl)octahydro-2H-pyrrolo[3,4-c]pyridine-2,7-dicarboxylate (3.5 g, 7.14 mmol; see synthesis of I-1) in DCM (40 mL) was added a solution of HCl in dioxane (4M, 20 mL). The resulting mixture was stirred for 3 h. The solvent was removed under vacuum to afford the product (3.0 g, quant.). LCMS m/z=390.2 [M+H]$^+$.

Step 2: ethyl 5-(2-(6-chloro-1H-indol-3-yl)acetyl)-2-(4-isopropoxy-3-methoxybenzoyl) octahydro-1H-pyrrolo[3,4-c]pyridine-7-carboxylate A mixture of ethyl 5-(2-(6-chloro-1H-indol-3-yl)acetyl) octahydro-1H-pyrrolo[3,4-c]pyridine-7-carboxylate hydrochloride (1.74 g, 4.1 mmol), 4-isopropoxy-3-methoxybenzoic acid (1.03 g, 4.92 mmol), EDCI (1.18 g, 6.15 mmol), HOBt (830 mg, 6.15 mmol) and DIEA (1.06 g, 8.2 mmol) in DMF (10 mL) was stirred overnight. The reaction mixture was diluted with water and extracted with EtOAc three times. The combined organic layers were washed with water and brine, dried over $Na_2SO_4$ and concentrated in vacuo. The residue was purified by column chromatography (2.5% MeOH/DCM) to give the product (2.1 g, 88%) as a white solid. LCMS m/z=582.3 $[M+H]^+$.

Step 3: 5-(2-(6-chloro-M-indol-3-yl)acetyl)-2-(4-isopropoxy-3-methoxybenzoyl)octahydro-1H-pyrrolo[3,4-c]pyridine-7-carboxylic acid To a solution of ethyl 5-(2-(6-chloro-1H-indol-3-yl)acetyl)-2-(4-isopropoxy-3-methoxybenzoyl) octahydro-1H-pyrrolo[3,4-c]pyridine-7-carboxylate (2.1 g, 3.61 mmol) in MeOH (20 mL) was added an aqueous solution of NaOH (1M, 7.2 mL). The resulting mixture was stirred for 3 h. The solvent was removed under vacuum and the residue obtained diluted with water. The pH was adjusted to ~1 by addition of 1M HCl and the aqueous layer extracted with EtOAc three times. The combined organic layers were washed with water and brine, dried over $Na_2SO_4$ and concentrated to afford the product (1.7 g, 85% yield) as a white solid. LCMS m/z=554.2 $[M+H]^+$.

Step 4: N—((R)-1-benzylpiperidin-3-yl)-5-(2-(6-chloro-1H-indol-3-yl)acetyl)-2-(4-isopropoxy-3-methoxybenzoyl)octahydro-1H-pyrrolo[3,4-c]pyridine-7-carboxamide (I-88)

To a solution of 5-(2-(6-chloro-1H-indol-3-yl)acetyl)-2-(4-isopropoxy-3-methoxybenzoyl)octahydro-1H-pyrrolo[3,4-c]pyridine-7-carboxylic acid (50 mg, 0.09 mmol) in DMA (1 mL) was added (R)-1-benzylpiperidin-3-amine (21 mg, 0.11 mmol), EDCI (26 mg, 0.14 mmol), HOBt (18 mg, 0.14 mmol) and DIPEA (44 mg, 0.27 mmol). The resulting mixture was stirred for 14 h. Water was added and the aqueous layer was extracted with EtOAc three times. The combined organic layers were washed with water and brine and dried over $Na_2SO_4$. The solvent was removed and the residue purified by prep-TLC (6% MeOH/DCM) to afford 1-88 (30 mg, 46%) as a white solid. LCMS m/z=726.3 $[M+H]^+$; $^1H$ NMR (400 MHz, $CD_3OD$) δ 7.59-6.69 (m, 12H), 4.75-4.30 (m, 2H), 3.92-3.46 (m, 12H), 3.22-2.48 (m, 7H), 2.34-1.65 (m, 5H), 1.41-1.26 (m, 8H).

The compounds listed in Table 3 were synthesized using analogous methods to those shown for 1-88, using the appropriate commercially available reagents and/or intermediates. Final examples were obtained as a mixture of diastereomers (or enantiomers where applicable) or separated by preparative chiral HPLC as indicated.

Table 3. Compounds made by a method analogous to I-88

| # | $^1H$ NMR Chromatography conditions, if applicable | LCMS |
|---|---|---|
| I-89 | $^1H$ NMR (400 MHz, $CD_3CD$) δ 7.76-6.62 (m, 12H), 4.78-4.54 (m, 1H), 4.53-4.09 (m, 2H), 4.08-3.75 (m, 6H), 3.73-3.37 (m, 4H), 3.22-2.94 (m, 3H), 2.79-2.27 (m, 4H), 2.24-1.81 (m, 2H), 1.80-1.46 (m,, 3H), 1.44-1.28 (m, 8H). | m/z = 740.4 $[M + H]^+$ |
| I-90 | $^1H$ NMR (400 MHz, $CD_3OD$) δ 7.74-6.63 (m, 12H), 4.78-4.30 (m, 2H), 4.26-3.77 (m, 8H), 3.76-3.60 (m, 3H), 3.58-3.37 (m, 3H), 3.26-2.72 (m, 5H), 2.71-1.80 (m, 5H), 1.78-1.49 (m, 2H), 1.41-1.22 (m, 8H). | m/z = 754.4 $[M + H]^+$ |
| I-91 | $^1H$ NMR (400 MHz, $CD_3OD$) δ 8.58-6.55 (m, 11H), 4.78-3.37 (m, 11H), 3.25-2.97 (m, 2H), 2.91-2.26 (m, 8H), 2.24-1.98 (m, 1H), 1.87-1.50 (m, 4H), 1.47-1.27 (m, 10H). | m/z = 743.3 $[M + H]^+$ |
| I-92 | $^1H$ NMR (400 MHz, $CD_3OD$) δ 7.64-6.63 (m, 12H), 4.76-3.73 (m, 12H), 3.72-3.57 (m, 1H), 3.50 (d, J = 6.4 Hz, 1H), 3.40 (s, 1H), 3.29-2.98 (m, 2H), 2.88-2.42 (m, 6H), 2.30-1.98 (m, 1H), 1.48-0.86 (m, 10H), 0.68 (d, J = 6.2 Hz, 1H). | m/z = 758.3 $[M + H]^+$ |
| I-93 | $^1H$ NMR (400 MHz, $CD_3OD$) δ 7.64-6.59 (m, 7H), 4.76-3.77 (m, 9H), 3.74-3.37 (m, 3H), 3.25-2.42 (m, 8H), 2.38-1.46 (m, 10H), 1.44-1.23 (m, 10H), 1.20-0.90 (m, 3H). | m/z = 734.4 $[M + H]^+$ |
| I-94 | $^1H$ NMR (400 MHz, $CD_3OD$) δ 8.58-6.52 (m, 7H), 4.79-3.36 (m, 11H), 3.27-2.38 (m, 8H), 2.37-1.44 (m, 8H), 1.44-1.08 (m, 13H), 1.08-0.62 (m, 3H). | m/z = 816.5 $[M + H]^+$ |
| I-95 | $^1H$ NMR (400 MHz, $CD_3OD$) δ 7.71-6.57 (m, 7H), 4.76-3.34 (m, 11H), 3.27-2.88 (m, 2H), 2.88-2.70 (m, 2H), 2.69-1.95 (m, 4H), 1.80-1.45 (m, 2H), 1.40-1.26 (m, 9H), 1.25-0.96 (m, 3H), 0.93-0.84 (m, 7H), 0.80-0.70 (m, 3H). | m/z = 722.4 $[M + H]^+$ |
| I-96 | $^1H$ NMR (400 MHz, $CD_3OD$) δ 7.69-6.60 (m, 7H), 4.78-4.23 (m, 3H), 4.22-3.89 (m, 2H), 3.87-3.78 (m, 3H), 3.76-3.33 (m, 3H), 3.25-2.98 (m, 2H), 2.95-2.67 (m, 3H), 2.67-1.98 (m, 4H), 1.82-1.41 (m, 2H), 1.41-1.29 (m, 8H), 1.28-0.96 (m, 4H), 0.93-0.84 (m, 6H), 0.81-0.70 (m, 3H). | m/z = 722.4 $[M + H]^+$ |
| I-97 | $^1H$ NMR (400 MHz, $CD_3OD$) δ 7.66-6.60 (m, 7H), 4.79-3.76 (m, 9H), 3.75-3.36 (m, 3H), 3.28-2.44 (m, 8H), 2.41-1.93 (m, 1H), 1.83-1.46 (m, 3H), 1.43-1.26 (m, 9H), 1.20 (m, 2H), 1.04-0.84 (m, 5H), 0.84-0.69 (m, 2H). | m/z = 708.4 $[M + H]^+$ |
| I-98 | $^1H$ NMR (400 MHz, $CD_3OD$) δ 7.66-6.59 (m, 12H), 4.78-4.35 (m, 2H), 4.33-3.96 (m, 2H), 3.95-3.38 (m, 8H), 3.26-2.75 (m, 5H), 2.72-2.15 (m, 5H), 1.90-1.60 (m, 2H), 1.43-1.19 (m, 9H). | m/z = 742.3 $[M + H]^+$ |
| I-99 | $^1H$ NMR (400 MHz, $CD_3OD$) δ 7.73-6.49 (m, 12H), 4.67-3.78 (m, 9H), 3.73-3.42 (m, 4H), 3.29-3.05 (m, 4H), 2.73-2.29 (m, 5H), 2.11-1.66 (m, 3H), 1.41-1.30 (m, 6H). | m/z = 728.3 $[M + H]^+$ |

-continued

| Table 3. Compounds made by a method analogous to I-88 | | |
|---|---|---|
| # | ¹H NMR Chromatography conditions, if applicable | LCMS |
| I-100 | ¹H NMR (400 MHz, CD₃OD) δ 7.70-6.46 (m, 12H), 4.74-3.78 (m, 9H), 3.74-3.34 (m, 5H), 3.28-3.05 (m, 2H), 3.01-2.81 (m, 4H), 2.68-2.44 (m, 4H), 2.10-1.72 (m, 3H), 1.42-1.22 (m, 7H). First eluting diastereomer purified by chiral prep-HPLC on a UniChiral CNZ-5H column (5 cm I.D. × 25 cm), using MeOH 0.1% DEA at a flow rate of 90 mL/min (wave length 254 nm). Rt = 12.5 min | m/z = 742.3 [M + H]⁺ |
| I-101 | ¹H NMR (400 MHz, CD₃OD) δ 7.68-6.47 (m, 12H), 4.76-3.79 (m, 9H), 3.76-3.33 (m, 5H), 3.28-3.05 (m, 2H), 3.01-2.81 (m, 4H), 2.70-2.48 (m, 4H), 2.08-1.75 (m, 3H), 1.42-1.24 (m, 7H). Second eluting diastereomer purified by chiral prep-HPLC on a UniChiral CNZ-5H column (5 cm I.D. × 25 cm), using MeOH 0.1% DEA at a flow rate of 90 mL/min (wave length 254 nm). Rt = 13.9 min | m/z = 742.4 [M + H]⁺ |
| I-102 | ¹H NMR (400 MHz, CD₃OD) δ 7.63-6.61 (m, 12H), 4.77-3.38 (m, 17H), 3.27-1.94 (m, 10H), 1.40-1.33 (m, 3H), 1.24-1.05 (m, 3H), 0.79-0.67 (m, 1H). | m/z = 758.4 [M + H]⁺ |
| I-103 | ¹H NMR (400 MHz, CD₃OD) δ 7.65-6.60 (m, 12H), 4.65 (m, 3H), 4.21-3.69 (m, 6H), 3.69-3.38 (m, 4H), 3.26-3.15 (m, 1H), 3.12-2.74 (m, 5H), 2.69-2.50 (m, 4H), 2.31-1.67 (m, 3H), 1.45-0.89 (m, 10H). | m/z = 756.4 [M + H]⁺ |
| I-104 | ¹H NMR (400 MHz, CD₃OD) δ 7.83-6.58 (m, 7H), 4.78-3.35 (m, 11H), 3.25-2.16 (m, 8H), 2.12-1.44 (m, 8H), 1.43-0.71 (m, 16H). | m/z = 816.4 [M + H]⁺ |
| I-105 | ¹H NMR (400 MHz, CD₃OD) δ 7.67-6.57 (m, 12H), 4.78-3.34 (m, 15H), 3.28-1.92 (m, 9H), 1.45-1.03 (m, 8H), 0.79-0.67 (m, 1H). | m/z = 758.4 [M + H]⁺ |
| I-106 | ¹H NMR (400 MHz, CD₃OD) δ 7.79-6.44 (m, 12H), 4.74-3.39 (m, 15H), 3.29-2.98 (m, 2H), 2.87-2.42 (m, 5H), 2.31-1.96 (m, 1H), 1.42-1.12 (m, 9H), 0.72-0.67 (m, 1H). | m/z = 758.4 [M + H]⁺ |
| I-107 | ¹H NMR (400 MHz, CD₃OD) δ 7.68-6.65 (m, 7H), 4.71-3.77 (m, 9H), 3.72-3.34 (m, 6H), 3.28-2.94 (m 4H), 2.83-2.58 (m, 5H), 2.32-1.96 (m, 1H), 1.68-1.58 (m, 6H), 1.43-1.27 (m, 10H), 1.24-1.04 (m, 5H), 0.93-0.83 (m, 2H), 0.65-0.63 (m, 1H). | m/z = 764.5 [M + H]⁺ |
| I-108 | ¹H NMR (400 MHz, CD₃OD) δ 7.81-6.44 (m, 7H), 4.81-4.41 (m, 3H), 4.39-4.08 (m, 1H), 4.07-3.79 (m, 5H), 3.73-3.52 (m, 2H), 3.47-3.36 (m, 1H), 3.24-2.94 (m, 3H), 2.80-2.61 (m, 4H), 2.57-2.14 (m, 2H), 1.70-1.56 (m, 5H), 1.41-1.35 (m, 9H), 1.23-1.05 (m, 5H), 0.92-0.81 (m, 4H). | m/z = 764.5 [M + H]⁺ |
| I-109 | ¹H NMR (400 MHz, CD₃OD) δ 7.64-6.59 (m, 12H), 4.78-3.36 (m, 12H), 3.27-2.51 (m, 6H), 2.48-1.96 (m, 2H), 1.84-1.55 (m, 3H), 1.43-1.22 (m, 7H). | m/z = 728.4 [M + H]⁺ |
| I-110 | ¹H NMR (400 MHz, CD₃OD) δ 7.63-6.57 (m, 12H), 4.77-3.73 (m, 8H), 3.70-2.86 (m, 9H), 2.83-2.29 (m, 6H), 1.42-1.16 (m, 6H). First eluting diastereomer purified by chiral prep-HPLC on a UniChiral CND-5H column (2.21 cm I.D. × 25 cm), using Hexane/EtOH (70/30) at a flow rate of 25 mL/min (wave length 254 nm). Rt = 9.1 min | m/z = 753.4 [M + H]⁺ |
| I-111 | ¹H NMR (400 MHz, CD₃OD) δ 7.64-6.40 (m, 12H), 4.76-4.16 (m, 3H), 4.02-3.34 (m, 9H), 3.28-2.22 (m, 10H), 1.41-1.24 (m, 7H). Second eluting diastereomer purified by chiral prep-HPLC on a UniChiral CND-5H column (2.21 cm I.D. × 25 cm), using Hexane/EtOH (70/30) at a flow rate of 25 mL/min (wave length 254 nm). Rt = 15.0 min | m/z = 753.4 [M + H]⁺ |
| I-112 | ¹H NMR (400 MHz, CD₃OD) δ 7.64-6.62 (m, 7H), 4.79-3.77 (m, 9H), 3.72-3.38 (m, 3H), 3.26-2.50 (m, 8H), 1.78-1.50 (m, 7H), 1.43-0.74 (m, 17H). | m/z = 748.4 [M + H]⁺ |
| I-113 | ¹H NMR (400 MHz, CD₃OD) δ 7.64-6.62 (m, 7H), 4.80-3.77 (m, 9H), 3.73-3.39 (m, 3H), 3.25-2.18 (m, 8H), 1.79-1.53 (m, 7H), 1.45-0.72 (m, 17H). | m/z = 748.4 [M + H]⁺ |
| I-114 | ¹H NMR (400 MHz, CD₃OD) δ 7.63-7.49 (m, 1H), 7.43-6.62 (m, 6H), 4.76-3.37 (m, 12H), 3.26-2.17 (m, 10H), 1.80-1.45 (m, 3H), 1.43-1.27 (m, 10H), 1.07-0.68 (m, 7H). | m/z = 708.5 [M + H]⁺ |
| I-115 | ¹H NMR (400 MHz, CD₃OD) δ 8.48-6.57 (m, 11H), 4.77-3.36 (m, 12H), 3.26-2.96 (m, 2H), 2.90-2.40 (m, 7H), 2.35-2.14 (m, 1H), 2.03-1.46 (m, 3H), 1.43-1.15 (m, 7H). | m/z = 758.4 [M + H]⁺ |
| I-116 | ¹H NMR (400 MHz, CD₃OD) δ 7.64-6.61 (m, 7H), 4.76-3.38 (m, 14H), 3.25-2.85 (m, 2H), 2.81-2.39 (m, 6H), 2.11-1.83 (m, 2H), 1.81-0.96 (m, 20H). | m/z = 764.5 [M + H]⁺ |
| I-117 | ¹H NMR (400 MHz, CD₃OD) δ 7.63-6.63 (m, 12H), 4.80-3.36 (m, 16H), 3.26-2.45 (m, 7H), 2.351.47 (m, 4H)1.45-1.27 (m, 8H). First eluting diastereomer purified by chiral prep-HPLC on a UniChiral CND-5H column (3 cm I.D. × 25 cm), using Hexane/EtOH (70/30) at a flow rate of 45 mL/min (wave length 254 nm). Rt = 10.3 min | m/z = 726.4 [M + H]⁺ |

Table 3. Compounds made by a method analogous to I-88

| # | ¹H NMR Chromatography conditions, if applicable | LCMS |
|---|---|---|
| I-118 | ¹H NMR (400 MHz, CD$_3$OD) δ 7.64-6.69 (m, 12H), 4.76-3.37 (m, 16H), 3.27-2.45 (m, 6H), 2.36-1.48 (m, 3H), 1.44-1.26 (m, 8H). Second eluting diastereomer purified by chiral prep-HPLC on a UniChiral CND-5H column (3 cm I.D. × 25 cm), using Hexane/EtOH (70/30) at a flow rate of 45 mL/min (wave length 254 nm). Rt = 13.8 min | m/z = 726.4 [M + H]$^+$ |
| I-119 | ¹H NMR (400 MHz, CD$_3$OD) δ 7.66-6.90 (m, 12H), 4.65-4.46 (m, 1H), 4.14-3.80 (m, 6H), 3.73-3.37 (m, 2H), 3.26-2.79 (m, 4H), 2.76-2.22 (m, 4H), 2.22-1.62 (m, 1H), 1.57-1.37 (m, 4H), 1.35-1.28 (m, 9H). | m/z = 685.3 [M + H]$^+$ |
| I-120 | ¹H NMR (400 MHz, CD$_3$OD) δ 7.66-6.55 (m, 12H), 4.78-3.38 (m, 11H), 3.17-2.81 (m, 4H), 2.75-2.48 (m, 5H), 2.44-2.02 (m, 1H), 1.41-1.30 (m, 8H). | m/z = 714.3 [M + H]$^+$ |
| I-121 | ¹H NMR (400 MHz, CD$_3$OD) δ 7.65-6.47 (m, 11H), 4.76-4.14 (m, 3H), 4.11-3.37 (m, 8H), 3.27-2.38 (m, 10H), 2.27-1.61 (m, 1H), 1.41-1.22 (m, 6H). | m/z = 730.3 [M + H]$^+$ |
| I-122 | ¹H NMR (400 MHz, CD$_3$OD) δ 7.65-6.50 (m, 12H), 4.80-4.36 (m, 2H), 4.36-3.93 (m, 1H), 3.92-3.60 (m, 6H), 3.59-3.34 (m, 2H), 3.21-2.78 (m, 4H), 2.77-2.31 (m, 6H), 1.46-1.20 (m, 8H). | m/z = 714.3 [M + H]$^+$ |
| I-123 | ¹H NMR (400 MHz, CD$_3$OD) δ 7.64-6.41 (m, 11H), 4.69-3.77 (m, 8H), 3.77-3.37 (m, 3H), 3.25-2.39 (m, 10H), 2.38-1.50 (m, 2H), 1.43-1.22 (m, 8H). | m/z = 730.2 [M + H]$^+$ |
| I-124 | ¹H NMR (400 MHz, CD$_3$OD) δ 8.52-6.62 (m, 7H), 4.74-3.75 (m, 8H), 3.74-3.37 (m, 3H), 3.28-2.76 (m, 3H), 2.76-2.41 (m, 5H), 2.38-1.71 (m, 1H), 1.42-1.09 (m, 11H). | m/z = 638.3 [M + H]$^+$ |
| I-125 | ¹H NMR (400 MHz, CD$_3$OD) δ 7.68-6.60 (m, 7H), 4.65-3.78 (m, 8H), 3.73-3.35 (m, 3H), 3.25-2.88 (m, 2H), 2.84-2.17 (m, 6H), 2.10-1.57 (m, 1H), 1.36-1.28 (m, 10H). | m/z = 638.3 [M + H]$^+$ |
| I-126 | ¹H NMR (400 MHz, CD$_3$OD) δ 8.55-6.50 (m, 11H), 4.78-4.00 (m, 4H), 3.99-3.77 (m, 5H), 3.74-3.37 (m, 3H), 3.27-2.41 (m, 10H), 1.87-1.54 (m, 3H), 1.42-1.24 (m, 8H). | m/z = 743.3 [M + H]$^+$ |
| I-127 | ¹H NMR (400 MHz, CD$_3$OD) δ 7.59-6.55 (m, 11H), 4.79-3.36 (m, 13H), 3.29-2.28 (m, 11H), 2.21-1.46 (m, 5H), 1.42-1.30 (m, 7H). | m/z = 758.4 [M + H]$^+$ |
| I-128 | ¹H NMR (400 MHz, CD$_3$OD) δ 7.72-6.42 (m, 11H), 4.78-4.12 (m, 4H), 4.11-3.34 (m, 9H), 3.23-1.52 (m, 14H), 1.37-1.26 (m, 7H). | m/z = 758.4 [M + H]$^+$ |
| I-129 | ¹H NMR (400 MHz, CD$_3$OD) δ 7.87-6.63 (m, 7H), 4.74-3.36 (m, 13H), 3.26-2.25 (m, 10H), 1.77-0.62 (m, 21H). | m/z = 764.5 [M + H]$^+$ |
| I-130 | ¹H NMR (400 MHz, CD$_3$OD) δ 7.66-6.61 (m, 7H), 4.76-3.99 (m, 4H), 3.97-3.37 (m, 11H), 3.28-2.76 (m, 3H), 2.75-1.65 (m, 7H), 1.61-0.87 (m, 17H). | m/z = 750.4 [M + H]$^+$ |
| I-131 | ¹H NMR (400 MHz, CD$_3$OD) δ 7.66-6.61 (m, 7H), 4.76-3.99 (m, 4H), 3.97-3.37 (m, 11H), 3.28-2.76 (m, 3H), 2.75-1.65 (m, 7H), 1.61-0.87 (m, 17H) | m/z = 750.4 [M + H]$^+$ |
| I-132 | ¹H NMR (400 MHz, CD$_3$OD) δ 7.70-6.58 (m, 7H), 4.79-3.77 (m, 9H), 3.76-3.35 (m, 3H), 3.30-2.98 (m, 2H), 2.96-2.41 (m, 6H), 1.86-1.45 (m, 9H), 1.42-1.26 (m, 9H), 1.17-0.87 (m, 3H). | m/z = 734.4 [M + H]$^+$ |
| I-133 | ¹H NMR (400 MHz, CD$_3$OD) δ 7.71-6.60 (m, 11H), 4.76-3.95 (m, 4H), 3.95-3.36 (m, 8H), 3.26-2.82 (m, 3H), 2.82-1.56 (m, 12H), 1.43-1.22 (m, 8H). | m/z = 810.4 [M + H]$^+$ |
| I-134 | ¹H NMR (400 MHz, CD$_3$OD) δ 7.74-6.59 (m, 11H), 4.78-3.35 (m, 12H), 3.24-2.37 (m, 10H), 2.33-1.45 (m, 5H), 1.43-1.19 (m, 7H). | m/z = 810.4 [M + H]$^+$ |
| I-135 | ¹H NMR (400 MHz, CD$_3$OD) δ 7.66-6.60 (m, 7H), 4.78-4.24 (m, 3H), 3.90 (m, 2H), 3.86 (m, 1H), 3.82 (m, 3H), 3.75-3.35 (m, 4H), 3.24-2.96 (m, 3H), 2.96-2.78 (m, 1H), 2.77-2.48 (m, 5H), 1.69 (m, 5H), 1.51 (m, 1H), 1.43-1.28 (m, 7H), 1.27-1.05 (m, 5H), 1.03-0.76 (m, 3H). | m/z = 764.5 [M + H]$^+$ |
| I-136 | ¹H NMR (400 MHz, CD$_3$OD) δ 7.72-6.04 (m, 12H), 4.75-3.98 (m, 3H), 3.96-3.36 (m, 8H), 3.26-2.88 (m, 2H), 2.84-2.17 (m, 7H), 1.41-1.22 (m, 6H). | m/z = 740.4 [M + H]$^+$ |
| I-137 | ¹H NMR (400 MHz, CD$_3$OD) δ 7.67-6.52 (m, 12H), 4.76-3.92 (m, 4H), 3.91-3.36 (m, 8H), 3.28-2.85 (m, 3H), 2.84-2.08 (m, 8H), 1.42-1.19 (m, 7H). | m/z = 738.3 [M + H]$^+$ |
| I-138 | ¹H NMR (400 MHz, CD$_3$OD) δ 8.77-8.51 (m, 2H), 8.00-6.65 (m, 9H), 4.79-3.79 (m, 9H), 3.73-3.39 (m, 3H), 3.24-2.12 (m, 11H), 1.92-1.57 (m, 3H), 1.45-1.23 (m, 7H). | m/z = 743.4 [M + H]$^+$ |
| I-139 | ¹H NMR (400 MHz, CD$_3$OD) δ 7.70-6.63 (m, 10H), 4.76-3.34 (m, 12H), 3.26-2.86 (m, 4H), 2.85-2.42 (m, 5H), 1.96-1.63 (m, 3H), 1.46-1.14 (m, 9H). | m/z = 783.4 [M + H]$^+$ |
| I-140 | ¹H NMR (400 MHz, CD$_3$OD) δ 7.66-6.64 (m, 7H), 4.75-3.38 (m, 12H), 3.26-2.36 (m, 9H), 1.75-1.01 (m, 25H). | m/z = 762.4 [M + H]$^+$ |
| I-141 | ¹H NMR (400 MHz, CD$_3$OD) δ 7.72-6.58 (m, 7H), 4.80-3.36 (m, 13H), 3.23-2.42 (m, 8H), 1.77-1.05 (m, 25H). | m/z = 762.4 [M + H]$^+$ |

-continued

Table 3. Compounds made by a method analogous to I-88

| # | ¹H NMR Chromatography conditions, if applicable | LCMS |
|---|---|---|
| I-142 | ¹H NMR (400 MHz, CD₃OD) δ 7.65-6.61 (m, 7H), 4.78-3.39 (m, 12H), 3.25-2.97 (m, 2H), 2.85-2.52 (m, 5H), 2.08-1.08 (m, 24H). | m/z = 764.4 [M + H]⁺ |
| I-143 | ¹H NMR (400 MHz, CD₃OD) δ 7.90-6.59 (m, 10H), 4.72-3.37 (m, 13H), 3.27-2.91 (m, 3H), 2.90-2.56 (m, 7H), 1.83-1.61 (m, 3H), 1.44-1.33 (m, 6H), 1.22-1.18 (m, 2H). | m/z = 783.5 [M + H]⁺ |
| I-144 | ¹H NMR (400 MHz, CD₃OD) δ 7.68-6.57 (m, 11H), 4.75-3.79 (m, 9H), 3.73-3.41 (m, 3H), 3.28-2.79 (m, 3H), 2.78-2.54 (m, 6H), 2.44-2.00 (m, 2H), 1.73-1.50 (m, 3H), 1.41-1.29 (m, 8H). | m/z = 760.4 [M + H]⁺ |
| I-145 | ¹H NMR (400 MHz, CD₃OD) δ 7.52-6.55 (m, 12H), 4.77-4.52 (m, 3H), 4.52-4.30 (m, 2H), 4.11-4.93 (m, 1H), 4.92-3.79 (m, 5H), 3.75-3.56 (m, 2H), 3.55-3.35 (m, 2H), 3.27-3.02 (m, 2H), 2.85-2.72 (m, 3H), 2.65-2.23 (m, 4H), 1.45-1.28 (m, 7H), 1.23-0.84 (m, 3H).<br>First eluting diastereomer purified by chiral prep-HPLC on a CHIRALPAK IF column (0.46 cm I.D. × 15 cm), using n-Hexane/EtOH 0.1% DEA (60/40) at a flow rate of 1.0 mL/min (wave length 210 nm). Rt = 8.2 min | m/z = 758.4 [M + H]⁺ |
| I-146 | ¹H NMR (400 MHz, CD₃OD) δ 7.55-6.60 (m, 12H), 4.66-4.12 (m, 6H), 4.05-3.75 (m, 6H), 3.70-3.58 (m, 1H), 3.52-3.35 (m, 3H), 3.26-3.01 (m, 2H), 2.84-2.47 (m, 6H), 1.40-1.97 (m, 9H), 1.46-1.35 (m, 9H), 0.71-0.66 (m, 2H).<br>Second eluting diastereomer purified by chiral prep-HPLC on a CHIRALPAK IF column (0.46 cm I.D. × 15 cm), using n-Hexane/EtOH 0.1% DEA (60/40) at a flow rate of 1.0 mL/min (wave length 210 nm). Rt = 10.5 min | m/z = 758.3 [M + H]⁺ |
| I-147 | ¹H NMR (400 MHz, CD₃OD) δ 8.07-6.76 (m, 12H), 4.80-3.98 (m, 6H), 3.97-3.58 (m, 7H), 3.55-3.33 (m, 2H), 3.29-1.63 (m, 8H), 1.37-0.88 (m, 9H).<br>First eluting diastereomer purified by prep-HPLC on an Agilent 10 Prep-C18 column (21.2 mm I.D. × 25 cm, 10 um), using H₂O/ACN 0.1% TFA at a flow rate of 20 mL/min (wave length 214 nm). Rt = 12.9 min | m/z = 758.4 [M + H]⁺ |
| I-148 | ¹H NMR (400 MHz, CD₃OD) δ7.62-6.88 (m, 12H), 4.67-4.23 (m, 5H), 4.13-3.68 (m, 8H), 3.63-3.33 (m, 2H), 3.28-2.58 (m, 5H), 2.54-2.13 (m, 3H), 1.38-1.27 (m, 6H), 1.23-1.06 (m, 3H).<br>Second eluting diastereomer purified by prep-HPLC on an Agilent 10 Prep-C18 column (21.2 mm I.D. × 25 cm, 10 um), using H₂O/ACN 0.1% TFA at a flow rate of 20 mL/min (wave length 214 nm). Rt = 13.9 min | m/z = 758.4 [M + H]⁺ |
| I-149 | ¹H NMR (400 MHz, CD₃OD) δ 7.92-6.63 (m, 14H), 4.80-3.45 (m, 11H), 3.27-2.07 (m, 8H), 1.77-1.18 (m, 11H) 1H), 1.80-1.52 (m, 2H), 1.48-0.86 (m, 9H). | m/z = 752.5 [M + H]⁺ |
| I-150 | ¹H NMR (400 MHz, CD₃OD) δ 8.58-6.67 (m, 16H), 4.79-3.39 (m, 12H), 3.23-1.96 (m, 9H), 1.88-1.33 (m, 9H). | m/z = 762.4 [M + H]⁺ |
| I-151 | ¹H NMR (400 MHz, CD₃OD) δ 8.78-8.71 (m, 1H), 8.70-8.61 (m, 0.5H), 8.40-8.29 (m, 0.5H), 7.61-6.65 (m, 13H), 4.79-3.75 (m, 8H), 3.70-3.35 (m, 3H), 3.29-2.94 (m, 2H), 2.84-2.39 (m, 5H), 2.22-2.00 (m, 1H), 1.87-1.49 (m, 3H), 1.42-1.31 (m, 5H), 1.29-1.23 (m, 3H). | m/z = 763.4 [M + H]⁺ |
| I-152 | ¹H NMR (400 MHz, CD₃OD) δ 7.68-6.41 (m, 11H), 4.77-4.13 (m, 3H), 4.11-3.33 (m, 9H), 3.28-1.51 (m, 14H), 1.44-1.21 (m, 7H).<br>First eluting diastereomer purified by chiral prep-HPLC on a UniChiral CND-5H column (21.2 mm I.D. × 250 mm), using ACN/IPA/DEA = 95/5/0.1, at a flow rate of 20 mL/min (wave length 254 nm). Rt = 5.7 min. | m/z = 758.4 [M + H]⁺ |
| I-153 | ¹H NMR (400 MHz, CD₃OD) δ 7.63-6.50 (m, 11H), 4.77-3.38 (m, 13H), 3.27-2.28 (m, 10H), 2.20-1.47 (m, 4H), 1.42-1.27 (m, 6H).<br>Second eluting diastereomer purified by chiral prep-HPLC on a UniChiral CND-5H column (21.2 mm I.D. × 250 mm), using ACN/IPA/DEA = 95/5/0.1, at a flow rate of 20 mL/min (wave length 254 nm). Rt = 6.3 min. | m/z = 758.4 [M + H]⁺ |
| I-261 | ¹H NMR (400 MHz, CD₃OD) δ 7.64-6.55 (m, 9H), 4.79-3.37 (m, 13H), 3.28-2.52 (m, 8H), 2.38-1.78 (m, 1H), 1.44-1.25 (m, 6H).<br>First eluting enantiomer purified by chiral prep-HPLC on a UniChiral CND-5H column (21.2 mm I.D. × 250 mm), using n-Hexane/EtOH = 70/30, at a flow rate of 20 mL/min (wave length 254 nm). Rt = 14.9 min. | m/z = 659.4 [M + H]⁺ |
| I-262 | ¹H NMR (400 MHz, CD₃OD) δ 7.64-6.54 (m, 9H), 4.74-3.39 (m, 13H), 3.27-2.47 (m, 8H), 2.43-1.93 (m, 1H), 1.42-1.28 (m, 6H).<br>Second eluting enantiomer purified by chiral prep-HPLC on a UniChiral CND-5H column (21.2 mm I.D. × 250 mm), using n-Hexane/EtOH = 70/30, at a flow rate of 20 mL/min (wave length 254 nm). Rt = 17.9 min. | m/z = 659.4 [M + H]⁺ |

343
Synthesis of 2-(4-isopropoxy-3-methoxybenzoyl)-N—((S)-1-(methylamino)-1-oxo-5-phenylpentan-2-yl)-5-(2-phenylacetyl)octahydro-1H-pyrrolo[3,4-c]pyridine-7-carboxamide I-154

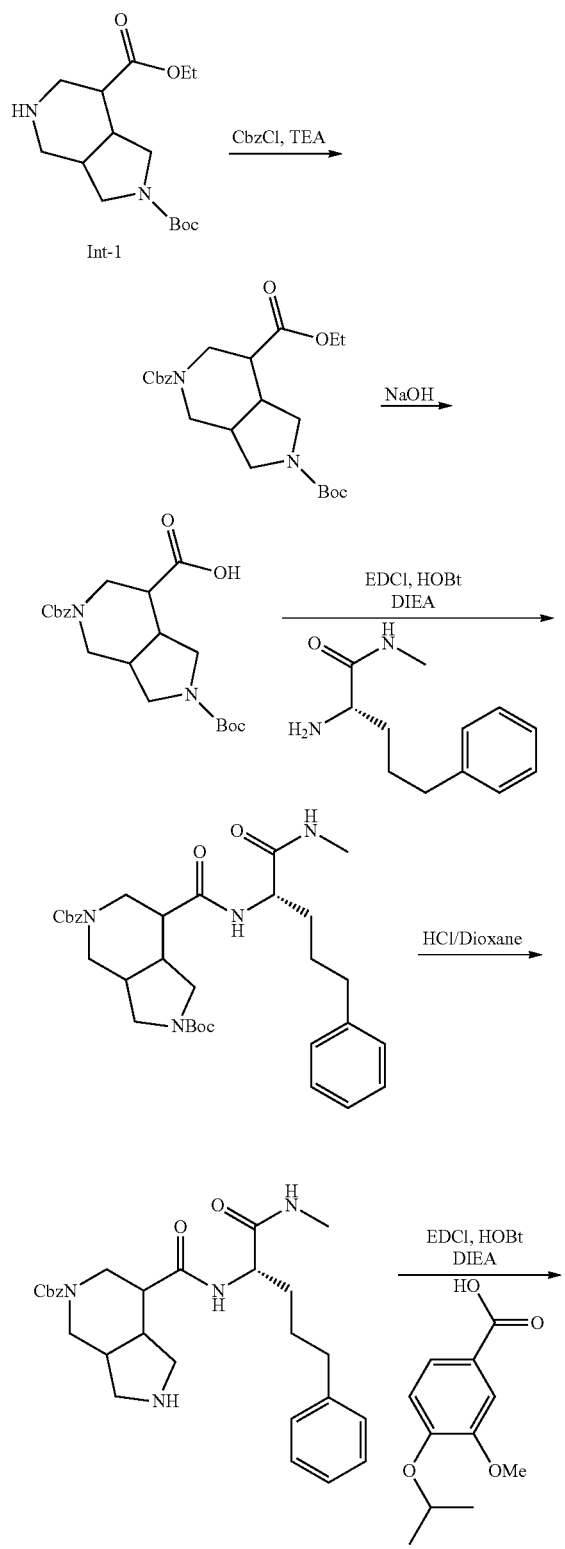

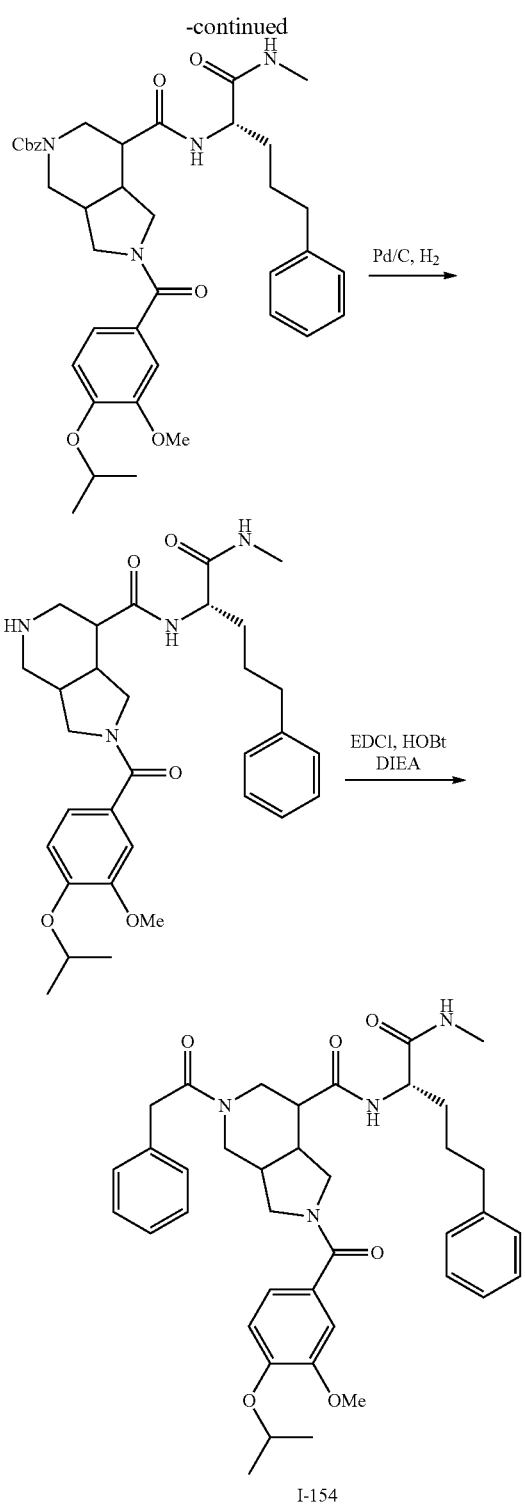

Step 1: 5-benzyl 2-(tert-butyl) 7-ethyl hexahydro-2H-pyrrolo[3,4-c]pyridine-2,5,7(3H)-tricarboxylate To a solution of Int-1 (5 g, 16.7 mmol) in DCM (50 mL) was added Et$_3$N (3.4 g, 33.5 mmol). After stirring for 30 min, CbzCl (3.1 g, 18.4 mmol) was added and stirring continued for 4 h. The reaction was quenched with water and extracted with EtOAc three times. The combined organic layers were washed with water, brine, and dried over Na$_2$SO$_4$. The solvent was removed in vacuo and the residue purified by column chromatography (20% EtOAc/PE) to afford the product (5.7 g, 79%) as a white solid. LCMS m/z=333.3 [M-Boc+H]$^+$; $^1$H NMR (400 MHz, CD$_3$OD) δ 7.39-7.26 (m, 5H), 5.13 (d, J=3.9 Hz, 2H), 4.31-3.47 (m, 4H), 3.46-3.32 (m, 3H), 3.30 (d, J=1.6 Hz, 1H), 3.24-1.58 (m, 5H), 1.46 (s, 9H), 1.29-1.23 (m, 3H).

Step 2: 5-((benzyloxy)carbonyl)-2-(tert-butoxycarbonyl)octahydro-1H-pyrrolo[3,4-c]pyridine-7-carboxylic acid To a solution of 5-benzyl 2-(tert-butyl) 7-ethyl hexahydro-2H-pyrrolo[3,4-c]pyridine-2,5,7(3H)-tricarboxylate (5.7 g, 13.2 mmol) in MeOH (60 mL) was added aqueous NaOH (1M, 20 mL). The mixture was stirred at room temperature for 3 h, then diluted with water and the pH adjusted to ~3 by addition of 1M HCl. The aqueous layer was extracted with EtOAc three times. The combined organic layers were washed with water, brine and dried over Na$_2$SO$_4$. Concentration afforded the product (4.7 g, 88%) as a white solid. LCMS m/z=305.3 [M-Boc+H]$^+$.

Step 3: 5-benzyl 2-(tert-butyl) 7-(((S)-1-(methylamino)-1-oxo-5-phenylpentan-2-yl)carbamoyl)hexahydro-2H-pyrrolo[3,4-c]pyridine-2,5(3H)-dicarboxylate To a solution of 5-((benzyloxy)carbonyl)-2-(tert-butoxycarbonyl)octahydro-1H-pyrrolo[3,4-c]pyridine-7-carboxylic acid (4.5 g, 11.1 mmol) in DMA (50 mL) was added (S)-2-amino-N-methyl-5-phenylpentanamide (3.4 g, 16.7 mmol), EDCI (3.2 g, 16.7 mmol), HOBt (1.7 g, 12.2 mmol) and DIEA (2.9 g, 22.3 mmol). The resulting mixture was stirred at room temperature overnight. The reaction was quenched with water and extracted with EtOAc three times. The combined organic layers were washed with water, brine and dried over Na$_2$SO$_4$. The solvent was removed and the residue purified by column chromatography (5% MeOH/DCM) to afford the product (5.3 g, 80%) as a white solid. LCMS m/z=493.4 [M-Boc+H]$^+$.

Step 4: benzyl 7-(((S)-1-(methylamino)-1-oxo-5-phenylpentan-2-yl)carbamoyl)octahydro-5H-pyrrolo[3,4-c]pyridine-5-carboxylate hydrochloride To a solution of 5-benzyl 2-(tert-butyl) 7-(((S)-1-(methylamino)-1-oxo-5-phenylpentan-2-yl)carbamoyl)hexahydro-2H-pyrrolo[3,4-c]pyridine-2,5(3H)-dicarboxylate (5.3 g, 8.9 mmol) in DCM (25 mL) was added a solution of HCl in dioxane (4M, 25 mL). The resulting mixture was stirred at room temperature for 1 h. The solvent was removed to afford the product (7.8 g, quant.). LCMS m/z=493.4 [M+H]$^+$.

Step 5: benzyl 2-(4-isopropoxy-3-methoxybenzoyl)-7-(((S)-1-(methylamino)-1-oxo-5-phenylpentan-2-yl)carbamoyl)octahydro-5H-pyrrolo[3,4-c]pyridine-5-carboxylate A mixture of benzyl 7-(((S)-1-(methylamino)-1-oxo-5-phenylpentan-2-yl)carbamoyl)octahydro-5H-pyrrolo[3,4-c]pyridine-5-carboxylate hydrochloride (5.1 g, 9.8 mmol), 4-isopropoxy-3-methoxybenzoic acid (2.47 g, 11.7 mmol), EDCI (2.8 g, 14.7 mmol), HOBt (2.0 g, 14.7 mmol) and DIEA (3.87 g, 30 mmol) in DMF (20 mL) was stirred overnight. The reaction mixture was diluted with water and extracted with EtOAc three times. The combined organic layers were washed with water and brine, dried over Na$_2$SO$_4$ and concentrated in vacuo. The residue was purified by column chromatography (5% MeOH/DCM) to give the product (6.7 g, quant.) as a colorless oil. LCMS m/z=685.4 [M+H]$^+$. $^1$H NMR (400 MHz, CD$_3$OD) δ 7.46-6.78 (m, 13H), 5.49 (s, 1H), 5.14 (d, J=2.7 Hz, 2H), 4.67-4.47 (m, 1H), 4.34-4.11 (m, 2H), 3.83 (d, J=7.0 Hz, 4H), 3.59 (d, J=3.7 Hz, 2H), 3.46-3.34 (m, 1H), 2.98 (d, J=53.8 Hz, 1H), 2.76-2.46 (m, 7H), 2.40 (t, J=7.3 Hz, 1H), 1.62 (d, J=33.2 Hz, 3H), 1.39-1.21 (m, 8H).

Step 6: 2-(4-isopropoxy-3-methoxybenzoyl)-N—((S)-1-(methylamino)-1-oxo-5-phenylpentan-2-yl)octahydro-1H-pyrrolo[3,4-c]pyridine-7-carboxamide To a solution of benzyl 2-(4-isopropoxy-3-methoxybenzoyl)-7-(((S)-1-(methylamino)-1-oxo-5-phenylpentan-2-yl)carbamoyl)octahydro-5H-pyrrolo[3,4-c]pyridine-5-carboxylate (6.7 g, 9.8 mmol) in MeOH (70 mL) was added Pd/C (10%, 600 mg). The resulting mixture was stirred under H$_2$ at room temperature overnight. The solution was filtered through celite and the filtrate concentrated to afford the product (5.2 g, 97%). LCMS m/z=551.4 [M+H]$^+$; $^1$H NMR (400 MHz, CD$_3$OD) δ 7.29-6.81 (m, 8H), 4.74-4.48 (m, 1H), 4.37-4.15 (m, 1H), 3.90-3.81 (m, 3H), 3.78-3.35 (m, 4H), 3.06-2.82 (m, 3H), 2.78-2.16 (m, 9H), 1.89-1.38 (m, 4H), 1.34-1.24 (m, 6H).

Step 7: 2-(4-isopropoxy-3-methoxybenzoyl)-N—((S)-1-(methylamino)-1-oxo-5-phenylpentan-2-yl)-5-(2-phenylacetyl)octahydro-1H-pyrrolo[3,4-c]pyridine-7-carboxamide (I-154)

A mixture of 2-(4-isopropoxy-3-methoxybenzoyl)-N—((S)-1-(methylamino)-1-oxo-5-phenylpentan-2-yl)octahydro-1H-pyrrolo[3,4-c]pyridine-7-carboxamide (55 mg, 0.1 mmol), 2-phenylacetic acid (16 mg, 0.12 mmol), EDCI (23 mg, 0.12 mmol), HOBt (20 mg, 0.15 mmol) and DIEA (32 mg, 0.25 mmol) in DMA (1.0 mL) was stirred at room temperature overnight. The reaction mixture was diluted with water and extracted with EtOAc three times. The combined organic layers were washed with water and brine, dried over Na$_2$SO$_4$ and concentrated in vacuo. The residue was purified by prep-HPLC to afford 1-154 (24.2 mg, 37%) as a white solid. LCMS m/z=669.4 [M+H]$^+$; $^1$H NMR (400 MHz, CD$_3$OD) δ 7.43-6.79 (m, 13H), 4.69-3.76 (m, 9H), 3.74-3.34 (m, 3H), 3.28-2.87 (m, 2H), 2.87-2.49 (m, 6H), 2.48-2.17 (m, 2H), 2.03-1.48 (m, 4H), 1.40-1.26 (m, 7H).

The compounds listed in Table 4 were synthesized using analogous methods to those shown for 1-154, using the appropriate commercially available reagents and/or intermediates. Final examples were obtained as a mixture of diastereomers or separated by preparative HPLC or preparative TLC as indicated.

TABLE 4

Compounds made by a method analogous to I-154

| # | $^1$H NMR Chromatography conditions, if applicable | LCMS |
|---|---|---|
| I-155 | $^1$H NMR (400 MHz, CD$_3$OD) δ 8.61-8.24 (m, 1H), 7.87-7.63 (m, 1H), 7.48-6.68 (m, 10H), 4.84-3.35 (m, 11H), 3.29-2.10 (m, 11H), 2.08-1.43 (m, 4H), 1.40-1.22 (m, 8H). | m/z = 670.4 [M + H]$^+$ |
| I-156 | $^1$H NMR (400 MHz, CD$_3$OD) δ 7.65-6.71 (m, 12H), 4.77-3.78 (m, 10H), 3.76-3.34 (m, 6H), 3.28-2.48 (m, 6H), 2.37-1.47 (m, 3H), 1.45-1.24 (m, 8H). | m/z = 743.4 [M + H]$^+$ |
| I-157 | $^1$H NMR (400 MHz, CD$_3$OD) δ 7.08-6.93 (m, 1H), 6.86-6.30 (m, 12H), 4.15-3.28 (m, 6H), 3.26-2.85 (m, 3H), 2.79-2.38 (m, 5H), 2.35-1.81 (m, 10H), 1.32-0.95 (m, 3H), 0.84-0.71 (m, 7H). | m/z = 722.5 [M + H]$^+$ |
| I-158 | $^1$H NMR (400 MHz, CD$_3$OD) δ 8.99-8.84 (m, 1H), 8.53-8.33 (m, 1H), 8.20-7.89 (m, 2H), 7.88-7.53 (m, 2H), 7.29-6.72 (m, 8H), 4.74-4.31 (m, 2H), 4.31-3.98 (m, 1H), 3.88-3.35 (m, 9H), 2.84-2.17 (m, 8H), 2.05-0.98 (m, 12H). | m/z = 706.5 [M + H]$^+$ |
| I-159 | $^1$H NMR (400 MHz, CD$_3$OD) δ 7.75-6.81 (m, 13H), 4.65-3.81 (m, 8H), 3.80-3.33 (m, 7H), 2.82-2.38 (m, 8H), 1.75-1.49 (m, 3H), 1.37-1.27 (m, 8H). | m/z = 708.5 [M + H]$^+$ |
| I-160 | $^1$H NMR (400 MHz, CD$_3$OD) δ 9.34-9.11 (m, 1H), 8.20-7.72 (m, 5H), 7.29-6.79 (m, 8H), 4.72-3.80 (m, 7H), 3.78-3.34 (m, 5H), 2.89-2.28 (m, 8H), 2.08-1.55 (m, 3H), 1.37-1.26 (m, 8H). | m/z = 706.4 [M + H]$^+$ |
| I-161 | $^1$H NMR (400 MHz, CD$_3$OD) δ 7.56-7.55 (m, 1H), 7.30-7.01 (m, 12H), 6.49-6.41 (m, 1H), 5.34-4.92 (m, 2H), 4.73-3.35 (m, 11H), 3.23-2.90 (m, 2H), 2.80-1.97 (m, 8H), 1.78-1.53 (m, 4H), 1.40-1.27 (m, 8H). | m/z = 708.5 [M + H]$^+$ |
| I-162 | $^1$H NMR (400 MHz, CD$_3$OD) δ 7.42-6.64 (m, 12H), 4.67-4.05 (m, 4H), 3.88-3.34 (m, 8H), 2.79-2.47 (m, 7H), 2.43-1.95 (m, 4H), 1.82-1.35 (m, 4H), 1.35-1.20 (m, 9H). | m/z = 708.4 [M + H]$^+$ |
| I-163 | $^1$H NMR (400 MHz, CD$_3$OD) δ 8.57-6.81 (m, 10H), 4.70-3.35 (m, 15H), 3.23-2.36 (m, 9H), 1.85-1.22 (m, 11H). | m/z = 687.4 [M + H]$^+$ |
| I-164 | $^1$H NMR (400 MHz, CD$_3$OD) δ 8.56-8.28 (m, 1H), 7.81-7.66 (m, 1H), 7.41-6.83 (m, 10H), 4.66-3.82 (m, 7H), 3.79-3.33 (m, 4H), 3.28-2.78 (m, 6H), 2.76-2.36 (m, 8H), 1.74-1.54 (m, 3H), 1.35-1.27 (m, 8H). | m/z = 684.4 [M + H]$^+$ |
| I-165 | $^1$H NMR (400 MHz, CD$_3$OD) δ 8.99-8.84 (m, 2H), 8.25-8.07 (m, 2H), 7.93-7.75 (m, 1H), 7.27-7.02 (m, 7H), 7.02-6.83 (m, 1H), 4.69-3.78 (m, 8H), 3.70-3.37 (m, 5H), 2.83-2.49 (m, 7H), 1.85-1.50 (m, 3H), 1.36-1.28 (m, 8H). | m/z = 707.4 [M + H]$^+$ |
| I-166 | $^1$H NMR (400 MHz, CD$_3$OD) δ 8.28-8.17 (m, 1H), 7.29-6.80 (m, 8H), 4.66-4.19 (m, 3H), 3.90-3.77 (m, 3H), 3.75-3.34 (m, 4H), 3.29-3.08 (m, 1H), 3.06-1.95 (m, 12H), 1.86-1.50 (m, 3H), 1.38-1.19 (m, 7H). | m/z = 660.4 [M + H]$^+$ |
| I-167 | $^1$H NMR (400 MHz, CD$_3$OD) δ 8.82-8.81 (m, 1H), 8.35-8.25 (m, 1H), 8.04-7.97 (m, 1H), 7.84-7.73 (m, 2H), 7.53-7.52 (m, 1H), 7.23-6.83 (m, 8H), 4.70-3.36 (m, 12H), 3.26-3.13 (m, 2H), 2.78-2.20 (m, 8H), 1.68-1.57 (m, 3H), 1.34-1.26 (m, 9H). | m/z = 720.5 [M + H]$^+$ |
| I-168 | $^1$H NMR (400 MHz, CD$_3$OD) δ 7.81-6.76 (m, 14H), 4.69-3.72 (m, 7H), 3.66-3.33 (m, 4H), 3.22-2.59 (m, 7H), 2.51-1.99 (m, 2H), 1.79-1.52 (m, 3H), 1.35-1.27 (m, 8H). | m/z = 721.5 [M + H]$^+$ |
| I-169 | $^1$H NMR (400 MHz, CD$_3$OD) δ 7.26-6.85 (m, 8H), 4.63-4.51 (m, 1H), 4.34-4.32 (m, 1H), 4.22-4.15 (m, 1H), 3.84-3.34 (m, 12H), 3.25-3.12 (m, 1H), 2.74-2.61 (m, 7H), 2.44-2.33 (m, 1H), 2.11-2.08 (m, 1H), 2.08-2.04 (m, 1H), 1.71-1.50 (m, 5H), 1.40-1.21 (m, 12H). | m/z = 677.5 [M + H]$^+$ |
| I-170 | $^1$H NMR (400 MHz, CD$_3$OD) δ 7.56-7.55 (m, 1H), 7.30-7.01 (m, 12H), 6.49-6.41 (m, 1H), 5.23-4.85 (m, 2H), 4.67-4.52 (m, 1H), 4.36-4.22 (m, 1H), 4.20-3.97 (m, 1H), 3.88-3.82 (m, 3H), 3.78-3.71 (m, 1H), 3.62-3.36 (m, 4H), 3.23-2.90 (m, 2H), 2.73-2.57 (m, 6H), 2.45-2.36 (m, 1H), 2.20-2.00 (m, 1H), 1.78-1.40 (m, 4H), 1.36-1.27 (m, 8H). | m/z = 708.4 [M + H]$^+$ |
| I-171 | $^1$H NMR (400 MHz, CD$_3$OD) δ 7.30-6.71 (m, 9H), 6.04-5.93 (m, 1H), 4.69-4.47 (m, 1H), 4.38-3.79 (m, 6H), 3.77-3.33 (m, 4H), 3.30-3.08 (m, 2H), 2.78-2.37 (m, 8H), 2.20-2.04 (m, 3H), 1.83-1.53 (m, 3H), 1.39-1.22 (m, 7H). | m/z = 658.5 [M + H]$^+$ |
| I-172 | $^1$H NMR (400 MHz, CD$_3$OD) δ 8.04-6.81 (m, 12H), 4.67-4.02 (m, 4H), 3.91-3.67 (m, 4H), 3.66-3.34 (m, 4H), 3.22-2.70 (m, 3H), 2.70-2.46 (m, 5H), 2.45-1.92 (m, 1H), 1.85-1.50 (m, 3H), 1.50-1.12 (m, 9H). | m/z = 728.4 [M + H]$^+$ |
| I-173 | $^1$H NMR (400 MHz, CD$_3$OD) δ 9.63-8.23 (m, 12H), 6.22-5.57 (m, 4H), 5.49-5.31 (m, 4H), 5.31-4.90 (m, 5H), 4.36-3.91 (m, 9H), 3.47-2.99 (m, 3H), 2.96-2.69 (m, 10H). | m/z = 726.5 [M + H]$^+$ |
| I-174 | $^1$H NMR (400 MHz, CD$_3$OD) δ 7.64-7.50 (m, 1H), 7.34-6.82 (m, 12H), 6.52-6.40 (m, 1H), 5.40-4.97 (m, 2H), 4.75-3.34 (m, 11H), 3.27-2.90 (m, 2H), 2.81-1.97 (m, 8H), 1.86-1.43 (m, 4H), 1.40-1.25 (m, 8H). | m/z = 726.5 [M + H]$^+$ |

TABLE 4-continued

Compounds made by a method analogous to I-154

| # | ¹H NMR Chromatography conditions, if applicable | LCMS |
|---|---|---|
| I-175 | ¹H NMR (400 MHz, CD$_3$OD) δ 7.53-6.67 (m, 12H), 4.72-4.24 (m, 2H), 4.23-3.60 (m, 7H), 3.60-3.34 (m, 2H), 3.28-2.79 (m, 2H), 2.78-2.48 (m, 9H), 2.48-1.92 (m, 2H), 1.86-1.43 (m, 3H), 1.40-1.18 (m, 10H). | m/z = 722.4 [M + H]$^+$ |
| I-176 | ¹H NMR (400 MHz, CD$_3$OD) δ 7.24-6.82 (m, 11H), 6.49-6.38 (m, 1H), 4.70-4.51 (m, 2H), 4.33-3.99 (m, 4H), 3.96-3.90 (m, 1H), 3.86-3.76 (m, 5H), 3.68-3.50 (m, 3H), 3.25-2.84 (m, 2H), 2.71-2.38 (m, 8H), 2.03-1.63 (m, 3H), 1.38-1.25 (m, 9H). | m/z = 738.5 [M + H]$^+$ |
| I-177 | ¹H NMR (400 MHz, CD$_3$OD) δ 7.59-6.73 (m, 13H), 4.84-3.94 (m, 3H), 3.94-3.80 (m, 3H), 3.81-3.36 (m, 2H), 3.25-2.77 (m, 2H), 2.77-2.46 (m, 6H), 2.46-1.93 (m, 2H), 1.84-1.53 (m, 9H), 1.50-1.04 (m, 10H). | m/z = 736.5 [M + H]$^+$ |
| I-178 | ¹H NMR (400 MHz, CD$_3$OD) δ 7.43-6.72 (m, 13H), 4.76-4.18 (m, 3H), 4.16-3.73 (m, 7H), 3.61-3.38 (m, 2H), 3.13-2.90 (m, 2H), 2.77-2.37 (m, 8H), 1.77-1.24 (m, 11H). | m/z = 708.4 [M + H]$^+$ |
| I-179 | ¹H NMR (400 MHz, CD$_3$OD) δ 8.25-6.67 (m, 12H), 4.76-4.30 (m, 2H), 4.30-3.35 (m, 10H), 3.28-2.93 (m, 2H), 2.80-2.15 (m, 8H), 1.90-1.21 (m, 11H). | m/z = 709.4 [M + H]$^+$ |
| I-180 | ¹H NMR (400 MHz, CD$_3$OD) δ 7.63-6.30 (m, 12H), 4.77-3.80 (m, 6H), 3.79-3.32 (m, 5H), 3.27-2.35 (m, 9H), 2.32-1.48 (m, 3H), 1.47-1.17 (m, 8H). | m/z = 694.5 [M + H]$^+$ |
| I-181 | ¹H NMR (400 MHz, CD$_3$OD) δ 9.02-6.80 (m, 14H), 4.75-3.99 (m, 3H), 3.89-3.82 (m, 3H), 3.81-3.36 (m, 6H), 2.88-2.25 (m, 8H), 2.08-1.39 (m, 3H), 1.36-1.14 (m, 8H). | m/z = 706.5 [M + H]$^+$ |
| I-182 | ¹H NMR (400 MHz, CD$_3$OD) δ 8.15-6.69 (m, 12H), 4.73-4.08 (m, 3H), 3.92-3.40 (m, 8H), 3.01-2.32 (m, 8H), 2.09-1.19 (m, 12H). | m/z = 695.4 [M + H]$^+$ |
| I-183 | ¹H NMR (400 MHz, CD$_3$OD) δ 7.28-6.28 (m, 9H), 4.71-4.16 (m, 3H), 3.89-3.71 (m, 4H), 3.663.53 (m, 2H), 2.82-2.49 (m, 8H), 2.44-2.24 (m, 4H), 1.81-1.50 (m, 3H), 1.34-1.24 (m, 10H). | m/z = 659.5 [M + H]$^+$ |
| I-184 | ¹H NMR (400 MHz, CD$_3$OD) δ 8.66-6.81 (m, 11H), 4.72-3.96 (m, 3H), 3.95-3.35 (m, 9H), 3.28-2.58 (m, 7H), 2.57-1.99 (m, 5H), 1.95-1.51 (m, 3H), 1.50-1.16 (m, 8H). | m/z = 670.5 [M + H]$^+$ |
| I-185 | ¹H NMR (400 MHz, CD$_3$OD) δ 7.28-6.83 (m, 8H), 4.72-3.35 (m, 12H), 2.94-2.25 (m, 14H), 1.77-1.52 (m, 3H), 1.35-1.24 (m, 8H). | m/z = 690.4 [M + H]$^+$ |
| I-186 | ¹H NMR (400 MHz, CD$_3$OD) δ 7.31-6.75 (m, 8H), 4.75-4.11 (m, 5H), 4.10-3.67 (m, 5H), 3.67-3.33 (m, 3H), 3.29-2.77 (m, 2H), 2.77-2.21 (m, 8H), 2.18-1.60 (m, 3H), 1.58-1.27 (m, 7H). | m/z = 661.4 [M + H]$^+$ |
| I-187 | ¹H NMR (400 MHz, CD$_3$OD) δ 8.30-6.72 (m, 9H), 4.68-3.36 (m, 12H), 2.84-2.24 (m, 11H), 1.87-1.20 (m, 11H). | m/z = 660.4 [M + H]$^+$ |
| I-188 | ¹H NMR (400 MHz, CD3OD) δ 7.28-6.83 (m, 8H), 4.72-3.35 (m, 12H), 2.94-2.25 (m, 14H), 1.77-1.52 (m, 3H), 1.35-1.24 (m, 8H). | m/z = 674.5 [M + H]$^+$ |
| I-189 | ¹H NMR (400 MHz, CD$_3$OD) δ 7.27-5.78 (m, 10H), 4.69-4.19 (m, 4H), 3.91-3.35 (m, 8H), 2.75-2.21 (m, 11H), 1.76-1.49 (m, 3H), 1.34-1.24 (m, 8H). | m/z = 658.5 [M + H]$^+$ |
| I-190 | 1H NMR (400 MHz, CD$_3$OD) δ 7.78-6.81 (m, 12H), 4.63-4.11 (m, 4H), 3.86-3.77 (m, 3H), 3.72-3.37 (m, 4H), 2.79-2.36 (m, 7H), 1.93-1.42 (m, 4H), 1.40-1.20 (m, 10H). | m/z = 712.4 [M + H]$^+$ |
| I-191 | ¹H NMR (400 MHz, CD$_3$OD) δ 7.74-6.77 (m, 12H), 4.65-4.07 (m, 4H), 3.99-3.33 (m, 8H), 2.80-2.35 (m, 11H), 1.92-1.43 (m, 3H), 1.41-1.08 (m, 8H). | m/z = 708.5 [M + H]$^+$ |
| I-192 | ¹H NMR (400 MHz, CD$_3$OD) δ 8.79-8.67 (m, 1H), 8.60-8.45 (m, 1H), 8.06-7.85 (m, 2H), 7.29-6.81 (m, 9H), 4.68-3.75 (m, 7H), 3.73-3.34 (m, 3H), 3.27-2.83 (m, 4H), 2.78-2.40 (m, 11H), 2.38-1.91 (m, 2H), 1.88-1.47 (m, 3H), 1.45-1.29 (m, 6H). | m/z = 698.5 [M + H]$^+$ |
| I-193 | ¹H NMR (400 MHz, CD$_3$OD) δ 8.10-7.70 (m, 1H), 7.29-6.80 (m, 8H), 4.74-4.16 (m, 4H), 3.88-3.79 (m, 3H), 3.71-3.34 (m, 4H), 3.28-2.83 (m, 1H), 2.81-2.34 (m, 11H), 1.86-1.37 (m, 4H), 1.35-1.20 (m, 7H). | m/z = 660.4 [M + H]$^+$ |
| I-194 | ¹H NMR (400 MHz, CD$_3$OD) δ 9.13-8.88 (m, 1H), 8.54-8.34 (m, 2H), 7.96-7.88 (m, 1H), 7.25-6.92 (m, 8H), 4.73-4.16 (m, 3H), 3.79-3.33 (m, 8H), 2.88-2.42 (m, 8H), 1.84-1.50 (m, 4H), 1.34-1.27 (m, 8H). First eluting diastereomer purified by Prep-TLC (6% MeOH/DCM). Rf = 0.45 | m/z = 696.4 [M + H]$^+$ |

TABLE 4-continued

Compounds made by a method analogous to I-154

| # | ¹H NMR Chromatography conditions, if applicable | LCMS |
|---|---|---|
| I-195 | ¹H NMR (400 MHz, CD₃OD) δ 9.24-8.88 (m, 1H), 8.57-8.32 (m, 2H), 7.97-7.88 (m, 1H), 7.28-6.81 (m, 8H), 4.80-4.15 (m, 4H), 3.87-3.33 (m, 7H), 3.06-2.35 (m, 9H), 2.07-1.51 (m, 3H), 1.35-1.23 (m, 8H).<br>Second eluting diastereomer purified by Prep-TLC (6% MeOH/DCM). Rf = 0.4 | m/z = 696.4 [M + H]⁺ |
| I-196 | ¹H NMR (400 MHz, CD₃OD) δ 9.03-8.73 (m, 2H), 7.31-6.78 (m, 8H), 4.74-4.10 (m, 3H), 3.91-3.36 (m, 9H), 3.27-2.92 (m, 1H), 2.84-2.37 (m, 8H), 1.84-1.56 (m, 3H), 1.38-1.23 (m, 9H). | m/z = 691.3 [M + H]⁺ |
| I-197 | ¹H NMR (400 MHz, CD₃OD) δ 7.30-6.49 (m, 9H), 4.66-4.14 (m, 3H), 3.89-3.56 (m, 6H), 3.52-3.33 (m, 2H), 2.81-2.54 (m, 7H), 1.84-1.48 (m, 3H), 1.39-1.21 (m, 11H). | m/z = 679.4 [M + H]⁺ |
| I-198 | ¹H NMR (400 MHz, CD₃OD) δ 7.75-6.93 (m, 9H), 6.30-6.13 (m, 1H), 4.74-4.36 (m, 2H), 4.35-3.97 (m, 2H), 3.93-3.75 (m, 4H), 3.72-3.35 (m, 4H), 3.26-2.97 (m, 2H), 2.76-2.49 (m, 7H), 1.80-1.54 (m, 4H), 1.41-1.23 (m, 8H) | m/z = 659.5 [M + H]⁺ |
| I-199 | ¹H NMR (400 MHz, CD₃OD) δ 8.43-6.43 (m, 12H), 4.74-3.33 (m, 12H), 3.25-2.34 (m, 8H), 2.04-1.47 (m, 3H), 1.45-1.19 (m, 8H). | m/z = 694.5 [M + H]⁺ |
| I-200 | ¹H NMR (400 MHz, CD₃OD) δ 7.37-6.70 (m, 12H), 4.75-4.25 (m, 3H), 4.20-3.76 (m, 9H), 3.70-3.35 (m, 3H), 3.24-2.96 (m, 2H), 2.94-2.51 (m, 7H), 2.46-2.36 (m, 1H), 1.77-1.55 (m, 3H), 1.40-1.24 (m, 8H). | m/z = 738.5 [M + H]⁺ |
| I-201 | ¹H NMR (400 MHz, CD₃OD) δ 7.50-6.73 (m, 12H), 4.80-3.90 (m, 4H), 3.88-3.47 (m, 4H), 3.69-3.35 (m, 3H), 3.28-2.49 (m, 9H), 2.44-2.29 (m, 4H), 1.91-1.45 (m, 4H), 1.42-1.23 (m, 8H). | m/z = 722.4 [M + H]⁺ |
| I-202 | ¹H NMR (400 MHz, CD₃OD) δ 8.56-8.40 (m, 2H), 7.44-6.87 (m, 10H), 4.67-4.13 (m, 3H), 4.07-3.45 (m, 9H), 3.24-2.81 (m, 2H), 2.76-2.40 (m, 7H), 1.83-1.42 (m, 4H), 1.37-1.22 (m, 8H). | m/z = 670.4 [M + H]⁺ |
| I-203 | ¹H NMR (400 MHz, CD₃OD) δ 7.91-6.65 (m, 12H), 4.77-4.06 (m, 3H), 4.04-3.34 (m, 9H), 3.29-2.72 (m, 3H), 2.71-2.21 (m, 7H), 1.63 (m, 3H), 1.40-1.23 (m, 8H). | m/z = 733.5 [M + H]⁺ |
| I-204 | ¹H NMR (400 MHz, CD₃OD) δ 7.83-6.80 (m, 12H), 4.77-3.79 (m, 9H), 3.76-3.34 (m, 4H), 3.29-2.86 (m, 2H), 2.75-2.57 (m, 6H), 2.46-2.30 (m, 1H), 1.78-1.52 (m, 3H), 1.40-1.28 (m, 7H), 0.94-0.86 (m, 1H). | m/z = 743.4 [M + H]⁺ |
| I-205 | ¹H NMR (400 MHz, CD₃OD) δ 7.88-6.35 (m, 11H), 4.75-3.39 (m, 12H), 3.27-2.50 (m 9H), 2.44-2.20 (m, 1H), 1.82-1.21 (m, 11H). | m/z = 743.4 [M + H]⁺ |
| I-206 | ¹H NMR (400 MHz, CD₃OD) δ 9.20-9.05 (m, 1H), 8.25-8.10 (m, 1H), 7.29-6.82 (m, 8H), 4.68-3.35 (m, 12H), 2.82-2.36 (m, 8H), 1.77-1.50 (m, 3H), 1.38-1.21 (m, 8H). | m/z = 662.4 [M + H]⁺ |
| I-207 | ¹H NMR (400 MHz, CD₃OD) δ 7.30-6.80 (m, 8H), 4.68-3.74 (m, 11H), 3.72-3.36 (m, 5H), 3.23-2.30 (m, 9H), 1.88-1.52 (m, 7H), 1.37-1.23 (m, 8H). | m/z = 663.5 [M + H]⁺ |
| I-208 | ¹H NMR (400 MHz, CD₃OD) δ 9.01-8.74 (m, 1H), 8.36-8.20 (m, 1H), 7.85-7.69 (m, 1H), 7.29-6.81 (m, 8H), 4.72-4.12 (m, 3H), 3.94-3.33 (m, 9H), 3.28-3.02 (m, 1H), 2.89-2.36 (m, 8H), 1.84-1.53 (m, 3H), 1.40-1.20 (m, 8H). | m/z = 681.4 [M + H]⁺ |
| I-209 | ¹H NMR (400 MHz, CD₃OD) δ 8.04-7.86 (m, 1H), 7.70-7.40 (m, 2H), 7.29-6.82 (m, 8H), 4.83-4.10 (m, 5H), 4.04-3.34 (m, 9H), 3.28-2.92 (m, 2H), 2.80-2.36 (m, 7H), 1.83-1.55 (m, 3H), 1.42-1.19 (m, 7H). | m/z = 686.4 [M + H]⁺ |
| I-210 | ¹H NMR (400 MHz, CD₃OD) δ 9.28-8.67 (m, 3H), 8.20-7.52 (m, 5H), 7.30-6.82 (m, 8H), 4.70-3.36 (m, 12H), 2.85-2.35 (m, 8H), 1.82-1.56 (m, 2H), 1.45-1.22 (m, 8H). | m/z = 732.5 [M + H]⁺ |
| I-211 | ¹H NMR (400 MHz, CD₃OD) δ 8.69-8.44 (m, 2H), 7.30-6.82 (m, 8H), 4.74-3.34 (m, 12H), 3.27-2.98 (m, 1H), 2.87-2.33 (m, 11H), 1.86-1.58 (m, 3H), 1.37-1.23 (m, 7H). | m/z = 671.4 [M + H]⁺ |
| I-212 | ¹H NMR (400 MHz, CD₃OD) δ 8.81-8.64 (m, 1H), 8.12-8.05 (m, 1H), 7.86-7.46 (m, 2H), 7.28-6.82 (m, 8H), 4.71-3.78 (m, 9H), 3.68-3.36 (m, 3H), 3.26-2.92 (m, 2H), 2.84-2.57 (m, 6H), 2.51-1.98 (m, 2H), 1.75-1.52 (m, 3H), 1.39-1.26 (m, 8H). | m/z = 709.4 [M + H]⁺ |
| I-213 | ¹H NMR (400 MHz, CDCl₃) δ 7.76-7.62 (m, 1H), 7.37-6.94 (m, 10H), 6.88-6.74 (m, 1H), 6.61-6.50 (m, 1H), 4.63-4.20 (m, 2H), 4.04-3.27 (m, 10H), 3.25-2.45 (m, 8H), 2.06-1.50 (m, 5H), 1.45-1.29 (m, 7H). | m/z = 694.5 [M + H]⁺ |
| I-214 | ¹H NMR (400 MHz, CD₃OD) δ 8.59-6.76 (m, 11H), 4.72-3.39 (m, 12H), 3.21-2.33 (m, 11H), 1.83-1.52 (m, 3H), 1.42-1.21 (m, 10H). | m/z = 684.5 [M + H]⁺ |
| I-215 | ¹H NMR (400 MHz, CD₃OD) δ 7.28-6.22 (m, 11H), 4.66-4.18 (m, 4H), 3.87-3.79 (m, 3H), 3.79-3.58 (m, 5H), 3.49-3.33 | m/z = 658.4 [M + H]⁺ |

TABLE 4-continued

Compounds made by a method analogous to I-154

| # | ¹H NMR Chromatography conditions, if applicable | LCMS |
|---|---|---|
| | (m, 2H), 2.76-2.36 (m, 8H), 1.82-1.54 (m, 3H), 1.35-1.25 (m, 9H). | |
| I-216 | ¹H NMR (400 MHz, CD₃OD) δ 7.87-7.68 (m, 1H), 7.35-6.82 (m, 9H), 4.73-4.46 (m, 2H), 4.43-4.20 (m, 1H), 4.19-3.92 (m, 4H), 3.87-3.34 (m, 8H), 3.27-2.38 (m, 9H), 1.77-1.47 (m, 3H), 1.37-1.25 (m, 8H). | m/z = 687.4 [M + H]⁺ |
| I-217 | ¹H NMR (400 MHz, CD₃OD) δ 7.28-6.67 (m, 12H), 4.70-3.33 (m, 13H), 3.27-2.93 (m, 2H), 2.79-2.36 (m, 10H), 1.79-1.52 (m, 3H), 1.39-1.23 (m, 8H). | m/z = 722.5 [M + H]⁺ |
| I-218 | ¹H NMR (400 MHz, CD₃OD) δ 7.96-6.45 (m, 13H), 4.72-3.36 (m, 16H), 3.26-2.15 (m, 13H), 1.81-1.17 (m, 11H). | m/z = 766.5 [M + H]⁺ |
| I-219 | ¹H NMR (400 MHz, CD₃OD) δ 7.47-6.70 (m, 12H), 4.75-3.39 (m, 11H), 3.27-2.33 (m, 13H), 1.82-1.52 (m, 3H), 1.45-1.18 (m, 9H). | m/z = 722.5 [M + H]⁺ |
| I-220 | ¹H NMR (400 MHz, CD₃OD) δ 7.74-6.57 (m, 12H), 4.65-3.97 (m, 4H), 3.96-3.65 (m, 6H), 3.63-3.36 (m, 2H), 3.24-2.77 (m, 2H), 2.76-2.36 (m, 7H), 2.33-1.93 (m, 1H), 1.64 (m, 4H), 1.35-1.19 (m, 7H). | m/z = 742.3 [M + H]⁺ |
| I-221 | ¹H NMR (400 MHz, CD₃OD) δ 7.35-6.85 (m, 12H), 4.72-3.35 (m, 12H), 3.27-2.82 (m, 2H), 2.81-2.24 (m, 8H), 1.89-1.42 (m, 4H), 1.35-1.22 (m, 7H). | m/z = 742.3 [M + H]⁺ |
| I-222 | ¹H NMR (400 MHz, CD₃OD) δ 7.63-6.76 (m, 12H), 4.75-3.37 (m, 11H), 3.30-3.00 (m, 2H), 2.99-2.24 (m, 8H), 2.01-1.46 (m, 4H), 1.43-1.19 (m, 8H). | m/z = 742.3 [M + H]⁺ |
| I-223 | ¹H NMR (400 MHz, CD₃OD) δ 7.68-6.69 (m, 13H), 4.73-3.76 (m, 9H), 3.75-3.32 (m, 3H), 3.26-2.90 (m, 2H), 2.77-2.45 (m, 6H), 2.43-2.34 (m, 1H), 2.32-1.85 (m, 1H), 1.79-1.38 (m, 4H), 1.38-1.22 (m, 7H). | m/z = 708.4 [M + H]⁺ |
| I-224 | ¹H NMR (400 MHz, CD₃OD) δ 8.53-8.33 (m, 2H), 7.81-7.66 (m, 1H), 7.47-6.83 (m, 9H), 4.75-3.80 (m, 9H), 3.79-3.38 (m, 4H), 2.77-2.54 (m, 7H), 2.46-2.34 (m, 1H), 1.73-1.44 (m, 4H), 1.39-1.25 (m, 8H). | m/z = 670.4 [M + H]⁺ |
| I-225 | ¹H NMR (400 MHz, CD₃OD) δ 7.67-6.64 (m, 12H), 4.77-3.79 (m, 9H), 3.77-3.63 (m, 3H), 3.62-3.36 (m, 3H), 3.27-3.02 (m, 2H), 2.97-2.79 (m, 1H), 2.77-2.55 (m, 6H), 2.44-2.37 (m, 1H), 2.24-2.00 (m, 1H), 1.86-1.50 (m, 4H), 1.41-1.26 (m, 8H). | m/z = 756.5 [M + H]⁺ |
| I-226 | ¹H NMR (400 MHz, CD₃OD) δ 7.74-6.31 (m, 12H), 4.77-4.11 (m, 4H), 4.08-3.38 (m, 6H), 3.26-2.81 (m, 2H), 2.81-2.07 (m, 9H), 2.07-1.55 (m, 3H), 1.54-1.16 (m, 12H). | m/z = 756.5 [M + H]⁺ |
| I-227 | ¹H NMR (400 MHz, CD₃OD) δ 7.97-6.38 (m, 11H), 4.75-3.90 (m, 4H), 3.87-3.40 (m, 7H), 3.20-2.52 (m, 8H), 2.46-1.51 (m, 5H), 1.42-1.17 (m, 10H). | m/z = 776.4 [M + H]⁺ |
| I-228 | ¹H NMR (400 MHz, CD₃OD) δ 7.64-6.79 (m, 12H), 4.66-4.08 (m, 3H), 3.89-3.34 (m, 8H), 3.29-2.34 (m, 12H), 1.85-1.46 (m, 3H), 1.43-1.17 (m, 8H). | m/z = 708.4 [M + H]⁺ |
| I-229 | ¹H NMR (400 MHz, CD₃OD) δ 7.31-6.54 (m, 12H), 4.74-3.97 (m, 4H), 3.96-3.69 (m, 8H), 3.67-3.36 (m, 3H), 3.27-2.78 (m, 3H), 2.79-1.91 (m, 8H), 1.75-1.43 (m, 3H), 1.39-1.23 (m, 7H). | m/z = 738.4 [M + H]⁺ |
| I-230 | ¹H NMR (400 MHz, CD₃OD) δ 8.65-8.31 (m, 3H), 7.28-6.88 (m, 8H), 4.73-3.35 (m, 14H), 3.25-2.33 (m, 10H), 1.80-1.54 (m, 3H), 1.38-1.26 (m, 8H). | m/z = 671.5 [M + H]⁺ |
| I-231 | ¹H NMR (400 MHz, CD₃OD) δ 7.59-6.69 (m, 12H), 4.83-3.38 (m, 12H), 3.29-2.21 (m, 14H), 2.02-1.58 (m, 3H), 1.49-1.21 (m, 8H). | m/z = 722.5 [M + H]⁺ |
| I-232 | ¹H NMR (400 MHz, CD₃OD) δ 8.41 (m, 1H), 7.27-6.84 (m, 9H), 4.68-4.19 (m, 4H), 3.87-3.77 (m, 4H), 3.70-3.57 (m, 2H), 2.78-2.58 (m, 7H), 2.48-2.36 (m, 2H), 1.74-1.57 (m, 2H), 1.36-1.22 (m, 9H).<br>First eluting diastereomer purified by prep-HPLC on an Agilent 10 Prep-C18 column (21.2 mm I.D. × 25 cm, 10 um), using H₂O/ACN 0.1% TFA at a flow rate of 20 mL/min (wave length 214 nm). Rt = 10.1 min | m/z = 680.4 [M + H]⁺ |
| I-233 | ¹H NMR (400 MHz, CD₃OD) δ 8.48-8.33 (m, 1H), 7.32-6.93 (m, 9H), 4.79-4.15 (m, 4H), 3.86-3.80 (m, 3H), 3.69-3.57 (m, 3H), 3.50-3.42 (m, 1H), 2.81-2.55 (m, 8H), 1.78-1.58 (m, 4H), 1.36-1.28 (m, 8H).<br>Second eluting diastereomer purified by prep-HPLC on an Agilent 10 Prep-C18 column (21.2 mm I.D. × 25 cm, 10 um), using H₂O/ACN 0.1% TFA at a flow rate of 20 mL/min (wave length 214 nm). Rt = 11.8 min | m/z = 680.4 [M + H]⁺ |
| I-234 | ¹H NMR (400 MHz, CD₃OD) δ 7.57-6.47 (m, 12H), 4.75-3.72 (m, 11H), 3.66-3.33 (m, 3H), 3.23-2.68 (m, 5H), 2.66-2.36 (m, 5H), 2.01-1.53 (m, 4H), 1.45-1.20 (m, 9H), 0.62-0.55 (m, 2H), 0.37-0.28 (m, 2H). | m/z = 778.5 [M + H]⁺ |

TABLE 4-continued

Compounds made by a method analogous to I-154

| # | ¹H NMR Chromatography conditions, if applicable | LCMS |
|---|---|---|
| I-235 | ¹H NMR (400 MHz, CD$_3$OD) δ 7.61-6.49 (m, 12H), 4.65-4.23 (m, 2H), 4.20-3.74 (m, 9H), 3.73-3.34 (m, 3H), 3.21-2.85 (m, 2H), 2.82-2.15 (m, 8H), 2.07-1.44 (m, 4H), 1.40-1.23 (m, 8H). | m/z = 738.4 [M + H]$^+$ |
| I-236 | ¹H NMR (400 MHz, CD$_3$OD) δ 7.83-6.37 (m, 13H), 4.72-4.14 (m, 3H), 3.92-3.74 (m, 3H), 3.67-3.42 (m, 1H), 3.27-2.22 (m, 11H), 1.85-1.27 (m, 11H), 1.27-0.72 (m, 6H). | m/z = 734.5 [M + H]$^+$ |
| I-237 | ¹H NMR (400 MHz, CD$_3$OD) δ 7.99-6.52 (m, 12H), 4.79-3.78 (m, 9H), 3.74-3.35 (m, 4H), 3.26-2.14 (m, 11H), 1.77-1.53 (m, 3H), 1.33 (m, 6H). | m/z = 786.3 [M + H]$^+$ |

Synthesis of N-(5-benzylpyridin-3-yl)-5-(2-(6-chloro-1H-indol-3-yl)acetyl)-2-(4-isopropoxy-3-methoxybenzoyl)octahydro-1H-pyrrolo[3,4-c]pyridine-7-carboxamide I-238

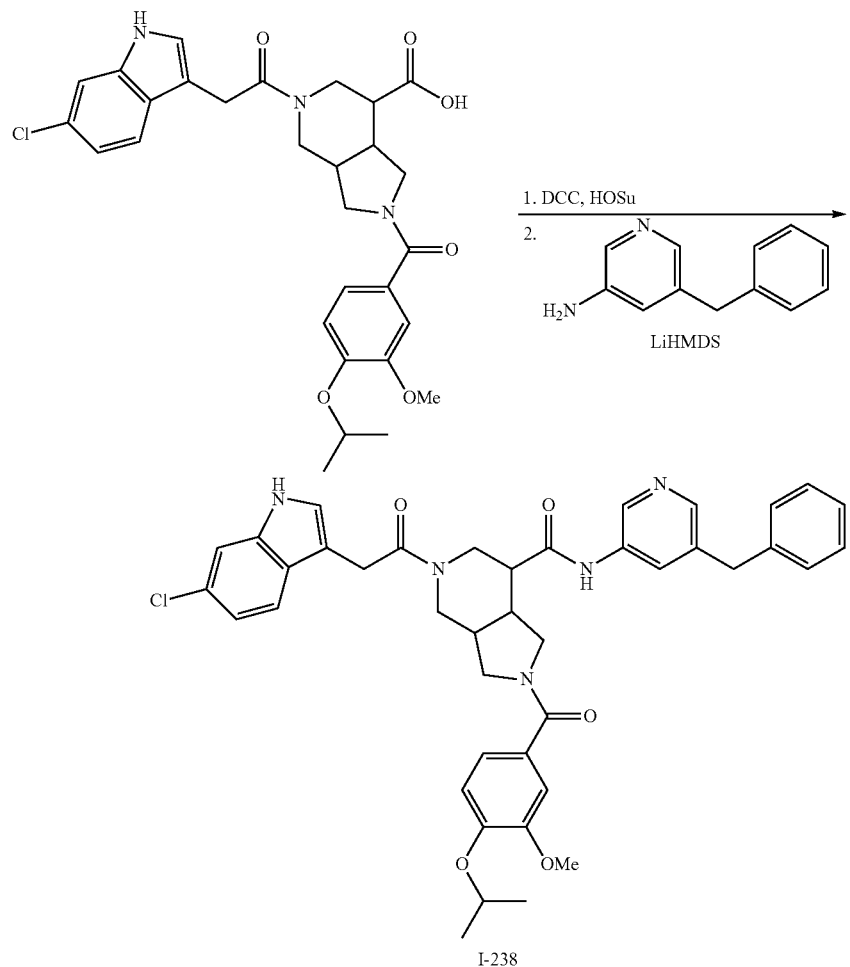

I-238

Step 1:

To a solution of 5-(2-(6-chloro-1H-indol-3-yl)acetyl)-2-(4-isopropoxy-3-methoxybenzoyl)octahydro-1H-pyrrolo[3,4-c]pyridine-7-carboxylic acid (100 mg, 0.18 mmol; see synthesis of I-88) in DCM (3 mL) was added DCC (31.0 mg, 0.27 mmol) and HOSu (42 mg, 0.36 mmol). The mixture was stirred for 8 h. The resulting mixture was filtered and concentrated to afford the active ester as a white solid. LCMS m/z=651.2 [M+H]$^+$.

Step 2:

To a solution of 5-benzylpyridin-3-amine (50 mg, 0.077 mmol) in THF (5 mL) was added LiHMDS (2M in THF, 0.153 mmol) dropwise at 0° C. After stirring for 30 min, the active ester was added to the mixture and stirred 1-238 (5 mg, 10%) as a white solid. LCMS m/z=720.3 [M+H]$^+$; $^1$H NMR (400 MHz, CD$_3$OD) δ 9.20-8.89 (m, 1H), 8.46-8.30 (m, 1H), 8.20-7.80 (m, 1H), 7.63-6.72 (m, 12H), 4.77-4.42 (m, 1H), 4.38-4.05 (m, 3H), 4.02-3.88 (m, 2H), 3.87-3.55 (m, 6H), 3.55-3.33 (m, 2H), 3.25-3.09 (m, 1H), 2.96-1.99 (m, 4H), 1.46-1.20 (m, 8H).

The compounds listed in Table 5 were synthesized using analogous methods to those shown for 1-238, using the appropriate commercially available reagents and/or intermediates. Final examples were obtained as a mixture of diastereomers.

TABLE 5

Compounds made by a method analogous to I-229

| # | $^1$H NMR | LCMS |
|---|---|---|
| I-239 | $^1$H NMR (400 MHz, CD$_3$OD) δ 9.07-6.28 (m, 15H), 4.79-4.19 (m, 3H), 4.19-3.35 (m, 11H), 3.27-3.00 (m, 1H), 2.96-1.99 (m, 4H), 1.45-1.18 (m, 7H). | m/z = 720.3 [M + H]$^+$ |
| I-240 | $^1$H NMR (400 MHz, CD$_3$OD) δ 8.51-8.29 (m, 1H), 8.08-7.68 (m, 2H), 7.57-7.26 (m, 4H), 7.24-6.69 (m, 8H), 4.81-4.29 (m, 2H), 4.27-3.70 (m, 7H), 3.60-3.47 (m, 2H), 3.27-2.24 (m, 5H), 1.42-1.25 (m, 7H). | m/z = 722.3 [M + H]$^+$ |
| I-241 | $^1$H NMR (400 MHz, CD$_3$OD) δ 9.25-8.90 (m, 1H), 8.32-8.06 (m, 1H), 7.72-6.75 (m, 13H), 4.80-4.23 (m, 4H), 4.06-3.35 (m, 10H), 3.23-3.03 (m, 1H), 2.90-2.61 (m, 2H), 2.57-2.34 (m, 1H), 1.68-0.98 (m, 8H). | m/z = 720.4 [M + H]$^+$ |

Synthesis of 5-(2-(6-chloro-1H-indol-3-yl)acetyl)-N-((2S,3R)-3-(cyclohexylmethoxy)-1-(methylamino)-1-oxobutan-2-yl)-2-(4-cyclopropoxybenzoyl)octahydro-1H-pyrrolo[3,4-c]pyridine-7-carboxamide I-242

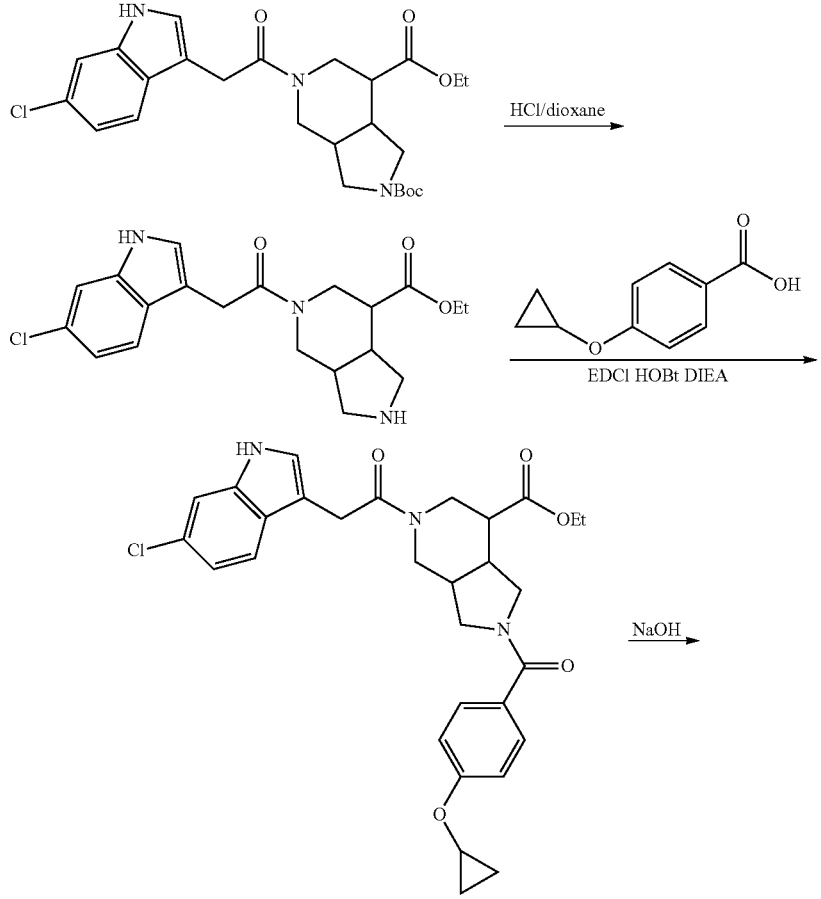

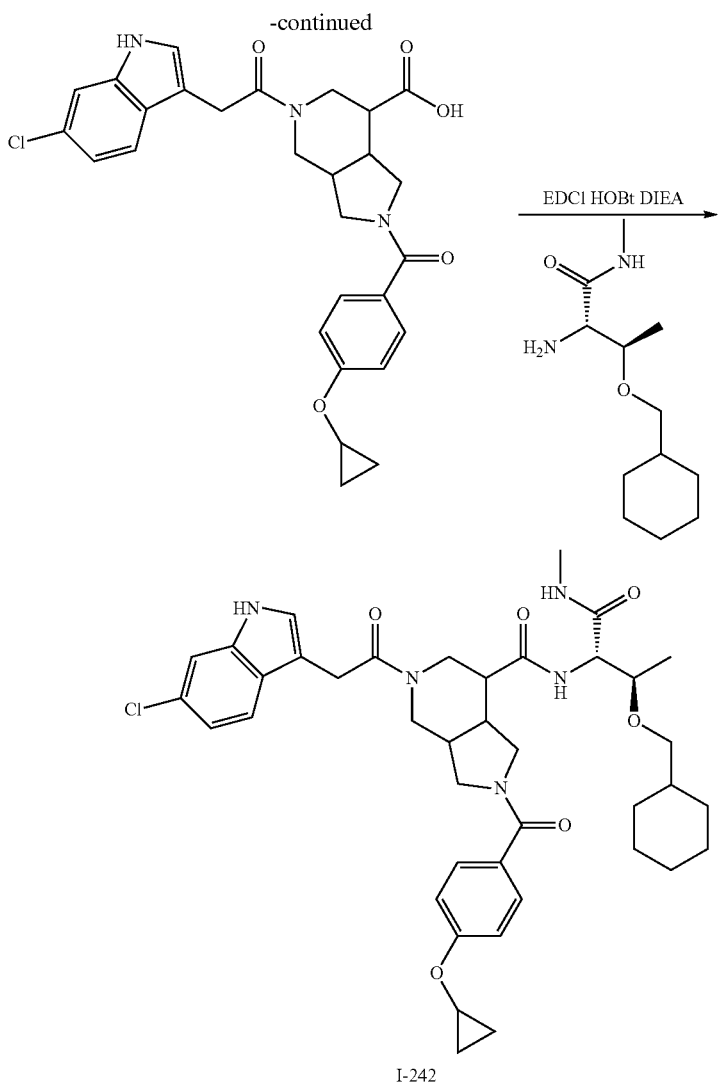

I-242

Step 1: ethyl 5-(2-(6-chloro-1H-indol-3-yl)acetyl)octahydro-1H-pyrrolo[3,4-c]pyridine-7-carboxylate To a solution of 2-(tert-butyl) 7-ethyl 5-(2-(6-chloro-1H-indol-3-yl)acetyl)octahydro-2H-pyrrolo[3,4-c]pyridine-2,7-dicarboxylate (500 mg, 1.02 mmol; see synthesis of I-1) in DCM (10 mL) was added HCl (4M in dioxane, 10 mL). The resulting mixture was stirred for 2 h. The solvent was removed to afford the product (500 mg, quant.). LCMS m/z=390.2 [M+H]$^+$.

Step 2: ethyl 5-(2-(6-chloro-1H-indol-3-yl)acetyl)-2-(4-cyclopropoxybenzoyl)octahydro-1H-pyrrolo[3,4-c]pyridine-7-carboxylate In a similar manner to the procedure reported in Step 1 of the preparation of I-1, the coupling of ethyl 5-(2-(6-chloro-1H-indol-3-yl)acetyl)octahydro-1H-pyrrolo[3,4-c]pyridine-7-carboxylate and 4-cyclopropoxybenzoic acid gave the product (413 mg, 76%) after column chromatography (2.5% MeOH/DCM) as a white solid.

Step 3: 5-(2-(6-chloro-1H-indol-3-yl)acetyl)-2-(4-cyclopropoxybenzoyl)octahydro-1H-pyrrolo[3,4-c]pyridine-7-carboxylic acid To a solution of ethyl 5-(2-(6-chloro-1H-indol-3-yl)acetyl)-2-(4-cyclopropoxybenzoyl)octahydro-1H-pyrrolo[3,4-c]pyridine-7-carboxylate (413 mg, 0.753 mmol) in MeOH (5 mL) was added aqueous NaOH (1M, 3 mL). The resulting mixture was stirred for 3 h. The solvent was removed under vacuum, the residue diluted with water and the pH adjusted to 1 by addition of 1M HCl. The aqueous layer was extracted with EtOAc three times. The combined organic layers were washed with water, brine and dried over Na$_2$SO$_4$. Removal of the solvent afforded the product (381.0 mg, 97%) as a white solid. LCMS m/z=522.3 [M+H]$^+$.

Step 4: 5-(2-(6-chloro-1H-indol-3-yl)acetyl)-N-((2S,3R)-3-(cyclohexylmethoxy)-1-(methylamino)-1-oxobutan-2-yl)-2-(4-cyclopropoxybenzoyl)octahydro-1H-pyrrolo[3,4-c]pyridine-7-carboxamide In a similar manner to the procedure in Step 1 of the preparation of I-1, the coupling of 5-(2-(6-chloro-1H-indol- 3-yl)acetyl)-2-(4-cyclopropoxybenzoyl)octahydro-1H-pyrrolo[3,4-c]pyridine-7-carboxylic acid and (2S,3R)-2-amino-3-(cyclohexylmethoxy)-N-methylbutanamide gave I-242 (40 mg, 51%) after column chromatography (2.8% MeOH/DCM) as a white solid. LCMS m/z=732.4 [M+H]+; 1H NMR (400 MHz, CD3OD) δ 8.06-6.94 (m, 8H), 4.68-3.35 (m, 10H), 3.27-2.07 (m, 9H), 1.80-1.58 (m, 5H), 1.57-1.39 (m, 1H), 1.38-1.06 (m, 7H), 1.04-0.72 (m, 7H).

The compounds listed in Table 6 were synthesized using analogous methods to those shown for 1-242, using the appropriate commercially available reagents and/or intermediates. Final examples were obtained as a mixture of diastereomers.

TABLE 6

Compounds made by a method analogous to I-242

| # | 1H NMR | LCMS |
|---|--------|------|
| I-243 | 1H NMR (400 MHz, CD3OD) δ 7.65-6.93 (m, 12H), 4.82-4.26 (m, 5H), 4.25-3.33 (m, 8H), 3.27-2.73 (m, 2H), 2.71-2.37 (m, 2H), 1.37-1.28 (m, 2H), 1.20-1.15 (m, 4H), 1.06-0.83 (m, 2H), 0.83-0.64 (m, 3H). | m/z = 730.4 [M + H]+ |
| I-244 | 1H NMR (400 MHz, CD3OD) δ 7.74-6.87 (m, 12H), 4.73-3.34 (m, 13H), 3.28-1.98 (m, 6H), 1.27-1.14 (m, 2H), 0.92-0.63 (m, 5H). | m/z = 730.4 [M + H]+ |
| I-245 | 1H NMR (400 MHz, CD3OD) δ 7.68-6.89 (m, 12H), 4.69-4.27 (m, 4H), 4.21-3.35 (m, 8H), 3.26-1.97 (m, 6H), 1.37-0.61 (m, 7H). | m/z = 730.4 [M + H]+ |
| I-246 | 1H NMR (400 MHz, CD3OD) δ 7.67-6.88 (m, 12H), 4.79-3.35 (m, 12H), 3.26-1.88 (m, 6H), 1.28-0.61 (m, 7H) | m/z = 730.4 [M + H]+ |

Synthesis of 2-(3,4-dichlorobenzoyl)-5-(2-(6-methoxy-1H-indol-3-yl)acetyl)-N—((S)-1-(methylamino)-1-oxo-5-phenylpentan-2-yl)octahydro-1H-pyrrolo[3,4-c]pyridine-7-carboxamide I-247

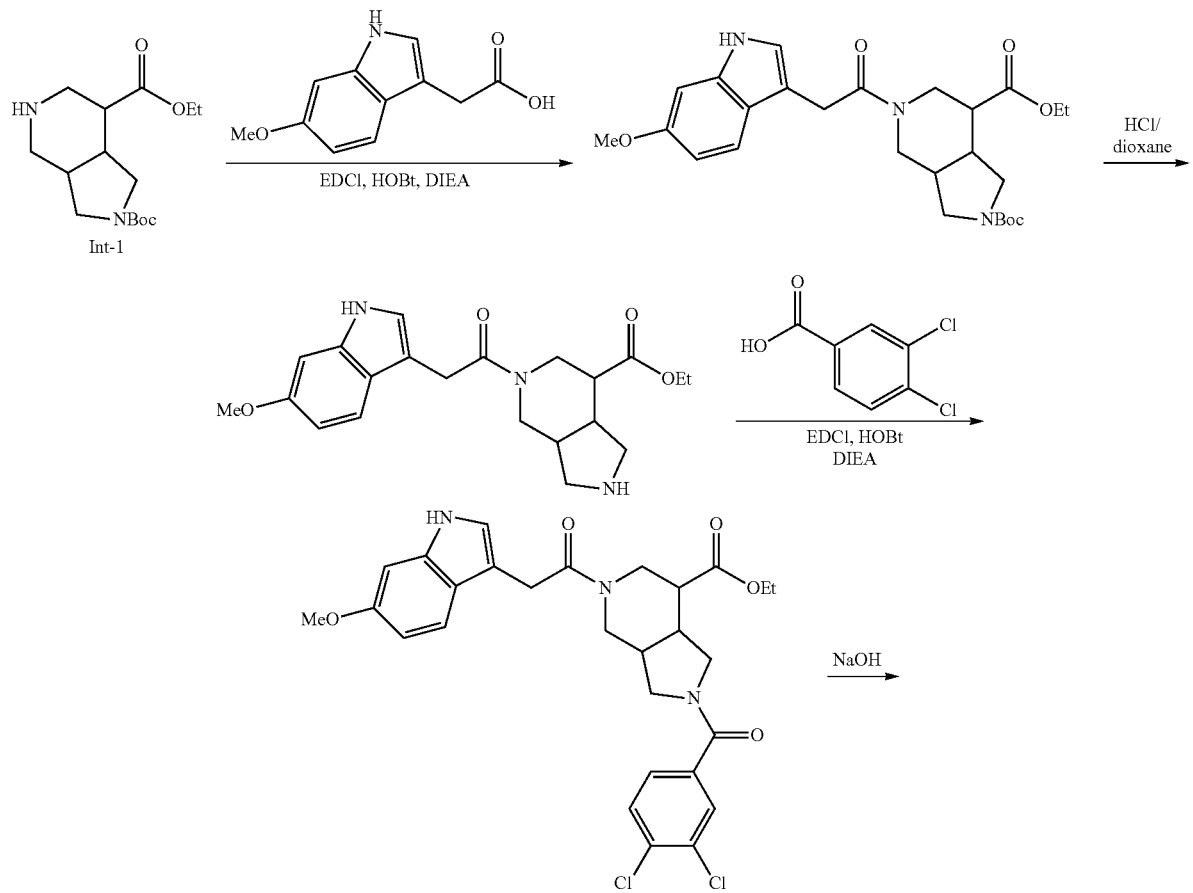

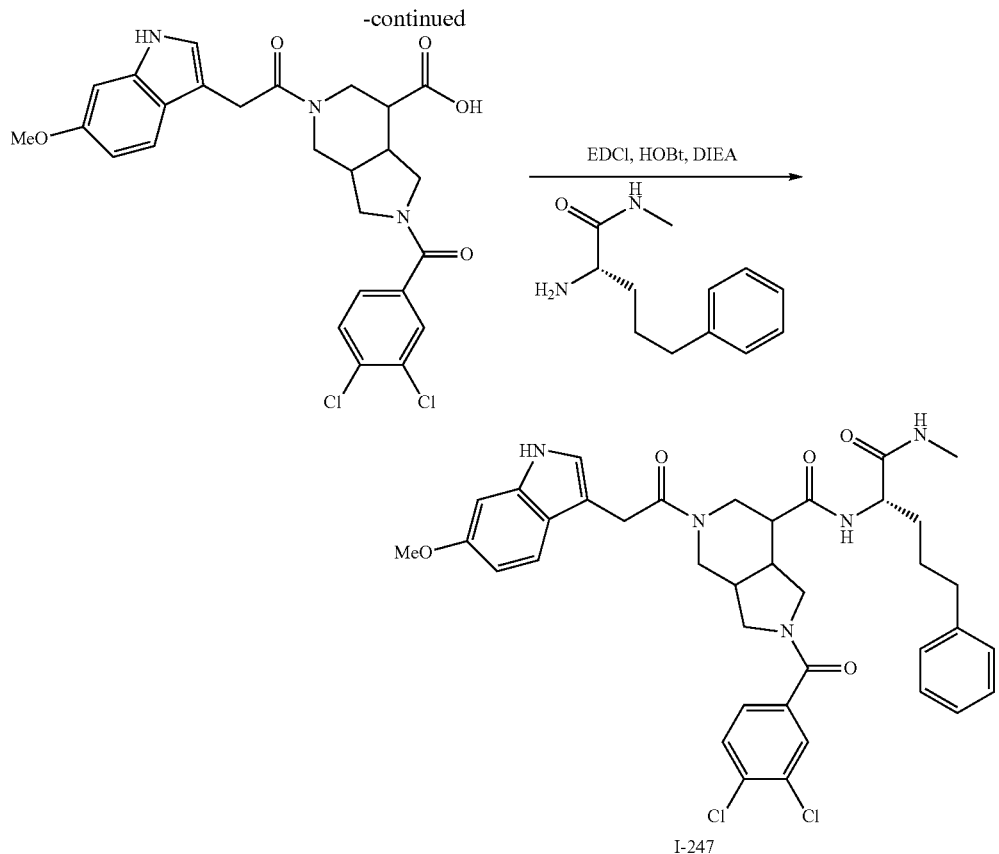

Step 1: 2-(tert-butyl) 7-ethyl 5-(2-(6-methoxy-1H-indol-3-yl)acetyl)octahydro-2H-pyrrolo[3,4-c]pyridine-2,7-dicarboxylate To a solution of Int-1 (400 mg, 1.34 mmol) in DMA (10 mL) was added 2-(6-methoxy-1H-indol-3-yl)acetic acid (330 mg, 1.61 mmol), EDCI (385 mg, 2.01 mmol), HOBt (217 mg, 1.61 mmol) and DIPEA (520 mg, 4.02 mmol). The resulting mixture was stirred overnight. Water was added and the mixture was extracted with EtOAc three times. The combined organic layers were washed with water, brine and dried over Na$_2$SO$_4$. The solvent was then removed and the crude purified by column chromatography (2% MeOH/DCM) to afford the product (410 mg, 63%) as a white solid. LCMS m/z=486 [M+H]$^+$; $^1$H NMR (400 MHz, CD$_3$OD) δ 7.46 (dd, J=21.3, 8.6 Hz, 1H), 7.07-6.99 (m, 1H), 6.92-6.85 (m, 1H), 6.69 (td, J=8.5, 3.9 Hz, 1H), 4.60 (s, 1H), 4.31 (dt, J=16.2, 12.8 Hz, 1H), 4.20-3.94 (m, 3H), 3.80 (d, J=4.9 Hz, 3H), 3.73 (t, J=13.9 Hz, 1H), 3.31 (dq, J=4.2, 2.9, 2.2 Hz, 3H), 3.05 (s, 3H), 2.92 (s, 3H), 1.45-1.36 (m, 9H), 1.28-1.17 (m, 3H).

Step 2: ethyl 5-(2-(6-methoxy-M-indol-3-yl)acetyl)octahydro-1H-pyrrolo[3,4-c]pyridine-7-carboxylate hydrochloride To a solution of 2-(tert-butyl) 7-ethyl 5-(2-(6-methoxy-1H-indol-3-yl)acetyl)octahydro-2H-pyrrolo[3,4-c]pyridine-2,7-dicarboxylate (410 mg, 0.84 mmol) in DCM (3 mL) was added HCl (4M in dioxane, 3 mL). The resulting mixture was stirred for 3 h. The solvent was removed to afford the target compound (443 mg, quant.). LCMS m/z=386 [M+H]$^+$.

Step 3: ethyl 2-(3,4-dichlorobenzoyl)-5-(2-(6-methoxy-M-indol-3-yl)acetyl)octahydro-M-pyrrolo[3,4-c]pyridine-7-carboxylate In a similar manner to the procedure in Step 1, the coupling of ethyl 5-(2-(6-methoxy-1H-indol-3-yl)acetyl)octahydro-1H-pyrrolo[3,4-c]pyridine-7-carboxylate hydrochloride and 3,4-dichlorobenzoic acid gave the desired product (86 mg, 26%) after column chromatography (2% MeOH/DCM) as a white solid. LCMS m/z=558 [M+H]$^+$; $^1$H NMR (400 MHz, CD$_3$OD) δ 8.30-6.46 (m, 7H), 4.54-4.08 (m, 1H), 4.08-3.83 (m, 1H), 3.82-3.61 (m, 4H), 3.61-3.34 (m, 2H), 3.28-3.12 (m, 1H), 3.12-2.88 (m, 1H), 2.81-2.32 (m, 2H), 2.30-1.19 (m, 6H), 1.18-0.61 (m, 3H).

Step 4: 2-(3,4-dichlorobenzoyl)-5-(2-(6-methoxy-M-indol-3-yl)acetyl)octahydro-M-pyrrolo[3,4-c]pyridine-7-carboxylic acid To a solution of ethyl 2-(3,4-dichlorobenzoyl)-5-(2-(6-methoxy-1H-indol-3-yl)acetyl)octahydro-1H-pyrrolo[3,4-c]pyridine-7-carboxylate (86 mg, 0.15 mmol) in MeOH (3 mL) was added aqueous NaOH (1M, 3 mL). The mixture was stirred at room temperature for 5 h then the solvent was removed under vacuum. The residue obtained was diluted with water and the pH adjusted to ~1 by addition of 1M HCl. The aqueous layer was extracted with EtOAc three times and the combined organic layers were washed with water, brine and dried over Na₂SO₄. Removal of the solvent afforded the product (48 mg, 59%) as a white solid. LCMS m/z=530 [M+H]⁺.

Step 5: 2-(3,4-dichlorobenzoyl)-5-(2-(6-methoxy-1H-indol-3-yl)acetyl)-N—((S)-1-(methylamino)-1-oxo-5-phenylpentan-2-yl)octahydro-1H-pyrrolo[3,4-c]pyridine-7-carboxamide In a similar manner to the procedure in Step 1, the coupling of 2-(3,4-dichlorobenzoyl)-5-(2-(6-methoxy-1H-indol-3-yl)acetyl)octahydro-1H-pyrrolo[3,4-c]pyridine-7-carboxylic acid and (S)-2-amino-N-methyl-5-phenylpentanamide gave 1-247 (10 mg, 15%) after column chromatography (2% MeOH/DCM) as a white solid. LC-MS m/z=718.3 [M+H]⁺; ¹H NMR (400 MHz, CD₃OD) δ 7.77-6.60 (m, 12H), 4.66-4.01 (m, 3H), 4.01-3.70 (m, 5H), 3.69-3.44 (m, 2H), 3.43-3.33 (m, 1H), 3.29-2.14 (m, 11H), 2.06-1.31 (m, 5H).

The compounds listed in Table 7 were synthesized using analogous methods to those shown for 1-247, using the appropriate commercially available reagents and/or intermediates. Final examples were obtained as a mixture of diastereomers.

TABLE 7

Compounds made by a method analogous to I-247

| Example | ¹H NMR | LCMS |
|---|---|---|
| I-248 | ¹H NMR (400 MHz, CD₃OD) δ 8.56-6.39 (m, 12H), 4.60-4.20 (m, 2H), 4.19-3.98 (m, 1H), 3.98-3.64 (m, 5H), 3.62-3.36 (m, 2H), 3.31-2.78 (m, 4H), 2.76-2.60 (m, 5H), 2.57-2.36 (m, 2H), 2.03-1.33 (m, 5H), 1.25-0.74 (m, 1H). | m/z = 751.2 [M + H]⁺ |

Synthesis of 5-(2-(6-chloro-1H-indol-3-yl)acetyl)-N-((2S,3S)-3-(cyclohexylmethoxy)-1-(methylamino)-1-oxobutan-2-yl)-2-(3-phenyl-1H-pyrazole-5-carbonyl)octahydro-1H-pyrrolo[3,4-c]pyridine-7-carboxamide I-249

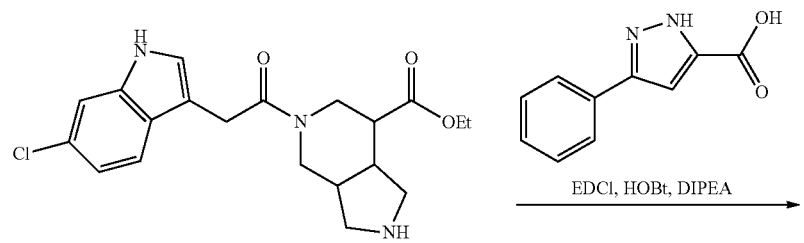

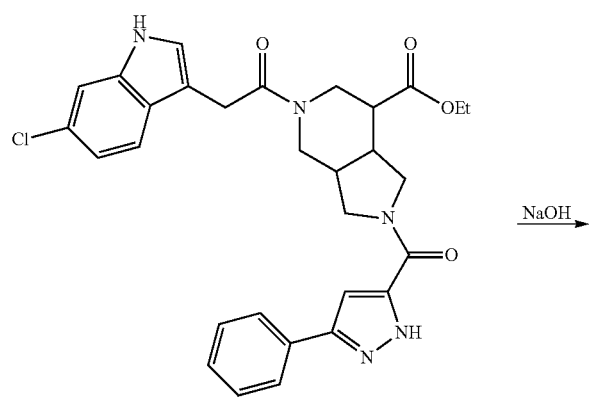

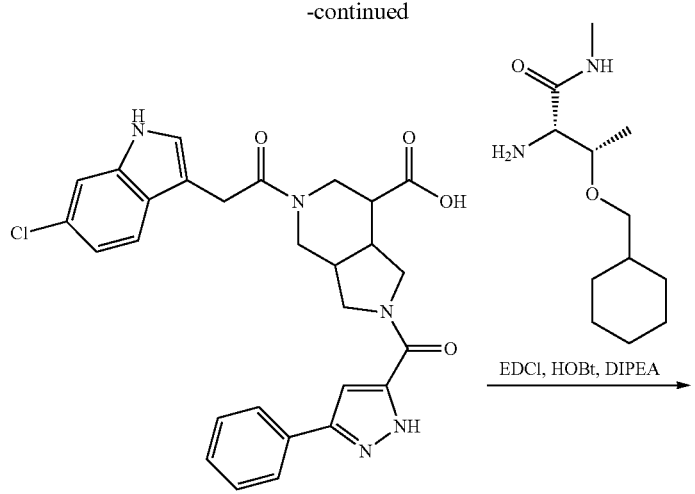

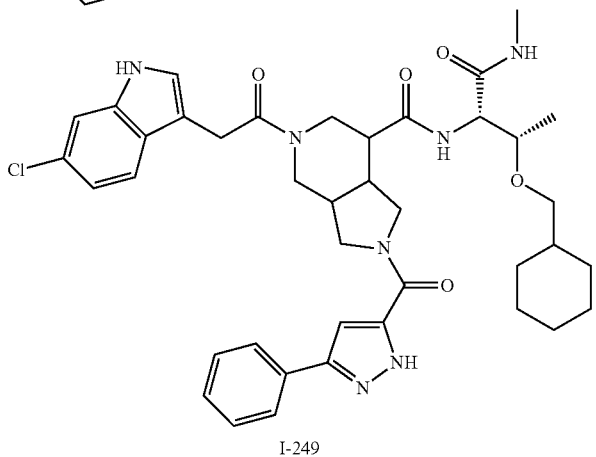

I-249

Step 1: ethyl 5-(2-(6-chloro-1H-indol-3-yl)acetyl)-2-(3-phenyl-1H-pyrazole-5-carbonyl)octahydro-1H-pyrrolo[3,4-c]pyridine-7-carboxylate To a solution of ethyl 5-(2-(6-chloro-1H-indol-3-yl)acetyl)octahydro-1H-pyrrolo[3,4-c]pyridine-7-carboxylate (358 mg, 0.92 mmol; see synthesis of I-242) in DMF (5.0 mL) was added 3-phenyl-1H-pyrazole-5-carboxylic acid (207 mg, 1.1 mmol), EDCI (264 mg, 1.38 mmol), HOBt (186 mg, 1.38 mmol) and DIPEA (593 mg, 4.59 mmol). The resulting mixture was stirred for 14 h. Water was then added and the aqueous extracted with EtOAc three times. The combined organic layers were washed with water and brine and dried over $Na_2SO_4$. The solvent was removed and the crude purified by column chromatography (2% MeOH/DCM) to give ethyl 5-(2-(6-chloro-1H-indol-3-yl)acetyl)-2-(3-phenyl-1H-pyrazole-5-carbonyl)octahydro-1H-pyrrolo[3,4-c]pyridine-7-carboxylate (350 mg, 68%) as a yellow solid.

Step 2: 5-(2-(6-chloro-1H-indol-3-yl)acetyl)-2-(3-phenyl-1H-pyrazole-5-carbonyl)octahydro-1H-pyrrolo[3,4-c]pyridine-7-carboxylic acid To the solution of ethyl 5-(2-(6-chloro-1H-indol-3-yl)acetyl)-2-(3-phenyl-1H-pyrazole-5-carbonyl)octahydro-1H-pyrrolo[3,4-c]pyridine-7-carboxylate (350 mg, 0.62 mmol) in a mixture of THF and $H_2O$ (5.0 mL/1.0 mL) was added NaOH (75 mg, 1.87 mmol) and the solution was stirred for 4 h. The pH was adjusted to 2 by addition of 1N HCl then concentrated to give the product (450 mg, quant.) as a white solid. LCMS m/z=532.1 $[M+H]^+$.

Step 3: 5-(2-(6-chloro-1H-indol-3-yl)acetyl)-N-((2S,3S)-3-(cyclohexylmethoxy)-1-(methylamino)-1-oxobutan-2-yl)-2-(3-phenyl-1H-pyrazole-5-carbonyl)octahydro-1H-pyrrolo[3,4-c]pyridine-7-carboxamide In a similar manner reported for synthesis of the product of Step 1, the coupling of 5-(2-(6-chloro-1H-indol-3-yl)acetyl)-2-(3-phenyl-1H-pyrazole-5-carbonyl)octahydro-1H-pyrrolo[3,4-c]pyridine-7-carboxylic acid and (2S,3S)-2-amino-3-(cyclohexylmethoxy)-N-methylbutanamide afforded I-249 (20 mg, 28%) as a white solid after prep-TLC (6% MeOH/DCM). LCMS m/z=742.3 $[M+H]^+$; $^1$H NMR (400 MHz, $CD_3OD$) δ 8.00-6.80 (m, 10H), 4.65-3.40 (m, 11H), 3.25-2.46 (m, 9H), 1.79-1.54 (m, 5H), 1.26-0.73 (m, 10H).

The compounds listed in Table 8 were synthesized using analogous methods to those shown for I-249, using the appropriate commercially available reagents and/or intermediates. Final examples were obtained as a mixture of diastereomers.

TABLE 8

Compounds made by a method analogous to I-249

| Example | ¹H NMR Chromatography conditions, if applicable | LCMS |
|---|---|---|
| I-250 | ¹H NMR (400 MHz, CD$_3$OD) δ 8.07-6.74 (m, 15H), 4.71-3.45 (m, 13H), 3.29-2.03 (m, 9H), 1.48-1.37 (m, 1H), 1.29-1.03 (m, 3H) | m/z = 736.5 [M + H]$^+$ |
| I-251 | ¹H NMR (400 MHz, CD$_3$OD) δ 8.00-6.73 (m, 10H), 4.67-3.42 (m, 11H), 3.24-2.21 (m, 10H), 1.82-1.39 (m, 6H), 1.22-0.83 (m, 7H). | m/z = 742.4 [M + H]$^+$ |
| I-252 | ¹H NMR (400 MHz, CD$_3$OD) δ 7.91-6.73 (m, 15H), 4.69-4.33 (m, 4H), 4.28-3.72 (m, 6H), 3.70-3.47 (m, 2H), 3.23-2.74 (m, 3H), 2.71-2.44 (m, 4H), 2.44-1.85 (m, 1H), 1.25-0.83 (m, 4H). | m/z = 736.5 [M + H]$^+$ |

Synthesis of 2-(4-isopropoxy-3-methoxybenzoyl)-N—((S)-1-(methylamino)-1-oxo-5-phenylpentan-2-yl)-5-(2-(quinolin-4-yl)acetyl)octahydro-1H-pyrrolo[3,4-c]pyridine-7-carboxamide I-253

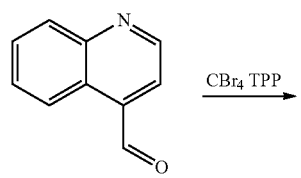

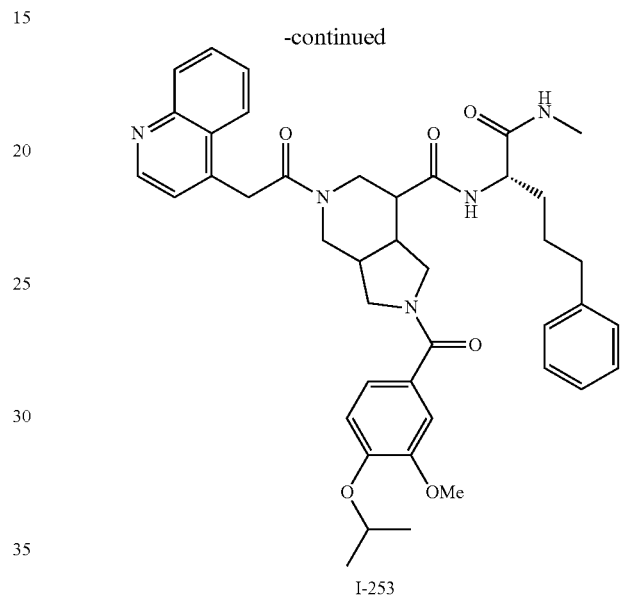

I-253

Step 1: 4-(2,2-dibromovinyl)quinoline

A mixture of quinoline-4-carbaldehyde (500 mg, 3.18 mmol), carbon tetrabromide (3.16 g, 9.54 mmol) and triphenylphosphine (5.19 g, 19.08 mmol) in DCM (10 mL) wad stirred at room temperature for 1.5 h under an atmosphere of N$_2$. Water was added and the aqueous extracted with EtOAc. The combined organic layers were washed with water, brine and dried over Na$_2$SO$_4$. The solvent was removed and the residue purified by column chromatography (6% MeOH/DCM) to afford 4-(2,2-dibromovinyl)quinoline (45.5 mg, 4.6%) as a brown solid.

Step 2: 2-(4-isopropoxy-3-methoxybenzoyl)-N—((S)-1-(methylamino)-1-oxo-5-phenylpentan-2-yl)-5-(2-(quinolin-4-yl)acetyl)octahydro-1H-pyrrolo[3,4-c]pyridine-7-carboxamide To a solution of 4-(2,2-dibromovinyl)quinoline (25 mg, 0.08 mmol) in DMF (1.5 ml) and H$_2$O (0.5 mL) was added 2-(4-isopropoxy-3-methoxybenzoyl)-N—((S)-1-(methylamino)-1-oxo-5-phenylpentan-2-yl)octahydro-1H-pyrrolo[3,4-c]pyridine-7-carboxamide (45 mg, 0.08 mmol; see synthesis of 1-154) and DIEA (31 mg, 0.24 mmol). The resulting mixture was stirred at room temperature for 4 h. Water was added and the aqueous extracted with EtOAc three times. The combined organic layers were washed with water, brine and dried over Na$_2$SO$_4$. The solvent was removed and the residue purified by prep-HPLC to afford the product (31 mg, 48%) as a yellow solid. LCMS m/z=720.4 [M+H]+ 1H NMR (400 MHz, CD3OD) δ 9.22-9.00 (m, 1H), 8.45-7.83 (m, 5H), 7.29-6.83 (m, 8H), 4.72-3.37 (m, 13H), 3.22-2.00 (m, 9H), 1.92-1.18 (m, 11H).

Synthesis of 5-(2-(6-chloro-1H-indol-3-yl)ethyl)-2-(4-isopropoxy-3-methoxybenzoyl)-N—((S)-1-(methylamino)-1-oxo-5-phenylpentan-2-yl)octahydro-1H-pyrrolo[3,4-c]pyridine-7-carboxamide I-254

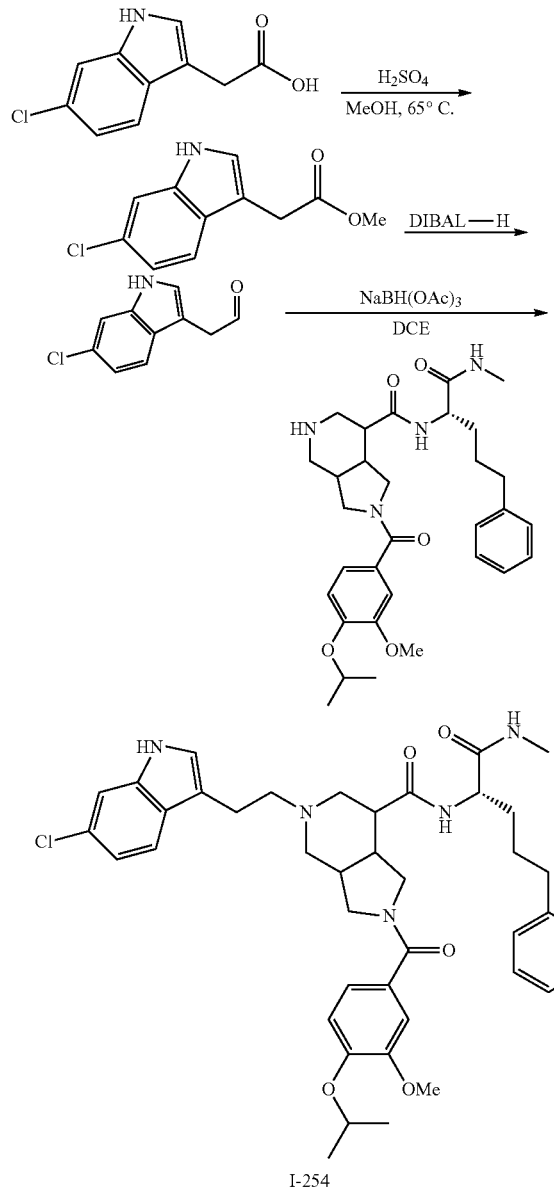

I-254

Step 1: methyl 2-(6-chloro-1H-indol-3-yl)acetate

To a solution of 2-(6-chloro-1H-indol-3-yl)acetic acid (210 mg, 1.0 mmol) in MeOH (5.0 mL) was added con. H2SO4 (3 mL). The mixture was heated at 65° C. for 1 h. The mixture was poured into ice-water and the aqueous extracted with EtOAc three times. The combined organic layers were washed with water, brine and dried over Na2SO4. The solvent was remove and the residue purified by column chromatography (20% EtOAc/PE) to afford methyl 2-(6-chloro-1H-indol-3-yl)acetate (121 mg, 54%) as a white solid.

Step 2: 2-(6-chloro-1H-indol-3-yl)acetaldehyde

To a solution of methyl 2-(6-chloro-1H-indol-3-yl)acetate (121 mg, 0.54 mmol) in DCM (1.0 mL) at −78° C. was added DIBAL-H (4M in Toluene, 0.2 mL). The resulting mixture was stirred at −78° C. under N2 for 3 h. The reaction mixture was quenched with saturated aq. NH4Cl and the aqueous extracted with EtOAc three times. The combined organic layers were washed with water, brine and dried over Na2SO4. The solvent was removed and the residue purified by column chromatography (33% EtOAc/PE) to afford 2-(6-chloro-1H-indol-3-yl)acetaldehyde (26 mg, 25% yield) as a white solid.

Step 3: 5-(2-(6-chloro-1H-indol-3-yl)ethyl)-2-(4-isopropoxy-3-methoxybenzoyl)-N—((S)-1-(methylamino)-1-oxo-5-phenylpentan-2-yl)octahydro-1H-pyrrolo[3,4-c]pyridine-7-carboxamide To 2-(4-isopropoxy-3-methoxybenzoyl)-N—((S)-1-(methylamino)-1-oxo-5-phenylpentan-2-yl)octahydro-1H-pyrrolo[3,4-c]pyridine-7-carboxamide (50 mg, 0.09 mmol; see synthesis of I-154) and 2-(6-chloro-1H-indol-3-yl)acetaldehyde (12.0 mg, 0.06 mmol) in DCE (2.0 mL) was added NaBH(OAc)3 (38.5 mg, 0.18 mmol) and the mixture stirred at room temperature overnight. The reaction mixture was concentrated in vacuo and the residue purified by prep-HPLC to afford the product (11.2 mg, 25.4%) as a white solid. LCMS m/z=728.5 [M+H]+; 1H NMR (400 MHz, CD3OD) δ 7.59-6.74 (m, 12H), 4.68-3.91 (m, 3H), 3.87-3.79 (m, 3H), 3.72-3.34 (m, 4H), 2.96-2.89 (m, 2H), 2.82-2.76 (m, 1H), 2.75-2.51 (m, 8H), 2.49-2.39 (m, 2H), 1.79-1.50 (m, 4H), 1.36-1.28 (m, 8H).

Synthesis of methyl (2S,3S)-3-(benzyloxy)-2-(5-(2-(6-chloro-1H-indol-3-yl)acetyl)-2-(4-isopropoxy-3-methoxybenzoyl)octahydro-1H-pyrrolo[3,4-c]pyridine-7-carboxamido)butanoate I-255

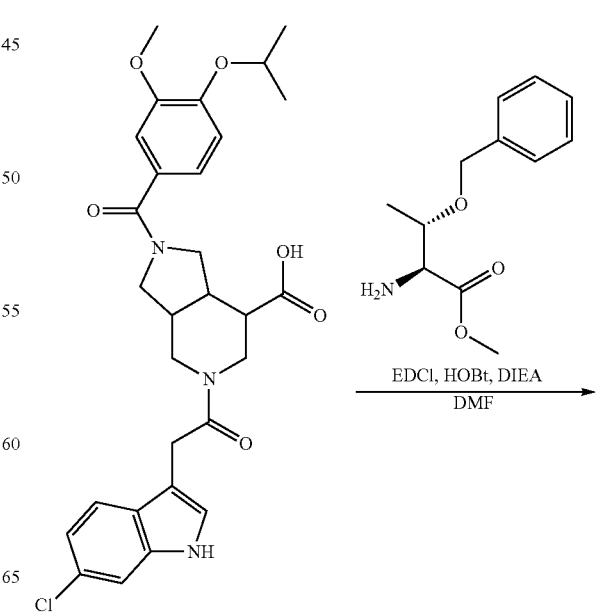

-continued

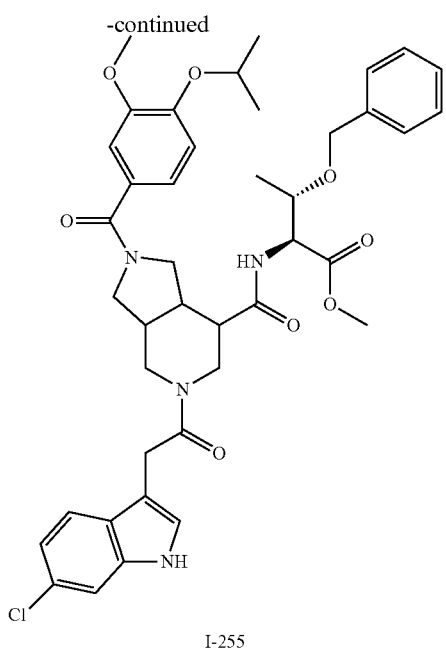

I-255

A mixture of methyl O-benzyl-L-allothreoninate (60.45 mg, 0.271 mmol), 5-(2-(6-chloro-1H-indol-3-yl)acetyl)-2-(4-isopropoxy-3-methoxybenzoyl)octahydro-1H-pyrrolo[3,4-c]pyridine-7-carboxylic acid (100 mg, 0.181 mmol) (I-88, Step 3), EDCI (52.0 mg, 0.271 mmol), HOBt (36.6 mg, 0.271 mmol) and DIEA (70.0 mg, 0.542 mmol) in DMF (5 mL) was stirred at room temperature overnight. Water was added and the aqueous extracted with EtOAc three times. The combined organic layers were washed with water and brine and dried over $Na_2SO_4$. The residue obtained after concentration was purified by prep-HPLC to afford methyl (2S,3S)-3-(benzyloxy)-2-(5-(2-(6-chloro-1H-indol-3-yl)acetyl)-2-(4-isopropoxy-3-methoxybenzoyl)octahydro-1H-pyrrolo[3,4-c]pyridine-7-carboxamido)butanoate (80 mg, 58%) as a white solid. LCMS m/z=759.4 [M+H]$^+$; $^1$H NMR (400 MHz, CD$_3$OD) δ 8.75-6.58 (m, 12H), 4.79-4.47 (m, 3H), 4.40-3.98 (m, 2H), 3.98-3.60 (m, 8H), 3.59-3.35 (m, 3H), 3.17-2.97 (m, 2H), 2.83-1.98 (m, 4H), 1.62-1.19 (m, 8H), 1.15-1.05 (m, 1H), 0.94-0.67 (m, 2H).

Synthesis of O-benzyl-N-(5-(2-(6-chloro-1H-indol-3-yl)acetyl)-2-(4-isopropoxy-3-methoxybenzoyl)octahydro-1H-pyrrolo[3,4-c]pyridine-7-carbonyl)-L-allothreonine I-256

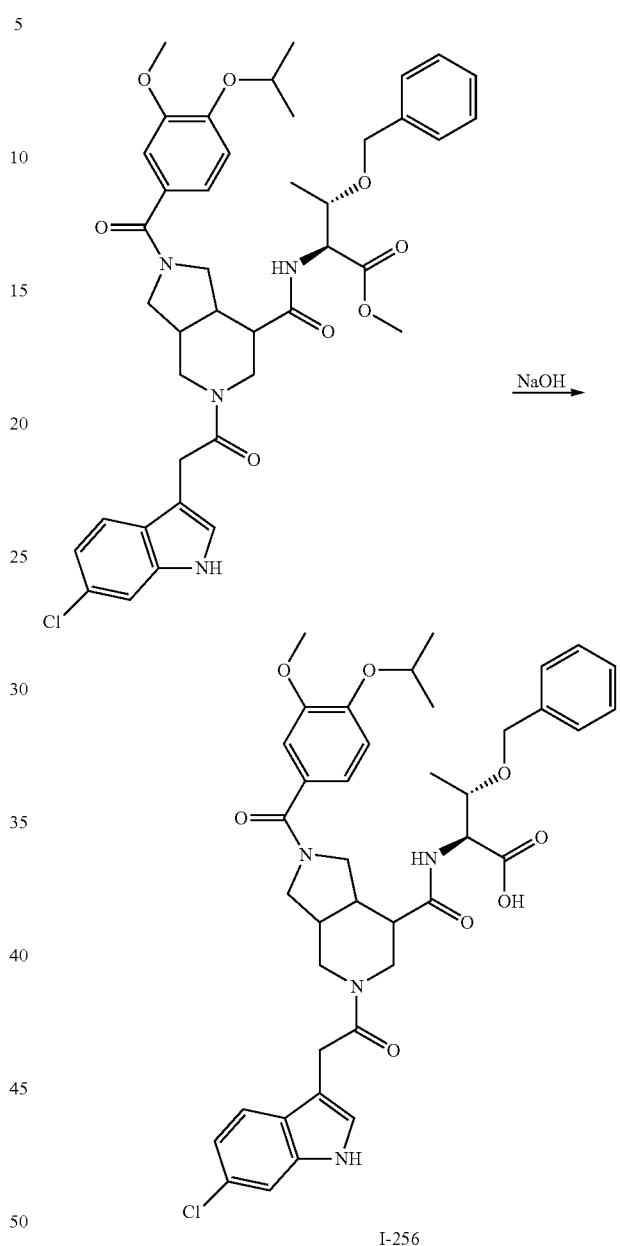

I-256

To a solution of I-255 in MeOH (5 mL) was added aqueous NaOH (1 M, 2 mL). The resulting mixture was stirred for 3 h then solvent was removed under vacuum. The residue obtained was diluted with water and the pH adjusted to ~1 by addition of 1 M HCl. The aqueous layer was extracted with EtOAc three times and the combined organic layers were washed with water, brine, dried over $Na_2SO_4$ and concentrated to afford O-benzyl-N-(5-(2-(6-chloro-1H-indol-3-yl)acetyl)-2-(4-isopropoxy-3-methoxybenzoyl)octahydro-1H-pyrrolo[3,4-c]pyridine-7-carbonyl)-L-allothreonine (500 mg, 90%) as a white solid. LCMS m/z=745.4 [M+H]$^+$; $^1$H NMR (400 MHz, CD$_3$OD) δ 7.78-6.64 (m, 12H), 4.80-4.39 (m, 3H), 4.38-3.95 (m, 2H), 3.94-3.68 (m, 5H), 3.67-3.37 (m, 3H), 3.24-2.96 (m, 1H), 2.92-2.16 (m, 3H), 1.45-1.37 (m, 3H), 1.36-1.10 (m, 8H), 0.97-0.67 (m, 2H). LCMS m/z=745.4 [M+H]$^+$.

Synthesis of N—((S)-1-((5-aminopentyl)amino)-5-(3-hydroxyphenyl)-1-oxopentan-2-yl)-5-(2-(6-chloro-1H-indol-3-yl)acetyl)-2-(4-isopropoxy-3-methoxybenzoyl)octahydro-1H-pyrrolo[3,4-c]pyridine-7-carboxamide I-257 and 1-258
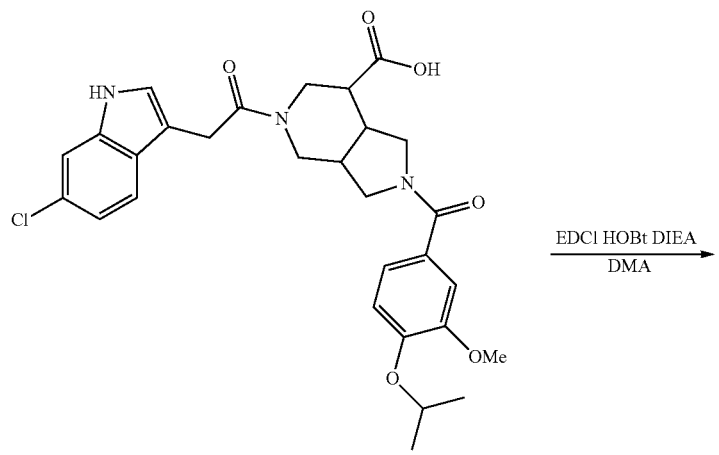
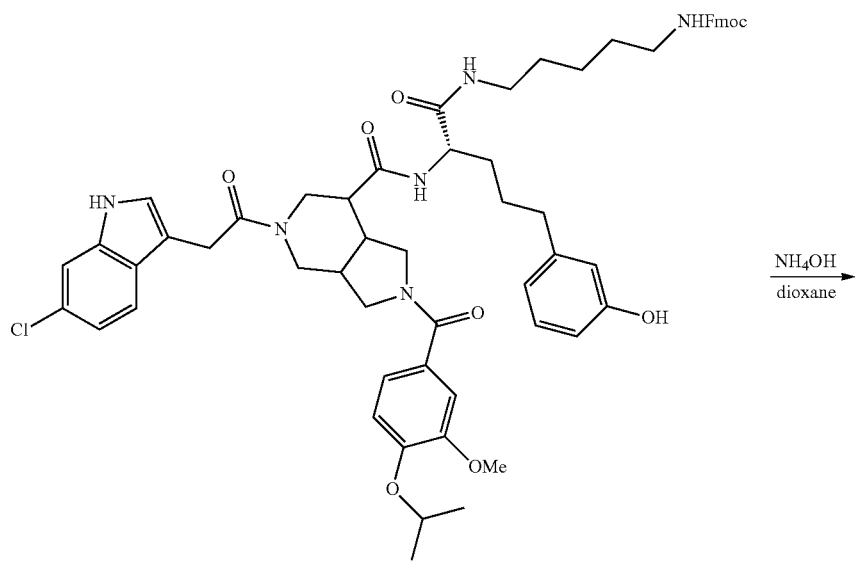

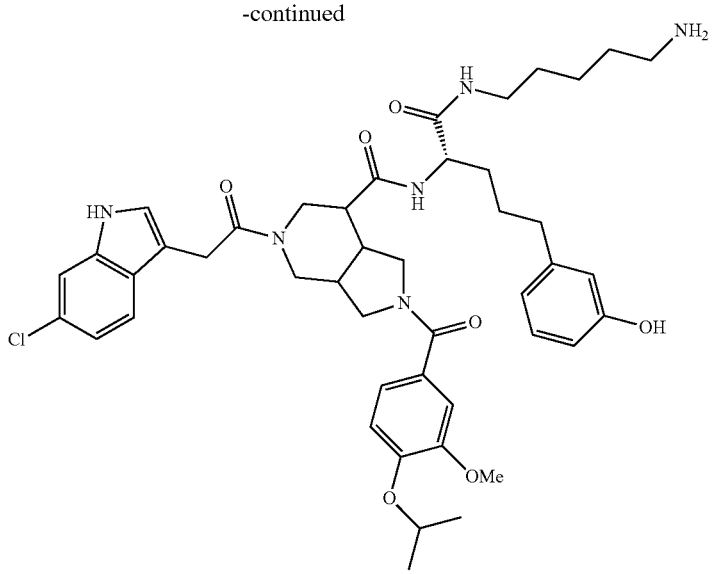

Step 1: (9H-fluoren-9-yl)methyl (5-((2S)-2-(5-(2-(6-chloro-1H-indol-3-yl)acetyl)-2-(4-isopropoxy-3-methoxybenzoyl)octahydro-1H-pyrrolo[3,4-c]pyridine-7-carboxamido)-5-(3-hydroxyphenyl)pentanamido)pentyl)carbamate Made using the same procedure reported for preparation of 1-255 using (9H-fluoren-9-yl)methyl (S)-(5-(2-amino-5-(3-hydroxyphenyl)pentanamido)pentyl)carbamate. Two diastereomers (30 mg each) were obtained after silica gel column (50% EtOAc/PE). LCMS m/z=1051.3 [M+H]⁺.

Step 2: N—((S)-1-((5-aminopentyl)amino)-5-(3-hydroxyphenyl)-1-oxopentan-2-yl)-5-(2-(6-chloro-1H-indol-3-yl)acetyl)-2-(4-isopropoxy-3-methoxybenzoyl)octahydro-1H-pyrrolo[3,4-c]pyridine-7-carboxamide To a solution of the first eluting diastereomer from Step 1 (40 mg, 0.038 mmol) in dioxane (1 mL) was added aq. NH₄OH (1 mL) and the mixture was heated at 65° C. in a sealed tube overnight. The solvent was removed under reduced pressure and the residue was purified by prep-HPLC to afford 1-257 (5.4 mg, 19%) as colorless solid. LCMS m/z=829.5 [M+H]⁺; ¹H NMR (400 MHz, CD₃OD) δ 7.62-6.48 (m, 11H), 4.70-3.75 (m, 9H), 3.69-3.35 (m, 3H), 3.22-2.74 (m, 6H), 2.69-2.04 (m, 5H), 1.79-1.49 (m, 7H), 1.43-1.25 (m, 10H). The second eluting diastereomer of from Step 1 was treated in the same fashion to afford I-258 (10.8 mg, 38%) as a colorless solid. LCMS m/z=829.5 [M+H]⁺; ¹H NMR (400 MHz, CD₃OD) δ 7.72-6.46 (m, 11H), 4.78-4.42 (m, 2H), 4.36-4.01 (m, 2H), 3.97-3.42 (m, 8H), 3.26-2.78 (m, 7H), 2.66-2.10 (m, 5H), 1.74-1.22 (m, 16H).

Synthesis of tert-butyl (5-((2S,3S)-3-(benzyloxy)-2-(5-(2-(6-chloro-1H-indol-3-yl)acetyl)-2-(4-isopropoxy-3-methoxybenzoyl)octahydro-1H-pyrrolo[3,4-c]pyridine-7-carboxamido)butanamido)pentyl)carbamate I-259 and I-260

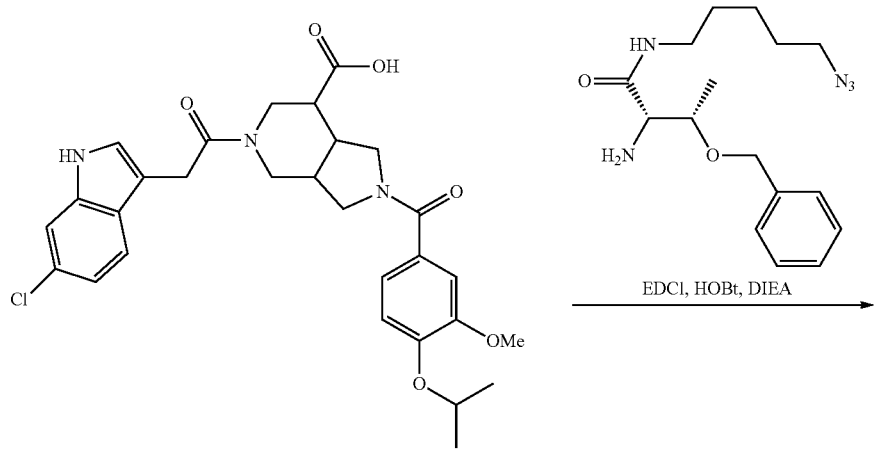

-continued
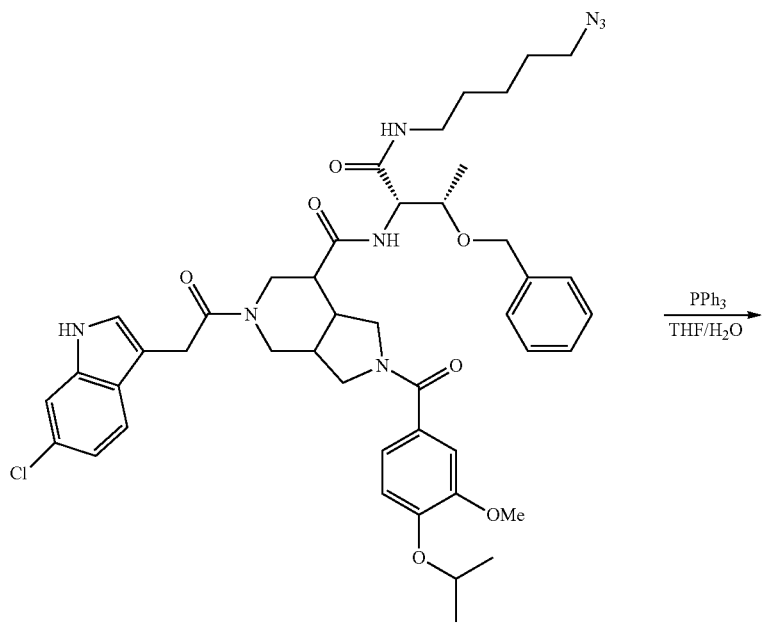
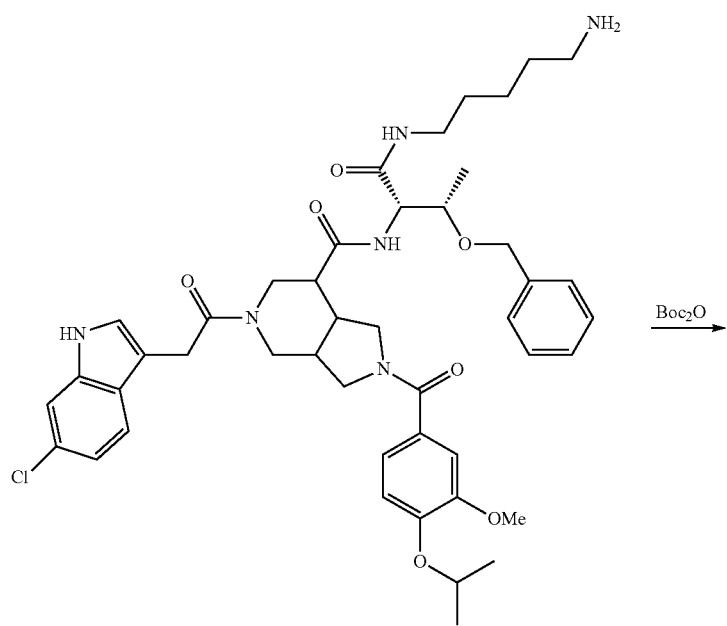

-continued

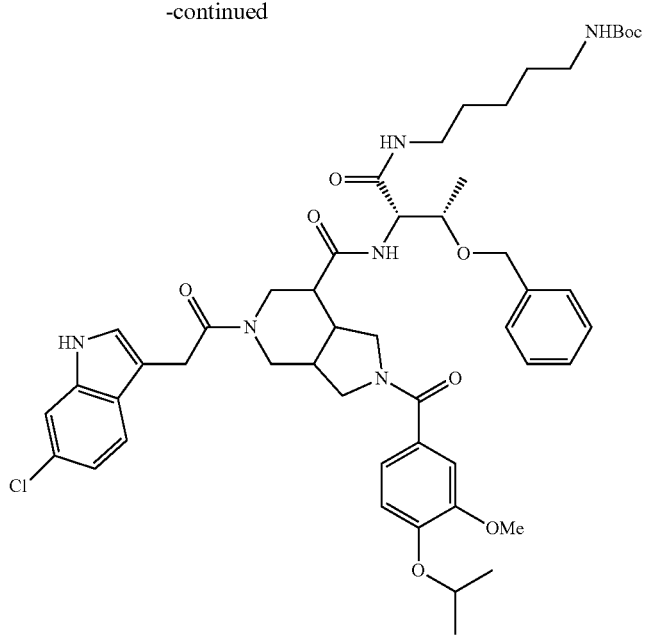

Step 1: N-((2S,3S)-1-((5-azidopentyl)amino)-3-(benzyloxy)-1-oxobutan-2-yl)-5-(2-(6-chloro-1H-indol-3-yl)acetyl)-2-(4-isopropoxy-3-methoxybenzoyl)octahydro-1H-pyrrolo[3,4-c]pyridine-7-carboxamide Made using the procedure reported for I-257/I-258, Step 1, using (2S,3S)-2-amino-N-(5-azidopentyl)-3-(benzyloxy) butanamide to give the titled product (100 mg, 20%) as a yellow solid. LCMS m/z=855.3 [M+H]$^+$.

Step 2: N-((2S,3S)-1-((5-aminopentyl)amino)-3-(benzyloxy)-1-oxobutan-2-yl)-5-(2-(6-chloro-1H-indol-3-yl)acetyl)-2-(4-isopropoxy-3-methoxybenzoyl)octahydro-1H-pyrrolo[3,4-c]pyridine-7-carboxamide To a solution of N-((2S,3S)-1-((5-azidopentyl)amino)-3-(benzyloxy)-1-oxobutan-2-yl)-5-(2-(6-chloro-1H-indol-3-yl)acetyl)-2-(4-isopropoxy-3-methoxybenzoyl)octahydro-1H-pyrrolo[3,4-c]pyridine-7-carboxamide (270 mg, 0.31 mmol) in a mixture of THF (2 mL) and H$_2$O (1 mL) was added PPh$_3$ (162 mg, 0.62 mmol). The resulting mixture was stirred at room temperature for 14 hours. The solvent was removed and the residue purified by prep-HPLC to afford the titled product (174 mg, 68%) as a white solid. LCMS m/z=829.5 [M+H]$^+$.

Step 3: tert-butyl (5-((2S,3S)-3-(benzyloxy)-2-(5-(2-(6-chloro-1H-indol-3-yl)acetyl)-2-(4-isopropoxy-3-methoxybenzoyl)octahydro-1H-pyrrolo[3,4-c]pyridine-7-carboxamido)butanamido)pentyl)carbamate To a solution of N-((2S,3S)-1-((5-aminopentyl)amino)-3-(benzyloxy)-1-oxobutan-2-yl)-5-(2-(6-chloro-1H-indol-3-yl)acetyl)-2-(4-isopropoxy-3-methoxybenzoyl)octahydro-1H-pyrrolo[3,4-c]pyridine-7-carboxamide (25 mg, 0.03 mmol) in DCM (1 mL) was added Boc$_2$O (6.5 mg, 0.03 mmol) and Et$_3$N (9 mg, 0.06 mmol). The resulting mixture was stirred at room temperature overnight. The solvent was removed in vacuo and the residue purified by prep-HPLC on an Agilent 10 Prep-C18 column (21.2 mm I.D.×25 cm, 10 um), using H$_2$O/ACN 0.1% TFA, at a flow rate of 20 mL/min (wave length 214 nm) to afford the first eluting (Rt=9.3 min) diastereomer (16 mg, 57%) 1-259 as a white solid; $^1$H NMR (400 MHz, CD$_3$OD) δ 7.63-6.66 (m, 12H), 4.73-4.31 (m, 5H), 4.15-3.36 (m, 9H), 3.26-2.90 (m, 6H), 2.87-1.99 (m, 5H), 1.43 (s, 9H), 1.39-1.13 (m, 15H). LCMS m/z=929.6 [M+H]$^+$, and the second eluting (Rt=10.5 min) diastereomer (10 mg, 35%) 1-260 also as a white solid; $^1$H NMR (400 MHz, CD$_3$OD) δ 7.67-6.63 (m, 12H), 4.75-3.35 (m, 16H), 3.28-2.93 (m, 7H), 2.85-2.44 (m, 3H), 2.29-1.97 (m, 1H), 1.42 (s, 9H), 1.38-1.18 (m, 11H), 0.93-0.67 (m, 2H). LCMS m/z=929.6 [M+H]$^+$.

Example A1: Caliper Assay

Inhibition of CDK2/Cyclin E1 activity in the presence of compounds of the present disclosure was evaluated using a Caliper LabChip® EZ Reader mobility shift assay. In the assay, activated CDK2/Cyclin E1 catalyzes the phosphorylation of a fluorescently tagged peptide 5-FAM-QSPKKG-CONH2 (PerkinElmer, FL Peptide 18) which induces a difference in capillary electrophoresis mobility. The peptide substrate and product were measured, and the conversion ratio was used to determine the inhibition (as % activity and IC$_{50}$ values) of CDK2/Cyclin E1. Reactions contained 50 mM HEPES pH 7.5, 10 mM MgCl$_2$, 1 mM EDTA, 2 mM DTT, 0.01% Brij35, 0.5 mg/mL BSA, 0.1% DMSO, 2.5 nM CDK2/Cyclin E1(14-475), 100 µM ATP, and 1.5 µM fluorescent peptide substrate.

Dose titrations of inhibitors in 100% DMSO were combined with 3.25 nM CDK2/Cyclin E1(14-475) and 130 µM of ATP in reaction buffer. The mixtures were incubated for 30 minutes before the addition of fluorescent peptide substrate to initiate the kinase reaction. The final conditions were 2.5 nM CDK2/Cyclin E1(14-475), 100 µM ATP, and 1.5 µM fluorescent peptide. The reactions were stopped after 100 minutes with the addition of EDTA (6 mM final EDTA concentration). The stopped reactions were analyzed on a Caliper LabChip® EZ Reader II. The conversion ratios were normalized to yield % activity, plotted against compound concentration, and fit to a four-parameter equation to determine the $IC_{50}$ for each compound.

The results of the Caliper Assay are reported in Table X, below. Compounds with an $IC_{50}$ less than or equal to 0.5 µM are designated as "A". Compounds with an $IC_{50}$ greater than 0.5 µM and less than or equal to 5.0 µM are designated as "B". Compounds with an $IC_{50}$ greater than 5.0 µM and less than or equal to 10.0 µM are designated as "C". Compounds with an $IC_{50}$ greater than 10.0 µM are designated as "D".

Example A2: BrdU Cell Proliferation Assay

A BrdU assay was used as a measure of proliferation based on the DNA replication process of proliferating cells. BrdU, a pyrimidine analog, is added to the cell culture and incorporated into the DNA of proliferating cells. The presence of the BrdU analog was then measured through a colorimetric ELISA. After fixation and permeabilization of cells, peroxidase-conjugated antibody recognizing BrdU is added and allowed to incubate, followed by thorough washing to remove unbound antibody. In order to quantify the amount of bound antibody, peroxidase substrate is added and produces a color that can be measured at 450 nm.

On day −1, Kuramochi cells (Sekisui XenoTech JCRB0098) were seeded at 2,000 cells/well in columns 2-12 of a 96 well plate (Corning, CLS3596) in 150 uL media and allowed to adhere overnight at 37 degree with 5% $CO_2$. In order to assess specificity of the compounds, Kuramochi $RB^{KO}$ cells were also plated and treated, as $RB^{KO}$ cells were not expected to show a proliferative response to CCNE/CDK specific inhibitors.

On day 0, the source plate was prepared by adding 10 mM compounds and performing 3-fold serial dilutions for a 4-point dose response of each compound. Using a multichannel pipette, 2 uL of the contents of the source plate were stamped into an intermediate plate with 500 uL of RPMI 1640 Media, GlutaMAX Supplement (Life Technologies, 61870127) in each well of a Nunc 96 DeepWell™ plate, non-treated 96 DeepWell plate, 2 mL/well, sterile, natural, 60/cs (Sigma Z717274) and mixed thoroughly. 50 uL from row A of this intermediate plate were added to rows A-H of one plate of previously seeded Kuramochi cells, and each subsequent row of the intermediate plate was added to a full plate of cells.

On day 4, the plates were developed using the BrdU ELISA Cell Proliferation Assay according to manufacturer's instructions (Roche, 11647229001). Briefly, BrdU was diluted 1:100 in Gibco®, Opti-MEM® and 20 µL/well was added, shaken for 10 minutes at 350 rpm, and then returned to the incubator for 1 hour. Following incubation, the medium was discarded, and the cells were fixed by adding 200 µL of Fix/Denature solution. The anti-BrdU peroxidase antibody was diluted 1:1000 in OptiMEM, added at 100 µL/well, and incubated while shaking (350 rpm) for one hour. Three washes with PBS were performed to remove any unbound antibody, followed by the addition of 100 µL of substrate solution to each well. µL/well of 1M sulfuric acid solution was then added to halt the reaction, and plates were read out using an Envision spectrophotometer (Perkin Elmer) set to read 450 nm absorbance. Background absorbance values from empty wells were subtracted from all samples and then normalized to DMSO treated wells.

The results of the BrdU cell proliferation assay are reported in Table X, below. Compounds with an $IC_{50}$ less than or equal to 0.5 µM are designated as "A". Compounds with an $IC_{50}$ greater than 0.5 µM and less than or equal to 5.0 µM are designated as "B". Compounds with an $IC_{50}$ greater than 5.0 µM and less than or equal to 10.0 µM are designated as "C". Compounds with an $IC_{50}$ greater than 10.0 µM are designated as "D".

Example A3: HotSpot™ Kinase Inhibition Assay

Inhibition of a select panel of CDK2/CCNE1 activities in the presence of compounds of the present disclosure was evaluated using the HotSpot™ assay (proprietary to Reaction Biology Corporation). In the assay, activated CDK2/Cyclin E1 catalyzes the transfer of radioactive phosphate to amino acid residues of peptide or protein substrates, which are detected radiometrically. After subtraction of background derived from control reactions containing inactive enzyme, kinase activity data is expressed as the percent remaining kinase activity in test samples compared to reactions without inhibitor present. Reactions contained 20 mM HEPES pH 7.5, 10 mM $MgCl_2$, 1 mM EGTA, 2 mM DTT, 0.02% Brij35, 0.02 mg/mL BSA, 0.1 mM $Na_3VO_4$, 1% DMSO, 1.5 nM CDK2/Cyclin E1(14-475), 10 µM ATP, and 20 µM Histone H1 protein isolated from calf thymus (Sigma).

CDK2/Cyclin E1 (14-75) and Histone H1 were mixed in reaction buffer. To this mixture, was added dose titrations of inhibitor compounds in 100% DMSO by acoustic transfer. The compound mixtures were incubated for 20 minutes, then the kinase reactions were initiated by the addition of a mixture of ATP and $^{33}P$ ATP for final concentrations of 10 µM total ATP, 20 µM Histone H1, and 1.5 nM CDK2/Cyclin E1 (14-475). The reactions were carried out for 120 minutes, then spotted on a P81 ion exchange filter paper, and extensively washed with 0.75% phosphoric acid. The resulting radioactive counts were normalized to yield % activity, plotted against compound concentration, and fit to a four-parameter equation to determine the $IC_{50}$ for each compound.

The results of the HotSpot™ assay are reported in Table X, below. Compounds with an $IC_{50}$ less than or equal to 1.0 µM are designated as "A". Compounds with an $IC_{50}$ greater than 1.0 µM and less than or equal to 10 µM are designated as "B". Compounds with an $IC_{50}$ greater than 10 µM and less than or equal to 100 µM are designated as "C". Compounds with an $IC_{50}$ greater than 100 µM are designated as "D".

Example A4: Incucyte® Cell Proliferation Assay

Kuramochi cells labeled with mApple-H2B and Kuramochi RB1−/− cells labeled with NucLight green (Sartorius, 4475) were co-plated on 384-well assay-ready plates along with test compounds at varying concentrations. Plates were placed in the IncuCyte® Sartorius and scanned at 0 and 72 hours. IncuCyte® software was used to count the number of fluorescent nuclei in each well. The fold change in cell count from 0 to 72 hours in wells treated with increasing compounds concentrations (10 pts, ½ log dilution, 20 uM top concentration) was normalized to DMSO control wells. The normalized cell counts were fit with dose response curves and a $GI_{50}$ was calculated.

The results of the Incucyte® Kuramochi cell viability assay are reported in Table X, below. Compounds with a $GI_{50}$ less than or equal to 1.0 µM are designated as "A". Compounds with a $GI_{50}$ greater than 1.0 µM and less than or equal to 10.0 µM are designated as "B". Compounds with a $GI_{50}$ greater than 10.0 µM and less than or equal to 20.0 µM are designated as "C". Compounds with a $GI_{50}$ greater than 20.0 μM are designated as "D".

TABLE X

Assay Results

| # | Caliper Assay | BrdU Cell Proliferation Assay | Kinase Inhibition Assay | Incucyte ® Cell Proliferation Assay |
|---|---|---|---|---|
| I-1 | A | D | | |
| I-2 | | D | C | |
| I-3 | D | D | | |
| I-4 | D | | | |
| I-5 | D | D | | |
| I-6 | B | D | | |
| I-7 | B | C | | |
| I-8 | D | D | | |
| I-9 | C | D | | |
| I-10 | D | D | | |
| I-11 | D | D | | |
| I-12 | D | D | | |
| I-13 | D | C | D | |
| I-14 | D | D | | |
| I-15 | D | D | | |
| I-16 | D | D | | |
| I-17 | | D | D | |
| I-18 | D | D | | |
| I-19 | D | B | A | |
| I-20 | D | D | | |
| I-21 | D | D | | |
| I-22 | D | D | | |
| I-23 | D | D | | |
| I-24 | D | D | | |
| I-25 | B | D | | |
| I-26 | C | D | | |
| I-27 | D | D | | |
| I-28 | D | D | | |
| I-29 | D | D | | |
| I-30 | D | D | | |
| I-31 | D | D | | |
| I-32 | | D | D | |
| I-33 | C | | | |
| I-34 | C | D | | |
| I-35 | | D | D | |
| I-36 | D | | | |
| I-37 | D | D | | |
| I-38 | D | D | | |
| I-39 | D | D | | |
| I-40 | D | D | | |
| I-41 | D | D | | |
| I-42 | | D | D | |
| I-43 | D | D | | |
| I-44 | D | D | | |
| I-45 | D | D | | |
| I-46 | B | D | | |
| I-47 | D | D | | |
| I-48 | D | D | | |
| I-49 | | D | | |
| I-50 | | D | B | |
| I-51 | | D | | |
| I-52 | C | D | | |
| I-53 | | D | | |
| I-54 | D | D | | |
| I-55 | D | D | | |
| I-56 | B | D | | |
| I-57 | D | D | | |
| I-58 | D | D | | |
| I-59 | D | D | | |
| I-60 | D | D | | |
| I-61 | D | D | | |
| I-62 | | D | D | |
| I-63 | | D | | |
| I-64 | | D | C | |
| I-65 | D | D | | |
| I-66 | D | D | | |
| I-67 | | | C | |
| I-68 | | D | | |
| I-69 | D | D | | |
| I-70 | D | D | | |
| I-71 | D | D | | |
| I-72 | D | D | | |
| I-73 | D | D | | |
| I-74 | D | D | | |
| I-75 | D | D | | |
| I-76 | | D | | |
| I-77 | | D | D | |
| I-78 | D | D | | |
| I-79 | C | D | | |
| I-80 | D | D | | |
| I-81 | | D | C | |
| I-82 | B | C | | |
| I-83 | A | D | | |
| I-84 | B | D | | |
| I-85 | A | D | | |
| I-86 | D | D | | |
| I-87 | A | D | | |
| I-88 | D | D | | |
| I-89 | D | D | | |
| I-90 | D | D | | |
| I-91 | B | D | | |
| I-92 | D | D | | |
| I-93 | B | D | | |
| I-94 | D | D | | |
| I-95 | B | D | | |
| I-96 | | | | |
| I-97 | B | D | | |
| I-98 | B | D | | |
| I-99 | B | D | | |
| I-100 | A | B | | |
| I-101 | D | D | | |
| I-102 | B | D | | |
| I-103 | B | D | | |
| I-104 | D | D | | |
| I-105 | D | D | | |
| I-106 | A | B | | B |
| I-107 | A | B | | |
| I-108 | D | D | | |
| I-109 | B | D | | |
| I-110 | D | D | | |
| I-111 | A | D | | |
| I-112 | C | D | | |
| I-113 | B | D | | |
| I-114 | D | D | | |
| I-115 | C | D | | |
| I-116 | D | D | | |
| I-117 | B | D | | |
| I-118 | D | D | | |
| I-119 | | D | | |
| I-120 | | D | | |
| I-121 | | D | | |
| I-122 | | | C | |
| I-123 | | | C | |
| I-124 | | D | D | |
| I-125 | | | C | |
| I-126 | B | D | | |
| I-127 | B | D | | |
| I-128 | C | B | | |
| I-129 | D | D | | |
| I-130 | B | D | | |
| I-131 | C | B | | |
| I-132 | B | D | | |
| I-133 | B | D | | |
| I-134 | D | D | | |
| I-135 | A | B | | |
| I-136 | B | D | | |
| I-137 | D | D | | |
| I-138 | D | D | | |
| I-139 | B | D | | |
| I-140 | B | D | | |
| I-141 | D | C | | |
| I-142 | D | D | | |
| I-143 | D | D | | |
| I-144 | B | D | | |

TABLE X-continued

Assay Results

| # | Caliper Assay | BrdU Cell Proliferation Assay | Kinase Inhibition Assay | Incucyte ® Cell Proliferation Assay |
|---|---|---|---|---|
| I-145 | A | B | | B |
| I-146 | A | D | | C |
| I-147 | D | D | | D |
| I-148 | B | D | | D |
| I-149 | B | D | | |
| I-150 | B | C | | |
| I-151 | A | B | | |
| I-152 | D | D | | |
| I-153 | B | D | | |
| I-154 | D | D | | |
| I-155 | D | D | | |
| I-156 | B | D | | |
| I-157 | D | D | | |
| I-158 | D | D | | |
| I-159 | D | D | | |
| I-160 | D | D | | |
| I-161 | D | D | | |
| I-162 | D | D | | |
| I-163 | D | D | | |
| I-164 | D | D | | |
| I-165 | D | D | | |
| I-166 | D | D | | |
| I-167 | D | D | | |
| I-168 | D | D | | |
| I-169 | D | D | | |
| I-170 | D | D | | |
| I-171 | D | D | | |
| I-172 | D | D | | |
| I-173 | B | D | | |
| I-174 | B | D | | |
| I-175 | D | D | | |
| I-176 | D | D | | |
| I-177 | D | D | | |
| I-178 | D | D | | |
| I-179 | D | D | | |
| I-180 | D | D | | |
| I-181 | D | D | | |
| I-182 | D | D | | |
| I-183 | D | D | | |
| I-184 | D | D | | |
| I-185 | D | D | | |
| I-186 | D | D | | |
| I-187 | D | D | | |
| I-188 | D | D | | |
| I-189 | D | D | | |
| I-190 | D | D | | |
| I-191 | D | D | | |
| I-192 | D | D | | |
| I-193 | D | D | | |
| I-194 | | D | | |
| I-195 | D | D | | |
| I-196 | D | D | | |
| I-197 | D | D | | |
| I-198 | D | D | | |
| I-199 | D | D | | |
| I-200 | C | D | | |
| I-201 | B | D | | |
| I-202 | D | D | | |
| I-203 | B | D | | |
| I-204 | B | D | | |
| I-205 | B | D | | |
| I-206 | D | D | | |
| I-207 | D | D | | |
| I-208 | D | D | | |
| I-209 | D | D | | |
| I-210 | D | D | | |
| I-211 | D | D | | |
| I-212 | D | D | | |
| I-213 | D | D | | |
| I-214 | D | D | | |
| I-215 | D | D | | |
| I-216 | D | D | | |
| I-217 | D | D | | |
| I-218 | D | D | | |
| I-219 | B | D | | |
| I-220 | D | D | | |
| I-221 | | D | D | |
| I-222 | | | B | |
| I-223 | D | D | | |
| I-224 | D | | | |
| I-225 | B | D | | |
| I-226 | B | C | | |
| I-227 | A | D | | |
| I-228 | D | D | | |
| I-229 | D | D | | |
| I-230 | D | D | | |
| I-231 | C | D | | |
| I-232 | D | D | | |
| I-233 | D | D | | |
| I-234 | D | D | | |
| I-235 | | | B | |
| I-236 | B | D | | |
| I-237 | A | D | | |
| I-238 | B | B | | |
| I-239 | B | D | | |
| I-240 | B | D | | |
| I-241 | D | D | | |
| I-242 | B | D | | |
| I-243 | B | D | | |
| I-244 | D | D | | |
| I-245 | D | D | | |
| I-246 | D | D | | |
| I-247 | D | D | | |
| I-248 | D | D | | |
| I-249 | D | D | | |
| I-250 | B | D | | |
| I-251 | D | C | D | |
| I-252 | D | D | | |
| I-253 | D | D | | |
| I-254 | D | | | |
| I-255 | A | B | | |
| I-256 | B | D | | |
| I-257 | B | D | | |
| I-258 | D | D | | |
| I-259 | A | B | | |
| I-260 | B | D | | |
| I-261 | D | | | D |
| I-262 | D | | | D |

We claim:

1. A compound, wherein the compound is of Formula I:

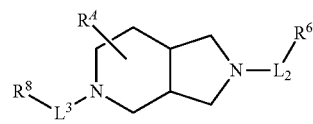

or a pharmaceutically acceptable salt thereof, wherein:
R$^A$ is

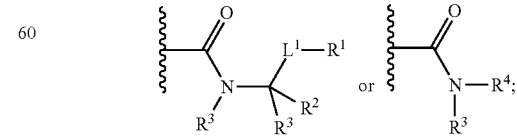

L$^1$ is a covalent bond or a saturated or unsaturated, straight or branched, optionally substituted bivalent $C_{1-6}$ hydrocarbon chain, wherein 0-2 methylene units of $L^1$ are independently replaced by —O—, —NR—, —S—, —OC(O)—, —C(O)O—, —C(O)—, —S(O)—, —S(O)$_2$—, —C(S)—, —NRS(O)$_2$—, —S(O)$_2$NR—, —NRC(O)—, —C(O)NR—, —OC(O)NR—, —NRC(O)O—, or —NRC(O)NR—;

$R^1$ is hydrogen, an optionally substituted $C_{1-6}$ aliphatic group, or an optionally substituted cyclic group selected from a 3-8 membered saturated or partially unsaturated monocyclic carbocyclic ring, a 7-12 membered saturated or partially unsaturated bicyclic carbocyclic ring, phenyl, an 8-10 membered bicyclic aromatic carbocyclic ring, a 3-8 membered saturated or partially unsaturated monocyclic heterocyclic ring (having 1-2 heteroatoms independently selected from nitrogen, oxygen, and sulfur), a 7-12 membered saturated or partially unsaturated bicyclic heterocyclic ring (having 1-4 heteroatoms independently selected from nitrogen, oxygen, and sulfur), a 5-6 membered monocyclic heteroaromatic ring (having 1-4 heteroatoms independently selected from nitrogen, oxygen, and sulfur), and an 8-10 membered bicyclic heteroaromatic ring (having 1-5 heteroatoms independently selected from nitrogen, oxygen, and sulfur);

$R^2$ is hydrogen, an optionally substituted $C_{1-6}$ aliphatic group, —C(O)OR, —C(O)NR$_2$, or an optionally substituted cyclic group selected from phenyl and a 5-6 membered monocyclic heteroaromatic ring (having 1-4 heteroatoms independently selected from nitrogen, oxygen, and sulfur);

each instance of $R^3$ is independently hydrogen or an optionally substituted $C_{1-6}$ aliphatic group;

$R^4$ is a cyclic group selected from a 3-8 membered saturated or partially unsaturated monocyclic carbocyclic ring, a 7-12 membered saturated or partially unsaturated bicyclic carbocyclic ring, phenyl, an 8-10 membered bicyclic aromatic carbocyclic ring, a 3-8 membered saturated or partially unsaturated monocyclic heterocyclic ring (having 1-2 heteroatoms independently selected from nitrogen, oxygen, and sulfur), a 7-12 membered saturated or partially unsaturated bicyclic heterocyclic ring (having 1-4 heteroatoms independently selected from nitrogen, oxygen, and sulfur), a 5-6 membered monocyclic heteroaromatic ring (having 1-4 heteroatoms independently selected from nitrogen, oxygen, and sulfur), and an 8-10 membered bicyclic heteroaromatic ring (having 1-5 heteroatoms independently selected from nitrogen, oxygen, and sulfur), wherein the cyclic group is optionally substituted with one or more instances of $R^5$;

each instance of $R^5$ is independently halogen, —CN, —NO$_2$, —OR, —SR, —NR$_2$, —S(O)$_2$R, —S(O)$_2$NR$_2$, —S(O)R, —S(O)NR$_2$, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)C(NR)NR$_2$, —N(R)S(O)$_2$NR$_2$, —N(R)S(O)$_2$R, an optionally substituted $C_{1-6}$ aliphatic group, or an optionally substituted —$C_{1-6}$ aliphatic-Cy group;

$L^2$ is a saturated or unsaturated, straight or branched, optionally substituted bivalent $C_{1-4}$ hydrocarbon chain, wherein 0-2 methylene units of $L^2$ are independently replaced by —O—, —NR—, —S—, —OC(O)—, —C(O)O—, —C(O)—, —S(O)—, —S(O)$_2$—, —C(S)—, —NRS(O)$_2$—, —S(O)$_2$NR—, —NRC(O)—, —C(O)NR—, —OC(O)NR—, —NRC(O)O—, or —NRC(O)NR—;

$R^6$ is an optionally substituted $C_{1-6}$ aliphatic group, or a cyclic group selected from a 3-8 membered saturated or partially unsaturated monocyclic carbocyclic ring, a 7-12 membered saturated or partially unsaturated bicyclic carbocyclic ring, phenyl, an 8-10 membered bicyclic aromatic carbocyclic ring, a 3-8 membered saturated or partially unsaturated monocyclic heterocyclic ring (having 1-2 heteroatoms independently selected from nitrogen, oxygen, and sulfur), a 7-12 membered saturated or partially unsaturated bicyclic heterocyclic ring (having 1-4 heteroatoms independently selected from nitrogen, oxygen, and sulfur), a 5-6 membered monocyclic heteroaromatic ring (having 1-4 heteroatoms independently selected from nitrogen, oxygen, and sulfur), and an 8-10 membered bicyclic heteroaromatic ring (having 1-5 heteroatoms independently selected from nitrogen, oxygen, and sulfur), wherein the cyclic group is optionally substituted with one or more instances of $R^7$;

each instance of $R^7$ is independently halogen, —CN, —NO$_2$, —OR, —SR, —NR$_2$, —S(O)$_2$R, —S(O)$_2$NR$_2$, —S(O)R, —S(O)NR$_2$, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)C(O)S(O)$_2$R, —N(R)C(NR)NR$_2$, —N(R)S(O)$_2$NR$^2$, —N(R)S(O)$_2$R, an optionally substituted $C_{1-6}$ aliphatic group, or Cy, or two instances of $R^6$ on the same carbon atom are taken together to form an oxo group;

$L^3$ is a saturated or unsaturated, straight or branched, optionally substituted bivalent $C_{1-4}$ hydrocarbon chain, wherein 0-2 methylene units of $L^3$ are independently replaced by —O—, —NR—, —S—, —OC(O)—, —C(O)O—, —C(O)—, —S(O)—, —S(O)$_2$—, —C(S)—, —NRS(O)$_2$—, —S(O)$_2$NR—, —NRC(O)—, —C(O)NR—, —OC(O)NR—, —NRC(O)O—, or —NRC(O)NR—;

$R^8$ is a cyclic group selected from a 3-8 membered saturated or partially unsaturated monocyclic carbocyclic ring, a 7-12 membered saturated or partially unsaturated bicyclic carbocyclic ring, phenyl, an 8-10 membered bicyclic aromatic carbocyclic ring, a 3-8 membered saturated or partially unsaturated monocyclic heterocyclic ring (having 1-2 heteroatoms independently selected from nitrogen, oxygen, and sulfur), a 7-12 membered saturated or partially unsaturated bicyclic heterocyclic ring (having 1-4 heteroatoms independently selected from nitrogen, oxygen, and sulfur), a 5-6 membered monocyclic heteroaromatic ring (having 1-4 heteroatoms independently selected from nitrogen, oxygen, and sulfur), and an 8-10 membered bicyclic heteroaromatic ring (having 1-5 heteroatoms independently selected from nitrogen, oxygen, and sulfur), wherein the cyclic group is optionally substituted with one or more instances of $R^9$;

each instance of $R^9$ is independently halogen, —CN, —NO$_2$, —OR, —SR, —NR$_2$, —S(O)$_2$R, —S(O)$_2$NR$_2$, —S(O)R, —S(O)NR$_2$, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)C(NR)NR$_2$, —N(R)S(O)$_2$NR$_2$, —N(R)S(O)$_2$R, an optionally substituted $C_{1-6}$ aliphatic group, an optionally substituted $C_{1-6}$ aliphatic-Cy group, or Cy;

each Cy is independently an optionally substituted cyclic group selected from a 3-8 membered saturated or partially unsaturated monocyclic carbocyclic ring, phenyl, a 3-8 membered saturated or partially unsaturated monocyclic heterocyclic ring (having 1-2 heteroatoms independently selected from nitrogen, oxygen, and sulfur), and a 5-6 membered monocyclic heteroaromatic ring (having 1-4 heteroatoms independently selected from nitrogen, oxygen, and sulfur); and each R is independently hydrogen, or an optionally substituted $C_{1-6}$ aliphatic group, an optionally substituted phenyl, an optionally substituted 3-7 membered saturated or partially unsaturated carbocyclic ring, an optionally substituted 3-7 membered saturated or partially unsaturated heterocyclic ring (having 1-2 heteroatoms independently selected from nitrogen, oxygen, and sulfur), or an optionally substituted 5-6 membered heteroaryl ring (having 1-4 heteroatoms independently selected from nitrogen, oxygen, and sulfur); or two R groups on the same nitrogen are taken together with their intervening atoms to form an optionally substituted 4-7 membered saturated, partially unsaturated, or heteroaryl ring (having 0-3 heteroatoms, in addition to the nitrogen, independently selected from nitrogen, oxygen, and sulfur);

wherein the compound is not 5-(2-(6-chloro-1H-indol-3-yl)acetyl)-2-(4-isopropoxy-3-methoxybenzoyl)-N-(1-(methylamino)-1-oxo-5-phenylpentan-2-yl)octahydro-1H-pyrrolo[3,4-c]pyridine-7-carboxamide.

2. The compound of claim 1, wherein $R^4$ is

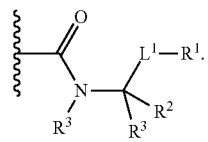

3. The compound of claim 1, wherein L is a covalent bond; or
wherein $L^1$ is a saturated or unsaturated, straight or branched, optionally substituted bivalent $C_{1-6}$ hydrocarbon chain, wherein 0-2 methylene units of $L^1$ are independently replaced by —O—, —NR—, —S—, —OC(O)—, —C(O)O—, —C(O)—, —S(O)—, —S(O)$_2$—, —C(S)—, —NRS(O)$_2$—, —S(O)$_2$NR—, —NRC(O)—, —C(O)NR—, —OC(O)NR—, —NRC(O)O—, or —NRC(O)NR—; or
wherein $L^1$ is an optionally substituted straight or branched $C_{1-4}$ alkylene chain, wherein 1-2 methylene units of $L^1$ are independently replaced by —O—, —NR—, —C(O)O—, or —NRC(O)—; or
wherein $L^1$ is

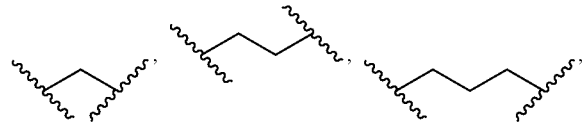

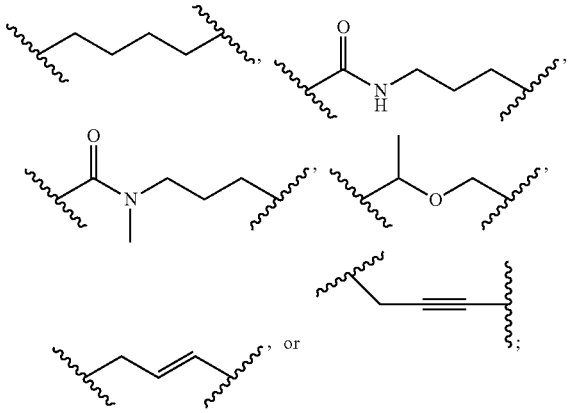

or
wherein $L^1$ is

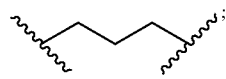 [SMILES: *CCC*]

or
wherein $L^1$ is

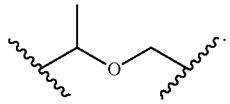 [SMILES: *COC(*)C]

4. The compound of claim 1, wherein $R^1$ is hydrogen; or
wherein $R^1$ is an optionally substituted $C_{1-6}$ aliphatic group; or
wherein $R^1$ is an optionally substituted cyclic group selected from a 3-8 membered saturated or partially unsaturated monocyclic carbocyclic ring, a 7-12 membered saturated or partially unsaturated bicyclic carbocyclic ring, phenyl, an 8-10 membered bicyclic aromatic carbocyclic ring, a 3-8 membered saturated or partially unsaturated monocyclic heterocyclic ring (having 1-2 heteroatoms independently selected from nitrogen, oxygen, and sulfur), a 7-12 membered saturated or partially unsaturated bicyclic heterocyclic ring (having 1-4 heteroatoms independently selected from nitrogen, oxygen, and sulfur), a 5-6 membered monocyclic heteroaromatic ring (having 1-4 heteroatoms independently selected from nitrogen, oxygen, and sulfur), and an 8-10 membered bicyclic heteroaromatic ring (having 1-5 heteroatoms independently selected from nitrogen, oxygen, and sulfur); or
wherein $R^1$ an optionally substituted cyclic group selected from a 3-8 membered saturated or partially unsaturated monocyclic carbocyclic ring, phenyl, a 3-8 membered saturated or partially unsaturated monocyclic heterocyclic ring (having 1-2 heteroatoms independently selected from nitrogen, oxygen, and sulfur), a 5-6 membered monocyclic heteroaromatic ring (having 1-4 heteroatoms independently selected from nitrogen, oxygen, and sulfur), and an 8-10 membered bicyclic heteroaromatic ring (having 1-5 heteroatoms independently selected from nitrogen, oxygen, and sulfur); or wherein R¹ is an optionally substituted cyclic group selected from phenyl, cyclohexyl, cyclopentyl, cycloheptyl, tetrahydrofuranyl, tetrahydropyranyl, indole, and benzotriazole; or wherein R¹ is optionally substituted cyclohexyl; or wherein R¹ is optionally substituted phenyl.

5. The compound of claim 1, wherein R² is an optionally substituted $C_{1-6}$ aliphatic group, —C(O)OR, —C(O)NR₂, or an optionally substituted cyclic group selected from phenyl and a 5-6 membered monocyclic heteroaromatic ring (having 1-4 heteroatoms independently selected from nitrogen, oxygen, and sulfur); or wherein R² is C(O)NR₂; or wherein R² is hydrogen, methyl, —C(O)NHCH₃, —C(O)NH₂, —C(O)OCH₃, or —C(O)OH; or wherein R² is a 5-6 membered monocyclic heteroaromatic ring (having 1-4 heteroatoms independently selected from nitrogen, oxygen, and sulfur); or wherein R² is an oxazolyl or pyrimidinyl group.

6. The compound of claim 1, wherein R⁴ is

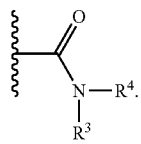

7. The compound of claim 1, wherein R⁴ is a cyclic group selected from a 3-8 membered saturated or partially unsaturated monocyclic heterocyclic ring (having 1-2 heteroatoms independently selected from nitrogen, oxygen, and sulfur), and a 5-6 membered monocyclic heteroaromatic ring (having 1-4 heteroatoms independently selected from nitrogen, oxygen, and sulfur), wherein the cyclic group is optionally substituted with one or more instances of R⁵; or wherein R⁴ is a cyclic group selected from phenyl, pyridine, and piperidine, wherein the cyclic group is optionally substituted with one or more instances of R⁵.

8. The compound of claim 1, wherein R⁵ is —OR, —C(O)R, an optionally substituted $C_{1-6}$ aliphatic group, or an optionally substituted —$C_{1-6}$ aliphatic-Cy group; or wherein R⁵ is an optionally substituted benzyl group, an optionally substituted benzoyl group, an optionally substituted phenoxy group, or an optionally substituted phenylacetyl group.

9. The compound of claim 1, wherein each R³ is hydrogen.

10. The compound of claim 1, wherein R⁴ is a substituent selected from:

TABLE A1

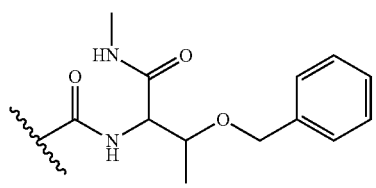 [SMILES: *C(=O)NC(C(=O)NC)C(C)OCc1ccccc1]

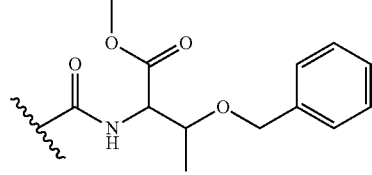 [SMILES: *C(=O)NC(C(=O)OC)C(C)OCc1ccccc1]

TABLE A1-continued

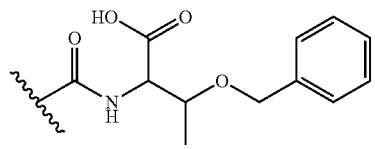 [SMILES: *C(=O)NC(C(=O)O)C(C)OCc1ccccc1]

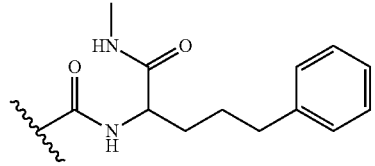 [SMILES: *C(=O)NC(CCCc1ccccc1)C(=O)NC]

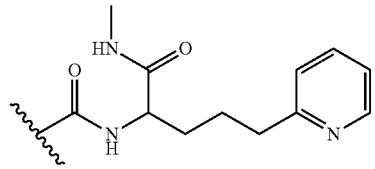 [SMILES: *C(=O)NC(CCCc1ccccn1)C(=O)NC]

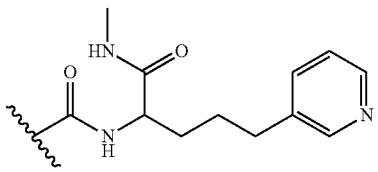 [SMILES: *C(=O)NC(CCCc1cccnc1)C(=O)NC]

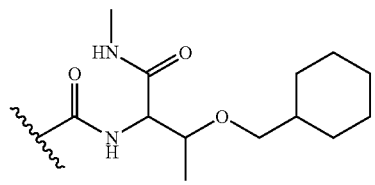 [SMILES: *C(=O)NC(C(=O)NC)C(C)OCC1CCCCC1]

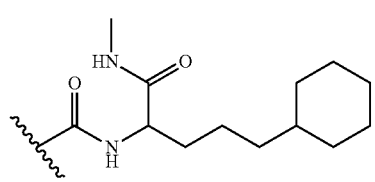 [SMILES: *C(=O)NC(CCCC1CCCCC1)C(=O)NC]

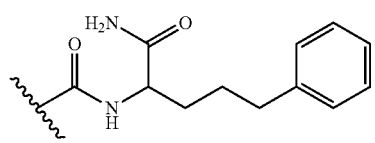 [SMILES: *C(=O)NC(CCCc1ccccc1)C(N)=O]

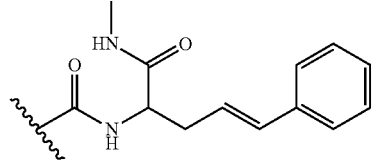 [SMILES: *C(=O)NC(C/C=C/c1ccccc1)C(=O)NC]

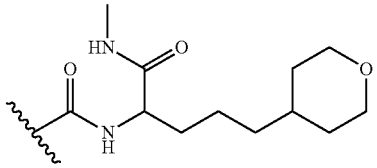 [SMILES: *C(=O)NC(CCCC1CCOCC1)C(=O)NC]

TABLE A1-continued
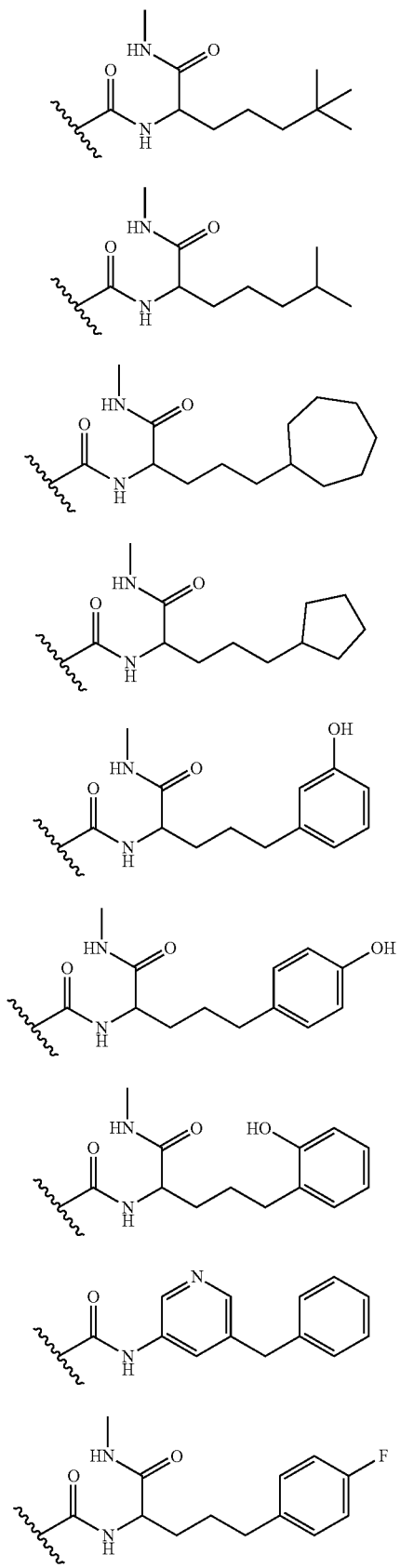
TABLE A1-continued
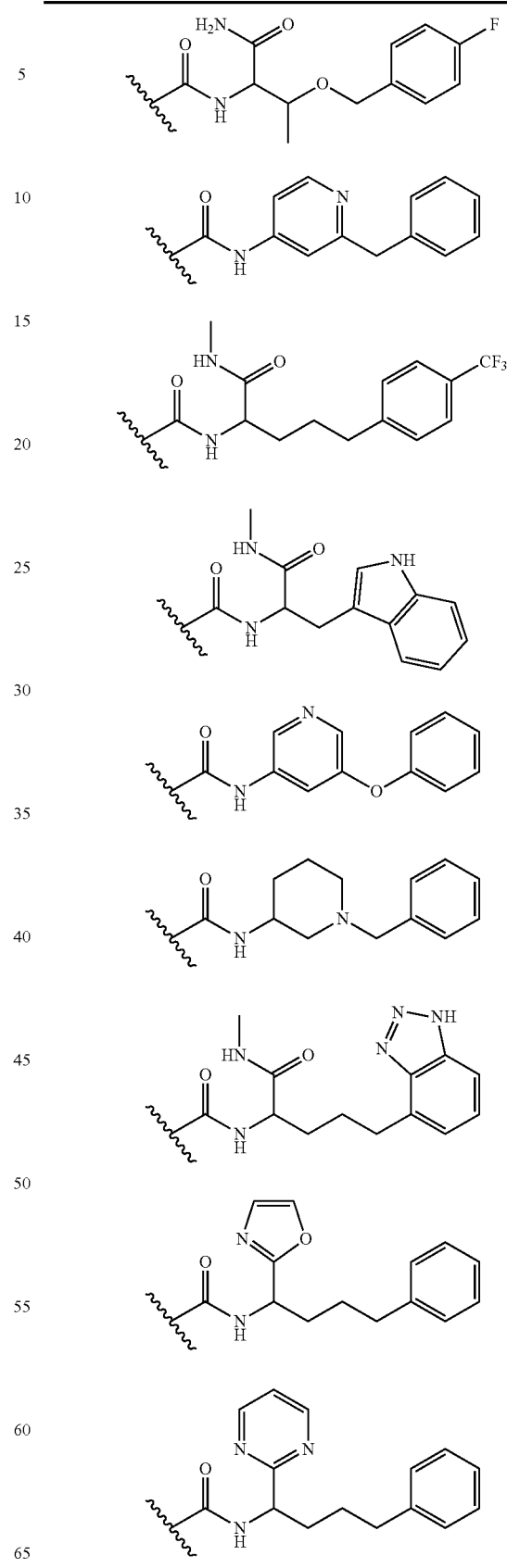

TABLE A1-continued
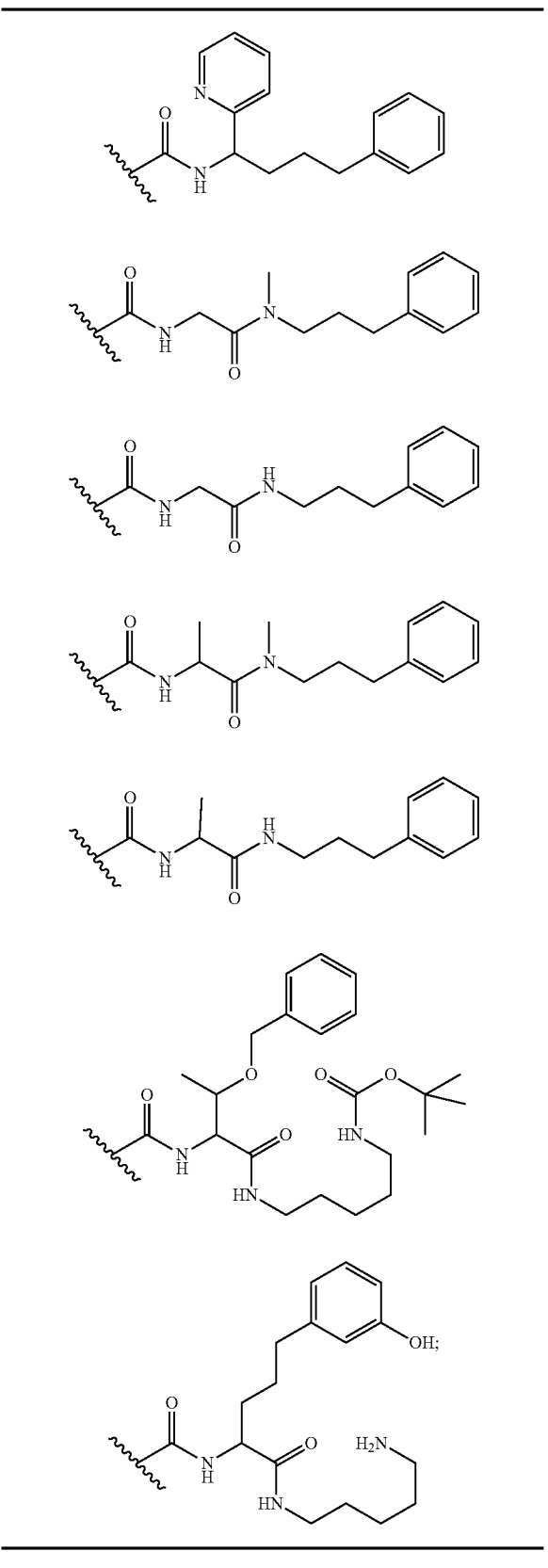
or
TABLE A2
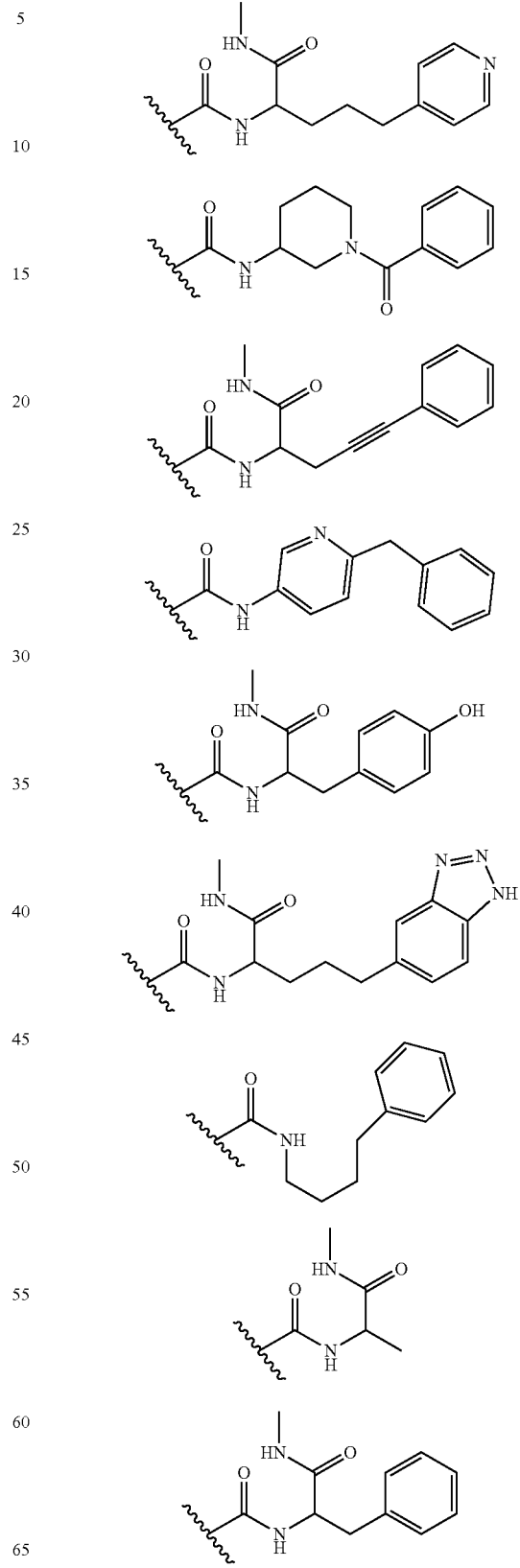

TABLE A2-continued

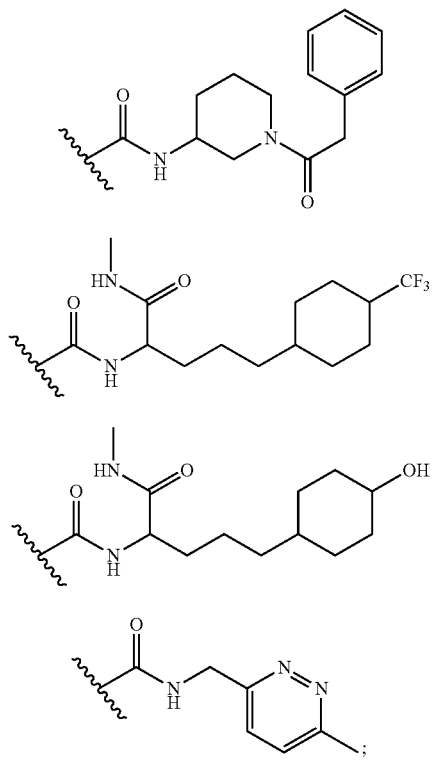

or
wherein $R^A$ is

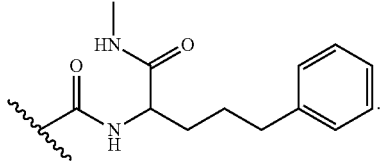 [SMILES: *C(=O)NC(CCCc1ccccc1)C(=O)NC]

11. The compound of claim 1, wherein $L^2$ is a saturated, straight, optionally substituted bivalent $C_{1-4}$ hydrocarbon chain, wherein 1 methylene unit of $L^2$ is replaced by —C(O)—; or
wherein $L^2$ is —C(O)—.

12. The compound of claim 1, wherein $R^6$ is a cyclic group selected from a 3-8 membered saturated or partially unsaturated monocyclic carbocyclic ring, a 7-12 membered saturated or partially unsaturated bicyclic carbocyclic ring, phenyl, an 8-10 membered bicyclic aromatic carbocyclic ring, a 3-8 membered saturated or partially unsaturated monocyclic heterocyclic ring (having 1-2 heteroatoms independently selected from nitrogen, oxygen, and sulfur), a 7-12 membered saturated or partially unsaturated bicyclic heterocyclic ring (having 1-4 heteroatoms independently selected from nitrogen, oxygen, and sulfur), a 5-6 membered monocyclic heteroaromatic ring (having 1-4 heteroatoms independently selected from nitrogen, oxygen, and sulfur), and an 8-10 membered bicyclic heteroaromatic ring (having 1-5 heteroatoms independently selected from nitrogen, oxygen, and sulfur), wherein the cyclic group is optionally substituted with one or more instances of $R^7$; or
wherein $R^6$ is a cyclic group selected from phenyl, an 8-10 membered bicyclic aromatic carbocyclic ring, a 5-6 membered monocyclic heteroaromatic ring (having 1-4 heteroatoms independently selected from nitrogen, oxygen, and sulfur), and an 8-10 membered bicyclic heteroaromatic ring (having 1-5 heteroatoms independently selected from nitrogen, oxygen, and sulfur), wherein the cyclic group is optionally substituted with one or more instances of $R^7$; or
wherein $R^6$ is a cyclic group selected from cyclohexyl, phenyl, quinolinyl, isoquinolinyl, quinoxalinyl, 2,3-dihydrobenzo[b][1,4]dioxinyl, pyrazolyl, isoxazolyl, imidazolyl, thiazolyl, pyridinyl, pyrazinyl, pyridazinyl, pyrimidinyl, 2,3-dihydrobenzo[d]furanyl, benzofuranyl, indolyl, benzo[1,2,3]triazole, benzimidazolyl, imidazo[1,2-a]pyrimidinyl, imidazo[1,2-a]pyrazinyl, indazolyl, indolinyl, indolizinyl, isoindolinyl, and 2,3,-dihydrobenzo[d]oxazolyl, wherein the cyclic group is optionally substituted with one or more instances of $R^7$.

13. The compound of claim 1, wherein each $R^7$ is independently halogen, —CN, —OR, —NR$_2$, —S(O)$_2$NR$_2$, —N(R)C(O)R, —N(R)C(O)S(O)$_2$R, an optionally substituted C$_{1-6}$ aliphatic group, or Cy, or two instances of $R^7$ on the same carbon atom are taken together to form an oxo group.

14. The compound of claim 1, wherein -$L^2$-$R^6$ is a substituent selected from:

TABLE B1

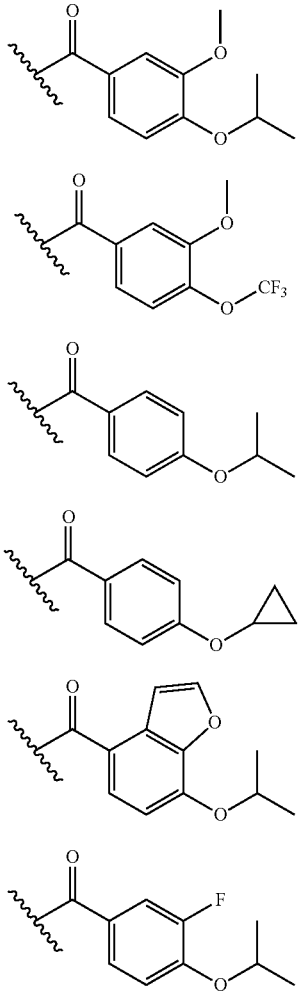

TABLE B1-continued
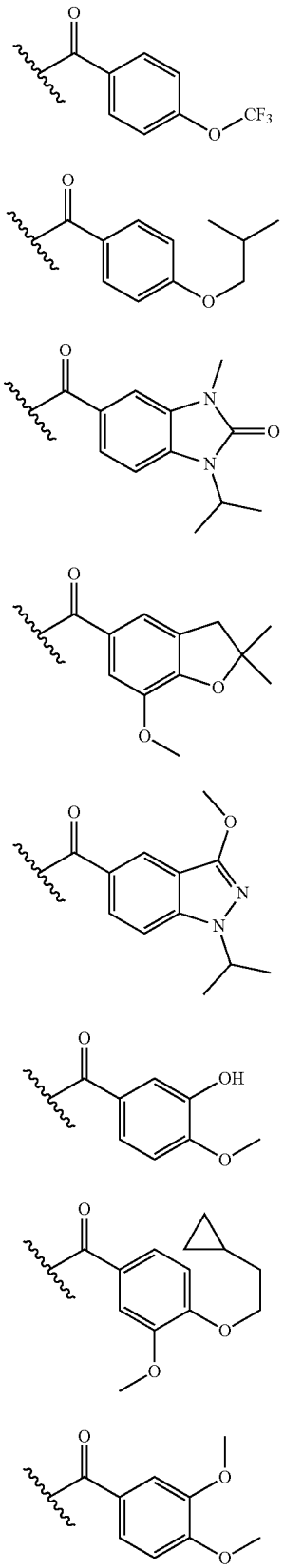
TABLE B1-continued
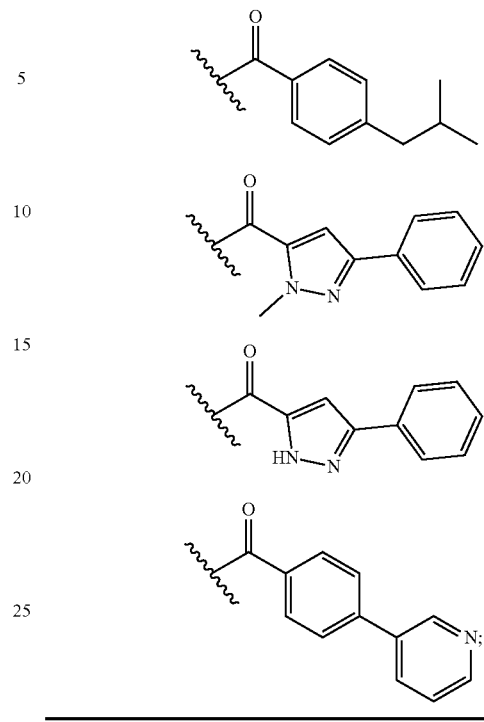
or,
TABLE B2
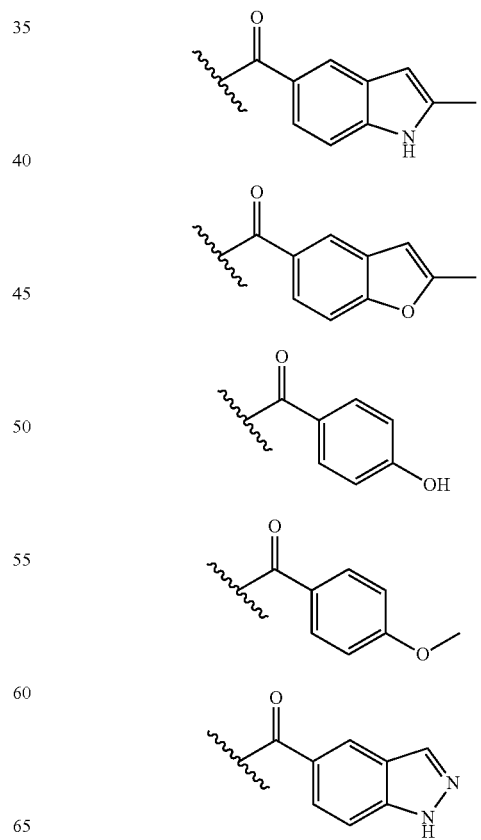

TABLE B2-continued
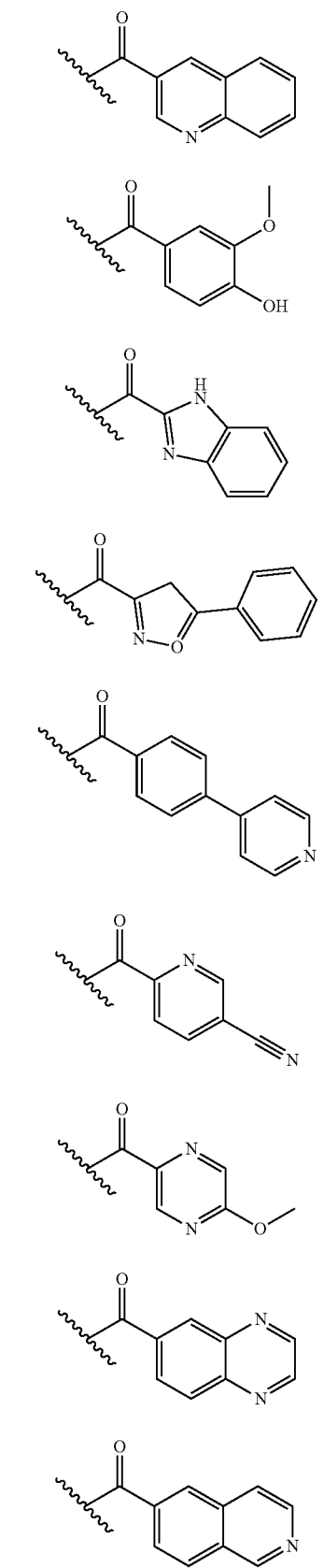
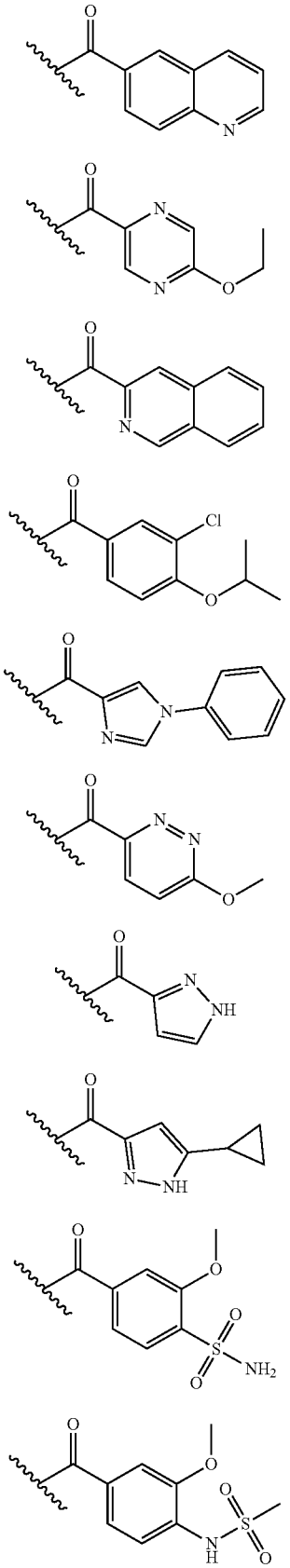

TABLE B2-continued
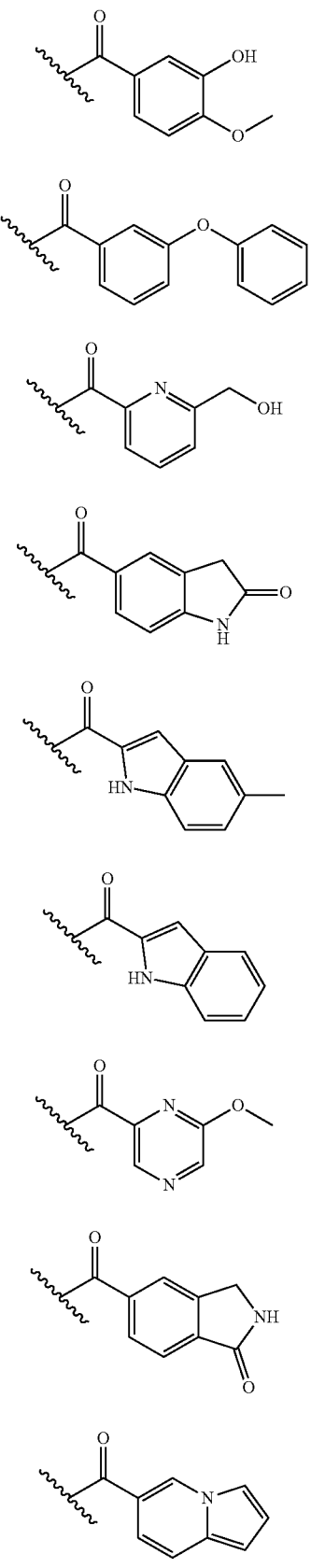
TABLE B2-continued
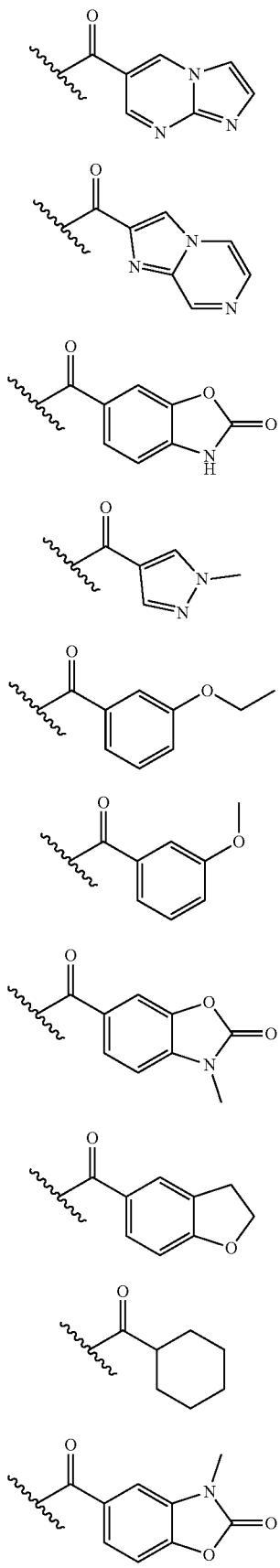

TABLE B2-continued
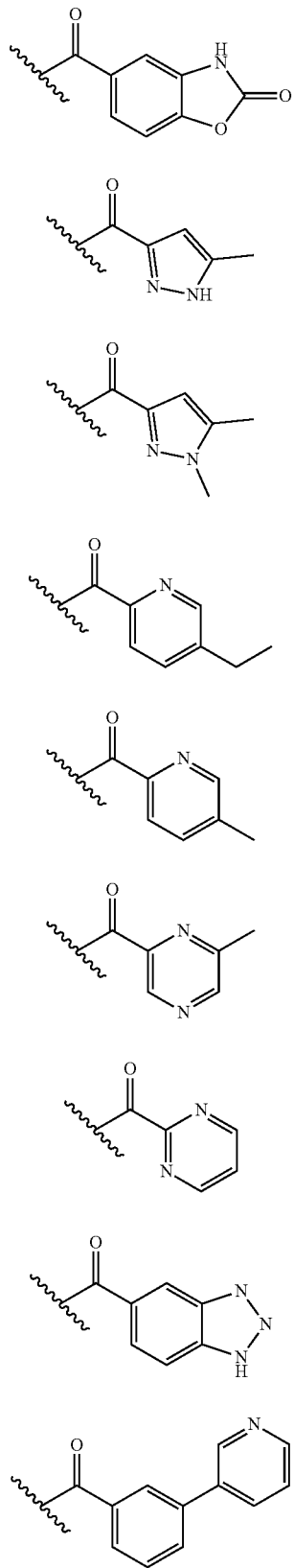
TABLE B2-continued
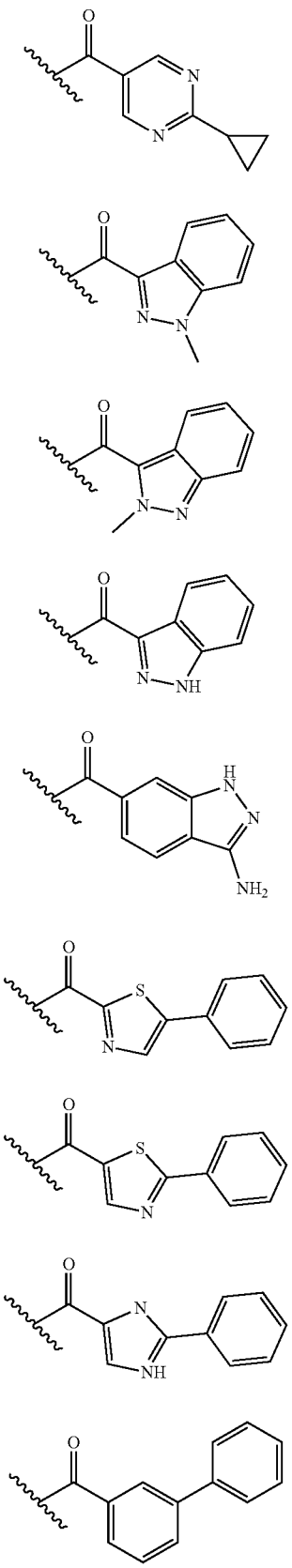

TABLE B2-continued

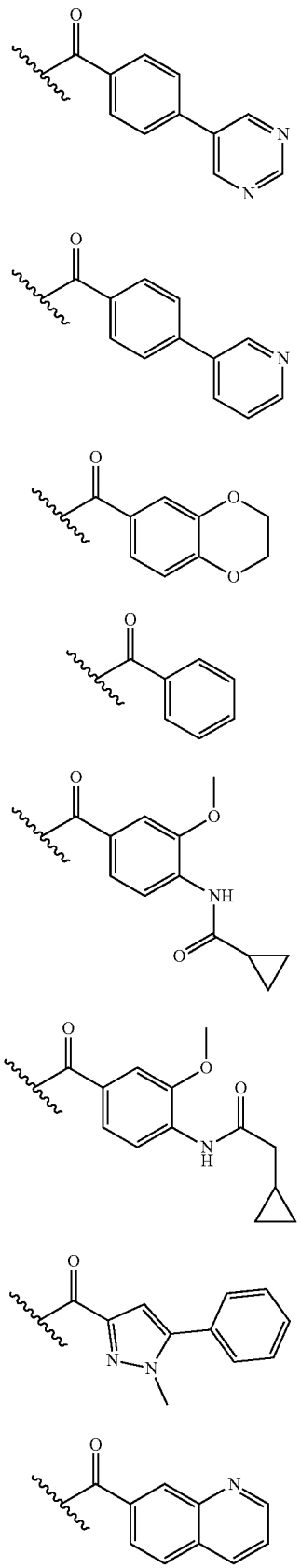

TABLE B2-continued

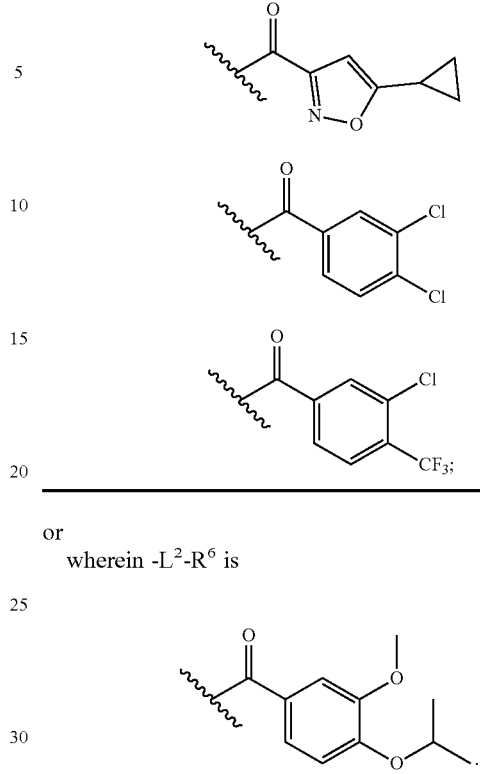

or
wherein -L²-R⁶ is

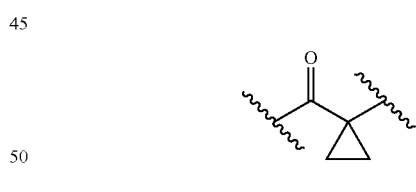

15. The compound of claim 1, wherein L³ is a saturated, straight, optionally substituted bivalent $C_{1-4}$ hydrocarbon chain, wherein 1 methylene unit of L³ is replaced by —O—, —NR—, —OC(O)—, —C(O)O—, —C(O)—, —NRC(O)—, or —C(O)NR; or
wherein L³ is a saturated, straight, optionally substituted bivalent $C_{1-4}$ hydrocarbon chain, wherein 1 methylene unit of L³ is replaced by —C(O)—; or
wherein L³ is —C(O)CH₂—, —C(O)C(CH₃)H—, —C(O)C(CH₃)₂—, —C(O)CH₂CH₂—, —C(O)CH₂CH₂CH₂—,

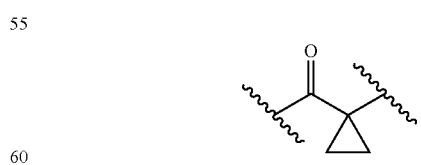

or —C(O)—; or
wherein L³ is —C(O)CH₂—, or —C(O)C(CH₃)H—.

16. The compound of claim 1, wherein R⁸ is a cyclic group selected from phenyl, a 3-8 membered saturated or partially unsaturated monocyclic heterocyclic ring (having 1-2 heteroatoms independently selected from nitrogen, oxygen, and sulfur), a 7-12 membered saturated or partially unsaturated bicyclic heterocyclic ring (having 1-4 heteroatoms independently selected from nitrogen, oxygen, and sulfur), a 5-6 membered monocyclic heteroaromatic ring (having 1-4 heteroatoms independently selected from nitrogen, oxygen, and sulfur), and an 8-10 membered bicyclic heteroaromatic ring (having 1-5 heteroatoms independently selected from nitrogen, oxygen, and sulfur), wherein the cyclic group is optionally substituted with one or more instances of $R^9$; or wherein $R^8$ is an 8-10 membered bicyclic heteroaromatic ring (having 1-5 heteroatoms independently selected from nitrogen, oxygen, and sulfur), optionally substituted with one or more instances of $R^9$; or wherein $R^8$ is a cyclic group selected from indolyl, indazolyl, benzimidazolyl, benzofuranyl, phenyl, pyridinyl, pyrimidinyl, pyridazinyl, pyrazinyl, quinolinyl, isoquinolinyl, pyrazolyl, tetrazolyl, quinoxalinyl, indolizinyl, thiazolyl, oxazolyl, pyrrolyl, imidazo[1,2-a]pyrazinyl, and tetrahydropyranyl wherein the cyclic group is optionally substituted with one or more instances of $R^9$.

17. The compound of claim 1, wherein each instance of $R^9$ is independently halogen, —CN, —OR, or an optionally substituted $C_{1-6}$ aliphatic group; or wherein each instance of $R^9$ is independently chloro, bromo, —CN, methyl, or methoxy.

18. The compound of claim 1, wherein -$L^3$-$R^8$ is a substituent selected from:

TABLE C1

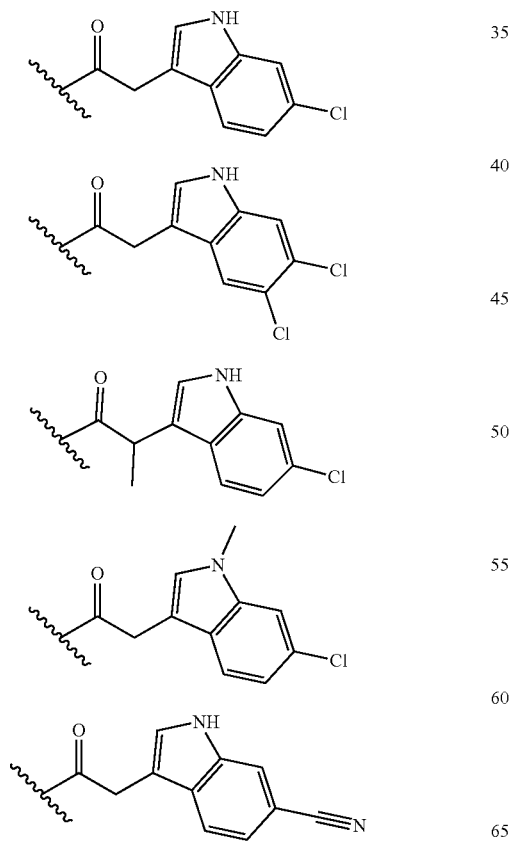

TABLE C1-continued

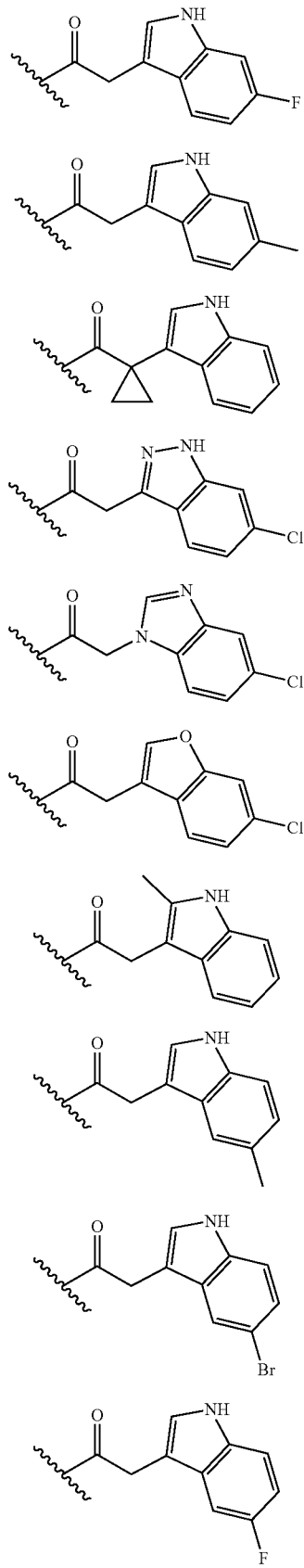

TABLE C1-continued
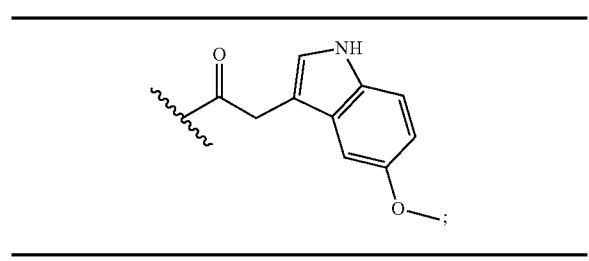
or
TABLE C2
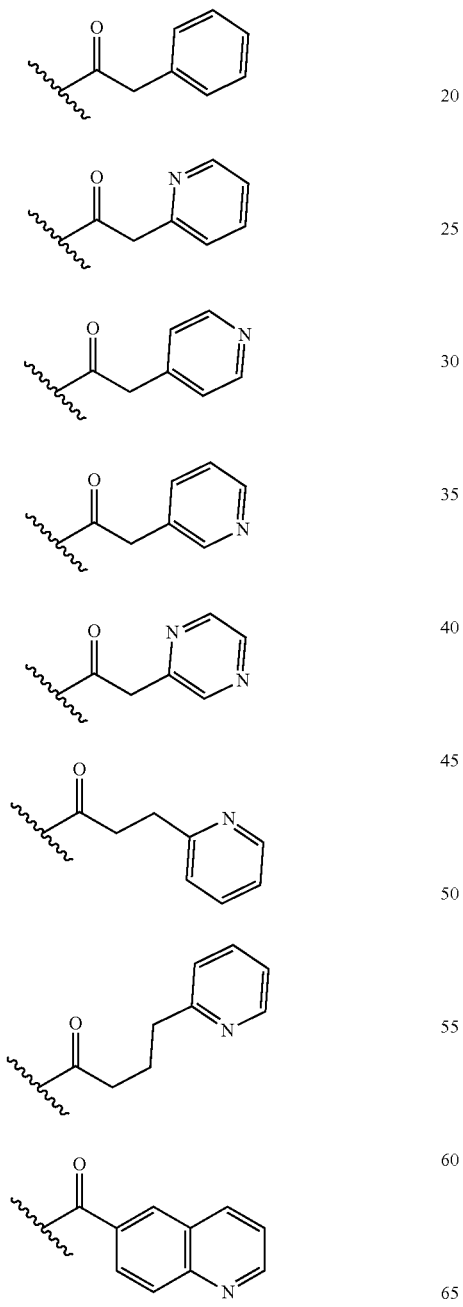
TABLE C2-continued
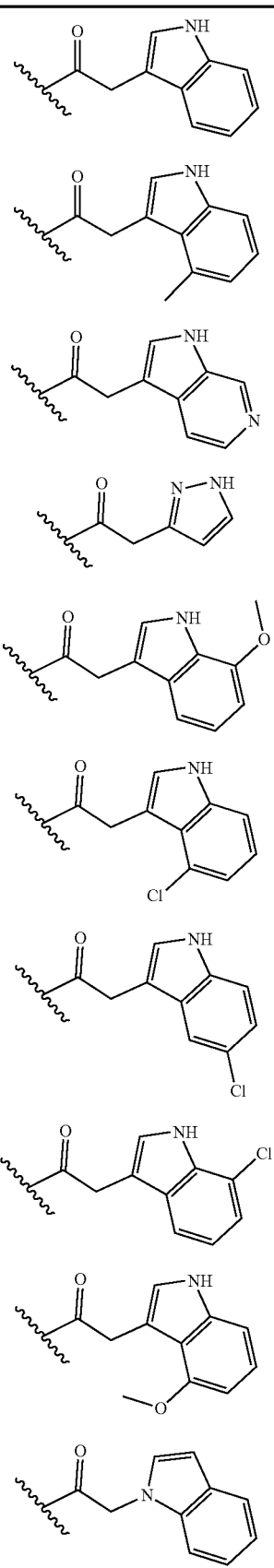

TABLE C2-continued
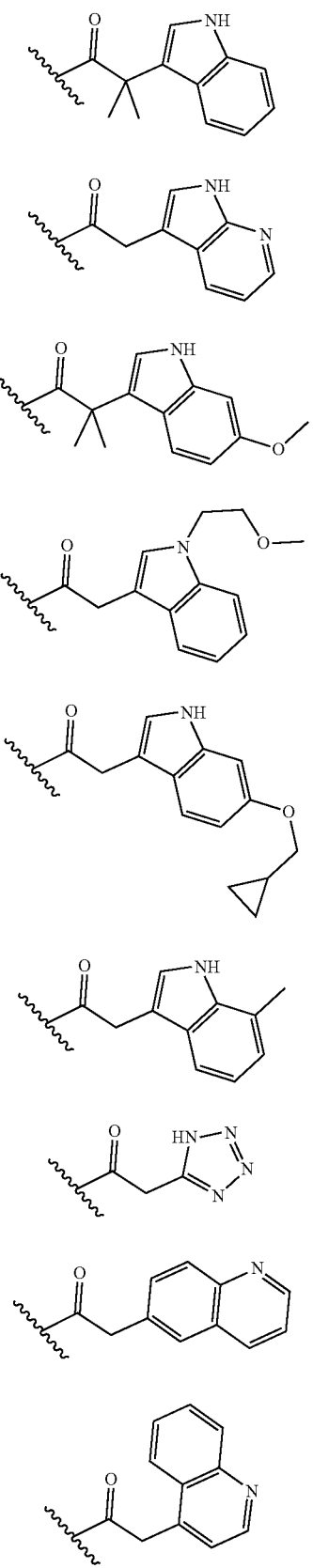
TABLE C2-continued
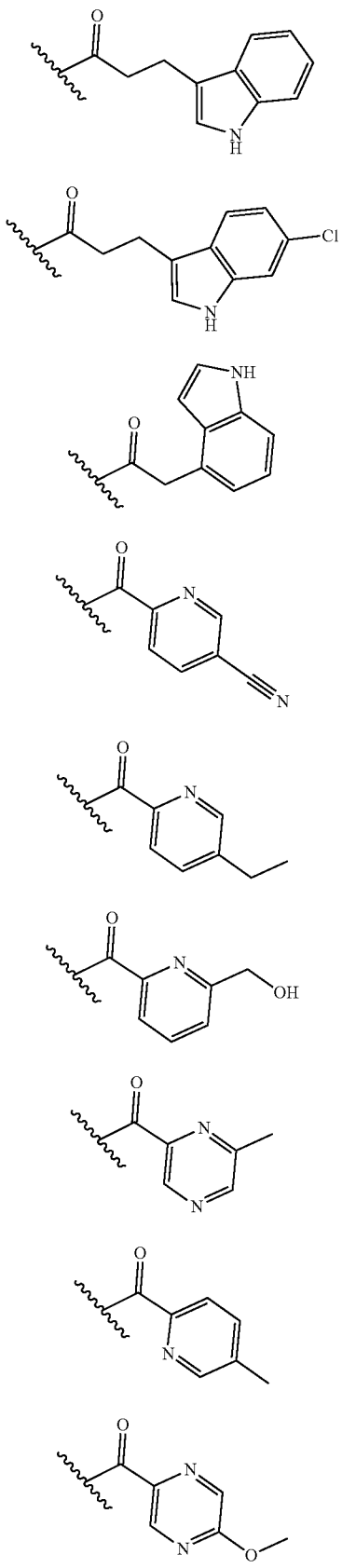

TABLE C2-continued
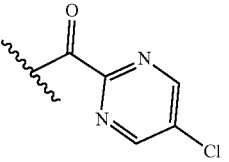 [SMILES: *C(=O)c1ncc(Cl)cn1]
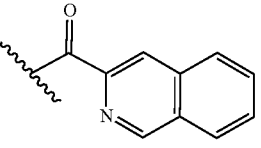 [SMILES: *C(=O)c1cc2ccccc2cn1]
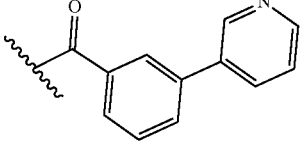
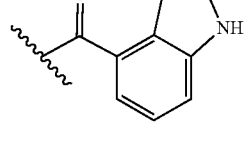
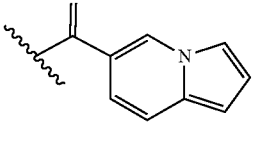
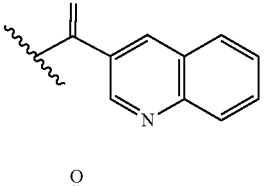
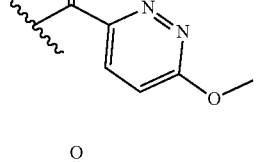
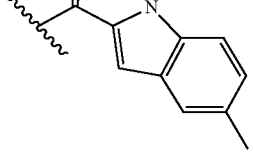
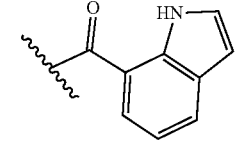 [SMILES: *C(=O)c1cccc2cc[nH]c12]
TABLE C2-continued
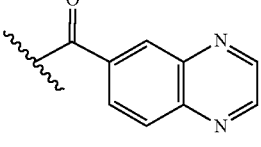
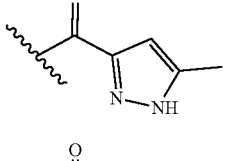
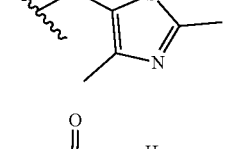
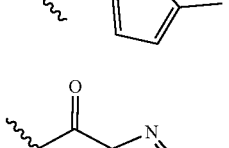
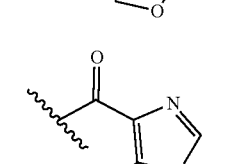
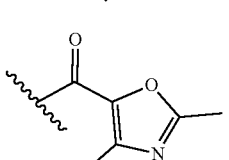
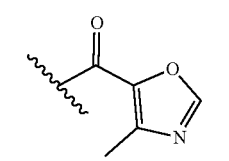 [SMILES: *C(=O)c1ocnc1C]
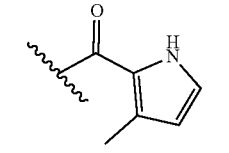 [SMILES: *C(=O)c1[nH]ccc1C]
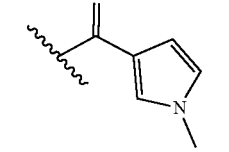

TABLE C2-continued
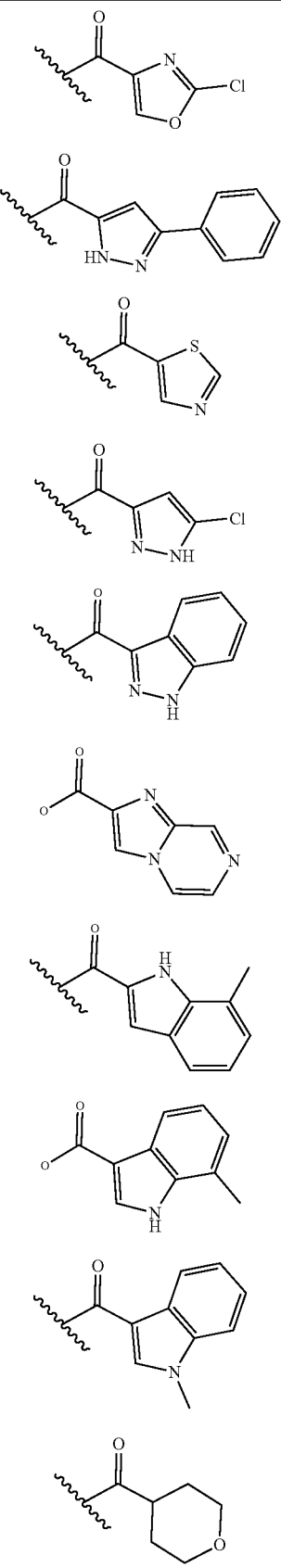
TABLE C2-continued
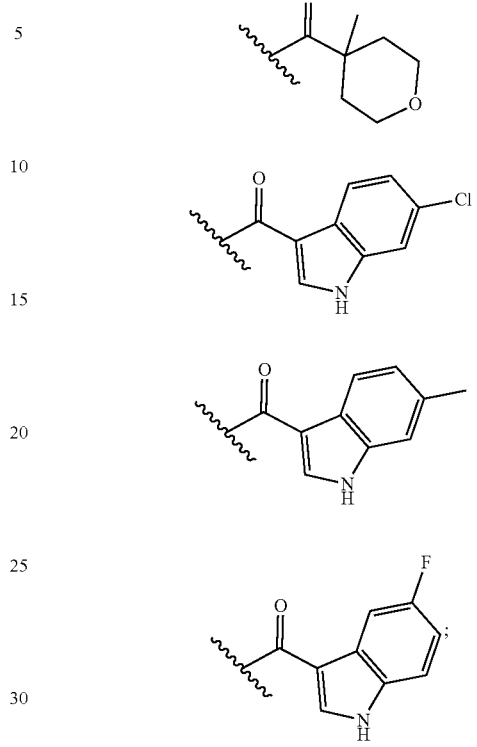
or,
wherein -L³-R⁸ is
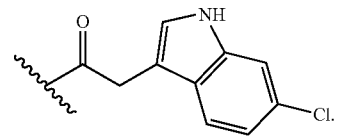 [SMILES: *C(=O)Cc1c[nH]c2cc(Cl)ccc12]
19. The compound of claim 1, wherein the compound of Formula I is a compound of any of the following Formulae:
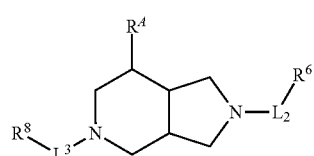
II
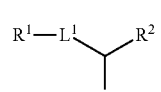
III
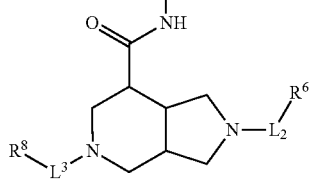

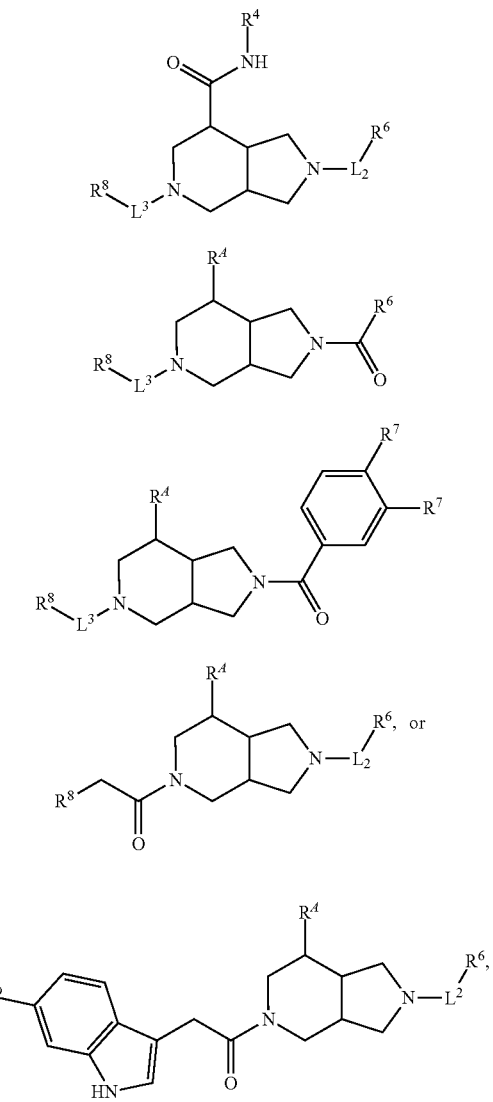

or a pharmaceutically acceptable salt thereof.

20. The compound of claim 1, wherein $R^A$ is

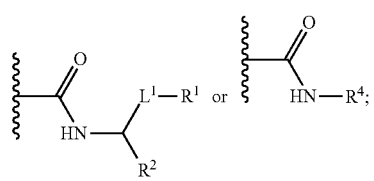

$L^1$ is

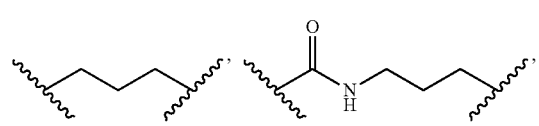

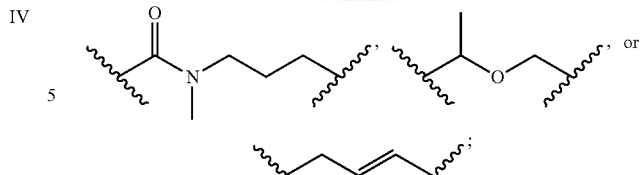

R¹ is a $C_{1-4}$ aliphatic group or an optionally substituted cyclic group selected from a 3-8 membered saturated or partially unsaturated monocyclic carbocyclic ring, phenyl, a 3-8 membered saturated or partially unsaturated monocyclic heterocyclic ring (having 1-2 heteroatoms independently selected from nitrogen, oxygen, and sulfur), a 5-6 membered monocyclic heteroaromatic ring (having 1-4 heteroatoms independently selected from nitrogen, oxygen, and sulfur), and an 8-10 membered bicyclic heteroaromatic ring (having 1-5 heteroatoms independently selected from nitrogen, oxygen, and sulfur);

R² is hydrogen, methyl, —C(O)NHCH₃, —C(O)NH₂, —C(O)OCH₃, —C(O)OH, or a 5-6 membered monocyclic heteroaromatic ring (having 1-4 heteroatoms independently selected from nitrogen, oxygen, and sulfur);

R⁴ is a cyclic group selected from a 3-8 membered saturated or partially unsaturated monocyclic heterocyclic ring (having 1-2 heteroatoms independently selected from nitrogen, oxygen, and sulfur), and a 5-6 membered monocyclic heteroaromatic ring (having 1-4 heteroatoms independently selected from nitrogen, oxygen, and sulfur), wherein the cyclic group is optionally substituted with one or more instances of R⁵;

each R⁵ is independently —OR, —C(O)R, an optionally substituted $C_{1-6}$ aliphatic group, or an optionally substituted —$C_{1-6}$ aliphatic-Cy group;

L² is —C(O)—;

R⁶ is a cyclic group selected from phenyl, an 8-10 membered bicyclic aromatic carbocyclic ring, a 5-6 membered monocyclic heteroaromatic ring (having 1-4 heteroatoms independently selected from nitrogen, oxygen, and sulfur), and an 8-10 membered bicyclic heteroaromatic ring (having 1-5 heteroatoms independently selected from nitrogen, oxygen, and sulfur), wherein the cyclic group is optionally substituted with one or more instances of R⁷;

each R⁷ is independently —OR, an optionally substituted $C_{1-6}$ aliphatic group, Cy or two instances of R⁷ on the same carbon atom are taken together to form an oxo group;

L³ is —C(O)CH₂—,

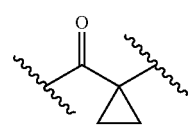 [SMILES: *C(=O)C1(*)CC1]

or —C(O)C(CH₃)H—;

R⁸ is an 8-10 membered bicyclic heteroaromatic ring (having 1-5 heteroatoms independently selected from nitrogen, oxygen, and sulfur), optionally substituted with one or more instances of R⁹;

each instance of R⁹ is independently halogen, —CN, —OR, or a $C_{1-6}$ aliphatic group; and each instance of Cy is independently phenyl or a 5-6 membered monocyclic heteroaromatic ring (having 1-4 heteroatoms independently selected from nitrogen, oxygen, and sulfur).

21. The compound of claim 1, wherein the compound is one of those in Table 1:

| # | Structure |
|---|---|
| I-1 | 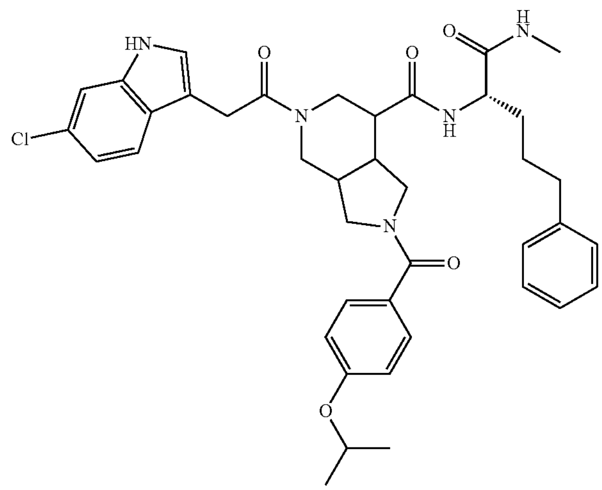 [SMILES: CNC(=O)[C@H](CCCc1ccccc1)NC(=O)C1CN(C(=O)Cc2c[nH]c3cc(Cl)ccc23)CC2CN(C(=O)c3ccc(OC(C)C)cc3)CC21] |
| I-2 | 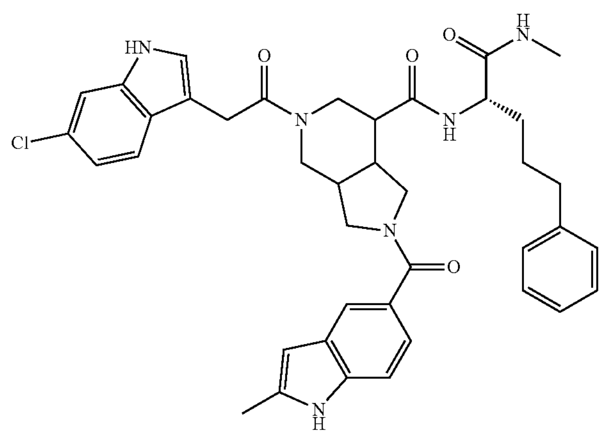 [SMILES: CNC(=O)[C@H](CCCc1ccccc1)NC(=O)C1CN(C(=O)Cc2c[nH]c3cc(Cl)ccc23)CC2CN(C(=O)c3ccc4[nH]c(C)cc4c3)CC21] |
| I-3 | 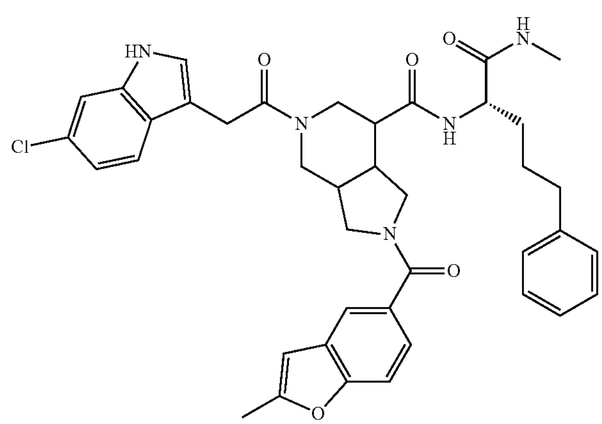 [SMILES: CNC(=O)[C@H](CCCc1ccccc1)NC(=O)C1CN(C(=O)Cc2c[nH]c3cc(Cl)ccc23)CC2CN(C(=O)c3ccc4oc(C)cc4c3)CC21] |

-continued
| # | Structure |
|---|---|
| I-4 | 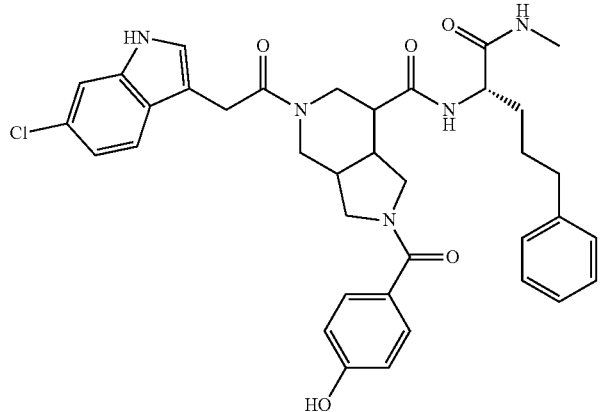 [SMILES: CNC(=O)[C@H](CCCc1ccccc1)NC(=O)C1CN(C(=O)Cc2c[nH]c3cc(Cl)ccc23)CC2CN(C(=O)c3ccc(O)cc3)CC21] |
| I-5 | 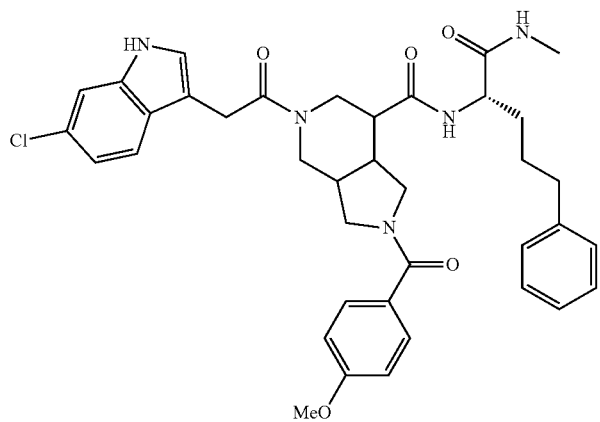 |
| I-6 | 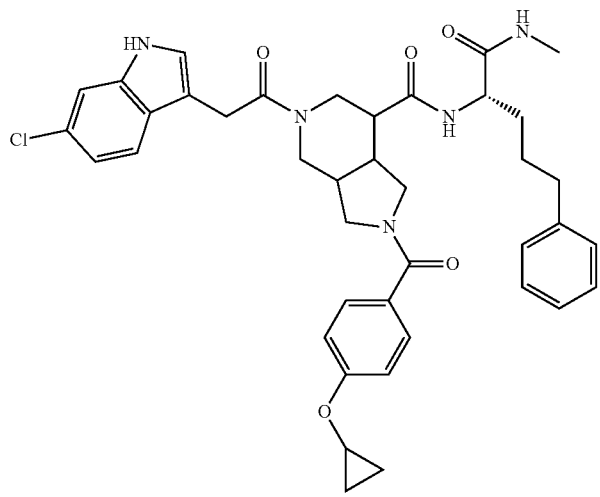 [SMILES: CNC(=O)[C@H](CCCc1ccccc1)NC(=O)C1CN(C(=O)Cc2c[nH]c3cc(Cl)ccc23)CC2CN(C(=O)c3ccc(OC4CC4)cc3)CC21] |

| # | Structure |
|---|---|
| I-7 | 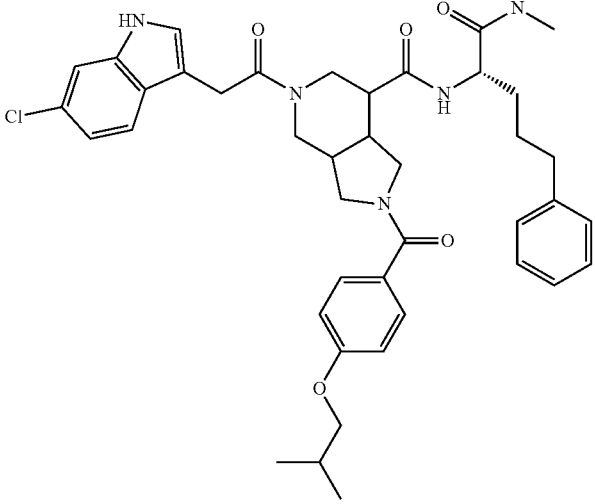 |
| I-8 | 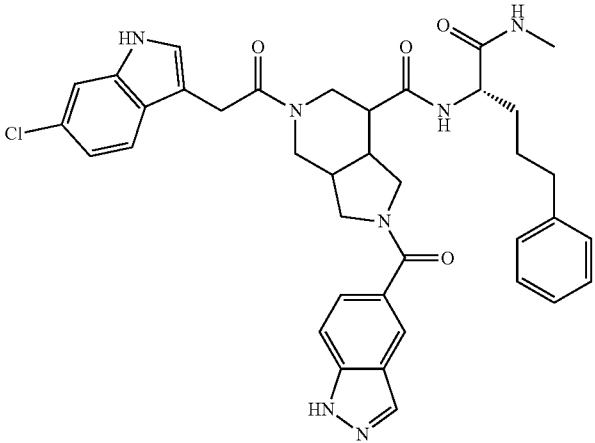 |
| I-9 | 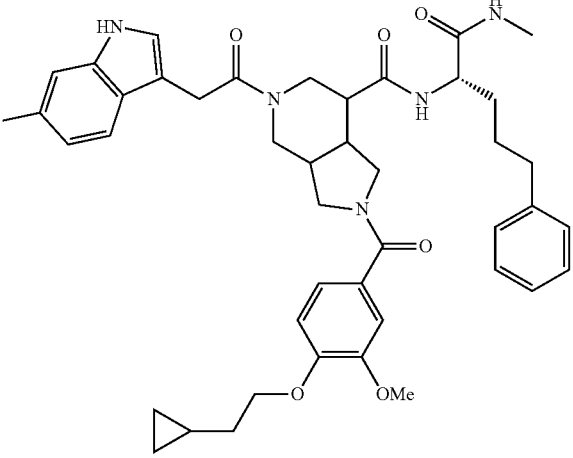 |

-continued
| # | Structure |
|---|---|
| I-10 | 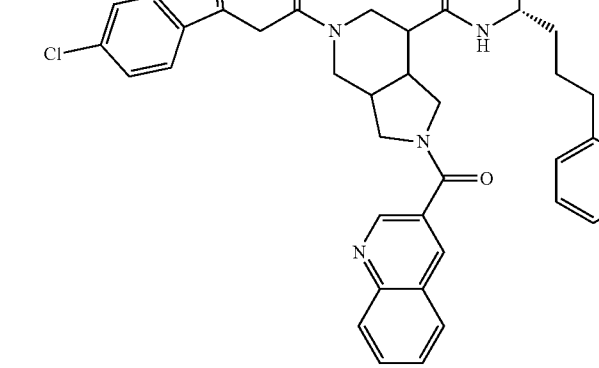 |
| I-11 | 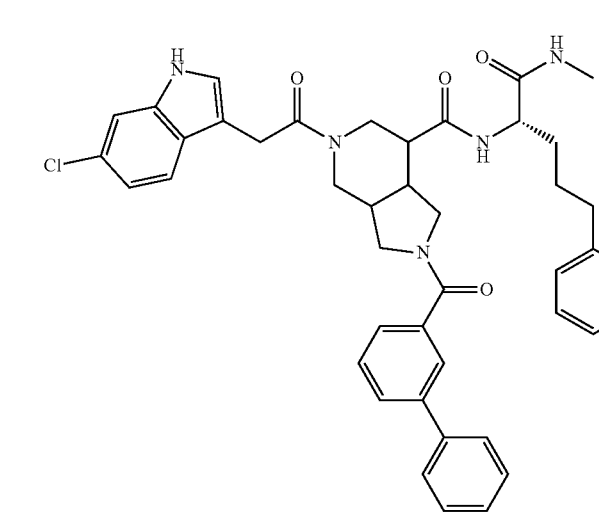 |
| I-12 | 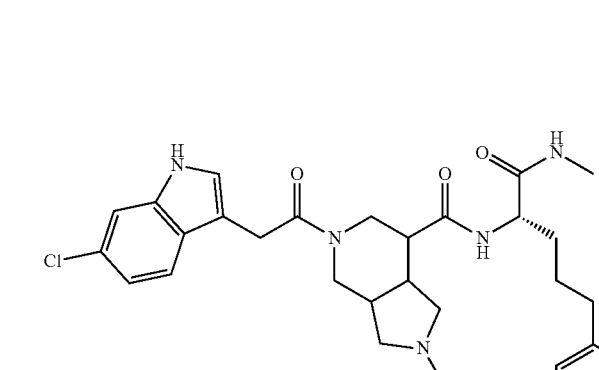 |

-continued
| # | Structure |
|---|---|
| I-13 | 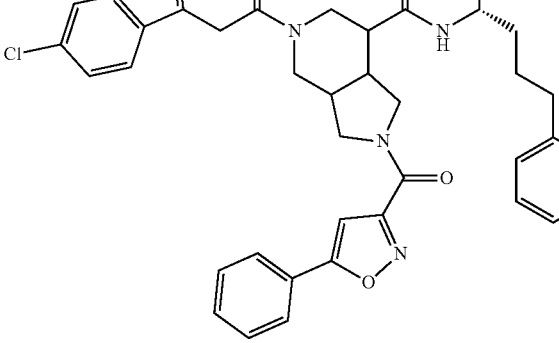 |
| I-14 | 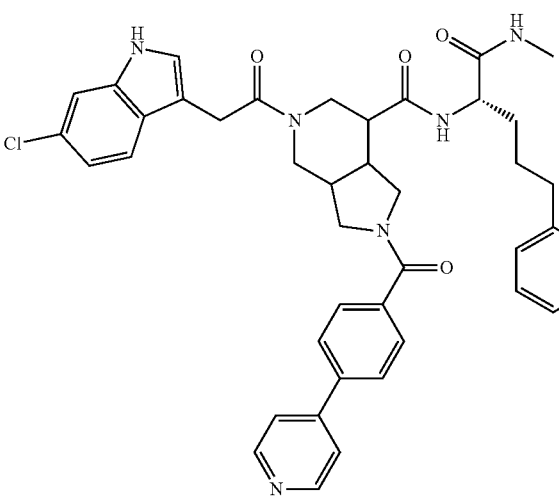 |
| I-15 | 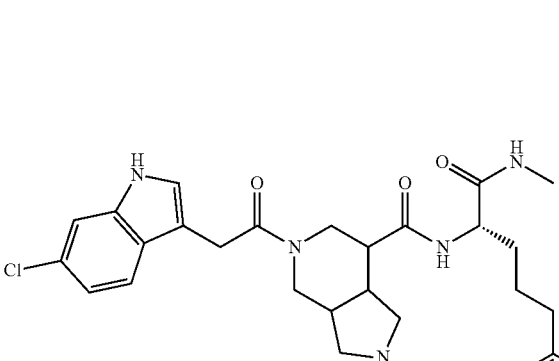 |

| # | Structure |
|---|---|
| I-16 | 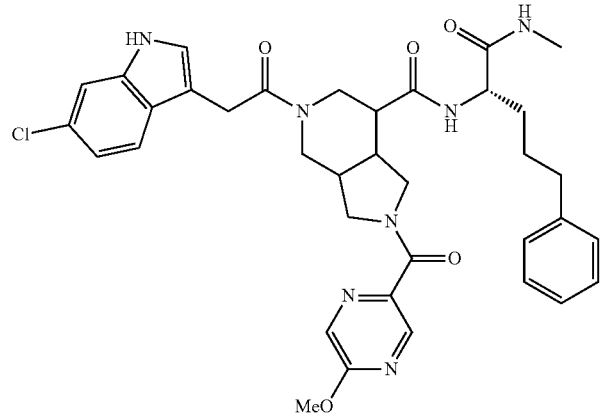 [SMILES: CNC(=O)[C@H](CCCc1ccccc1)NC(=O)C1CN(C(=O)Cc2c[nH]c3cc(Cl)ccc23)CC2CN(C(=O)c3cnc(OC)cn3)CC21] |
| I-17 | 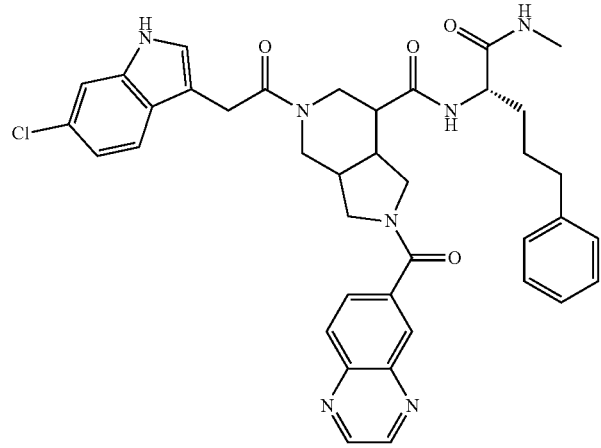 |
| I-18 | 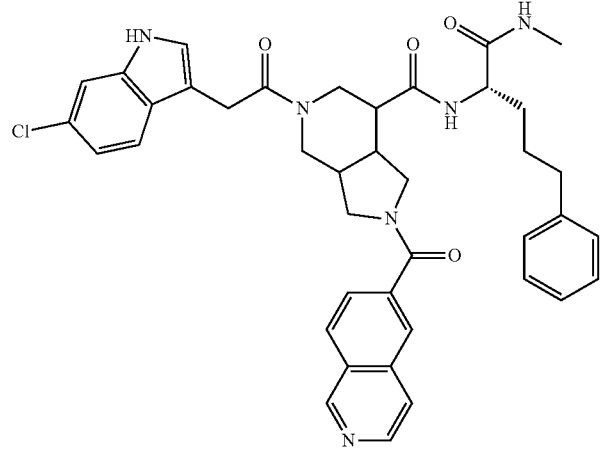 [SMILES: CNC(=O)[C@H](CCCc1ccccc1)NC(=O)C1CN(C(=O)Cc2c[nH]c3cc(Cl)ccc23)CC2CN(C(=O)c3ccc4cnccc4c3)CC21] |

-continued
| # | Structure |
|---|---|
| I-19 | 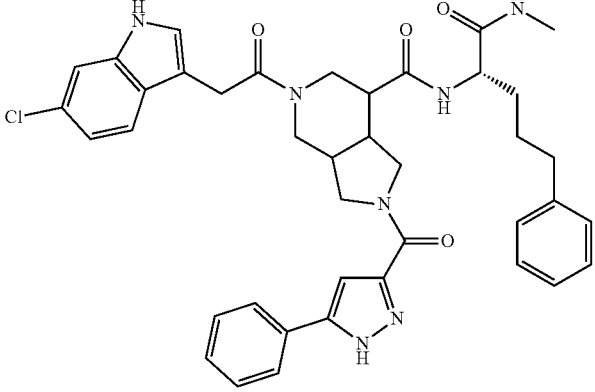 |
| I-20 | 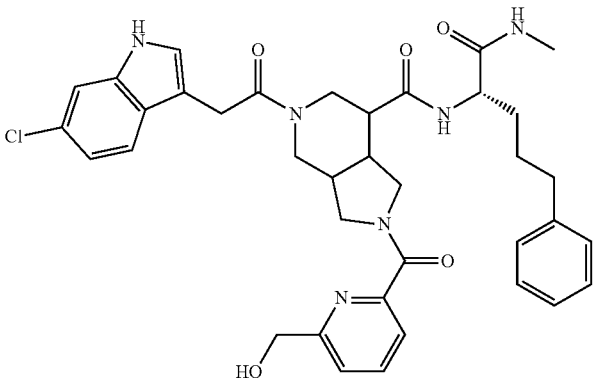 [SMILES: CNC(=O)[C@H](CCCc1ccccc1)NC(=O)C1CN(C(=O)Cc2c[nH]c3cc(Cl)ccc23)CC2CN(C(=O)c3cccc(CO)n3)CC21] |
| I-21 | 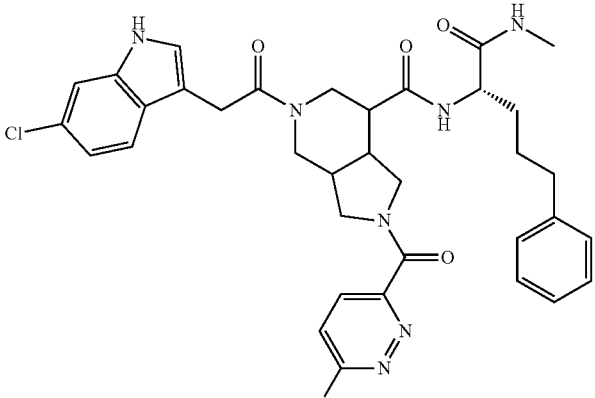 |

| # | Structure |
|---|---|
| I-22 | 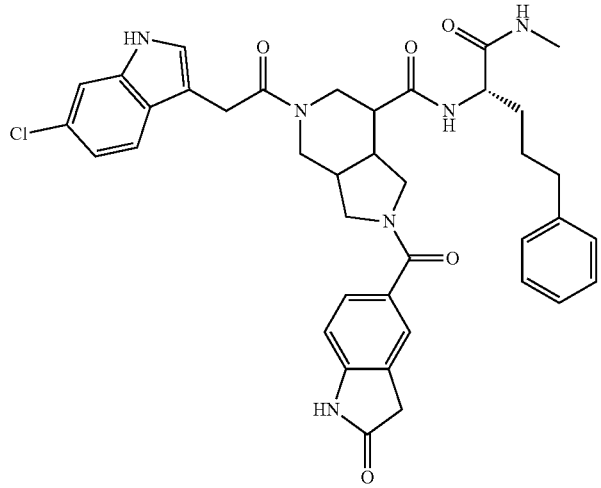
First eluting diastereomer |
| I-23 | 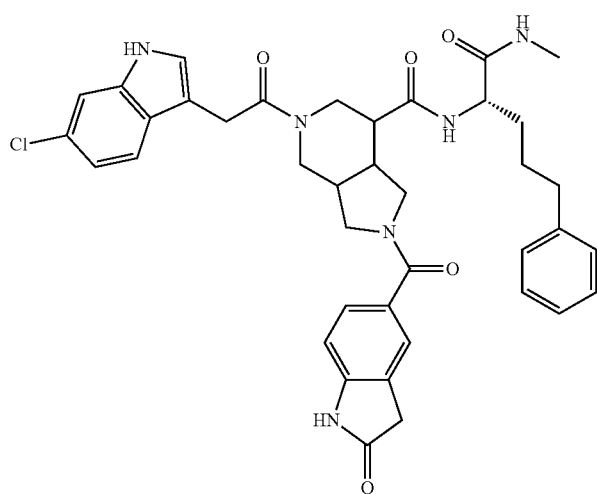
Second eluting diastereomer |
| I-24 | 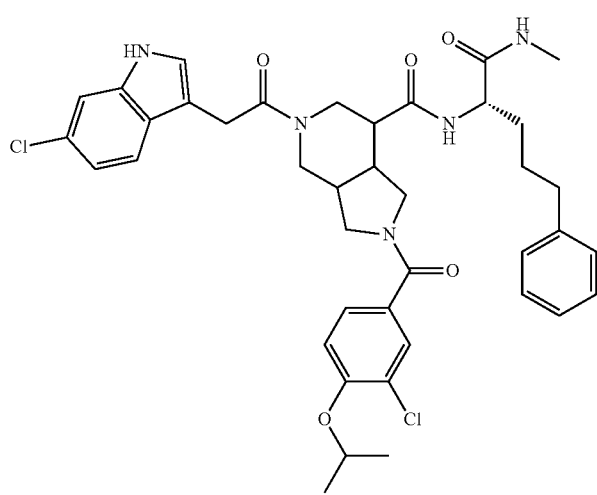 |

| # | Structure |
|---|---|
| I-25 | 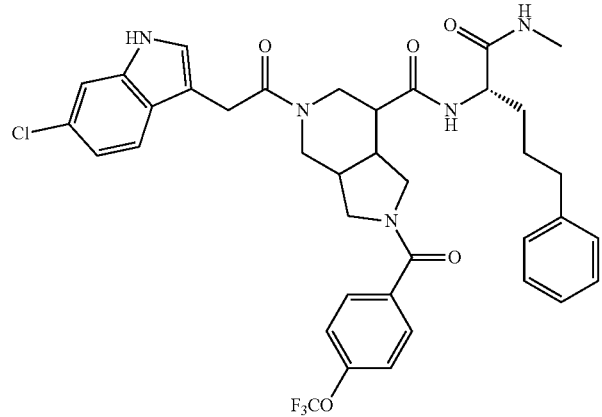 [SMILES: CNC(=O)[C@H](CCCc1ccccc1)NC(=O)C1CN(C(=O)Cc2c[nH]c3cc(Cl)ccc23)CC2CN(C(=O)c3ccc(OC(F)(F)F)cc3)CC21] |
| I-26 | 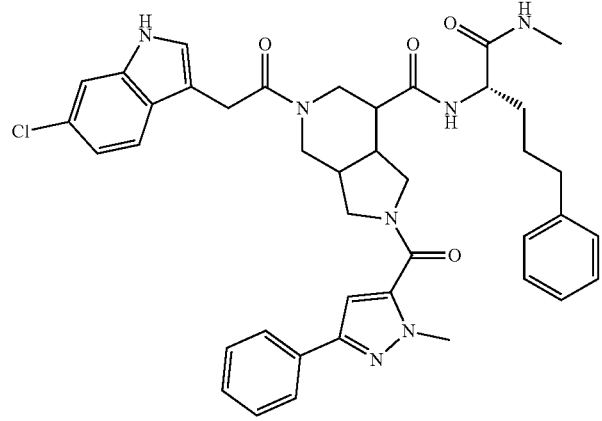 [SMILES: CNC(=O)[C@H](CCCc1ccccc1)NC(=O)C1CN(C(=O)Cc2c[nH]c3cc(Cl)ccc23)CC2CN(C(=O)c3cc(-c4ccccc4)nn3C)CC21] |
| I-27 | 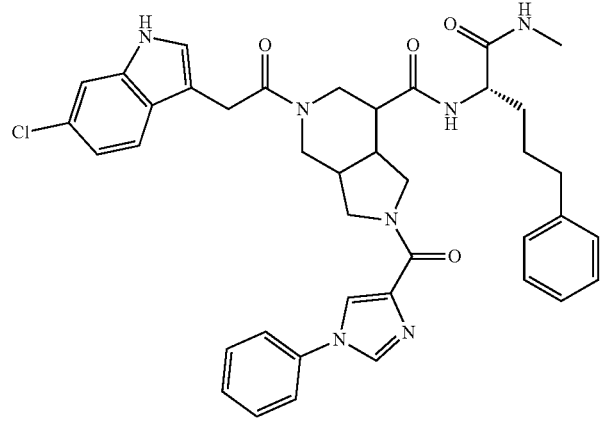 [SMILES: CNC(=O)[C@H](CCCc1ccccc1)NC(=O)C1CN(C(=O)Cc2c[nH]c3cc(Cl)ccc23)CC2CN(C(=O)c3cn(-c4ccccc4)cn3)CC21] |

-continued
| # | Structure |
|---|---|
| I-28 | 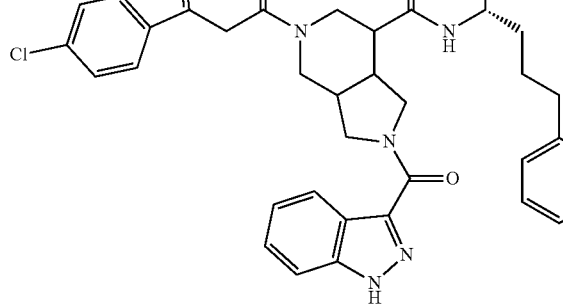 |
| I-29 | 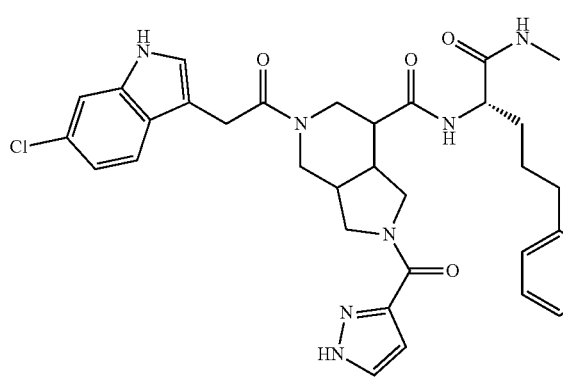 |
| I-30 | 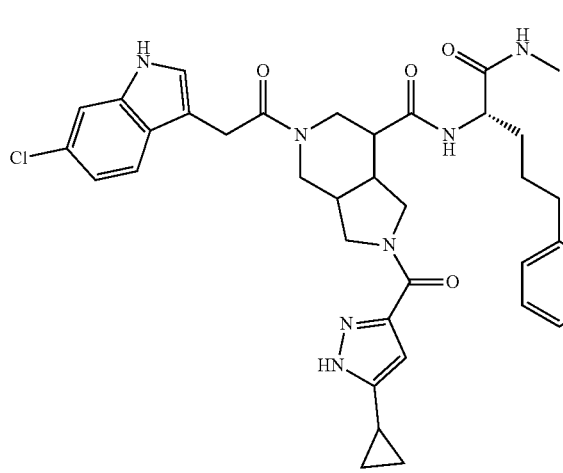 |

| # | Structure |
|---|---|
| I-31 | 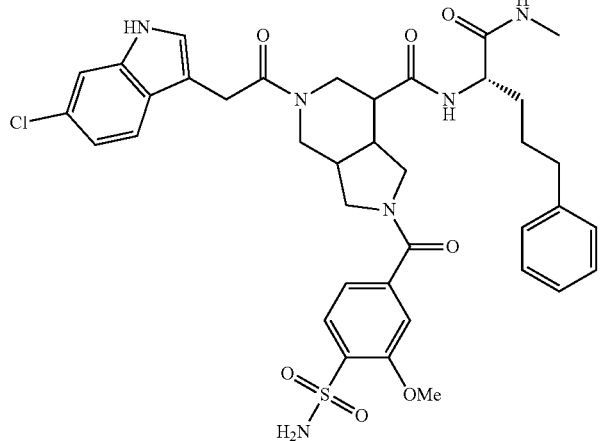 |
| I-32 | 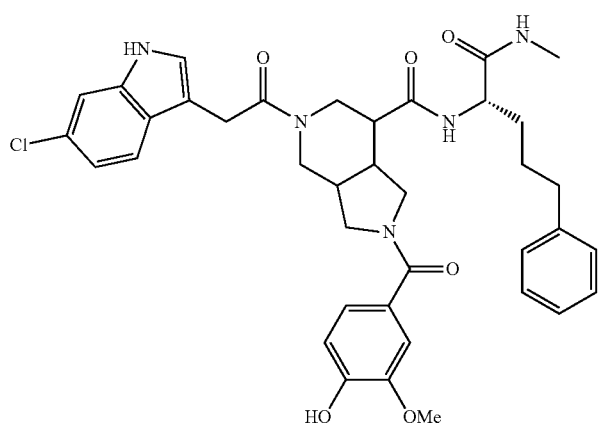 [SMILES: CNC(=O)[C@H](CCCc1ccccc1)NC(=O)C1CN(C(=O)Cc2c[nH]c3cc(Cl)ccc23)CC2CN(C(=O)c3ccc(O)c(OC)c3)CC21] |
| I-33 | 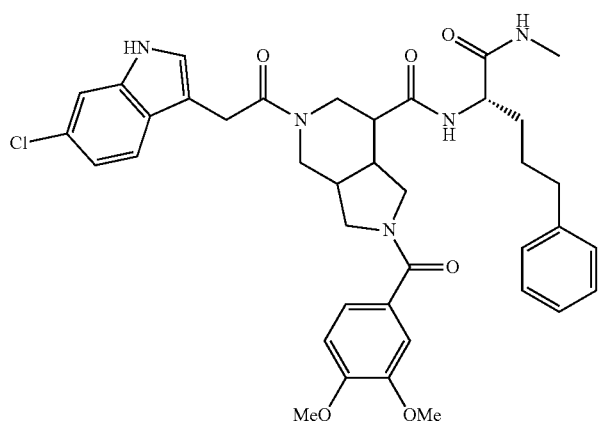 [SMILES: CNC(=O)[C@H](CCCc1ccccc1)NC(=O)C1CN(C(=O)Cc2c[nH]c3cc(Cl)ccc23)CC2CN(C(=O)c3ccc(OC)c(OC)c3)CC21] |

-continued
| # | Structure |
|---|---|
| I-34 | 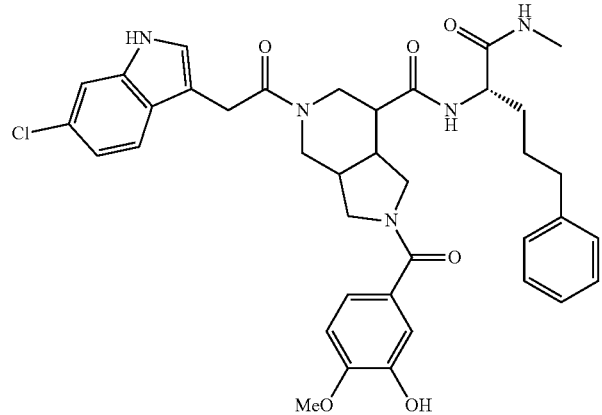 [SMILES: CNC(=O)[C@H](CCCc1ccccc1)NC(=O)C1CN(C(=O)Cc2c[nH]c3cc(Cl)ccc23)CC2CN(C(=O)c3ccc(OC)c(O)c3)CC21] |
| I-35 | 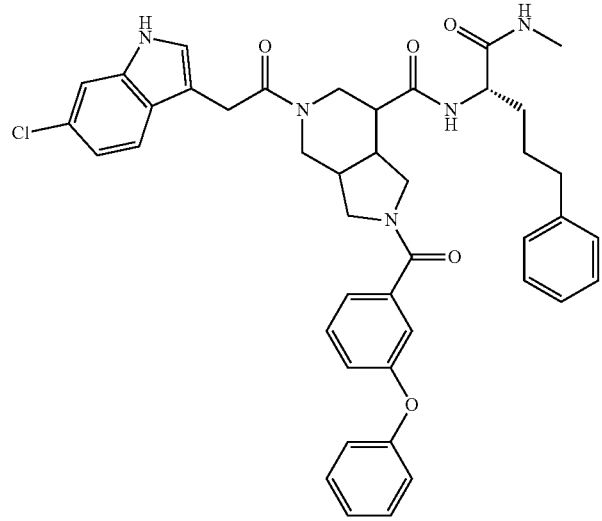 [SMILES: CNC(=O)[C@H](CCCc1ccccc1)NC(=O)C1CN(C(=O)Cc2c[nH]c3cc(Cl)ccc23)CC2CN(C(=O)c3cccc(Oc4ccccc4)c3)CC21] |
| I-36 | 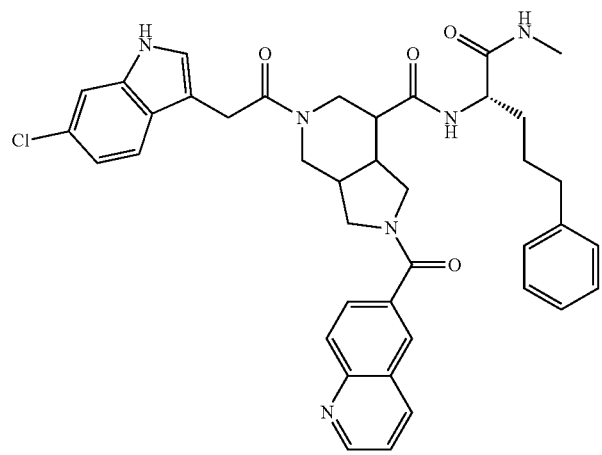 |

| # | Structure |
|---|---|
| I-37 | 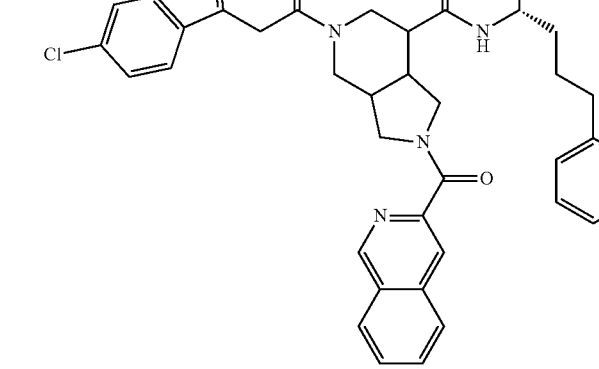 |
| I-38 | 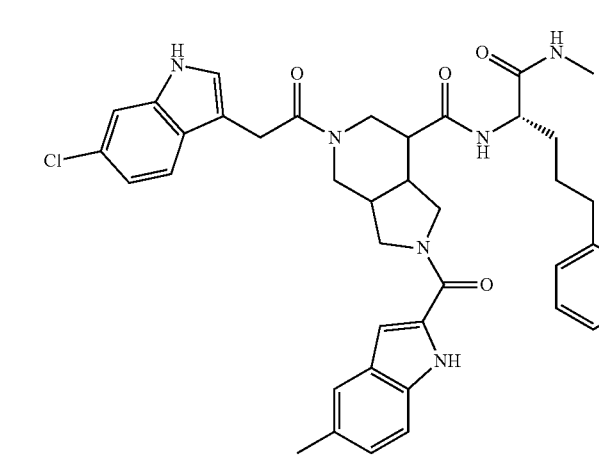 |
| I-39 | 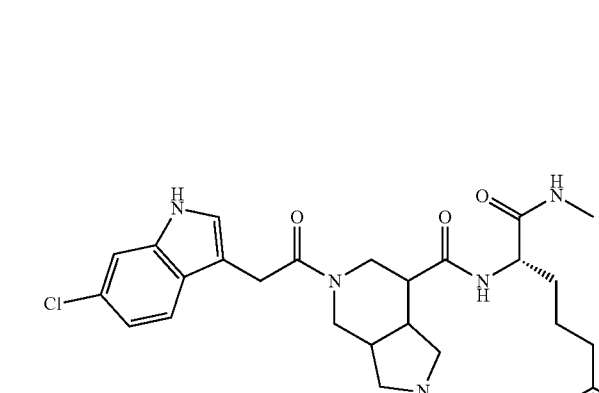 |

| # | Structure |
|---|---|
| I-40 | 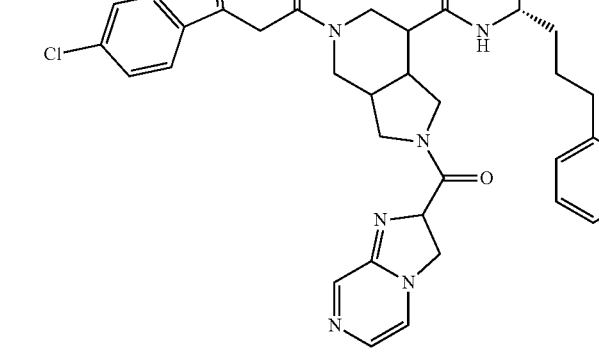 |
| I-41 | 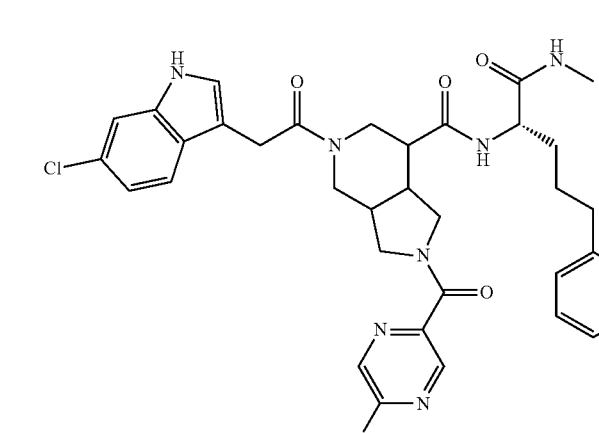 |
| I-42 | 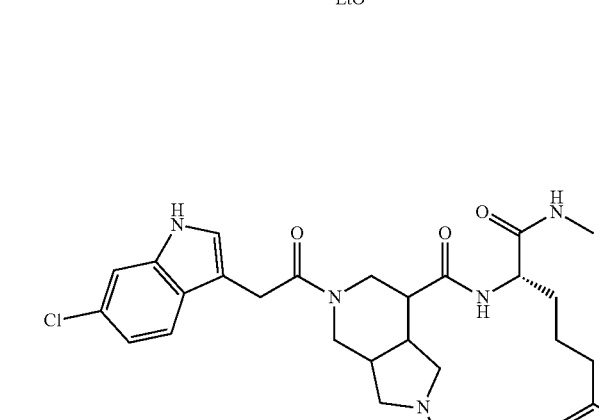 |

| # | Structure |
|---|---|
| I-43 | 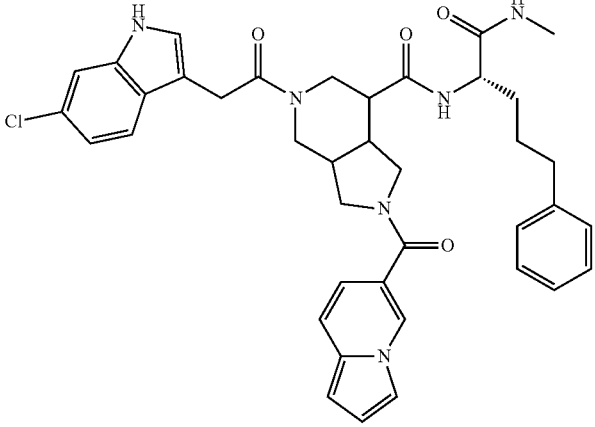 |
| I-44 | 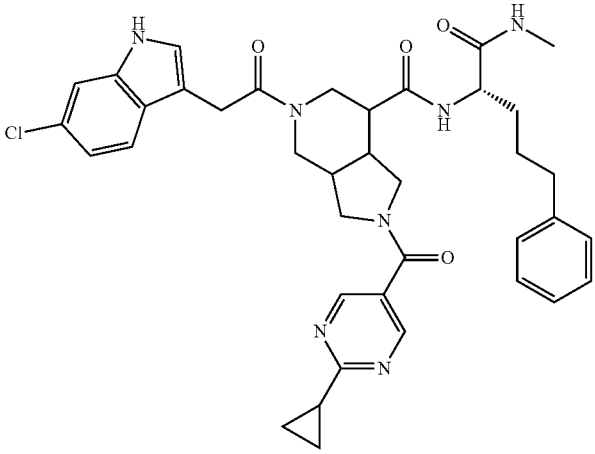 [SMILES: CNC(=O)[C@H](CCCc1ccccc1)NC(=O)C1CN(C(=O)Cc2c[nH]c3cc(Cl)ccc23)CC2CN(C(=O)c3cnc(C4CC4)nc3)CC21] |
| I-45 | 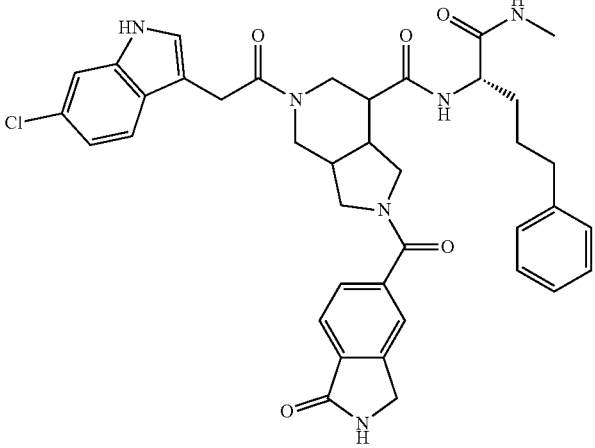 |

| # | Structure |
|---|---|
| I-46 | 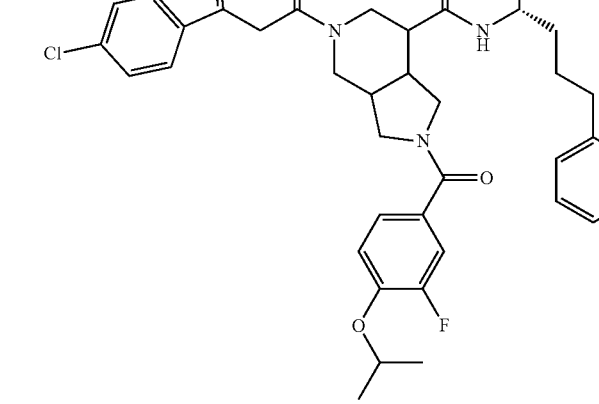 |
| I-47 | 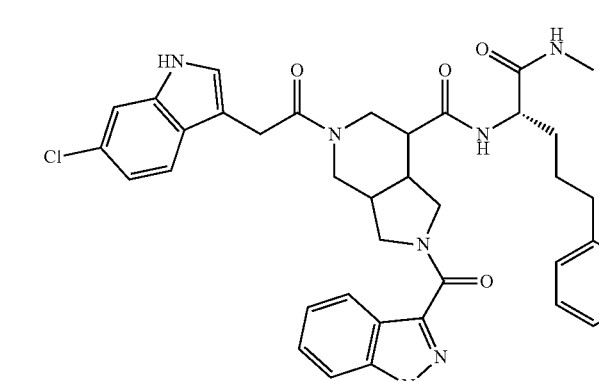 |
| I-48 | 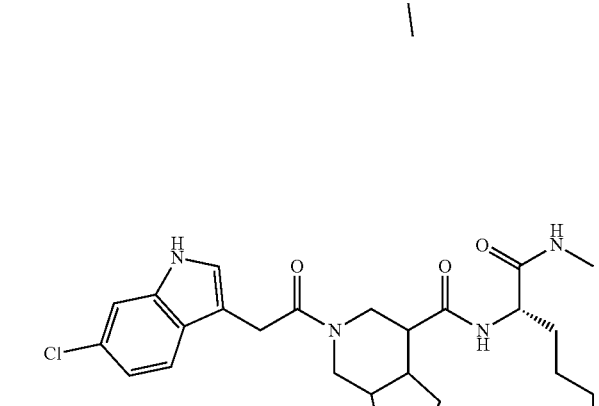 |

-continued
| # | Structure |
|---|---|
| I-49 | 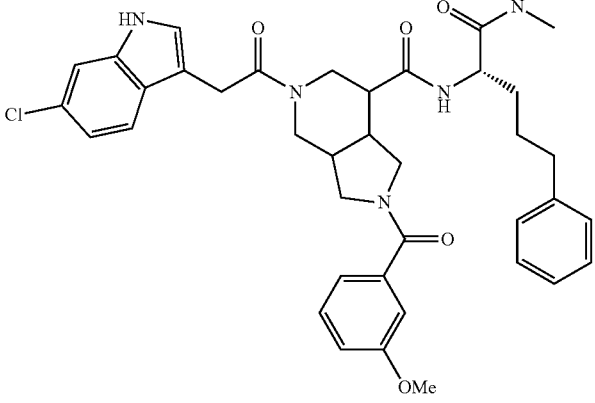 |
| I-50 | 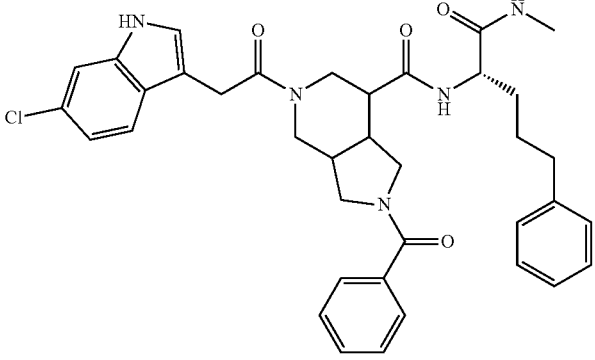 |
| I-51 | 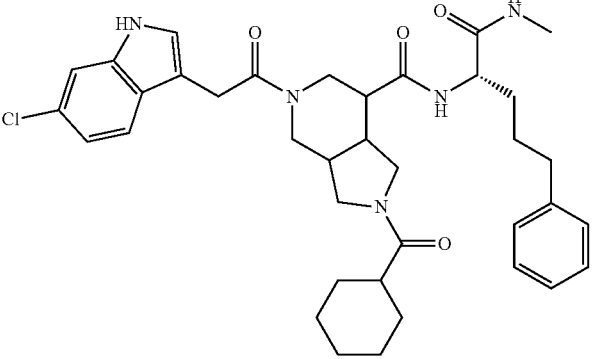 |

-continued
| # | Structure |
|---|---|
| I-52 | 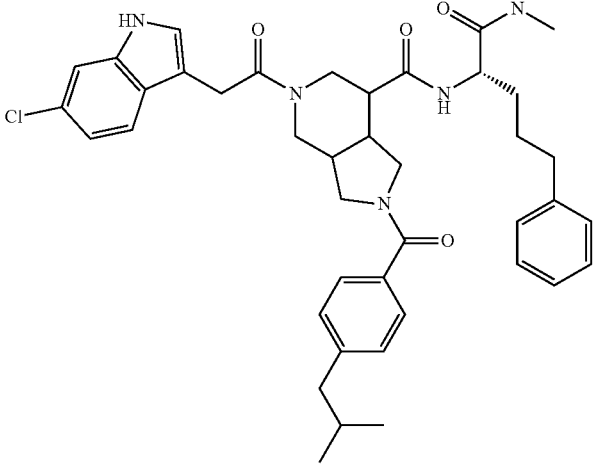 |
| I-53 | 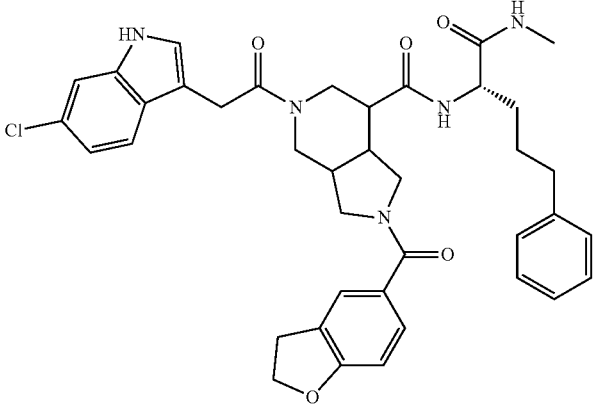 [SMILES: CNC(=O)[C@H](CCCc1ccccc1)NC(=O)C1CN(C(=O)Cc2c[nH]c3cc(Cl)ccc23)CC2CN(C(=O)c3ccc4c(c3)CCO4)CC21] |
| I-54 | 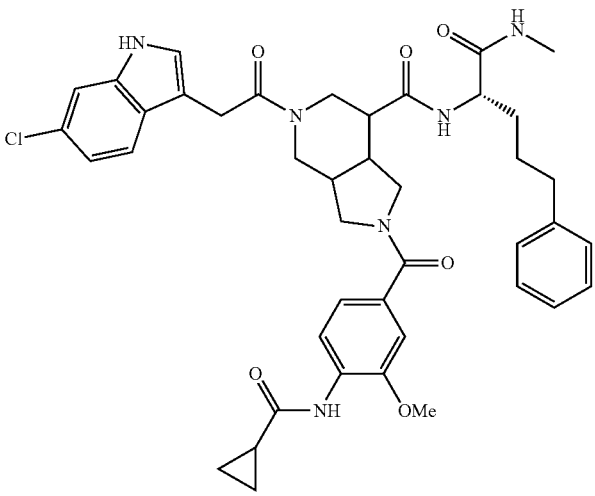 [SMILES: CNC(=O)[C@H](CCCc1ccccc1)NC(=O)C1CN(C(=O)Cc2c[nH]c3cc(Cl)ccc23)CC2CN(C(=O)c3ccc(NC(=O)C4CC4)c(OC)c3)CC21] |

| # | Structure |
|---|---|
| I-55 | 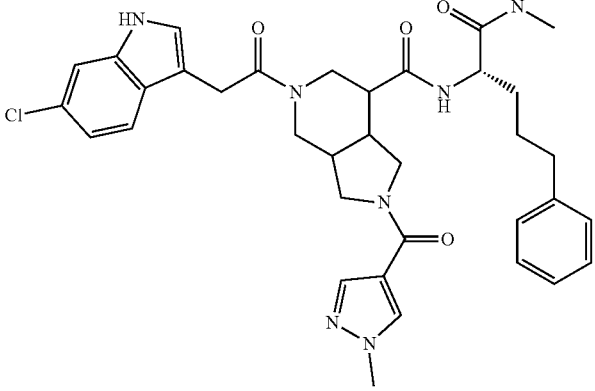 |
| I-56 | 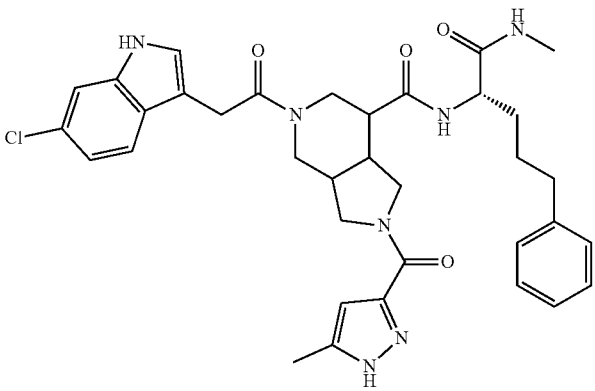 [SMILES: CNC(=O)[C@H](CCCc1ccccc1)NC(=O)C1CN(C(=O)Cc2c[nH]c3cc(Cl)ccc23)CC2CN(C(=O)c3cc(C)[nH]n3)CC21] |
| I-57 | 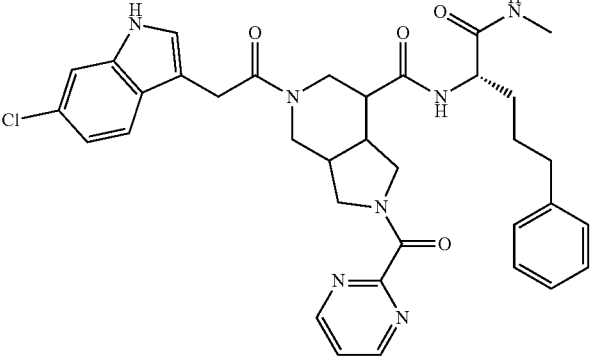 |

| # | Structure |
|---|---|
| I-58 | 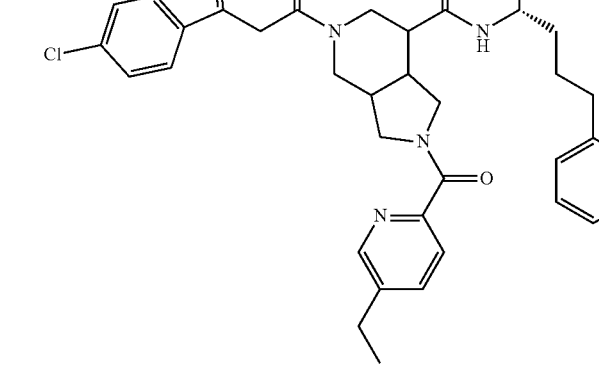 |
| I-59 | 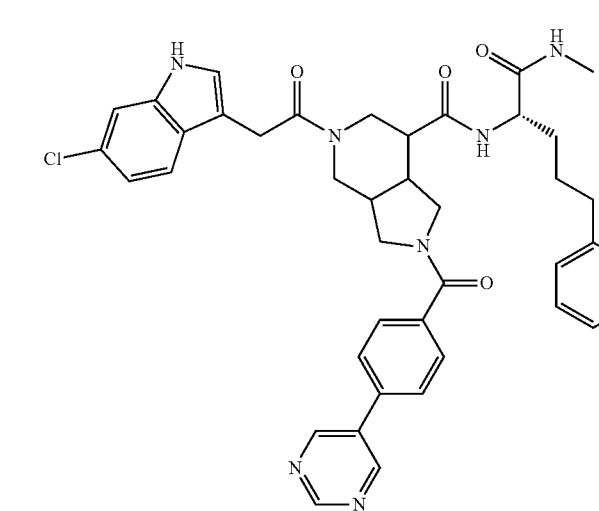 |
| I-60 | 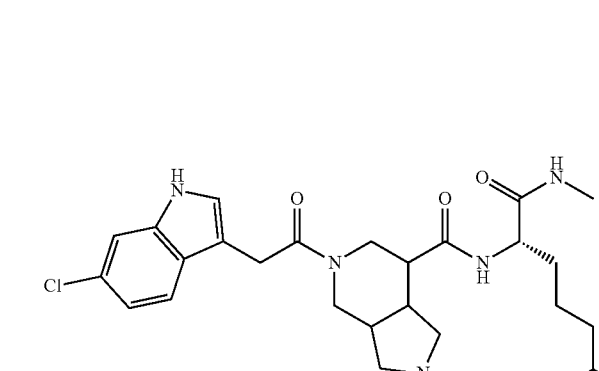 |

| # | Structure |
|---|---|
| I-61 | 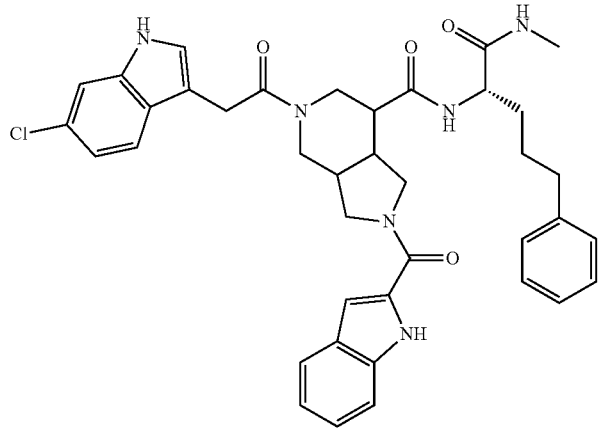 |
| I-62 | 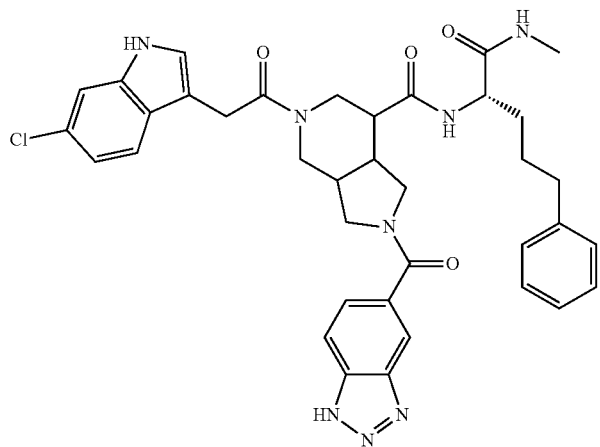 |
| I-63 | 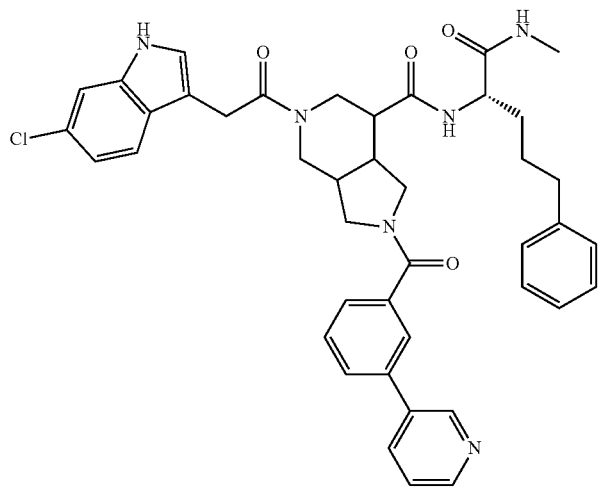 |

| # | Structure |
|---|---|
| I-64 | 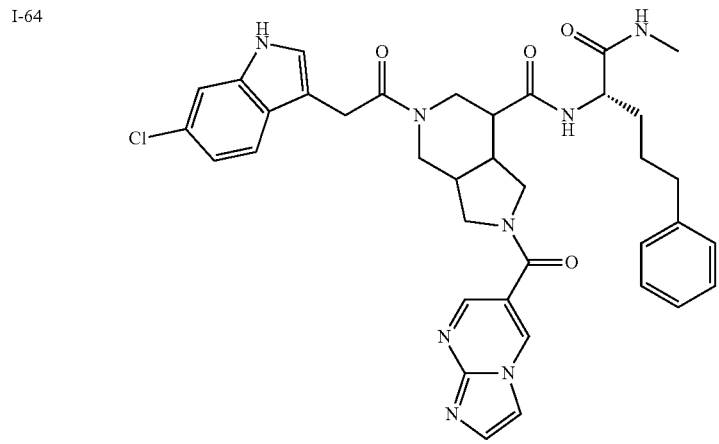 |
| I-65 | 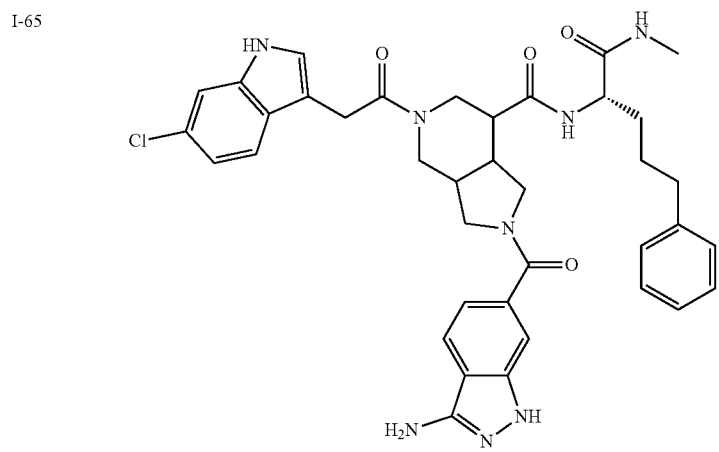 |
| I-66 | 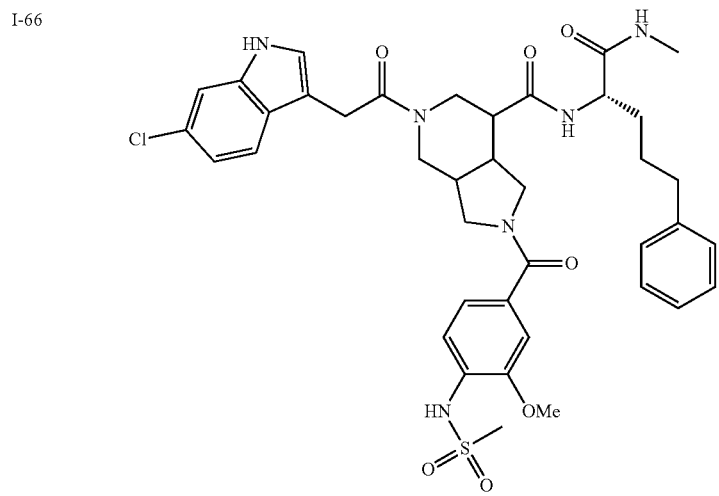 |

| # | Structure |
|---|---|
| I-67 | 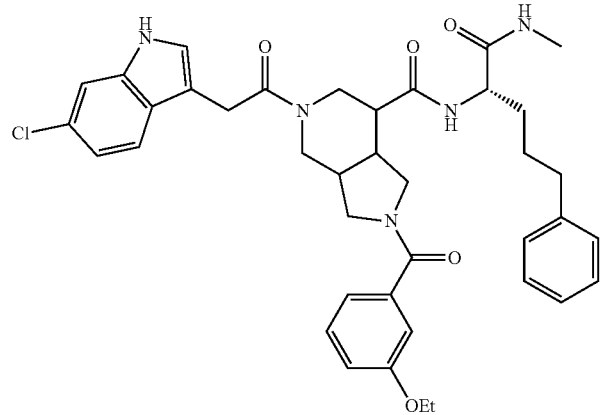 [SMILES: CCOc1cccc(C(=O)N2CC3CN(C(=O)Cc4c[nH]c5cc(Cl)ccc45)CC(C(=O)N[C@@H](CCCc4ccccc4)C(=O)NC)C3C2)c1] |
| I-68 | 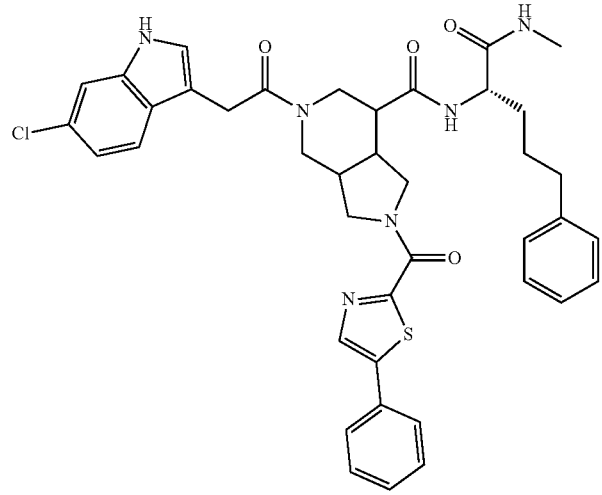 [SMILES: CNC(=O)[C@H](CCCc1ccccc1)NC(=O)C1CN(C(=O)Cc2c[nH]c3cc(Cl)ccc23)CC2CN(C(=O)c3ncc(-c4ccccc4)s3)CC21] |
| I-69 | 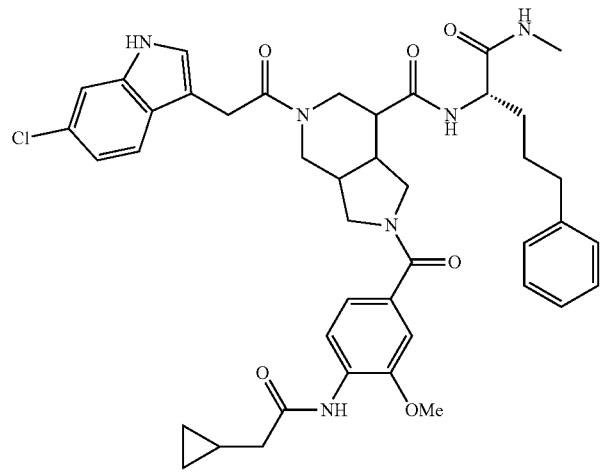 [SMILES: CNC(=O)[C@H](CCCc1ccccc1)NC(=O)C1CN(C(=O)Cc2c[nH]c3cc(Cl)ccc23)CC2CN(C(=O)c3ccc(NC(=O)CC4CC4)c(OC)c3)CC21] |

| # | Structure |
|---|---|
| I-70 | 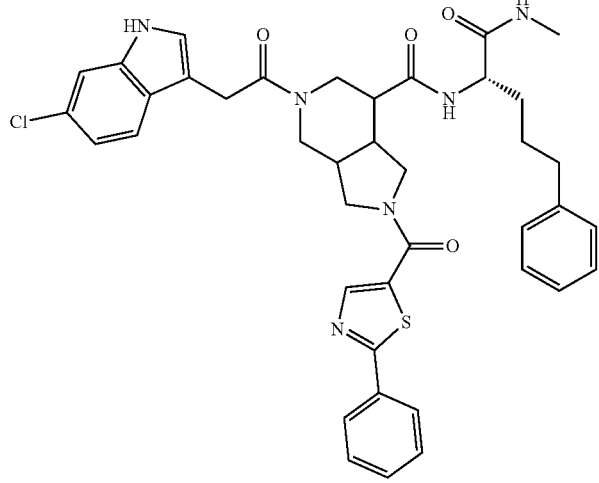 |
| I-71 | 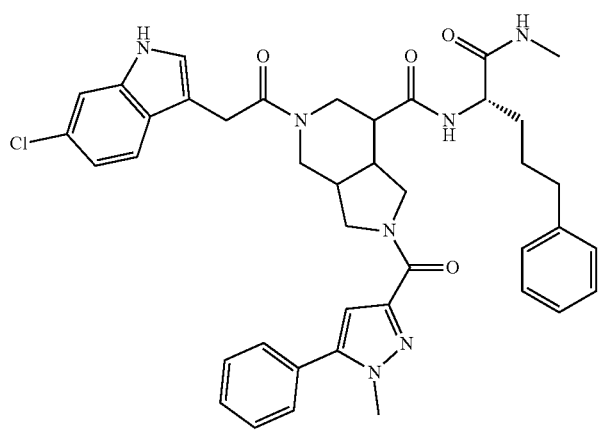 [SMILES: CNC(=O)[C@H](CCCc1ccccc1)NC(=O)C1CN(C(=O)Cc2c[nH]c3cc(Cl)ccc23)CC2CN(C(=O)c3cc(-c4ccccc4)n(C)n3)CC21] |
| I-72 | 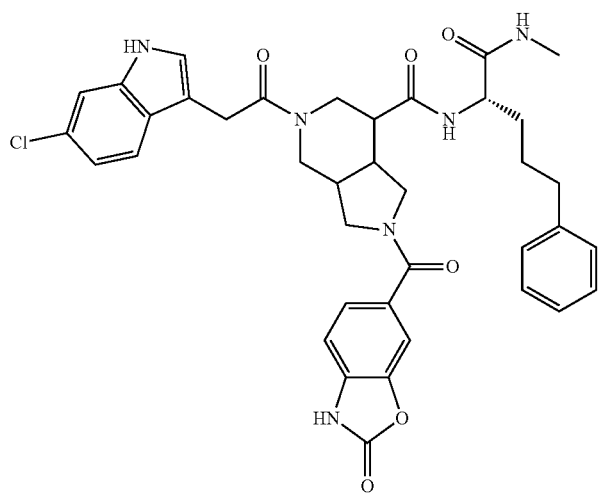 |

-continued
| # | Structure |
|---|---|
| I-73 | 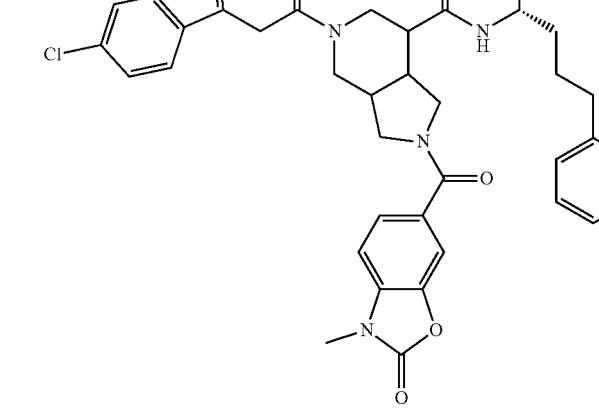 |
| I-74 | 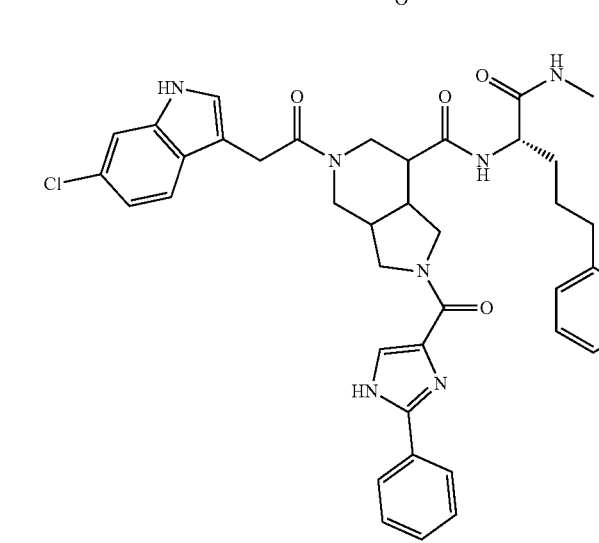 |
| I-75 | 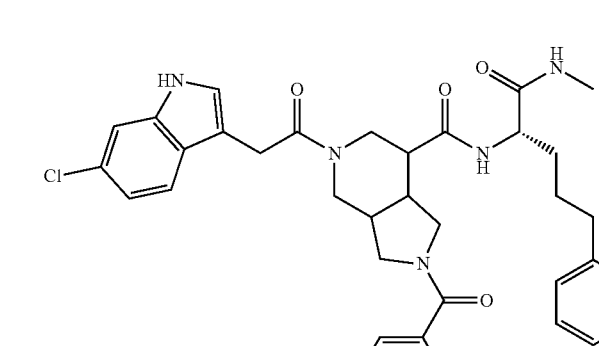 |

-continued
| # | Structure |
|---|---|
| I-76 | 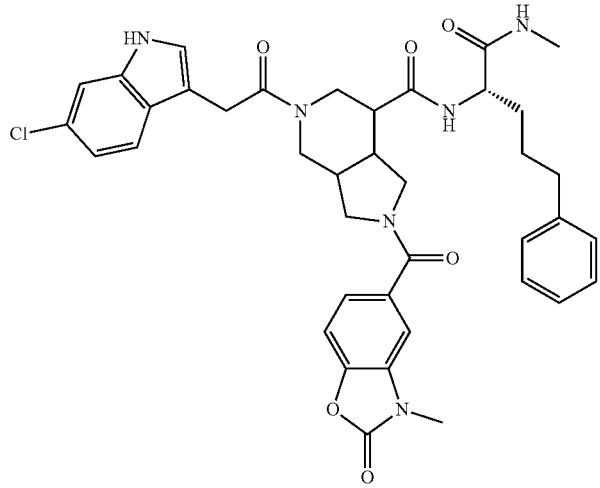 [SMILES: CNC(=O)[C@H](CCCc1ccccc1)NC(=O)C1CN(C(=O)Cc2c[nH]c3cc(Cl)ccc23)CC2CN(C(=O)c3ccc4oc(=O)n(C)c4c3)CC21] |
| I-77 | 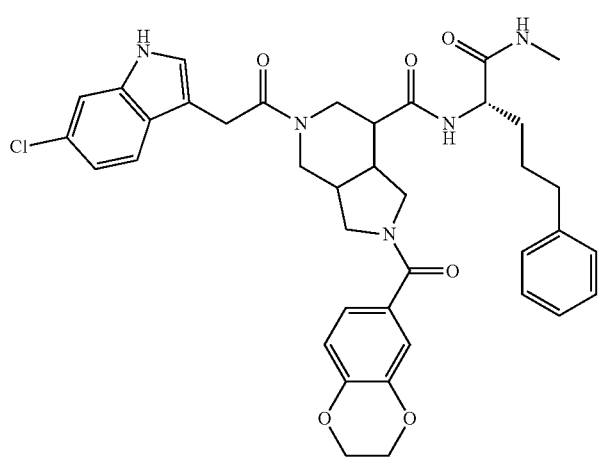 |
| I-78 | 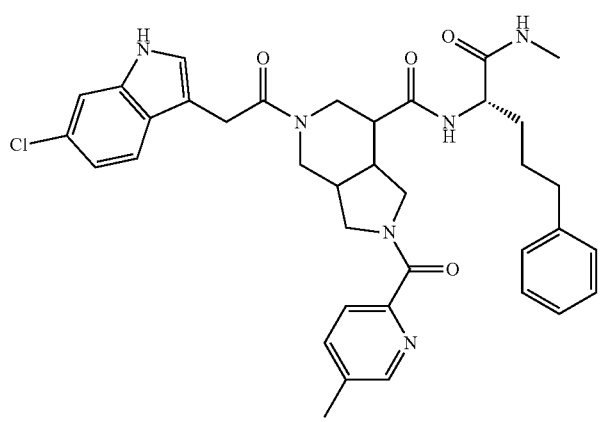 [SMILES: CNC(=O)[C@H](CCCc1ccccc1)NC(=O)C1CN(C(=O)Cc2c[nH]c3cc(Cl)ccc23)CC2CN(C(=O)c3ccc(C)cn3)CC21] |

-continued
| # | Structure |
|---|---|
| I-79 | 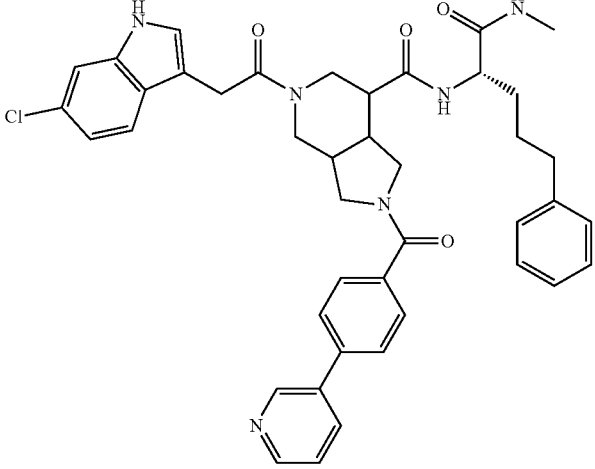 |
| I-80 | 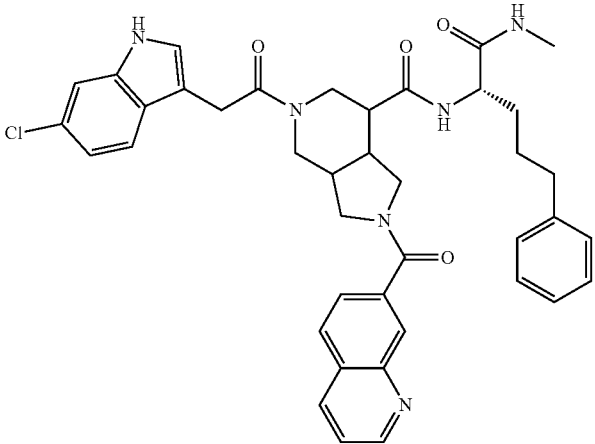 |
| I-81 | 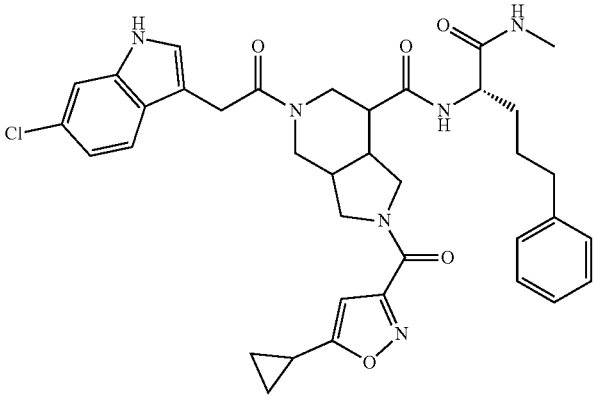 [SMILES: CNC(=O)[C@H](CCCc1ccccc1)NC(=O)C1CN(C(=O)Cc2c[nH]c3cc(Cl)ccc23)CC2CN(C(=O)c3cc(C4CC4)on3)CC21] |

| # | Structure |
|---|---|
| I-82 | 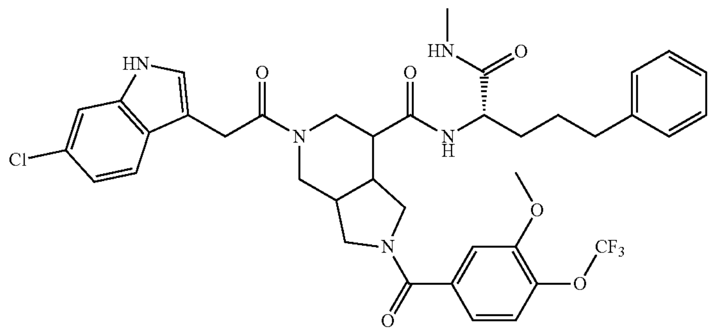 [SMILES: CNC(=O)[C@H](CCCc1ccccc1)NC(=O)C1CN(C(=O)Cc2c[nH]c3cc(Cl)ccc23)CC2CN(C(=O)c3ccc(OC(F)(F)F)c(OC)c3)CC21] |
| I-83 | 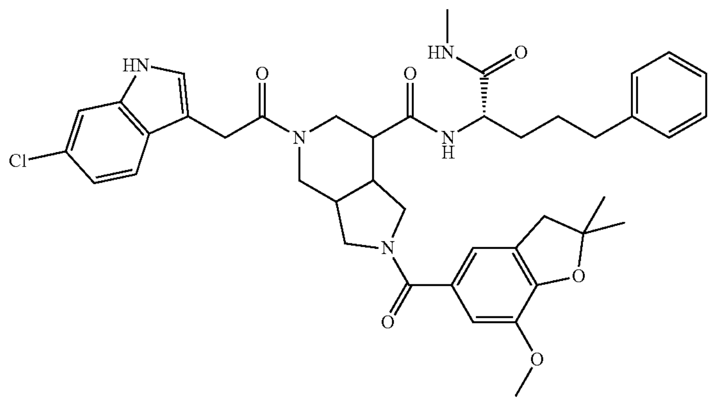 [SMILES: CNC(=O)[C@H](CCCc1ccccc1)NC(=O)C1CN(C(=O)Cc2c[nH]c3cc(Cl)ccc23)CC2CN(C(=O)c3cc4c(c(OC)c3)OC(C)(C)C4)CC21] |
| I-84 | 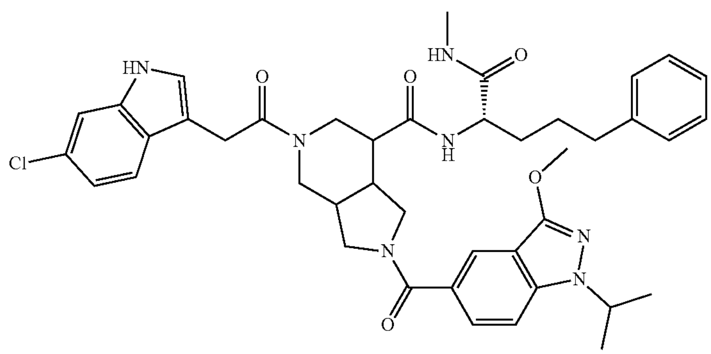 [SMILES: CNC(=O)[C@H](CCCc1ccccc1)NC(=O)C1CN(C(=O)Cc2c[nH]c3cc(Cl)ccc23)CC2CN(C(=O)c3ccc4c(c3)c(OC)nn4C(C)C)CC21] |
| I-85 | 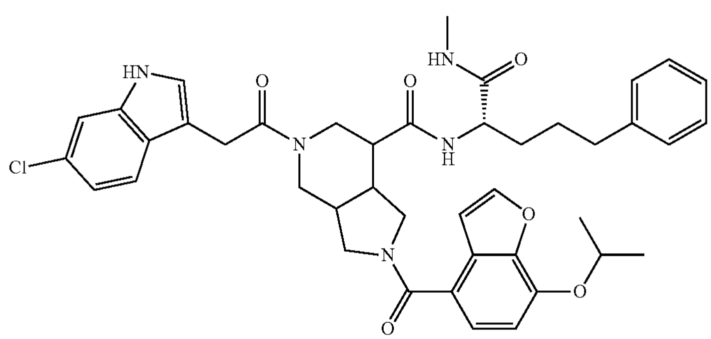 [SMILES: CNC(=O)[C@H](CCCc1ccccc1)NC(=O)C1CN(C(=O)Cc2c[nH]c3cc(Cl)ccc23)CC2CN(C(=O)c3ccc(OC(C)C)c4occc34)CC21] |

| # | Structure |
|---|---|
| I-86 | 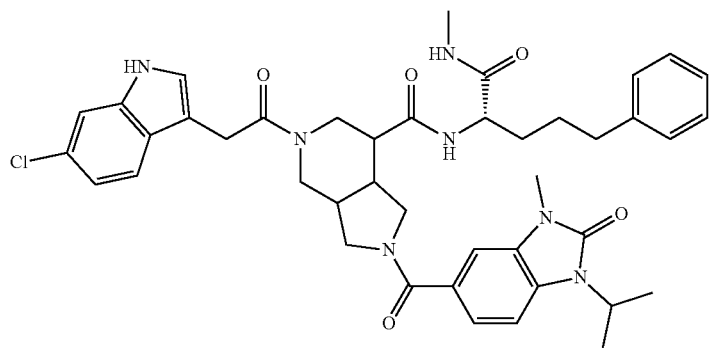<br>First eluting diastereomer |
| I-87 | 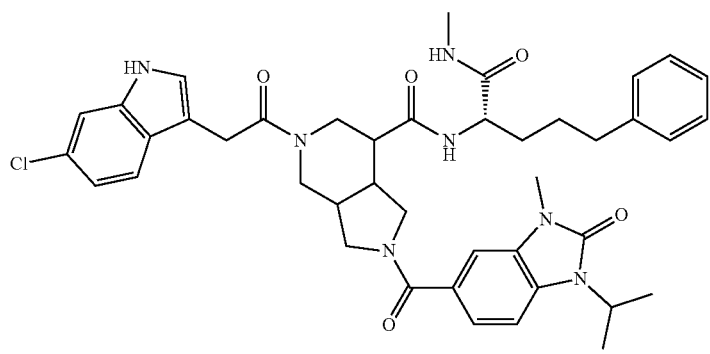<br>Second eluting diastereomer |
| I-88 | 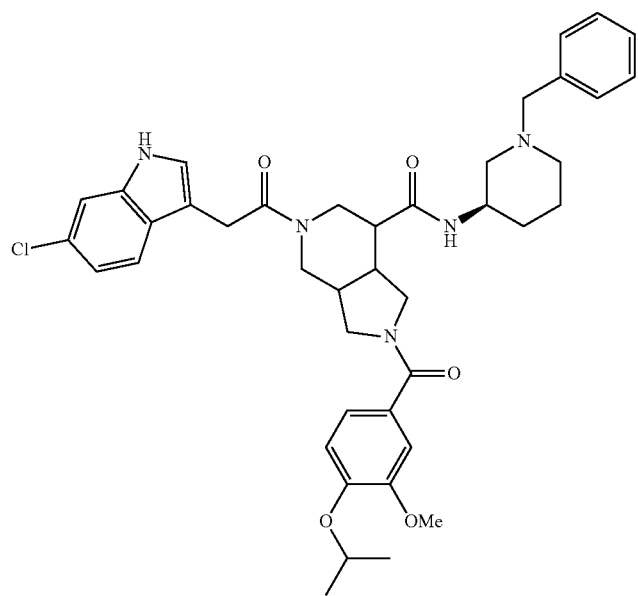 [SMILES: COc1cc(C(=O)N2CC3CN(C(=O)Cc4c[nH]c5cc(Cl)ccc45)CC(C(=O)N[C@@H]4CCCN(Cc5ccccc5)C4)C3C2)ccc1OC(C)C] |

-continued
| # | Structure |
|---|-----------|
| I-89 | 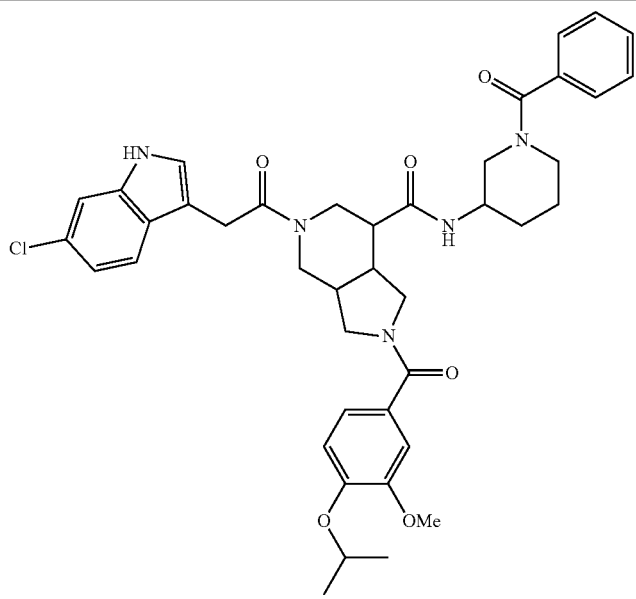 [SMILES: COc1cc(C(=O)N2CC3CN(C(=O)Cc4c[nH]c5cc(Cl)ccc45)CC(C(=O)NC4CCCN(C(=O)c5ccccc5)C4)C3C2)ccc1OC(C)C] |
| I-90 | 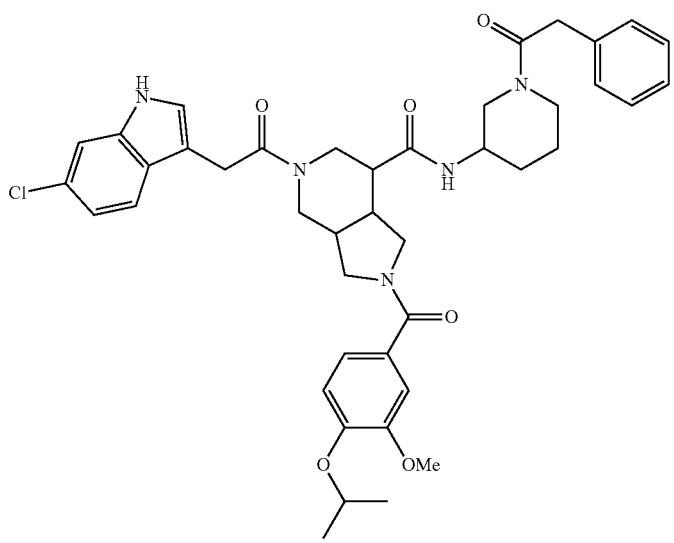 [SMILES: COc1cc(C(=O)N2CC3CN(C(=O)Cc4c[nH]c5cc(Cl)ccc45)CC(C(=O)NC4CCCN(C(=O)Cc5ccccc5)C4)C3C2)ccc1OC(C)C] |
| I-91 | 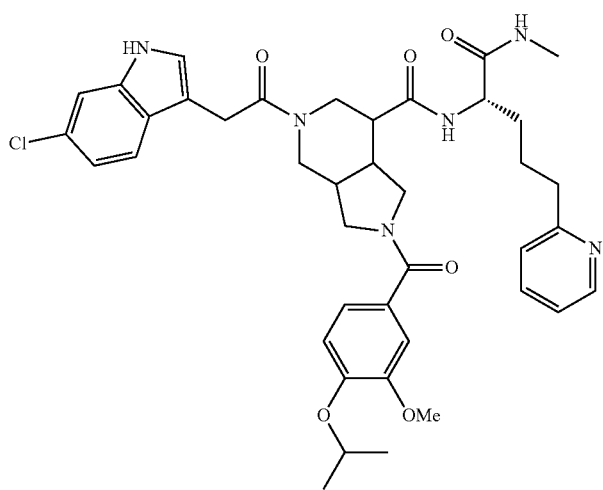 [SMILES: CNC(=O)[C@H](CCCc1ccccn1)NC(=O)C1CN(C(=O)Cc2c[nH]c3cc(Cl)ccc23)CC2CN(C(=O)c3ccc(OC(C)C)c(OC)c3)CC21] |

-continued
| # | Structure |
|---|---|
| I-92 | 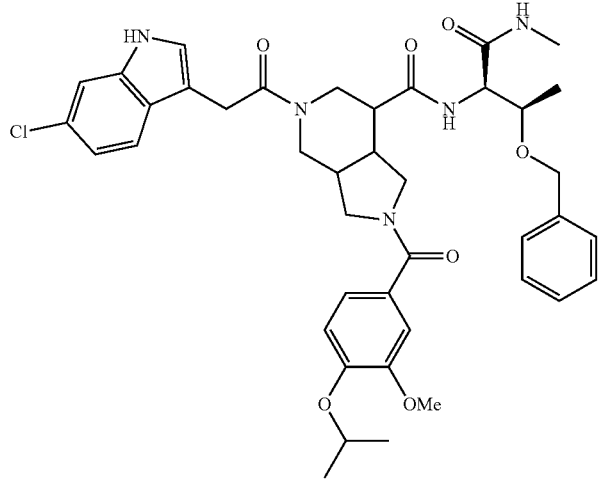 [SMILES: CNC(=O)[C@H](NC(=O)C1CN(C(=O)Cc2c[nH]c3cc(Cl)ccc23)CC2CN(C(=O)c3ccc(OC(C)C)c(OC)c3)CC21)[C@@H](C)OCc1ccccc1] |
| I-93 | 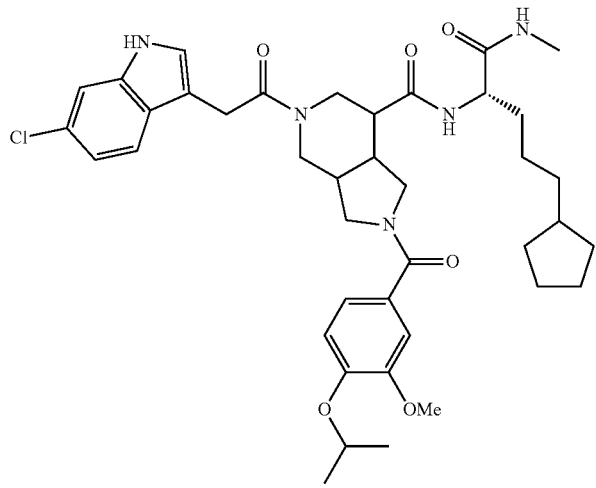 [SMILES: CNC(=O)[C@H](CCCC1CCCC1)NC(=O)C1CN(C(=O)Cc2c[nH]c3cc(Cl)ccc23)CC2CN(C(=O)c3ccc(OC(C)C)c(OC)c3)CC21] |
| I-94 | 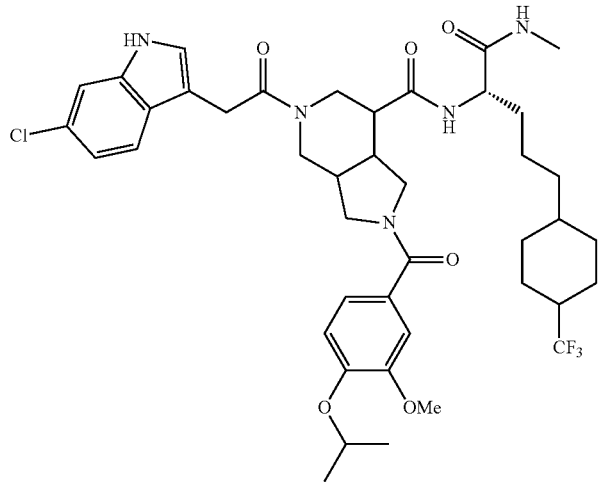 [SMILES: CNC(=O)[C@H](CCCC1CCC(C(F)(F)F)CC1)NC(=O)C1CN(C(=O)Cc2c[nH]c3cc(Cl)ccc23)CC2CN(C(=O)c3ccc(OC(C)C)c(OC)c3)CC21] |

| # | Structure |
|---|---|
| I-95 | 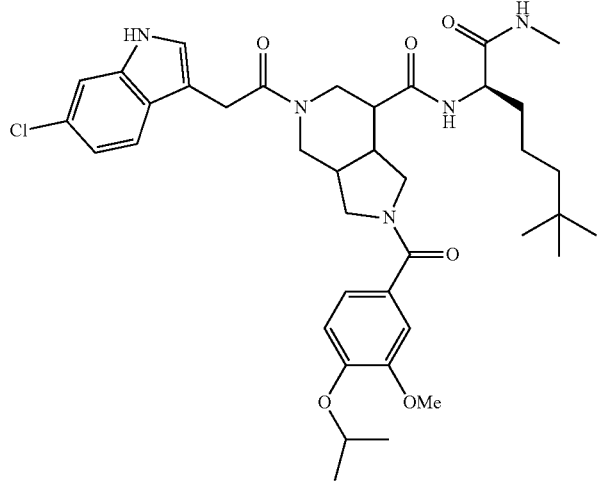 [SMILES: CNC(=O)[C@@H](CCCC(C)(C)C)NC(=O)C1CN(C(=O)Cc2c[nH]c3cc(Cl)ccc23)CC2CN(C(=O)c3ccc(OC(C)C)c(OC)c3)CC21] |
| I-96 | 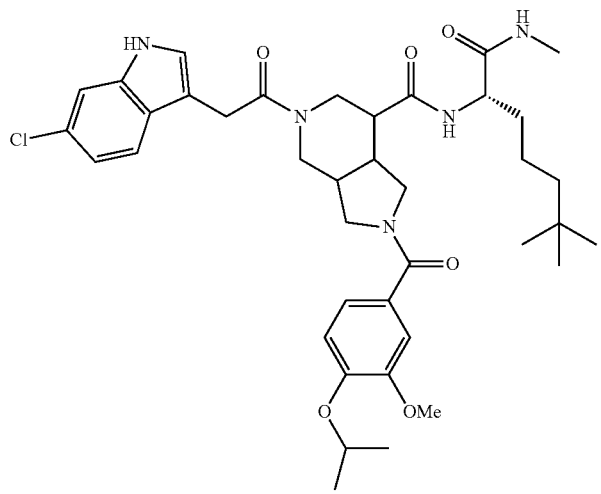 [SMILES: CNC(=O)[C@H](CCCC(C)(C)C)NC(=O)C1CN(C(=O)Cc2c[nH]c3cc(Cl)ccc23)CC2CN(C(=O)c3ccc(OC(C)C)c(OC)c3)CC21] |
| I-97 | 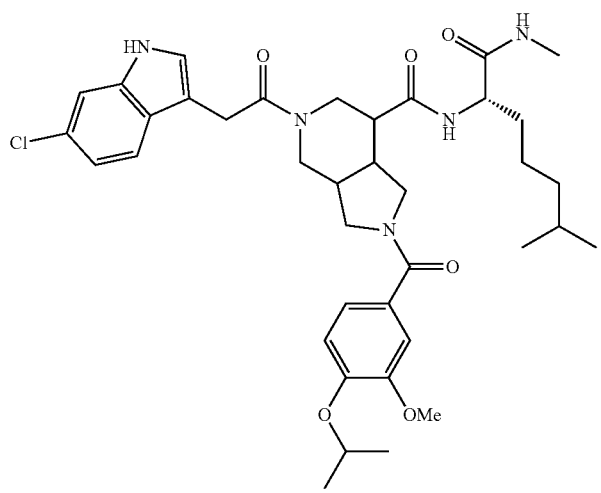 [SMILES: CNC(=O)[C@H](CCCC(C)C)NC(=O)C1CN(C(=O)Cc2c[nH]c3cc(Cl)ccc23)CC2CN(C(=O)c3ccc(OC(C)C)c(OC)c3)CC21] |

| # | Structure |
|---|---|
| I-98 | 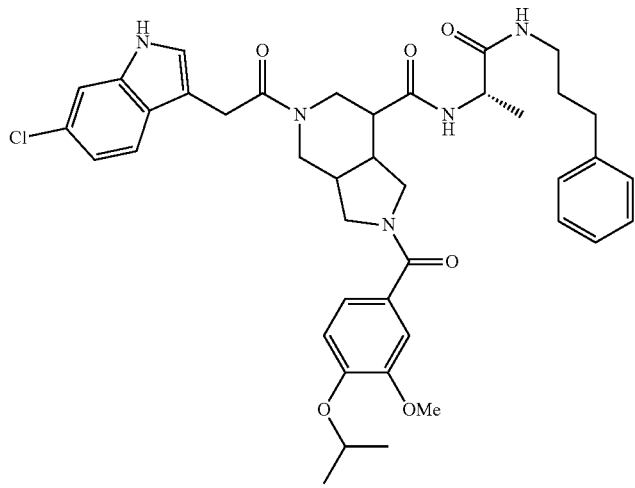 [SMILES: COc1cc(C(=O)N2CC3CN(C(=O)Cc4c[nH]c5cc(Cl)ccc45)CC(C(=O)N[C@@H](C)C(=O)NCCCc4ccccc4)C3C2)ccc1OC(C)C] |
| I-99 | 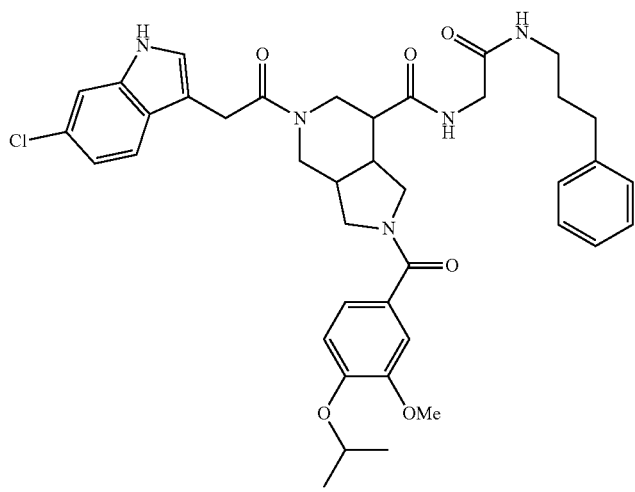 [SMILES: COc1cc(C(=O)N2CC3CN(C(=O)Cc4c[nH]c5cc(Cl)ccc45)CC(C(=O)NCC(=O)NCCCc4ccccc4)C3C2)ccc1OC(C)C] |
| I-100 | 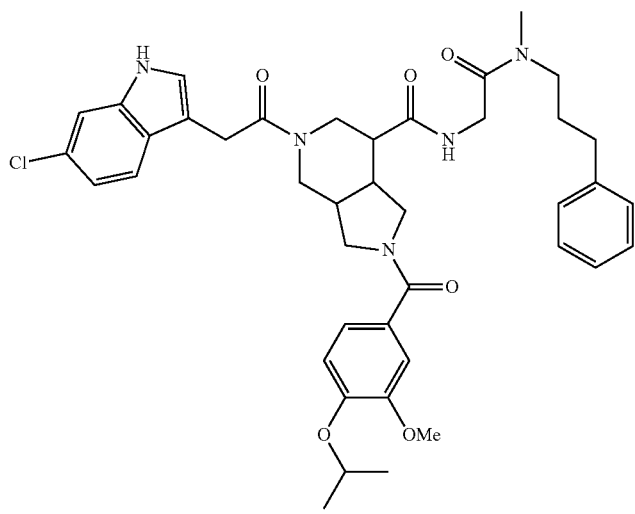
First eluting diastereomer |

| # | Structure |
|---|---|
| I-101 | 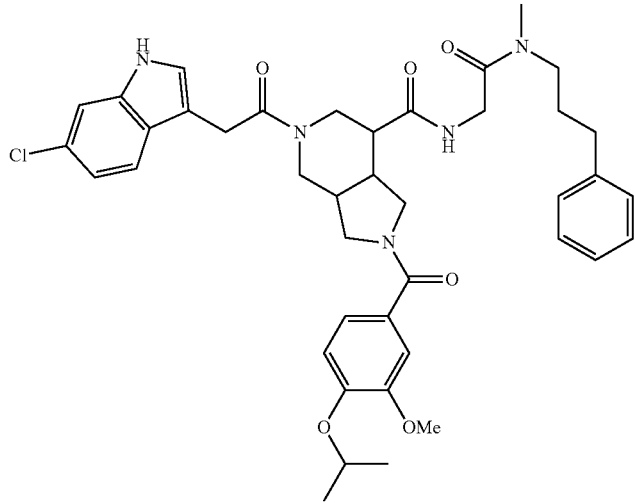<br>Second eluting diastereomer |
| I-102 | 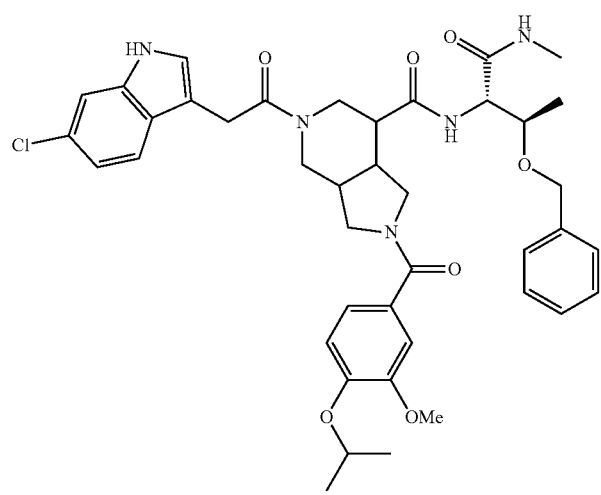 [SMILES: CNC(=O)[C@@H](NC(=O)C1CN(C(=O)Cc2c[nH]c3cc(Cl)ccc23)CC2CN(C(=O)c3ccc(OC(C)C)c(OC)c3)CC21)[C@@H](C)OCc1ccccc1] |
| I-103 | 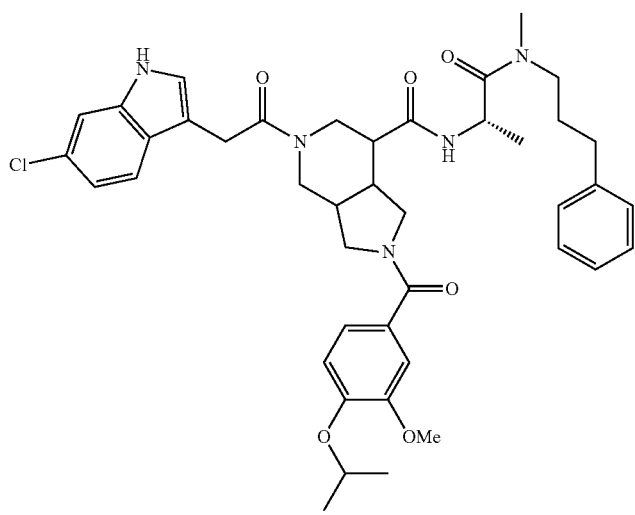 [SMILES: COc1cc(C(=O)N2CC3CN(C(=O)Cc4c[nH]c5cc(Cl)ccc45)CC(C(=O)N[C@@H](C)C(=O)N(C)CCCc4ccccc4)C3C2)ccc1OC(C)C] |

| # | Structure |
|---|---|
| I-104 | 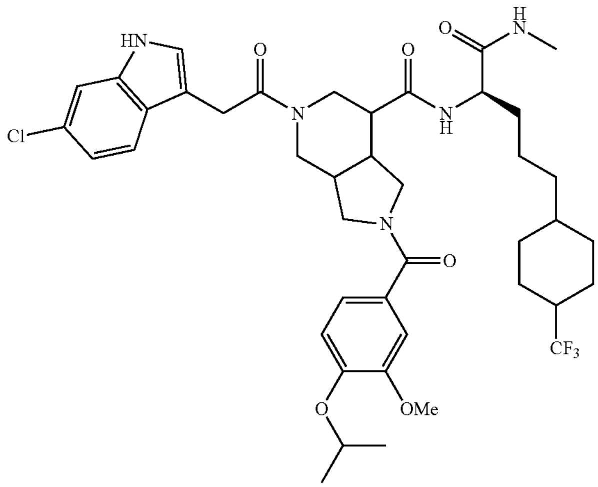 [SMILES: CNC(=O)[C@@H](CCCC1CCC(C(F)(F)F)CC1)NC(=O)C1CN(C(=O)Cc2c[nH]c3cc(Cl)ccc23)CC2CN(C(=O)c3ccc(OC(C)C)c(OC)c3)CC21] |
| I-105 | 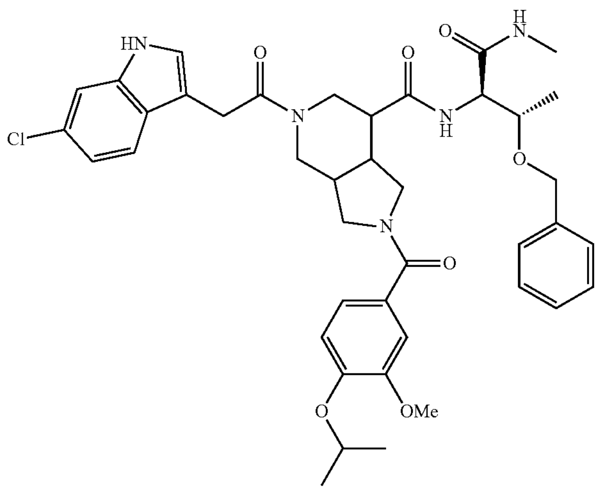 [SMILES: CNC(=O)[C@H](NC(=O)C1CN(C(=O)Cc2c[nH]c3cc(Cl)ccc23)CC2CN(C(=O)c3ccc(OC(C)C)c(OC)c3)CC21)[C@H](C)OCc1ccccc1] |
| I-106 | 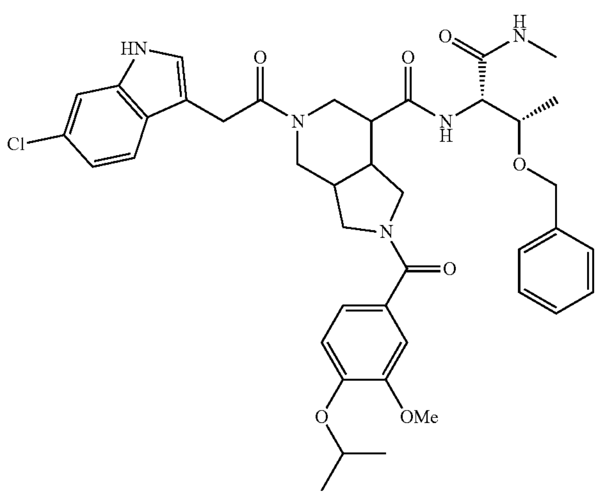 [SMILES: CNC(=O)[C@@H](NC(=O)C1CN(C(=O)Cc2c[nH]c3cc(Cl)ccc23)CC2CN(C(=O)c3ccc(OC(C)C)c(OC)c3)CC21)[C@H](C)OCc1ccccc1] |

-continued
| # | Structure |
|---|---|
| I-107 | 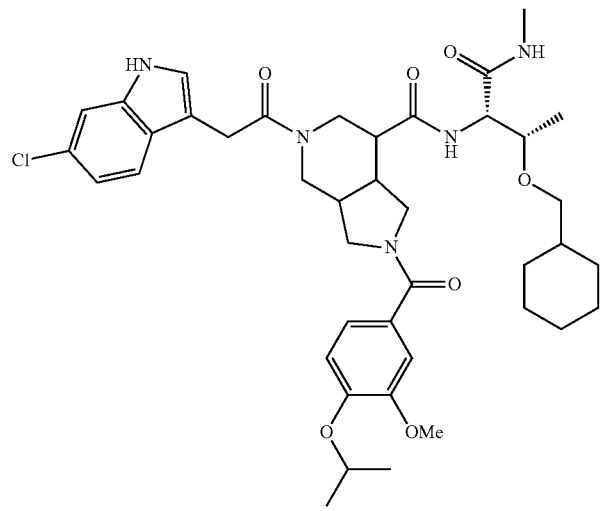 [SMILES: CNC(=O)[C@@H](NC(=O)C1CN(C(=O)Cc2c[nH]c3cc(Cl)ccc23)CC2CN(C(=O)c3ccc(OC(C)C)c(OC)c3)CC21)[C@H](C)OCC1CCCCC1] |
| I-108 | 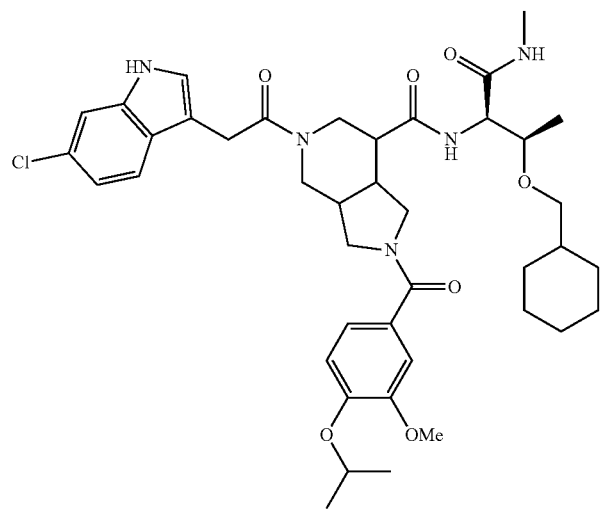 [SMILES: CNC(=O)[C@H](NC(=O)C1CN(C(=O)Cc2c[nH]c3cc(Cl)ccc23)CC2CN(C(=O)c3ccc(OC(C)C)c(OC)c3)CC21)[C@@H](C)OCC1CCCCC1] |
| I-109 | 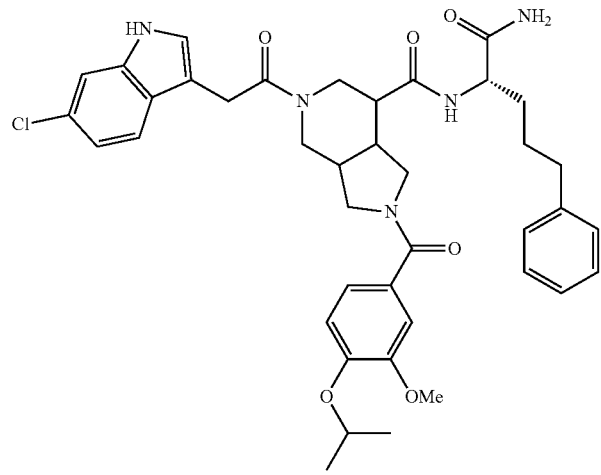 [SMILES: COc1cc(C(=O)N2CC3CN(C(=O)Cc4c[nH]c5cc(Cl)ccc45)CC(C(=O)N[C@@H](CCCc4ccccc4)C(N)=O)C3C2)ccc1OC(C)C] |

| # | Structure |
|---|---|
| I-110 | 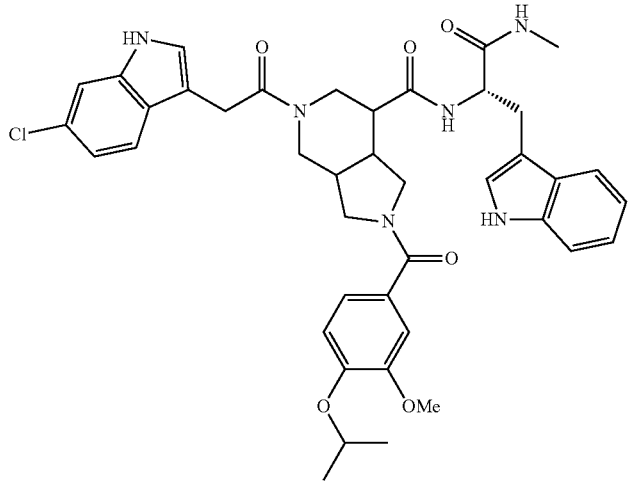<br>First eluting diastereomer |
| I-111 | 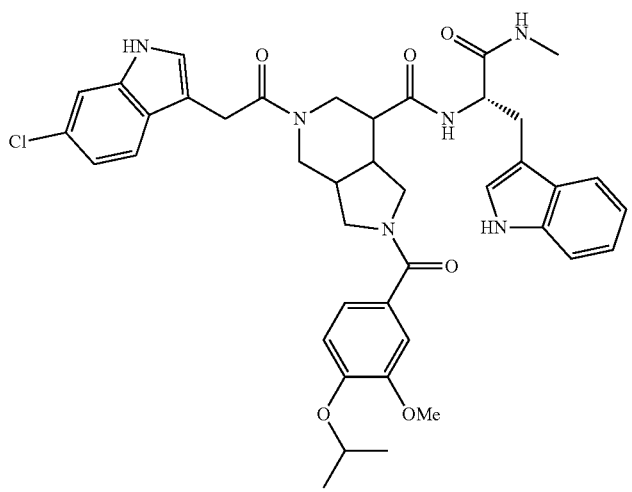<br>Second eluting diastereomer |
| I-112 | 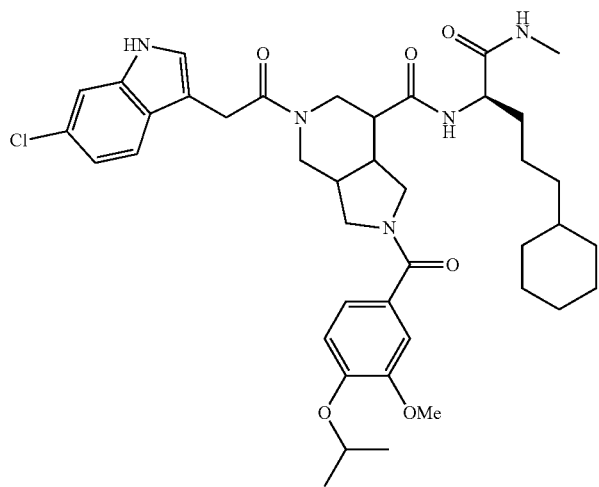 [SMILES: CNC(=O)[C@@H](CCCC1CCCCC1)NC(=O)C1CN(C(=O)Cc2c[nH]c3cc(Cl)ccc23)CC2CN(C(=O)c3ccc(OC(C)C)c(OC)c3)CC21] |

| # | Structure |
|---|---|
| I-113 | 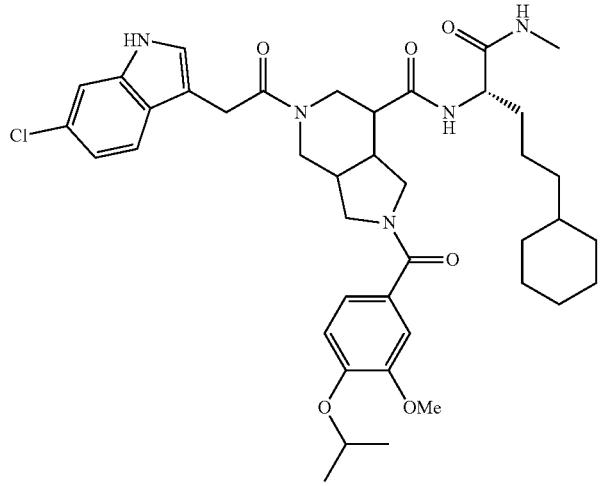 |
| I-114 | 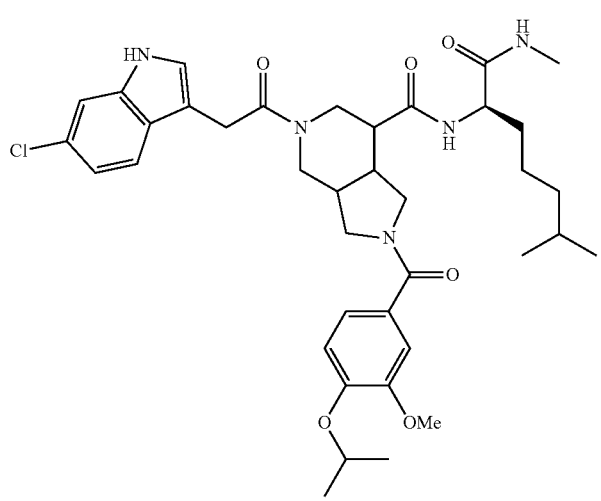 [SMILES: CNC(=O)[C@@H](CCCC(C)C)NC(=O)C1CN(C(=O)Cc2c[nH]c3cc(Cl)ccc23)CC2CN(C(=O)c3ccc(OC(C)C)c(OC)c3)CC21] |
| I-115 | 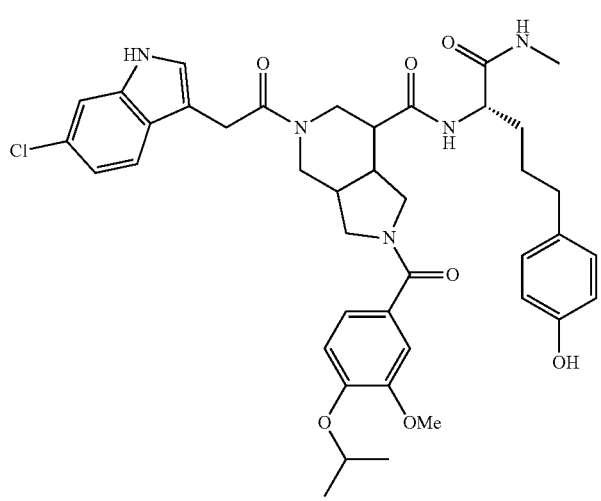 [SMILES: CNC(=O)[C@H](CCCc1ccc(O)cc1)NC(=O)C1CN(C(=O)Cc2c[nH]c3cc(Cl)ccc23)CC2CN(C(=O)c3ccc(OC(C)C)c(OC)c3)CC21] |

| # | Structure |
|---|---|
| I-116 | 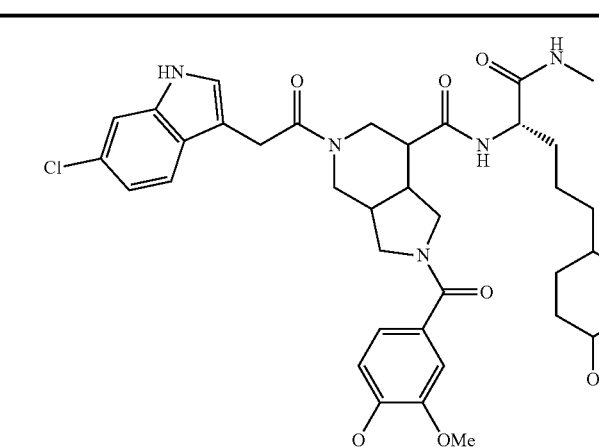 |
| I-117 | 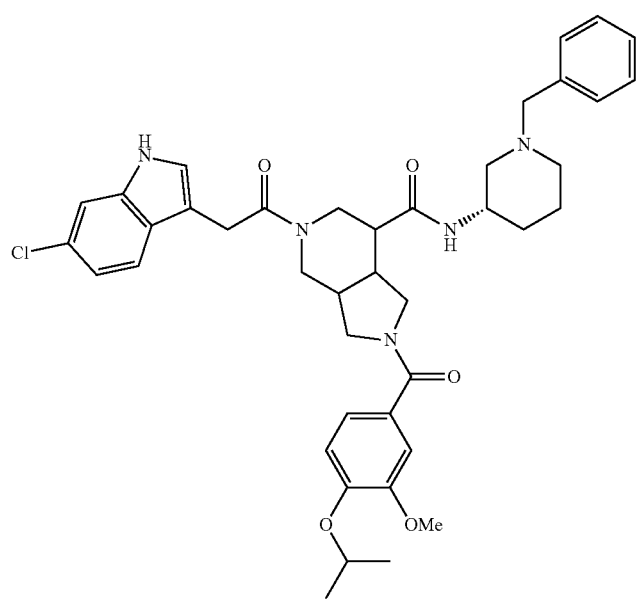
First eluting diastereomer |

| # | Structure |
|---|---|
| I-118 | 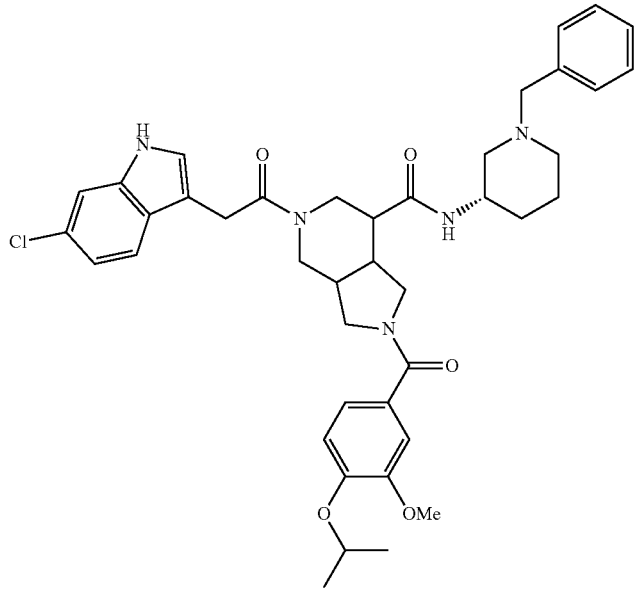<br>Second eluting diastereomer |
| I-119 | 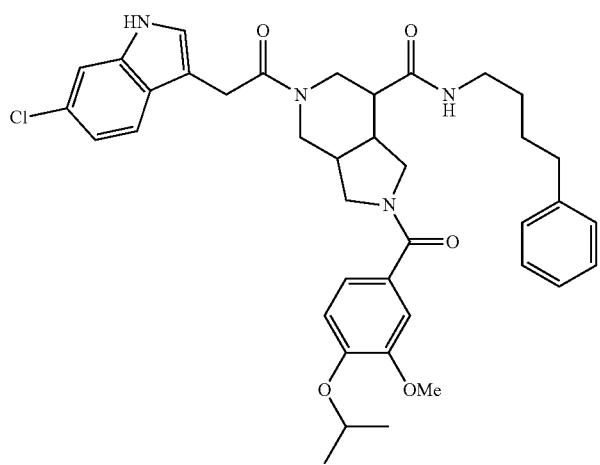 [SMILES: COc1cc(C(=O)N2CC3CN(C(=O)Cc4c[nH]c5cc(Cl)ccc45)CC(C(=O)NCCCCc4ccccc4)C3C2)ccc1OC(C)C] |
| I-120 | 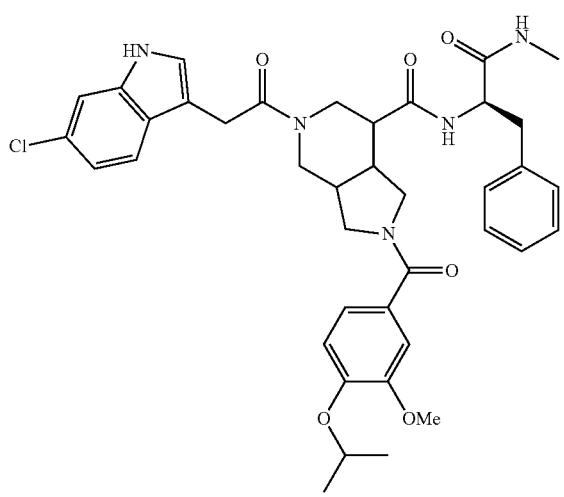 [SMILES: CNC(=O)[C@@H](Cc1ccccc1)NC(=O)C1CN(C(=O)Cc2c[nH]c3cc(Cl)ccc23)CC2CN(C(=O)c3ccc(OC(C)C)c(OC)c3)CC21] |

-continued
| # | Structure |
|---|---|
| I-121 | 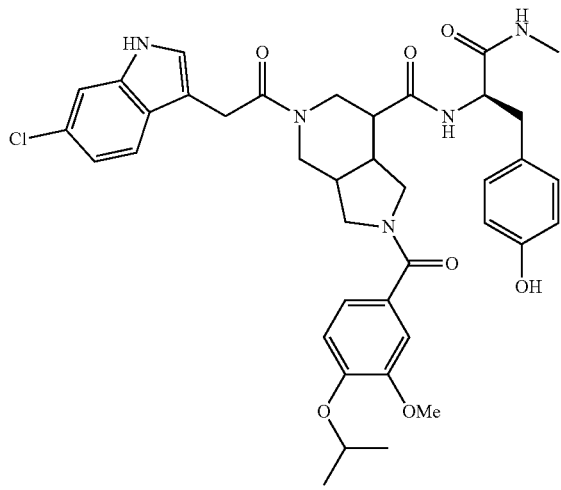 [SMILES: CNC(=O)[C@@H](Cc1ccc(O)cc1)NC(=O)C1CN(C(=O)Cc2c[nH]c3cc(Cl)ccc23)CC2CN(C(=O)c3ccc(OC(C)C)c(OC)c3)CC21] |
| I-122 | 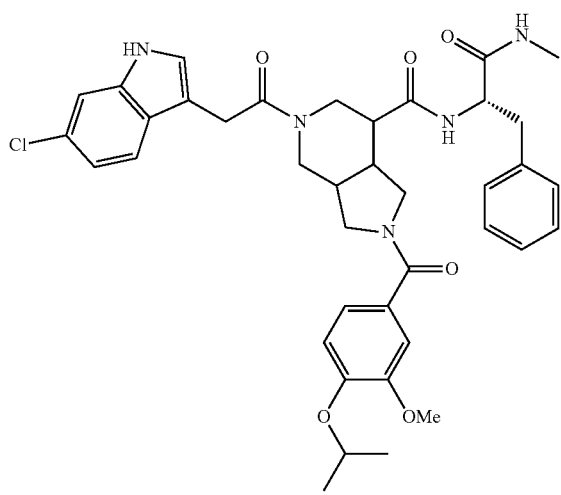 [SMILES: CNC(=O)[C@H](Cc1ccccc1)NC(=O)C1CN(C(=O)Cc2c[nH]c3cc(Cl)ccc23)CC2CN(C(=O)c3ccc(OC(C)C)c(OC)c3)CC21] |
| I-123 | 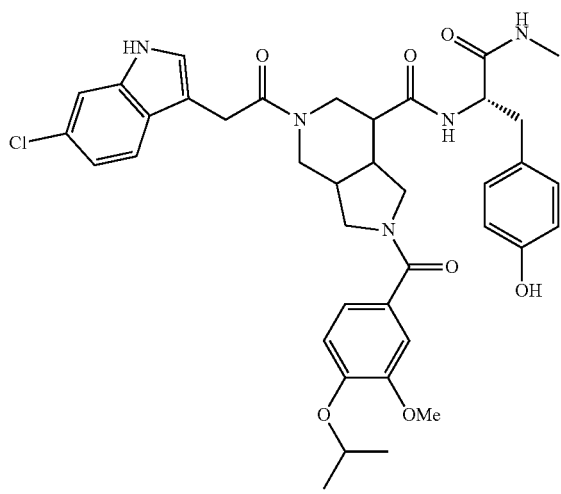 [SMILES: CNC(=O)[C@H](Cc1ccc(O)cc1)NC(=O)C1CN(C(=O)Cc2c[nH]c3cc(Cl)ccc23)CC2CN(C(=O)c3ccc(OC(C)C)c(OC)c3)CC21] |

| # | Structure |
|---|---|
| I-124 | 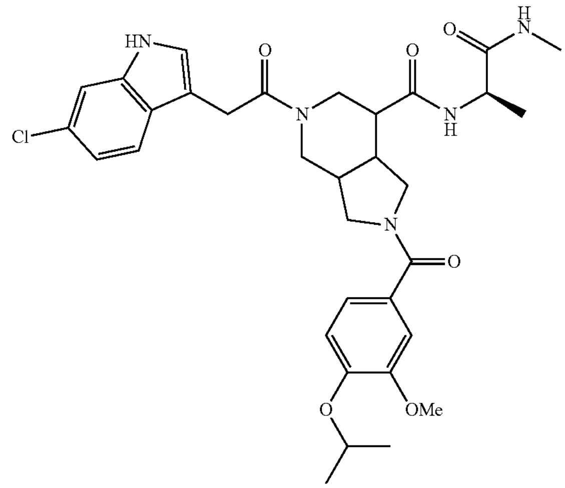 [SMILES: CNC(=O)[C@@H](C)NC(=O)C1CN(C(=O)Cc2c[nH]c3cc(Cl)ccc23)CC2CN(C(=O)c3ccc(OC(C)C)c(OC)c3)CC21] |
| I-125 | 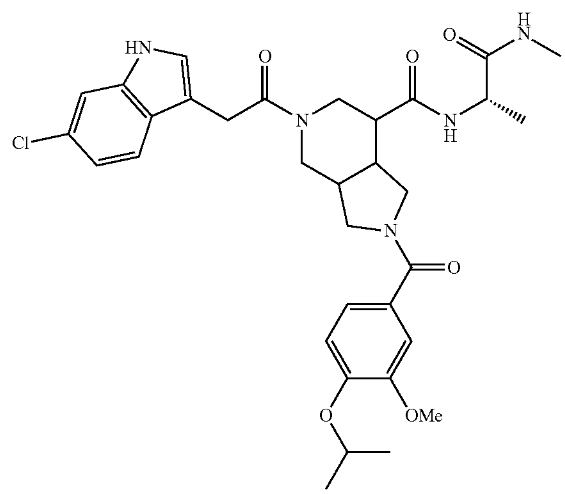 [SMILES: CNC(=O)[C@H](C)NC(=O)C1CN(C(=O)Cc2c[nH]c3cc(Cl)ccc23)CC2CN(C(=O)c3ccc(OC(C)C)c(OC)c3)CC21] |
| I-126 | 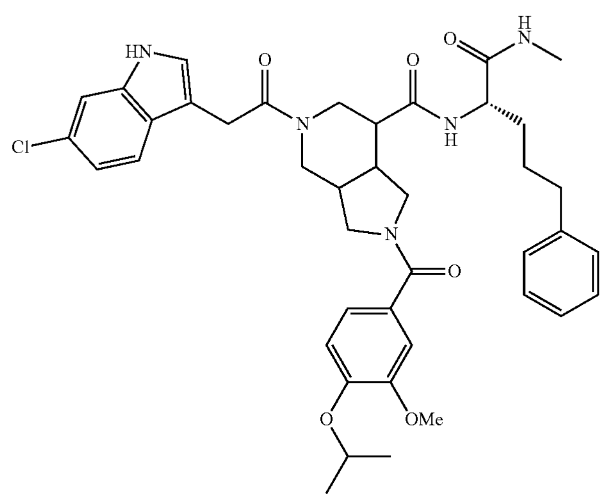 |

-continued
| # | Structure |
|---|---|
| I-127 | 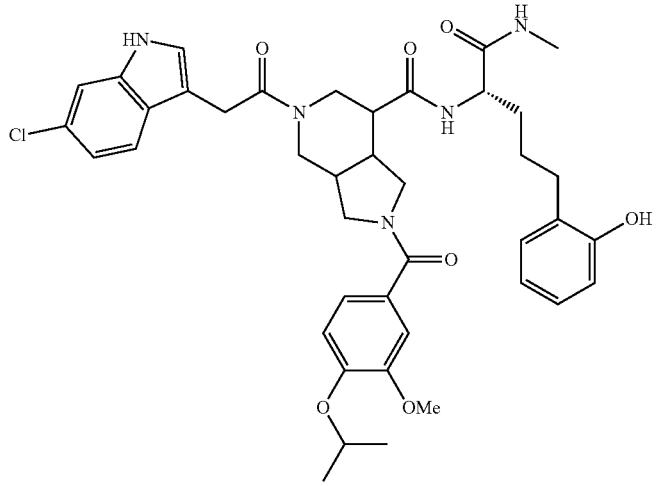 [SMILES: CNC(=O)[C@H](CCCc1ccccc1O)NC(=O)C1CN(C(=O)Cc2c[nH]c3cc(Cl)ccc23)CC2CN(C(=O)c3ccc(OC(C)C)c(OC)c3)CC21] |
| I-128 | 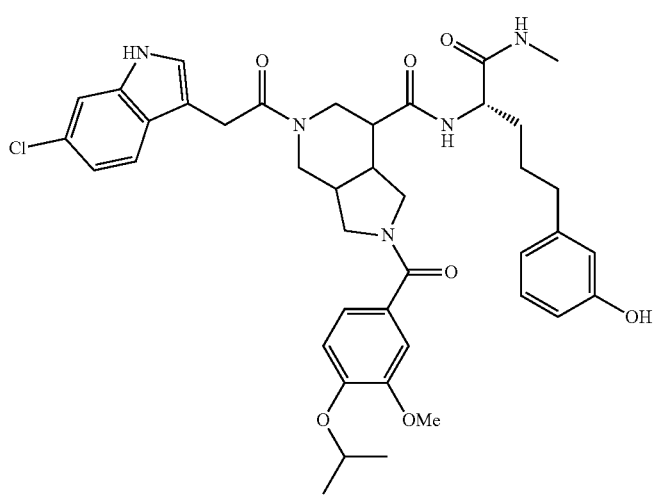 [SMILES: CNC(=O)[C@H](CCCc1cccc(O)c1)NC(=O)C1CN(C(=O)Cc2c[nH]c3cc(Cl)ccc23)CC2CN(C(=O)c3ccc(OC(C)C)c(OC)c3)CC21] |
| I-129 | 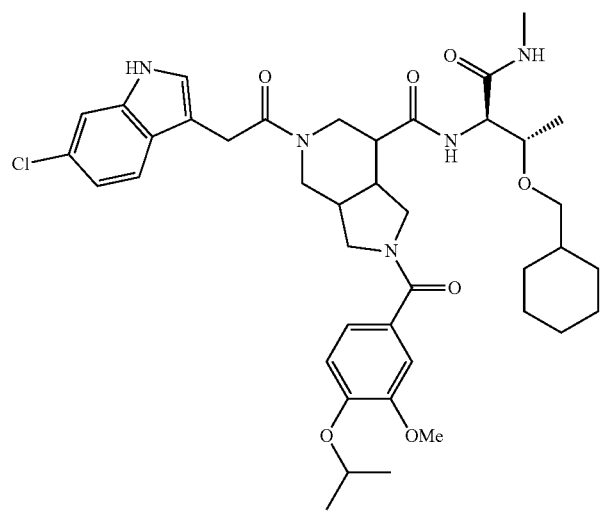 [SMILES: CNC(=O)[C@H](NC(=O)C1CN(C(=O)Cc2c[nH]c3cc(Cl)ccc23)CC2CN(C(=O)c3ccc(OC(C)C)c(OC)c3)CC21)[C@H](C)OCC1CCCCC1] |

| # | Structure |
|---|---|
| I-130 | 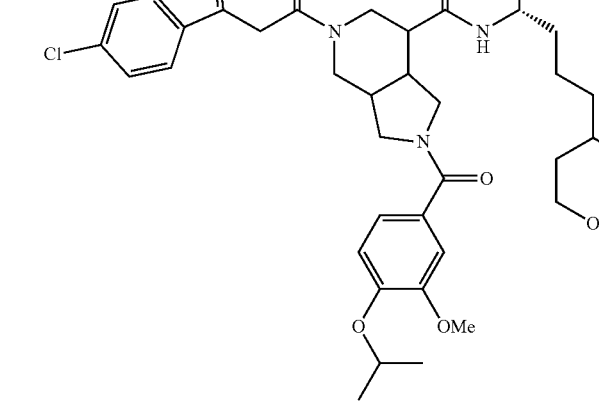 |
| I-131 | 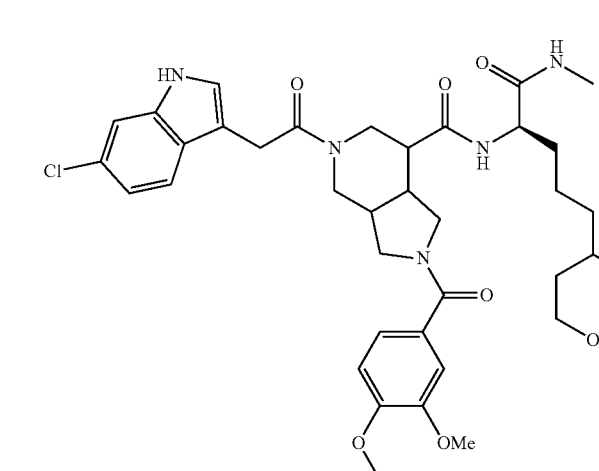 |
| I-132 | 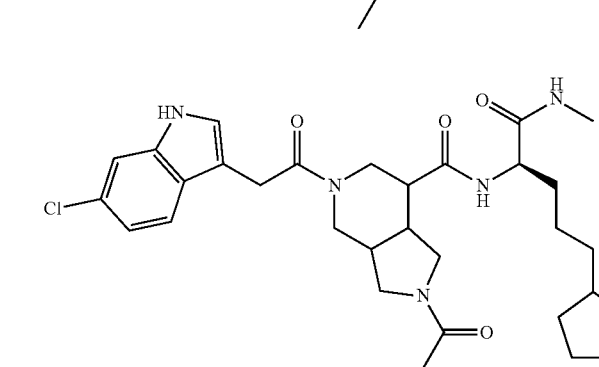 |

| # | Structure |
|---|---|
| I-133 | 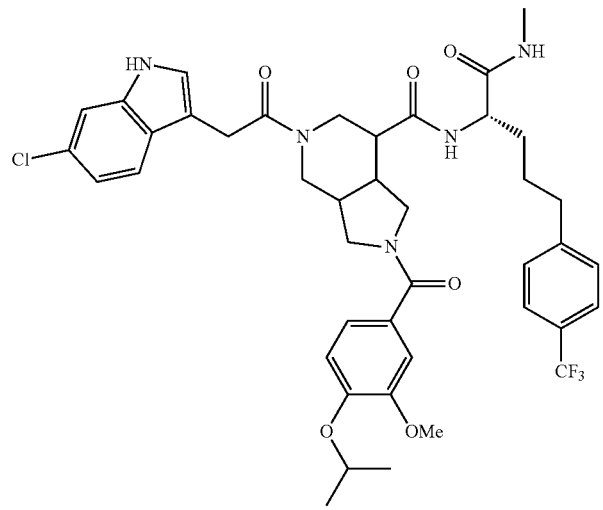 [SMILES: CNC(=O)[C@H](CCCc1ccc(C(F)(F)F)cc1)NC(=O)C1CN(C(=O)Cc2c[nH]c3cc(Cl)ccc23)CC2CN(C(=O)c3ccc(OC(C)C)c(OC)c3)CC21] |
| I-134 | 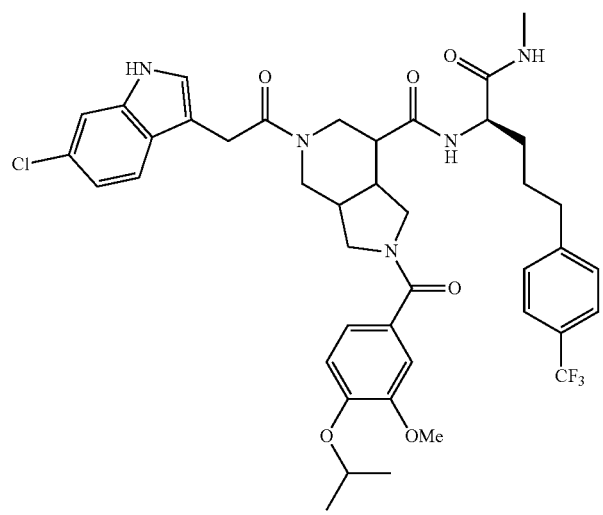 [SMILES: CNC(=O)[C@@H](CCCc1ccc(C(F)(F)F)cc1)NC(=O)C1CN(C(=O)Cc2c[nH]c3cc(Cl)ccc23)CC2CN(C(=O)c3ccc(OC(C)C)c(OC)c3)CC21] |
| I-135 | 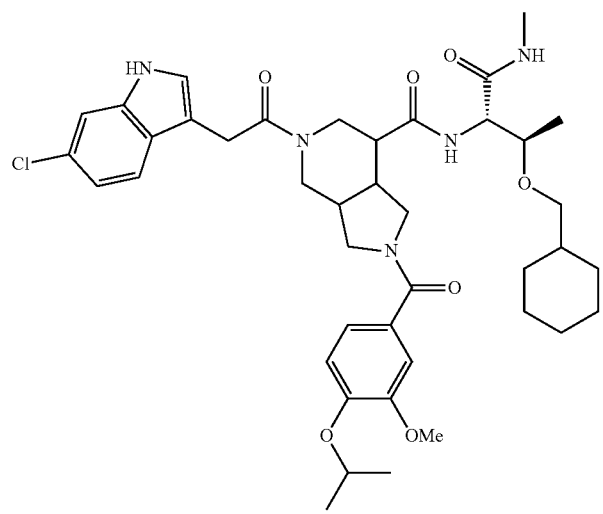 [SMILES: CNC(=O)[C@@H](NC(=O)C1CN(C(=O)Cc2c[nH]c3cc(Cl)ccc23)CC2CN(C(=O)c3ccc(OC(C)C)c(OC)c3)CC21)[C@@H](C)OCC1CCCCC1] |

| # | Structure |
|---|---|
| I-136 | 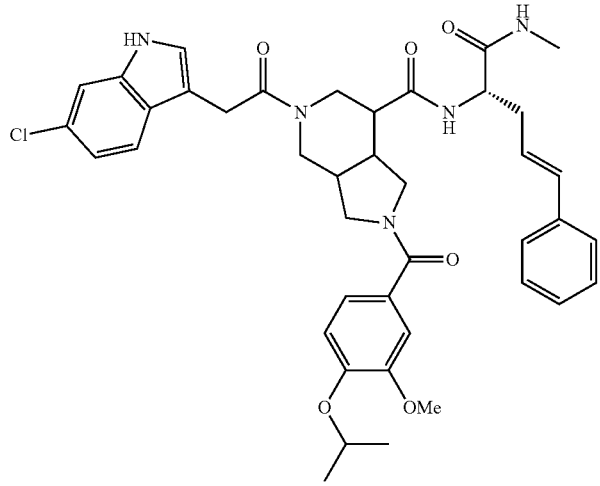 [SMILES: CNC(=O)[C@H](C/C=C/c1ccccc1)NC(=O)C1CN(C(=O)Cc2c[nH]c3cc(Cl)ccc23)CC2CN(C(=O)c3ccc(OC(C)C)c(OC)c3)CC21] |
| I-137 | 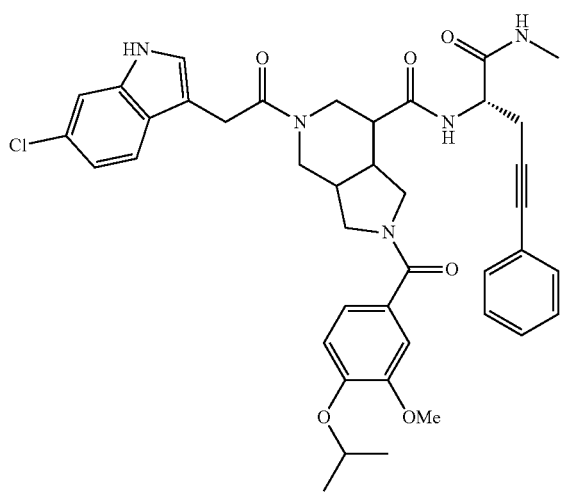 [SMILES: CNC(=O)[C@H](CC#Cc1ccccc1)NC(=O)C1CN(C(=O)Cc2c[nH]c3cc(Cl)ccc23)CC2CN(C(=O)c3ccc(OC(C)C)c(OC)c3)CC21] |
| I-138 | 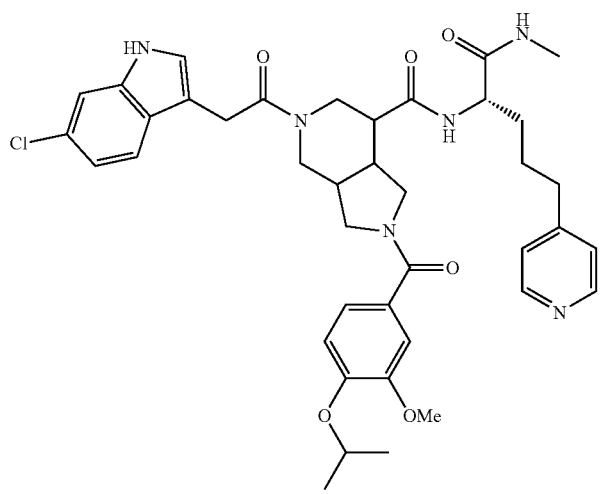 [SMILES: CNC(=O)[C@H](CCCc1ccncc1)NC(=O)C1CN(C(=O)Cc2c[nH]c3cc(Cl)ccc23)CC2CN(C(=O)c3ccc(OC(C)C)c(OC)c3)CC21] |

| # | Structure |
|---|---|
| I-139 | 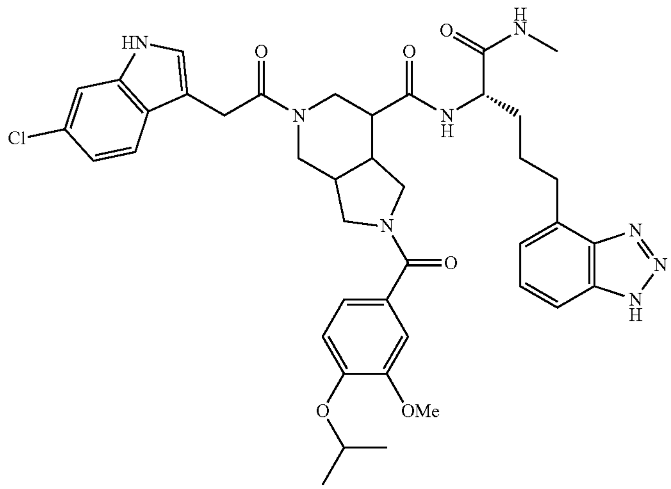 [SMILES: CNC(=O)[C@H](CCCc1cccc2[nH]nnc12)NC(=O)C1CN(C(=O)Cc2c[nH]c3cc(Cl)ccc23)CC2CN(C(=O)c3ccc(OC(C)C)c(OC)c3)CC21] |
| I-140 | 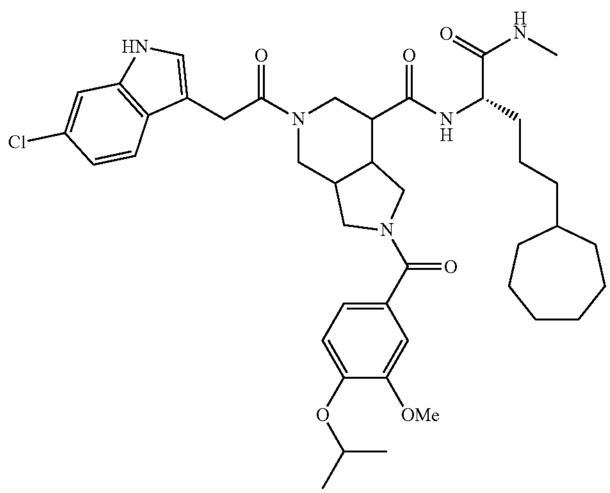 [SMILES: CNC(=O)[C@H](CCCC1CCCCCC1)NC(=O)C1CN(C(=O)Cc2c[nH]c3cc(Cl)ccc23)CC2CN(C(=O)c3ccc(OC(C)C)c(OC)c3)CC21] |
| I-141 | 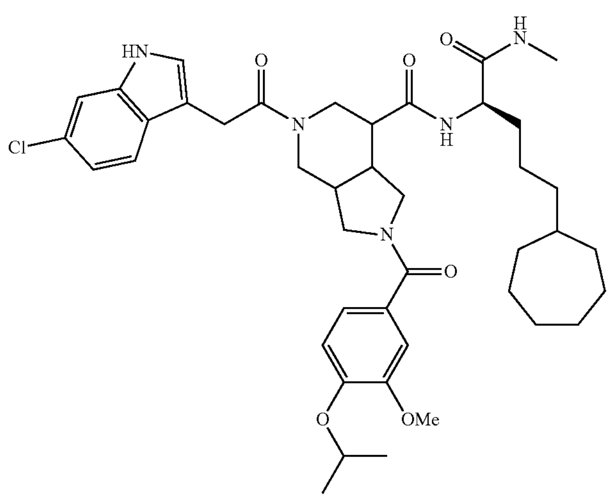 [SMILES: CNC(=O)[C@@H](CCCC1CCCCCC1)NC(=O)C1CN(C(=O)Cc2c[nH]c3cc(Cl)ccc23)CC2CN(C(=O)c3ccc(OC(C)C)c(OC)c3)CC21] |

| # | Structure |
|---|---|
| I-142 | 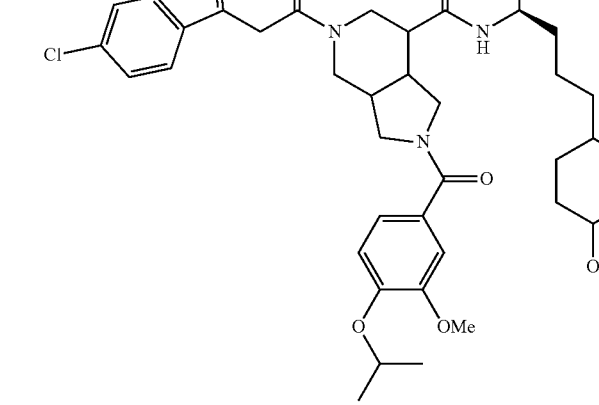 |
| I-143 | 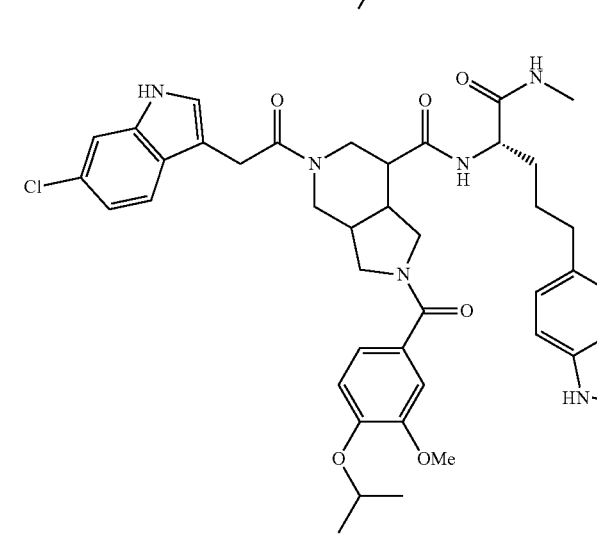 |
| I-144 | 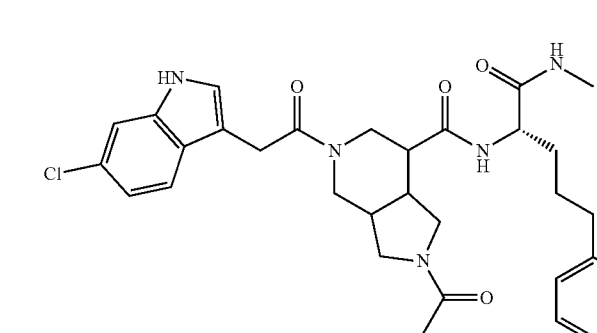 |

| # | Structure |
|---|---|
| I-145 | 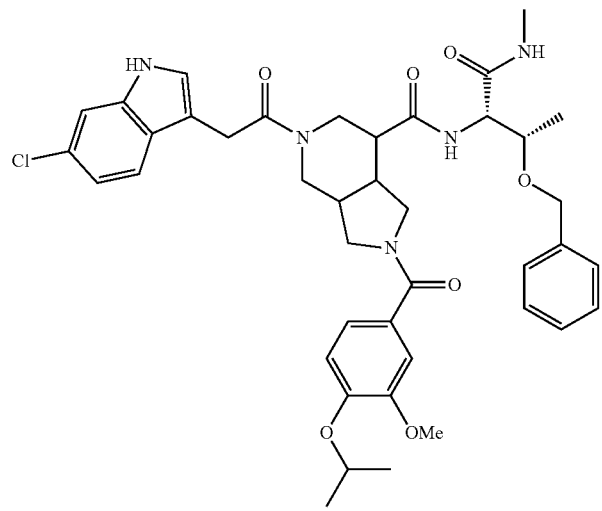<br>First eluting diastereomer—n-Hexane/EtOH |
| I-146 | 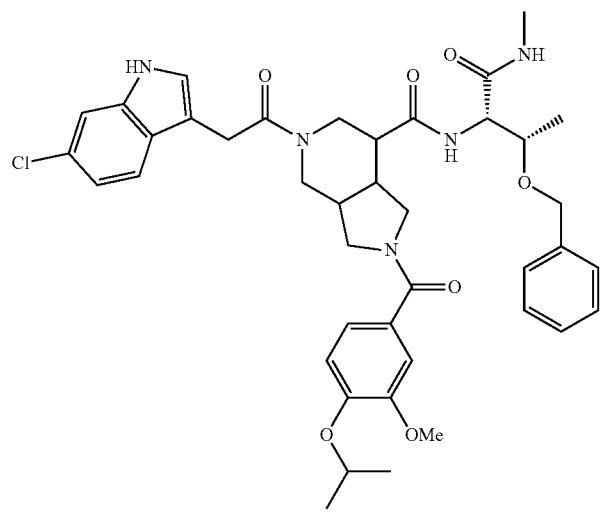<br>Second eluting diastereomer—n-Hexane/EtOH |

| # | Structure |
|---|---|
| I-147 | 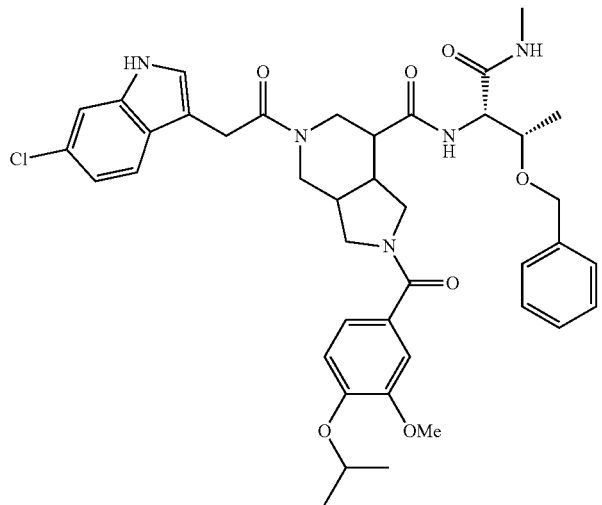<br>First eluting diastereomer—H$_2$O/Acetonitrile |
| I-148 | 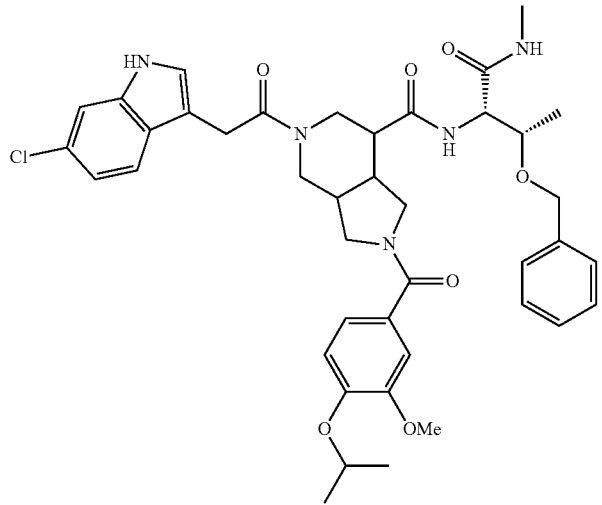<br>Second eluting diastereomer—H$_2$O/Acetonitrile |
| I-149 | 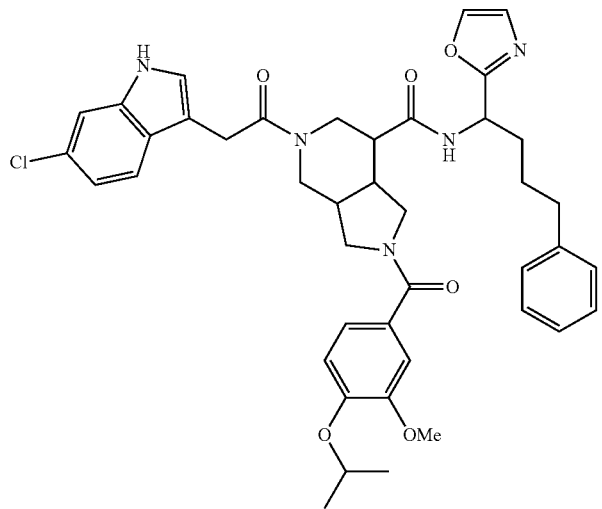 [SMILES: COc1cc(C(=O)N2CC3CN(C(=O)Cc4c[nH]c5cc(Cl)ccc45)CC(C(=O)NC(CCCc4ccccc4)c4ncco4)C3C2)ccc1OC(C)C] |

| # | Structure |
|---|---|
| I-150 | 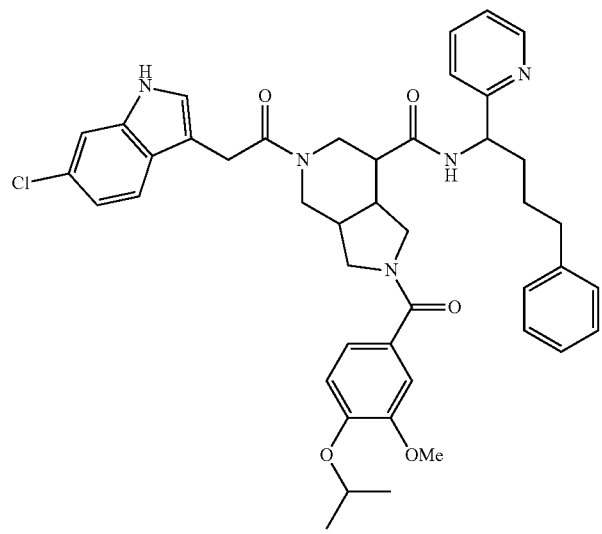 |
| I-151 | 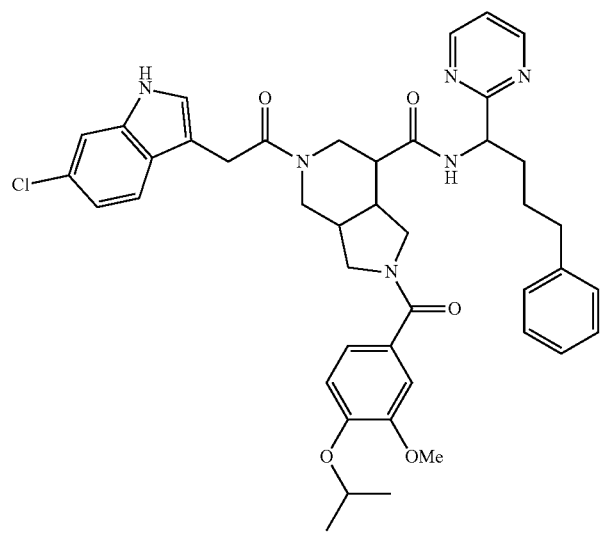 [SMILES: COc1cc(C(=O)N2CC3CN(C(=O)Cc4c[nH]c5cc(Cl)ccc45)CC(C(=O)NC(CCCc4ccccc4)c4ccccn4)C3C2)ccc1OC(C)C] |
| I-152 | 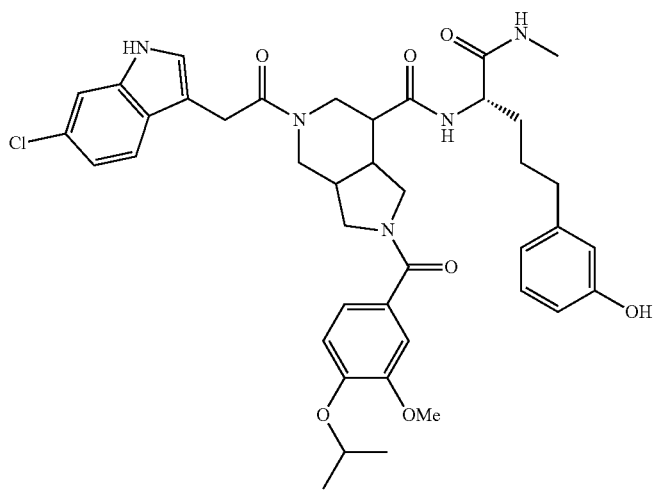<br>First eluting diastereomer |

| # | Structure |
|---|-----------|
| I-153 | 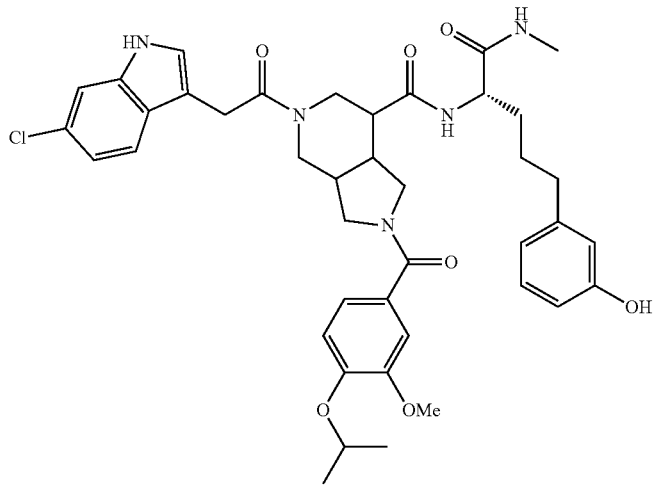<br>Second eluting diastereomer |
| I-154 | 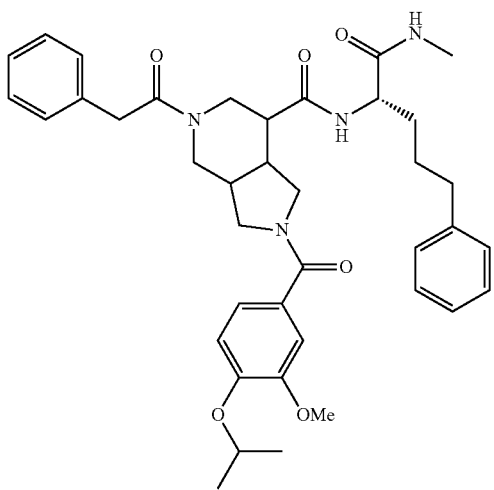 [SMILES: CNC(=O)[C@H](CCCc1ccccc1)NC(=O)C1CN(C(=O)Cc2ccccc2)CC2CN(C(=O)c3ccc(OC(C)C)c(OC)c3)CC21] |
| I-155 | 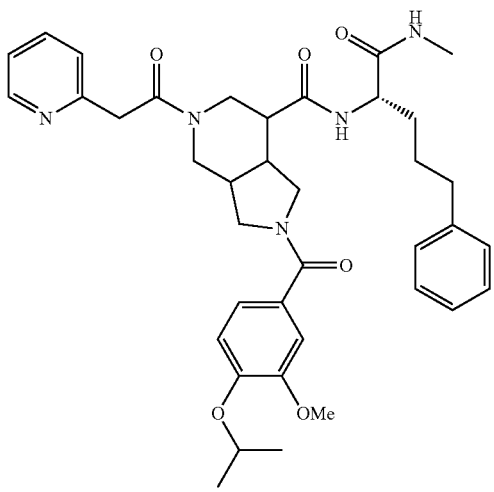 [SMILES: CNC(=O)[C@H](CCCc1ccccc1)NC(=O)C1CN(C(=O)Cc2ccccn2)CC2CN(C(=O)c3ccc(OC(C)C)c(OC)c3)CC21] |

| # | Structure |
|---|---|
| I-156 | 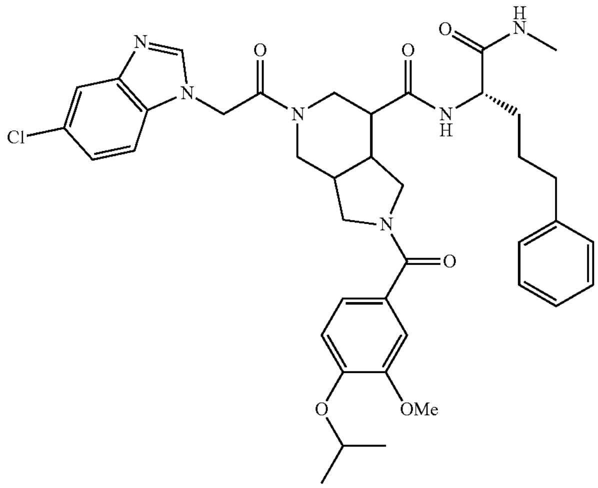 [SMILES: CNC(=O)[C@H](CCCc1ccccc1)NC(=O)C1CN(C(=O)Cn2cnc3cc(Cl)ccc32)CC2CN(C(=O)c3ccc(OC(C)C)c(OC)c3)CC21] |
| I-157 | 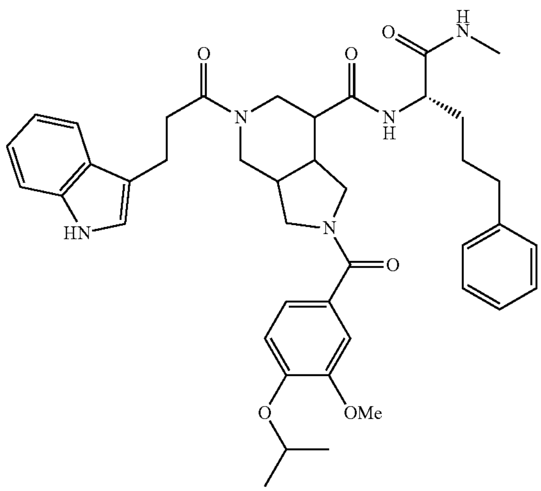 [SMILES: CNC(=O)[C@H](CCCc1ccccc1)NC(=O)C1CN(C(=O)CCc2c[nH]c3ccccc23)CC2CN(C(=O)c3ccc(OC(C)C)c(OC)c3)CC21] |
| I-158 | 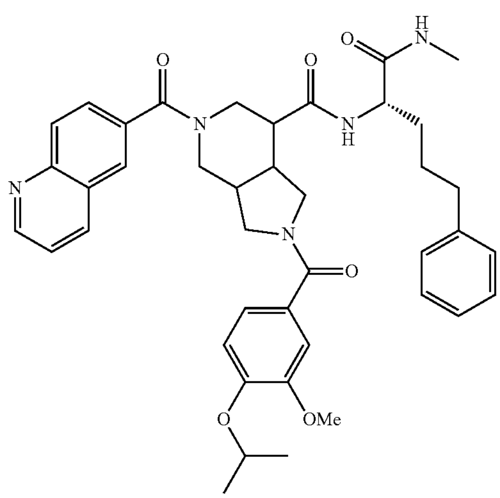 [SMILES: CNC(=O)[C@H](CCCc1ccccc1)NC(=O)C1CN(C(=O)c2ccc3ncccc3c2)CC2CN(C(=O)c3ccc(OC(C)C)c(OC)c3)CC21] |

-continued
| # | Structure |
|---|---|
| I-159 | 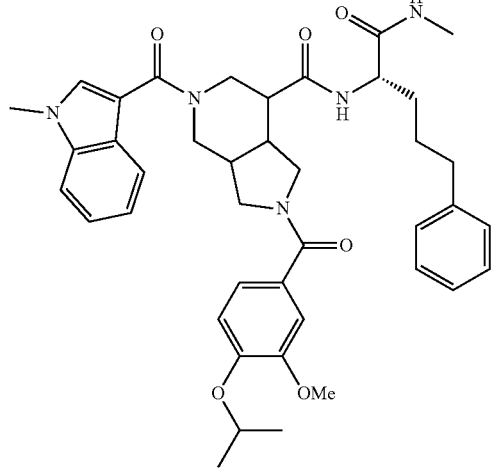 |
| I-160 | 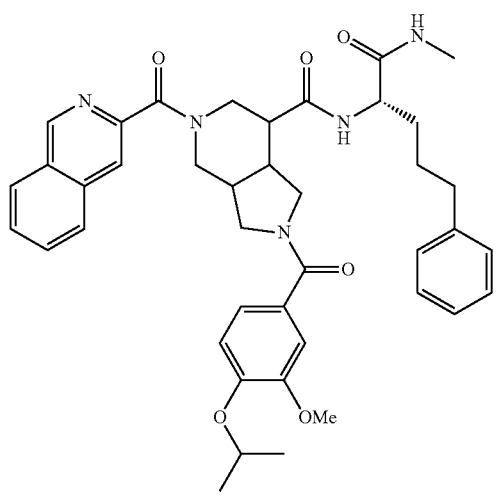 [SMILES: CNC(=O)[C@H](CCCc1ccccc1)NC(=O)C1CN(C(=O)c2cc3ccccc3cn2)CC2CN(C(=O)c3ccc(OC(C)C)c(OC)c3)CC21] |
| I-161 | 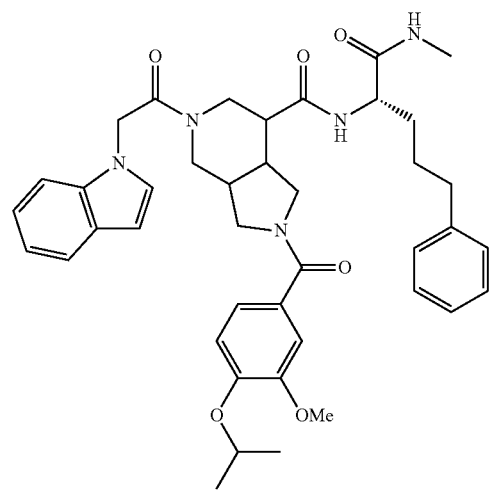 [SMILES: CNC(=O)[C@H](CCCc1ccccc1)NC(=O)C1CN(C(=O)Cn2ccc3ccccc32)CC2CN(C(=O)c3ccc(OC(C)C)c(OC)c3)CC21] |

| # | Structure |
|---|---|
| I-162 | 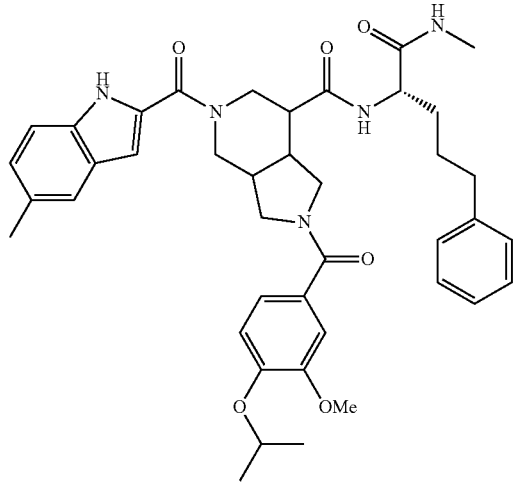 [SMILES: CNC(=O)[C@H](CCCc1ccccc1)NC(=O)C1CN(C(=O)c2cc3cc(C)ccc3[nH]2)CC2CN(C(=O)c3ccc(OC(C)C)c(OC)c3)CC21] |
| I-163 | 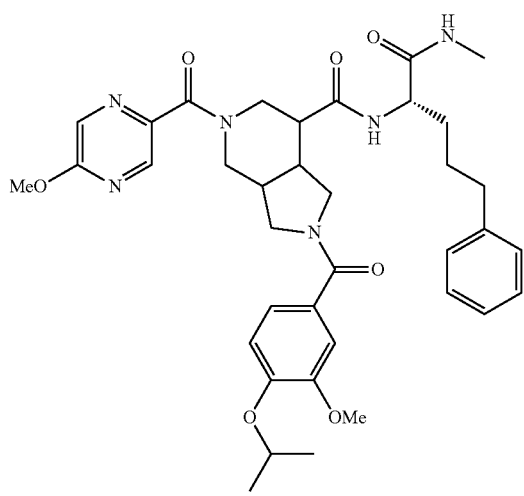 [SMILES: CNC(=O)[C@H](CCCc1ccccc1)NC(=O)C1CN(C(=O)c2cnc(OC)cn2)CC2CN(C(=O)c3ccc(OC(C)C)c(OC)c3)CC21] |
| I-164 | 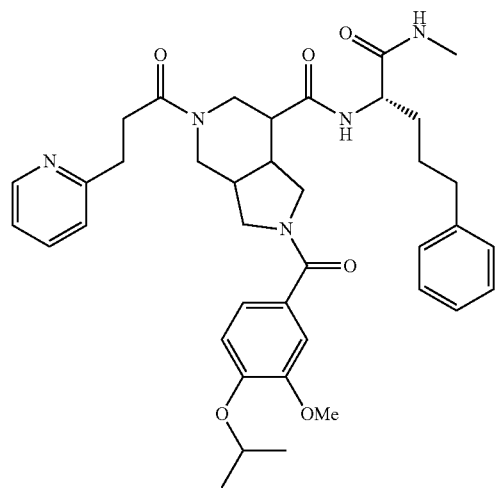 [SMILES: CNC(=O)[C@H](CCCc1ccccc1)NC(=O)C1CN(C(=O)CCc2ccccn2)CC2CN(C(=O)c3ccc(OC(C)C)c(OC)c3)CC21] |

| # | Structure |
|---|---|
| I-165 | 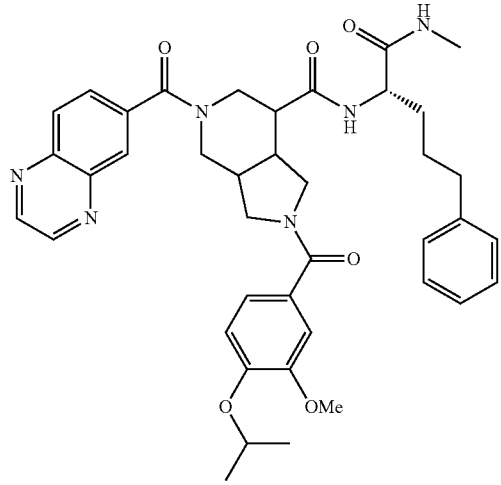 [SMILES: CNC(=O)[C@H](CCCc1ccccc1)NC(=O)C1CN(C(=O)c2ccc3nccnc3c2)CC2CN(C(=O)c3ccc(OC(C)C)c(OC)c3)CC21] |
| I-166 | 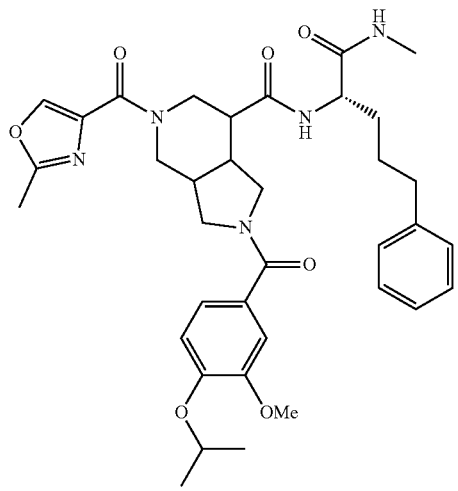 [SMILES: CNC(=O)[C@H](CCCc1ccccc1)NC(=O)C1CN(C(=O)c2coc(C)n2)CC2CN(C(=O)c3ccc(OC(C)C)c(OC)c3)CC21] |
| I-167 | 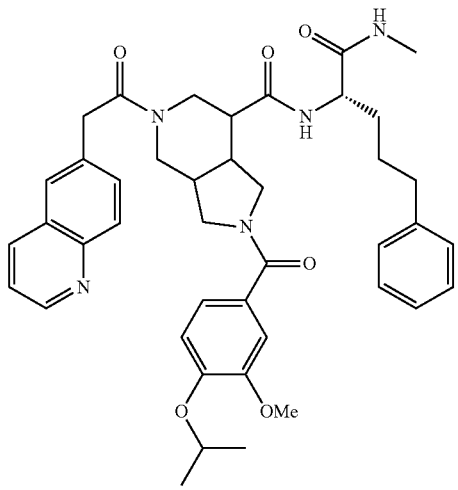 [SMILES: CNC(=O)[C@H](CCCc1ccccc1)NC(=O)C1CN(C(=O)Cc2ccc3ncccc3c2)CC2CN(C(=O)c3ccc(OC(C)C)c(OC)c3)CC21] |

| # | Structure |
|---|---|
| I-168 | 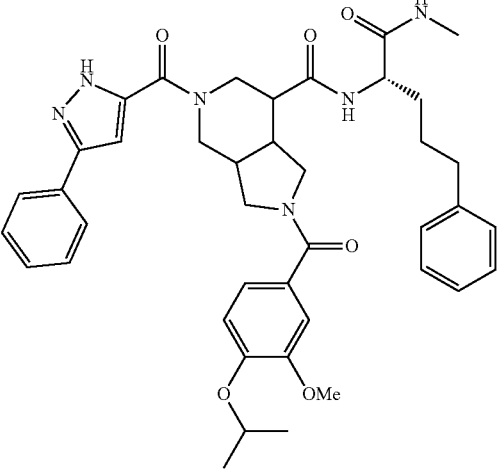 |
| I-169 | 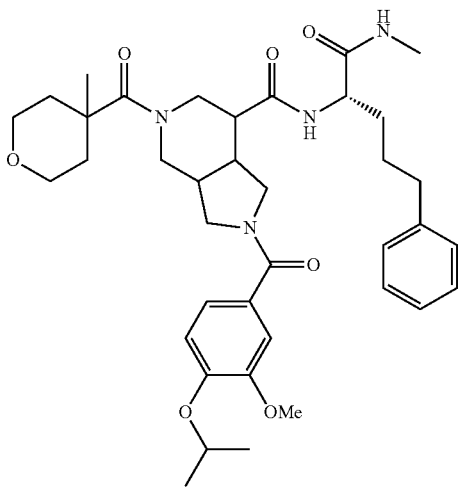 |
| I-170 | 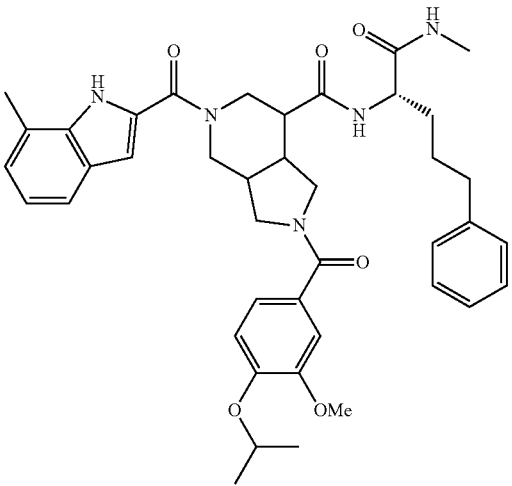 [SMILES: CNC(=O)[C@H](CCCc1ccccc1)NC(=O)C1CN(C(=O)c2cc3cccc(C)c3[nH]2)CC2CN(C(=O)c3ccc(OC(C)C)c(OC)c3)CC21] |

| # | Structure |
|---|-----------|
| I-171 | 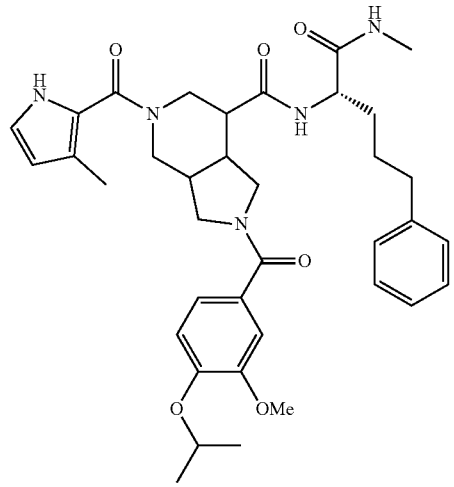 [SMILES: CNC(=O)[C@H](CCCc1ccccc1)NC(=O)C1CN(C(=O)c2[nH]ccc2C)CC2CN(C(=O)c3ccc(OC(C)C)c(OC)c3)CC21] |
| I-172 | 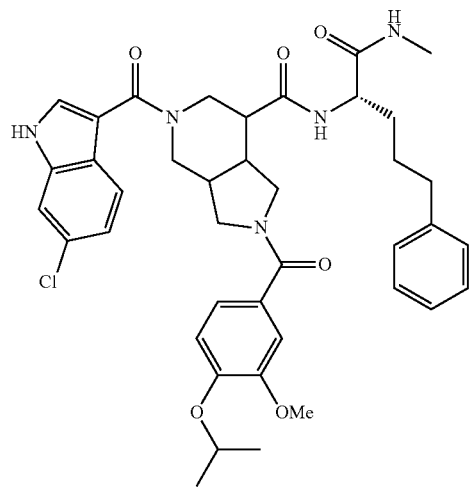 |
| I-173 | 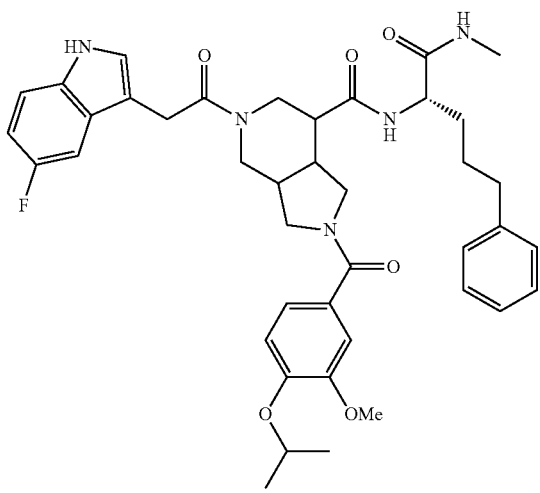 |

| # | Structure |
|---|---|
| I-174 | 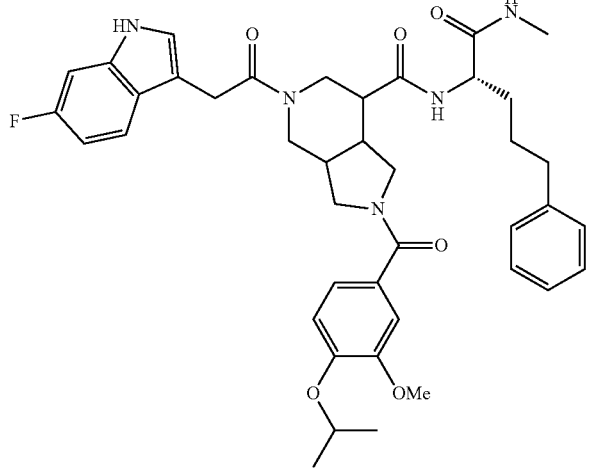 |
| I-175 | 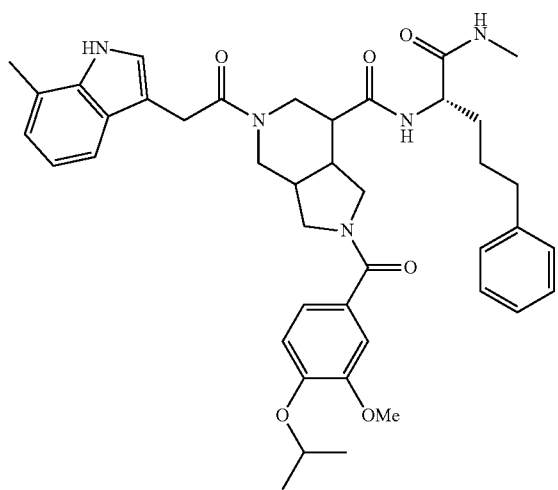 [SMILES: CNC(=O)[C@H](CCCc1ccccc1)NC(=O)C1CN(C(=O)Cc2c[nH]c3c(C)cccc23)CC2CN(C(=O)c3ccc(OC(C)C)c(OC)c3)CC21] |
| I-176 | 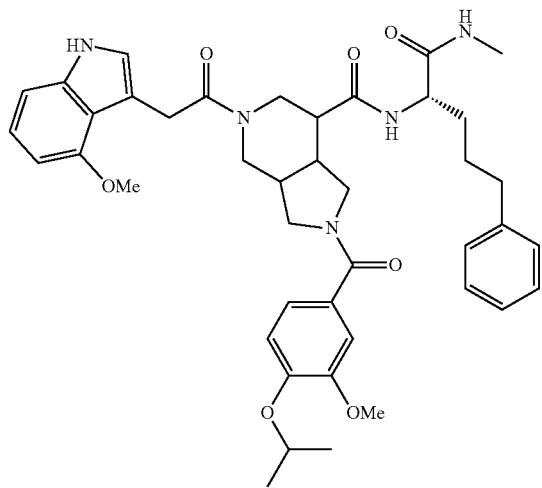 [SMILES: CNC(=O)[C@H](CCCc1ccccc1)NC(=O)C1CN(C(=O)Cc2c[nH]c3cccc(OC)c23)CC2CN(C(=O)c3ccc(OC(C)C)c(OC)c3)CC21] |

| # | Structure |
|---|---|
| I-177 | 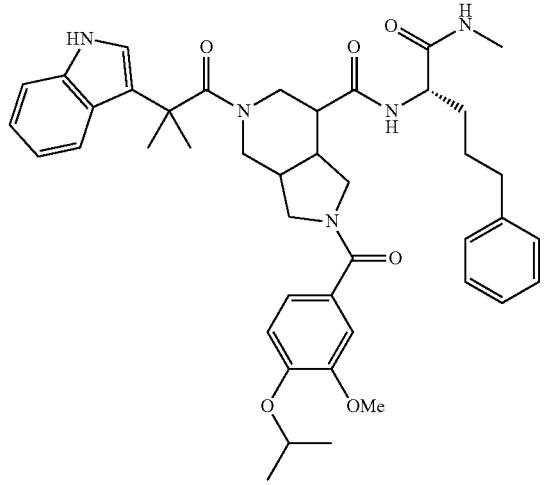 [SMILES: CNC(=O)[C@H](CCCc1ccccc1)NC(=O)C1CN(C(=O)C(C)(C)c2c[nH]c3ccccc23)CC2CN(C(=O)c3ccc(OC(C)C)c(OC)c3)CC21] |
| I-178 | 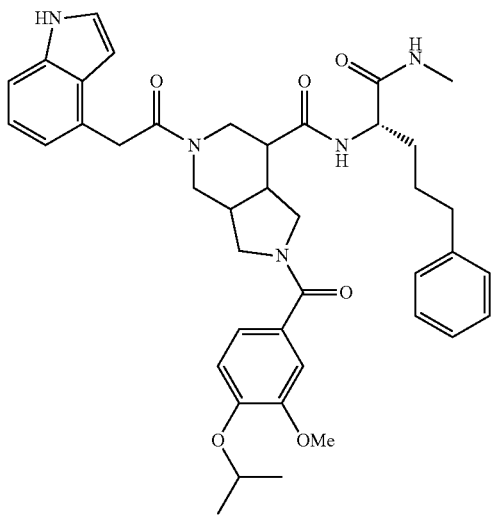 [SMILES: CNC(=O)[C@H](CCCc1ccccc1)NC(=O)C1CN(C(=O)Cc2cccc3[nH]ccc23)CC2CN(C(=O)c3ccc(OC(C)C)c(OC)c3)CC21] |
| I-179 | 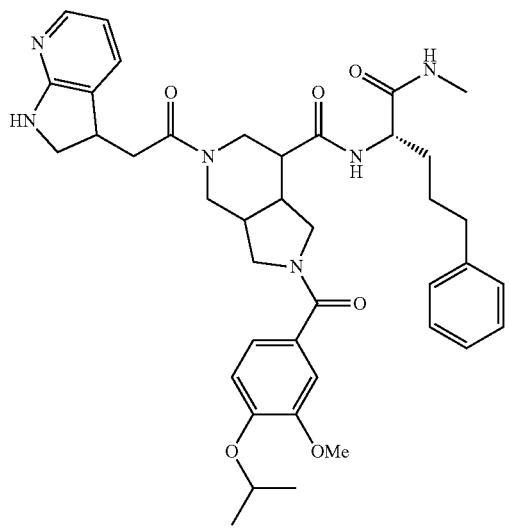 [SMILES: CNC(=O)[C@H](CCCc1ccccc1)NC(=O)C1CN(C(=O)CC2CNc3ncccc32)CC2CN(C(=O)c3ccc(OC(C)C)c(OC)c3)CC21] |

| # | Structure |
|---|---|
| I-180 | 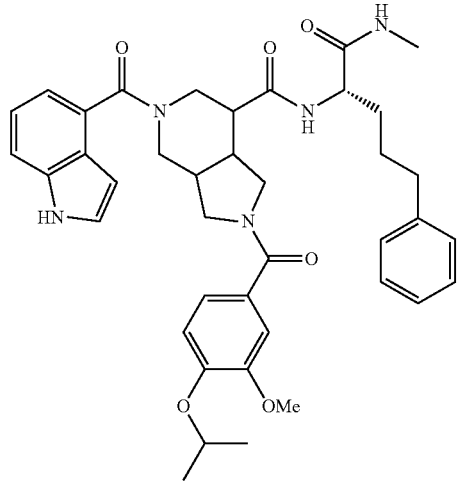 [SMILES: CNC(=O)[C@H](CCCc1ccccc1)NC(=O)C1CN(C(=O)c2cccc3[nH]ccc23)CC2CN(C(=O)c3ccc(OC(C)C)c(OC)c3)CC21] |
| I-181 | 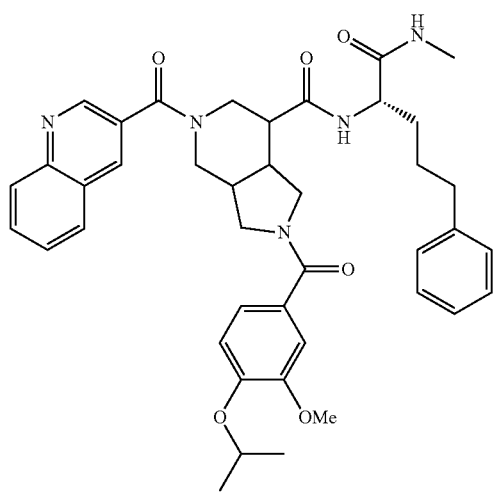 [SMILES: CNC(=O)[C@H](CCCc1ccccc1)NC(=O)C1CN(C(=O)c2cnc3ccccc3c2)CC2CN(C(=O)c3ccc(OC(C)C)c(OC)c3)CC21] |
| I-182 | 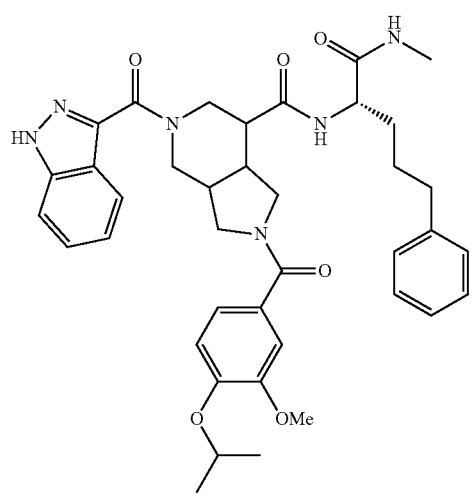 [SMILES: CNC(=O)[C@H](CCCc1ccccc1)NC(=O)C1CN(C(=O)c2n[nH]c3ccccc23)CC2CN(C(=O)c3ccc(OC(C)C)c(OC)c3)CC21] |

| # | Structure |
|---|---|
| I-183 | 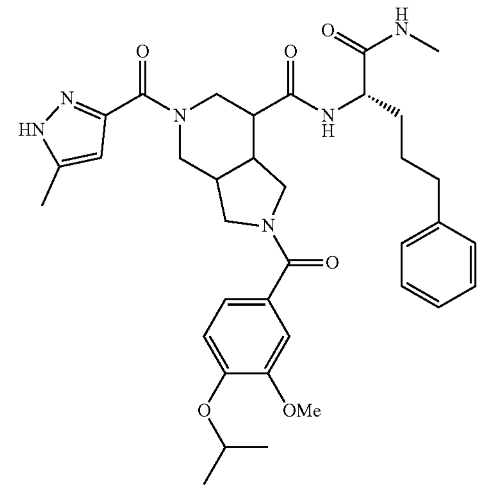 [SMILES: CNC(=O)[C@H](CCCc1ccccc1)NC(=O)C1CN(C(=O)c2cc(C)[nH]n2)CC2CN(C(=O)c3ccc(OC(C)C)c(OC)c3)CC21] |
| I-184 | 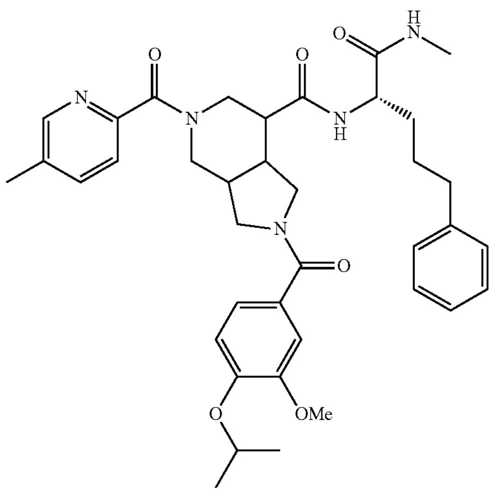 [SMILES: CNC(=O)[C@H](CCCc1ccccc1)NC(=O)C1CN(C(=O)c2ccc(C)cn2)CC2CN(C(=O)c3ccc(OC(C)C)c(OC)c3)CC21] |
| I-185 | 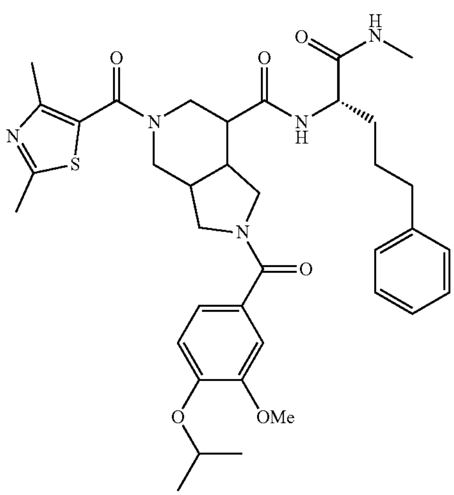 |

| # | Structure |
|---|---|
| I-186 | 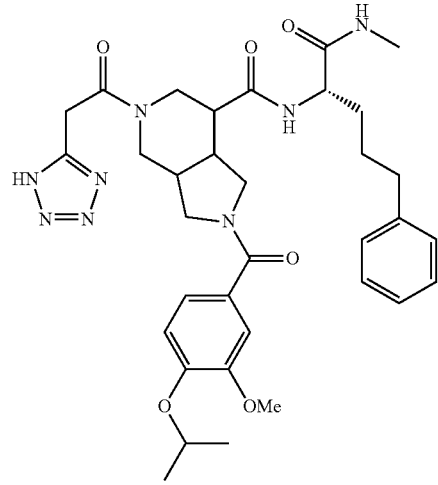 [SMILES: CNC(=O)[C@H](CCCc1ccccc1)NC(=O)C1CN(C(=O)Cc2nnn[nH]2)CC2CN(C(=O)c3ccc(OC(C)C)c(OC)c3)CC21] |
| I-187 | 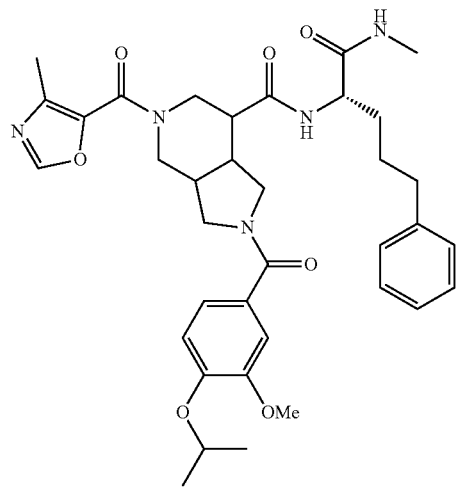 |
| I-188 | 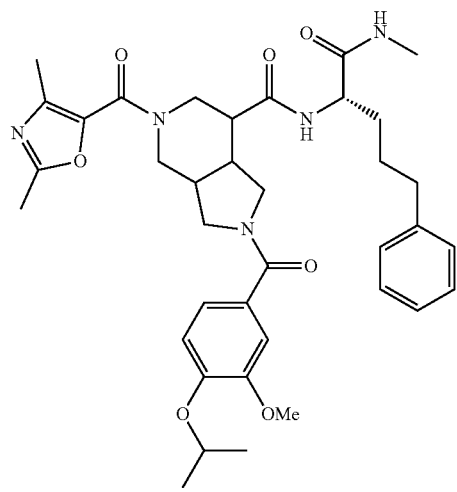 [SMILES: CNC(=O)[C@H](CCCc1ccccc1)NC(=O)C1CN(C(=O)c2oc(C)nc2C)CC2CN(C(=O)c3ccc(OC(C)C)c(OC)c3)CC21] |

-continued

| # | Structure |
|---|---|
| I-189 | 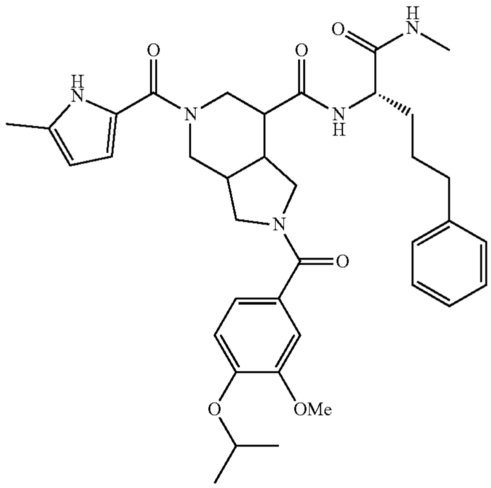 [SMILES: CNC(=O)[C@H](CCCc1ccccc1)NC(=O)C1CN(C(=O)c2ccc(C)[nH]2)CC2CN(C(=O)c3ccc(OC(C)C)c(OC)c3)CC21] |
| I-190 | 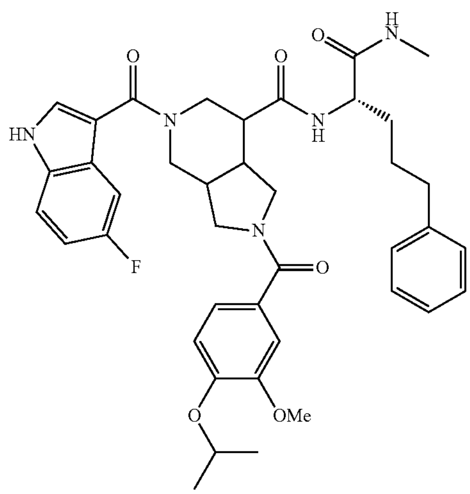 [SMILES: CNC(=O)[C@H](CCCc1ccccc1)NC(=O)C1CN(C(=O)c2c[nH]c3ccc(F)cc23)CC2CN(C(=O)c3ccc(OC(C)C)c(OC)c3)CC21] |
| I-191 | 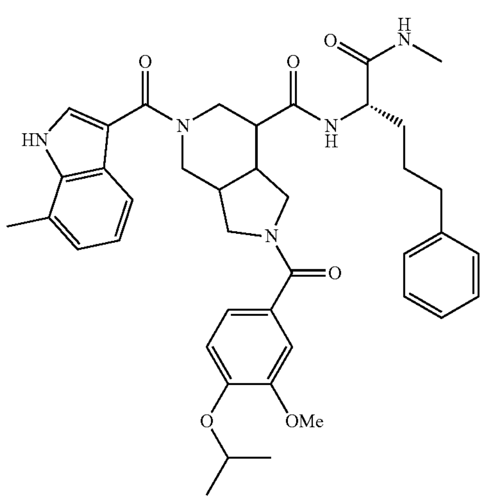 [SMILES: CNC(=O)[C@H](CCCc1ccccc1)NC(=O)C1CN(C(=O)c2c[nH]c3c(C)cccc23)CC2CN(C(=O)c3ccc(OC(C)C)c(OC)c3)CC21] |

| # | Structure |
|---|---|
| I-192 | 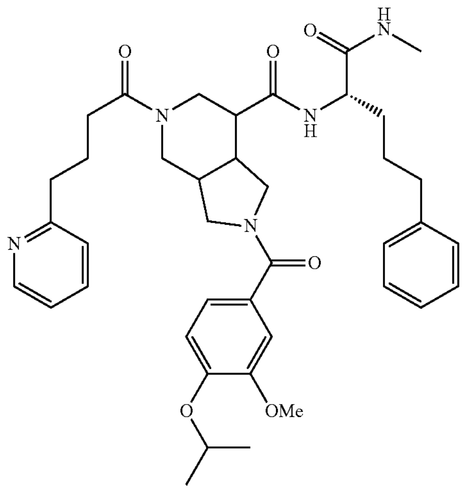 [SMILES: CNC(=O)[C@H](CCCc1ccccc1)NC(=O)C1CN(C(=O)CCCc2ccccn2)CC2CN(C(=O)c3ccc(OC(C)C)c(OC)c3)CC21] |
| I-193 | 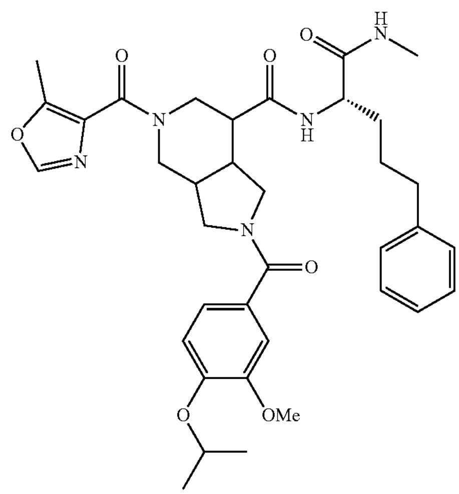 [SMILES: CNC(=O)[C@H](CCCc1ccccc1)NC(=O)C1CN(C(=O)c2ncoc2C)CC2CN(C(=O)c3ccc(OC(C)C)c(OC)c3)CC21] |
| I-194 | 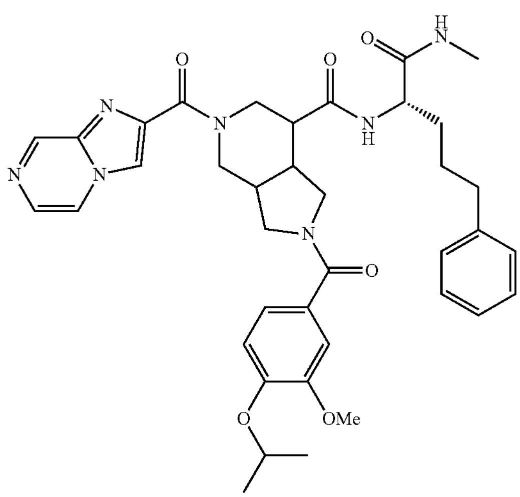 |

First eluting diastereomer

-continued
| # | Structure |
|---|---|
| I-195 | 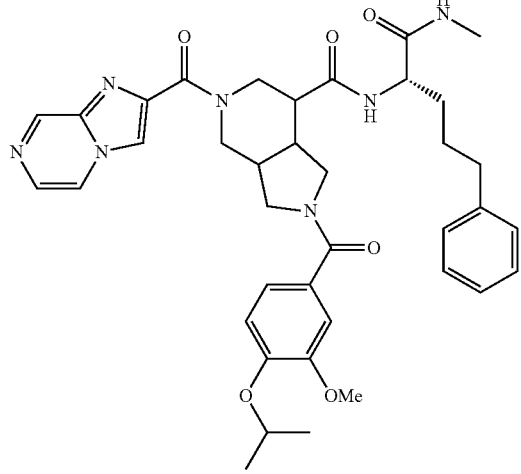
Second eluting diastereomer |
| I-196 | 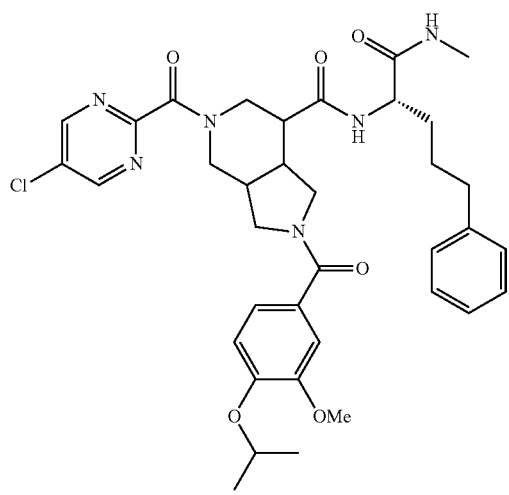 [SMILES: CNC(=O)[C@H](CCCc1ccccc1)NC(=O)C1CN(C(=O)c2ncc(Cl)cn2)CC2CN(C(=O)c3ccc(OC(C)C)c(OC)c3)CC21] |
| I-197 | 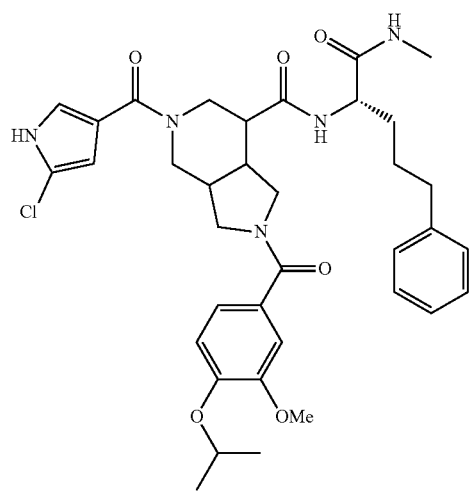 [SMILES: CNC(=O)[C@H](CCCc1ccccc1)NC(=O)C1CN(C(=O)c2c[nH]c(Cl)c2)CC2CN(C(=O)c3ccc(OC(C)C)c(OC)c3)CC21] |

| # | Structure |
|---|---|
| I-198 | 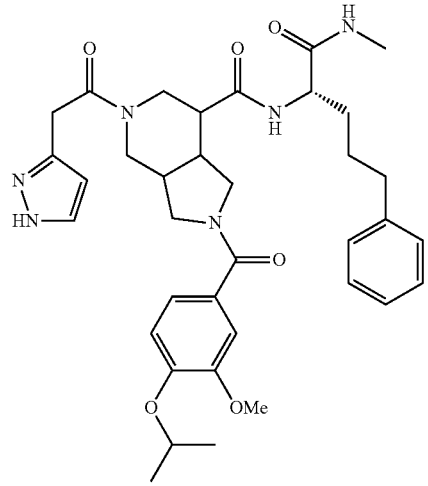 [SMILES: CNC(=O)[C@H](CCCc1ccccc1)NC(=O)C1CN(C(=O)Cc2cc[nH]n2)CC2CN(C(=O)c3ccc(OC(C)C)c(OC)c3)CC21] |
| I-199 | 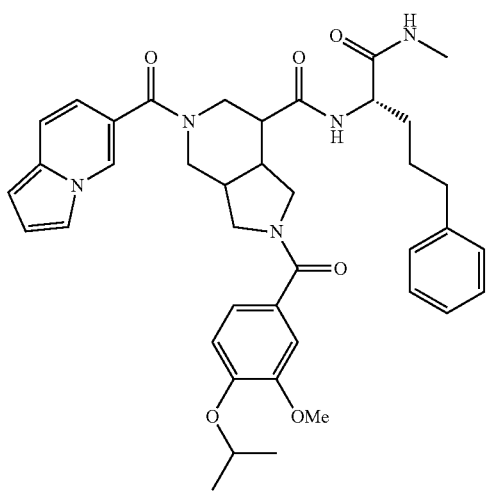 [SMILES: CNC(=O)[C@H](CCCc1ccccc1)NC(=O)C1CN(C(=O)c2ccc3cccn3c2)CC2CN(C(=O)c3ccc(OC(C)C)c(OC)c3)CC21] |
| I-200 | 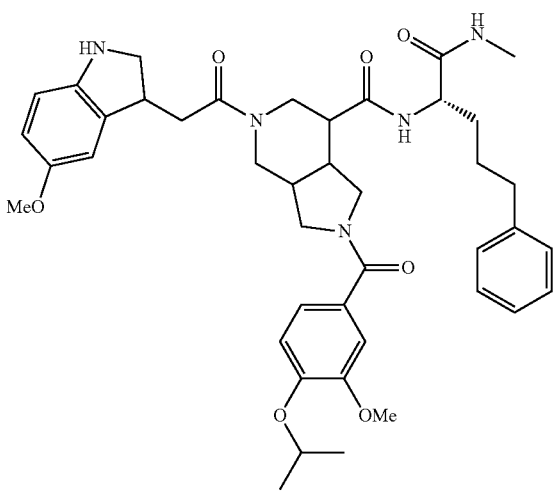 [SMILES: CNC(=O)[C@H](CCCc1ccccc1)NC(=O)C1CN(C(=O)CC2CNc3ccc(OC)cc32)CC2CN(C(=O)c3ccc(OC(C)C)c(OC)c3)CC21] |

-continued
| # | Structure |
|---|---|
| I-201 | 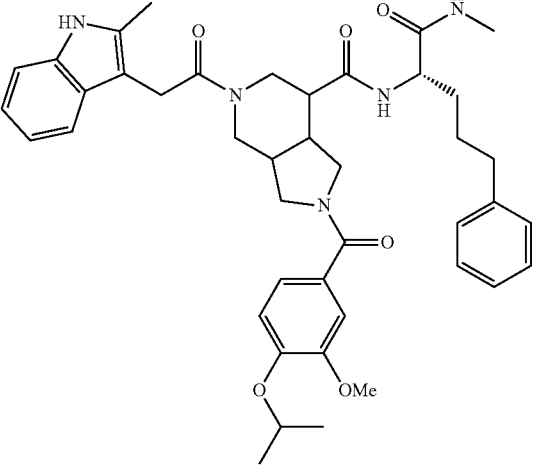 |
| I-202 | 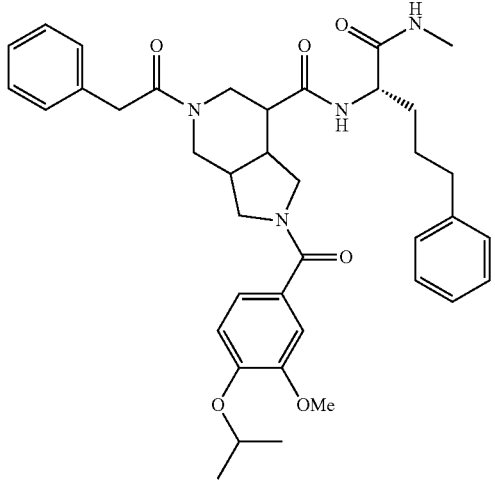 [SMILES: CNC(=O)[C@H](CCCc1ccccc1)NC(=O)C1CN(C(=O)Cc2ccccc2)CC2CN(C(=O)c3ccc(OC(C)C)c(OC)c3)CC21] |
| I-203 | 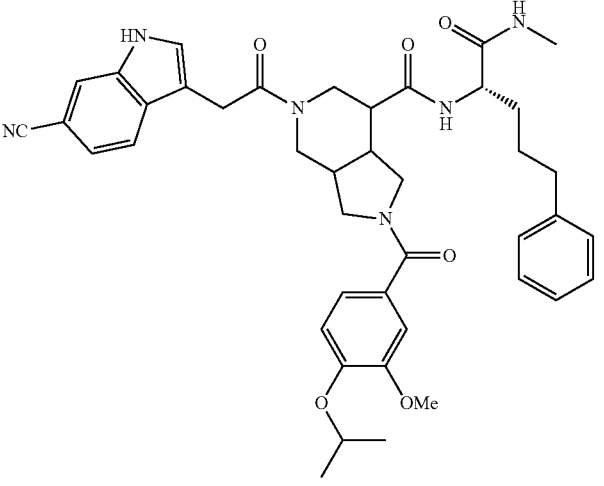 [SMILES: CNC(=O)[C@H](CCCc1ccccc1)NC(=O)C1CN(C(=O)Cc2c[nH]c3cc(C#N)ccc23)CC2CN(C(=O)c3ccc(OC(C)C)c(OC)c3)CC21] |

-continued

| # | Structure |
|---|---|
| I-204 | 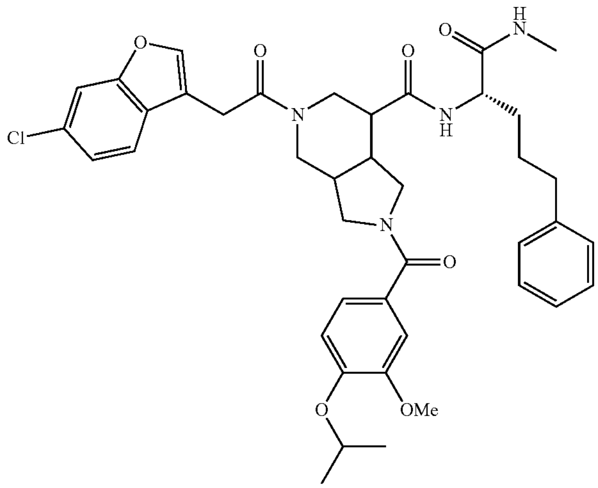 [SMILES: CNC(=O)[C@H](CCCc1ccccc1)NC(=O)C1CN(C(=O)Cc2coc3cc(Cl)ccc23)CC2CN(C(=O)c3ccc(OC(C)C)c(OC)c3)CC21] |
| I-205 | 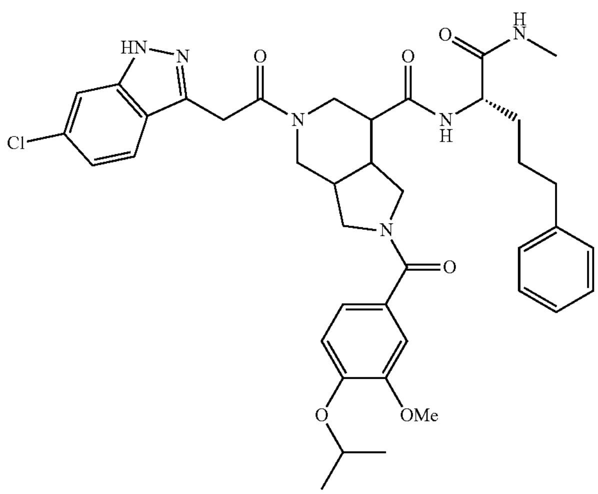 [SMILES: CNC(=O)[C@H](CCCc1ccccc1)NC(=O)C1CN(C(=O)Cc2n[nH]c3cc(Cl)ccc23)CC2CN(C(=O)c3ccc(OC(C)C)c(OC)c3)CC21] |
| I-206 | 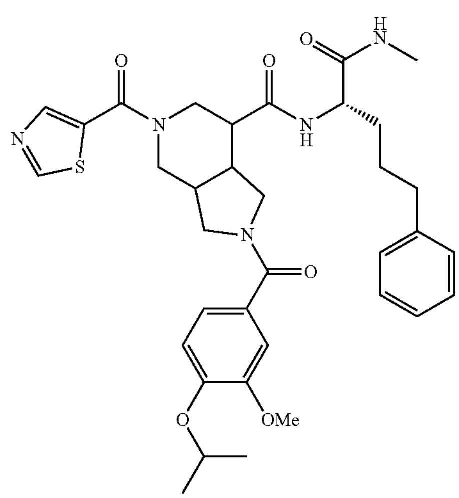 [SMILES: CNC(=O)[C@H](CCCc1ccccc1)NC(=O)C1CN(C(=O)c2cncs2)CC2CN(C(=O)c3ccc(OC(C)C)c(OC)c3)CC21] |

| # | Structure |
|---|---|
| I-207 | 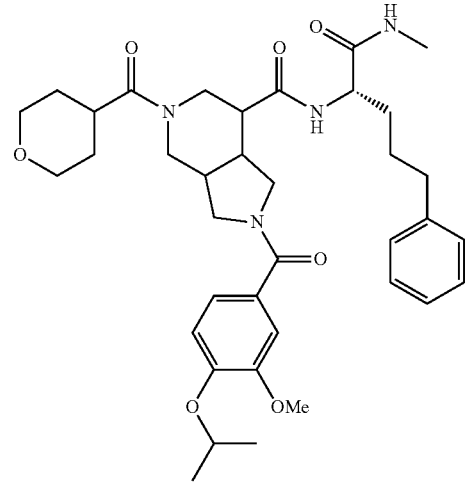 [SMILES: CNC(=O)[C@H](CCCc1ccccc1)NC(=O)C1CN(C(=O)C2CCOCC2)CC2CN(C(=O)c3ccc(OC(C)C)c(OC)c3)CC21] |
| I-208 | 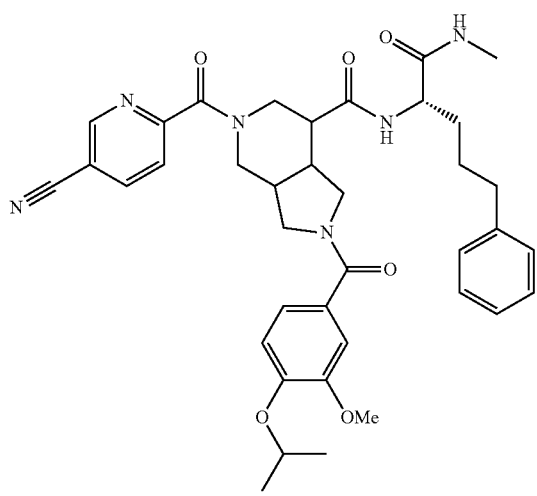 [SMILES: CNC(=O)[C@H](CCCc1ccccc1)NC(=O)C1CN(C(=O)c2ccc(C#N)cn2)CC2CN(C(=O)c3ccc(OC(C)C)c(OC)c3)CC21] |
| I-209 | 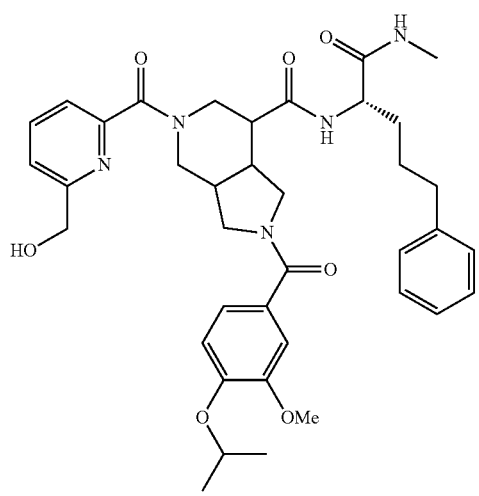 [SMILES: CNC(=O)[C@H](CCCc1ccccc1)NC(=O)C1CN(C(=O)c2cccc(CO)n2)CC2CN(C(=O)c3ccc(OC(C)C)c(OC)c3)CC21] |

-continued

| # | Structure |
|---|---|
| I-210 | 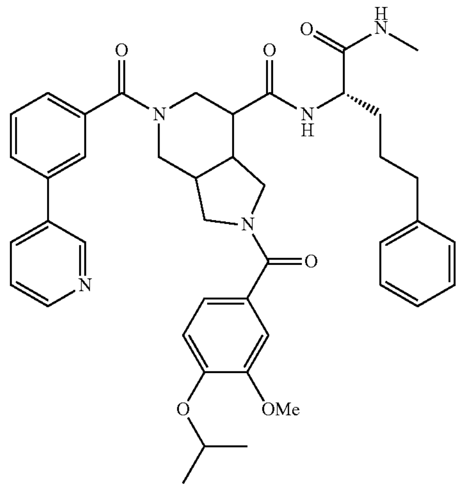 [SMILES: CNC(=O)[C@H](CCCc1ccccc1)NC(=O)C1CN(C(=O)c2cccc(-c3cccnc3)c2)CC2CN(C(=O)c3ccc(OC(C)C)c(OC)c3)CC21] |
| I-211 | 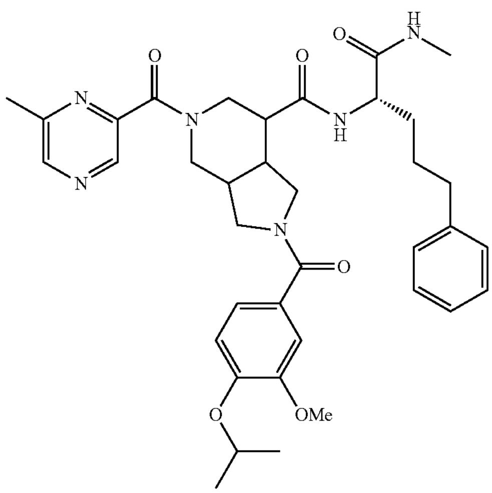 [SMILES: CNC(=O)[C@H](CCCc1ccccc1)NC(=O)C1CN(C(=O)c2cncc(C)n2)CC2CN(C(=O)c3ccc(OC(C)C)c(OC)c3)CC21] |
| I-212 | 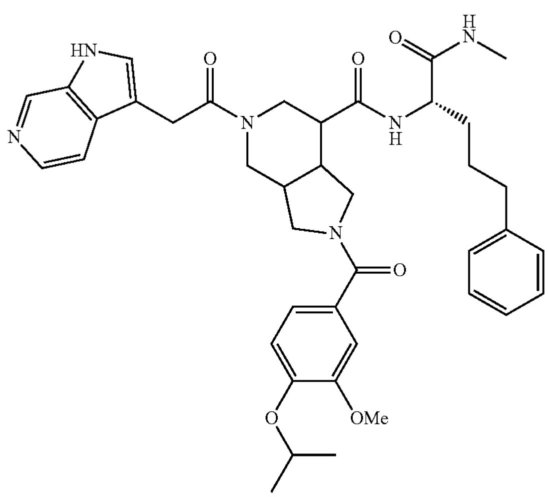 [SMILES: CNC(=O)[C@H](CCCc1ccccc1)NC(=O)C1CN(C(=O)Cc2c[nH]c3cnccc23)CC2CN(C(=O)c3ccc(OC(C)C)c(OC)c3)CC21] |

| # | Structure |
|---|---|
| I-213 | 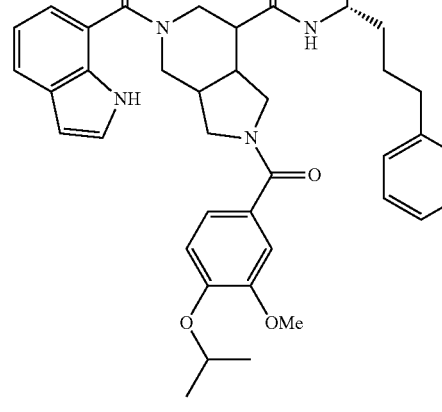 |
| I-214 | 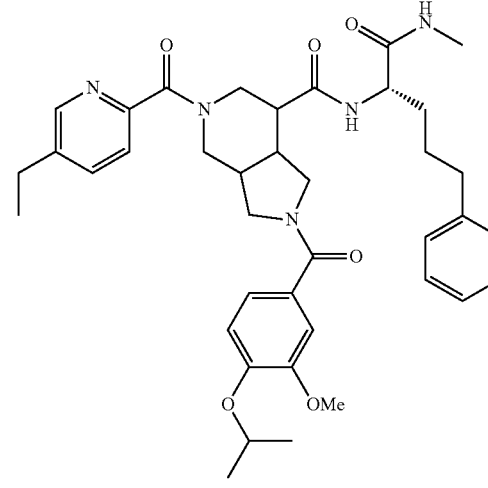 |
| I-215 | 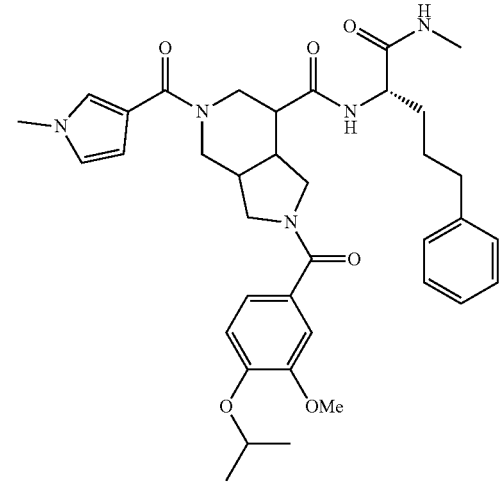 [SMILES: CNC(=O)[C@H](CCCc1ccccc1)NC(=O)C1CN(C(=O)c2ccn(C)c2)CC2CN(C(=O)c3ccc(OC(C)C)c(OC)c3)CC21] |

| # | Structure |
|---|---|
| I-216 | 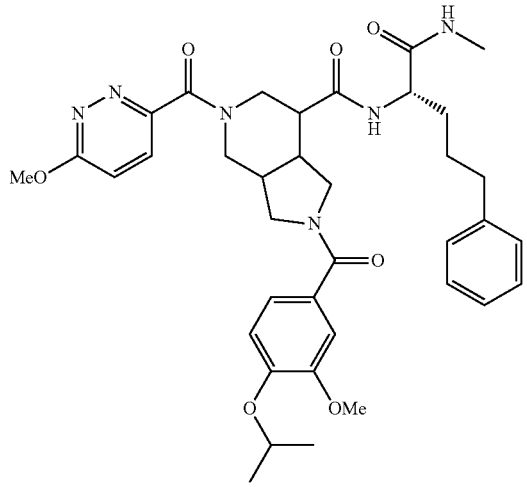 [SMILES: CNC(=O)[C@H](CCCc1ccccc1)NC(=O)C1CN(C(=O)c2ccc(OC)nn2)CC2CN(C(=O)c3ccc(OC(C)C)c(OC)c3)CC21] |
| I-217 | 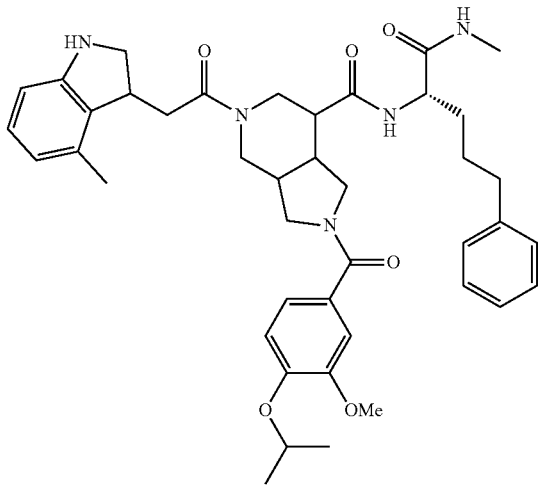 [SMILES: CNC(=O)[C@H](CCCc1ccccc1)NC(=O)C1CN(C(=O)CC2CNc3cccc(C)c32)CC2CN(C(=O)c3ccc(OC(C)C)c(OC)c3)CC21] |
| I-218 | 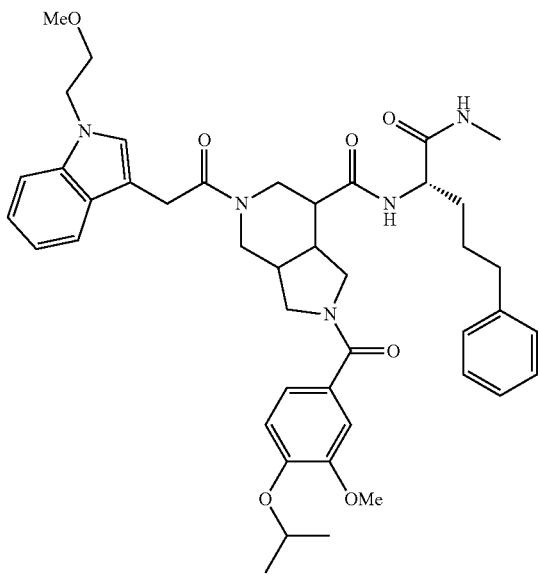 [SMILES: CNC(=O)[C@H](CCCc1ccccc1)NC(=O)C1CN(C(=O)Cc2cn(CCOC)c3ccccc23)CC2CN(C(=O)c3ccc(OC(C)C)c(OC)c3)CC21] |

-continued

| # | Structure |
|---|---|
| I-219 | 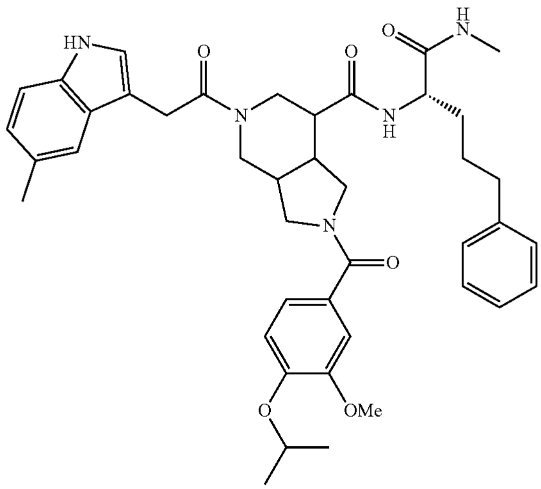 [SMILES: CNC(=O)[C@H](CCCc1ccccc1)NC(=O)C1CN(C(=O)Cc2c[nH]c3ccc(C)cc23)CC2CN(C(=O)c3ccc(OC(C)C)c(OC)c3)CC21] |
| I-220 | 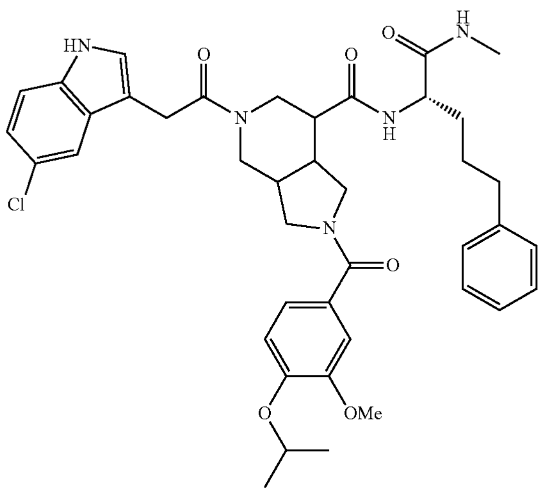 |
| I-221 | 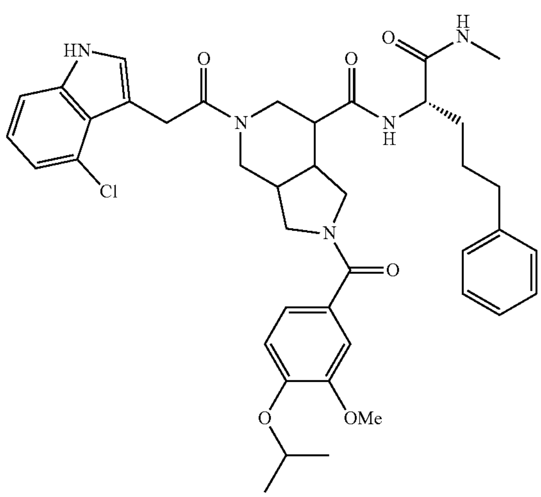 [SMILES: CNC(=O)[C@H](CCCc1ccccc1)NC(=O)C1CN(C(=O)Cc2c[nH]c3cccc(Cl)c23)CC2CN(C(=O)c3ccc(OC(C)C)c(OC)c3)CC21] |

| # | Structure |
|---|---|
| I-222 | 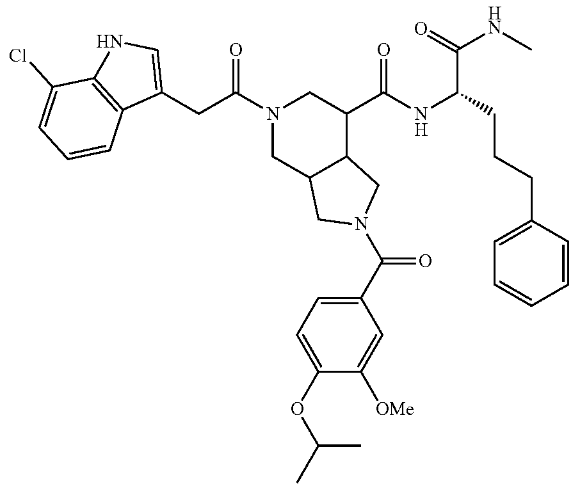 [SMILES: CNC(=O)[C@H](CCCc1ccccc1)NC(=O)C1CN(C(=O)Cc2c[nH]c3c(Cl)cccc23)CC2CN(C(=O)c3ccc(OC(C)C)c(OC)c3)CC21] |
| I-223 | 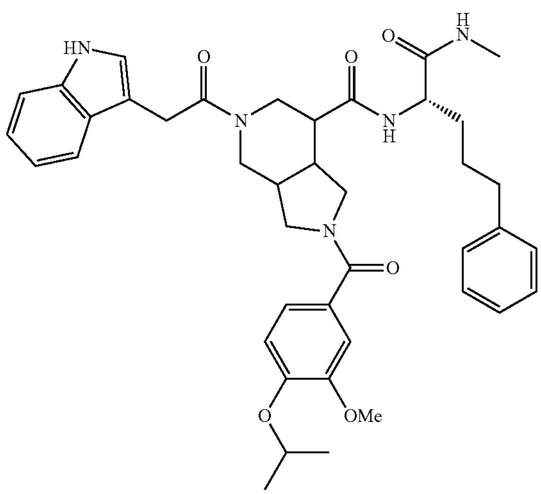 [SMILES: CNC(=O)[C@H](CCCc1ccccc1)NC(=O)C1CN(C(=O)Cc2c[nH]c3ccccc23)CC2CN(C(=O)c3ccc(OC(C)C)c(OC)c3)CC21] |
| I-224 | 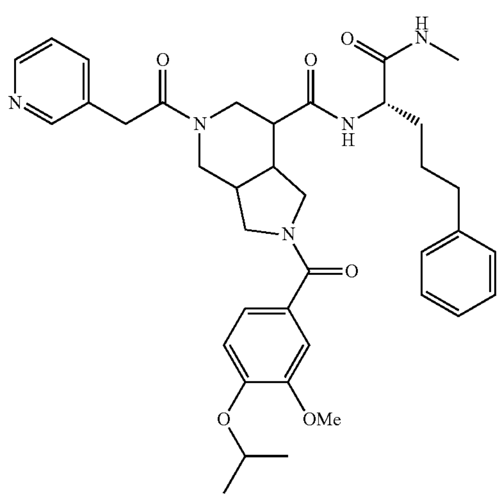 [SMILES: CNC(=O)[C@H](CCCc1ccccc1)NC(=O)C1CN(C(=O)Cc2cccnc2)CC2CN(C(=O)c3ccc(OC(C)C)c(OC)c3)CC21] |

| # | Structure |
|---|---|
| I-225 | 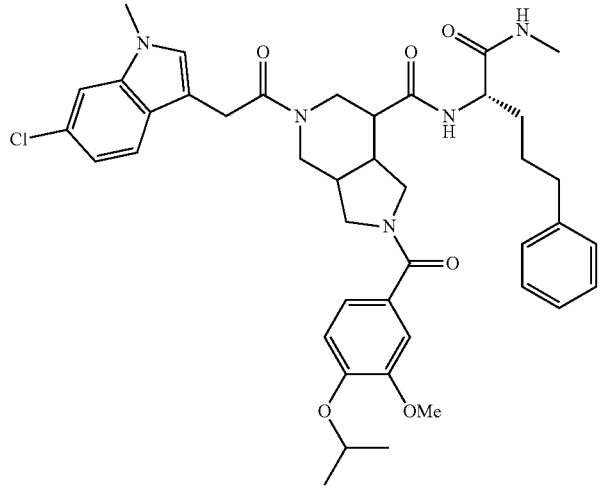 [SMILES: CNC(=O)[C@H](CCCc1ccccc1)NC(=O)C1CN(C(=O)Cc2cn(C)c3cc(Cl)ccc23)CC2CN(C(=O)c3ccc(OC(C)C)c(OC)c3)CC21] |
| I-226 | 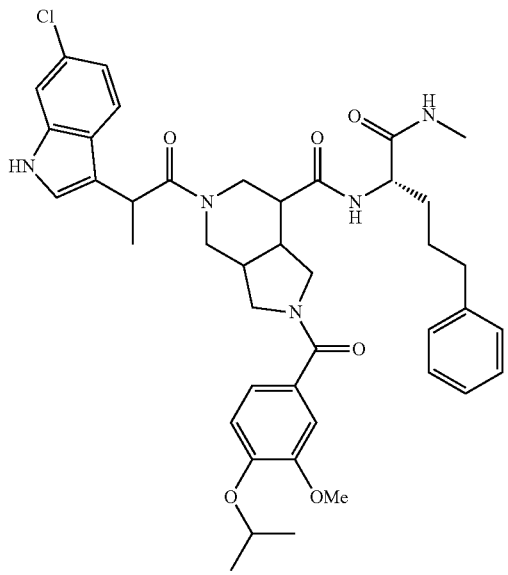 [SMILES: CNC(=O)[C@H](CCCc1ccccc1)NC(=O)C1CN(C(=O)C(C)c2c[nH]c3cc(Cl)ccc23)CC2CN(C(=O)c3ccc(OC(C)C)c(OC)c3)CC21] |
| I-227 | 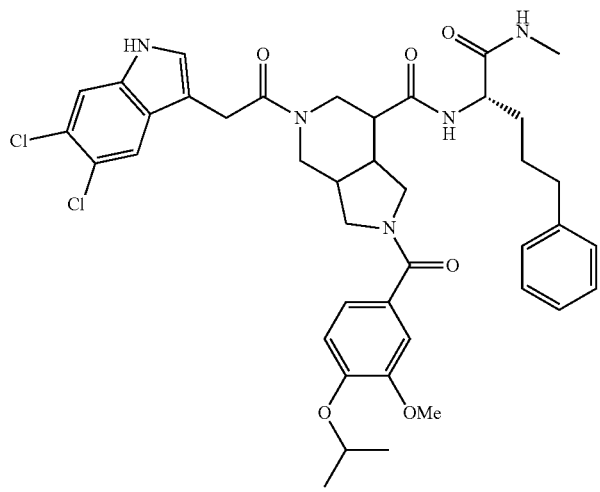 [SMILES: CNC(=O)[C@H](CCCc1ccccc1)NC(=O)C1CN(C(=O)Cc2c[nH]c3cc(Cl)c(Cl)cc23)CC2CN(C(=O)c3ccc(OC(C)C)c(OC)c3)CC21] |

| # | Structure |
|---|-----------|
| I-228 | 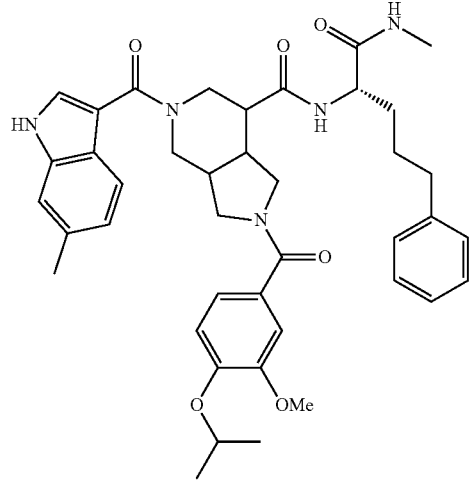 |
| I-229 | 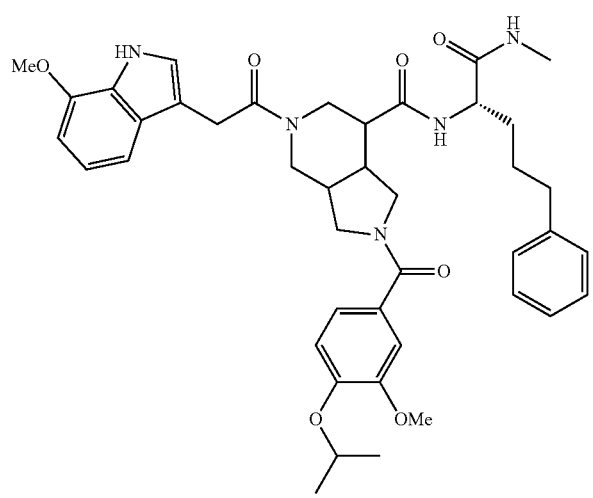 [SMILES: CNC(=O)[C@H](CCCc1ccccc1)NC(=O)C1CN(C(=O)Cc2c[nH]c3c(OC)cccc23)CC2CN(C(=O)c3ccc(OC(C)C)c(OC)c3)CC21] |
| I-230 | 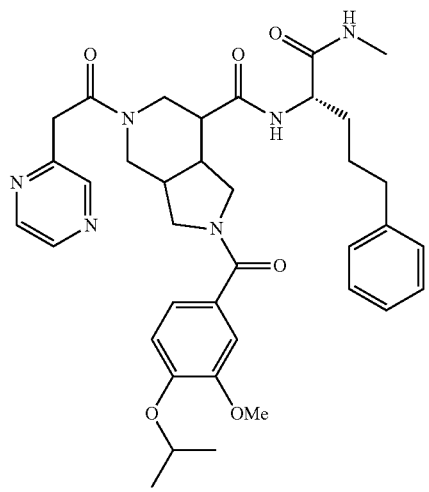 [SMILES: CNC(=O)[C@H](CCCc1ccccc1)NC(=O)C1CN(C(=O)Cc2cnccn2)CC2CN(C(=O)c3ccc(OC(C)C)c(OC)c3)CC21] |

| # | Structure |
|---|---|
| I-231 | 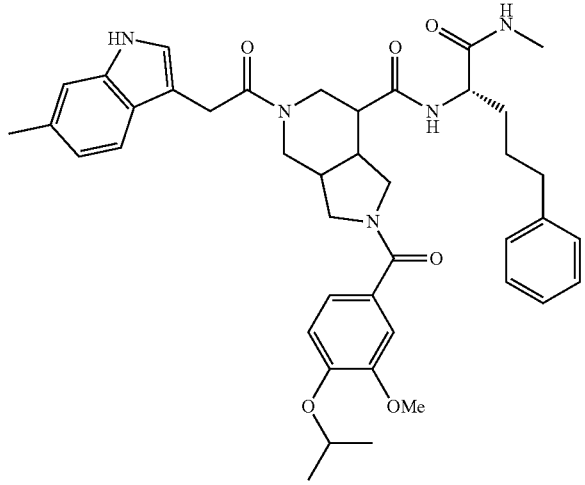 [SMILES: CNC(=O)[C@H](CCCc1ccccc1)NC(=O)C1CN(C(=O)Cc2c[nH]c3cc(C)ccc23)CC2CN(C(=O)c3ccc(OC(C)C)c(OC)c3)CC21] |
| I-232 | 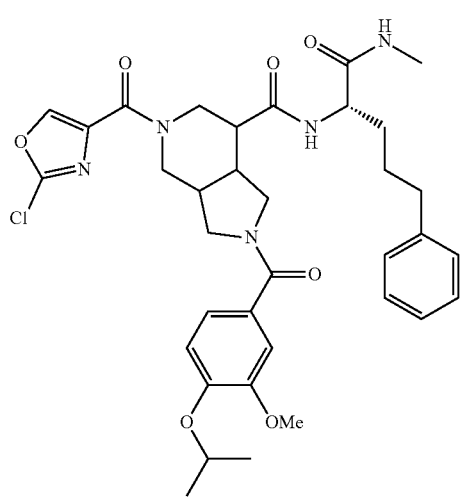
First eluting diastereomer |
| I-233 | 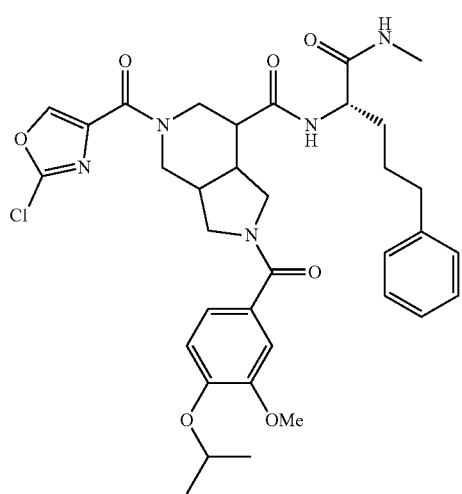
Second eluting diastereomer |

-continued
| # | Structure |
|---|---|
| I-234 | 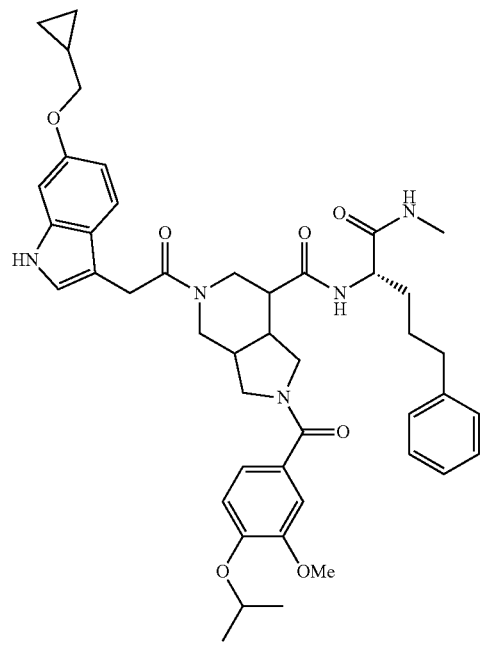 [SMILES: CNC(=O)[C@H](CCCc1ccccc1)NC(=O)C1CN(C(=O)Cc2c[nH]c3cc(OCC4CC4)ccc23)CC2CN(C(=O)c3ccc(OC(C)C)c(OC)c3)CC21] |
| I-235 | 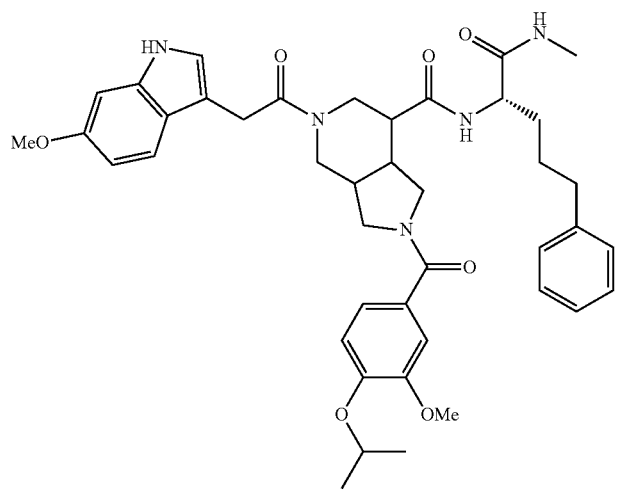 [SMILES: CNC(=O)[C@H](CCCc1ccccc1)NC(=O)C1CN(C(=O)Cc2c[nH]c3cc(OC)ccc23)CC2CN(C(=O)c3ccc(OC(C)C)c(OC)c3)CC21] |
| I-236 | 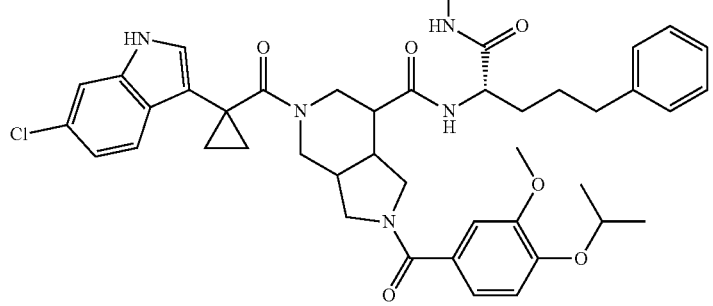 |

-continued
| # | Structure |
|---|---|
| I-237 | 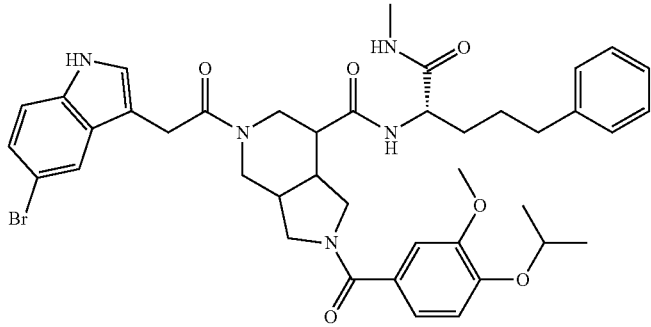 [SMILES: CNC(=O)[C@H](CCCc1ccccc1)NC(=O)C1CN(C(=O)Cc2c[nH]c3ccc(Br)cc23)CC2CN(C(=O)c3ccc(OC(C)C)c(OC)c3)CC21] |
| I-238 | 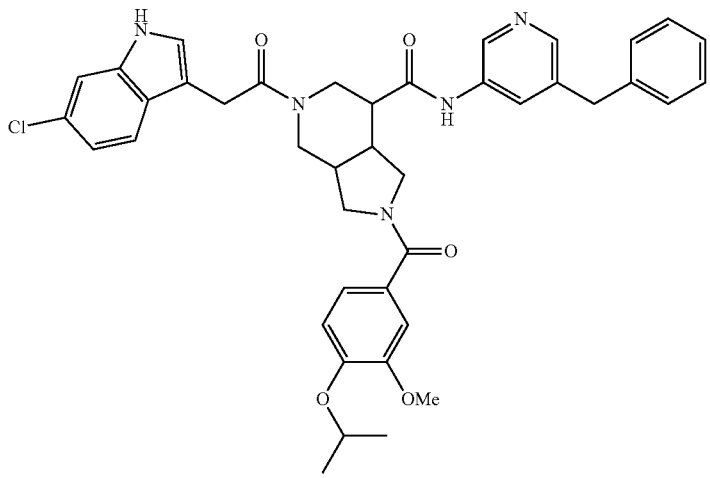 [SMILES: COc1cc(C(=O)N2CC3CN(C(=O)Cc4c[nH]c5cc(Cl)ccc45)CC(C(=O)Nc4cncc(Cc5ccccc5)c4)C3C2)ccc1OC(C)C] |
| I-239 | 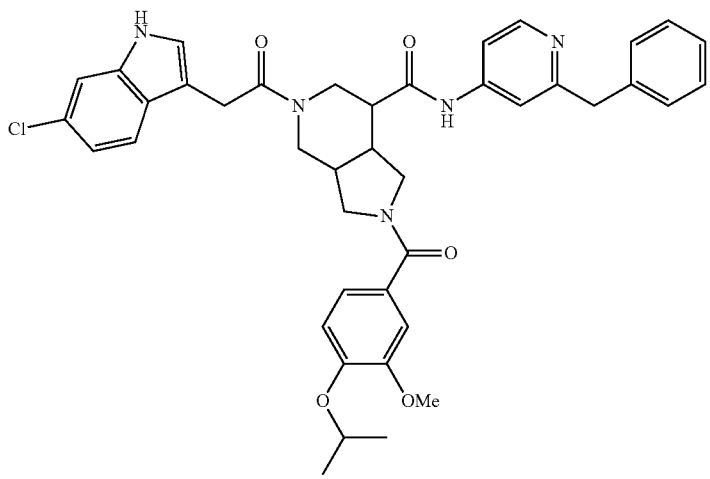 [SMILES: COc1cc(C(=O)N2CC3CN(C(=O)Cc4c[nH]c5cc(Cl)ccc45)CC(C(=O)Nc4ccnc(Cc5ccccc5)c4)C3C2)ccc1OC(C)C] |

| # | Structure |
|---|---|
| I-240 | 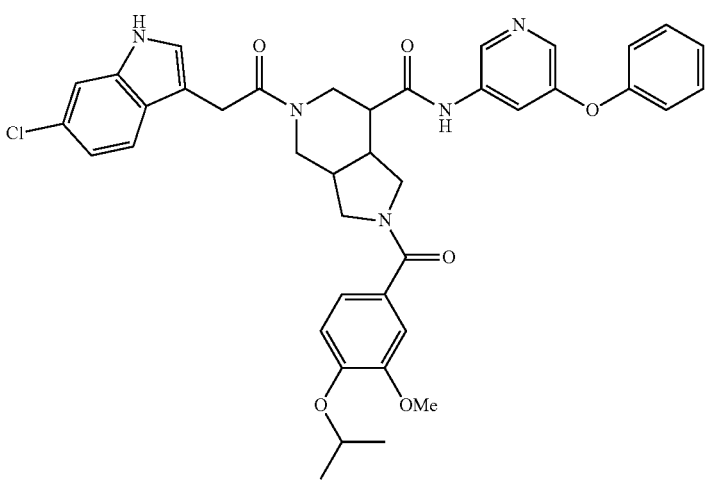 |
| I-241 | 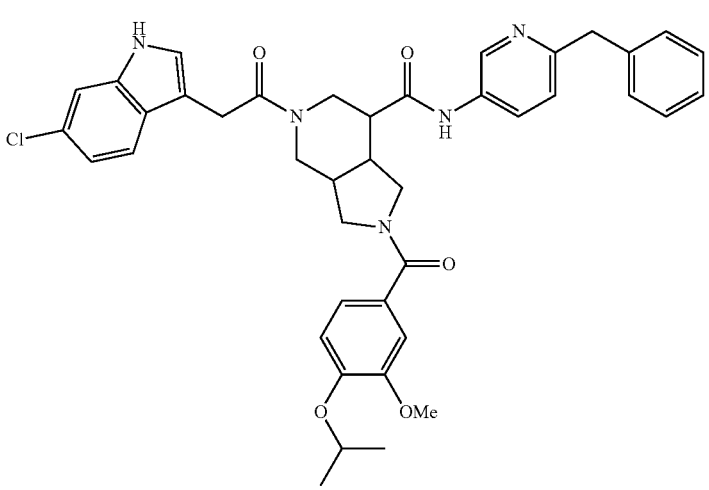 [SMILES: COc1cc(C(=O)N2CC3CN(C(=O)Cc4c[nH]c5cc(Cl)ccc45)CC(C(=O)Nc4ccc(Cc5ccccc5)nc4)C3C2)ccc1OC(C)C] |
| I-242 | 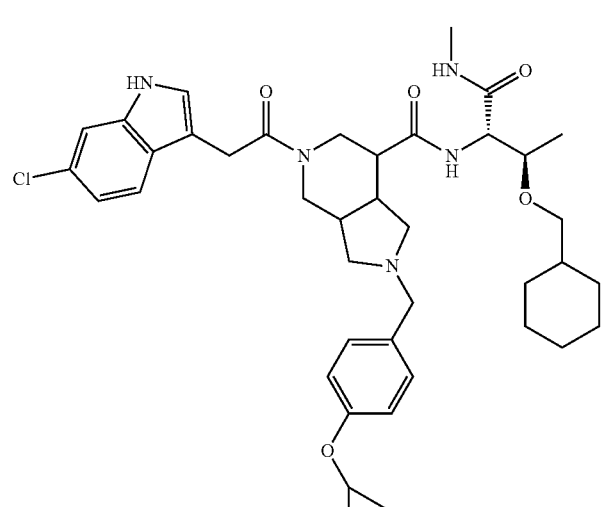 |

-continued
| # | Structure |
|---|---|
| I-243 | 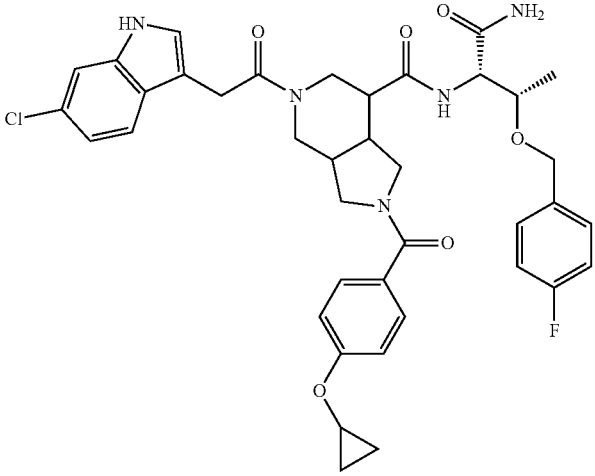 [SMILES: C[C@H](OCc1ccc(F)cc1)[C@H](NC(=O)C1CN(C(=O)Cc2c[nH]c3cc(Cl)ccc23)CC2CN(C(=O)c3ccc(OC4CC4)cc3)CC21)C(N)=O] |
| I-244 | 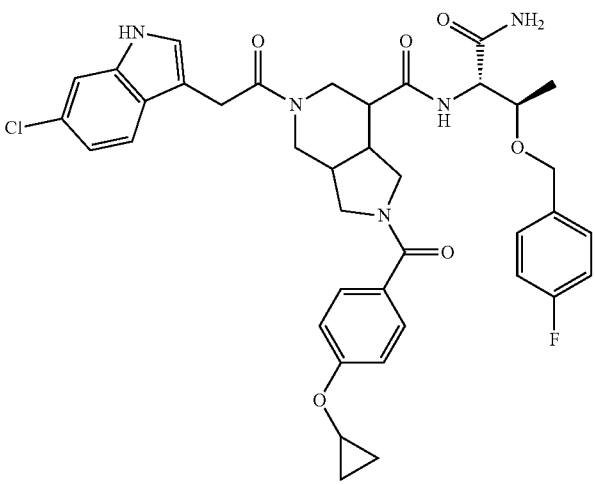 [SMILES: C[C@@H](OCc1ccc(F)cc1)[C@H](NC(=O)C1CN(C(=O)Cc2c[nH]c3cc(Cl)ccc23)CC2CN(C(=O)c3ccc(OC4CC4)cc3)CC21)C(N)=O] |
| I-245 | 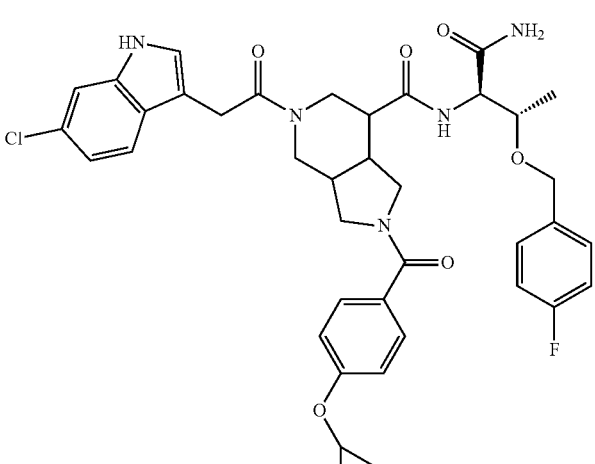 |

| # | Structure |
|---|---|
| I-246 | 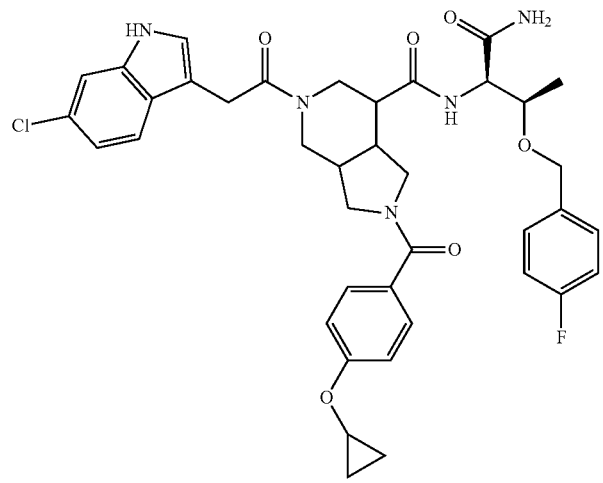 [SMILES: C[C@@H](OCc1ccc(F)cc1)[C@@H](NC(=O)C1CN(C(=O)Cc2c[nH]c3cc(Cl)ccc23)CC2CN(C(=O)c3ccc(OC4CC4)cc3)CC21)C(N)=O] |
| I-247 | 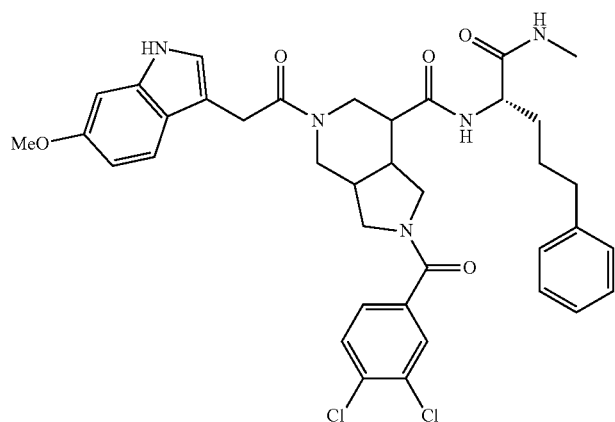 [SMILES: CNC(=O)[C@H](CCCc1ccccc1)NC(=O)C1CN(C(=O)Cc2c[nH]c3cc(OC)ccc23)CC2CN(C(=O)c3ccc(Cl)c(Cl)c3)CC21] |
| I-248 | 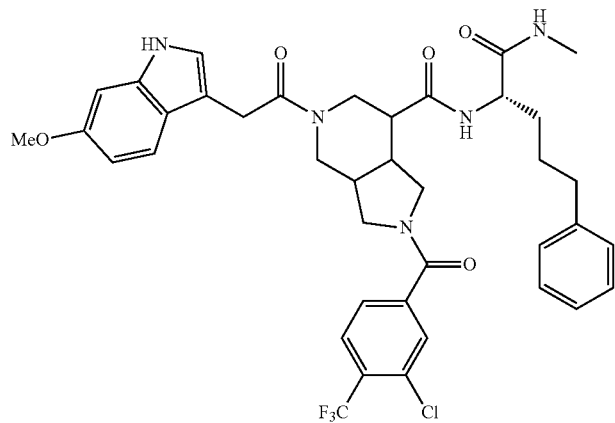 [SMILES: CNC(=O)[C@H](CCCc1ccccc1)NC(=O)C1CN(C(=O)Cc2c[nH]c3cc(OC)ccc23)CC2CN(C(=O)c3ccc(C(F)(F)F)c(Cl)c3)CC21] |

| # | Structure |
|---|---|
| I-249 | 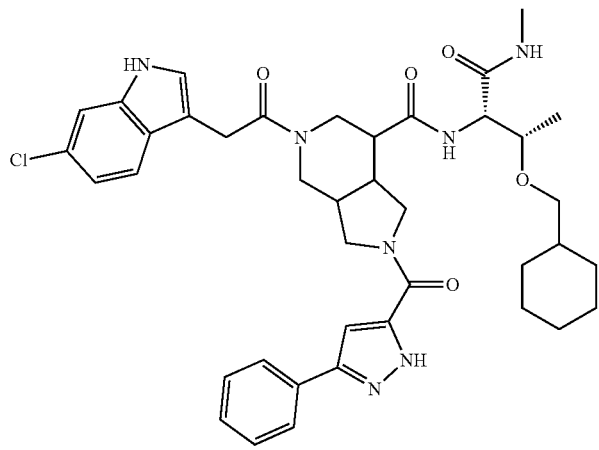 [SMILES: CNC(=O)[C@@H](NC(=O)C1CN(C(=O)Cc2c[nH]c3cc(Cl)ccc23)CC2CN(C(=O)c3cc(-c4ccccc4)n[nH]3)CC21)[C@H](C)OCC1CCCCC1] |
| I-250 | 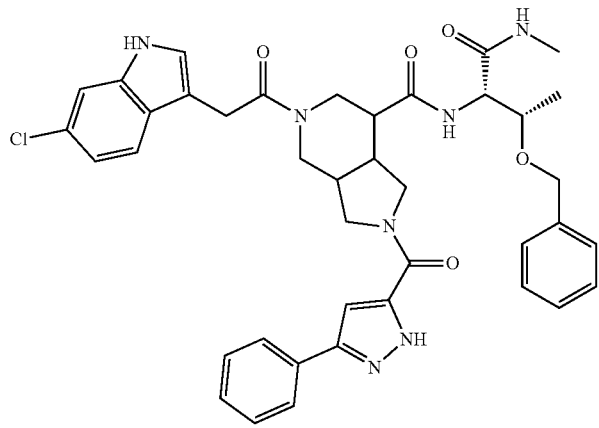 [SMILES: CNC(=O)[C@@H](NC(=O)C1CN(C(=O)Cc2c[nH]c3cc(Cl)ccc23)CC2CN(C(=O)c3cc(-c4ccccc4)n[nH]3)CC21)[C@H](C)OCc1ccccc1] |
| I-251 | 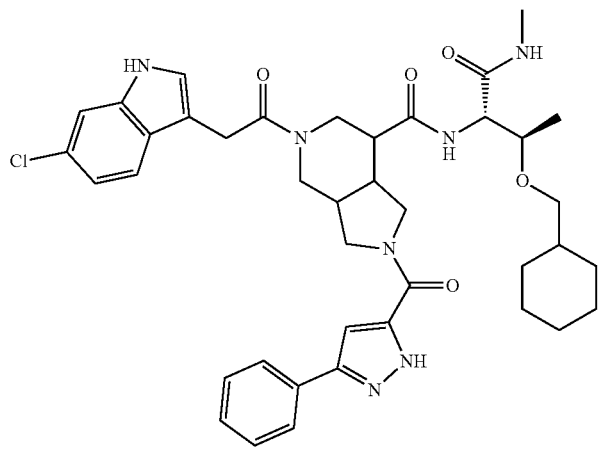 [SMILES: CNC(=O)[C@@H](NC(=O)C1CN(C(=O)Cc2c[nH]c3cc(Cl)ccc23)CC2CN(C(=O)c3cc(-c4ccccc4)n[nH]3)CC21)[C@@H](C)OCC1CCCCC1] |

| # | Structure |
|---|---|
| I-252 | 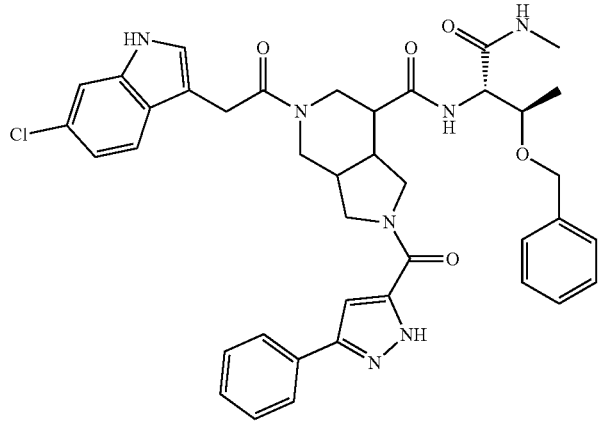 [SMILES: CNC(=O)[C@@H](NC(=O)C1CN(C(=O)Cc2c[nH]c3cc(Cl)ccc23)CC2CN(C(=O)c3cc(-c4ccccc4)n[nH]3)CC21)[C@@H](C)OCc1ccccc1] |
| I-253 | 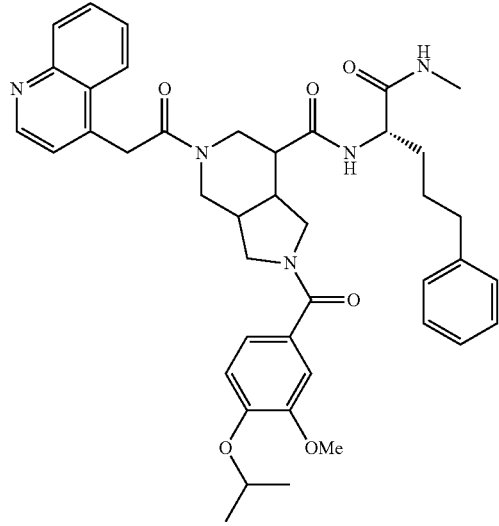 |
| I-254 | 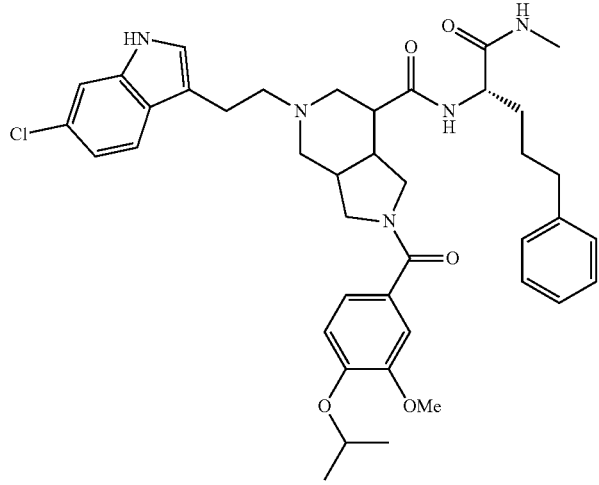 [SMILES: CNC(=O)[C@H](CCCc1ccccc1)NC(=O)C1CN(CCc2c[nH]c3cc(Cl)ccc23)CC2CN(C(=O)c3ccc(OC(C)C)c(OC)c3)CC21] |

| # | Structure |
|---|---|
| I-255 | 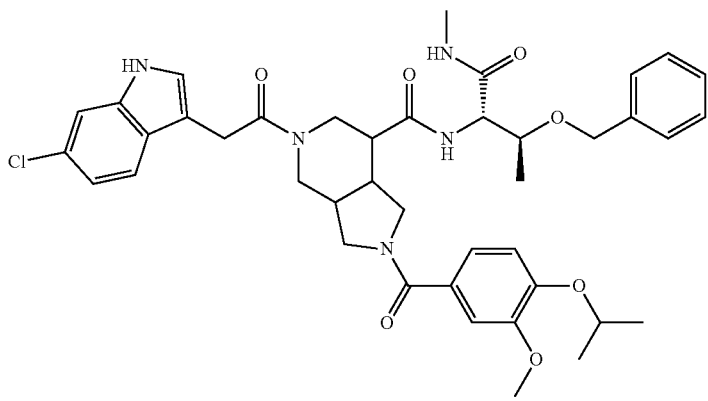 [SMILES: CNC(=O)[C@@H](NC(=O)C1CN(C(=O)Cc2c[nH]c3cc(Cl)ccc23)CC2CN(C(=O)c3ccc(OC(C)C)c(OC)c3)CC21)[C@H](C)OCc1ccccc1] |
| I-256 | 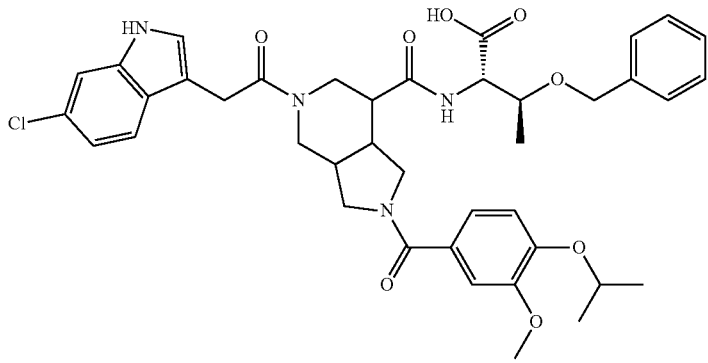 [SMILES: COc1cc(C(=O)N2CC3CN(C(=O)Cc4c[nH]c5cc(Cl)ccc45)CC(C(=O)N[C@H](C(=O)O)[C@H](C)OCc4ccccc4)C3C2)ccc1OC(C)C] |
| I-257 | 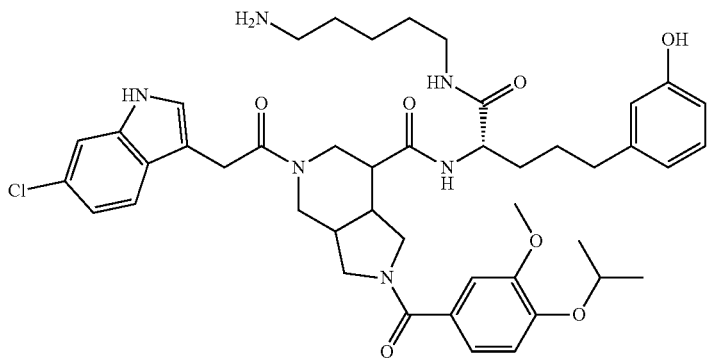<br>Synthesized from first eluting intermediate |
| I-258 | 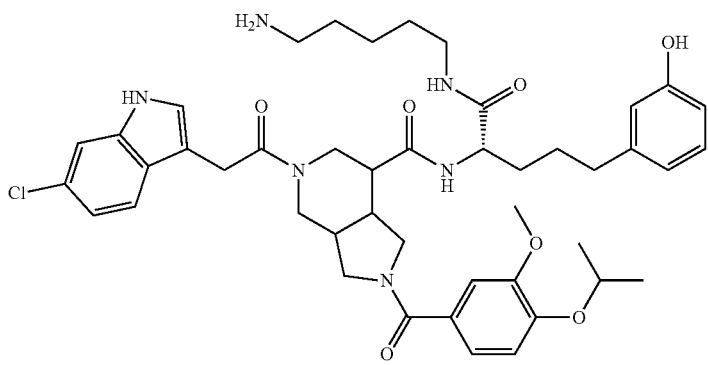<br>Synthesized from second eluting intermediate |

| # | Structure |
|---|---|
| I-259 | 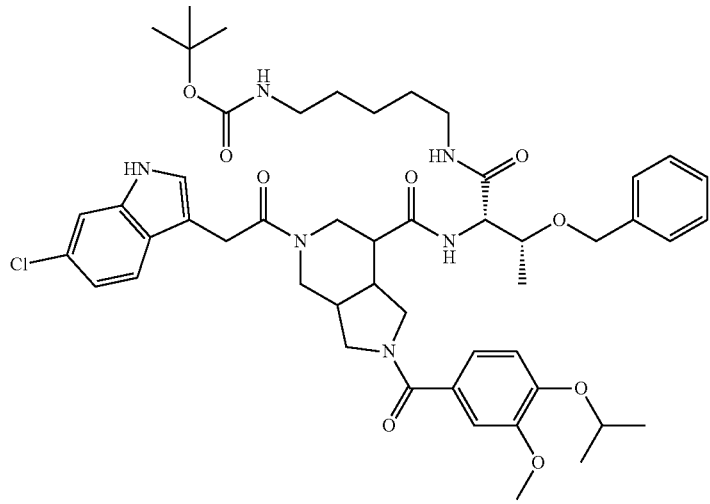<br>First eluting diastereomer |
| I-260 | 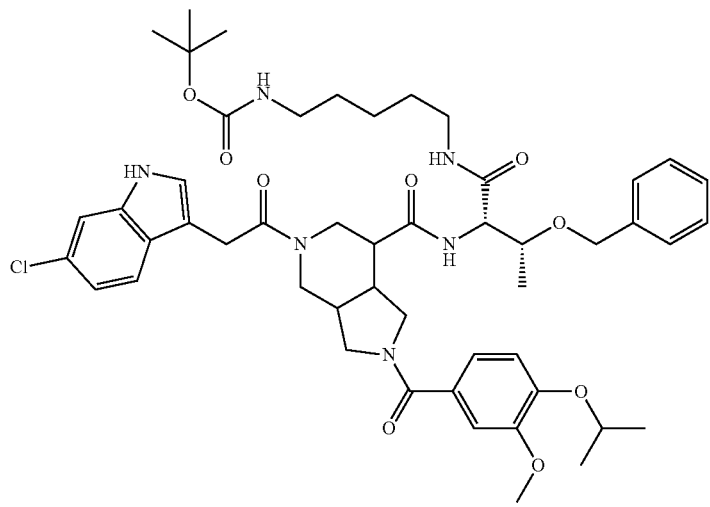<br>Second eluting diastereomer |
| I-261 | 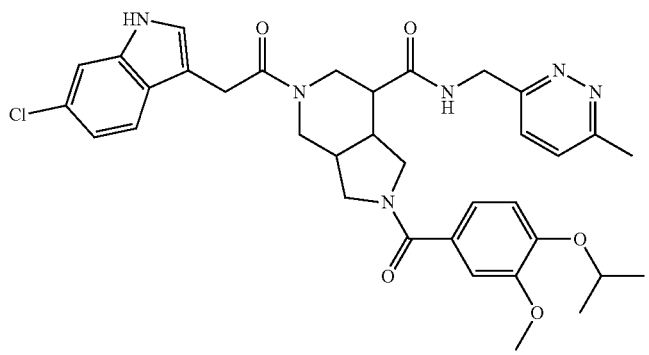<br>First eluting enantiomer |

| # | Structure |
|---|---|
| I-262 | 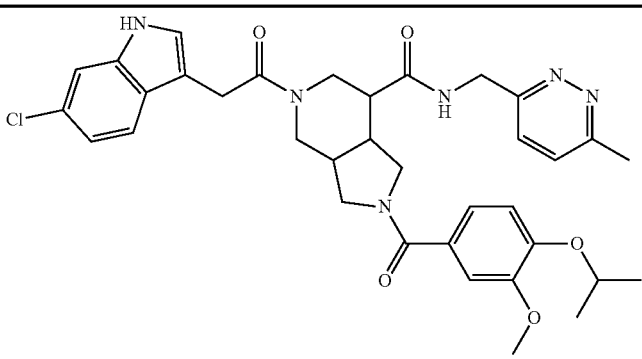<br>Second eluting enantiomer | or a pharmaceutically acceptable salt thereof.

22. A pharmaceutically acceptable composition comprising a compound of claim 1, and a pharmaceutically acceptable carrier, excipient, vehicle, adjuvant or diluent; optionally further comprising an additional therapeutic agent.

23. A method of reducing male fertility comprising administering to the patient in need thereof a compound of claim 1.

\* \* \* \* \*